US010941162B2

(12) United States Patent
Castro et al.

(10) Patent No.: US 10,941,162 B2
(45) Date of Patent: Mar. 9, 2021

(54) HETEROCYCLIC COMPOUNDS AND USES THEREOF

(71) Applicant: Infinity Pharmaceuticals, Inc., Cambridge, MA (US)

(72) Inventors: Alfredo C. Castro, Woburn, MA (US); Catherine A. Evans, Somerville, MA (US); Martin R. Tremblay, Melrose, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/290,545

(22) Filed: Mar. 1, 2019

(65) Prior Publication Data

US 2019/0330240 A1   Oct. 31, 2019

Related U.S. Application Data

(60) Division of application No. 15/621,815, filed on Jun. 13, 2017, now Pat. No. 10,253,047, which is a continuation of application No. 14/874,328, filed on Oct. 2, 2015, now Pat. No. 9,708,348.

(60) Provisional application No. 62/216,261, filed on Sep. 9, 2015, provisional application No. 62/059,426, filed on Oct. 3, 2014.

(51) Int. Cl.

| *C07D 471/04* | (2006.01) |
|---|---|
| *C07D 519/00* | (2006.01) |
| *C07D 487/04* | (2006.01) |
| *C07D 491/04* | (2006.01) |
| *C07D 495/04* | (2006.01) |
| *C07D 498/04* | (2006.01) |
| *C07D 513/04* | (2006.01) |

(52) U.S. Cl.
CPC ......... *C07D 519/00* (2013.01); *C07D 471/04* (2013.01); *C07D 487/04* (2013.01); *C07D 491/04* (2013.01); *C07D 495/04* (2013.01); *C07D 498/04* (2013.01); *C07D 513/04* (2013.01)

(58) Field of Classification Search
CPC ........................... A61K 31/519; C07D 471/04
USPC ........................................ 514/259.3; 544/281
See application file for complete search history.

(56) References Cited

U.S. PATENT DOCUMENTS

| 4,547,508 A | 10/1985 | Konz et al. |
|---|---|---|
| 4,656,159 A | 4/1987 | McPherson et al. |
| 4,704,381 A | 11/1987 | Schaumann et al. |
| 4,795,627 A | 1/1989 | Fisher et al. |
| 4,981,856 A | 1/1991 | Hughes |
| 5,240,941 A | 8/1993 | Bruneau |
| 5,272,158 A | 12/1993 | Hartman et al. |
| 5,294,612 A | 3/1994 | Bacon et al. |
| 5,310,731 A | 5/1994 | Olsson et al. |
| 5,364,862 A | 11/1994 | Spada et al. |
| 5,409,930 A | 4/1995 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,504,103 A | 4/1996 | Bonjouklian et al. |
| 5,506,347 A | 4/1996 | Erion et al. |
| 5,527,811 A | 6/1996 | Natsugari et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,679,677 A | 10/1997 | Pill et al. |
| 5,686,455 A | 11/1997 | Adams et al. |
| 5,736,554 A | 4/1998 | Spada et al. |
| 5,747,235 A | 5/1998 | Farid et al. |
| 5,756,502 A | 5/1998 | Padia |
| 5,756,711 A | 5/1998 | Zilch et al. |
| 5,763,596 A | 6/1998 | Boyer et al. |
| 5,763,597 A | 6/1998 | Ugarkar et al. |
| 5,763,608 A | 6/1998 | Bhattacharya et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,869,665 A | 2/1999 | Padia |
| 5,872,136 A | 2/1999 | Anthony et al. |
| 5,914,488 A | 6/1999 | Sone |
| 5,919,808 A | 7/1999 | Petrie et al. |

(Continued)

FOREIGN PATENT DOCUMENTS

| CA | 1338379 C | 6/1996 |
|---|---|---|
| CN | 1502608 | 6/2004 |

(Continued)

OTHER PUBLICATIONS

Pitt et al., "Resistance Mechanisms to Immune-Checkpoint Blockade in Cancer: Tumor-Intrinsic and -Extrinsic Factors", Immunity, 2016, 44, 1255-1269.

(Continued)

*Primary Examiner* — Jeffrey H Murray

(74) *Attorney, Agent, or Firm* — Jones Day

(57) ABSTRACT

Trisubstituted bicyclic heterocyclic compounds (e.g., pyridopyrimidinones) and pharmaceutical compositions that modulate kinase activity, including PI3 kinase activity, and methods of treatment of diseases and conditions associated with kinase activity, including PI3 kinase activity, are described herein.

15 Claims, No Drawings

(56) References Cited

U.S. PATENT DOCUMENTS

| | | |
|---|---|---|
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,977,134 A | 11/1999 | Ciccarone et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,037,474 A | 3/2000 | Drauz et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,184,377 B1 | 2/2001 | Gao |
| 6,191,170 B1 | 2/2001 | Medina |
| 6,207,697 B1 | 3/2001 | Han et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,429,311 B2 | 8/2002 | Gao |
| 6,455,534 B2 | 9/2002 | Bridges et al. |
| 6,469,026 B2 | 10/2002 | Marlowe et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,004 B1 | 4/2003 | Finer et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,562,831 B1 | 5/2003 | Finer et al. |
| 6,583,161 B1 | 6/2003 | Medina |
| 6,596,497 B1 | 7/2003 | Jiang et al. |
| 6,596,718 B1 | 7/2003 | Flohr et al. |
| 6,596,723 B1 | 7/2003 | Watkins et al. |
| 6,613,798 B1 | 9/2003 | Porter et al. |
| 6,630,479 B1 | 10/2003 | Finer et al. |
| 6,630,495 B1 | 10/2003 | Cooke et al. |
| 6,632,789 B1 | 10/2003 | June |
| 6,645,989 B2 | 11/2003 | Adams et al. |
| 6,649,565 B1 | 11/2003 | Feucht et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,683,108 B1 | 1/2004 | Baxter et al. |
| 6,683,192 B2 | 1/2004 | Baxter et al. |
| 6,689,782 B2 | 2/2004 | Watkins et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,753,428 B2 | 6/2004 | Yao et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,794,379 B2 | 9/2004 | Medina et al. |
| 6,800,620 B2 | 10/2004 | Sadhu et al. |
| 6,831,085 B1 | 12/2004 | Bergnes et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,870,055 B2 | 3/2005 | Claremon et al. |
| 6,900,219 B2 | 5/2005 | Ibrahim et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 6,964,967 B2 | 11/2005 | Medina et al. |
| 6,995,144 B2 | 2/2006 | Ozaki et al. |
| 7,009,049 B2 | 3/2006 | Bergnes et al. |
| 7,026,461 B1 | 4/2006 | Shokat |
| 7,038,048 B2 | 5/2006 | Dhanak et al. |
| 7,041,676 B2 | 5/2006 | McDonald et al. |
| 7,049,116 B2 | 5/2006 | Shokat |
| 7,049,312 B1 | 5/2006 | Rafferty et al. |
| 7,053,215 B2 | 5/2006 | Medina et al. |
| 7,053,216 B2 | 5/2006 | Sun et al. |
| 7,064,218 B2 | 6/2006 | Dyatkina et al. |
| 7,067,662 B2 | 6/2006 | Medina et al. |
| 7,071,355 B2 | 7/2006 | Leban et al. |
| 7,105,668 B1 | 9/2006 | Bergnes et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,148,214 B1 | 12/2006 | Janssens et al. |
| 7,157,487 B2 | 1/2007 | Nakayama et al. |
| 7,161,002 B2 | 1/2007 | Bergnes et al. |
| 7,166,293 B2 | 1/2007 | Teng et al. |
| 7,166,595 B2 | 1/2007 | Zhou et al. |
| 7,192,949 B2 | 3/2007 | Fraley et al. |
| 7,208,601 B2 | 4/2007 | Mjalli et al. |
| 7,214,800 B2 | 5/2007 | Feng et al. |
| 7,217,794 B2 | 5/2007 | Abdel-Meguid et al. |
| 7,230,000 B1 | 6/2007 | Finer et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,187 B2 | 8/2007 | Fraley et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,294,634 B2 | 11/2007 | Finer et al. |
| 7,329,765 B2 | 2/2008 | Burli et al. |
| 7,332,497 B2 | 2/2008 | Hirst et al. |
| 7,332,498 B2 | 2/2008 | Dhanak et al. |
| 7,345,046 B2 | 3/2008 | Wang et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,405,235 B2 | 7/2008 | Levy et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,528,137 B2 | 5/2009 | Feng et al. |
| 7,534,797 B2 | 5/2009 | Arnold et al. |
| 7,538,135 B2 | 5/2009 | Vedananda |
| 7,541,373 B2 | 6/2009 | Polisetti et al. |
| 7,550,590 B2 | 6/2009 | Feng et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,589,098 B2 | 9/2009 | Finer et al. |
| 7,608,594 B2 | 10/2009 | Blagg et al. |

(56) References Cited

U.S. PATENT DOCUMENTS

| | | |
|---|---|---|
| 7,615,552 B2 | 11/2009 | Ono et al. |
| 7,615,554 B2 | 11/2009 | Selliah et al. |
| 7,622,451 B2 | 11/2009 | Blagg et al. |
| 7,632,839 B2 | 12/2009 | Coleman et al. |
| 7,650,848 B2 | 1/2010 | Brennan et al. |
| 7,652,061 B2 | 1/2010 | Ksander et al. |
| 7,671,200 B2 | 3/2010 | Finer et al. |
| 7,678,803 B2 | 3/2010 | Huang et al. |
| 7,700,607 B2 | 4/2010 | Hu et al. |
| 7,705,018 B2 | 4/2010 | Chen et al. |
| 7,745,485 B2 | 6/2010 | Durden |
| 7,763,628 B2 | 7/2010 | Finer et al. |
| 7,799,795 B2 | 9/2010 | Bergeron et al. |
| 7,825,126 B2 | 11/2010 | Jacobson et al. |
| 7,893,260 B2 | 2/2011 | Chong et al. |
| 7,932,260 B2 | 4/2011 | Fowler et al. |
| 7,939,538 B2 | 5/2011 | Fu et al. |
| 7,939,539 B2 | 5/2011 | Wang et al. |
| 8,013,003 B2 | 9/2011 | Sreet et al. |
| 8,030,318 B2 | 10/2011 | Simmen et al. |
| 8,106,146 B2 | 1/2012 | Benz et al. |
| 8,133,998 B2 | 3/2012 | Pajouhesh et al. |
| 8,193,182 B2 | 6/2012 | Ren et al. |
| 8,232,285 B2 | 7/2012 | Liu et al. |
| 8,236,808 B2 | 8/2012 | Collingwood et al. |
| 8,247,436 B2 | 8/2012 | Baettig et al. |
| 8,389,544 B2 | 3/2013 | Wong et al. |
| 8,399,483 B2 | 3/2013 | Allen et al. |
| 8,399,493 B2 | 3/2013 | Bolea et al. |
| 8,569,316 B2 | 10/2013 | Ettmayer et al. |
| 8,569,323 B2 | 10/2013 | Ren et al. |
| 8,586,619 B2 | 11/2013 | Wu et al. |
| 8,604,032 B2 | 12/2013 | Ren et al. |
| 8,637,666 B2 | 1/2014 | Charrier et al. |
| 8,642,609 B2 | 2/2014 | Makings et al. |
| 8,648,084 B2 | 2/2014 | Bunnelle et al. |
| 8,703,777 B2 | 4/2014 | Ren et al. |
| 8,716,297 B2 | 5/2014 | Woods et al. |
| 8,748,440 B2 | 6/2014 | Martin et al. |
| 8,785,470 B2 | 7/2014 | Castro et al. |
| 8,809,349 B2 | 8/2014 | Ren et al. |
| 8,809,530 B1 | 8/2014 | Wu et al. |
| 8,822,453 B2 | 9/2014 | Matsumura et al. |
| 8,901,133 B2 | 12/2014 | Ren et al. |
| 8,940,742 B2 | 1/2015 | Castro et al. |
| 8,969,363 B2 | 3/2015 | Castro et al. |
| 9,056,877 B2 | 6/2015 | Castro et al. |
| 9,115,141 B2 | 8/2015 | Castro et al. |
| 9,255,108 B2 | 2/2016 | Castro et al. |
| 9,359,365 B2 | 6/2016 | Castro et al. |
| 9,388,183 B2 | 7/2016 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0198236 A1 | 12/2002 | Baxter et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0144350 A1 | 7/2003 | Stevenson et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0220338 A1 | 11/2003 | Watkins et al. |
| 2003/0229097 A1 | 12/2003 | Watkins et al. |
| 2003/0232832 A1 | 12/2003 | Lombardo et al. |
| 2003/0232849 A1 | 12/2003 | Noe et al. |
| 2003/0235822 A1 | 12/2003 | Lokhov et al. |
| 2004/0023996 A1 | 2/2004 | Finer et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0082567 A1 | 4/2004 | McDonald et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0132732 A1 | 7/2004 | Han et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0242596 A1 | 12/2004 | Kim et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0065169 A1 | 3/2005 | Wang et al. |
| 2005/0070578 A1 | 3/2005 | Baxter et al. |
| 2005/0080138 A1 | 4/2005 | Guicherit et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0152940 A1 | 7/2005 | Hezi-Yamit et al. |
| 2005/0153997 A1 | 7/2005 | Simon et al. |
| 2005/0171148 A1 | 8/2005 | Mjalli et al. |
| 2005/0178286 A1 | 8/2005 | Brennan et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0203110 A1 | 9/2005 | Coleman et al. |
| 2005/0209254 A1 | 9/2005 | Wang et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282834 A1 | 12/2005 | Malik et al. |
| 2006/0019988 A1 | 1/2006 | McDonald et al. |
| 2006/0036093 A1 | 2/2006 | Lin et al. |
| 2006/0041128 A1 | 2/2006 | Aquila et al. |
| 2006/0063751 A1 | 3/2006 | Aquila et al. |
| 2006/0069034 A1 | 3/2006 | Burli et al. |
| 2006/0069106 A1 | 3/2006 | Fu et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |

(56) References Cited

U.S. PATENT DOCUMENTS

| | | |
|---|---|---|
| 2006/0205694 A1 | 9/2006 | Alonso et al. |
| 2006/0235031 A1 | 10/2006 | Arnold et al. |
| 2006/0270849 A1 | 11/2006 | Nishino et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0021493 A1 | 1/2007 | Guicherit et al. |
| 2007/0027193 A1 | 2/2007 | Leban et al. |
| 2007/0032640 A1 | 2/2007 | Varghese et al. |
| 2007/0049593 A1 | 3/2007 | Oka et al. |
| 2007/0054915 A1 | 3/2007 | Arora et al. |
| 2007/0066632 A1 | 3/2007 | Hart et al. |
| 2007/0072897 A1 | 3/2007 | Mahaney et al. |
| 2007/0099871 A1 | 5/2007 | Davis et al. |
| 2007/0135454 A1 | 6/2007 | Hollingworth et al. |
| 2007/0142405 A1 | 6/2007 | Dong et al. |
| 2007/0155730 A1 | 7/2007 | Leit et al. |
| 2007/0161644 A1 | 7/2007 | Stockwell |
| 2007/0179151 A1 | 8/2007 | Chen et al. |
| 2007/0207996 A1 | 9/2007 | Auger et al. |
| 2007/0224672 A1 | 9/2007 | Leban et al. |
| 2007/0244133 A1 | 10/2007 | Bower et al. |
| 2007/0249598 A1 | 10/2007 | Wang et al. |
| 2007/0249680 A1 | 10/2007 | Illig et al. |
| 2007/0265231 A1 | 11/2007 | Hofmann et al. |
| 2007/0270452 A1 | 11/2007 | Blagg et al. |
| 2008/0004253 A1 | 1/2008 | Branstetter et al. |
| 2008/0032960 A1 | 2/2008 | Knight et al. |
| 2008/0058521 A1 | 3/2008 | Krishnan et al. |
| 2008/0070864 A1 | 3/2008 | Martin et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0194552 A1 | 8/2008 | Jones et al. |
| 2008/0200465 A1 | 8/2008 | Burli et al. |
| 2008/0234299 A1 | 9/2008 | Buchstaller et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0030036 A1 | 1/2009 | Dalton et al. |
| 2009/0053192 A1 | 2/2009 | Millan et al. |
| 2009/0088452 A1 | 4/2009 | Coleman et al. |
| 2009/0099210 A1 | 4/2009 | Aquila et al. |
| 2009/0099214 A1 | 4/2009 | Fairhurst et al. |
| 2009/0105233 A1 | 4/2009 | Chua et al. |
| 2009/0118261 A1 | 5/2009 | Aquila et al. |
| 2009/0118283 A1 | 5/2009 | Defert et al. |
| 2009/0124638 A1 | 5/2009 | Shokat et al. |
| 2009/0124641 A1 | 5/2009 | Coleman et al. |
| 2009/0124654 A1 | 5/2009 | Mjalli et al. |
| 2009/0130097 A1 | 5/2009 | Liu et al. |
| 2009/0137581 A1 | 5/2009 | Chen et al. |
| 2009/0149484 A1 | 6/2009 | Aquila et al. |
| 2009/0163481 A1 | 6/2009 | Murphy et al. |
| 2009/0163525 A1 | 6/2009 | Aquila et al. |
| 2009/0163545 A1 | 6/2009 | Goldfarb |
| 2009/0163709 A1 | 6/2009 | Blagg |
| 2009/0170834 A1 | 7/2009 | Venkat et al. |
| 2009/0170849 A1 | 7/2009 | Aquila et al. |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0214465 A1 | 8/2009 | Becklin et al. |
| 2009/0221488 A1 | 9/2009 | Wood et al. |
| 2009/0232768 A1 | 9/2009 | Birkus et al. |
| 2009/0233907 A1 | 9/2009 | Austin et al. |
| 2009/0233947 A1 | 9/2009 | Bayliss et al. |
| 2009/0247513 A1 | 10/2009 | Burli et al. |
| 2009/0247567 A1 | 10/2009 | Do et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0280153 A1 | 11/2009 | Hunter et al. |
| 2009/0291442 A1 | 11/2009 | Hedge et al. |
| 2009/0298856 A1 | 12/2009 | Brown et al. |
| 2009/0306069 A1 | 12/2009 | Rueckle et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0099871 A1 | 4/2010 | Miller et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0189685 A1 | 7/2010 | Byrd et al. |
| 2010/0190749 A1 | 7/2010 | Ren et al. |
| 2010/0226943 A1 | 9/2010 | Brennan et al. |
| 2010/0249030 A1 | 9/2010 | Basso-Porcaro |
| 2010/0280010 A1 | 11/2010 | Gudmundsson et al. |
| 2010/0292188 A1 | 11/2010 | Denonne et al. |
| 2010/0310503 A1 | 12/2010 | Li et al. |
| 2010/0323973 A1 | 12/2010 | Leamon et al. |
| 2011/0014186 A1 | 1/2011 | Ehrhardt et al. |
| 2011/0046165 A1 | 2/2011 | Ren et al. |
| 2011/0059953 A1 | 3/2011 | Fersht et al. |
| 2011/0071148 A1 | 3/2011 | Ding et al. |
| 2011/0123486 A1 | 5/2011 | Robbins et al. |
| 2011/0124641 A1 | 5/2011 | Ren et al. |
| 2011/0144134 A1 | 6/2011 | Shokat et al. |
| 2011/0152242 A1 | 6/2011 | Bayliss et al. |
| 2011/0172228 A1 | 7/2011 | Ren et al. |
| 2011/0217300 A1 | 9/2011 | Liu et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2011/0313156 A1 | 12/2011 | Engelhardt et al. |
| 2012/0041683 A1 | 2/2012 | Vaske et al. |
| 2012/0059000 A1 | 3/2012 | Ren et al. |
| 2012/0065154 A1 | 3/2012 | Tanaka et al. |
| 2012/0065205 A1 | 3/2012 | Mercer et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0157306 A1 | 6/2012 | Frankenpohl et al. |
| 2012/0184568 A1 | 7/2012 | Ren et al. |
| 2012/0202784 A1 | 8/2012 | Aronov et al. |
| 2012/0220575 A1 | 8/2012 | Chang et al. |
| 2012/0225866 A1 | 9/2012 | Oshima et al. |
| 2012/0245136 A1 | 9/2012 | Hadida-Ruah et al. |
| 2012/0245166 A1 | 9/2012 | Grimaldi et al. |
| 2012/0245169 A1 | 9/2012 | Ren et al. |
| 2012/0270863 A1 | 10/2012 | Williams et al. |
| 2012/0289493 A1 | 11/2012 | Corkey et al. |
| 2012/0329776 A1 | 12/2012 | Ren et al. |
| 2013/0005802 A1 | 1/2013 | Chen et al. |
| 2013/0029982 A1 | 1/2013 | Castro et al. |
| 2013/0029984 A1 | 1/2013 | Castro et al. |
| 2013/0053362 A1 | 2/2013 | Castro et al. |
| 2013/0116277 A1 | 5/2013 | Dalton et al. |
| 2013/0190308 A1 | 7/2013 | Jain et al. |
| 2013/0267521 A1 | 10/2013 | Castro et al. |
| 2013/0267542 A1 | 10/2013 | Chern et al. |

(56) References Cited

U.S. PATENT DOCUMENTS

| | | |
|---|---|---|
| 2013/0289033 A1 | 10/2013 | Griffioen et al. |
| 2013/0344061 A1 | 12/2013 | Palombella et al. |
| 2013/0345216 A1 | 12/2013 | Ren et al. |
| 2014/0045825 A1 | 2/2014 | Leahy |
| 2014/0088099 A1 | 3/2014 | Ren et al. |
| 2014/0100214 A1 | 4/2014 | Castro et al. |
| 2014/0120060 A1 | 5/2014 | Palombella et al. |
| 2014/0120083 A1 | 5/2014 | Stern et al. |
| 2014/0155387 A1 | 6/2014 | No et al. |
| 2014/0194417 A1 | 7/2014 | Greenwood et al. |
| 2014/0227321 A1 | 8/2014 | Iadonato et al. |
| 2014/0249145 A1 | 9/2014 | Marugan et al. |
| 2015/0225410 A1 | 8/2015 | Castro et al. |
| 2015/0290207 A1 | 10/2015 | Kutok et al. |
| 2016/0122365 A1 | 5/2016 | Castro et al. |

FOREIGN PATENT DOCUMENTS

| | | |
|---|---|---|
| CN | 101602768 A | 12/2009 |
| DE | 2139107 A1 | 2/1973 |
| DE | 19940859 | 3/2001 |
| DE | 102010013716 | 10/2011 |
| EP | 773023 A1 | 5/1997 |
| EP | 1020445 B1 | 8/2008 |
| EP | 2070932 | 6/2009 |
| GB | 812366 A | 4/1959 |
| GB | 937725 A | 9/1963 |
| GB | 2373186 | 9/2002 |
| JP | 61-109797 A | 5/1986 |
| JP | H05239036 | 9/1993 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2001250689 | 9/2001 |
| JP | 2002131859 A | 5/2002 |
| JP | 2003073357 A | 3/2003 |
| JP | 2004161716 A | 6/2004 |
| JP | 2005035933 | 2/2005 |
| JP | 2006265107 | 10/2006 |
| JP | 2012184225 | 9/2012 |
| JP | 5569437 | 10/2012 |
| WO | WO 1983/001446 A1 | 4/1983 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/040706 A1 | 12/1996 |
| WO | WO 1997/010221 | 3/1997 |
| WO | WO 1997/028133 A1 | 8/1997 |
| WO | WO 1997/028161 A1 | 8/1997 |
| WO | WO 1997/036901 | 10/1997 |
| WO | WO 1998/002162 | 1/1998 |
| WO | WO 1998/041525 A1 | 9/1998 |
| WO | WO 1998/052611 A1 | 11/1998 |
| WO | WO 1998/057952 A1 | 12/1998 |
| WO | WO 1999/024416 | 5/1999 |
| WO | WO 2000/017202 A1 | 3/2000 |
| WO | WO 2001/002369 A2 | 1/2001 |
| WO | WO 2001/016114 A2 | 3/2001 |
| WO | WO 2001/019829 A2 | 3/2001 |
| WO | WO 2001/025238 A2 | 4/2001 |
| WO | WO 2001/031063 A1 | 5/2001 |
| WO | WO 2001/038584 A2 | 5/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/019829 A3 | 9/2001 |
| WO | WO 2001/025238 A3 | 10/2001 |
| WO | WO 2001/038584 A3 | 10/2001 |
| WO | WO 2001/081346 A2 | 11/2001 |
| WO | WO 2001/098278 | 12/2001 |
| WO | WO 2002/006192 A1 | 1/2002 |
| WO | WO 2001/081346 A3 | 3/2002 |
| WO | WO 2002/024655 A1 | 3/2002 |
| WO | WO 2001/002369 A3 | 4/2002 |
| WO | WO 2002/030944 A2 | 4/2002 |
| WO | WO 2002/050091 | 6/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/083884 | 10/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/016275 A1 | 2/2003 |
| WO | WO 2003/020279 | 3/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/045385 | 6/2003 |
| WO | WO 2003/059884 A1 | 7/2003 |
| WO | WO 2003/076418 | 9/2003 |
| WO | WO 2003/020880 A3 | 10/2003 |
| WO | WO 2003/082341 A1 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |
| WO | WO 2004/018058 A3 | 7/2004 |
| WO | WO 2004/039774 A3 | 7/2004 |
| WO | WO 2004/058717 A1 | 7/2004 |
| WO | WO 2003/000187 A3 | 8/2004 |
| WO | WO 2004/069145 | 8/2004 |
| WO | WO 2004/087053 A2 | 10/2004 |
| WO | WO 2004/092123 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/061707 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |

(56) References Cited

FOREIGN PATENT DOCUMENTS

| | | |
|---|---|---|
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/121522 | 11/2006 |
| WO | WO 2006/068760 A3 | 12/2006 |
| WO | WO 2006/089106 A3 | 12/2006 |
| WO | WO 2006/135479 | 12/2006 |
| WO | WO 2007/002293 A2 | 1/2007 |
| WO | WO 2007/006547 A1 | 1/2007 |
| WO | WO 2007/008541 | 1/2007 |
| WO | WO 2007/015877 | 2/2007 |
| WO | WO 2007/020046 A1 | 2/2007 |
| WO | WO 2007/002293 A3 | 3/2007 |
| WO | WO 2007/025090 A2 | 3/2007 |
| WO | WO 2006/050501 A3 | 5/2007 |
| WO | WO 2007/056155 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/076055 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2008/013840 | 1/2008 |
| WO | WO 2008/013987 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/054252 | 5/2008 |
| WO | WO 2008/063625 A2 | 5/2008 |
| WO | WO 2008/064018 A1 | 5/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2008/094909 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/120098 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2008/153701 | 12/2008 |
| WO | WO 2009/000412 A1 | 12/2008 |
| WO | WO 2009/002808 | 12/2008 |
| WO | WO 2009/004621 A1 | 1/2009 |
| WO | WO 2009/010925 A2 | 1/2009 |
| WO | WO 2009/018811 | 2/2009 |
| WO | WO 2009/021163 | 2/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/065919 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/097233 | 8/2009 |
| WO | WO 2009/100406 A2 | 8/2009 |
| WO | WO 2009/114826 A2 | 9/2009 |
| WO | WO 2009/117157 A1 | 9/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/118207 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/046780 | 4/2010 |
| WO | WO 2010/019210 A3 | 5/2010 |
| WO | WO 2010/051391 | 5/2010 |
| WO | WO 2010/056758 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/096680 | 8/2010 |
| WO | WO 2010/127208 | 11/2010 |
| WO | WO 2010/133836 A1 | 11/2010 |
| WO | WO 2011/003065 | 1/2011 |
| WO | WO 2011/008302 A1 | 1/2011 |
| WO | WO 2011/020849 | 2/2011 |
| WO | WO 2011/025774 A1 | 3/2011 |
| WO | WO 2011/048111 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/146882 A1 | 11/2011 |
| WO | WO 2011/150201 | 12/2011 |
| WO | WO 2012/009097 A1 | 1/2012 |
| WO | WO 2012/032334 A1 | 3/2012 |
| WO | WO 2012/037204 | 3/2012 |
| WO | WO 2012/040634 | 3/2012 |
| WO | WO 2012/052753 | 4/2012 |
| WO | WO 2012/061696 A1 | 5/2012 |
| WO | WO 2012/064973 A2 | 5/2012 |
| WO | WO 2012/065019 A2 | 5/2012 |
| WO | WO 2012/065057 A2 | 5/2012 |
| WO | WO 2012/165606 | 6/2012 |
| WO | WO 2012/097000 A1 | 7/2012 |
| WO | WO 2012/177997 | 12/2012 |
| WO | WO 2013/012915 | 1/2013 |
| WO | WO 2013/012918 A1 | 1/2013 |
| WO | WO 2013/032591 | 3/2013 |
| WO | WO 2013/038381 | 3/2013 |
| WO | WO 2013/065725 | 5/2013 |
| WO | WO 2013/136076 | 9/2013 |
| WO | WO 2013/154878 A1 | 10/2013 |
| WO | WO 2013/188432 | 12/2013 |
| WO | WO 2013/190555 | 12/2013 |
| WO | WO 2014/034750 | 3/2014 |

(56) References Cited

FOREIGN PATENT DOCUMENTS

| WO | WO 2014/158528 | 10/2014 |
|---|---|---|
| WO | WO 2015/010641 | 1/2015 |
| WO | WO 2015/048318 | 4/2015 |
| WO | WO 2015/051241 | 4/2015 |
| WO | WO 2015/051244 | 4/2015 |
| WO | WO 2015/091685 | 6/2015 |
| WO | WO 2015/143012 | 9/2015 |
| WO | WO 2016/054491 | 4/2016 |

OTHER PUBLICATIONS

Kushner et al., "Pharmacological uses and perspectives of heavy water and deuterated compounds", Can. J. Physiol. Pharmacol. 77: 79-88 (1999).
Tung, "The Development of Deuterium-Containing Drugs", 2010.
Anderson et al., "The Use of Esters of N-Hydroxysuccinimide in Peptide Synthesis," Journal of the American Chemical Society, 1964, 86:1839-1842.
El-Faham et al., "Peptide Coupling Reagents, More than a Letter Soup," Chem. Rev. 2011, 111:6557-6602.
Abdel-Rahman et al., "Synthesis of heterobicyclic quinazolinones derived from N-[2-(2-chloro-phenyl)-1-(6,8-dibromo-4-oxo-4H-benzo[d][1,3]oxazin-2-yl)-vinyl]-benzamide as antimicrobial agents," Egyptian Journal of Chemistry (2006), 49(4), 461-474.
Abdel-Rahman et al., "Synthesis, reactions and antifungal agents of 2-[benzoylamino-2-(naphthyl- and/or 2'-furyl)]vinyl-4-H-3,1-benzoxazin-4-ones derivatives," Egyptian Journal of Chemistry (2006), 49(2), 169-184.
Abdel-Rahman, T., "Reactivity of 3-amino-3H-quinazolin-4-one derivatives towards some electrophilic and nucleophilic reagents and using of the products in the building of some interesting heterocycles as anticancer agent," Journal of Heterocyclic Chemistry (2006), 43(3), 527-534.
Abdel-Rahman, T., "Reactivity of 3-amino-3H-quinazolin-4-one derivatives towards some electrophilic and nucleophilic reagents and using of the products in the building of some interesting heterocycles as anticancer agent," Bollettino Chimico Farmaceutico (2005), 144(3), 124-138.
Afantitis et al., "A combined LS-SVM & MLR QSAR workflow for predicting the inhibition of CXCR3 receptor by quinazolinone analogs," Molecular Diversity (2010), 14(2), 225-235.
Afify, A.A. et al., "Synthesis and reactions of substituted benzoxazinones bearing a bulky group at position-2," Indian Journal of Chemistry, Section B: Organic Chemistry Including Medicinal Chemistry (1988), 27B(10), 920-25.
Afify, A.A. et al., Synthesis and reactions of substituted benzoxazinones bearing a bulky group at position-2. Part I, Revue Roumaine de Chimie (1990), 35(4), 567-75.
Ahmad, S. et al., "Monoamine oxidase inhibitory activity of 4(3H)-quinazolinones of dopamine," Indian Journal of Pharmaceutical Sciences (1979), 41(3), 126-7.
Avila, M.A. et al., "New therapies for hepatocellular carcinoma," Oncogene (2006), 25(27), 3866-3884.
Barili, P.L. et al., "A facile one pot synthesis of 2,9-disubstituted 8-azapurin-6-ones (3,5-disubstituted 7-hydroxy-3H-1,2,3-triazolo[4,5-d]pyrimidines)," Journal of Heterocyclic Chemistry (1985), 22(6), 1607-9.
Basso et al., "SCH 1473759, a novel Aurora inhibitor, demonstrates enhanced anti-tumor activity in combination with taxanes and KSP inhibitors", Cancer Chemotherapy and Pharmacology (2011), 68(4), 923-933.
Beer, T. et al., "Southwest oncology group phase II study of ispinesib in androgen-independent prostate cancer previously treated with taxanes," Clinical Genitourinary Cancer (2008), 6(2), 103-109.
Birk et al., "Cell cycle-dependent cytotoxicity and mitotic spindle checkpoint dependency of investigational and approved antimitotic agents", International Journal of Cancer (2012), 130(4), 798-807.

Blagden, S.P. et al., "A phase I trial of ispinesib, a kinesin spindle protein inhibitor, with docetaxel in patients with advanced solid tumours," British Journal of Cancer (2008), 98(5), 894-899.
Bol'But, A.V. et al., "Condensed pyrimidine systems. 5.6-methyl-functionalized in pyrazolo[3,4-d]pyrimidin-4(5H)-ones," Zhurnal Organichnoi ta Farmatsevtichnoi Khimii (2006), 4(3), 57-61.
Brunton, S. et al., "Potent Inhibitors of the Hedgehog Signaling Pathway," Journal of Medicinal Chemistry (2008), 51(5), 1108-1110.
Burris et al., "A phase I study of ispinesib, a kinesin spindle protein inhibitor, administered weekly for three consecutive weeks of a 28-day cycle in patients with solid tumors", Investigational New Drugs (2011), 29(3), 467-472.
Chau et al., "The association between EGFR variant III, HPV, p16, c-MET, EGFR gene copy number and response to EGFR inhibitors in patients with recurrent or metastatic squamous cell carcinoma of the head and neck", Head & Neck Oncology (2011), 3(11), 1-11.
Davis et al., "Increased therapeutic potential of an experimental anti-mitotic inhibitor SB715992 by genistein in PC-3 human prostate cancer cell line," BMC Cancer (2006), 6, 22.
Debnath, A. et al., "Structure-Based Identification of Small Molecule Antiviral Compounds Targeted to the gp41 Core Structure of the Human Immunodeficiency Virus Type 1," Journal of Medicinal Chemistry (1999), 42(17), 3203-3209.
El-Bassiouny et al., "Synthesis and some reactions of 2-[a-benzoylamino-b-2-furylvinyl]-6,8-dibromobenzoxazin-4(3H)-one and 3-aminoquinazolin-4(3H)-one derivatives," Asian Journal of Chemistry (1990), 2(1), 67-72.
El-Farargy et al., "Study on the reactivity of 2-[benzamido-(a-naphthylidene)]-4H-3,1-benzoxazin-4 one towards different carbon and nitrogen nucleophiles," Egyptian Journal of Chemistry (1993), Volume Date 1992, 35(5), 603-9.
El-Farargy, A.F., "Study on the stability and behavior of 2-[benzamido(naphthylidene)methyl]-4(3H)-quinazolinone," Egyptian Journal of Pharmaceutical Sciences (1991), 32(3-4), 565-74.
Elkafrawy, et al., "Steric and polar factors involving heteroring opening of 2-(a-benzoylamino-p-methoxystyryl)-6,8-dibromo-3,1-benzoxazin-4(H)-one," Indian Journal of Chemistry, Section B: Organic Chemistry Including Medicinal Chemistry (1992), 31B(1), 19-23.
El-Khamry et al., "Synthesis and reactions of 2-(a-benzoylamino-p-chlorostyryl)-3,1(4H)-benzoxazin-4-one with some nucleophilic reagents: synthesis of quinazolinone, tetrazole and benzimidazole derivatives," Egyptian Journal of Chemistry (1990), Volume Date 1988, 31(2), 261-9.
El-Nagdy, S. et al., "Behavior of benzoxazinone derivatives bearing a bulky group at position 2 toward some nitrogen and carbon nucleophiles. Part 2," Revue Roumaine de Chimie (1990), 35(1), 55-62.
El-Nagdy, S. et al., "Behavior of benzoxazinone derivatives bearing a bulky group at position-2 towards some nitrogen and carbon nucleophiles," Indian Journal of Chemistry, Section B: Organic Chemistry Including Medicinal Chemistry (1989), 28B(2), 126-30.
El-Nagdy, S. et al., "Synthesis and some reactions of 2-(a-benzoylaminostyryl)-3,1(4H)-benzoxazin-4-one and 3-amino-2-(a-benzoylaminostyrylquinazolin-4(3H)-one," Revue Roumaine de Chimie (1988), 33(8), 827-32.
El-Nagdy, S. et al., "Synthesis and some reactions of 2-(a-benzoylaminostyryl)-3,1(4H)-benzoxazin-4-one and 3-amino-2-(a-benzoylaminostyryl)quinazolin-4(3H)-one," Egyptian Journal of Chemistry (1990), Volume Date 1988, 31(5), 599-606.
El-Nagdy, S., "Synthesis and some reactions of 2-[a-(benzoylamino)styryl]-6,8-dibromo-3,1-benzoxazin-4(H)-one, quinazolin-4(3H)-one, and chloroquinazoline derivatives with some nucleophilic reagents," Asian Journal of Chemistry (1990), 2(4), 368-78.
El-Sharief et al., "Oxidation of 3-aminoquinazolinones with lead tetraacetate. A novel synthesis of naphtho-fused azirino-pyrazolo- and 1,4,5-oxadiazepinoquinazolinones," Journal of Chemical Research, Synopses (2002), (5), 205-208.
Essawy et al., "Behavior of 2-(a-phenylimido-b-p-nitrophenyl) vinyl-(4H)-3,1-benzoxazin-4-one towards some nucleophiles," Journal of Pure and Applied Sciences (1990), 9(2), 29-35 (abstract only).

(56) References Cited

OTHER PUBLICATIONS

Gao, H. et al., "A Dramatic Substituent Effect in Silver(I)-Catalyzed Regioselective Cyclization of ortho-Aikynylaryl Aldehyde Oxime Derivatives," Advanced Synthesis & Catalysis (2009), 351 (1-2), 85-88.
Garg, P. et al., "Synthesis and anti-implantation activity of 2-[2-[2-aryl-4(3H)-oxoquinazolin-3-yl]ethyl]-5-benzylidenecyclohexanone thiosemicarbazones," Biological Memoirs (1988), 14(2), 180-6.
Ghosh, T., "Quinazolines. I," Journal of the Indian Chemical Society (1937), 14, 411-13.
Guirguis, D., "The behaviour of some nucleophiles towards 2-[a-(benzoylamino)-b-(2-thienyl)vinyl]benzoxazin-4(3H)-one," Indian Journal of Chemistry, Section B: Organic Chemistry Including Medicinal Chemistry (2000), 39B(4), 264-269.
Hassanein et al., "Synthesis of 2-substituted-10H-[1,2,4]triazino[6,1-b]quinazoline-10-ones and 8,13,14,16-tetrahydronaphtho[2',3':3,4][1,2,5]triazepino[7,1-b]quinazoline-8,13,16-triones with biological interest," Al-Azhar Bulletin of Science (1997), 8(2), 417-434.
Heiser et al., "Subtype and pathway specific responses to anticancer compounds in breast cancer", Proceedings of the National Academy of Sciences of the United States of America (2012), 109(8), 2724-2729.
Huang, W. et al., "Synthesis and evaluation of quinazolin-4-ones as hypoxia-inducible factor-1 inhibitors," Bioorganic & Medicinal Chemistry Letters (2011), 21(18), 5239-5243.
Jackson, J. et al., "Targeted anti-mitotic therapies: can we improve on tubulin agents?" Nature Reviews Cancer (2007), 7(2), 107-117.
Jankowski, F. et al., "Efficient microwave-assisted two-step procedure for the synthesis of 1,3-disubstituted-imidazo[1,5-a]quinazolin-5(4H)-ones," Tetrahedron (2010), 66(1), 128-133.
Jiang, C. et al., "De novo design, synthesis and biological evaluation of 1,4-dihydroquinolin-4-ones and 1,2,3,4-tetrahydroquinazolin-4-ones as potent kinesin spindle protein (KSP) inhibitors", Bioorganic & Medicinal Chemistry (2011), 19(18), 5612-5627.
Jiang, C. et al., "Docking studies on kinesin spindle protein inhibitors: an important cooperative 'minor binding pocket' which increases the binding affinity significantly," Journal of Molecular Modeling (2007), 13(9), 987-992.
Johnson, M. et al., "Discovery and optimization of a series of quinazolinone-derived antagonists of CXCR3," Bioorganic & Medicinal Chemistry Letters (2007), 17(12), 3339-3343.
Karanov et al., "Cytokinin and anticytokinin activity of some 4-substituted 1H-pyrazoles and 8-aza analogs of adenine," Plant Growth Regulation (1993), 13(1), 7-11.
Kathman, S. et al., "A Bayesian population PK-PD model for ispinesib/docetaxel combination-induced myelosuppression," Cancer Chemotherapy and Pharmacology (2009), 63(3), 469-476.
Kathman, S. et al., "A bayesian population PK-PD model of ispinesib-induced myelosuppression," Clinical Pharmacology & Therapeutics (New York, NY, United States) (2007), 81(1), 88-94.
Kirmani et al., "Studies on the reactivity of 2-methyl-3-phenyl-4(3H)-quinazolinone," Indian Journal of Chemistry, Section B: Organic Chemistry Including Medicinal Chemistry (1979), 17B(5), 445-9.
Knox, J. et al., "A phase II and pharmacokinetic study of SB-715992, in patients with metastatic hepatocellular carcinoma: a study of the National Cancer Institute of Canada Clinical Trials Group (NCIC CTG IND.168)," Investigational New Drugs (2008), 26(3), 265-272.
Lad, L. et al., "Mechanism of Inhibition of Human KSP by Ispinesib," Biochemistry (2008), 47(11), 3576-3585.
Lee, C. et al., "A phase II study of ispinesib (SB-715992) in patients with metastatic or recurrent malignant melanoma: a National Cancer Institute of Canada Clinical Trials Group trial," Investigational New Drugs (2008), 26(3), 249-255.
Lee, R. et al., "A University of Chicago consortium phase II trial of SB-715992 in advanced renal cell cancer," Clinical Genitourinary Cancer (2008), 6(1), 21-24.
Liu F. et al., "Discovery of tetrahydro-b-calbolines as inhibitors of the mitotic kinesin KSP," Bioorganic & Medicinal Chemistry (2010), 18(12), 4167-4177.
Liu F. et al., "Pharmacophore identification of KSP inhibitors," Bioorganic & Medicinal Chemistry Letters (2007), 17(3), 722-726.
Liu, D. et al., "Impurity identification in process chemistry by mass spectrometry", Characterization of Impurities and Degradants Using Mass Spectrometry, First Edition, John Wiley & Sons, Inc., Hoboken, NJ, (2011), pp. 251-277.
Mahmoud et al., "Heteroannulated quinazoline and quinazolinone derivatives from (Z)-2-[1-benzamido-2-(3,4,5-trimethoxyphenyl)vinyl]-3,1-benzoxazin-4(3H)-one," Synthetic Communications (2010), 40(10), 1516-1529.
Mahmoud et al., "Synthesis of new thiadiazoles, 1,2,4-triazolo[3,4-b]-1,3,4-thiadiazoles, and 1,2,4-triazolo[2,3-c]quinazoline derivatives from 4H-3,1-benzoxazin-4-one derivative," Phosphorus, Sulfur and Silicon and the Related Elements (2007), 182(6), 1275-1289.
Mahmoud et al., "Synthesis of novel quinazolinone and fused quinazolinones", European Journal of Chemistry (2011), 2(3), 404-409.
Marone et al., "Targeting phosphoinositide 3-kinase—Moving towards therapy," Biochimica et Biophysica Acta 1784 (2008) 159-185.
Mealy, et al., "Drugs under development for the treatment of head and neck cancer," Drugs of the Future (2006), 31(7), 627-639.
Morsy, J.M., "Use of 2-(substituted vinyl)-4(3H)-quinazolinone and -4H-3,1-benzoxazinone in synthesis of heterocycles," Bulgarian Chemical Communications (2007), 39(2), 146-151.
Mossetti et al., "Imides: forgotten players in the Ugi reaction. One-pot multicomponent synthesis of quinazolinones", Chemical Communications, (2011), 47(24), 6966-6968.
Natsugari, H. et al., "Novel, Potent, and Orally Active Substance P Antagonists: Synthesis and Antagonist Activity of N-Benzylcarboxamide Derivatives of Pyrido[3,4-b]pyridine," Journal of Medicinal Chemistry (1995), 38(16), 3106-20.
Pandey, V.K. et al., "Quinazolylthiazoles as CNS acting agents," Acta Pharmaceutica (Zagreb) (1996), 46(1), 51-9.
Pandey, V.K. et al., "Synthesis and antiviral activity of quinazolinyl sydnones," Indian Journal of Heterocyclic Chemistry (2006), 15(4), 399-400.
Pandey, V.K. et al., "Synthesis of 1-(2'-aryl-4'-oxo(3H)quinazolyl)-3-aryl-5-phenyl-formazans as potential anti-viral agents," Indian Drugs (1999), 36(1), 37-40.
Pandey, V.K., "Antiparkinsonism and CNS activities of (±)-2-aryl/alkyl-3-{b-(3',4'-dihydroxyphenyl)ethyl}quinazolin-4(3H)-ones," Biological Memoirs (1985), 11(2), 213-15.
Pandey, V.K., "Possible antiparkinsonian compounds. Part XI. Synthesis of 2-aryl/alkyl-3-[b-(3':4'-dihydroxyphenyl)ethyl]-quinazoline(3H)-4-one and 2-aryl/alkyl-3-[(7'-(phenothiazinyl)-ethyl]quinazoline(3H)-4-one," Acta Ciencia Indica (1978), 4(3), 230-5.
Parrish, C. et al., "Novel ATP-Competitive Kinesin Spindle Protein Inhibitors," Journal of Medicinal Chemistry (2007), 50(20), 4939-4952.
Pattan, S. et al., "Synthesis and microbiological evaluation of N'-3-(4-(4-chlorophenyl)thiazol-2-yl)quinazolin-4(3H)-ones," Indian Journal of Heterocyclic Chemistry (2005), 15(1), 79-80.
Pattan, S. et al., "Synthesis of N-3(4-(4-chlorophenyl thiazole-2-yl)-(2-(amino)methyl)-quinazoline-4(3H)-one and their derivatives for antitubercular activity," Indian Journal of Chemistry, Section B: Organic Chemistry Including Medicinal Chemistry (2006), 45B(7), 1778-1781.
Pinkerton, A. et al., "Synthesis and SAR of thiophene containing kinesin spindle protein (KSP) inhibitors," Bioorganic & Medicinal Chemistry Letters (2007), 17(13), 3562-3569.
Poupert, J.H., "Drug Design: Basic Principles and Applications", 2 Encyclopedia of Pharmaceutical Technology, 1362-1369, (James Swarbrick ed., 3rd ed., 2007).
Purcell, J. et al., "Activity of the kinesin spindle protein inhibitor ispinesib (SB-715992) in models of breast cancer," Clinical Cancer Research (2010), 16(2), 566-576.

(56) References Cited

OTHER PUBLICATIONS

Rodriguez et al., "Synthesis and characterization of tritylthioethanamine derivatives with potent KSP inhibitory activity", Bioorganic & Medicinal Chemistry (2011), 19(18), 5446-5453.
Sakowicz, R. et al., "Antitumor Activity of a Kinesin Inhibitor," Cancer Research (2004), 64(9), 3276-3280.
Saleh, R.M. et al., "Synthesis and reactions of 2-[1-benzamido-2-(o-chlorophenyl)vinyl]-4H-3,1-benzoxazin-4-one," Revue Roumaine de Chimie (1994), 39(5), 567-76.
Saleh, R.M. et al., "Synthesis and some reactions of 2-(a-benzamido-p-chlorostyryl)-3,1-benzoxazin-4-one," Pakistan Journal of Scientific and Industrial Research (1991), 34(11), 417-21.
Sheth, P. et al., "Novel Benzimidazole Inhibitors Bind to a Unique Site in the Kinesin Spindle Protein Motor Domain," Biochemistry (2010), 49(38), 8350-8358.
Sheth, P. et al., "Thermodynamics of Nucleotide and Inhibitor Binding to Wild-Type and Ispinesib-Resistant Forms of Human Kinesin Spindle Protein," Biochemistry (2009), 48(46), 11045-11055.
Singh, B. et al., "4-Quinazolones. II. Synthesis of some imidazo[1,5-a]quinazolin-5(4H)ones," Journal of the Indian Chemical Society (1969), 46(1), 21-5.
Singh, R. et al., "Synthesis and pharmacological screening of some 2-aryl-3-(phenyl-aryl-hydrazonyl)quinazolin-(3H)4-ones," Indian Drugs (1990), 28(2), 70-4.
Soliman et al., "Synthesis and reactions of substituted benzoxazinones bearing a bulky group at position 2," Revue Roumaine de Chimie (1992), 37(10), 1153-8.
Soliman et al., "Synthesis and reactions of substituted benzoxazinones bearing a bulky group at position 2," Delta Journal of Science (1990), 14(1), 166-80.
Sorbera, L.A. et al., "Ispinesib mesilate," Drugs of the Future (2006), 31(9), 778-787.
Storelli, S. et al., "Synthesis and structure-activity relationship of 3-phenyl-3H-quinazolin-4-one derivatives as CXCR3 chemokine receptor antagonists," Bioorganic & Medicinal Chemistry Letters (2005), 15(11), 2910-2913.
Storelli, S. et al., "Synthesis and structure-activity relationships of 3H-quinazolin-4-ones and 3H-pyrido[2,3-d]pyrimidin-4-ones as CXCR3 receptor antagonists," Archiv der Pharmazie (Weinheim, Germany) (2007), 340(6), 281-291.
Tang, P. et al., "Phase II study of ispinesib in recurrent or metastatic squamous cell carcinoma of the head and neck," Investigational New Drugs (2008), 26(3), 257-264.
Theoclitou et al., "Discovery of(+)-N-(3-Aminopropyl)-N-[1-(5-benzyl-3-methyl-4-oxo-[1,2]thiazolo[5,4-d ]pyrimidin-6-yl)-2-methylpropyl]-4-methylbenzamide (AZD4877), a Kinesin Spindle Protein Inhibitor and Potential Anticancer Agent," Journal of Medicinal Chemistry (2011), 54(19), 6734-6750.
Tiwari, A. et al., "Synthesis and biological properties of 4-(3H)-quinazolone derivatives," European Journal of Medicinal Chemistry (2007), 42(9), 1234-1238.
Tiwari, S. et al., "Possible antifertility compounds—Part III: Synthesis of 2-hippuryl-3-arylquinazolinones," Journal of the Chemical Society of Pakistan (1981), 3(4), 215-17.
Tiwari, S. et al., "Synthesis and central nervous systems activity of 2-aryl-3(3',4'-dihydroxyphenylethyl)-6,8-substituted 4(3H)-quinazolinones," Indian Journal of Pharmaceutical Sciences (1978), 40(2), 40-3.
Tiwari, S. et al., "Synthesis of possible antiparkinsonian compounds. X. Synthesis of 2,6,8-trisubstituted benzoxazinones and their corresponding 3-hydroxyquinazolinones," Journal of the Indian Chemical Society (1975), 52(8), 736-7.
Valensin S., et al., "KIF11 inhibition for glioblastoma treatment: reason to hope or a struggle with the brain?" BMC Cancer (2009), 9.
Voultsiadou et al., "Recent advances of kinesin motor inhibitors and their clinical progress", Reviews on Recent Clinical Trials (2011), 6(3), 271-277.

Wang, F. et al., "Triphenylbutanamines: Kinesin Spindle Protein Inhibitors with in Vivo Antitumor Activity," Journal of Medicinal Chemistry (2012), 55 (4), 1511-1525.
Watkins, W. et al., "Quinazolinone fungal efflux pump inhibitors. Part 2: In vitro structure-activity relationships of (N-methylpiperazinyl)-containing derivatives," Bioorganic & Medicinal Chemistry Letters (2004), 14(20), 5133-5137.
White, M., "Targeting mitotic fragility in cancer," Future Oncology (2009), 5(5), 613-615.
Zhang, B. et al., "Crystal structure of HsEg5 in complex with clinical candidate CK0238273 provides insight into inhibitory mechanism, potency, and specificity," Biochemical and Biophysical Research Communications (2008), 72(4), 565-570.
Zhang, B. et al., "Development of a high-throughput robotic fluorescence-based assay for HsEg5 inhibitor screening," Analytical Biochemistry (2005), 345(2), 326-335.
Aksoy et al., "The p110d isoform of the kinase PI(3)K controls the subcellular compartmentalization of TLR4 signaling and protects from endotoxic shock", Nature Immunology, 2012, vol. 13(11), pp. 1045-1054.
Ali et al., "Leukocyte Extravasation: An Immunoregulatory Role for-L-Fucosidase?", J Immunol 2008, vol. 181, pp. 2407-2413.
Balla et al. (Eds.), Phosphoinositides I: Enzymes of Synthesis and Degradation, Chapter 5: PI3Ks—Drug Targets in Inflammation and Cancer Series: Subcellular Biochemistry, vol. 58, 2012, XVI, 356 p.
Burger et al, "CXCR4: a key receptor in the crosstalk between tumor cells and their microenvironment", Blood, Mar. 1, 2006;107(5), pp. 1761-1767.
Burger et al., "The microenvironment in chronic lymphocytic leukemia (CLL) and other B cell malignancies: insight into disease biology and new targeted therapies", Semin Cancer Biol., Feb. 2014; vol. 24:pp. 71-81.
Curran et al., "PD-1 and CTLA-4 combination blockade expands infiltrating T cells and reduces regulatory T and myeloid cells within B16 melanoma tumors," PNAS, Mar. 2, 2010, vol. 107(9), pp. 4275-4280.
De Palma and Lewis, "Macrophage Regulation of Tumor Responses to Anticancer Therapies", Cancer Cell, vol. 23, Issue 3, Mar. 18, 2013, pp. 277-286.
Denardo et al., "Leukocyte Complexity Predicts Breast Cancer Survival and Functionally Regulates Response to Chemotherapy", Cancer Discovery, Jun. 2011, vol. 1, pp. 54-67.
Duraiswamy et al., "Dual Blockade of PD-1 and CTLA-4 Combined with Tumor Vaccine Effectively Restores T-Cell Rejection Function in Tumors," Cancer Research, Jun. 5, 2013;73(12):3591-603.
Feig et al., "Targeting CXCL12 from FAP-expressing carcinoma associated fibroblasts synergizes with anti-PD-L1 immunotherapy in pancreatic cancer," PNAS, Dec. 10, 2013, vol. 110, No. 50, pp. 20212-20217.
Ferrandi et al., "Phosphoinositide 3-Kinase Inhibition Plays a Crucial Role in Early Steps of Inflammation by Blocking Neutrophil Recruitment", J Pharmacol Exp Ther, Sep. 2007, vol. 322, pp. 923-930.
Fruman, D., "Phosphoinositide 3-kinase and its targets in B-cell and T-cell signaling", Current Opinion in Immunology, vol. 16, Issue 3, Jun. 2004, pp. 314-320.
Ghia et al., "Chronic lymphocytic leukemia B cells are endowed with the capacity to attract CD4+, CD40L+ T cells by producing CCL22", Eur J Immunol., May 2002; vol. 32(5): pp. 1403-1413.
Hardamon et al., "Inhibition of myeloid cell PI3K is a potential therapeutic approach to treat pancreatic cancer", Cancer Research, Apr. 15, 2012; vol. 72, Issue 8, Supplement 1, Abstract 5228.
Herman et al., "Molecular pathways: targeting phosphoinositide 3-kinase p110-delta in chronic lymphocytic leukemia", Clin Cancer Res., Aug. 1, 2012; vol. 18(15): pp. 4013-4018.
Hirsch et al., "Phosphoinositide 3-kinases as a common platform for multi-hormone signaling", J Endocrinol, 2007, vol. 194 (2), pp. 243-256.
Kaneda et al., "PI3-kinase gamma controls the macrophage M1-M2 switch, thereby promoting tumor immunosuppression and progression", AACR; Cancer Res 2014, vol. 74 (19 Suppl), Abstract 3650.

(56) References Cited

OTHER PUBLICATIONS

Lewis and Pollard, "Distinct Role of Macrophages in Different Tumor Microenvironments", Cancer Res 2006, vol. 66 (2), pp. 605-612.
Monjazeb et al., "Immunoediting and antigen loss: overcoming the Achilles heel of immunotherapy with antigen non-specific therapies", Front. Oncol., 2013, vol. 3, Article 197, pp. 1-10.
Mraz et al., "miR-34a, miR-29c and miR-17-5p are downregulated in CLL patients with TP53 abnormalities", Leukemia (2009), vol. 23(6), pp. 1159-1163.
Ni et al., "Functional Characterization of an Isoform-Selective Inhibitor of PI3K-p110b as a Potential Anticancer Agent", Cancer Discovery, May 2012, vol. 2, pp. 425-433.
Okkenhaug, K., "Signaling by the Phosphoinositide 3-Kinase Family in Immune Cells", Annu. Rev. Immunol., 2013, vol. 31, pp. 675-704.
Ries, et al., "Targeting Tumor-Associated Macrophages with Anti-CSF-1R Antibody Reveals a Strategy for Cancer Therapy", Cancer Cell, vol. 25, Issue 6, Jun. 16, 2014, pp. 846-859.
Rommel et al., Taking PI3Kδ and PI3Kγ One Step Ahead: Dual Active PI3Kδ/γ Inhibitors for the Treatment of Immune-Mediated Inflammatory Diseases, Phosphoinositide 3-Kinase in Health and Disease, 2011, vol. 1, pp. 279-299.
Roy et al., "DDB2 Suppresses Epithelial-to-Mesenchymal Transition in Colon Cancer", Cancer Res Jun. 15, 2013, 73(12), pp. 3771-3782.
Schmid et al., "PI3 Kinase gamma control of Arginase-1 expression promotes tumor immunosuppression", Cancer Research, Apr. 15, 2012, vol. 72, Issue 8, Supplement 1, Abstract 411.
Schmid et al., "ReceptorTyrosineKinasesandTLR/IL1Rs Unexpectedly Activate Myeloid Cell PI3Kg, A Single Convergent Point Promoting Tumor Inflammation and Progression", Cancer Cell, vol. 19, Issue 6, Jun. 14, 2011, pp. 715-727.
Topalian et al., "Safety, Activity, and Immune Correlates of Anti-PD-1 Antibody in Cancer", N Engl J Med 2012, 366(26), pp. 2443-2454.
Wolchok et al., "Antitumor response and new lesions in advanced melanoma patients on ipilimumab treatment", Wolchok et al., J. Clin. Oncology, 2008 ASCO (Post-Meeting Edition), vol. 26, No. 15S (May 20 Suppl), Abstract 3020.
Wolchok et al., "Nivolumab plus Ipilimumab in Advanced Melanoma", NEJM, 2013, vol. 369, pp. 122-133.
Wurth et al., "CXCL12 modulation of CXCR4 and CXCR7 activity in human glioblastoma stem-like cells and regulation of the tumor microenvironment," Frontiers in Cellular Neuroscience, May 2014, vol. 8, Article 144, pp. 1-19.
Brachman et al., "PI3K and mTOR inhibitors—a new generation of targeted anticancer agents", Current Opinion in Cell Biology (2009), vol. 21, pp. 194-198.
Dagia et al., "A preferential p110α/γ PI3K inhibitor attenuates experimental inflammation by suppressing the production of proinflammatory mediators in a NF-κB-dependent manner", American Journal of Physiology—Cell Physiology (2010), vol. 298, pp. 929-941.
Dushianthan et al., "Acute respiratory distress syndrome and acute lung injury", Post Graduate Medical Journal (2011), vol. 87, pp. 612-622.
Engelman, J. "Targeting PI3K signalling in cancer: opportunities, challenges and limitations", Nature Reviews: Cancer. vol. 9 (2009), pp. 550-562.
Ghigo et al., "PI3K Inhibition in Inflammation: Toward tailored therapies for specific diseases," BioEssays 32 (2010), pp. 185-196.
Hirsch, E. et al., "Taming the PI3K team to hold inflammation and cancer at bay", Pharmacology & Therapeutics (2008), vol. 118, pp. 192-205.
Kolliputi, N. et al., "IL-6 cytoprotection in hyperoxic acute lung injury occurs via PI3K/Akt-mediated Bax phosphorylation", American Journal of Physiology, Lung Cellular and Molecular Physiology (2009), vol. 297, pp. L6-L16.

Kong, D. et al., "Phosphatidylinositol 3-kinase inhibitors: promising drug candidates for cancer therapy", Cancer Science (2008), vol. 9, pp. 1734-1740.
Liu, Q. et al. "mTOR mediated anti-cancer drug discovery", Drug Discovery Today: Therapeutic Strategies, (2009), vol. 6, pp. 47-55.
Shuttleworth et al., "Progress in the Preclinical Discovery and Clinical Development of Class I and Dual Class I/IV Phosphoinositide 3-Kinase (PI3K) Inhibitors", Current Medicinal Chemistry (2011), vol. 18, pp. 2686-2714.
Evans, "Principles of Radiopharmacology", Colombett, L.G editor, CRC Press, 1979, pp. 11-13 and 24.
Banham-Hall et al., "The therapeutic potential for PI3K inhibitors in autoimmune and rheumatic diseases", Open Rheumatol. J. 2012, 6, 245-258.
Bell et al., "SAR studies around a series of triazolopyridines as potent and selective PI3Kc inhibitors", Bioorg. Med. Chem. Lett. 2012, 22, 5257-5263.
Bergamini et al., "A selective inhibitor reveals PI3Kγ dependence of TH17 cell differentiation", Nat. Chem. Biol. 2012, 8, 576-582.
Bruce et al., "Development of isoform selective PI3K-kinase inhibitors as pharmacological tools for elucidating the PI3K pathway", Bioorg. Med. Chem. Lett. 2012, 22, 5445-5450.
Cantley, L.C., "The phosphoinositide 3-kinase pathway", Science, 2002, 296, 1655-1657.
Collier et al., "Discovery of highly isoform selective thiazolopiperidine inhibitors of phosphoinositide 3-kinase γ", J. Med. Chem. 2015, 58, 5684-5688.
Collier et al., "Structural basis for isoform selectivity in a class of benzothiazole inhibitors of phosphoinositide 3-kinase γ", J. Med Chem. 2015, 58, 517-521.
DeHenau et al., "Checkpoint Blockade Therapy is Improved by Altering the Immune-Suppressive Microenvironment with IPI-549, a Potent and Selective Inhibitor of PI3K-γ, in Preclinical Models," AACR Annual Meeeting 2016, Apr. 17, 2016, New Orleans, Poster 554.
Gunderson et al., "Bruton tryrosine kinase-dependent immune cell cross-talk drives pancreas cancer", Cancer Discovery 2016, 6, 270-285.
Hawkins et al., PI3K signalling in inflammation. Biochim. Biophys. Acta, Mol. Cell Biol. Lipids 2015, 1851, 882-897.
Joshi et al., "A macrophage-dominant PI3K isoform controls hypoxia-induced HIF1alpha nad HIF2alpha stability and tumor growth, angiogenesis, and metastasis", Mol. Cancer. Res. 2014, 12, 1520-1531.
Kutok et al., "The Potent and Selective Phosphoinositide-3-Kinase (PI3K)-γ Inhibitor, IPI-549, Inhibits Tumor Growth in Murine Syngeneic Solid Tumor Models through Alterations in the Immune Suppressive Microenvironment", CRI-CIMT-EATI-AACR—The Inaugural International Cancer Immunotherapy Conference, Sep. 18, 2015, New York, NY, Poster.
Leahy et al., "Discovery of a novel series of potent and orally bioavailable phosphoinositide 3-kinase γ inhibitiors", J. Med. Chem. 2012, 55, 5467-5482.
NCT02637531: A dose-escalation study to evaluate the safety, tolerability, pharmacokinetics, and pharmacodynamics of IPI-549. www.clinicaltrials.gov, May 19, 2016.
Oka et al., "Discovery of N-{5-[3-(3-hydroxypiperdin-1-yl)-1,2,4-oxadiazol-5-yl]-4-methyl-1,3-thiazol-2-yl}acetamide (TASP0415914) as an orally potent phosphosititide 3-kinase γ inhibitor for the treatment of inflammatory diseases", Bioorg. Med. Chem. 2013, 21, 7578-7583.
Reif et al., "Cutting Edge: Differential Roles for Phosphoinositide 3-Kinases, p110γ and p110δ, in Lymphocyte Chemotaxis and Homing," J. Immunol. 173:2236-2240 (2004).
Rivera et al., "Intratumoral myeloid cells regulate repsoniveness and resistance to antiangiogenic therapy", Cell Rep. 2015, 11, 577-591.
Sunose et al., "Discovery of 5-(2-amino-[1,2,4]triazolo[1,5-a]yridin-7-yl)-N-(tert-butyl)pyridine-3-sulfonamide (CZC24758), as a potent, orally bioavailable and selective inhibitor of PI3K for the treatment of inflammatory disease", Bioorg. Med. Chem. Lett. 2012, 22, 4613-4618.

(56) References Cited

OTHER PUBLICATIONS

Thorpe et al., "PI3K in cancer: divergent rols of isoforms, modes of activation and therapeutic targeting", Nat. Rev. Cancer 2015, 15, 7-24.
Tolcher et al., "A Phase 1/1b First-In-Human Study of IPI-549, a PI3K-g Inhibitor, as Monotherapy and in Combination with an Anti-PD1 Antibody in Subjects with Advanced Solid Tumors", ASCO Annual Meeting Jun. 3-7, 2016, Chicago, IL, Poster.
Vanhaesebroeck et al., "Molecules in medicine mini-review: isoforms of PI3K in biology and disease", J. Mol. Med. 2016, 94, 5-11.
Winkler et al., "PI3K-d and PI3K-g Inhibition by IPI-145 Abrogates Immune Responses and Suppresses Activity in Autoimmune and Inflammatory Disease Models," Chem. Biol. 2013, 20, 1364-1374.
Brunk et al., "Anti-PD-L1 therapy yielded durable responses in early NSCLC trials, Oncology Practice Digital Network", Feb. 2014, pp. 1-3.
Tomasini et al., "Ipilimumab: its potential in non-small cell lung cancer", Ther Ad Med Oncol, 2012, Issue 4, No. 2, pp. 43-50.
Evans et al., "Discovery of a Selective Phosphoinositide-3-Kinase {PI3K}-γ lnhibitor (IPI-549) as an lmmuno-Oncology Clinical Candidate," ACS Med. Chem. Lett., 2016, 7, 862-867.
Golub, T.R., et al., "Molecular classification of Cancer: Class Discover and Class Predication by Expression Monitoring," Science, 286:531-537, 1999.
Pomel et al, "Furan-2-ylmethylene Thiazolidinediones as Novel, Potent, and Selective Inhibitors of Phosphoinositide 3-Kinase γ," J. Med. Chem. 49:3857-3871, 2006.
Braga et al., "Crystal polymorphism and multiple crystal forms," Struct. Bond. 132:25-50 (2009).
Zell et al., "Investigation of polymorphism in aspartame and neotame using solid-state NMR spectroscopy," Tetrahedron, 56:6603-6616 (2000).
Pirrung, "Handbook of Synthetic Organic Chemistry," $2^{nd}$ Ed., 2017, p. 178.
Bernstein, "Polymorphism in Molecular Crystals," Oxford, 2002, p. 46.
Guillory, "Generation of Polymorphs, Hydrates, Solvates, and Amorphous Solids". Chapter 5 in Polymorphism in Pharmaceutical Solids, Ed. by Harry G. Brittain, Dekker: New York, 1999, pp. 183-226.
Brittain, "Effects of Pharmaceutical Processing on Drug Polymorphs and Solvates", Chapter 8 in Polymorphism is Pharmaceutical Solids, Ed. by Harry G. Brittain, Dekker: New York, 1999, pp. 331-360.
Sapey et al., "Abnormal Neutrophil Migration Is a Feature of Early COPO, Present Across Disease Phenotypes and Causally Related to Increased PhosphoINOSitide-3-Kinase Signalling", American Journal of Respiratoly and Critical Care Medicine, 2013, vol. 187, Supp., A3492.
Abdel-Mohsen, "Synthesis, Reactions and Antimicrobial Activity of 2-Amino-4-(8-quinolinol-5-yl)-1-(p-tolyl)-pyrrole-3-carbonitrile," Bull. Korean Chem. Soc. 26(5):719-728 (2005).
Abe et al., "T cell receptor-mediated recognition of self-ligand induces signaling in immature thymocytes before negative selection," J. Exp. Med. 176(2):459-468 (1992).
Abrahamian et al., "Immunological and Clinical Profile of Adult Patients with Selective Immunoglobulin Subclass deficiency: response to intravenous immunoglobulin therapy," Clin. Exp. Immunol. 159(3):344-350 (2010).
Abraham, T., "Thermally induced intramolecular cycloaddition reaction of N-phenyl-2-phenylethynlbenzamide potential cure reaction for thermosetting polymers," J. Polym. Sci. Polym. Chem. Ed. 20(7):1953-1957 (1982).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," J.C.S. Perkin I 1390-1395 (1975).
Anderson et al., "Paradoxical inhibition of T-cell function in response to CTLA-4 blockade; heterogeneity within the human T-cell population," Nat. Med. 6(2):211-214 (2000).

Andrews et al., "Effects of the 11β-hydroxysteroid dehydrogenase inhibitor carbenoxolone on insulin sensitive in men with type 2 diabetes," J. Clin. Endocrinol. Metab. 88(1):285-291 (2003).
Arcaro et al., "Wortmannin is a potent phosphatidylinositol 3-kinase inhibitor: the role of phosphatidylinositol 3,4,5-triphosphate in neutrophil responses," Biochem. J., 296(Pt 2):297-301 (1993).
Arnold et al., "Pyrrolo[2,3-d]pyrimidines containing an extended 5-substituent as potent and selective inhibitors of Ick I," Bioorg. Med. Chem. Lett. 10(19):2167-2170 (2000).
Augustine et al., "Interleukin 2- and polyomavirus middle T antigen-induced modification of phosphatidylinositol 3-kinase activity in activated T lymphocytes," Mol. Cell. Biol. 11(9):4431-4440 (1991).
Baggiolini et al., "Inhibition of the phagocytosis-induced respiratory burst by the fungal metabolite wortmannin and some analogues," Exp. Cell. Res. 169(2): 408-418 (1987).
Ballell et al. "New Thiopyrazolo[3,4-d] pyrimidine derivatives as anti-mycobacterial agents," Bioorg. Med. Chem. Lett. 17(6):1736-1740 (2007).
Banker et al., Modern Pharmaceutics, pp. 451, 596, $3^{rd}$ ed, Marcel Dekker, New York (1996).
Bansal et al., "The Molecular Biology of Endometrial Cancers and the Implications for Pathogenesis, Classification, and Targeted Therapies," Cancer Control 16(1):8-13 (2009).
Barber et al., "PI3Kgamma inhibition blocks glomerulonephritis and extends lifespan in a mouse model of systemic lupus," Nat. Med. 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxysteroid dehydrogenase Type 1," J. Med. Chem. 45(18):3813-3815 (2002).
Barnes et al., "Efficacy and Safety of Inhaled Corticosteroids in Asthma—Report of a Workshop Held in Eze, France Oct. 1992," Am. Rev. Respir. Dis. 148:S1-S26 (1993).
Bartholomeusz et al., "Targeting the PI3K Signaling Pathway in Cancer Therapy," Expert Opin. Ther. Targets 16(1):121-130 (2012).
BASOTEST®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retreived from the Internet Nov. 29, 2011.
Beeram et al., "Akt-induced endocrine therapy resistance is reversed by inhibition of mTOR signaling," Ann Oncol. 18(8):1323-1328 (2007).
Bell et al., "Glucokinase mutations insulin secretion, and diabetes mellitus", Annu. Rev. Physiol. 58:171-186 (1996).
Berndt et al., "The p110δ crystal structure uncovers mechanisms for selectivity and potency of novel PI3K inhibitors," Nat. Chem. Biol. 6(2):117-124 (2010).
Bhat et al., "Pyrazolopyrimidine nucleosides. 12. Synthesis and biological activity of certain pyrazolo[3,4-d]pyrimidine nucleosides related to adenosine," J. Med. Chem. 24(10):1165-1172 (1981).
Bhatt et al., "Dual inhibition of PI3K and mTOR inhibits autocrine and paracrine proliferative loops in PI3K/Akt/mTOR-addicted lymphomas," Blood 115(22):4455-4463 (2010).
Bi et al., "Proliferative defect and embryonic lethality in mice homozygous for a deletion in the p110α subunit of phosphoinositide 3-kinase," J. Biol. Chem. 274:10963-10968 (1999).
Billottet et al., "A selective inhibitor of the p110δ isoform of PI 3-kinase inhibits AML cell proliferation and survival and increases the cytotoxic effects of VP16," Oncogene 25:6648-6659 (2006).
Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," Cancer Res. 69(3):1027-1036 (2009).
Bishop et al., "Generation of monospecific nanomolar tyrosine kinase inhibitors via a chemical genetic approach," J. Am. Chem. Soc. 121(4):627-631 (1999).
Blunden et al., "Mycotoxins in food," Med. Lab. Sci. 48(4):271-282 (1991).
Bochner et al., "Immunological aspects of allergic asthma," Annu. Rev. Immunol. 12:295-335 (1994).
Bohren et al., "Expression, crystallization and preliminary crystallographic analysis of human carbonyl reductase," J. Mol. Biol. 224:659-664 (1994).

(56) References Cited

OTHER PUBLICATIONS

Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Hematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).
Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.*(Tokyo) 47(6):900-902 (1999).
Clayton et al., "A crucial role for the p110delta subunit of phosphatidylinositol 3-kinase in B cell development and activation," *J. Exp. Med.* 196:753-763 (2002).

Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Dijksman et al., "271.1 : 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).
European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).

(56) References Cited

OTHER PUBLICATIONS

Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C-C bonds on solid support," *Can. J. Chem.* 78:957-962 (2000).
Funder et al., "Mineralocorticoid action: target tissue specificity is enzyme, not receptor, mediated," *Science* 242:583-585 (1998).
Fung-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," *Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," *Cancer Res.* 55(20):4646-4650 (1995).
Graber et al., "The protein tyrosine kinase inhibitor herbimycin A, but not genistein, specifically inhibits signal transduction by the T cell antigen receptor," *Int. Immunol.* 4(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from Fusarium oxysporum," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin 1* 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/Al2O3-basensystemen; 2-arylbenzofurane and 2,3-diarylisochinolin-1(2H)-one," *Synthesis* 1995(9):1135-1141 (1995).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.

(56) References Cited

OTHER PUBLICATIONS

International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).

Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio- and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," Curr. Med. Chem. 17(36):4433-4447 (2010).

(56) References Cited

OTHER PUBLICATIONS

Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," Blood (ASH Annual Meeting Abstracts), 116:Abstract 3926 (2010).
Mellinghoff et al., "TORward AKTually useful mouse models," Nat. Med. 10(6):579-580 (2004).
Merida et al., "IL-2 binding activates a tyrosine-phosphorylated phosphatidylinositol-3-kinase," J. Immunol. 147(7): 2202-2207 (1991).
Miyaura et al., "Palladium-catalyzed cross-coupling reactions of organoboron compounds," Chem. Rev. 95(7):2457-2483 (1995).
Modi et al., "Isoquinolones; part IV—synthesis of methyl, 3-formyl & other 3-substituted N-arylisoquinolones." Indian J. Chem. 18B:304-306 (1979).
Moon et al., "A novel microtubule destabilizing entity from orthogonal synthesis of triazine library and zebrafish embryo screening," J. Am. Chem. Soc. 124(39):11608-11609 (2002).
Mosmann et al., "The expanding universe of T-cell subsets: Th1, Th2 and more," Immunology Today 17(3):138-146 (1996).
Nakanishi et al., "Cloning and sequence analysis of a cDNA encoding tetrameric carbonyl reductase of pig lung," Biochem. Biophys. Res. Commun. (3):1311-1316 (1993).
Nemazanyi et al., "3-Amino-4-aryl-1(2H)-isoquinolones," Chemistry of Heterocyclic Compounds 27(3):307-308 (1991).
Newman et al., "Solid state analysis of the active pharmaceutical ingredient in drug products," Drug Discov. Today 8(19):898-905 (2003).
Nisitani et al., "Posttranscriptional regulation of Bruton's tyrosine kinase expression in antigen receptor-stimulated splenic B cells," PNAS 97(6):2737-2742 (2000).
Niswender et al., "Protein engineering of protein kinase a catalytic subunits results in the acquisition of novel inhibitor sensitivity," J. Biol. Chem. 277(32):28916-28922 (2002).
Nobel et al., "Purification of full-length recombinant human and rat type 1 11β-hydroxysteroid dehydrogenases with retained oxidoreductase activities," Protein Expr. Purif. 26(3):349-356 (2002).
Norman, "Selective PI3K-delta Inhibitors, A Review of the Patent Literature," Expert Opinion on Therapeutic Patents, 21(11): 1773-1790 (2011).
Nunes et al., "Signalling through CD28 T-cell activation pathway involves an inositol phospholipid-specific phospholipase C activity," Biochem. J. 293(Pt 3):835-842 (1993).
Oda et al., "PIK3CA cooperates with other phosphatidylinositol 3'-kinase pathway mutations to effect oncogenic transformation," Cancer Res. 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," J. Biol. Chem. 269(5):3568-3573 (1994).
Okada et al., "Blockage of chemotactic peptide-induced stimulation of neutrophils by wortmannin as a result of selective inhibition of phosphatidylinositol 3-kinase," J. Biol. Chem. 269(5):3563-3567 (1994).
Oppermann et al., "Forms and functions of human SDR enzymes," Chem. Biol. Interact. 130-132(1-3):699-705 (2001).
O'Shea et al., "Activation of human peripheral blood T lymphocytes by pharmacological induction of protein-tyrosine phosphorylation," Proc. Natl. Acad. Sci. U. S. A. 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," Chem. Pharm. Bull. 32(6):2160-2164 (1984).
Ozol et al., "Autoxidative transformations of 2-substituted 3-alkyl-4-hydroxy-1-oxo-1, 2-dihydroisoquinolines," Chemistry of Heterocyclic Compounds 14(6):644-648 (1978).
Patel et al., "Immunopathological aspects of age-related macular degeneration," Semin. Immunopathol. 30(2):97-110 (2008).

Pérez-Blas et al., "Impaired T cell signal transduction through CD28 in a patient with idiopathic thrombocytopenia," Clin. Exp. Immunol. 85(3):424-428 (1991).
Persson, "Glucocorticoids for asthma—early contributions," Pulm. Pharmacol. 2(3):163-166 (1989).
Petrie et al., "Novel biotinylated adenylate analogue derived from pyrazolo[3,4-d]pyrimidine for labeling DNA probes," Bioconjug. Chem. 2(6):441-446 (1991).
Pighi et al., "Phospho-proteomic analysis of mantle cell lymphoma cells suggests a pro-survival role of B-cell receptor signaling," Cell Oncol. (Dordr) 34(2):141-153 (2011).
Polak et al., "The PI3K/PKB signaling module as key regulator of hematopoiesis: implications for therapeutic strategies in leukemia," Blood 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," J. Urol. 182(6):2569-2577 (2009).
Prasad et al., "Phosphatidylinositol (PI) 3-kinase and PI 4-kinase binding to the CD4-p56$^{lck}$ complex: the p56$^{lck}$ SH3 domain binds to PI 3-kinase but not PI 4-kinase," Mol. Cell. Biol. 13(12): 7708-7717 (1993).
Prasad et al., "Src-homology 3 domain of protein kinase p59$^{fyn}$ mediates binding to phosphatidylinositol 3-kinase in T cells," Proc. Natl. Acad. Sci. U. S. A. 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," Proc. Natl. Acad. Sci. U. S. A. 91(7): 2834-2838 (1994).
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," J. Med. Chem. 33(7):1984-1992 (1990).
Puri and Gold, "Selective inhibitors of phosphoinositide 3-kinase delta: modulators of B-cell function with potential for treating autoimmune inflammatory disease and B-cell malignancies," Front. Immunol. 3:256 (2012).
Quiroga et al., "B-cell antigen receptor signaling enhances chronic lymphocytic leukemia cell migration and survival: specific targeting with a novel spleen tyrosine kinase inhibitor, R406," Blood 114(5):1029-1037 (2009).
Reif et al., "Divergent regulation of phosphatidylinositol 3-kinase P85α and P85β isoforms upon T cell activation," J. Biol. Chem. 268(15):10780-10788 (1993).
Report of the Expert Committee on the Diagnosis and Classification of Diabetes Mellitus, Diabetes Care 2( Suppl. 1):S5-S19 (1992).
Rizzatti et al., "Gene expression profiling of mantle cell lymphoma cells reveals aberrant expression of genes from the PI3K-AKT, WNT and TGFβ signaling pathways," Brit. J. Haematol. 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," J. Immunol. 189:4612-4620 (2012).
Romero et al., "Cloning and expression of the bovine 11b-hydroxysteroid dehydrogenase type-2," J. Steroid Biochem. Mol. Biol. 72(5):231-237 (2000).
Rommel et al., "PI3Kδ and PI3Kγ: partners in crime in inflammation in rheumatoid arthritis and beyond?" Nat. Rev. Immunol. 7:191-201 (2007).
Rott et al., "Recent developments in the use of biologics in psoriasis and autoimmune disorders. The role of autoantibodies," BMJ 330(7493):716-720 (2005).
Rudelius et al., "Constitutive activation of Akt contributes to the pathogenesis and survival of mantle cell lymphoma," Blood 108(5):1668-1676 (2006).
Saif and Chu, "Biology of colorectal cancer," Cancer J. 16(3):196-201 (2010).
Salmena et al., "Tenets of PTEN Tumor Suppression," Cell 133(3):403-414 (2008).
Sarker et al., "Targeting the PI3K/AKT pathway for the treatment of prostate cancer," Clin. Cancer Res. 15(15):4799-4805 (2009).

(56) References Cited

OTHER PUBLICATIONS

Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, a PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 ( Pt 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).
Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).

Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "P13K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecalboxylic Acids into N-Amino Pyrazolopyridinones," *Journal of Heterocyclic Chemistry* 39(6):1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).
Vogt et al., "Phosphatidylinositol 3-kinase the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (ASH Annual Meeting Abstracts)* 118: Abstract 3490 (2011).
Ward et al., "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines-potent inhibitors of the tyrosine kinase c-Src," Bioorg. Med. Chem. Lett. 11(6):849-852 (2001).
Wiesinger et al., "Antiinflammatory activity of the new mould metabolite 11-desacetoxy-wortmannin and of some of its derivatives," *Experientia* 30(2):135-136 (1974).
Wolff, Burger's Medicinal Chemistry, 5th ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).

(56) References Cited

OTHER PUBLICATIONS

Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(41):5486-5496 (2008).
U.S. Appl. No. 12/811,695, filed Nov. 11, 2010, filed U.S. Pat. No. 8,703,777, Substituted Bicyclic Compounds and Methods of Use Thereof, Patented.
U.S. Appl. No. 16/085,536, filed Sep. 14, 2018, 2019-0202835, Isotopologues of Isoquinolinone and Quinazolinone Compounds and Uses Thereof as PI3K Kinase Inhibitors, Published.
U.S. Appl. No. 16/312,896, filed Dec. 21, 2018, Unpublished, Combination Therapies, Pending.
U.S. Appl. No. 15/599,378, filed May 18, 2017, 2018-0098983, Certain Chemical Entities, Compositions and Methods, Published.
U.S. Appl. No. 15/672,964, filed Aug. 9, 2017, 2018-0055852, Heterocyclic Compounds and Uses Thereof, Published.
U.S. Appl. No. 15/799,612, filed Oct. 31, 2017, 2018-0273535, Processes for Preparing Isoquinolinones and Solid Forms of Isoquinolinones, Published.
U.S. Appl. No. 16/172,539, filed Oct. 26, 2018, Unpublished, Certain Chemical Entities, Compositions and Methods, Pending.
U.S. Appl. No. 16/417,420, filed May 20, 2019, Unpublished, Heterocyclic Compounds and Uses Thereof, Pending.
U.S. Appl. No. 13/552,460, filed Jul. 18, 2012, U.S. Pat. No. 8,969,363, Heterocyclic Compounds and Uses Thereof, Patented.
U.S. Appl. No. 13/552,473, filed Jul. 18, 2012, U.S. Pat. No. 9,056,877, Heterocyclic Compounds and Uses Thereof, Patented.
U.S. Appl. No. 13/552,516, filed Jul. 18, 2012, U.S. Pat. No. 8,785,470, Heterocyclic Compounds and Uses Thereof, Patented.
U.S. Appl. No. 13/841,265, filed Mar. 15, 2013, U.S. Pat. No. 8,940,742, Heterocyclic Compounds and Uses Thereof, Patented.
U.S. Appl. No. 13/839,912, filed Mar. 15, 2013, 2014-0120060, Treatment of Rheumatoid Arthritis and Asthma Using PI3 Kinase Inhibitors, Abandoned.
U.S. Appl. No. 14/209,842, filed Mar. 13, 2014, U.S. Pat. No. 9,481,667, Salts and Solid Forms of Isoquinolinones and Composition Comprising and Methods of Using the Same, Patented.
U.S. Appl. No. 13/840,822, filed Mar. 15, 2013, 2014-0120083, Treatment of Cancers Using PI3 Kinase Isoform Modulators, Published.
U.S. Appl. No. 12/811,695, filed Nov. 11, 2010, U.S. Pat. No. 8,703,777, Substituted Bicyclic Compounds and Methods of Use Thereof, Patented.
U.S. Appl. No. 12/503,776, filed Jul. 15, 2009, U.S. Pat. No. 8,193,182, Substituted Isoquinolin-1(2H)-Ones, and Methods of Use Thereof, Patented.
U.S. Appl. No. 13/403,394, filed Feb. 23, 2012, U.S. Pat. No. 8,785,456, Certain Chemical Entities, Compositions and Methods, Patented.
U.S. Appl. No. 13/350,444, filed Jan. 13, 2012, U.S. Pat. No. 8,569,323, Substituted Isoquinolin-1(2H)-One Compounds, Compositions, and Methods Thereof, Patented.
U.S. Appl. No. 13/121,157, filed Aug. 2, 2011, U.S. Pat. No. 8,703,778, Heterocyclic Kinase Inhibitors, Patented.
U.S. Appl. No. 13/289,540, filed Nov. 4, 2011, U.S. Pat. No. 8,785,454, Heterocyclic Compounds and Uses Thereof, Patented.
U.S. Appl. No. 13/293,828, filed Nov. 10, 2011, U.S. Pat. No. 8,901,133, Heterocyclic Compounds and Uses Thereof, Patented.
U.S. Appl. No. 13/112,611, filed May 20, 2011, U.S. Pat. No. 8,604,032, Chemical Compounds, Compositions and Methods for Kinase Modulation, Patented.
U.S. Appl. No. 13/347,423, filed Jan. 10, 2012, U.S. Pat. No. 8,809,349, Processes for Preparing Isoquinolinones and Solid Forms of Isoquinolinones, Patented.
U.S. Appl. No. 13/837,195, filed Mar. 15, 2013, U.S. Pat. No. 8,828,998, Treatment of Lupus, Fibrotic Conditions, and Inflammatory Myopathies and Other Disorders Using PI3 Kinase Inhibitors, Patented.
U.S. Appl. No. 14/222,488, filed Mar. 21, 2014, 2014-0206684, Certain Chemical Entities, Compositions and Methods, Abandoned.
U.S. Appl. No. 14/085,660, filed Nov. 20, 2013, U.S. Pat. No. 9,181,221, Chemical Compounds, Compositions and Methods for Kinase Modulation, Patented.
U.S. Appl. No. 14/099,831, filed Dec. 6, 2013, U.S. Pat. No. 9,115,141, Heterocyclic Compounds and Uses Thereof, Patented.
U.S. Appl. No. 14/776,604, filed Sep. 14, 2015, 2016-0024051, Salts and Solid Forms of Isoquinolinones and Composition Comprising and Methods of Using the Same, Abandoned.
U.S. Appl. No. 13/971,793, filed Aug. 20, 2013, U.S. Pat. No. 9,206,182, Certain Chemical Entities, Compositions and Methods, Patented.
U.S. Appl. No. 15/026,947, filed Apr. 1, 2016, U.S. Pat. No. 9,751,888, Heterocyclic Compounds and Uses Thereof, Patented.
U.S. Appl. No. 14/506,429, filed Oct. 3, 2014, U.S. Pat. No. 9,359,365, Heterocyclic Compounds and Uses Thereof, Patented.
U.S. Appl. No. 14/222,500, filed Mar. 21, 2014, U.S. Pat. No. 9,296,742, Heterocyclic Kinase Inhibitors, Patented.
U.S. Appl. No. 14/292,475, filed May 30, 2014, 2014-0377258, Treatment of Cancers Using PI3 Kinase Isoform Modulators, Published.
U.S. Appl. No. 15/030,701, filed Apr. 20, 2016, 2016-0244452, Heterocyclic Compounds and Uses Thereof, Abandoned.
U.S. Appl. No. 14/297,526, filed Jun. 5, 2014, U.S. Pat. No. 9,546,180, Heterocyclic Compounds and Uses Thereof, Patented.
U.S. Appl. No. 14/296,953, filed Jun. 5, 2014, U.S. Pat. No. 9,216,982, Certain Chemical Entities, Compositions and Methods, Patented.
U.S. Appl. No. 14/302,340, filed Jun. 11, 2014, U.S. Pat. No. 9,315,505, Heterocyclic Compounds and Uses Thereof, Patented.
U.S. Appl. No. 14/327,499, filed Jul. 9, 2014, U.S. Pat. No. 9,290,497, Processes for Preparing Isoquinolinones and Solid Forms of Isoquinolinones, Patented.
U.S. Appl. No. 14/439,965, filed Apr. 30, 2015, 2015-0283142, Treatment of Cancers Using PI3 Kinase Isoform Modulators, Published.
U.S. Appl. No. 14/448,998, filed Jul. 31, 2014, U.S. Pat. No. 9,527,847, Treatment of Lupus, Fibrotic Conditions, and Inflammatory Myopathies and Other Disorders Using PI3 Kinase Inhibitors, Patented.
U.S. Appl. No. 14/512,262, filed Oct. 10, 2014, U.S. Pat. No. 9,388,183, Heterocyclic Compounds and Uses Thereof, Patented.
U.S. Appl. No. 14/573,961, filed Dec. 17, 2014, U.S. Pat. No. 9,255,108, Heterocyclic Compounds and Uses Thereof, Patented.
U.S. Appl. No. 15/059,962, filed Mar. 3, 2016, U.S. Pat. No. 9,822,131, Certain Chemical Entities, Compositions and Methods, Patented.
U.S. Appl. No. 14/661,656, filed Mar. 18, 2015, U.S. Pat. No. 9,775,844, Heterocyclic Compounds and Uses Thereof, Patented.
U.S. Appl. No. 14/592,628, filed Jan. 8, 2015, U.S. Pat. No. 9,718,815, Heterocyclic Compounds and Uses Thereof, Patented.
U.S. Appl. No. 14/687,714, filed Apr. 15, 2015, 2015-0320754, Combination Therapies, Published.
U.S. Appl. No. 14/687,768, filed Apr. 15, 2015, 2015-0320755, Combination Therapies, Published.

(56) References Cited

OTHER PUBLICATIONS

U.S. Appl. No. 14/695,699, filed Apr. 24, 2015, U.S. Pat. No. 9,828,377, Heterocyclic Compounds and Uses Thereof, Patented.
U.S. Appl. No. 14/710,336, filed May 12, 2015, U.S. Pat. No. 9,605,003, Heterocyclic Compounds and Uses Thereof, Patented.
U.S. Appl. No. 15/051,529, filed Feb. 23, 2016, Re. 46,621, Processes for Preparing Isoquinolinones and Solid Forms of Isoquinolinones, Patented.
U.S. Appl. No. 14/874,328, filed Oct. 2, 2015, U.S. Pat. No. 9,708,348, Heterocyclic Compounds and Uses Thereof, Patented.
U.S. Appl. No. 15/264,417, filed Sep. 13, 2016, U.S. Pat. No. 10,160,761, Solid Forms of Isoquinolinones, and Process of Making, Composition Comprising, and Methods of Using the Same, Patented.
U.S. Appl. No. 14/869,637, filed Sep. 29, 2015, U.S. Pat. No. 9,738,644, Chemical Compounds, Compositions and Methods for Kinase Modulation, Patented.
U.S. Appl. No. 14/876,589, filed Oct. 6, 2015, 2016-0022692, Treatment of Rheumatoid Arthritis and Asthma Using PI3 Kinase Inhibitors, Abandoned.
U.S. Appl. No. 14/884,612, filed Oct. 15, 2015, U.S. Pat. No. 9,522,146, Certain Chemical Entities, Compositions and Methods, Patented.
U.S. Appl. No. 14/894,854, filed Nov. 30, 2015, 2016-0113932, Treatment of Cancers Using PI3 Kinase Isoform Modulators, Abandoned.
U.S. Appl. No. 14/938,647, filed Nov. 11, 2015, U.S. Pat. No. 9,655,892, Certain Chemical Entities, Compositions and Methods, Patented.
U.S. Appl. No. 14/971,954, filed Dec. 16, 2015, 2016-0207940, Heterocyclic Compounds and Uses Thereof, Abandoned.
U.S. Appl. No. 15/016,117, filed Feb. 4, 2016, U.S. Pat. No. 9,840,505, Processes for Preparing Isoquinolinones and Solid Forms of Isoquinolinones, Patented.
U.S. Appl. No. 16/085,536, filed Sep. 14, 2018, 2019-0202835, Isotopologues of Isoquinolinone and Quinazolinone Compounds and Uses Thereof as PI3K Kinase Inhibitors, Allowed.
U.S. Appl. No. 15/050,029, filed Feb. 22, 2016, U.S. Pat. No. 9,790,228, Heterocyclic Kinase Inhibitors, Patented.
U.S. Appl. No. 16/312,896, filed Dec. 21, 2018, 2019-0216816, Combination Therapies, Published.
U.S. Appl. No. 16/308,377, filed Dec. 7, 2018, 2019-0135833, Heterocyclic Compounds and Uses Thereof, Published.
U.S. Appl. No. 15/179,570, filed Jun. 10, 2016, Unpublished, Heterocyclic Compounds and Uses Thereof, Abandoned.
U.S. Appl. No. 15/333,803, filed Oct. 25, 2016, 2017-0137407, Heterocyclic Compounds and Uses Thereof, Abandoned.
U.S. Appl. No. 15/347,489, filed Nov. 9, 2016, 2017-0281614, Certain Chemical Entities, Compositions and Methods, Abandoned.
U.S. Appl. No. 15/599,378, filed May 18, 2017, 2018-0098983, Certain Chemical Entities, Compositions and Methods, Abandoned.
U.S. Appl. No. 15/621,815, filed Jun. 13, 2017, U.S. Pat. No. 10,253,047, Heterocyclic Compounds and Uses Thereof, Patented.
U.S. Appl. No. 15/621,764, filed Jun. 13, 2017, Unpublished, Chemical Compounds, Compositions and Methods for Kinase Modulation, Abandoned.
U.S. Appl. No. 15/672,964, filed Aug. 9, 2017, 2018-0055852, Heterocyclic Compounds and Uses Thereof, Allowed.
U.S. Appl. No. 15/675,185, filed Aug. 11, 2017, Unpublished, Heterocyclic Compounds and Uses Thereof, Abandoned.
U.S. Appl. No. 15/794,816, filed Oct. 26, 2017, U.S. Pat. No. 10,329,299, Heterocyclic Compounds and Uses Thereof, Patented.
U.S. Appl. No. 15/799,612, filed Oct. 31, 2017, 2018-0273535, Processes for Preparing Isoquinolinones and Solid Forms of Isoquinolinones, Allowed.
U.S. Appl. No. 15/789,868, filed Oct. 20, 2017, 2018-0258103, Certain Chemical Entities, Compositions and Methods, Published.
U.S. Appl. No. 16/172,539, filed Oct. 26, 2018, 2019-0290636, Certain Chemical Entities, Compositions and Methods, Published.
U.S. Appl. No. 16/197,195, filed Nov. 20, 2018, 2019-0185477, Solid Forms of Isoquinolinones, and Process of Making, Composition Comprising, and Methods of Using the Same, Published.
U.S. Appl. No. 16/417,420, filed May 20, 2019, 2019-0367521, Heterocyclic Compounds and Uses Thereof, Published.
U.S. Appl. No. 16/556,048, filed Aug. 29, 2019, Unpublished, Certain Chemical Entities, Compositions and Methods, Pending.

HETEROCYCLIC COMPOUNDS AND USES THEREOF

CROSS REFERENCES TO RELATED APPLICATIONS

This application is a divisional application of U.S. patent application Ser. No. 15/621,815, filed on Jun. 13, 2017, which is a continuation application of U.S. patent application Ser. No. 14/874,328, filed on Oct. 2, 2015, now U.S. Pat. No. 9,708,348, which claims priority to U.S. Provisional Application Nos. 62/059,426, filed Oct. 3, 2014, and 62/216,261, filed Sep. 9, 2015, the entireties of which are incorporated herein by reference.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphotylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in man different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K-δ is expressed primarily in hematopoietic cells including leukocytes such as T-cells, dendritic cells, neutrophils, mast cells. B-cells, and macrophages. PI3K-δ is integrally involved in mammalian immune system functions such as T-cell function. B-cell activation, mast cell activation, dendritic cell function, and neutrophil activity. Due to its integral role in immune system function. PI3K-δ is also involved in a number of diseases related to undesirable immune response such as allergic reactions, inflammatory diseases, inflammation mediated angiogenesis, rheumatoid arthritis, and auto-immune diseases such as lupus, asthma, emphysema and other respiratory diseases. Other class I PI3K involved immune system function includes PI3K-γ, which plays a role in leukocyte signaling and has been implicated in inflammation, rheumatoid arthritis, and autoimmune diseases such as lupus. For example, PI3K-γ and PI3K-δ are highly expressed in leukocytes and have been associated with adaptive and innate immunity; thus, these PI3K isoforms can be important mediators in inflammatory disorders and hematologic malignancies.

The gamma (γ) isoform of class I PI3K consists of a catalytic subunit p110γ, which is associated with a p101 regulatory subunit. PI3K-γ is regulated by G protein-coupled receptors (GPCRs) via association with the β/γ subunits of heterotrimeric G proteins. PI3K-γ is expressed primarily in hematopoietic cells and cardiomyocytes and is involved in inflammation and mast cell function. Inhibitors of PI3K-γ are useful for treating a variety of inflammatory diseases, allergies, and cardiovascular diseases, among others.

Unlike PI3K-δ, the beta (β) isoform of class I PI3K appears to be ubiquitously expressed. PI3K-β has been implicated primarily in various types of cancer including PTEN-negative cancer (Edgar et al. *Cancer Research* (2010) 70(3):1164-1172), and HER2-overexpressing cancer such as breast cancer and ovarian cancer.

SUMMARY

Described herein are compounds capable of selectively inhibiting one or more isoform(s) of class I PI3K without substantially affecting the activity of the remaining isoforms of the same class. For example, in some embodiments, non-limiting examples of inhibitors capable of selectively inhibiting PI3K-δ and/or PI3K-γ, but without substantially affecting the activity of PI3K-α and/or PI3K-β are disclosed. In one embodiment, the inhibitors provided herein can be effective in ameliorating disease conditions associated with PI3K-δ and/or PI3K-γ activity. In one embodiment, the compounds are capable of selectively inhibiting PI3K-γ over PI3K-δ.

Provided herein are compounds of Formula I' or Formula II':

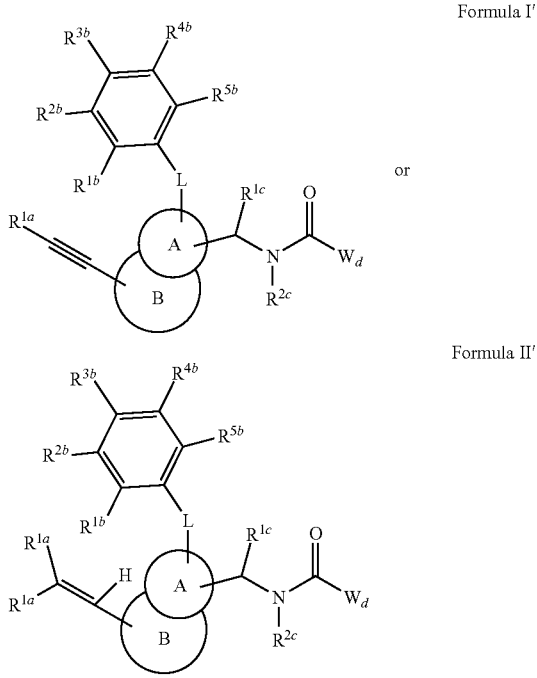

Formula I' or

Formula II' or a pharmaceutically acceptable form thereof, wherein A, B, L, $W_d$, $R^{1a}$, $R^{1b}$, $R^{2b}$, $R^{3b}$, $R^{4b}$, $R^{5b}$, $R^{1c}$, and $R^{2c}$ are as described herein.

In one embodiment, the compound provided herein is predominately in an (S)-stereochemical configuration. In one embodiment, the compound provided herein is the S enantiomer having an enantiomeric excess selected from greater than about 25%, greater than about 55%, greater than about 80%, greater than about 90%, and greater than about 95%. In one embodiment, the compound is present in a pharmaceutical composition comprising the compound, or a pharmaceutically acceptable salt thereof, and one or more pharmaceutically acceptable excipients.

In certain embodiments, a compound disclosed herein selectively modulates PI3K gamma isoform. In certain embodiments, the compound selectively inhibits the gamma isoform over the alpha or beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of PI3K gamma isoform over PI3K alpha or beta isoform is measured by the ratio of the $IC_{50}$ value against PI3K alpha or beta isoform to the $IC_{50}$ value against PI3K gamma isoform. In certain embodiments, the PI3K gamma isoform $IC_{50}$ activity of a compound disclosed herein can be less than about 1000 nM, less than about 100 nM, less than about 10 nM, or less than about 1 nM.

In certain embodiments, a compound disclosed herein selectively modulates PI3K gamma isoform over the delta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of PI3K gamma isoform over PI3K delta isoform is measured by the ratio of the $IC_{50}$ value against PI3K delta isoform to the $IC_{50}$ value against PI3K gamma isoform.

In certain embodiments, a compound as disclosed herein selectively modulates PI3K delta isoform. In certain embodiments, the compound selectively inhibits the delta isoform over the alpha or beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of PI3K delta isoform over PI3K alpha or beta isoform is measured by the ratio of the $IC_5$, value against PI3K alpha or beta isoform to the $IC_{50}$ value against PI3K delta isoform. In certain embodiments, the PI3K delta isoform ICs activity of a compound disclosed herein can be less than about 1000 nM, less than about 100 nM, less than about 10 nM, or less than about 1 nM.

In certain embodiments, provided herein is a composition (e.g., a pharmaceutical composition) comprising a compound described herein and a pharmaceutically acceptable excipient. In some embodiments, provided herein is a method of inhibiting a PI3 kinase, comprising contacting the PI3 kinase with an effective amount of a compound or a pharmaceutical composition described herein. In certain embodiments, a method is provided for inhibiting a PI3 kinase wherein said PI3 kinase is present in a cell. The inhibition can take place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, among others. In certain embodiments, a second therapeutic agent is administered to the subject.

In certain embodiments, a method is provided for selectively inhibiting a PI3 kinase gamma isoform over PI3 kinase alpha or beta isoform wherein the inhibition takes place in a cell. Non-limiting examples of the methods disclosed herein can comprise contacting PI3 kinase gamma isoform with an effective amount of a compound or a pharmaceutical composition disclosed herein. In an embodiment, such contact can occur in a cell.

In certain embodiments, a method is provided for selectively inhibiting a PI3 kinase gamma isoform over PI3 kinase alpha or beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase gamma isoform over PI3 kinase alpha or beta isoform by administering an amount of a compound or a pharmaceutical composition provided herein to said subject, wherein said amount is sufficient for selective modulation of PI3 kinase gamma isoform over PI3 kinase alpha or beta isoform.

In certain embodiments, a method is provided for selectively inhibiting a PI3 kinase delta isoform over PI3 kinase alpha or beta isoform wherein the inhibition takes place in a cell. Non-limiting examples of the methods disclosed herein can comprise contacting PI3 kinase delta isoform with an effective amount of a compound or a pharmaceutical composition disclosed herein. In an embodiment, such contact can occur in a cell.

In certain embodiments, a method is provided for selectively inhibiting a PI3 kinase delta isoform over PI3 kinase alpha or beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase delta isoform over PI3 kinase alpha or beta isoform by administering an amount of a compound or a pharmaceutical composition provided herein to said subject, wherein said amount is sufficient for selective modulation of PI3 kinase delta isoform over PI3 kinase alpha or beta isoform.

In certain embodiments, a method is provided for selectively inhibiting a PI3 kinase gamma isoform over PI3 kinase delta isoform wherein the inhibition takes place in a cell. Non-limiting examples of the methods disclosed herein can comprise contacting PI3 kinase gamma isoform with an effective amount of a compound or a pharmaceutical composition disclosed herein. In an embodiment, such contact can occur in a cell.

In certain embodiments, a method is provided for selectively inhibiting a PI3 kinase gamma isoform over PI3 kinase delta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or a pharmaceutical composition provided herein to said subject. In certain embodiments, provided herein is a method of treating a subject suffering from a disorder associated with PI3 kinase, said method comprising selectively modulating the PI3 kinase gamma isoform over PI3 kinase delta isoform by administering an amount of a compound or a pharmaceutical composition provided herein to said subject, wherein said amount is sufficient for selective modulation of PI3 kinase gamma isoform over PI3 kinase delta isoform.

In certain embodiments, provided herein is a method of inhibiting a PI3 kinase in a subject suffering from an inflammatory disease, an immune disease, or a respiratory disease, comprising administering to the subject an effective amount of a compound provided herein (e.g., a compound of Formula I', Formula II', Formula I, or Formula II). In one embodiment, the subject is a mammal. In one embodiment, the mammal is a human. In one embodiment, the subject is a human.

In some embodiments, the disorder suffered by the subject is a cancer. In one embodiment, the cancer is a hematological cancer. In one embodiment, the cancer is acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus type 1 (HTLV-1) leukemia/lymphoma, AIDS-related lymphoma, adult T-cell lymphoma, acute lymphocytic leukemia (ALL), T-cell acute lymphocytic leukemia. B-cell acute lymphoblastic leukemia, chronic lymphocytic leukemia, or multiple myeloma (MM). In one embodiment, the cancer is leukemia or lymphoma. In one embodiment, the leukemia is B-cell acute lymphoblastic leukemia (B-ALL), acute myeloid leukemia (AML), acute lymphocytic leukemia, chronic myeloid leukemia, hairy cell leukemia, myelodysplasia, myeloproliferative disorders, acute myelogenous leukemia (AML), chronic myelogenous leukemia (CML), chronic lymphocytic leukemia (CLL), multiple myeloma (MM), myelodysplastic syndrome (MDS), or mast cell cancer. In one embodiment, the lymphoma is diffuse large B-cell lymphoma, B-cell immunoblastic lymphoma, small non-cleaved cell lymphoma, human lymphotrophic virus-type 1 (HTLV-1) leukemia/lymphoma, adult T-cell lymphoma, Hodgkin disease, or non-Hodgkin lymphomas.

In one embodiment, the cancer is a solid tumor. In one embodiment, the cancer is lung cancer, e.g., non-small cell lung cancer, small cell lung cancer, melanoma; prostate cancer, glioblastoma; endometrial cancer, pancreatic cancer, renal cell carcinoma; colorectal cancer, breast cancer, thyroid cancer, or ovarian cancer. In one embodiment, the solid tumor is prostate cancer, breast cancer, or glioblastomas.

In some embodiments, the disorder suffered by the subject is an inflammatory disease or an immune disease. In one embodiment, the inflammatory disease or the immune disease is asthma, emphysema, allergy, dermatitis, rheumatoid arthritis, psoriasis, lupus erythematosus, graft versus host disease, inflammatory bowel disease, eczema, scleroderma, Crohn's disease, or multiple sclerosis. In one embodiment, the disorder is rheumatoid arthritis. In one embodiment, the disorder is rheumatoid arthritis, and the amount of the compound is effective to ameliorate one or more symptoms associated with rheumatoid arthritis, wherein the symptom associated with rheumatoid arthritis is independently a reduction in the swelling of the joints, a reduction in serum anti collagen levels, a reduction in bone resorption a reduction in cartilage damage, a reduction in pannus, or a reduction in inflammation.

In some embodiments, the disorder suffered by the subject is a respiratory disease. In one embodiment, the respiratory disease is asthma, chronic obstructive pulmonary disease (COPD), chronic bronchitis, emphysema, or bronchiectasis. In one embodiment, the disorder is asthma.

In one embodiment, the methods provided herein further comprise administration of one or more therapeutic agents selected from chemotherapeutic agents, cytotoxic agents, and radiation. In one embodiment, the compound is administered in combination with an mTOR inhibitor. In one embodiment, the compound is administered in combination with one or more of: an agent that inhibits IgE production or activity, 2-(4-(6-cyclohexyloxy-2-naphtyloxy)phenylacetamide)benzoic acid, an mTOR inhibitor, rapamycin, a TORC1 inhibitor, a TORC2 inhibitor, an anti-IgE antibody, prednisone, corticosteroid, a leukotriene inhibitor, XOLAIR, ADVAIR, SINGULAIR, or SPIRIVA. In one embodiment, the compound is administered in combination with one or more of: a mitotic inhibitor, an alkylating agent, an anti-metabolite, an intercalating antibiotic, a growth factor inhibitor, a cell cycle inhibitor, an enzyme, a topoisomerase inhibitor, an anti-hormone, an angiogenesis inhibitor, an anti-androgen, or an anti-receptor kinase antibody. In one embodiment, the compound is administered in combination with one or more of: Imatinib Mesylate, bortezomib, bicalutamide, gefitinib, ADRIAMYCIN, alkylating agents, alkyl sulfonates, ethylenimines, altretamine, triethylenemelamine, trietylenephosphoramide, triethylenethiophosphaoramide, trimethylolomelamine, nitrogen mustards, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, nitrosureas, antibiotics, anti-metabolites, denopterin, methotrexate, pteropterin, trimetrexate, 5-fluorouracil (5-FU), fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens, anti-adrenals, folic acid replenisher, arabinoside, cyclophosphamide, thiotepa, taxanes, anti-hormonal agents, anti-estrogens, tamoxifen, raloxifene, aromatase inhibiting 4(5)-imidazoles, 4-hydroxytamoxifen, trioxifene, keoxifene, onapristone, toremifene, anti-androgens, chlorambucil, gemcitabine, 6-thioguanine; mercaptopurine, cisplatin, carboplatin, vincristine; vinorelbine, vinblastin, ifosfamide, mitomycin C, daunorubicin, doxorubicin, mitoxantrone, HERCEPTIN, AVASTIN, ERBITUX, RITUXAN, TAXOL, ARIMIDEX, TAXOTERE, or an anti-receptor tyrosine kinase antibody selected from cetuximab, panitumumab, trastuzumab, anti CD20 antibody, rituximab, tositumomab, alemtuzumab, bevacizumab, and gemtuzamab. In one embodiment, the compound is administered in combination with one or more of: bortezomib, ADRIAMYCIN, alkylating agents, anti-metabolites, denopterin, pteropterin, trimetrexate, a nitrogen mustard, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, methotrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens, cyclophosphamide, taxanes, anti-hormonal agents, gemcitabine; cisplatin, carboplatin, vincristine, vinorelbine, vinblastin, ifosfamide, mitomycin C, daunorubicin, doxorubicin, mitoxantrone, HERCEPTIN, AVASTIN, ERBITUX, RITUXAN, TAXOL, ARIMIDEX, or TAXOTERE. In one embodiment, the compound is administered in combination with one or more of: non-steroidal anti-inflammatory drugs (NSAIDs), corticosteroids, prednisone, chloroquine, hydroxychloroquine, azathioprine, cyclophosphamide, methotrexate, cyclosporine, anti-CD20 antibodies, ENBREL, REMICADE, HUMIRA, AVONEX, or REBIF.

In one embodiment, provided herein is a method of inhibiting a PI3 kinase in a subject suffering from a cancer, comprising administering to the subject an effective amount of a compound provided herein (e.g., a compound of Formula I'). In one embodiment, the cancer is selected from acute myeloid leukemia (AML), chronic myeloid leukemia (CML), myelodysplastic syndrome (MDS), myeloproliferative disorders, mast cell cancer, Hodgkin disease, non-Hodgkin lymphomas, diffuse large B-cell lymphoma, human lymphotrophic virus-type 1 (HTLV-1) leukemia/lymphoma, AIDS-related lymphoma, adult T-cell lymphoma, acute lymphocytic leukemia (ALL), B-cell acute lymphoblastic leukemia. T-cell acute lymphoblastic leukemia, chronic lymphocytic leukemia, or multiple myeloma (MM). In one embodiment, the cancer is leukemia or lymphoma. In one embodiment, the leukemia is selected from B-cell acute lymphoblastic leukemia (B-ALL), acute lymphocytic leukemia, hairy cell leukemia, myelodysplasia, myeloproliferative disorders, acute myelogenous leukemia (AML), chronic myelogenous leukemia (CML), chronic lymphocytic leukemia (CLL), multiple myeloma (MM), myelodysplastic syndrome (MDS), or mast cell cancer. In one embodiment, the lymphoma is selected from diffuse large B-cell lymphoma. B-cell immunoblastic lymphoma, small non-cleaved cell lymphoma, human lymphotrophic virus-type 1 (HTLV-1) leukemia/lymphoma, AIDS-related lymphoma, adult T-cell lymphoma, Hodgkin disease, or non-Hodgkin lymphomas. In one embodiment, the compound is administered in combination with one or more therapeutic agents provided herein.

In one embodiment, provided herein is a method of inhibiting a PI3 kinase in a subject suffering from an inflammatory disease or an immune disease, comprising administering to the subject an effective amount of a compound provided herein (e.g., a compound of Formula I'). In one embodiment, the inflammatory disease or immune disease is asthma, emphysema, allergy, dermatitis, rheumatoid arthritis, psoriasis, lupus erythematosus, graft versus host disease, inflammatory bowel disease, eczema, scleroderma. Crohn's disease, or multiple sclerosis. In one embodiment, the inflammatory disease or immune disease is rheumatoid arthritis. In one embodiment, the compound is administered in combination with one or more therapeutic agents provided herein.

In one embodiment, provided herein is a method of inhibiting a PI3 kinase in a subject suffering from a respiratory disease, comprising administering to the subject an effective amount of a compound provided herein (e.g., a compound of Formula I'). In one embodiment, the respiratory disease is asthma, chronic obstructive pulmonary disease (COPD), chronic bronchitis, emphysema, or bronchiectasis. In one embodiment, the respiratory disease is asthma. In one embodiment, the compound is administered in combination with one or more therapeutic agents provided herein.

In certain embodiments, provided herein is a method of inhibiting PI3K-γ in a subject comprising administering to the subject an effective amount of a compound provided herein (e.g., a compound of Formula I').

In certain embodiments, provided herein is a method of inhibiting PI3K-δ in a subject, comprising administering to the subject an effective amount of a compound provided herein (e.g., a compound of Formula I').

In certain embodiments, provided herein is a method of making a compound described herein.

In certain embodiments, provided herein is a reaction mixture comprising a compound described herein.

In certain embodiments, provided herein is a kit comprising a compound described herein.

In some embodiments, a method is provided for treating a disease or disorder described herein, the method comprising administering a therapeutically effective amount of a compound or a pharmaceutical composition described herein to a subject.

In some embodiments, a method is provided for treating a PI3K mediated disorder in a subject, the method comprising administering a therapeutically effective amount of a compound or a pharmaceutical composition described herein to a subject.

In some embodiments, provided herein is a use of a compound or a pharmaceutical composition described herein for the treatment of a disease or disorder described herein in a subject.

In some embodiments, provided herein is a use of a compound or a pharmaceutical composition described herein for the treatment of a PI3K mediated disorder in a subject.

In some embodiments, provided herein is a use of a compound or a pharmaceutical composition described herein in the manufacture of a medicament for the treatment of a disease or disorder described herein in a subject.

In some embodiments, provided herein is use of a compound or a pharmaceutical composition described herein in the manufacture of a medicament for the treatment of a PI3K mediated disorder in a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DETAILED DESCRIPTION

In one embodiment, provided are heterocyclyl compounds, and pharmaceutically acceptable forms thereof, including, but not limited to, salts, hydrates, solvates, isomers, prodrugs, and isotopically labeled derivatives thereof.

In another embodiment, provided are methods of treating and/or managing various diseases and disorders, which comprises administering to a patient a therapeutically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In another embodiment, provided are methods of preventing various diseases and disorders, which comprises administering to a patient in need of such prevention a prophylactically effective amount of a compound provided herein or a pharmaceutically acceptable form (e.g., salts, hydrates, solvates, isomers, prodrugs, and isotopically labeled derivatives) thereof. Examples of diseases and disorders are described herein.

In other embodiments, a compound provided herein, or a pharmaceutically acceptable form (e.g., salts, hydrates, solvates, isomers, prodrugs, and isotopically labeled derivatives) thereof, is administered in combination with another drug ("second active agent") or treatment. Second active agents include small molecules and large molecules (e.g., proteins and antibodies), examples of which are provided herein, as well as stem cells. Other methods or therapies that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, prodrugs, and isotopically labeled derivatives) thereof, and optionally one or more second active agents.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5% or 0.05% of a given value or range.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of this disclosure.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of which the target protein or polypeptide are also specifically included within this definition. Non-limiting examples of biological activity inhibited by an antagonist include those associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, or buccal administration, or inhalation, or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompass administration of two or more agents to subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, the terms "treatment". "treating", "palliating" and "ameliorating" are used interchangeably herein. These terms refer to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, the terms "prevention" and "preventing" are used herein to refer to an approach for obtaining beneficial or desired results including, but not limited to, prophylactic benefit. For prophylactic benefit, the pharmaceutical compositions can be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

"Signal transduction" is a process during which stimulatory or inhibitory signals are transmitted into and within a cell to elicit an intracellular response. A "modulator" of a signal transduction pathway refers to a compound which modulates the activity of one or more cellular proteins mapped to the same specific signal transduction pathway. A modulator can augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target. For example, a compound that selectively inhibits one isoform of PI3K over another isoform of PI3K has an activity of at least greater than about 1× against a first isoform relative to the compound's activity against the second isoform (e.g., at least about 2×, 3×, 5×, 10×, 20×, 50×, 100×, 200×, 500×, or 1000×). In certain embodiments, these terms refer to (1) a compound of described herein that selectively inhibits the gamma isoform over the alpha, beta, or delta isoform; or (2) a compound described herein that selectively inhibits the delta isoform over the alpha or beta isoform. By way of non-limiting example, the ratio of selectivity can be greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by $IC_{50}$ e.g., in vitro or in vivo assays such as those described in Examples 222, 224, 225, 226, 247, 248, etc. In certain embodiments, the $IC_{50}$ can be measured by in vitro or in vivo assays such as those described in Examples 247 and 248. In certain embodiments, the PI3K gamma isoform $IC_{50}$ activity of a compound of provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM. In certain embodiments, the PI3K delta isoform $IC_{50}$ activity of a compound provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM.

"Radiation therapy" means exposing a patient, using routine methods and compositions known to the practitioner, to radiation emitters such as, but not limited to, alpha-particle emitting radionuclides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons.

"Subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body.

The term "in vitro" refers to an event that takes places outside of a subject's body. For example, an in vitro assay encompasses any assay conducted outside of a subject In vitro assays encompass cell-based assays in which cells, alive or dead, are employed. In vitro assays also encompass a cell-free assay in which no intact cells are employed.

As used herein, "pharmaceutically acceptable esters" include, but are not limited to, alkyl, alkenyl, alkynyl, aryl, aralkyl, and cycloalkyl esters of acidic groups, including, but not limited to, carboxylic acids, phosphoric acids, phosphic acids, sulfonic acids, sulfonic acids, and boronic acids.

As used herein, "pharmaceutically acceptable enol ethers" include, but are not limited to, derivatives of formula —C=C(OR) where R can be selected from alkyl, alkenyl, alkynyl, aryl, aralkyl, and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl, and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al, describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a solvate (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmaceutically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*. Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or min vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as D-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy) ethyl, 1-methyl-1-(($C_1$-$C_6$)alkanoyloxy)ethyl ($C_1$-$C_6$) alkoxycarbonyloxy methyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from naturally occurring L-amino acids, P(O)(OH)$_2$, —P(OXO($C_1$-C6)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$) alkyl or mono-N— or di-N,N—($C_1$-$C_6$)alkylaminoalkyl, —C(Y$^4$)$^5$ wherein Y$^4$ is H or methyl and Y$^5$ is mono-N— or di-N,N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Atropisomers" are stereoisomers from hindered rotation about single bonds and can be resolved or isolated by methods known to those skilled in the art. For example, certain substituents with ortho or meta substituted phenyl may form atropisomers, where they may be separated and isolated.

"Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

In certain embodiments, the symbol ═══ denotes a bond that can be a single or double as described herein.

In certain embodiments, provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of the plane of the ring are designated "cis/trans."

"Enantiomers" are a pair of stereoisomers that are non-superimposable mirror images of each other. A mixture of a pair of enantiomers in any proportion can be known as a "racemic" mixture. The term "(i)" is used to designate a racemic mixture where appropriate. "Diastereoisomers" are stereoisomers that have at least two asymmetric atoms, but which are not mirror-images of each other. The absolute stereochemistry can be specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-, The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., an S enantiomer, and 10% of the other enantiomer, e.g., an R enantiomer.

$$ee=(90-10)/100=80\%.$$

Thus, a composition containing 90% of one enantiomer and 10% of the other enantiomer is said to have an enantiomeric excess of 80%. Some compositions described herein contain an enantiomeric excess of at least about 1%, about 5%, about 10%, about 20%, about 30%, about 40%, about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 1%, about 5%, about 10%, about 20%, about 30%, about 40% about 50%, about 75%, about 90% about 95% or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers), such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30% greater than about 40% greater than about 50%, greater than about 55%, greater than about 60%, greater than about 65%, greater than about 70% greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about %9%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5% about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities (i.e., (S)- or (R)-stereoisomers). In some embodiments, the mixture of identical chemical entities (i.e., mixture of stereoisomers) is a racemic mixture of (S)- and (R)-isomers. In another embodiment, the mixture of the identical chemical entities (i.e., mixture of stereoisomers) contains predominately (S)-isomer or predominately (R)-isomer. For example, in some embodiments, the (S)-isomer in the mixture of identical chemical entities (i.e., mixture of stereoisomers) is present at about 55%, about 60%, about 65%, about 70%, about 75% about 80%, about 85%, about 90%, about 95%, about 96% about 97%, about 98%, about 99%, or about 99.5% by weight, or more, relative to the total weight of the mixture of (S)- and (R)-isomers. In some embodiments, the (S)-isomer in the mixture of identical chemical entities (i.e., mixture of stereoisomers) is present at an (S)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90%, to about 99.5%, about 95% to about 99.5%, about 96% to about 99.5%, about 97% to about 99.5%, about 98% to about 99.5%, or about 99% to about 99.5%, or more than about 99.5%.

In other embodiments, the (R)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (R)-isomers in the mixture of identical chemical entities (i.e., mixture of stereoisomers) is present at an (R)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90%, to about 99.5%, about 95% to about 99.5%, about 96% to about 99.5%, about 97% to about 99.5%, about 98% to about 99.5%, or about 99% to about 99.5%, or more than about 99.5%.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques. Ed., Wiley Interscience, New York, 1981); Wilen et al., *Tetrahedron* 33:2725 (1977); *Stereochemistry of Carbon Compounds* (E. L. Eliel, Ed., McGraw-Hill, NY, 1962); and *Tables of Resolving Agents and Optical Resolutions* p. 268 (E. L. Eliel, Ed., Univ. of Notre Dame Press, Notre Dane, Ind. 1972).

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen phosphorus, sulfur, fluorine, and chlorine, such as, e.g., $^{2}H$, $^{3}H$, $^{13}C$, $^{14}C$, $^{15}N$, $^{18}O$, $^{17}O$, $^{31}P$, $^{35}S$, $^{18}F$, and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5th ed., John Wiley & Sons. Inc., New York, 2001; Larock, Comprehensive Organic Transformations. Inc., New York, 1989; and Carruthers, Some *Modern Methods of Organic Synthesis,* 3rd ed., Cambridge University Press. Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain radical consisting solely of carbon and hydrogen atoms, containing no unsaturation, having, in some embodiments, from one to ten carbon atoms (e.g., $C_1$-$C_{10}$ alkyl). Linear or straight alkyl refers to an alkyl with no branching, e.g., methyl, ethyl, n-propyl. Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, 4 carbon atoms, etc., up to and including 10 carbon atoms, although the present definition also covers the occurrence of the term "alkyl" where no numerical range is designated. In some embodiments, an alkyl is a $C_1$-$C_6$ alkyl group. In some embodiments, alkyl groups have 1 to 10, 1 to 6, 1 to 4, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t R^a$ (where t is 1 or 2), —S(O)$_t$O$R^a$ (where t is 1 or 2), —S(O)$_t$N(R)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl and the like. "Haloalkyl" refers to an alkyl group in which one or more of the hydrogen atoms have been replaced with a halogen independently selected from fluoro, chloro, bromo, and iodo.

"Alkyl-cycloalkyl" refers to an -(alkyl)cycloalkyl radical where alkyl and cycloalkyl are as disclosed herein and which are optionally substituted by one or more of the substituents described as suitable substituents for alkyl and cycloalkyl respectively. The "alkyl-cycloalkyl" is bonded to the parent molecular structure through the alkyl group. The terms "alkenyl-cycloalkyl" and "alkynyl-cycloalkyl" mirror the above description of "alkyl-cycloalkyl" wherein the term "alkyl" is replaced with "alkenyl" or "alkynyl" respectively, and "alkenyl" or "alkynyl" are as described herein.

"Alkylaryl" refers to an -(alkyl)aryl radical where aryl and alkyl are as disclosed herein and which are optionally substituted by one or more of the substituents described as suitable substituents for aryl and alkyl respectively. The "alkylaryl" is bonded to the parent molecular structure through the alkyl group. The terms "-(alkenyl)aryl" and "-(alkynyl)aryl" mirror the above description of "-(alkyl)aryl" wherein the term "alkyl" is replaced with "alkenyl" or "alkynyl" respectively, and "alkenyl" or "alkynyl" are as described herein.

"Alkyl-heteroaryl" refers to an -(alkyl)heteroaryl radical where heteroaryl and alkyl are as disclosed herein and which are optionally substituted by one or more of the substituents described as suitable substituents for heteroaryl and alkyl respectively. The "alkyl-heteroaryl" is bonded to the parent molecular structure through the alkyl group. The terms "-(alkenyl)heteroaryl" and "-(alkynyl)heteroaryl" mirror the above description of "-(alkyl) heteroaryl" wherein the term "alkyl" is replaced with "alkenyl" or "alkynyl" respectively, and "alkenyl" or "alkynyl" are as described herein.

"Alkyl-heterocyclyl" refers to an -(alkyl)heterocyclyl radical where alkyl and heterocyclyl are as disclosed herein and which are optionally substituted by one or more of the substituents described as suitable substituents for heterocyclyl and alkyl respectively. The "alkyl-heterocyclyl" is bonded to the parent molecular structure through the alkyl group. The terms "-(alkenyl)heterocycyl" and "-(alkynyl) heterocyclyl" mirror the above description of "-(alkyl)heterocyclyl" wherein the term "alkyl" is replaced with "alkenyl" or "alkynyl" respectively, and "alkenyl" or "alkynyl" are as described herein.

"Alkenyl" refers to a straight or branched hydrocarbon chain radical group consisting solely of carbon and hydrogen atoms, containing at least one double bond, and in some embodiments, having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, 4 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkynyl" refers to a straight or branched hydrocarbon chain radical group consisting solely of carbon and hydrogen atoms, containing at least one triple bond, having, in some embodiments, from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, 4 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_8$ alkynyl). The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$. —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkoxy" refers to the group —O-alkyl (in some embodiments, including from 1 to 10 carbon atoms), of a straight branched, cyclic configuration and combinations thereof, attached to the parent molecular structure through an oxygen. Examples include methoxy, ethoxy, propoxy, isopropoxy, cyclopropyloxy, cyclohexyloxy, and the like. "Lower alkoxy" refers to alkoxy groups containing one to six carbons. In some embodiments, $C_1$-$C_6$ alkoxy is an alkoxy group which encompasses both straight and branched chain alkyls of from 1 to 4 carbon atoms. Unless stated otherwise in the specification, an alkoxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$. —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "alkoxycarbonyl" refers to a group of the formula (alkoxy)(C=O)— attached to the parent molecular structure through the carbonyl carbon (in some embodiments, having from 1 to 10 carbon atoms). Thus a $C_1$-$C_8$ alkoxycarbonyl group comprises an alkoxy group having from 1 to 6 carbon atoms attached through its oxygen to a carbonyl linker. The $C_1$-$C_6$ designation does not include the carbonyl carbon in the atom count. "Lower alkoxycarbonyl" refers to an alkoxycarbonyl group wherein the alkyl portion of the alkoxy group is a lower alkyl group. In some embodiments, $C_1$-$C_4$ alkoxycarbonyl comprises an alkoxy group which encompasses both straight and branched chain alkoxy groups of from 1 to 4 carbon atoms. Unless stated otherwise in the specification, an alkoxycarbonyl group is optionally substituted by one or more substituents which independently include: acyl, alkyl, alkenyl, alkenyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R)$_3$, —OR$^a$, —SR$^a$, —OC(O)—R$^a$, —N(R$^1$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. The terms "alkenoxycarbonyl" and "alkynoxycarbonyl" mirror the above description of "alkoxycarbonyl" wherein the prefix "alk" is replaced with "alken" or "alkyn" respectively, and the parent "alkenyl" or "alkynyl" terms are as described herein.

"Acyl" refers to R—C(O)— groups such as, but not limited to, H, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, provided herein is a $C_1$-$C_{10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Acyloxy" refers to a R(C=O)O— radical wherein "R" can be H, alkyl, alkenyl, alkynyl, heteroalkyl, heteroalkenyl, heteroalkynyl, aryl, cyclohexyl, heteroaryl, or heterocycloalkyl, which are as described herein. The acyloxy group is attached to the parent molecular structure through the oxygen functionality. In some embodiments, an acyloxy group is a $C_1$-$C_4$ acyloxy radical which refers to the total number of chain or ring atoms of the alkyl, alkenyl, alkynyl, aryl, cyclohexyl, heteroaryl or heterocycloalkyl portion of the acyloxy group plus the carbonyl carbon of acyl, e.g., a $C_4$-acyloxy has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$. —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl and each of these moieties can be optionally substituted as defined herein.

"Amino" or "amine" refers to a —N(R$^b$)$_2$, —N(R$^b$)R$^b$—, or —R$^b$N(R$^b$)R$^b$— radical group, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. When a —N(R$^b$) group has two R$^b$ other than hydrogen, they can be combined with the nitrogen atom to form a 3-, 4-, 5-, 6-, 7-, or 8-membered ring. For example, —N(R$^b$)$_2$ is meant to include, but not be limited to, 1-pyrolidinyl and 4-morpholinyl. Unless stated otherwise in the specification, an amino group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2). —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

The terms "amine" and "amino" can also refer to N-oxides of the groups —N$^+$(H)(R$^a$)O$^-$, and —N$^+$(R)(R$^a$)O$^-$, where R$^a$ is as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NR$^b$C(O)R$^b$, where R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. In some embodiments, an amido or amide radical is a $C_1$-$C_4$ amido or amide radical, which includes the amide carbonyl in the total number of carbons in the radical. When a —C(O)N(R$^b$)$_2$ has two R$^b$ other than hydrogen, they can be combined with the nitrogen atom to form a 3-, 4-, 5-, 6-, 7-, or 8-membered ring. For example, N(R$^b$)$_2$ portion of a —C(O)N(R$^b$)$_2$ radical is meant to include, but not be limited to, 1-pyrrolidinyl and 4-morpholinyl. Unless stated otherwise in the specification, an amido R$^b$ group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2). —S(O)$_t$OR$^a$ (where t is 1 or 2), —S(O)$_1$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

The term "amide" or "amido" is inclusive of an amino acid or a peptide molecule. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis,* 4th Ed., John Wiley & Sons, New York, N.Y., 2006, which is incorporated herein by reference in its entirety.

"Amidino" refers to the $-C(=NR^b)N(R^b)_2$, $-N(R^b)-C(=NR^b)-R^b$, and $-N(R^b)-C(=NR^b)-$ radicals, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Aryl" refers to a radical with six to fourteen ring atoms (e.g., $C_6$-$C_{14}$ or $C_6$-$C_{10}$ aryl) which has at least one carbocyclic ring having a conjugated pi electron system which is aromatic (e.g., having 6, 10, or 14 π electrons shared in a cyclic array) (e.g., phenyl, fluorenyl, and naphthyl). In one embodiment, bivalent radicals formed from substituted benzene derivatives and having the free valences at ring atoms are named as substituted phenylene radicals. In other embodiments, bivalent radicals derived from univalent monocyclic or polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea. $-Si(R^a)_3$, $-OR^a$, $-SR^a$, $-OC(O)-R^a$, $-N(R^a)_2$, $-C(O)R^a$, $-C(O)OR^a$, $-OC(O)N(R^a)_2$, $-C(O)N(R^a)_2$, $-N(R^a)C(O)OR^a$, $-N(R)C(O)R^a$, $-N(R^a)C(O)N(R^a)_2$, $-N(R^a)C(NR^a)N(R^a)_2$, $-N(R^a)S(O)_tR^a$ (where t is 1 or 2), $-S(O)_tOR^a$ (where t is 1 or 2), $-S(O)_tN(R^a)_2$ (where t is 1 or 2), or $-O-P(=O)(OR^a)_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise. "aryl" also includes ring systems wherein the aryl ring, as defined above, is fused with one or more cycloalkyl or heterocyclyl groups wherein the point of attachment to the parent molecular structure is on the aryl ring.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively. The "aralkyl" or "arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as descried herein.

"Azide" refers to a $-N_3$ radical.

"Carbamate" refers to any of the following radicals: $-O-(C=O)-N(R^b)-$, $-O-(C=O)-N(R^b)_2$, $-N(R^b)-(C=O)-O-$, and $-N(R^b)-(C=O)-OR^b$, wherein each $R^b$ is independently selected from H, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Carbonate" refers to a $-O-(C=O)-O-$ or $-O-(C=O)-OR$ radical, where R can be hydrogen, alkyl, alkenyl, alkynyl, heteroalkyl, heteroalkenyl, heteroalkynyl, aryl, cyclohexyl, heteroaryl, or heterocycloalkyl, which are as described herein.

"Carbonyl" refers to a $-(C=O)-$ radical.

"Carboxaldehyde" refers to a $-(C=O)H$ radical.

"Carboxyl" refers to a $-(C=O)OH$ radical.

"Cyano" refers to a $-CN$ radical.

"Cycloalkyl," or alternatively, "carbocyclyl." refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl, and the like. Unless stated otherwise in the specification, a cycloalkyl group is optionally substituted by one or more substituents which independently include: aryl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR)N(R$^a$)$_2$, —N(R$^a$)S(O)$_t$R (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "cycloalkyl" or "carbocyclyl" also includes ring systems wherein the cycloalkyl or carbocyclyl ring, as defined above, is fused with one or more aryl or heteroaryl groups wherein the point of attachment to the parent molecular structure is on the cycloalkyl or carbocyclyl ring.

"Cycloalkyl-alkyl" refers to a -(cycloalkyl)alkyl radical where cycloalkyl and alkyl are as disclosed herein and which are optionally substituted by one or more of the substituents described as suitable substituents for cycloalkyl and alkyl respectively. The "cycloalkyl-alkyl" is bonded to the parent molecular structure through the cycloalkyl group. The terms "cycloalkyl-alkenyl" and "cycloalkyl-alkynyl" mirror the above description of "cycloalkyl-alkyl" wherein the term "alkyl" is replaced with "alkenyl" or "alkynyl" respectively, and "alkenyl" or "alkynyl" are as described herein.

"Cycloalkyl-heterocycloalkyl" refers to a -(cycloalkyl)heterocyclylalkyl radical where cycloalkyl and heterocycloalkyl are as disclosed herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for heteroaryl and cycloalkyl respectively. The "cycloalkyl-heteroaryl" is bonded to the parent molecular structure through the cycloalkyl group.

As used herein, a "covalent bond" or "direct bond" refers to a single bond joining two groups.

"Ester" refers to a radical of formula —COOR, where R is selected from alkyl, alkenyl, alkynyl, haloalkyl, heteroalkyl (bonded through a chain carbon), cycloalkyl, cycloalkylalkyl, aryl, alkyl, heterocycloalkyl (bonded through a ring carbon), heterocyclolkylalalkyl, heteroaryl (bonded through a ring carbon), and heteroarylalkyl. Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis*, 4th Ed., John Wiley & Sons, New York, N.Y., 2006, which is incorporated herein by reference in its entirely. Unless stated otherwise in the specification, an ester group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR)N(R$^a$)$_2$, —N(R$^a$)S(O)$_t$R$^a$ (where t is 1 or 2), —S(O)$_t$OR$^a$ (where t is 1 or 2). —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Ether" refers to a —R$^b$—OR$^b$ radical where each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Halo", "halide", or, alternatively. "halogen" means fluoro, chloro, bromo, or iodo. The terms "haloalkyl." "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, and phosphorus, or combinations thereof. A numerical range can be given, e.g., $C_1$-$C_4$ heteroalkyl which refers to the chain length in total, which in this example can be up to 4 atoms long. For example, a —CH$_2$OCH$_2$CH$_3$ radical is referred to as a "C$_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_1$), (methoxymethoxy)ethanyl (—CH$_2$CH$_2$—OCH$_2$OCH$_3$), (methoxymethoxy)methanyl (—CH$_2$OCH$_2$OCH$_3$), and (methoxyethoxy)methanyl (—CH$_2$OCH$_2$CH$_2$OCH$_3$), and the like; amines such as —CH$_2$CH$_2$NHCH$_3$. —CH$_2$CH$_2$N(CH$_3$)$_2$, —CH$_2$NHCH$_2$CH$_3$, —CH$_2$N(CH$_2$CH$_3$)(CH$_3$), and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heteroalkyl-aryl" refers to a -(heteroalkyl)aryl radical where heteroalkyl and aryl are as disclosed herein and which are optionally substituted by one or more of the substituents described as suitable substituents for heteroalkyl and aryl respectively. The "heteroalkyl-aryl" is bonded to the parent molecular structure through an atom of the heteroalkyl group.

"Heteroalkyl-heteroaryl" refers to a -(heteroalkyl)heteroaryl radical where heteroalkyl and heteroaryl are as disclosed herein and which are optionally substituted by one or more of the substituents described as suitable substituents for heteroalkyl and heteroaryl respectively. The "heteroalkyl-heteroaryl" is bonded to the parent molecular structure through an atom of the heteroalkyl group.

"Heteroalkyl-heterocycloalkyl" refers to a -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl respectively. The "heteroalkyl-heterocycloalkyl" is bonded to the parent molecular structure through an atom of the heteroalkyl group.

"Heteroalkyl-cycloalkyl" refers to a -(heteroalkyl)cycloalkyl radical where heteroalkyl and cycloalkyl are as disclosed herein and which are optionally substituted by one or more of the substituents described as suitable substituents for heteroalkyl and cycloalkyl respectively. The "heteroalkyl-cycloalkyl" is bonded to the parent molecular structure through an atom of the heteroalkyl group.

"Heteroaryl", or alternatively, "heteroaromatic", refers to a radical of a 5- to 18-membered monocyclic or polycyclic (e.g., bicyclic or tricyclic) aromatic ring system (e.g., having 6, 10 or 14 π electrons shared in a cyclic array) having ring carbon atoms and 1 to 6 ring heteroatoms provided in the aromatic ring system, wherein each heteroatom is independently selected from nitrogen, oxygen, phosphorous, and sulfur ("5- to 18-membered heteroaryl"). Heteroaryl polycyclic ring systems can include one or more heteroatoms in one or more rings. Whenever it appears herein, a numerical range such as "5 to 18" refers to each integer in the given range; e.g., "5 to 18 ring atoms" means that the heteroaryl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either the ring bearing a heteroatom (e.g., 2-indolyl) or the ring that does not contain a heteroatom (e.g., 5-indolyl). In some embodiments, a heteroaryl group is a 5 to 10 membered aromatic ring system having ring carbon atoms and 1 to 4 ring heteroatoms provided in the aromatic ring system, wherein each heteroatom is independently selected from nitrogen, oxygen, phosphorous, and sulfur ("5- to 10-membered heteroaryl"). In some embodiments, a heteroaryl group is a 5- to 8-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 8-membered heteroaryl"). In some embodiments, a heteroaryl group is a 5- to 6-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 6-membered heteroaryl"). In some embodiments, the 5- to 6-membered heteroaryl has 1 to 3 ring heteroatoms independently selected from nitrogen, oxygen, phosphorous, and sulfur. In some embodiments, the 5- to 6-membered heteroaryl has 1 to 2 ring heteroatoms independently selected from nitrogen, oxygen, phosphorous, and sulfur. In some embodiments, the 5- to 6-membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, cabazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6.7]cyclohepta[1,2-c]pyridazinyl, dibenzofuranyl, dibenzothiophenyl, furanyl, furazanyl, furanonyl, furo[3,2-c]pyridinyl 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinoyl, oxadiazolyl, 2-oxoazepinyl, oxazolyl, oxiranyl, 5,6,6a,7,8,9,10,10a-octahdrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl).

Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen alkyl, haloalkyl, carbocyclyl, carbocyclylalkyl, aryl, aralkyl, heterocycloalkyl, heterocycloalkylalkyl heteroaryl, or heteroarylalkyl, and each of these moieties can be optionally substituted as defined herein.

"Heteroaryl-alkyl" refers to a -(heteroaryl)alkyl radical where heteroaryl and alkyl are as disclosed herein and which are optionally substituted by one or more of the substituents described as suitable substituents for heteroaryl and alkyl respectively. The "heteroaryl-alkyl" is bonded to the parent molecular structure through any atom of the heteroaryl group.

"Heteroaryl-heterocycloalkyl" refers to an -(heteroaryl)heterocycloalkyl radical where heteroaryl and heterocycloalkyl are as disclosed herein and which are optionally substituted by one or more of the substituents described as suitable substituents for heteroaryl and heterocycloalkyl respectively. The "heteroaryl-heterocycloalkyl" is bonded to the parent molecular structure through an atom of the heteroaryl group.

"Heteroaryl-cycloalkyl" refers to an -(heteroaryl)cycloalkyl radical where heteroaryl and cycloalkyl are as disclosed herein and which are optionally substituted by one or more of the substituents described as suitable substituents for heteroaryl and cycloalkyl respectively. The "heteroaryl-cycloalkyl" is bonded to the parent molecular structure through a carbon atom of the heteroaryl group.

"Heterocyclyl", "heterocycloalkyl" or "heterocarbocyclyl" each refer to any 3- to 18-membered non-aromatic radical monocyclic or polycyclic moiety comprising at least one ring heteroatom selected from nitrogen, oxygen, phosphorous, and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or more rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heterocyclyl radicals whose names end in "-yl" by removal of one hydrogen atom from the atom with the free valence are named by adding "-idene" to the name of the corresponding univalent radical, e.g., a piperidyl group with two points of attachment is a piperidylidene.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3- to 10-membered non-aromatic ring system having ring carbon atoms and 1 to 4 ring heteroatoms, wherein each heteroatom is independently selected from nitrogen, oxygen, phosphorous, and sulfur ("3- to 10-membered heterocyclyl"). In some embodiments, a heterocyclyl group is a 5- to 8-membered non-aromatic ring system having ring carbon atoms and 1 to 4 ring heteroatoms, wherein each heteroatom is independently selected from nitrogen, oxygen, phosphorous, and sulfur ("5- to 8-membered heterocyclyl"). In some embodiments, a heterocyclyl group is a 5- to 6-membered non-aromatic ring system having ring carbon atoms and 1 to 4 ring heteroatoms, wherein each heteroatom is independently selected from nitrogen, oxygen, phosphorous, and sulfur ("5- to 6-membered heterocyclyl"). In some embodiments, the 5- to 6-membered heterocyclyl has 1 to 3 ring heteroatoms independently selected from nitrogen, oxygen, phosphorous, and sulfur. In some embodiments, the 5- to 6-membered heterocyclyl has 1 to 2 ring heteroatoms independently selected from nitrogen, oxygen, phosphorous, and sulfur. In some embodiments, the 5- to 6-membered heterocyclyl has 1 ring heteroatom selected from nitrogen, oxygen, phosphorous, and sulfur.

Exemplary 3-membered heterocyclyls containing 1 heteroatom include, without limitation, aziridinyl, oxiranyl, thiorenyl. Exemplary 4-membered heterocyclyls containing 1 heteroatom include, without limitation azetidinyl, oxetanyl and thietanyl. Exemplary 5-membered heterocyclyls containing 1 heteroatom include, without limitation tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation triazolinyl, oxadiazolinyl, and thiadiazolinyl, Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and thiazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$), —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heterocyclyl-alkyl" refers to a -(heterocyclyl)alkyl radical where heterocyclyl and alkyl are as disclosed herein and which are optionally substituted by one or more of the substituents described as suitable substituents for heterocyclyl and alkyl respectively. The "heterocyclyl-alkyl" is bonded to the parent molecular structure through any atom of the heterocyclyl group. The terms "heterocyclyl-alkenyl" and "heterocyclyl-alkynyl" mirror the above description of "heterocyclyl-alkyl" wherein the term "alkyl" is replaced with "alkenyl" or "alkynyl" respectively, and "alkenyl" or "alkynyl" are as described herein.

"Imino" refers to the "—C(=N—$R^b$)—$R^b$" radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphate" refers to a —O—P(=O)(O$R^b$)$_2$ radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Phosphonate" refers to a —O—P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) and heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Phosphinate" refers to a —P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

A "leaving group or atom" is any group or atom that will, under the reaction conditions, cleave from the starting material, thus promoting reaction at a specified site. Suitable non-limiting examples of such groups, unless otherwise specified, include halogen atoms, mesyloxy, p-nitrobenzensulphonyloxy, trifluoromethyloxy, and tosyloxy groups.

"Protecting group" has the meaning conventionally associated with it in organic synthesis, e.g., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Fourth Edition, John Wiley & Sons, New York (2006), incorporated herein by reference in its entirety. For example, a hydroxy protected form is where at least one of the hydroxy groups present in a compound is protected with a hydroxy protecting group. Likewise, amines and other reactive groups can similarly be protected.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents can include one or more group(s) individually and independently selected from acyl, alkyl, alkenyl, alkynyl, alkoxy, alkylaryl, cycloalkyl, aralkyl, aryl, aryloxy, amino, amido, azide, carbonate, carbonyl, heteroalkyl, heteroaryl, heteroarylalkyl, heterocycloalkyl, hydroxy, cyano, halo, haloalkoxy, haloalkyl ester, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$^2$, —N(R$^a$)C(O)OR$^a$, —N(R$^a$)C(O)R$^a$, —N(R$^a$)C(O)N(R$^a$)$_2$, —N(R$^a$)C(NR$^a$)N(R)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), and —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

"Silyl" refers to a —Si(R$^b$)$_3$ radical where each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Sulfanyl", "sulfide", and "thio" each refer to the radical —S—R$^b$, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. For instance, an "alkylthio" refers to the "alkyl-S—" radical, and "arylthio" refers to the "aryl-S—" radical, each of which are bound to the parent molecular group through the S atom. The terms "sulfide". "thiol". "mercapto", and "mercaptan" can also each refer to the group —R$^b$SH.

"Sulfinyl" or "sulfoxide" refers to the —S(O)—R$^b$ radical, wherein for "sulfinyl", R$^b$ is H, and for "sulfoxide", R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Sulfonyl" or "sulfone" refers to the —S(O$_2$)—R$^b$ radical, wherein R$^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Sulfonamidyl" or "sulfonamido" refers to the following radicals: —S(=O)$_2$—N(R)$_2$, —N(R$^b$)—S(=O)$_2$—R$^b$, —S(=O)$_2$—N(R$^b$)—, or —N(R$^b$)—S(=O)$_2$—, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein. The R$^b$ groups in —S(=O)$_2$—N(R$^b$)$_2$ or —N(R$^b$)—S(=O)$_2$—R$^b$ can be taken together with the nitrogen to which they are attached to form a 4-, 5-, 6-, 7-, or 8-membered heterocyclyl ring. In some embodiments, the term designates a $C_1$-$C_4$ sulfonamido, wherein each R$^b$ in the sulfonamido contains 1 carbon, 2 carbons, 3 carbons, or 4 carbons total.

"Sulfoxyl" refers to a —S(=O)$_2$OH radical.

"Sulfonate" refers to a —S(=O)$_2$—OR$^b$ radical, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

"Thiocarbonyl" refers to a —(C=S)— radical.

"Urea" refers to a —N(R$^b$)—(C=O)—N(R$^b$)$_2$ or —N(R$^b$)(C=O)—N(R$^b$)— radical, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon), and heteroarylalkyl, unless stated otherwise in the specification, each of which moiety can itself be optionally substituted as described herein.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds

Provided herein are compounds of Formula I' or Formula II':

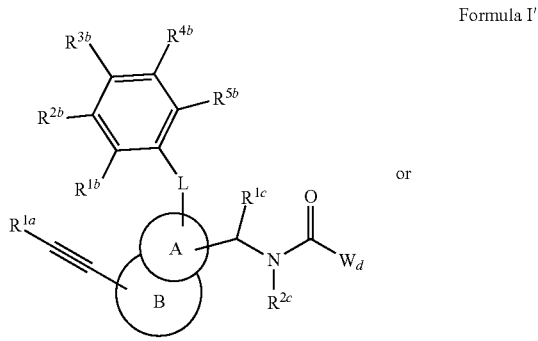

Formula I' or

-continued

Formula II'

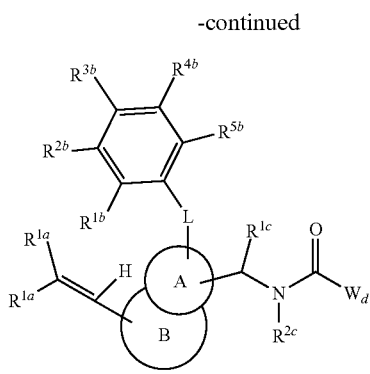

or a pharmaceutically acceptable form thereof.
wherein

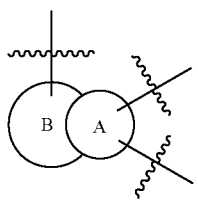

is a (5-14 membered fused bicyclic saturated, unsaturated, or aromatic heterocycle containing one or more heteroatoms selected from the group consisting of N, O, and S) or (5-14 membered fused bicyclic saturated, unsaturated, or aromatic carbocycle); wherein the heterocycle or carbocycle is optionally substituted with one or more substituents selected from $R^{2a}$, $R^{3a}$, $R^{4a}$, $R^{6a}$, $(R^{5a})_n$, and $R^{1d}$; n is 1, 2, or 3;
L is a bond or —$NR^{1e}$;
$W_d$ is a (3-14 membered saturated, unsaturated, or aromatic carbocycle) or a (3-14 membered saturated, unsaturated or aromatic heterocycle containing one or more heteroatoms selected from the group consisting of N, O, and S); wherein the carbocycle or heterocycle is optionally substituted with $R^{1f}$, $R^{2f}$, $R^{3f}$, $R^{4f}$, and $R^{5f}$; each instance of $R^{1a}$ is independently selected from the group consisting of hydrogen, $C_1$-$C_8$ alkyl, $C_2$-$C_8$ alkenyl, $C_2$-$C_8$ alkynyl, OH, $OR^{10}$, $NH_2$, $NHR^{10}$, $NR^{10}R^{10}$, $NR^{10}COR^{10}$, COH, $C(O)R^{10}$, COOH, $COOR^{10}$, $CONH_2$, $CONHR^{10}$, $CONR^{10}R^{10}$, CN, halo, $NO_2$, haloalkyl, (3-14 membered saturated, unsaturated, or aromatic carbocycle), and (3-14 membered saturated, unsaturated, or aromatic heterocycle containing one or more heteroatoms selected from the group consisting of N, O, and S); wherein each of alkyl, alkenyl, alkynyl, haloalkyl, carbocycle, or heterocycle is optionally substituted with one or more $R^{11}$;
each instance of $R^{10}$ is independently selected from the group consisting of hydrogen, $C_1$-$C_8$ alkyl, $C_2$-$C_8$ alkenyl, $C_2$-$C_8$ alkynyl, halo, OH, $O(C_1$-$C_8$ alkyl), $NH_2$, $NH(C_1$-$C_8$ alkyl), $N(C_1$-$C_8$ alkyl)$_2$, haloalkyl CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl). $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected front the group consisting of N, O, and S):
each instance of $R^{11}$ is independently selected from the group consisting of hydrogen, $C_1$-$C_8$ alkyl, $C_2$-$C_8$ alkenyl, $C_2$-$C_8$ alkynyl, halo, OH, $O(C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S): each instance of $R^{2a}$, $R^{3a}$, $R^{4a}$, $R^{5a}$, and $R^{6a}$ is independently selected from the group consisting of hydrogen, $C_1$-$C_8$ alkyl, $C_2$-$C_8$ alkenyl, $C_2$-$C_8$ alkynyl, halo, oxo, OH, $O(C_1$-$C_8$ alkyl), $OCF_3$, $OCF_2H$, $OCFH_2$, $NH_2$, $NH(C_1$-$C_8$ alkyl). $N(C_1$-$C_8$ alkyl), haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl). COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);
$R^{1b}$, $R^{2b}$, $R^{3b}$, $R^{4b}$, and $R^{5b}$ each is independently selected from the group consisting of hydrogen, $C_1$-$C_8$ alkyl, $C_2$-$C_8$ alkenyl, $C_2$-$C_8$ alkynyl, halo, OH, $O(C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), CON $(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);
$R^{1c}$ is selected from the group consisting of hydrogen, $C_1$-$C_8$ alkyl, $C_2$-$C_8$ alkenyl, $C_2$-$C_8$ alkynyl, halo, OH. $O(C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);
$R^{2c}$ is selected from the group consisting of hydrogen, $C_1$-$C_8$ alkyl, $C_2$-$C_8$ alkenyl, $C_2$-$C_8$ alkynyl, halo, OH, $O(C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S); and
$R^{1d}$ is selected from the group consisting of hydrogen $C_1$-$C_8$ alkyl, $C_2$-$C_8$ alkenyl, and $C_2$-$C_8$ alkynyl;
$R^{1e}$ is selected from the group consisting of hydrogen, $C_1$-$C_8$ alkyl, $C_2$-$C_8$ alkenyl, and $C_2$-$C_8$ alkynyl;
$R^{1f}$ is selected from the group consisting of $NH_2$, $NH(C_1$-$C_8$ alkyl), $N(C_1$-$C_8$ alkyl)$_2$, hydrogen, $C_1$-$C_8$ alkyl, $C_2$-$C_8$ alkenyl, $C_2$-$C_8$ alkynyl, halo, OH, $O(C_1$-$C_8$ alkyl), $OCF_3$, $OCF_2H$, $OCFH_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);

$R^{2f}$, $R^{3f}$, $R^{4f}$, and $R^{5f}$ each is independently selected from the group consisting of hydrogen, $C_1$-$C_8$ alkyl, $C_2$-$C_8$ alkenyl, $C_2$-$C_8$ alkynyl, halo, OH. $O(C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);

provided

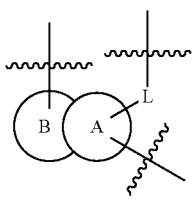

is not

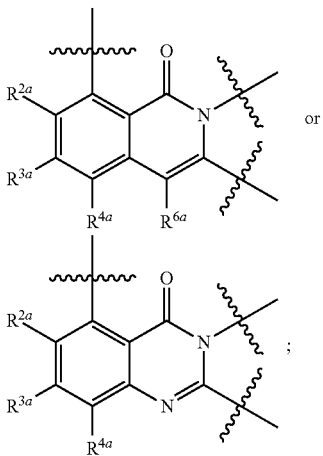

and provided the compound is not

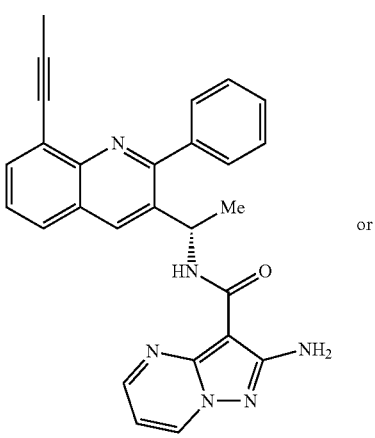

or

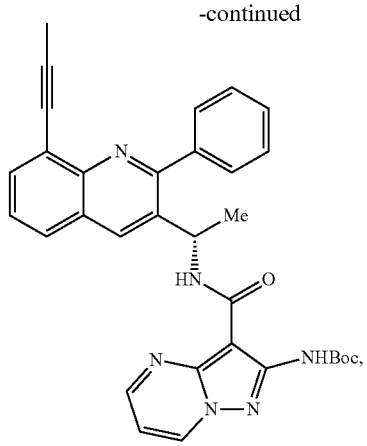

or an enantiomer, a mixture of enantiomers thereof.

In one embodiment, provided herein is a compound of Formula I':

Formula I'

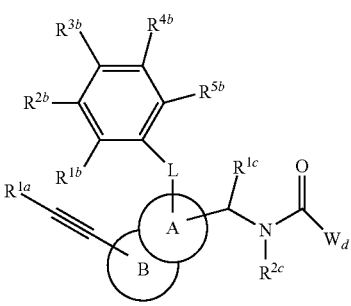

or a pharmaceutically acceptable form thereof.

In one embodiment, provided herein is a compound of Formula II':

Formula II'

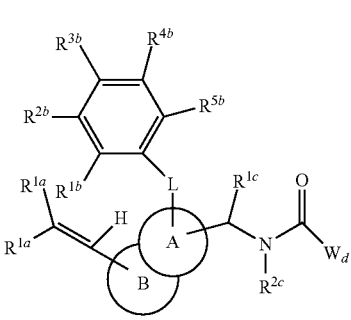

or a pharmaceutically acceptable form thereof.

In one embodiment, $W_d$ is

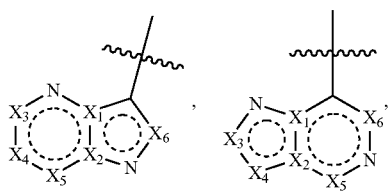

-continued

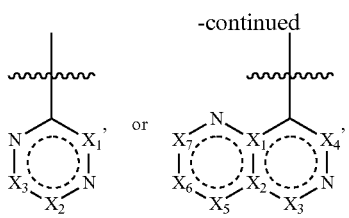

$X_1$, $X_2$, $X_3$, $X_4$, $X_5$, $X_6$, and $X_7$ are each independently C, N, S, or O, wherein each of C and N is optionally substituted with $R^{1f}$, $R^{2f}$, $R^{3f}$, $R^{4f}$ and $R^{5f}$.

In one embodiment, $W^d$ is

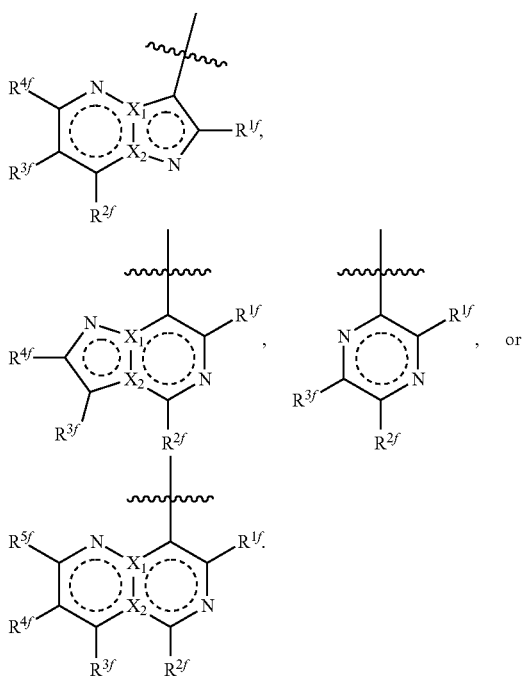

In certain embodiments, $W^d$ is

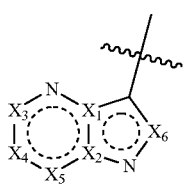

wherein $X_1$, $X_2$, $X_3$, $X_4$, $X_5$, and $X_6$ are as defined herein.

In certain embodiments. $W^d$ is

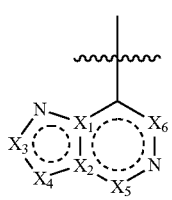

wherein $X_1$, $X_2$, $X_3$, $X_4$, $X_5$, and $X_6$ are as defined herein.

In certain embodiments, $W^d$ is

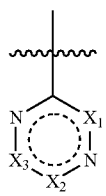

wherein $X_1$, $X_2$, and $X_3$ are as defined herein.

In certain embodiments, $W^d$ is

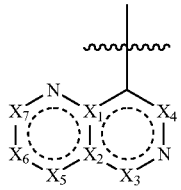

wherein $X_1$, $X_2$, $X_3$, $X_4$, $X_5$, $X_6$, and $X_7$ are as defined herein.

In some embodiments, $W^d$ is

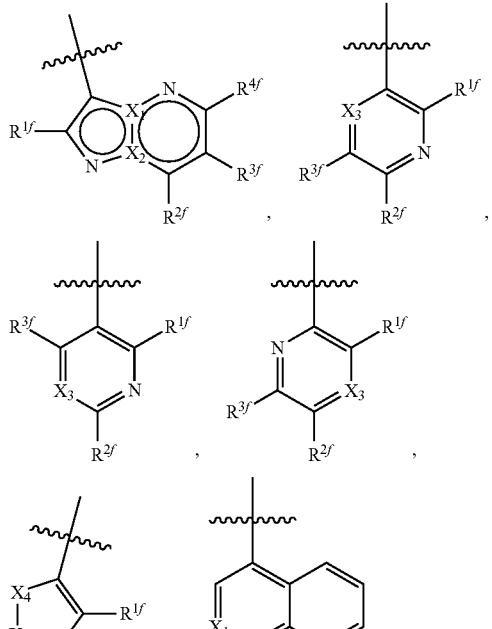

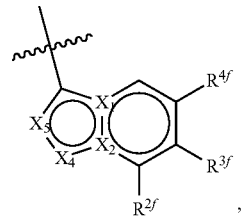

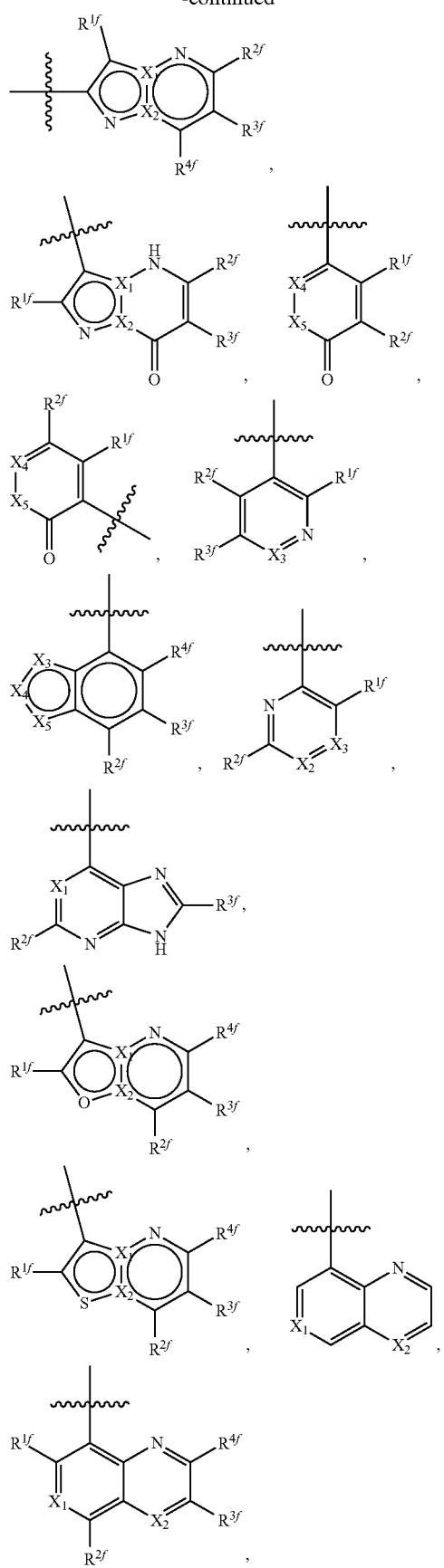
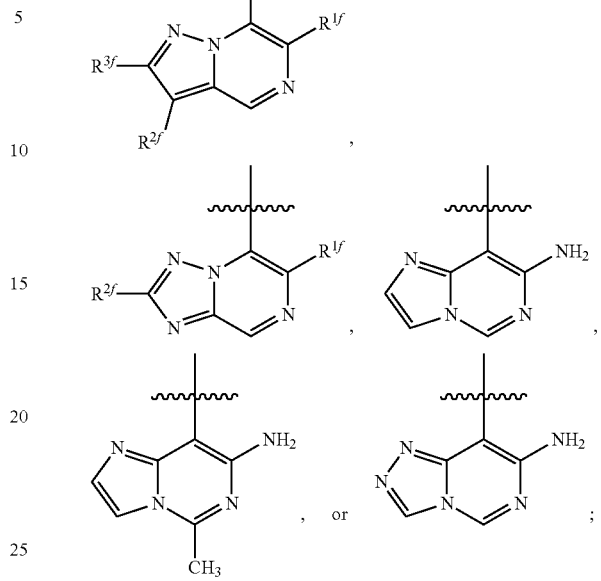
wherein
$X_1$, $X_2$, $X_3$, $X_4$, $X_5$, $X_6$, $R^{1f}$, $R^{2f}$, $R^{3f}$, and $R^{4f}$ are as defined herein.
In exemplary embodiments. $W_d$ is one of the following moieties:
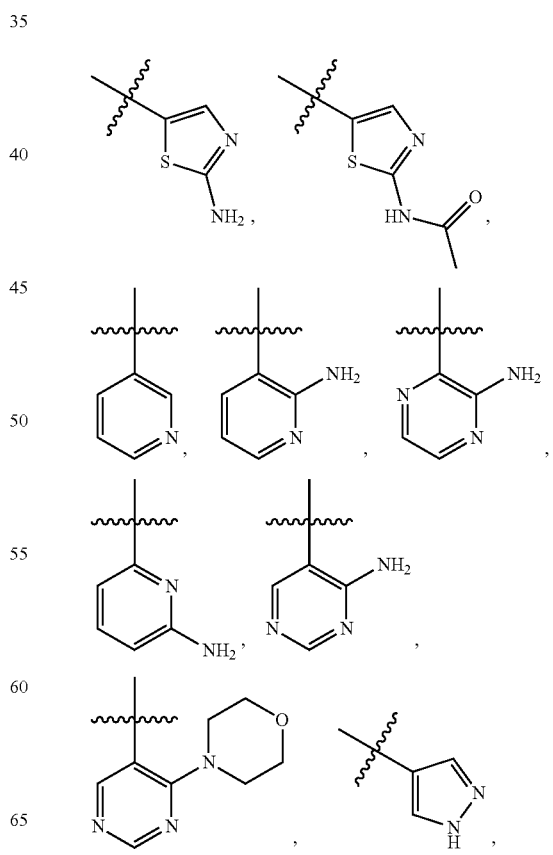

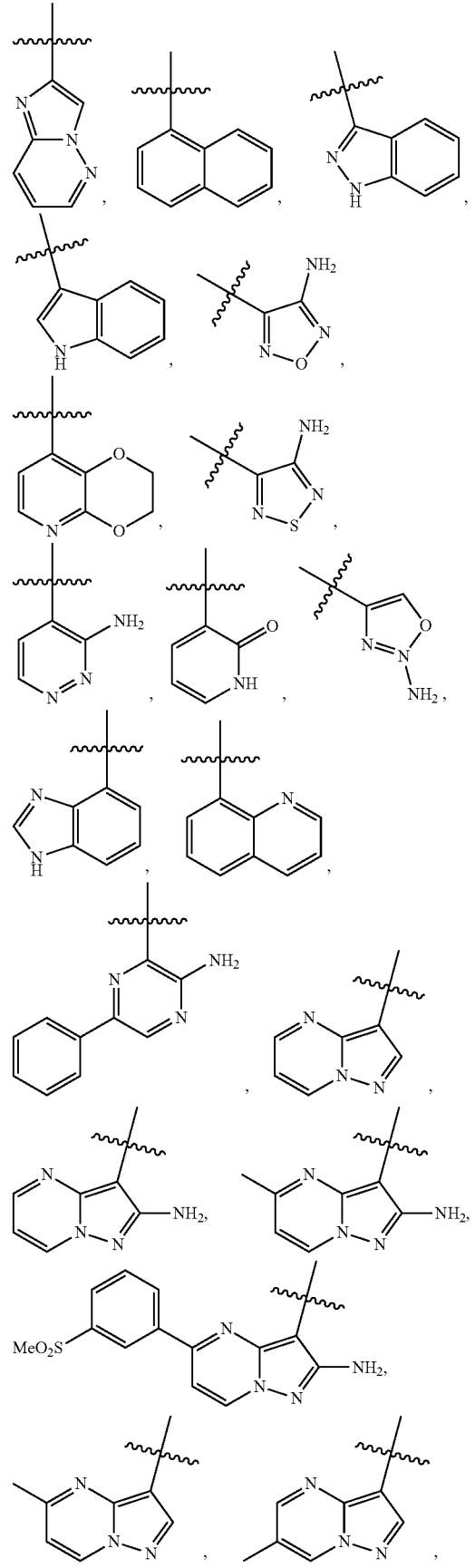

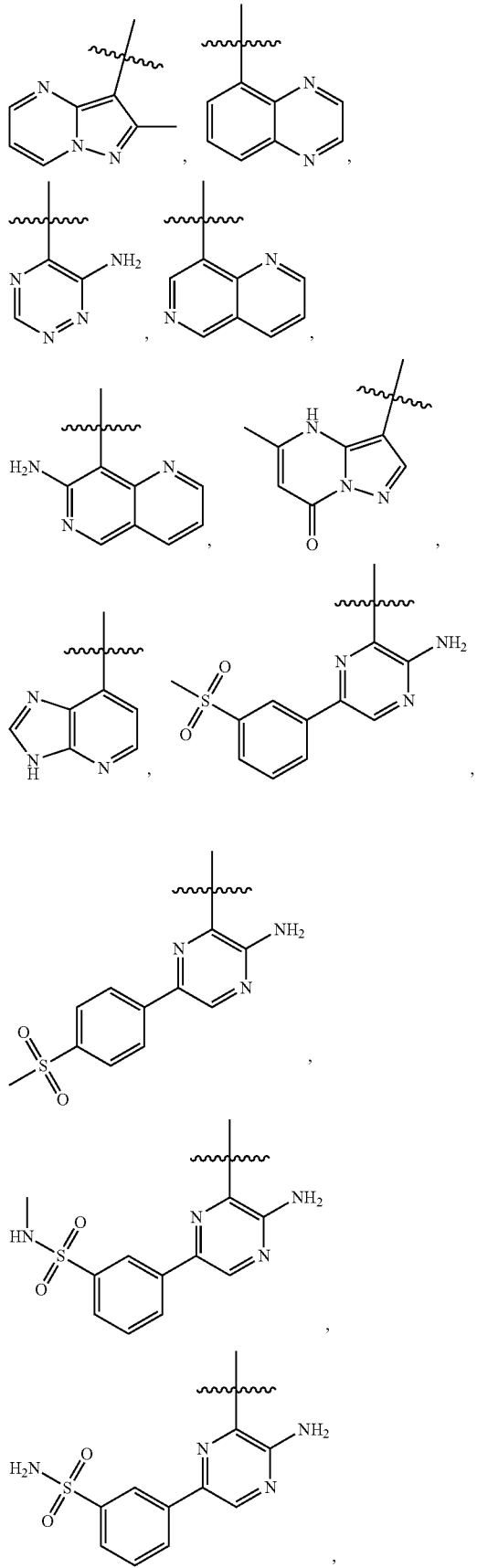
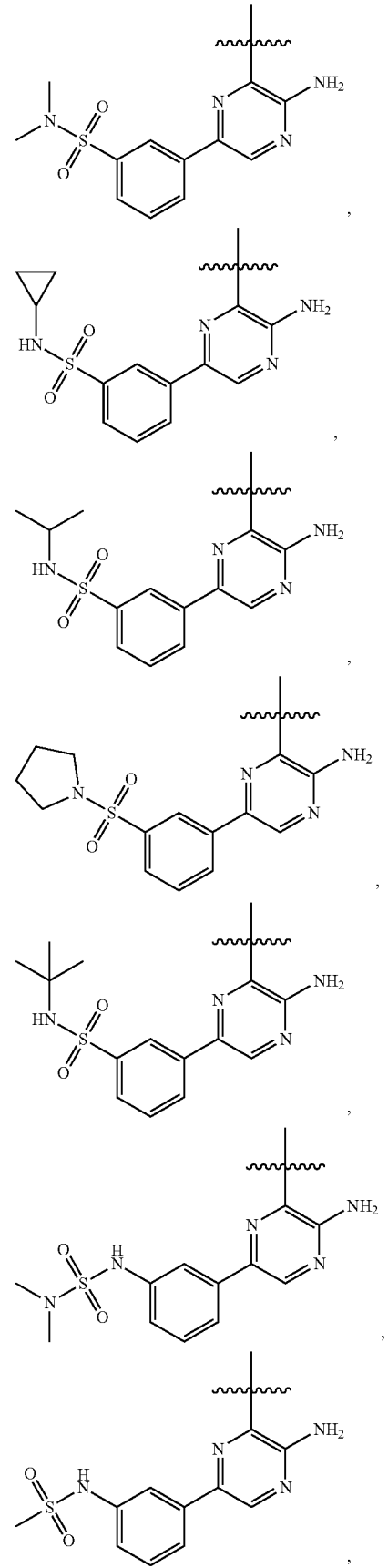

-continued
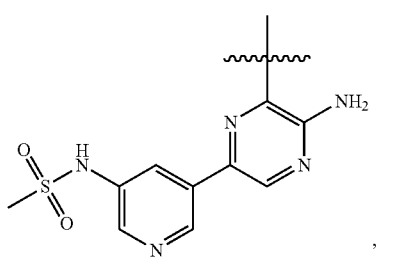
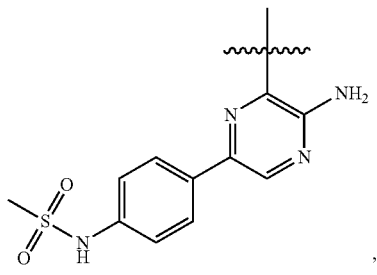
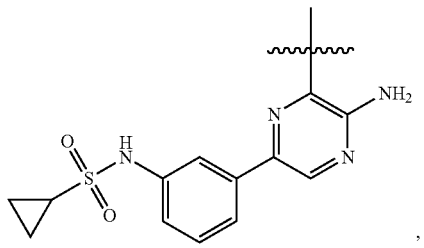
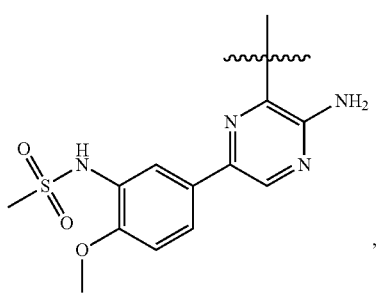
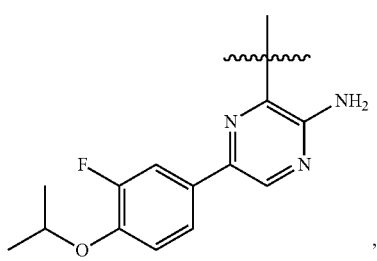
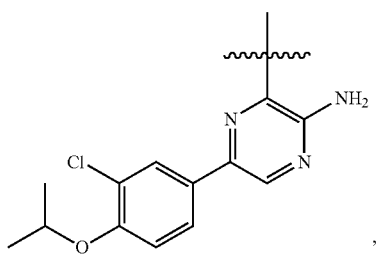
-continued
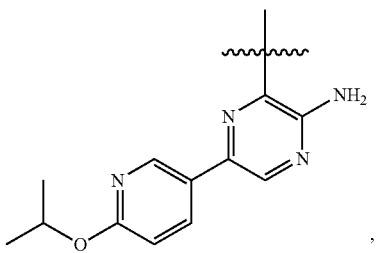
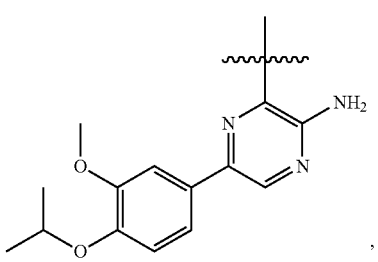
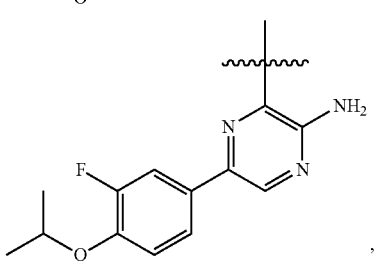
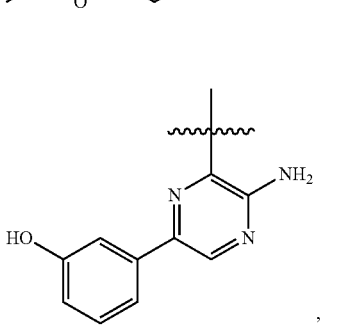
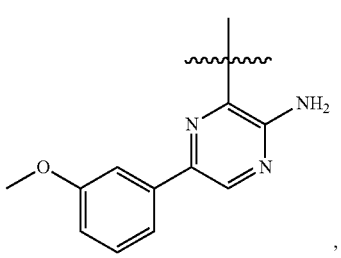
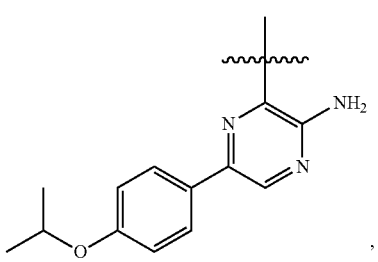

-continued
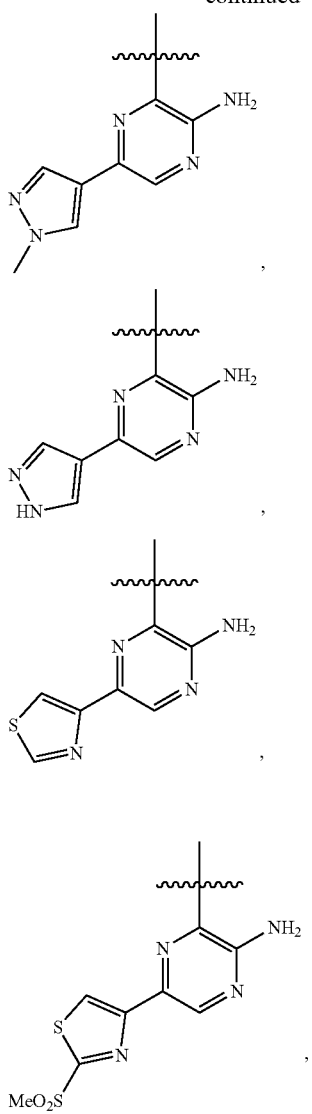
wherein $R^{2f}$ is as defined herein.
In one embodiment, $W^d$ is
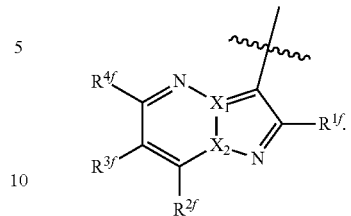
In one embodiment, $W_d$ is
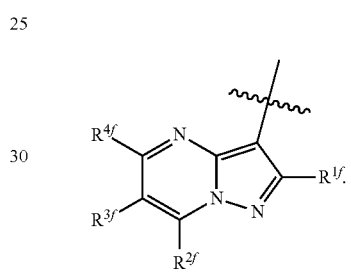
In one embodiment, the compound of Formula I' is a compound of formula I:
Formula I
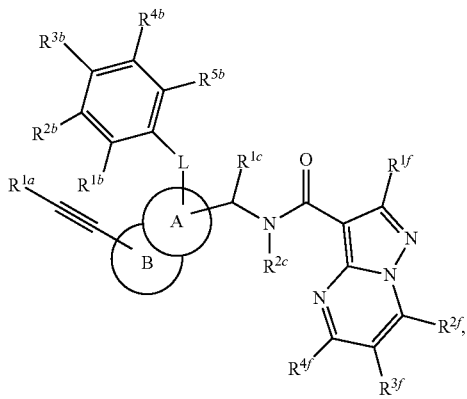
or a pharmaceutically acceptable form thereof.
In one embodiment, the compound of Formula II' is a compound of formula II:

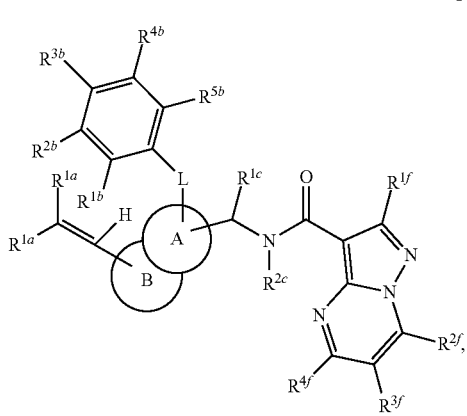

Formula II

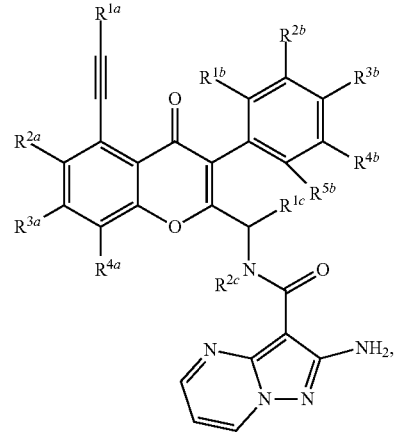

Formula A1 or a pharmaceutically acceptable form thereof.

In one embodiment, $R^{1f}$ is $NH_2$, $NH(C_1-C_8$ alkyl), or $N(C_1-C_8$ alkyl$)_2$. In one embodiment, $R^{1f}$ is $NH_2$. In one embodiment, $R^{2d}$, $R^{3f}$, and $R^{4f}$ each is independently selected from the group consisting of hydrogen, $C_1-C_8$ alkyl, $C_2-C_8$ alkenyl, $C_2-C_8$ alkynyl, halo, OH, $O(C_1-C_8$ alkyl), $OCF_3$, $OCF_2H$, $OCFH_2$, $NH_2$, $NH(C_1-C_8$ alkyl), $N(C_1-C_8$ alkyl), haloalkyl, CN, $NO_2$, $CONH_2$, $CONH(C_1-C_8$ alkyl), $CON(C_1-C_8$ alkyl$)_2$, COH, $CO(C_1-C_8$ alkyl), COOH, COO $(C_1-C_8$ alkyl), $NHCO(C_1-C_8$ alkyl), and $N(C_1-C_8$ alkyl)CO $(C_1-C_8$ alkyl). In one embodiment, $R^{2f}$, $R^{3f}$, and $R^{4f}$ each is independently hydrogen, $C_1-C_8$ alkyl, $C_2-C_8$ alkenyl, or $C_2-C_8$ alkynyl. In one embodiment, $R^{2f}$, $R^{3f}$, and $R^{4f}$ are hydrogen.

In one embodiment,

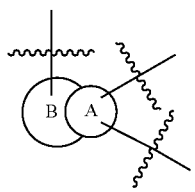

Formula A2

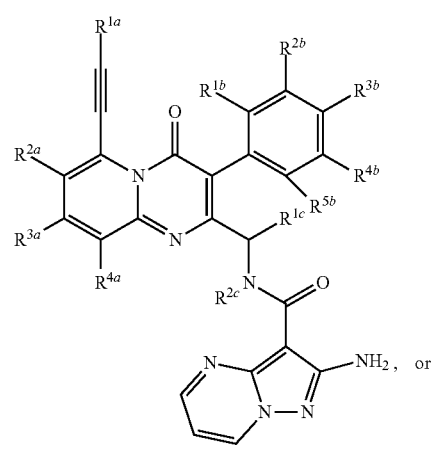

, or is a (8-10 membered fused bicyclic saturated, unsaturated, or aromatic heterocycle containing one or more heteroatoms selected from the group consisting of N, O, and S) or (8-10 membered fused bicyclic saturated, unsaturated, or aromatic carbocycle).

In one embodiment, A is 6-membered heterocycle or carbocycle and B is 6-membered heterocycle or carbocycle. In one embodiment, A is 6-membered heterocycle and B is 6-membered carbocycle. In one embodiment, A is 6-membered heterocycle and B is 6-membered heterocycle.

In one embodiment, the compound of Formula I' is a compound of the formula:

Formula A3

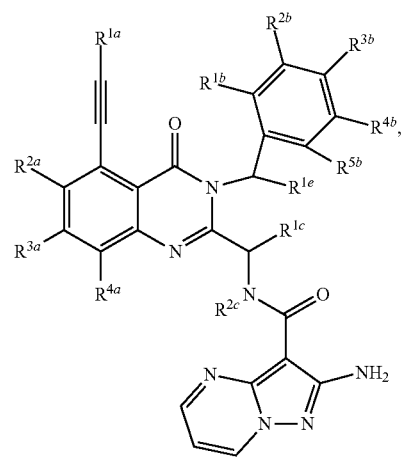

or a pharmaceutically acceptable form thereof.

In one embodiment, the compound of Formula I' is a compound of the formula:

Formula A1S
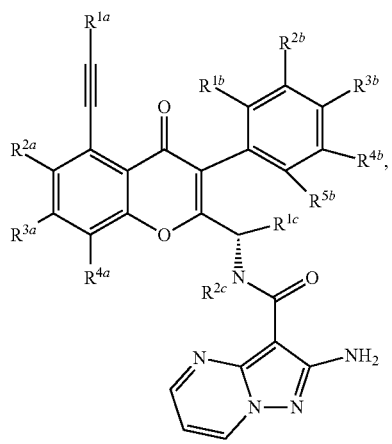
Formula A1R
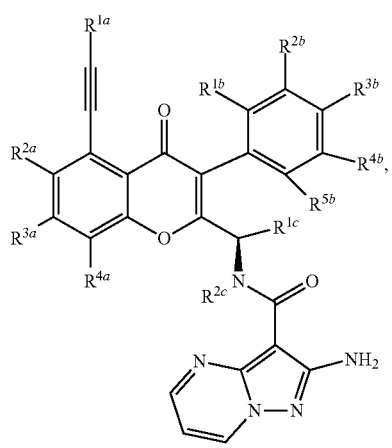
Formula A2S
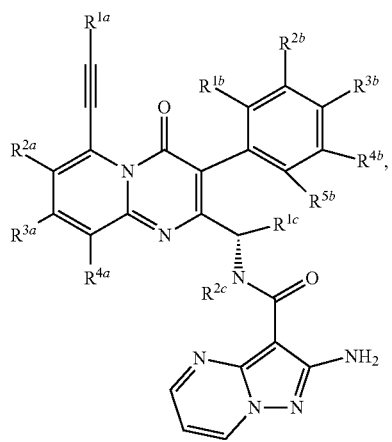
Formula A2R
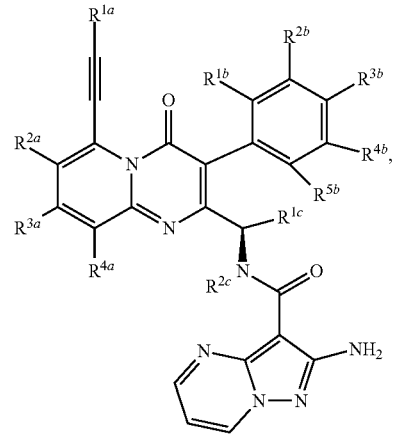
Formula A3S
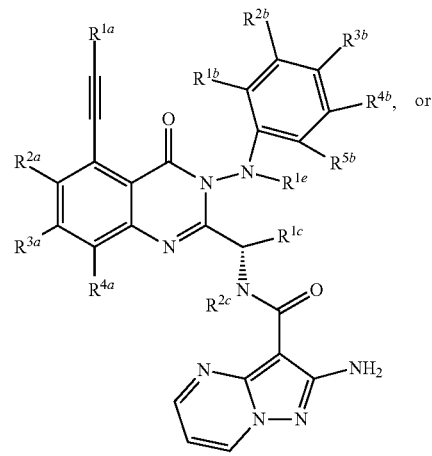
Formula A3R, or
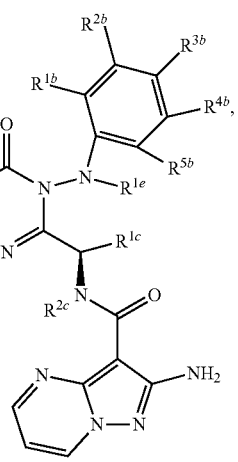
or a pharmaceutically acceptable form thereof.
In one embodiment, the compound of Formula II' is a compound of the formula:

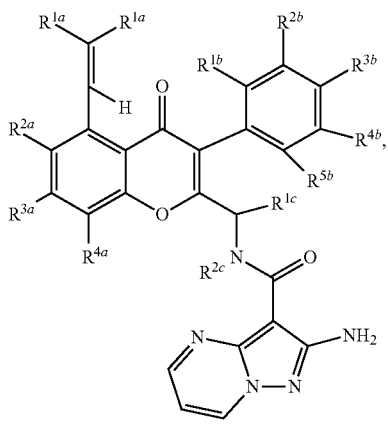
Formula A4
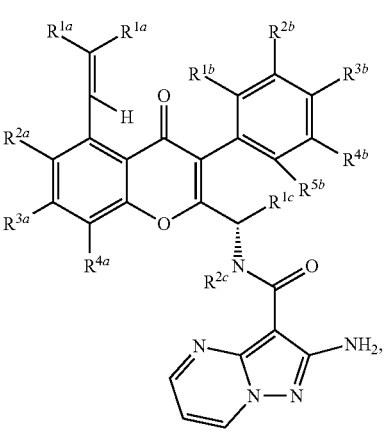
Formula A4S
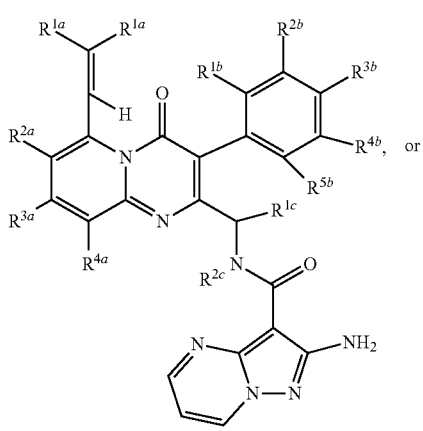
Formula A5
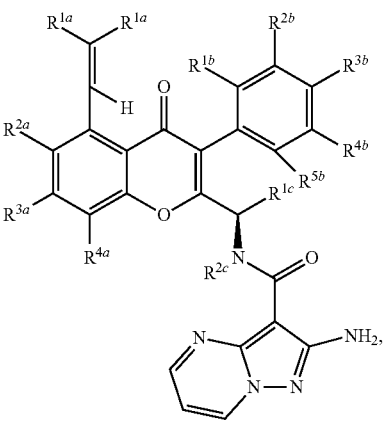
Formula A4R
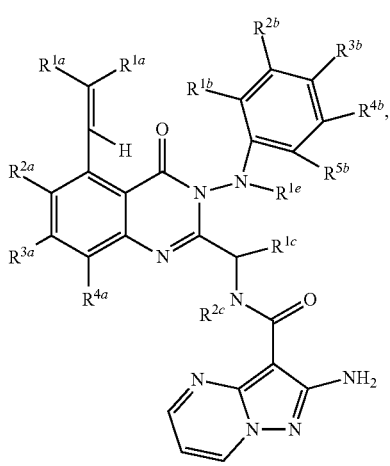
Formula A6
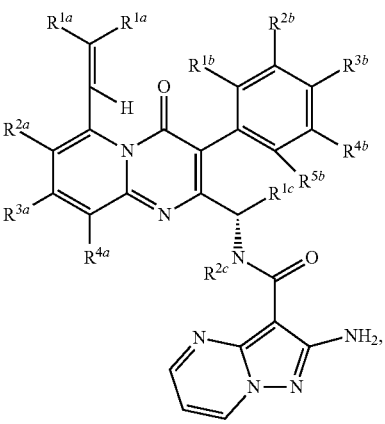
Formula A5S
or a pharmaceutically acceptable form thereof.
In one embodiment, the compound of Formula I' is a compound of the formula:

Formula A5R

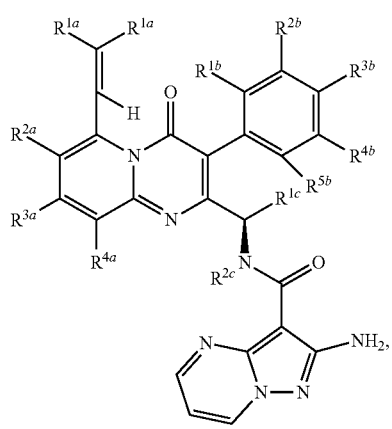

Formula A6S

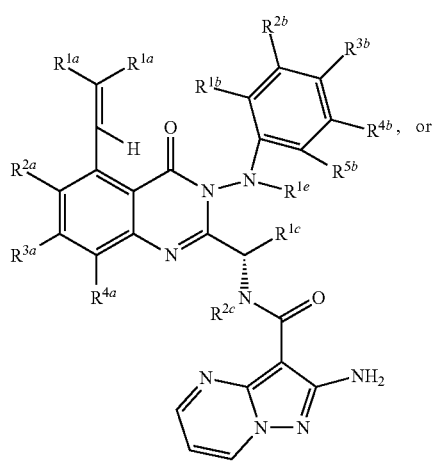

or

Formula A6R

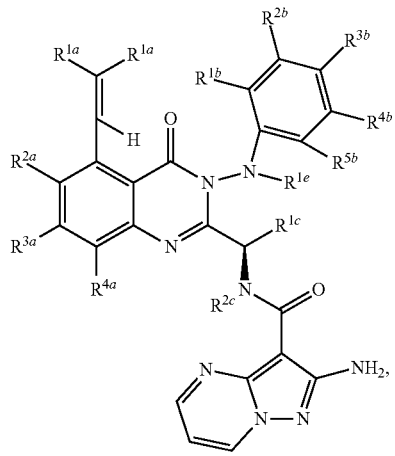

or a pharmaceutically acceptable form thereof.

In one embodiment, $R^{2a}$, $R^{3a}$, and $R^{4a}$ each is independently hydrogen, $C_1$-$C_8$ alkyl, or halo. In one embodiment, $R^{2a}$, $R^{3a}$, and $R^{4a}$ are hydrogen. In one embodiment, $R^{2a}$ is halo, and $R^{3a}$ and $R^{4a}$ are hydrogen.

In one embodiment, the compound of Formula I' is a compound of the formula:

Formula B1

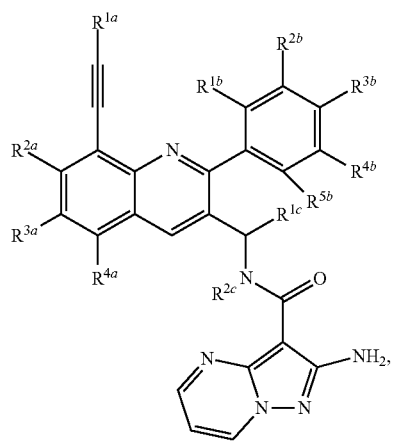

Formula B2

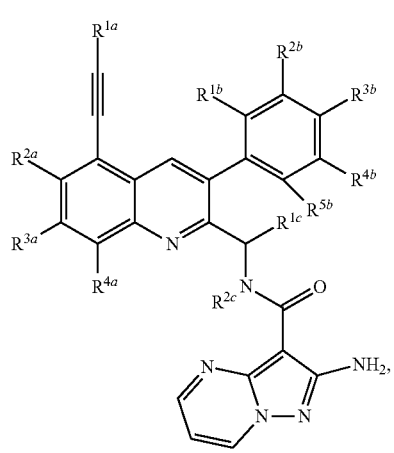

Formula B3

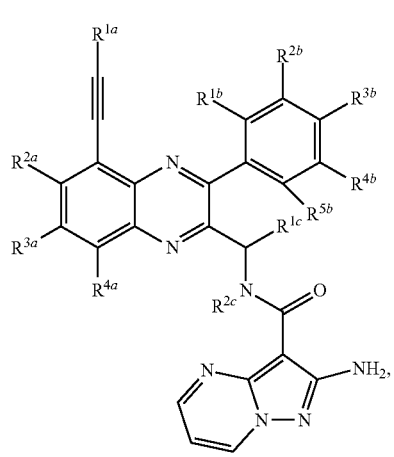

-continued
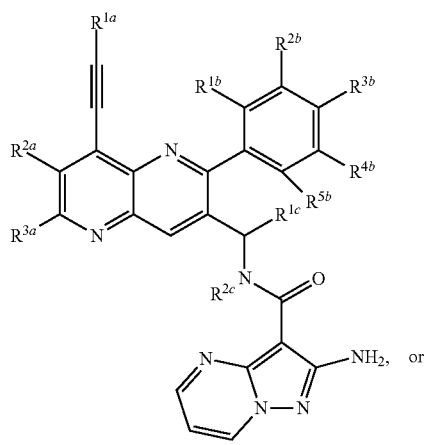
Formula B4
or
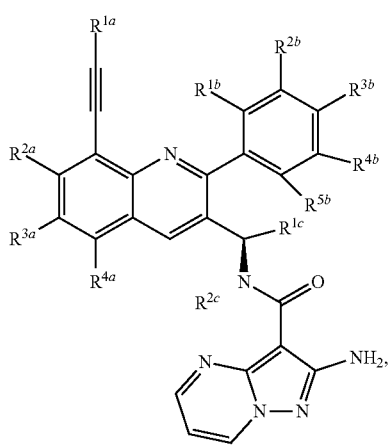
Formula B1R
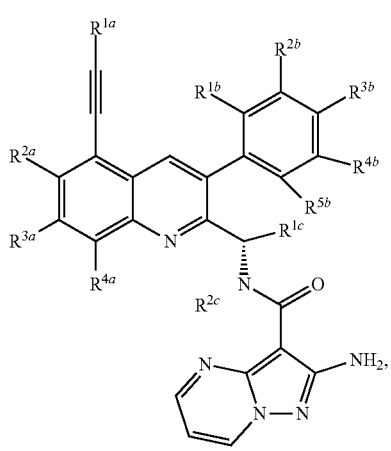
Formula B2S
Formula B5
or a pharmaceutically acceptable form thereof.
In one embodiment, the compound of Formula I' is a compound of the formula:
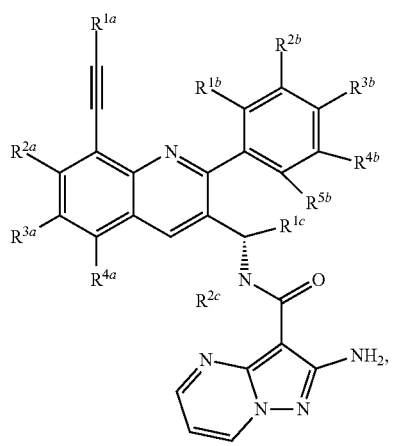
Formula B1S
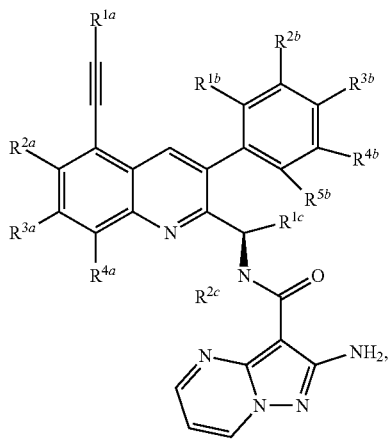
Formula B2R Formula B3S
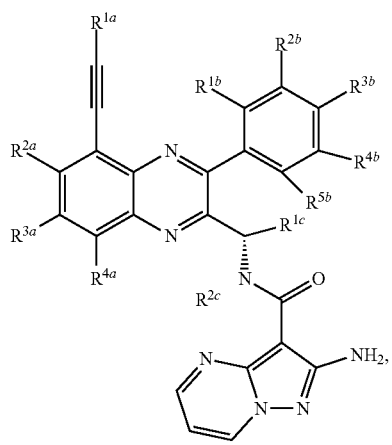
Formula B3R
Formula B4S
Formula B4R
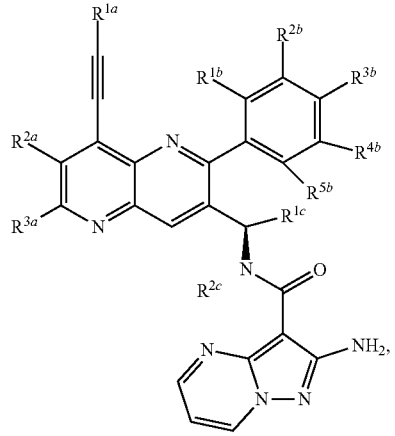
Formula B5S
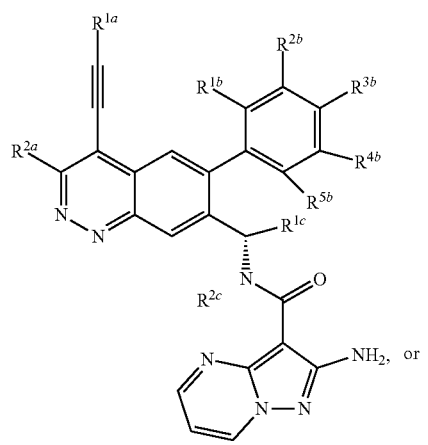
Formula B5R
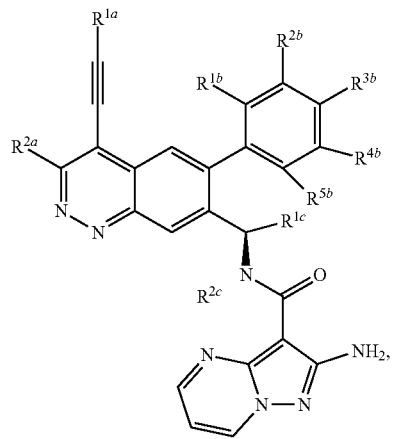
or a pharmaceutically acceptble form thereof.
In one embodiment, the compound of Formula II' is a compound of the formula:

Formula B6
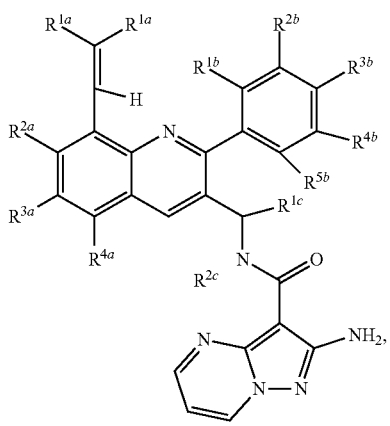
Formula B7
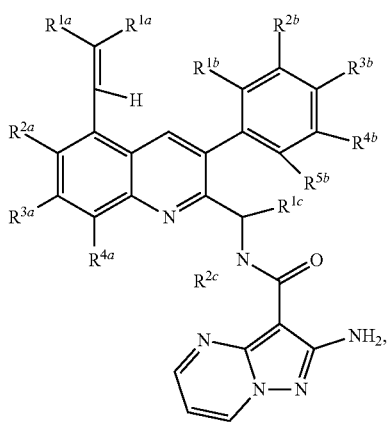
Formula B8
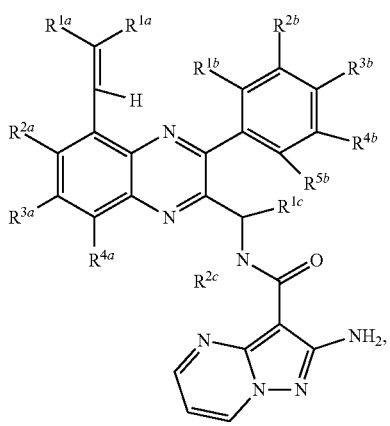
Formula B9
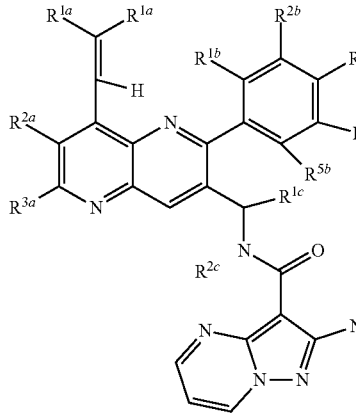
Formula B10
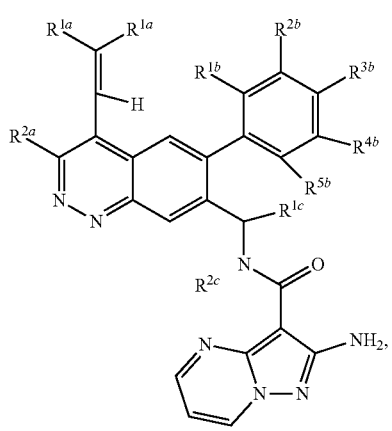
or a pharmaceutically acceptble form thereof.
In one embodiment, the compound of Formula II' is a compound of the formula:
Formula B6S
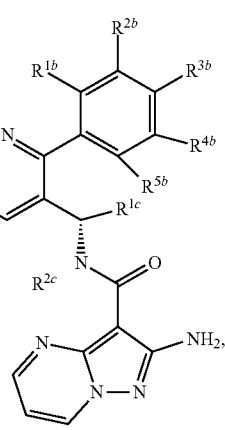

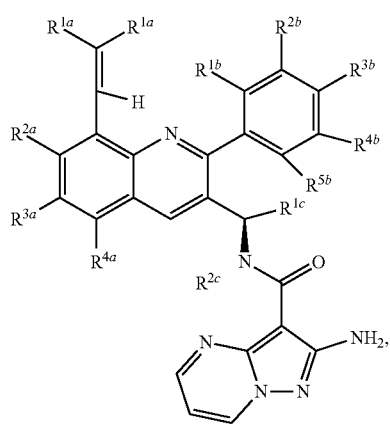
Formula B6R
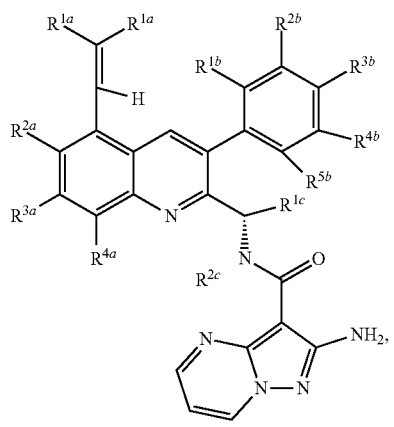
Formula B7S

Formula B7R
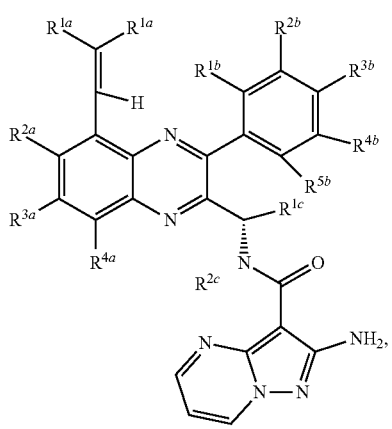
Formula B8S
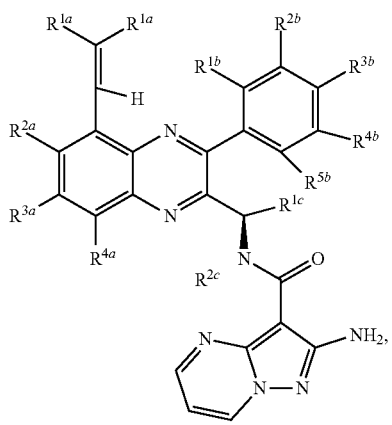
Formula B8R
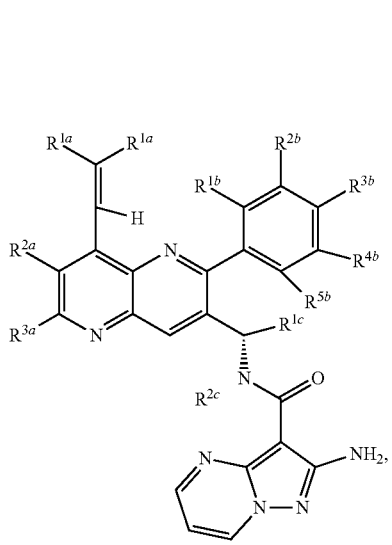
Formula B9S -continued

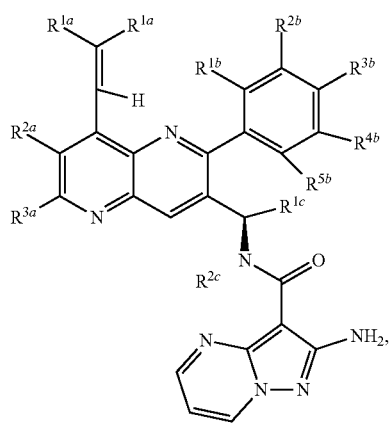
Formula B9R

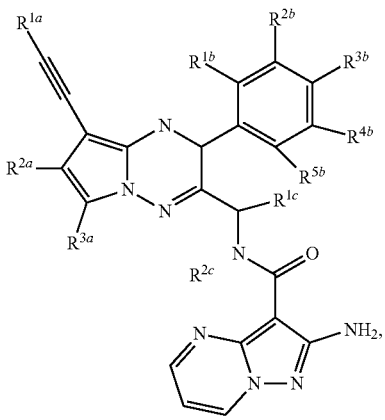
Formula C1

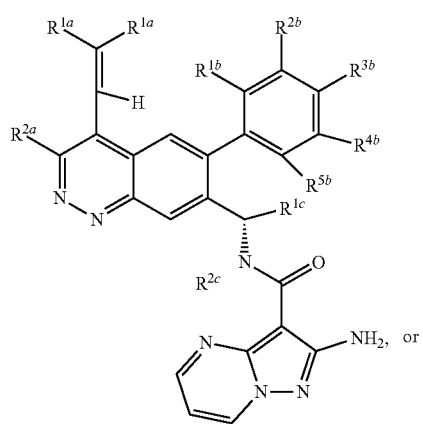
Formula B10S

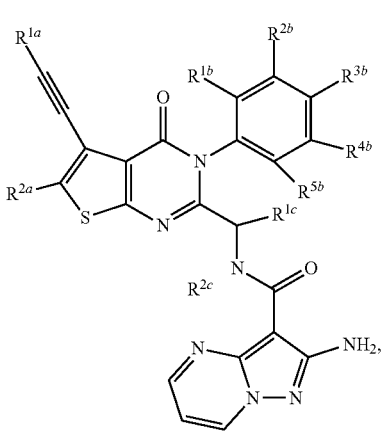
Formula C2

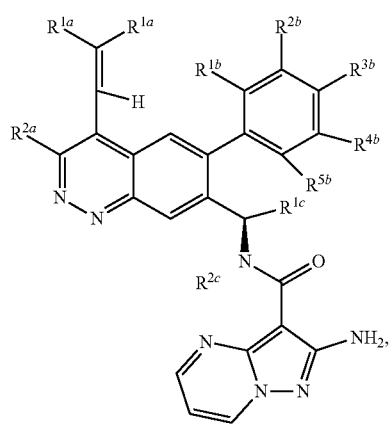
Formula B10R

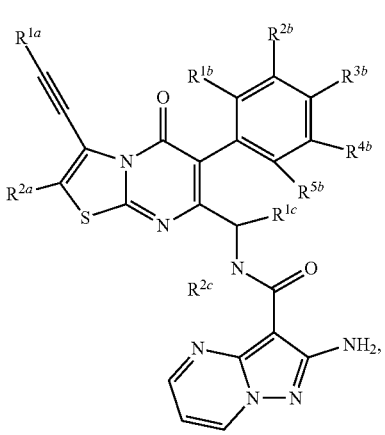
Formula C3 or a pharmaceutically acceptable form thereof.

In one embodiment, $R^{2a}$, $R^{3a}$, and $R^{4a}$ each is independently hydrogen, $C_1$-$C_8$ alkyl, or halo. In one embodiment, $R^{2a}$, $R^{3a}$, and $R^{4a}$ are hydrogen. In one embodiment, $R^{2a}$ is halo, and $R^{3a}$ and $R^{4a}$ are hydrogen.

In one embodiment, A is 6-membered heterocycle or carbocycle and B is 5-membered heterocycle or carbocycle. In one embodiment, A is 6-membered heterocycle and B is 5-membered heterocycle. In one embodiment, A is 6-membered heterocycle and B is 5-membered carbocycle.

In one embodiment, the compound of Formula I' is a compound of the formula:

Formula C4
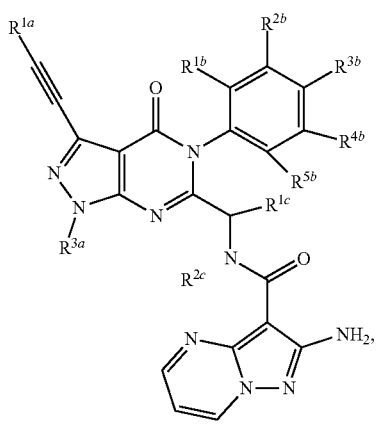
Formula C5
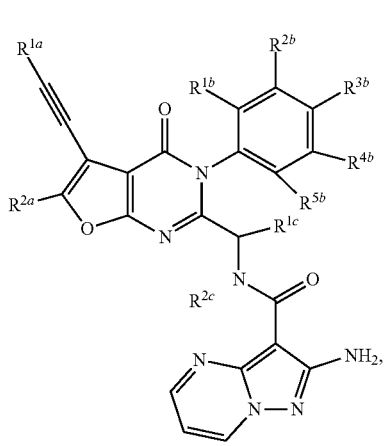
Formula C6
Formula C7
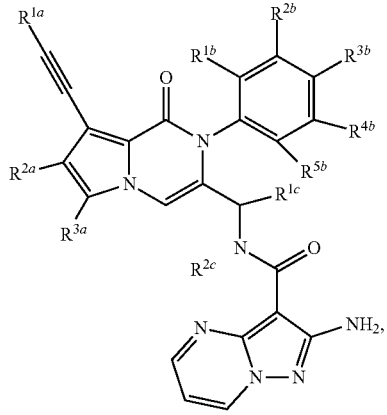
Formula C8
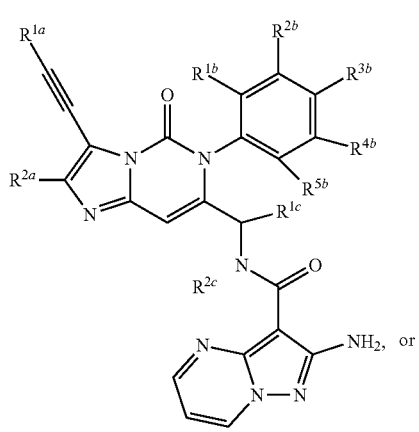
Formula C9
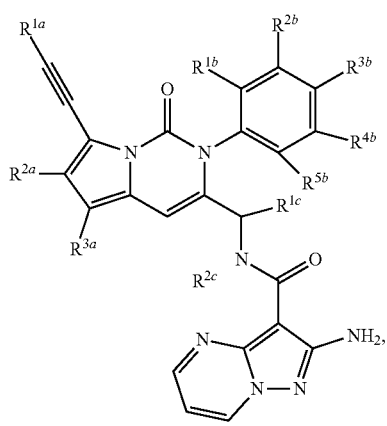
or a pharmaceutically acceptable form thereof.
In one embodiment, the compound of Formula I' is a compound of the formula:

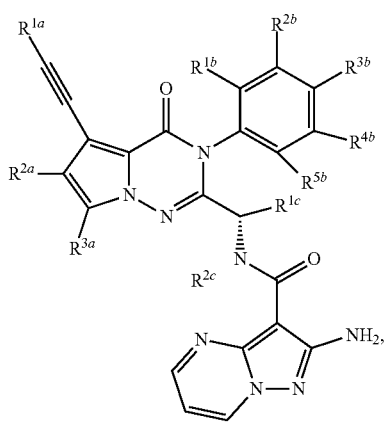
Formula C1S
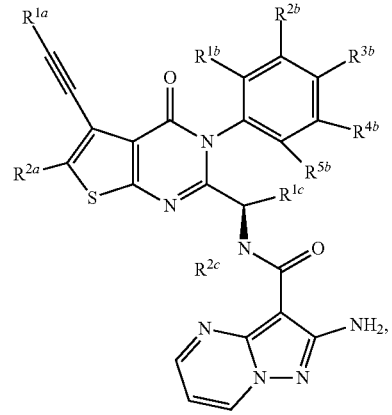
Formula C2R
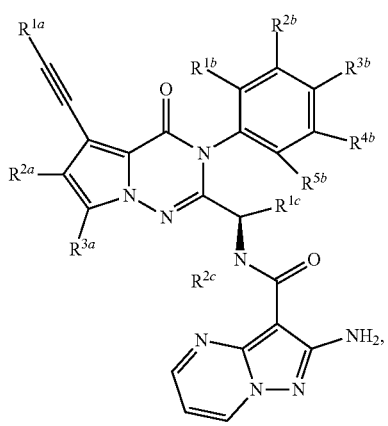
Formula C1R
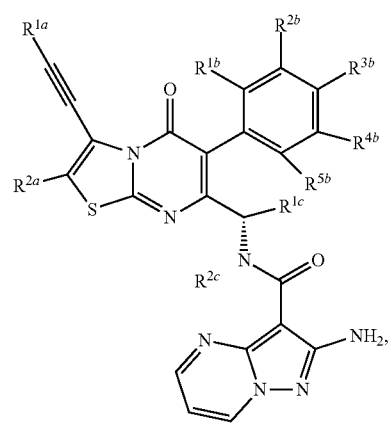
Formula C3S
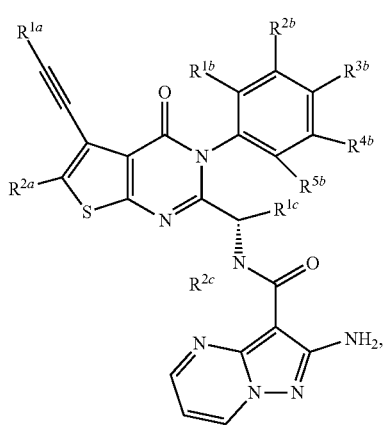
Formula C2S Formula C4S
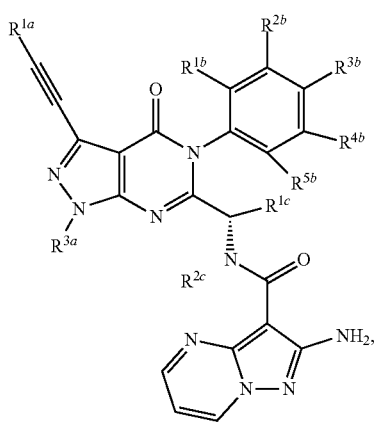
Formula C4R
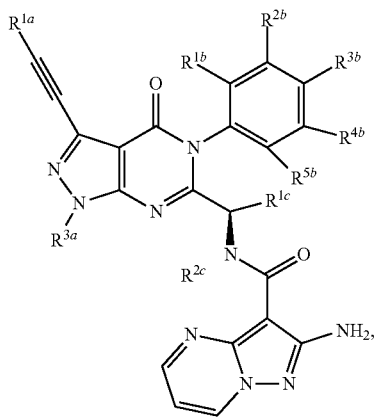
Formula C5S
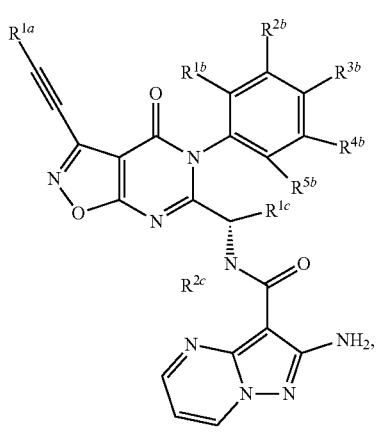
Formula C5R
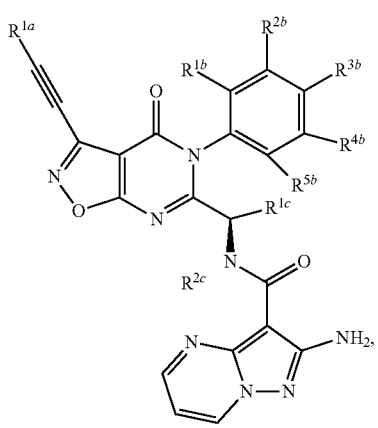
Formula C6S
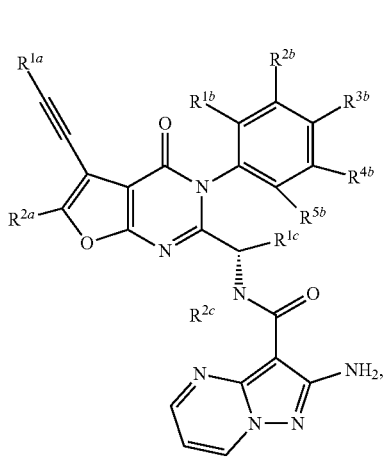
Formula C6R
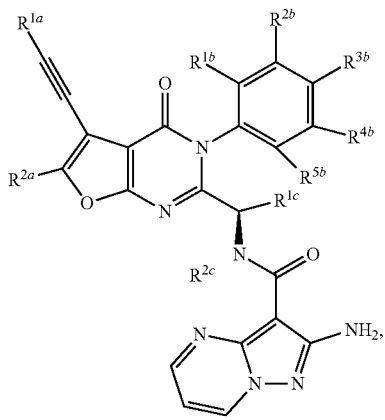

-continued
Formula C7S
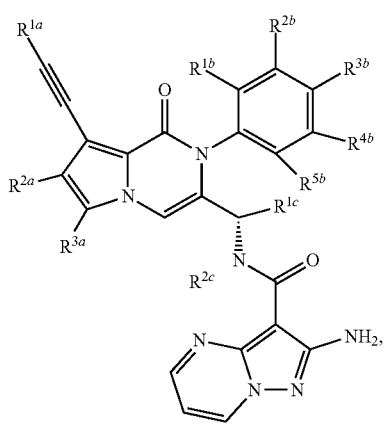
Formula C8R
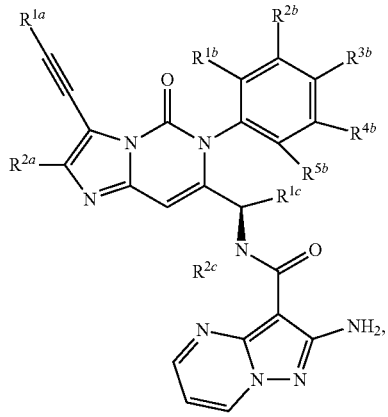
Formula C7R
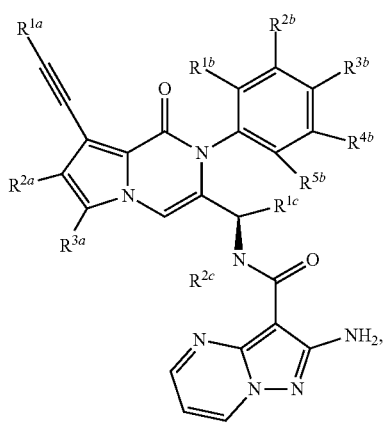
Formula C8S
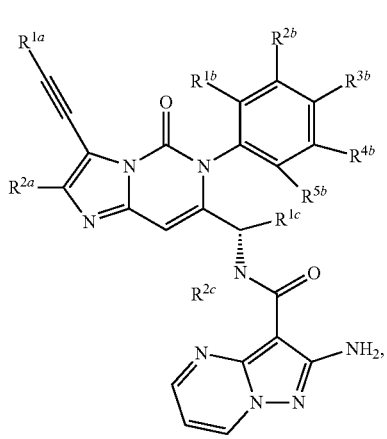
Formula C9S
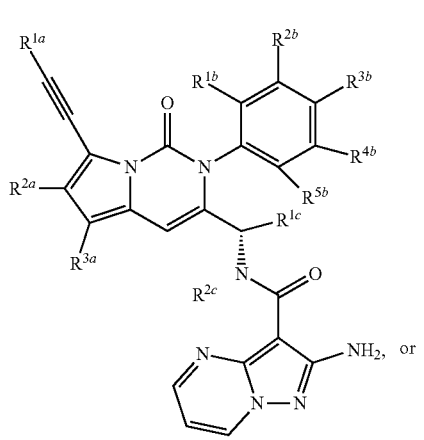
Formula C9R
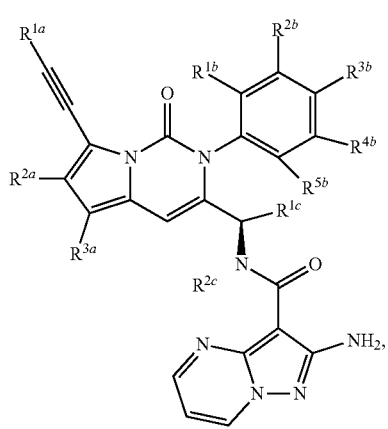
or a pharmaceutically acceptable form thereof.
In one embodiment, the compound of Formula II' is a compound of the formula:

Formula C10
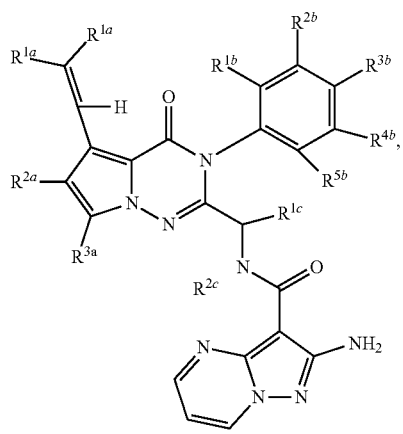
Formula C11
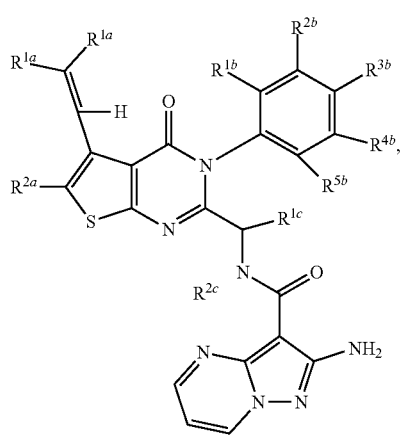
Formula C12
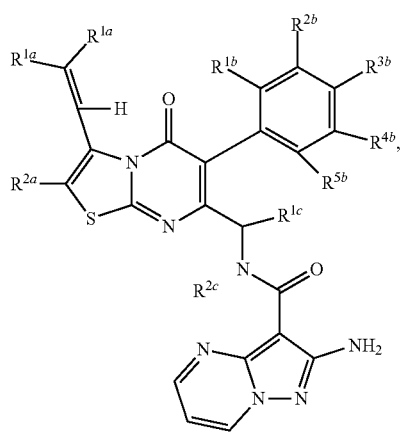
Formula C13
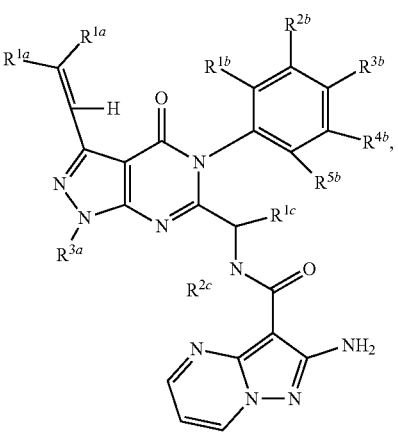
Formula C14
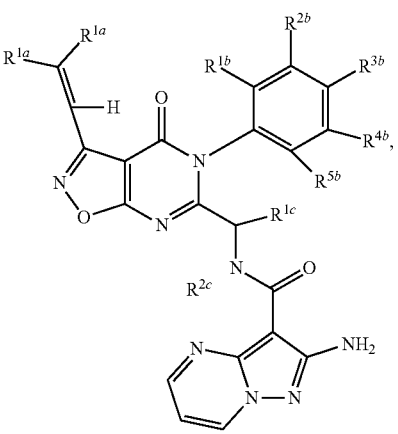
Formula C15
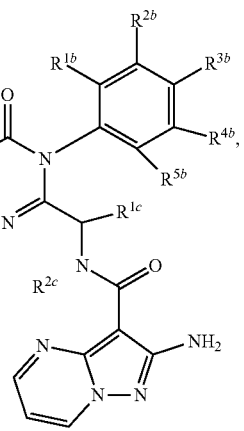

Formula C16
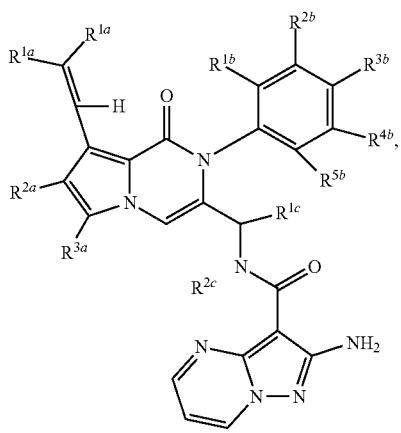
Formula C17
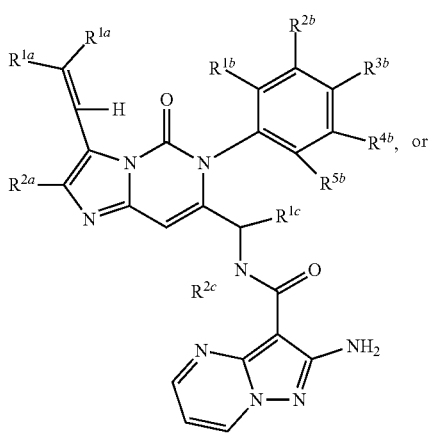
, or
Formula C18
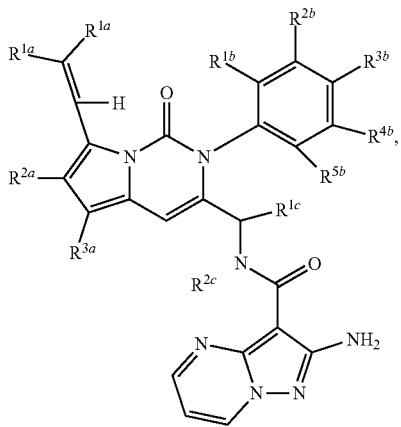
or a pharmaceutically acceptable form thereof.
In one embodiment, the compound of Formula II' is a compound of the formula:
Formula C10S
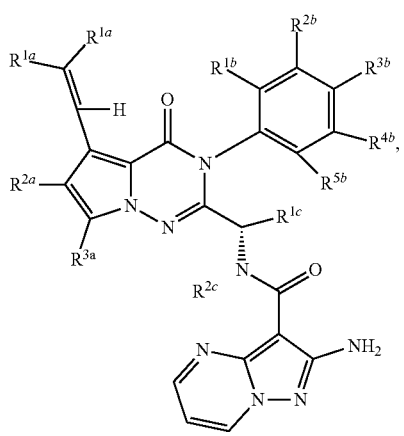
Formula C10R
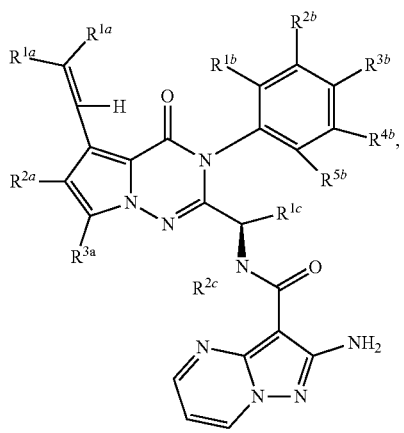
Formula C11S
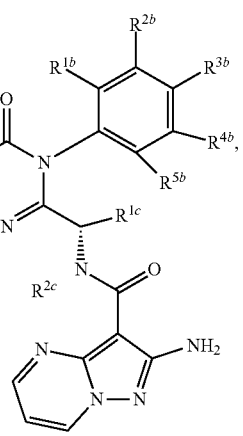

-continued
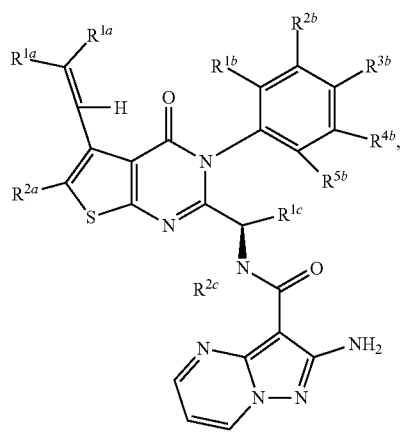
Formula C11R
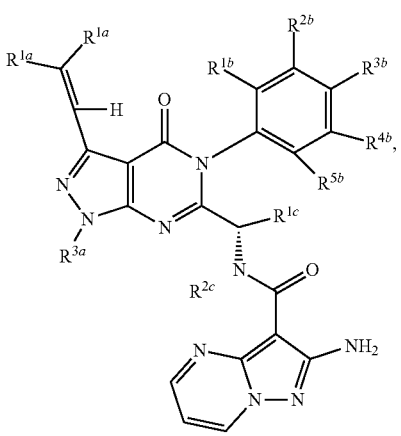
Formula C13S
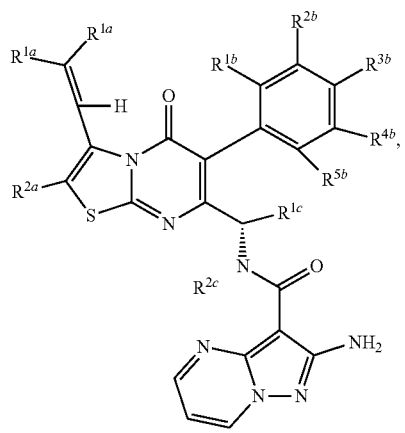
Formula C12S
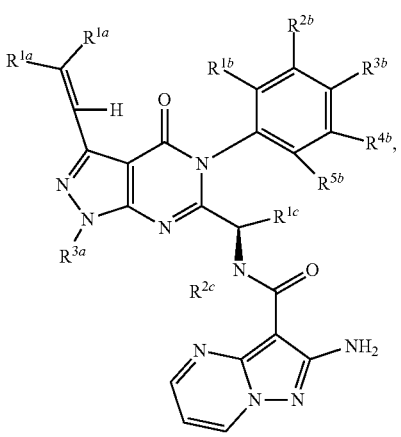
Formula C13R
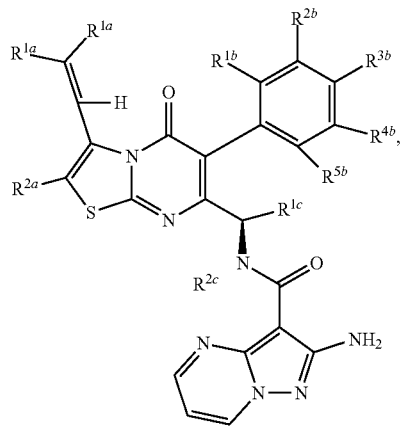
Formula C12R
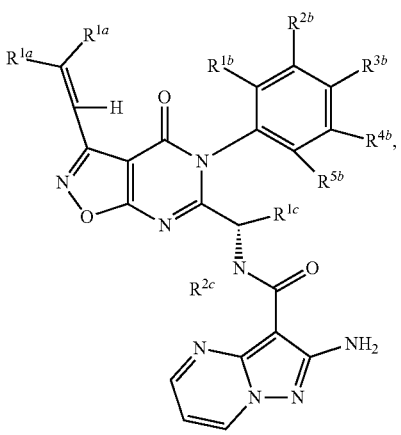
Formula C14S -continued
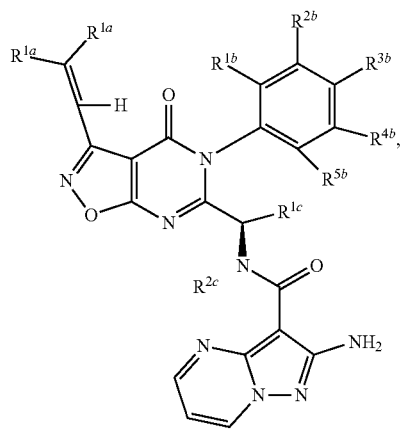
Formula C14R
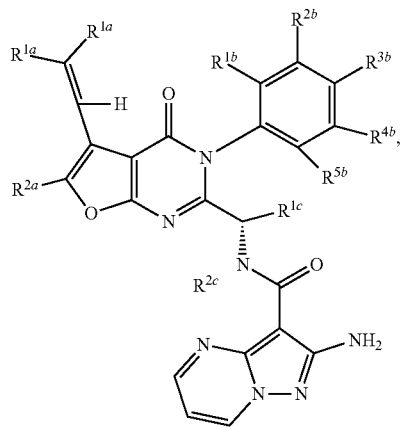
Formula C15S
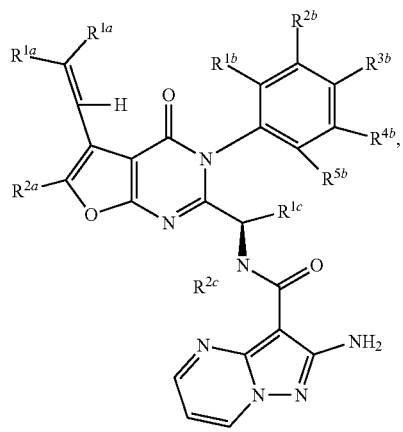
Formula C15R
-continued
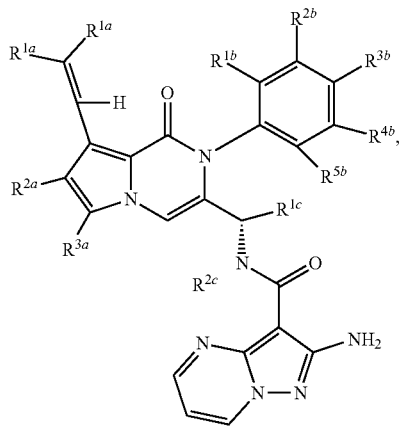
Formula C16S
Formula C16R
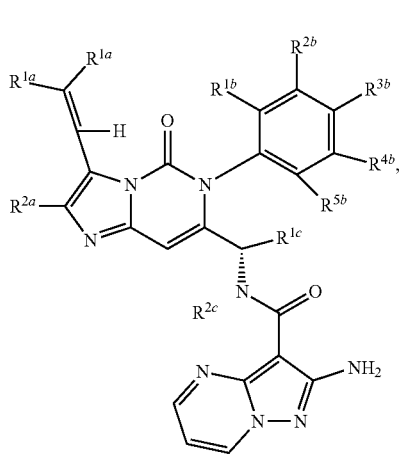
Formula C17S Formula C17R

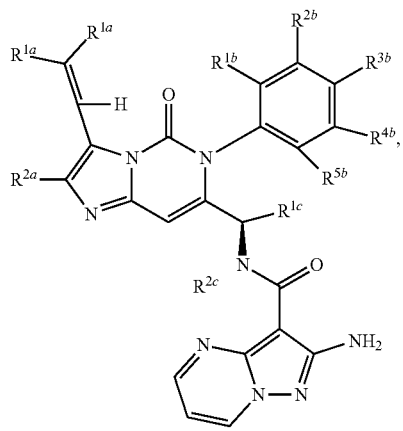

Formula C18S

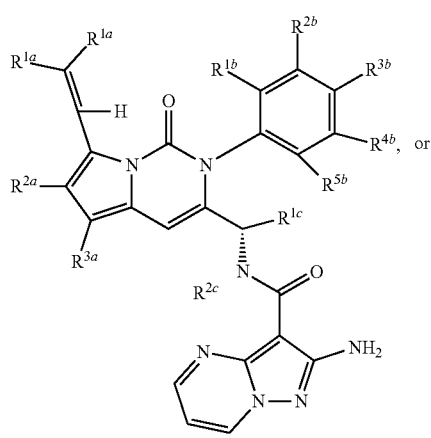
or

Formula C18R

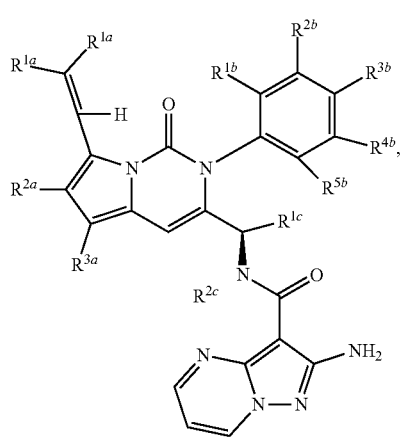

or a pharmaceutically acceptable form thereof.

In one embodiment, $R^{2a}$ and $R^{3a}$ each is independently hydrogen, $C_1$-$C_8$ alkyl, or halo. In one embodiment, $R^{2a}$ and $R^{3a}$ are hydrogen. In one embodiment, $R^{2a}$ is halo, and $R^{3a}$ is hydrogen.

In one embodiment, the compound of Formula I' is a compound of the formula:

Formula D1

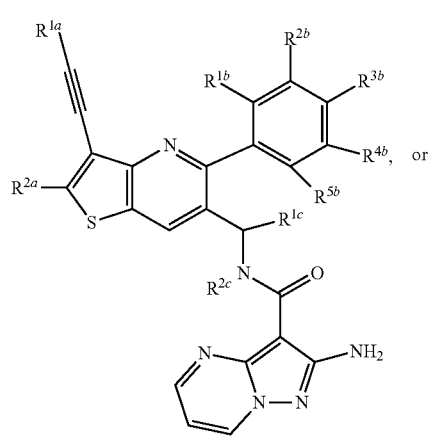
or

Formula D2

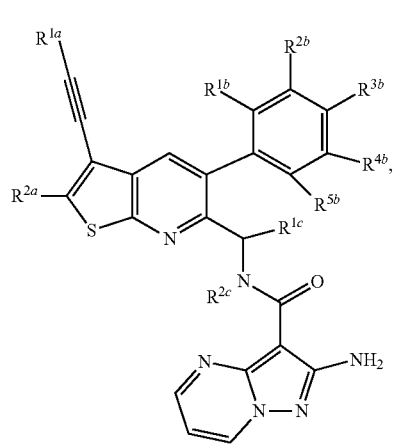

or a pharmaceutically acceptable form thereof.

In one embodiment, the compound of Formula I' is a compound of the formula:

Formula D1S

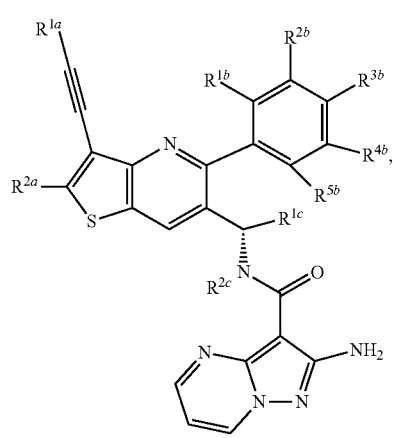

Formula D1R
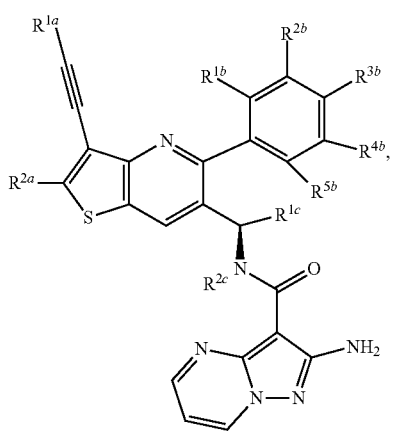
Formula D2S
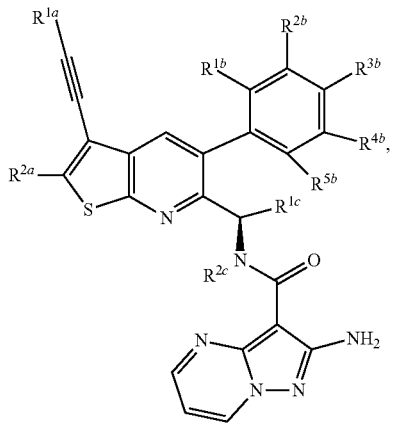
or
Formula D2R
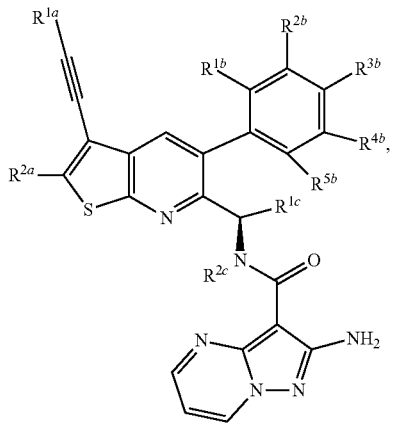
or a pharmaceutically acceptable form thereof.
In one embodiment, the compound of Formula II' is a compound of the formula:
Formula D3
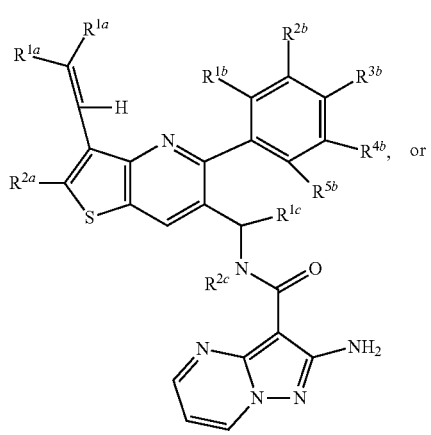
or
Formula D4
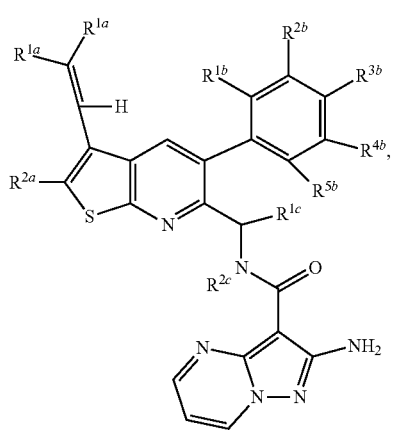
or a pharmaceutically acceptable form thereof.
In one embodiment, the compound of Formula II' is a compound of the formula:
Formula D3S
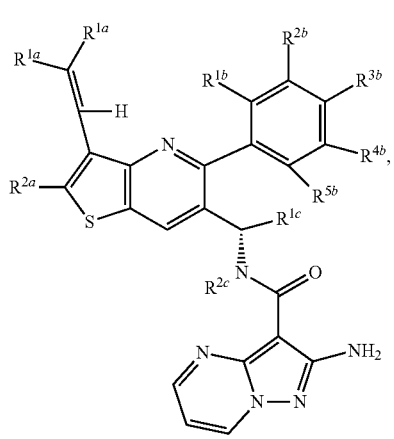

Formula D3R

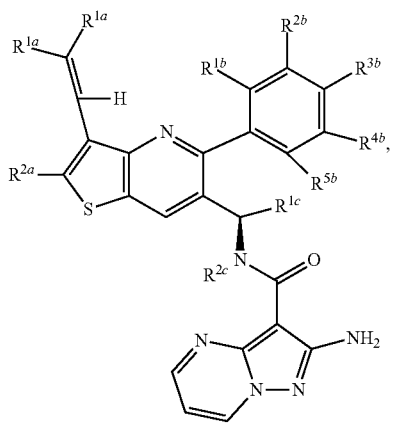

Formula D4S

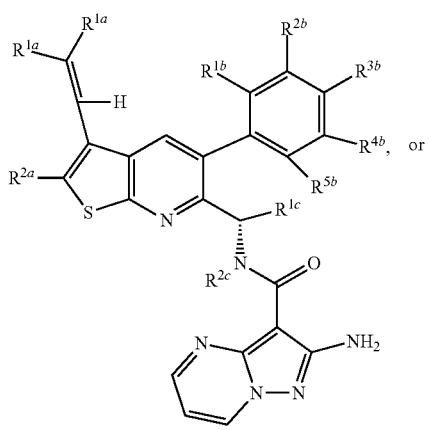

Formula D4R

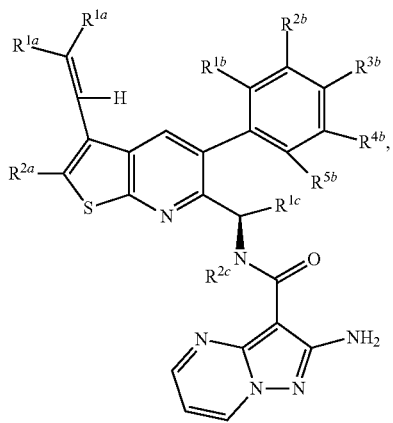

or a pharmaceutically acceptable form thereof.

In one embodiment, $R^{2a}$ is hydrogen, $C_1$-$C_8$ alkyl, or halo. In one embodiment, $R^{2a}$ is hydrogen. In one embodiment, $R^{2a}$ is halo.

In one embodiment, A is 5-membered heterocycle or carbocycle and B is 6-membered heterocycle or carbocycle. In one embodiment, A is 5-membered heterocycle and B is 6-membered heterocycle. In one embodiment, A is 5-membered heterocycle and B is 6-membered carbocycle.

In one embodiment, the compound of Formula I' is a compound of the formula:

Formula E1

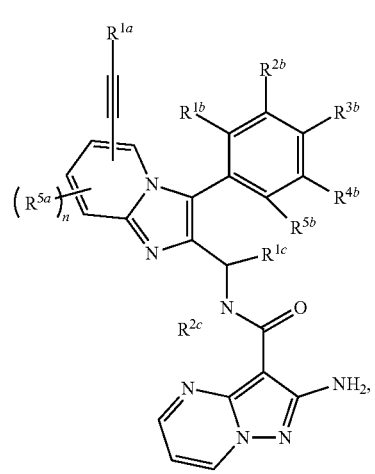

Formula E2

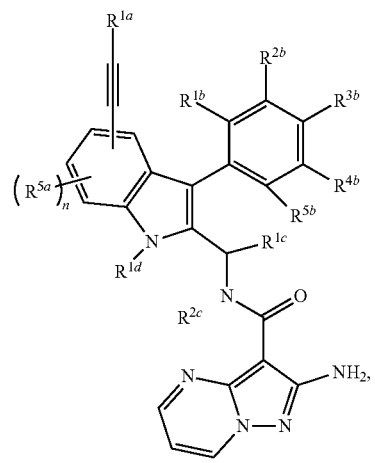

Formula E3

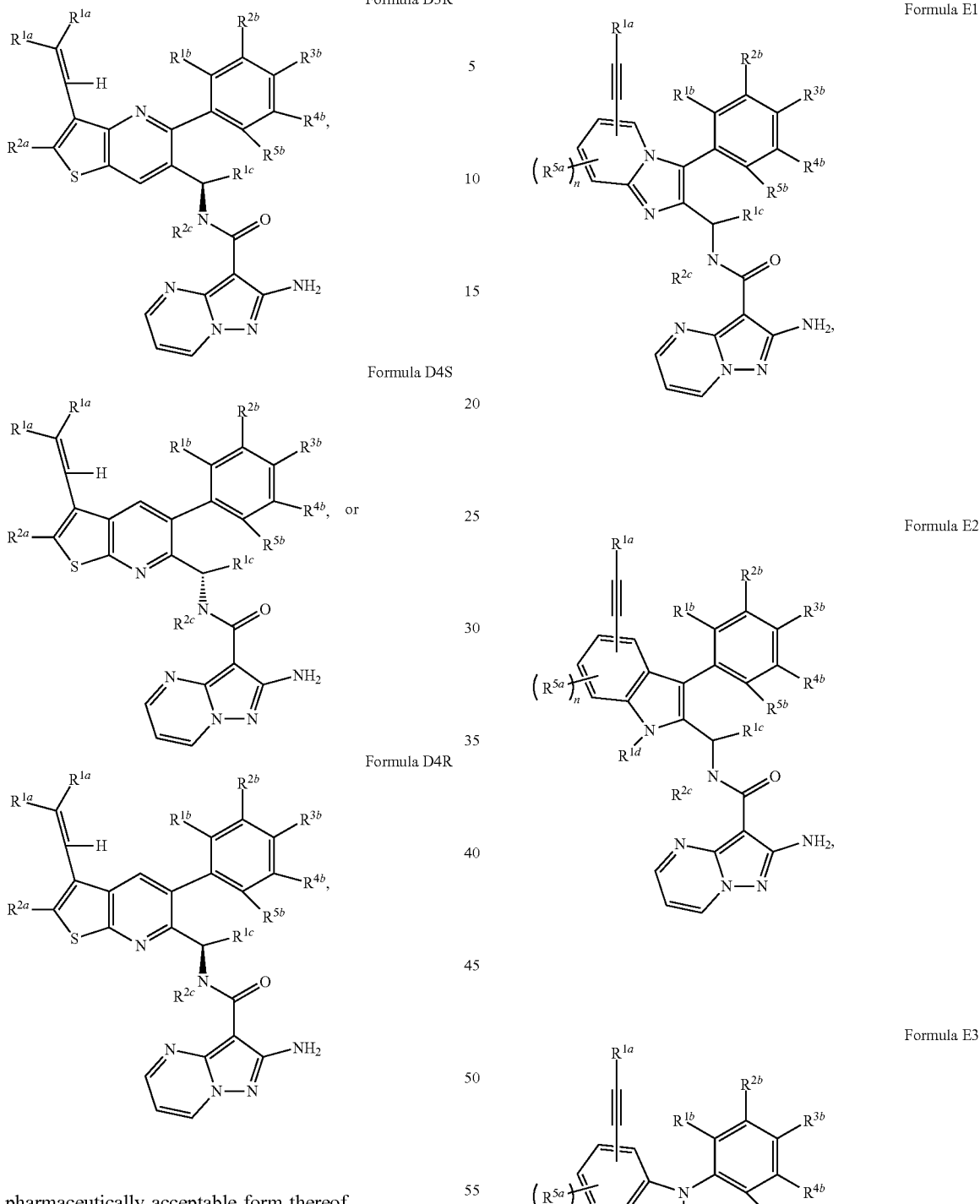

-continued
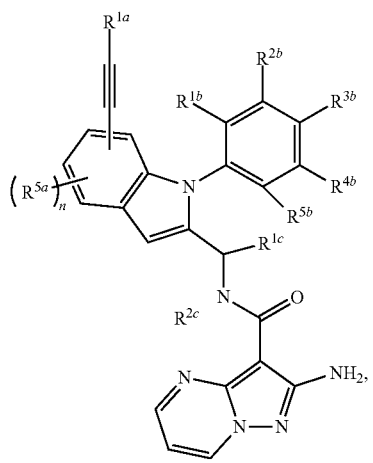
Formula E4
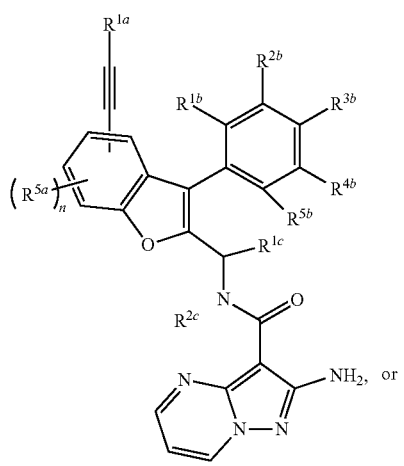
Formula E5
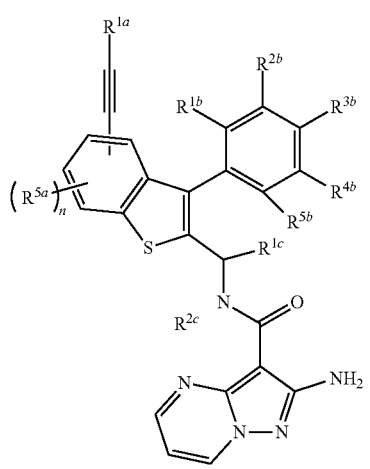
Formula E6
or a pharmaceutically acceptable form thereof.
In one embodiment, the compound of Formula I' is a compound of the formula:
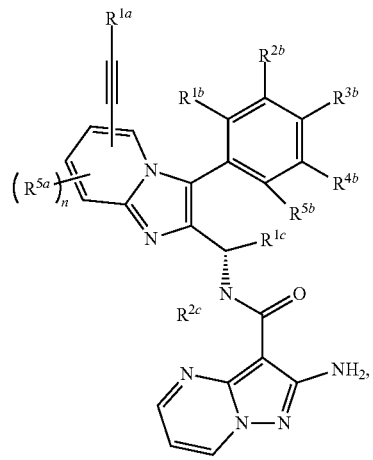
Formula E1S
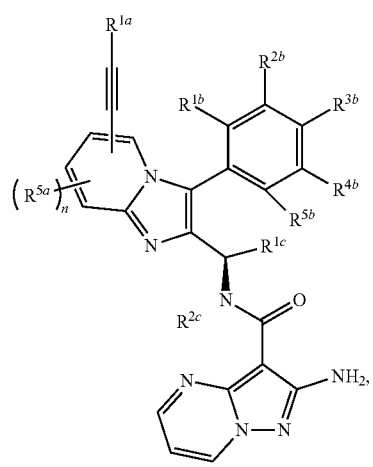
Formula E1R
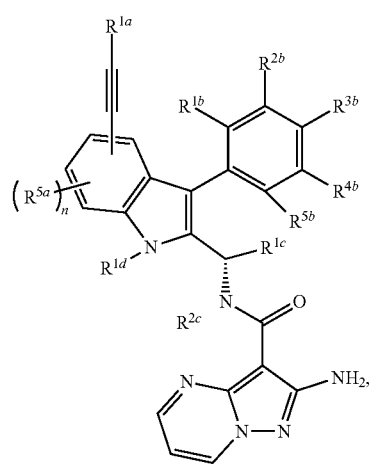
Formula E2S -continued
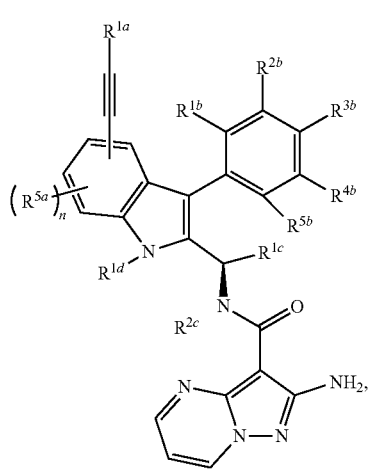
Formula E2R
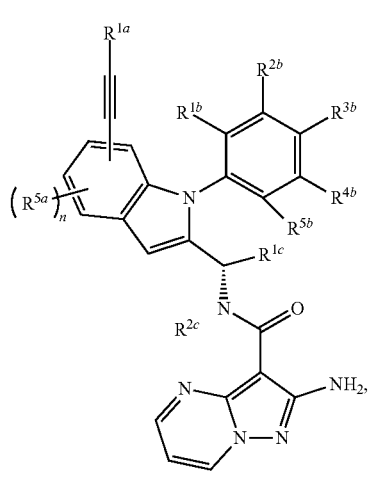
Formula E4S

Formula E3S

Formula E4R
Formula E3R
Formula E5S Formula E5R
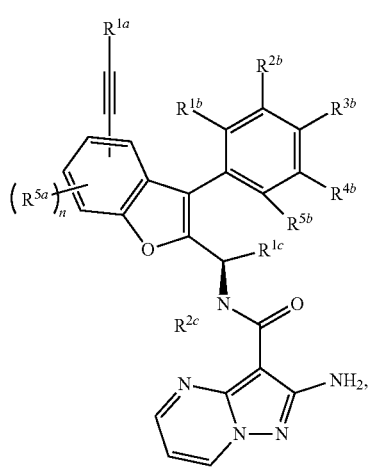
Formula E7
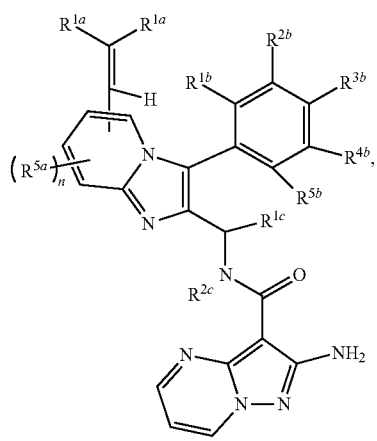
Formula E6S
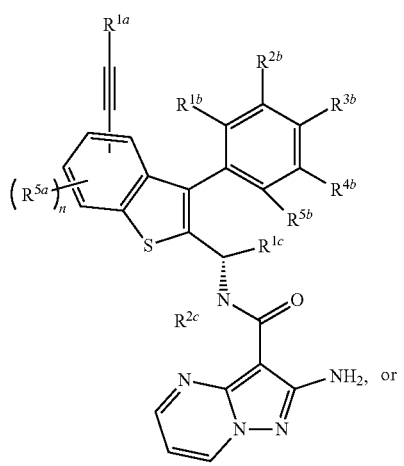
Formula E8
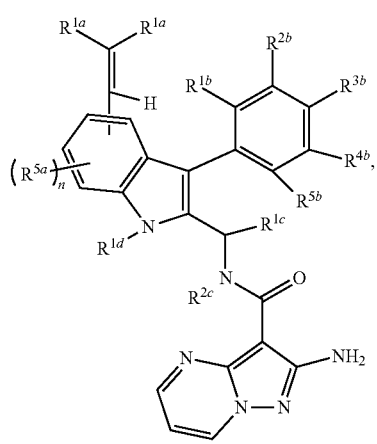
Formula E6R
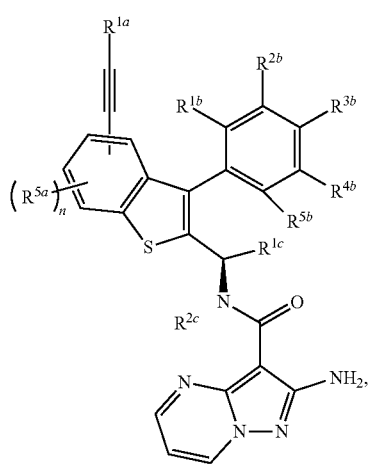
Formula E9
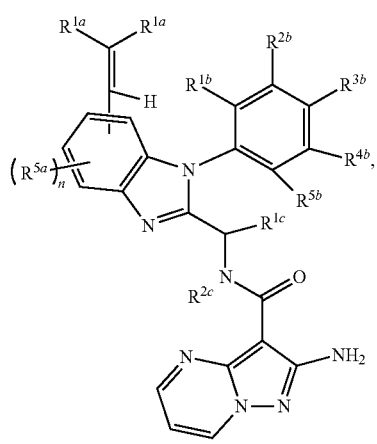
or a pharmaceutically acceptable form thereof.
In one embodiment, the compound of Formula II' is a compound of the formula:

Formula E10
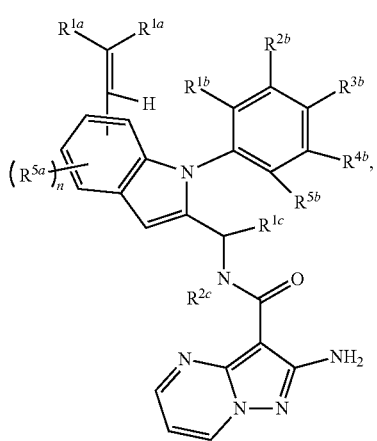
Formula E7S
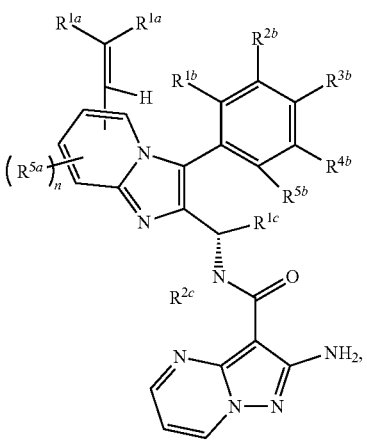
Formula E11
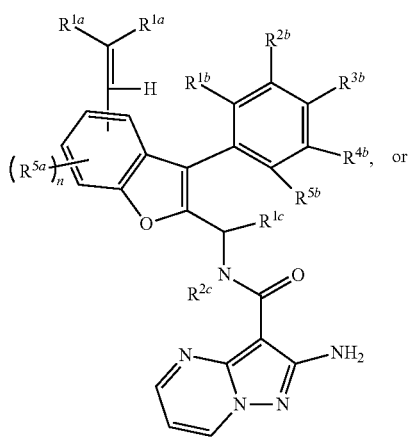
or
Formula E7R
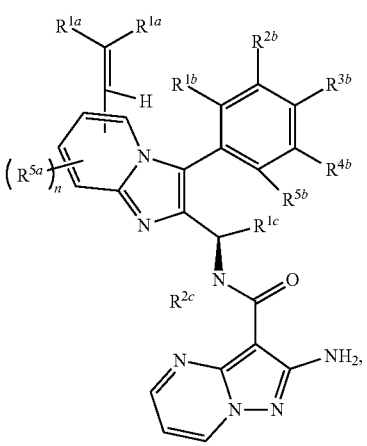
Formula E12
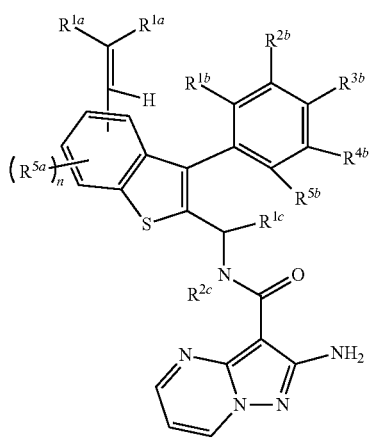
Formula E8S
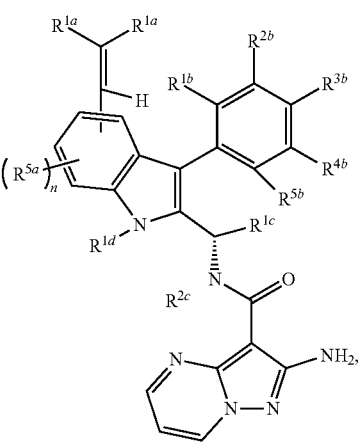
or a pharmaceutically acceptable form thereof.
In one embodiment, the compound of Formula II' is a compound of the formula:

103
-continued
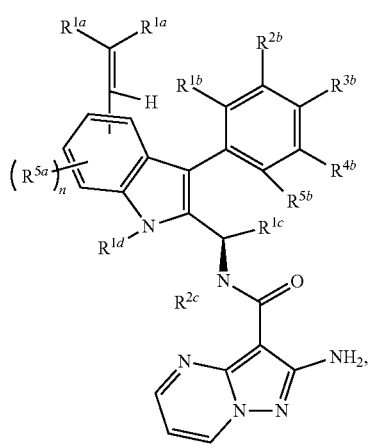
Formula E8R
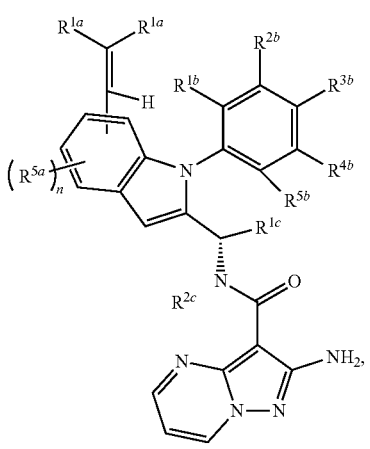
Formula E10S
Formula E9S
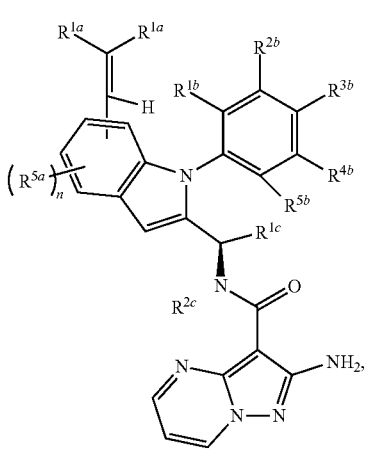
Formula E10R
Formula E9R
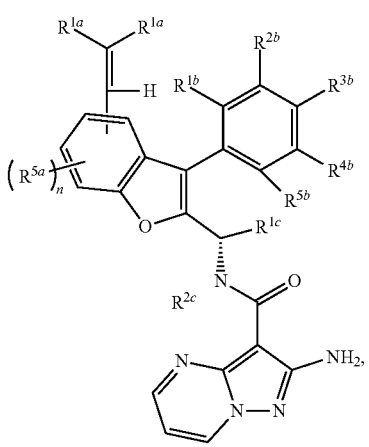
Formula E11S

105

-continued

Formula E11R

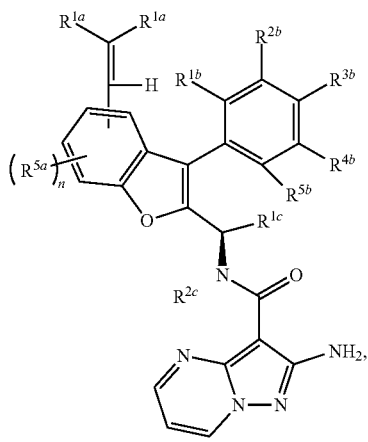

Formula E12S

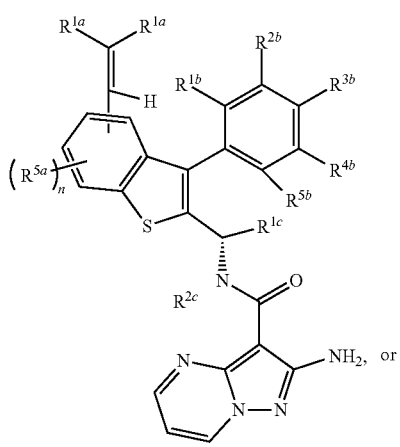

Formula E12R

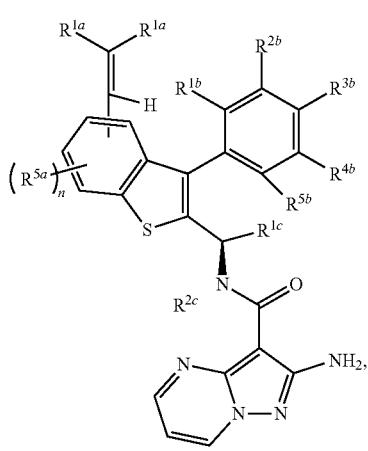

or a pharmaceutically acceptable form thereof.

In one embodiment, $R^{1d}$ is hydrogen or $C_1$-$C_8$ alkyl. In one embodiment, $R^{1d}$ is hydrogen. In one embodiment, $R^{1d}$ is methyl. In one embodiment, each instance of $R^{5a}$ is independently hydrogen, $C_1$-$C_8$ alkyl, or halo. In one embodiment, each instance of $R^{5a}$ is independently hydrogen. In one embodiment, n is 1. In one embodiment, n is 2. In one embodiment, n is 3.

In one embodiment, A is 5-membered heterocycle or carbocycle and B is 5-membered heterocycle or carbocycle. In one embodiment, A is 5-membered heterocycle and B is 5-membered heterocycle.

106

In one embodiment, the compound of Formula I' is a compound of the formula:

Formula F1

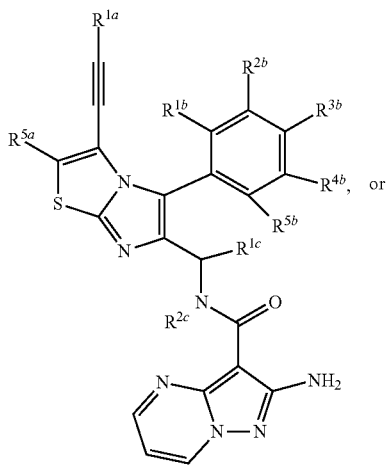

Formula F2

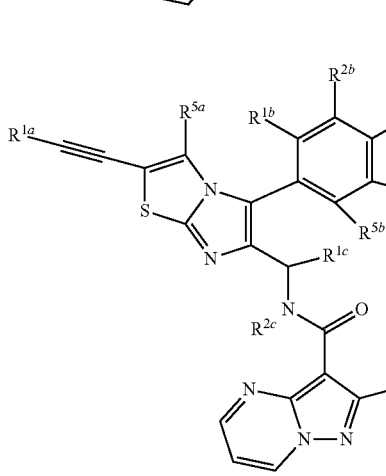

or a pharmaceutically acceptable form thereof.

In one embodiment, the compound of Formula I' is a compound of the formula:

Formula F1S

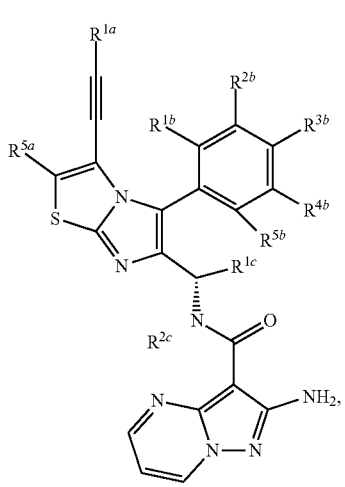

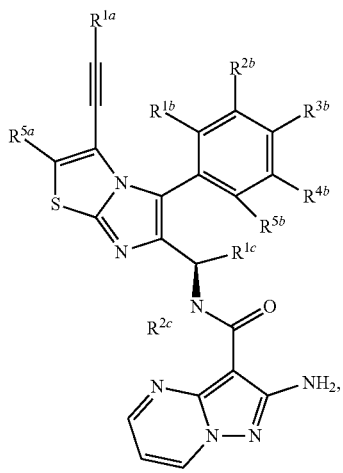
Formula F1S
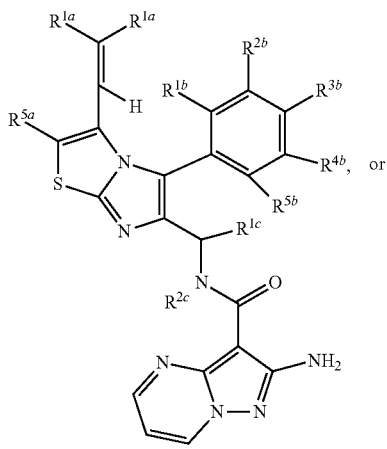
Formula F3
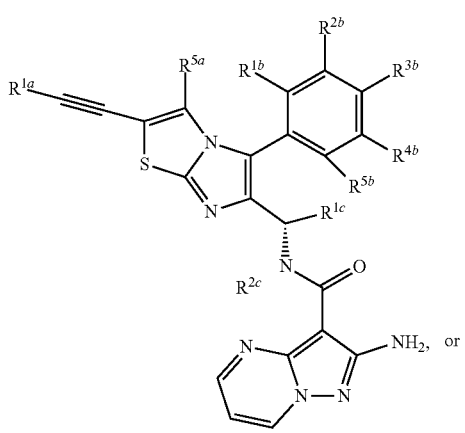
Formula F2S
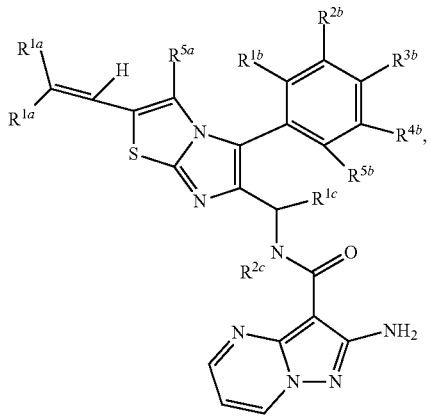
Formula F4
or a pharmaceutically acceptable form thereof.
In one embodiment, the compound of Formula II' is a compound of the formula:
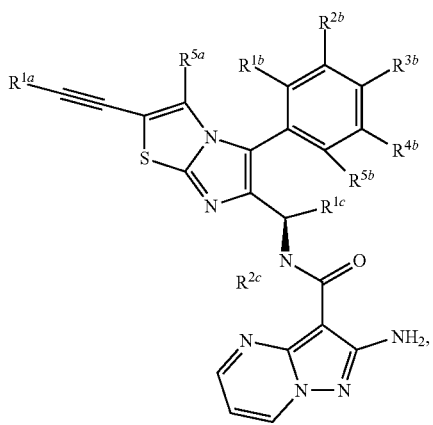
Formula F2S
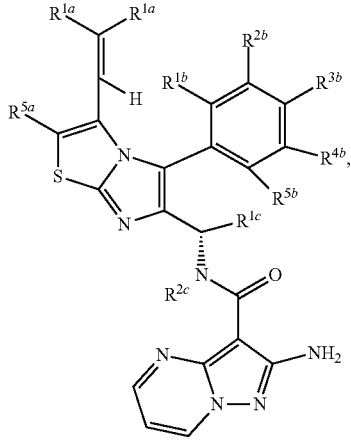
Formula F3S
or a pharmaceutically acceptable form thereof.
In one embodiment, the compound of Formula II' is a compound of the formula:

Formula F3S

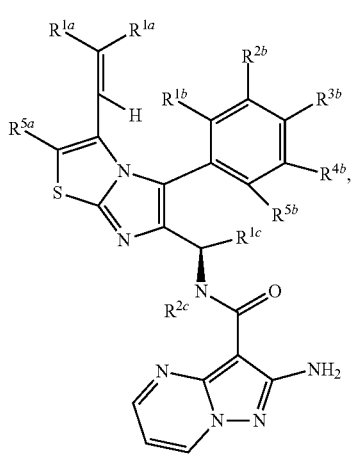

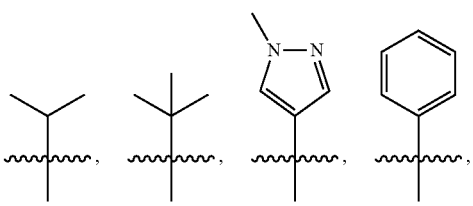

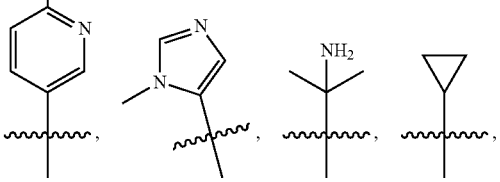

Formula F4S

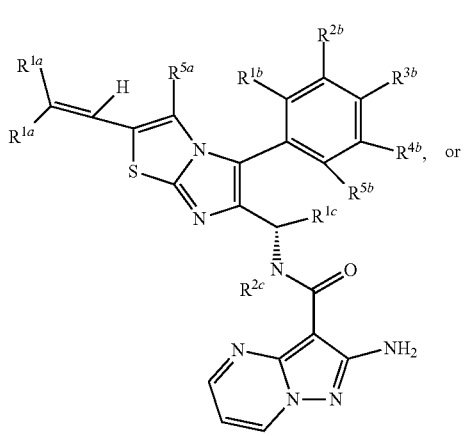

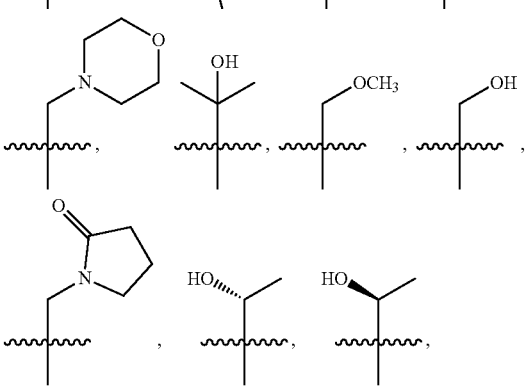

Formula F4S

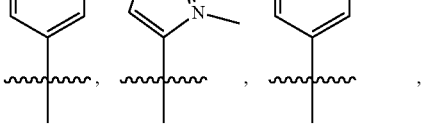

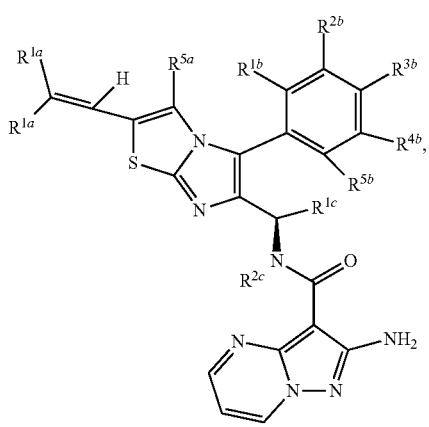

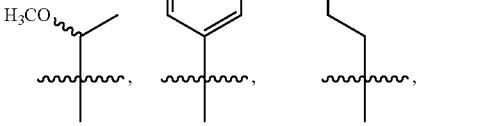

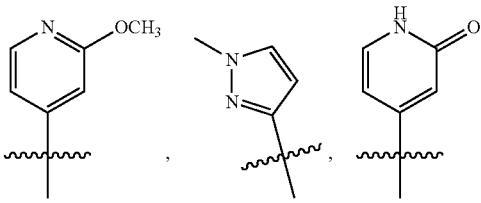

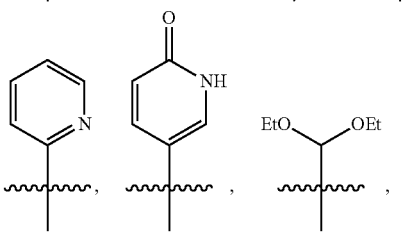

In one embodiment, each instance of $R^{5a}$ is independently hydrogen, $C_1$-$C_8$ alkyl, or halo. In one embodiment, $R^{5a}$ is hydrogen. In one embodiment, $R^{1a}$ is hydrogen, $C_1$-$C_8$ alkyl, or 3-14 membered saturated, unsaturated, or aromatic heterocycle containing one or more heteroatoms selected from the group consisting of N, O, and S.

In one embodiment, $R^{1a}$ is $C_1$-$C_8$ alkyl. In one embodiment, $R^{1a}$ is 3-14 membered saturated, unsaturated, or aromatic heterocycle containing one or more heteroatoms selected from the group consisting of N, O, and S. In one embodiment, $R^{1a}$ is 5- or 6-membered aromatic heterocycle containing one or more N heteroatoms.

In some embodiments, $R^{1a}$ is: methyl,

-continued
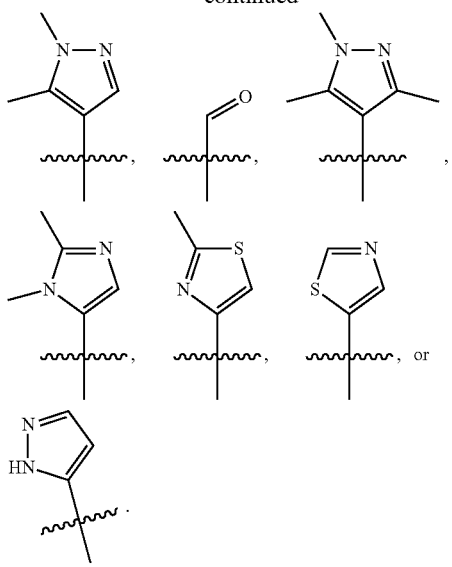
In one embodiment, the heterocycle is optionally substituted with one or more $C_1$-$C_8$ alkyl. In one embodiment, $R^{1b}$, $R^{2b}$, $R^{3b}$, $R^{4b}$, and $R^{5b}$ are hydrogen.
In one embodiment, $R^{1c}$ is $C_1$-$C_8$ alkyl. In one embodiment, $R^{1c}$ is methyl. In one embodiment, $R^{2c}$ is hydrogen or $C_1$-$C_8$ alkyl. In one embodiment, $R^{2c}$ is hydrogen.
In one embodiment,
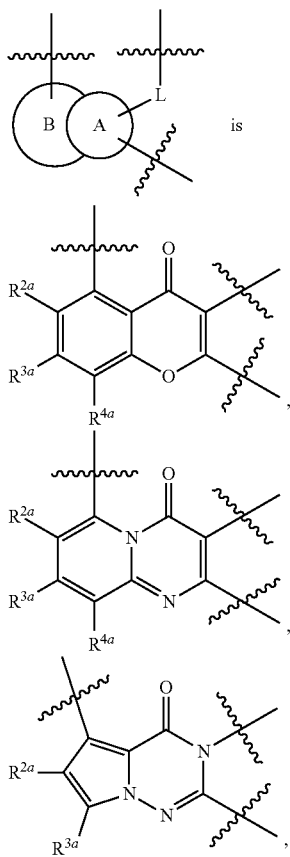
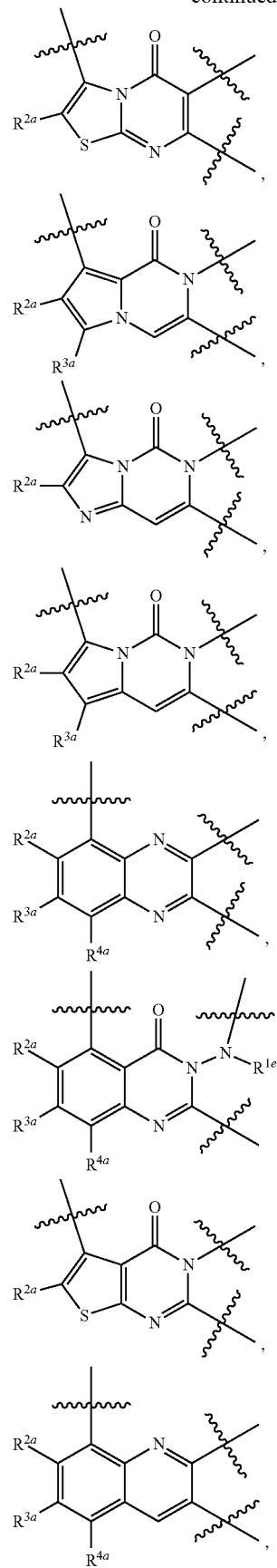

-continued

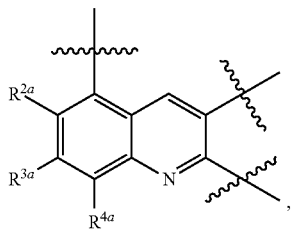,

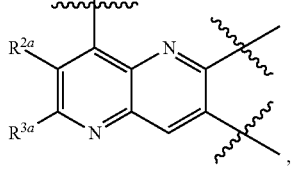,

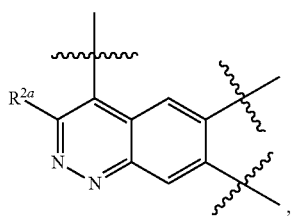,

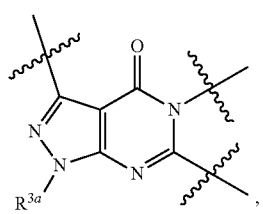,

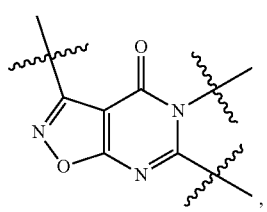,

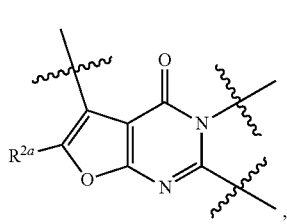,

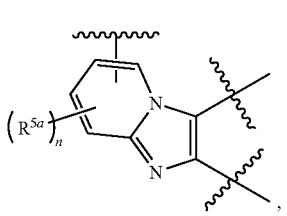,

-continued

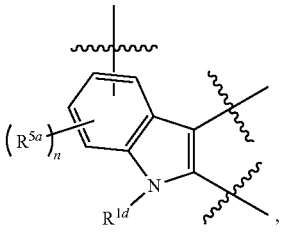,

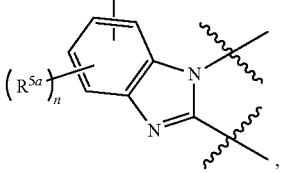,

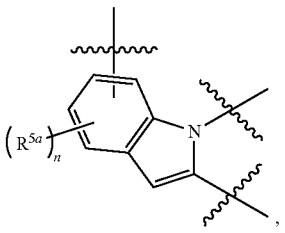,

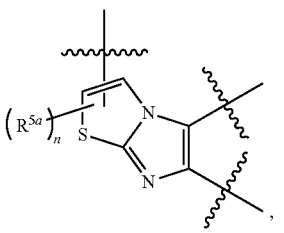,

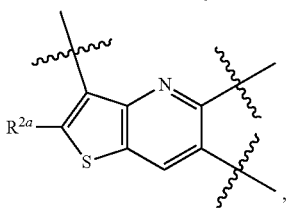, or

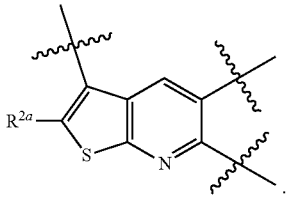.

In one embodiment, provided herein is a compound selected from Table 1, Table 2, and Table 3, or a pharmaceutically acceptable form thereof.

In one embodiment, provided herein is a compound selected from Table 1.

In one embodiment, provided herein is a compound selected from Table 2.

In one embodiment, provided herein is a compound selected from Table 3.

TABLE 1
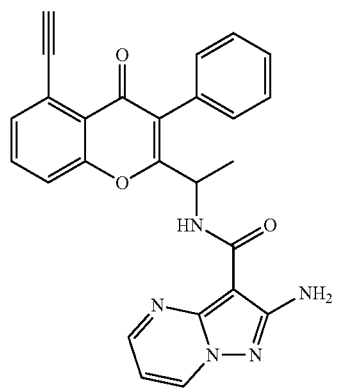 [SMILES: C#Cc1cccc2oc(C(C)NC(=O)c3c(N)nn4cccnc34)c(-c3ccccc3)c(=O)c12] 101
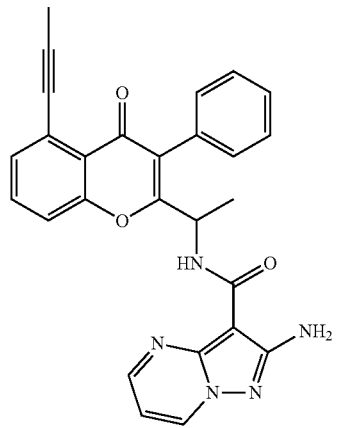 [SMILES: CC#Cc1cccc2oc(C(C)NC(=O)c3c(N)nn4cccnc34)c(-c3ccccc3)c(=O)c12] 102
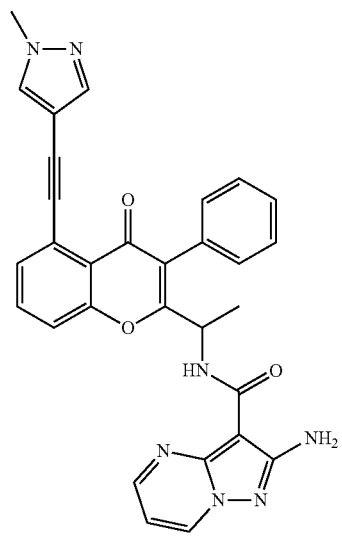 [SMILES: CC(NC(=O)c1c(N)nn2cccnc12)c1oc2cccc(C#Cc3cnn(C)c3)c2c(=O)c1-c1ccccc1] 103
TABLE 1-continued
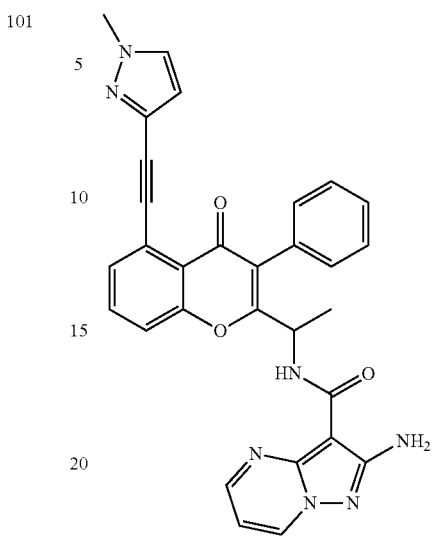 104
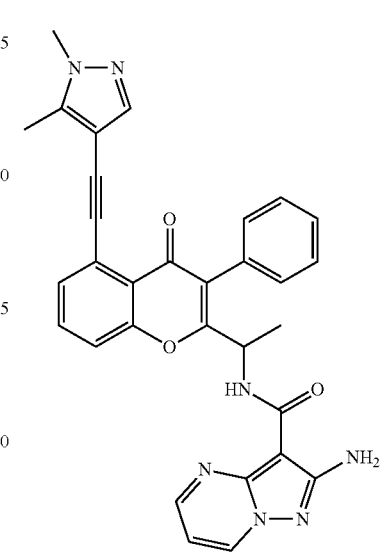 105
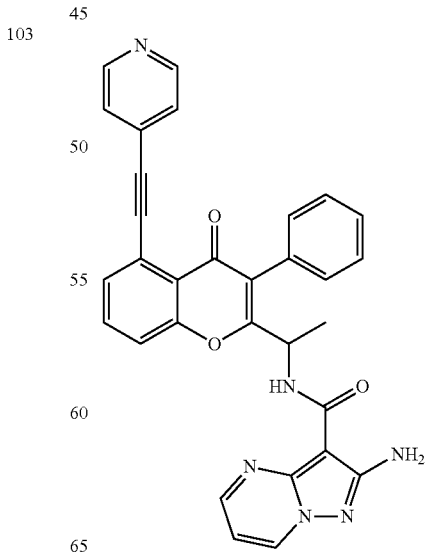 106

TABLE 1-continued
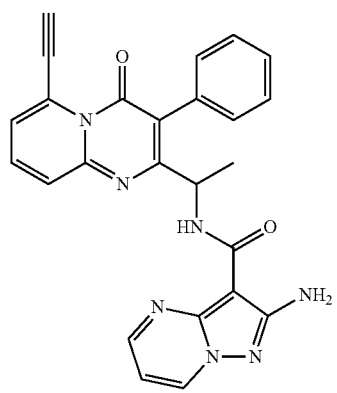 [SMILES: C#Cc1cccc2nc(C(C)NC(=O)c3c(N)nn4cccnc34)c(-c3ccccc3)c(=O)n12]
107
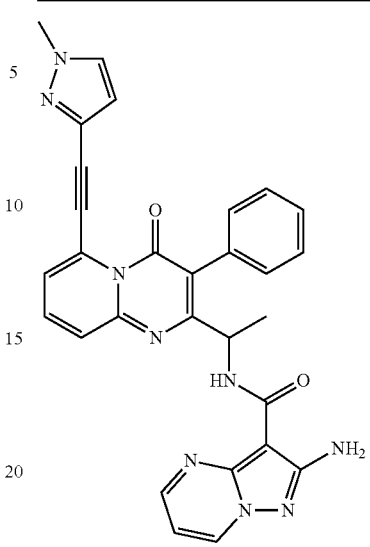
110
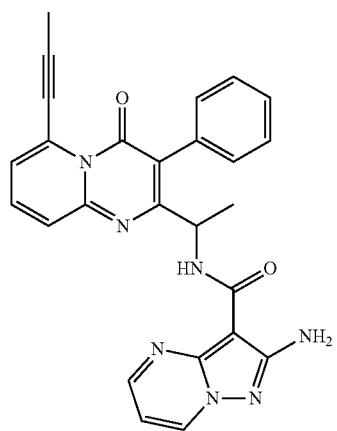 [SMILES: CC#Cc1cccc2nc(C(C)NC(=O)c3c(N)nn4cccnc34)c(-c3ccccc3)c(=O)n12]
108
111
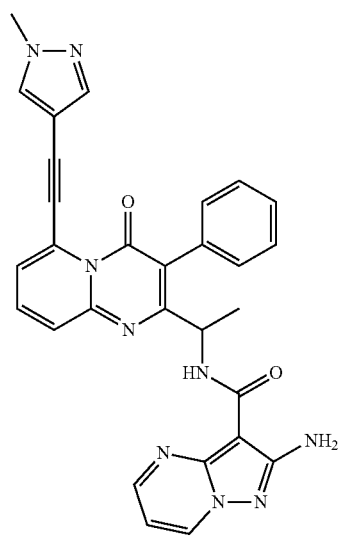 [SMILES: CC(NC(=O)c1c(N)nn2cccnc12)c1nc2cccc(C#Cc3cnn(C)c3)n2c(=O)c1-c1ccccc1]
109
112

TABLE 1-continued
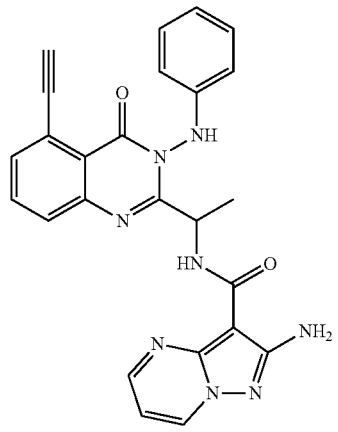 [SMILES: C#Cc1cccc2nc(C(C)NC(=O)c3c(N)nn4cccnc34)n(Nc3ccccc3)c(=O)c12]
113
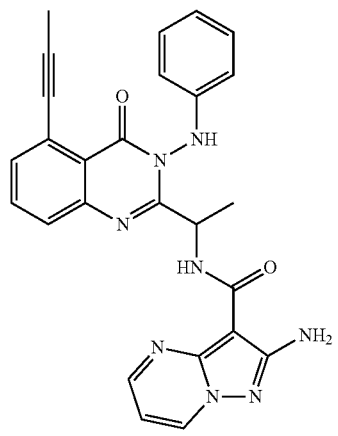 [SMILES: CC#Cc1cccc2nc(C(C)NC(=O)c3c(N)nn4cccnc34)n(Nc3ccccc3)c(=O)c12]
114
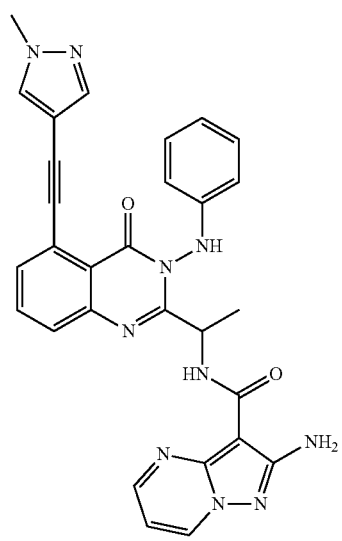 [SMILES: CC(NC(=O)c1c(N)nn2cccnc12)c1nc2cccc(C#Cc3cnn(C)c3)c2c(=O)n1Nc1ccccc1]
115
TABLE 1-continued
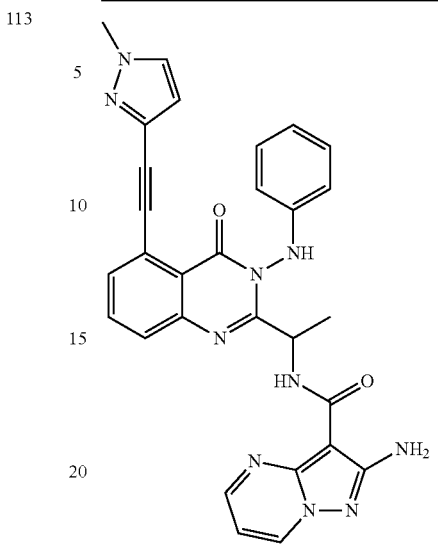
116
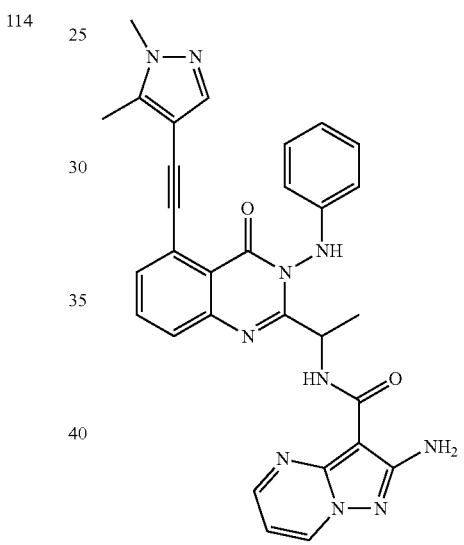
117
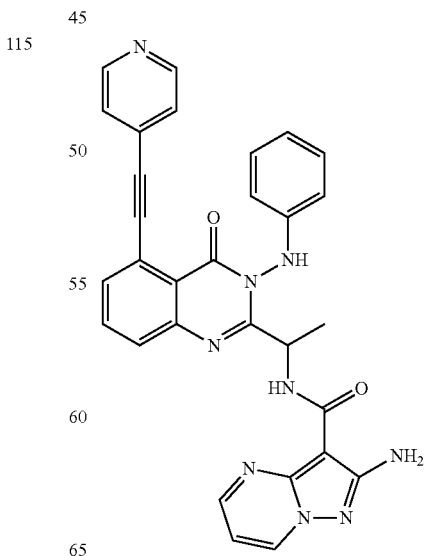
118

TABLE 1-continued
| | |
|---|---|
| 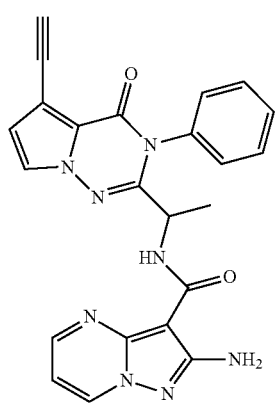 [SMILES: C#Cc1ccn2nc(C(C)NC(=O)c3c(N)nn4cccnc34)n(-c3ccccc3)c(=O)c12] 119 | 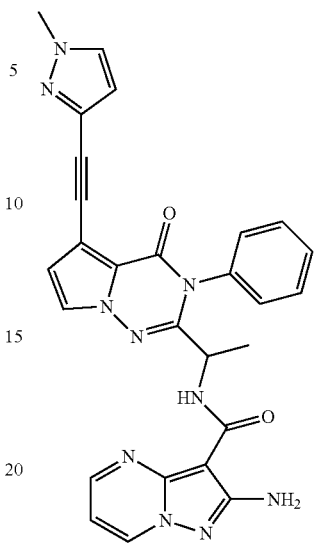 122 |
| 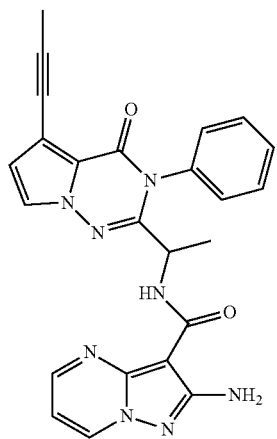 [SMILES: CC#Cc1ccn2nc(C(C)NC(=O)c3c(N)nn4cccnc34)n(-c3ccccc3)c(=O)c12] 120 | 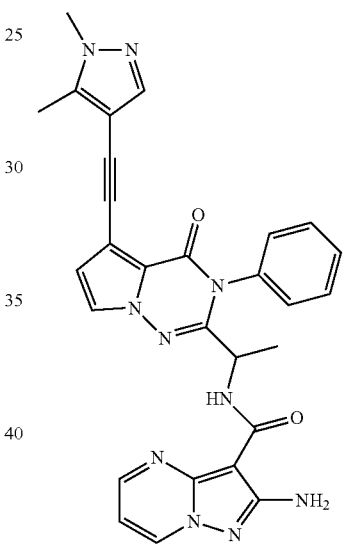 123 |
| 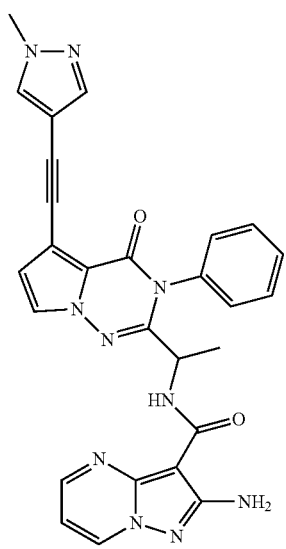 [SMILES: CC(NC(=O)c1c(N)nn2cccnc12)c1nn2ccc(C#Cc3cnn(C)c3)c2c(=O)n1-c1ccccc1] 121 | 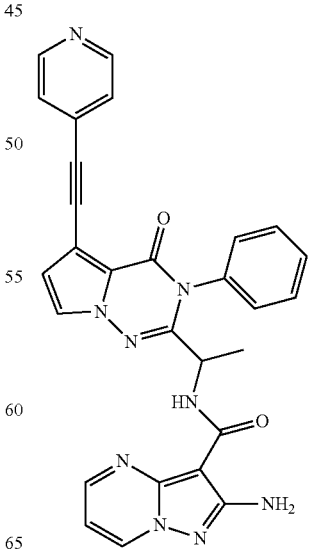 124 |

TABLE 1-continued
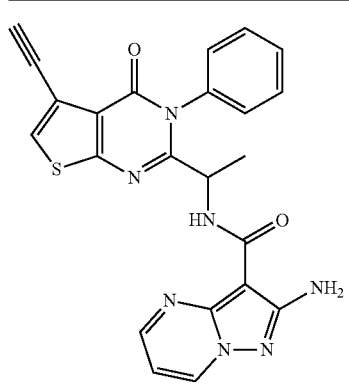
125
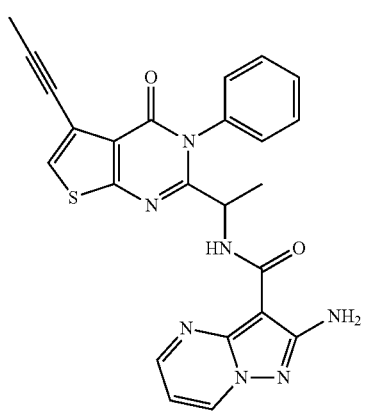 [SMILES: CC#Cc1csc2nc(C(C)NC(=O)c3c(N)nn4cccnc34)n(-c3ccccc3)c(=O)c12]
126
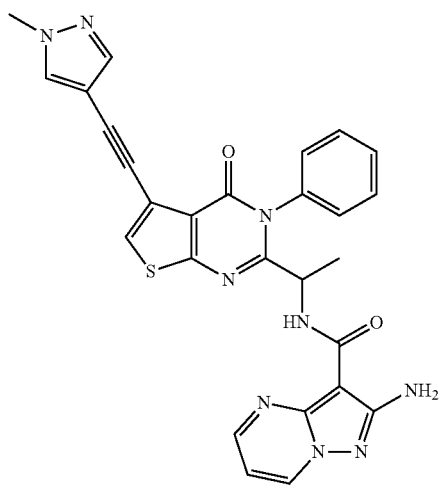
127
TABLE 1-continued
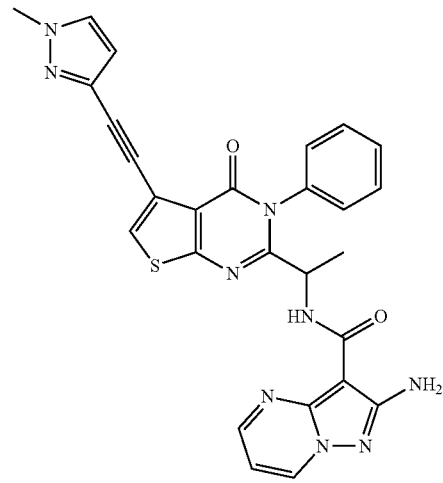
128
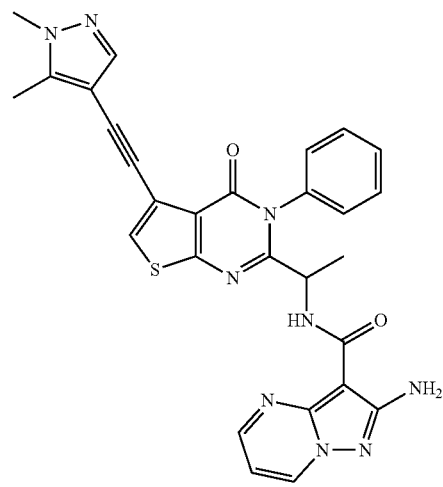
129
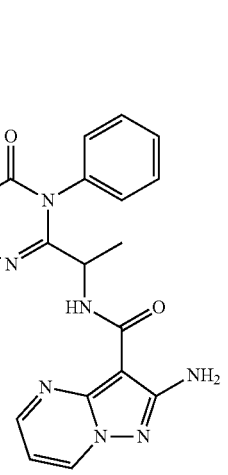
130

TABLE 1-continued
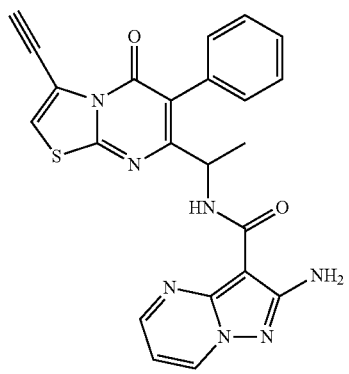 [SMILES: C#Cc1csc2nc(C(C)NC(=O)c3c(N)nn4cccnc34)c(-c3ccccc3)c(=O)n12]
131
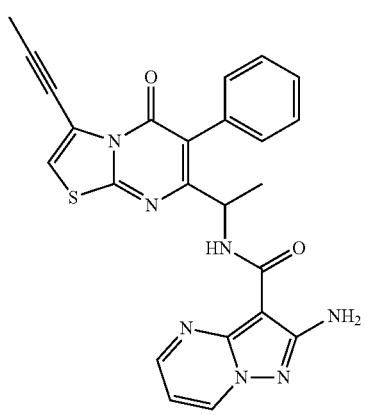 [SMILES: CC#Cc1csc2nc(C(C)NC(=O)c3c(N)nn4cccnc34)c(-c3ccccc3)c(=O)n12]
132
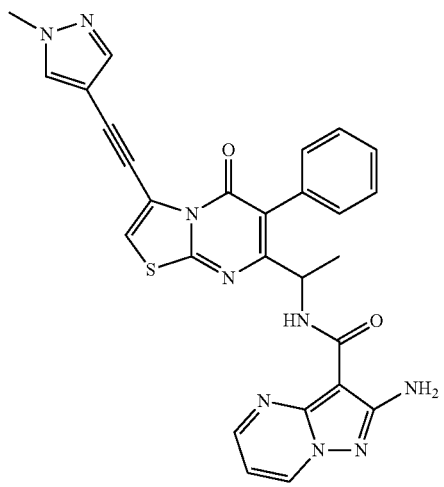 [SMILES: CC(NC(=O)c1c(N)nn2cccnc12)c1nc2scc(C#Cc3cnn(C)c3)n2c(=O)c1-c1ccccc1]
133
TABLE 1-continued
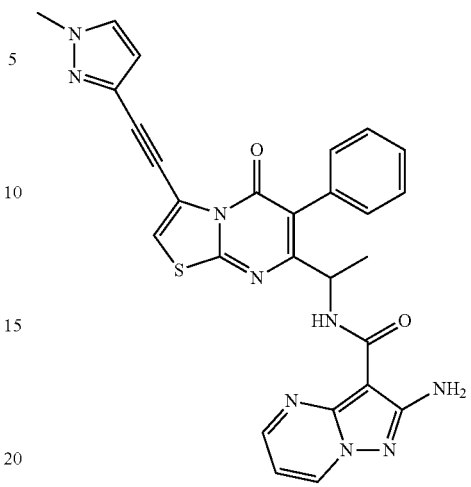
134
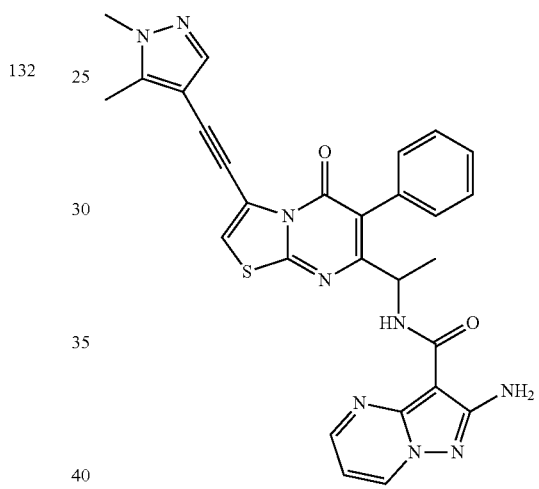
135
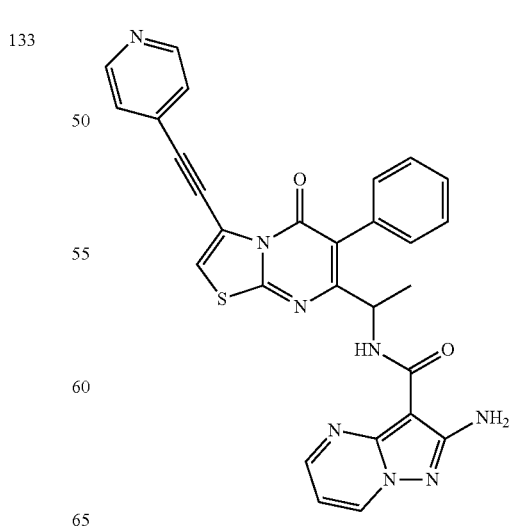
136

TABLE 1-continued
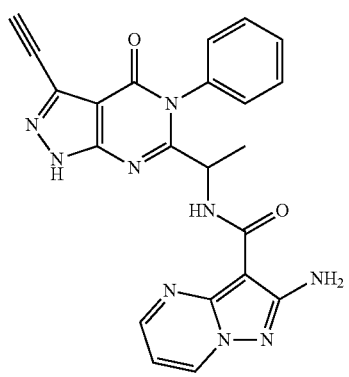 [SMILES: C#Cc1n[nH]c2nc(C(C)NC(=O)c3c(N)nn4cccnc34)n(-c3ccccc3)c(=O)c12] 137
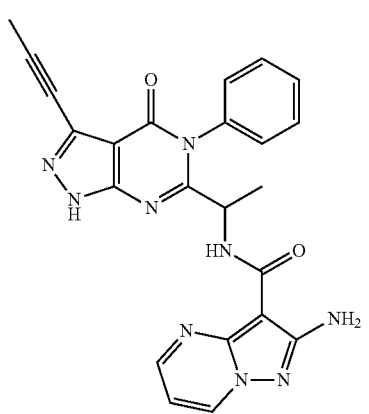 [SMILES: CC#Cc1n[nH]c2nc(C(C)NC(=O)c3c(N)nn4cccnc34)n(-c3ccccc3)c(=O)c12] 138
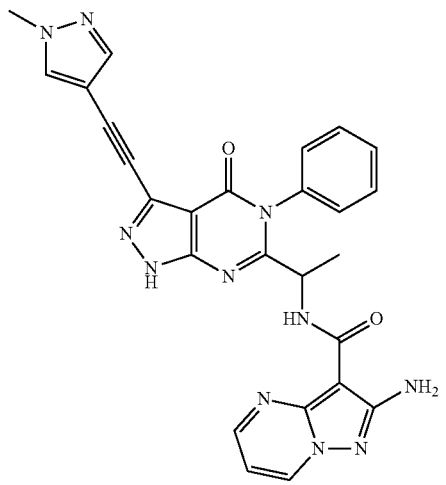 [SMILES: CC(NC(=O)c1c(N)nn2cccnc12)c1nc2[nH]nc(C#Cc3cnn(C)c3)c2c(=O)n1-c1ccccc1] 139
TABLE 1-continued
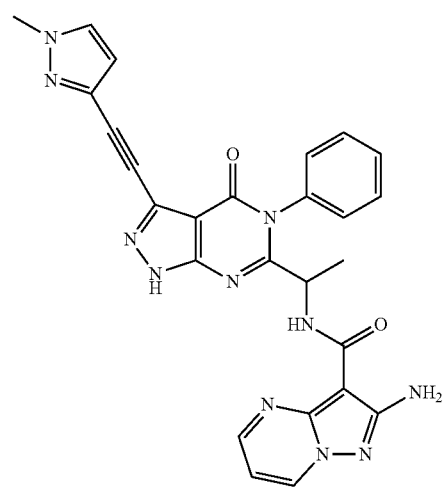 [SMILES: CC(NC(=O)c1c(N)nn2cccnc12)c1nc2[nH]nc(C#Cc3ccn(C)n3)c2c(=O)n1-c1ccccc1] 140
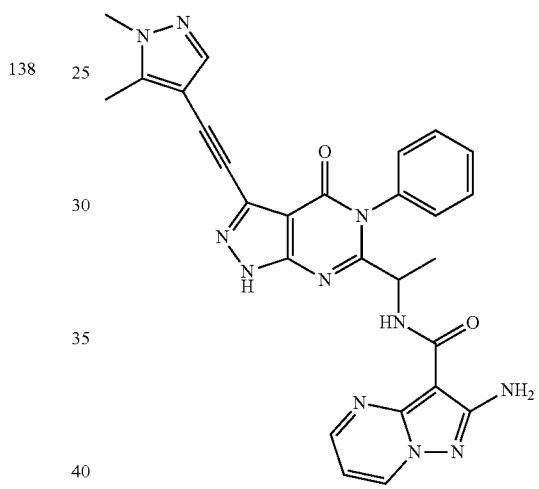 141
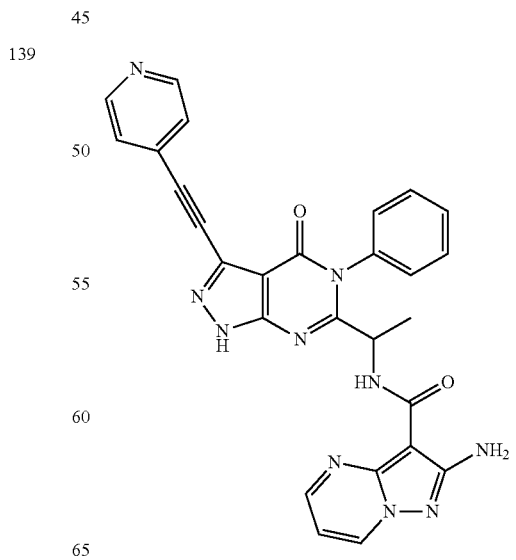 142

TABLE 1-continued
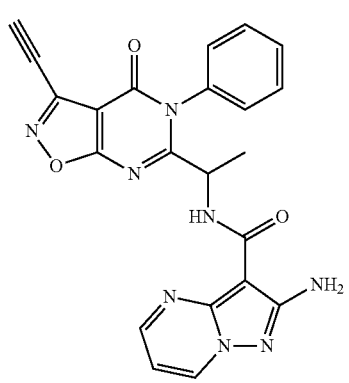 [SMILES: C#Cc1noc2nc(C(C)NC(=O)c3c(N)nn4cccnc34)n(-c3ccccc3)c(=O)c12]
143
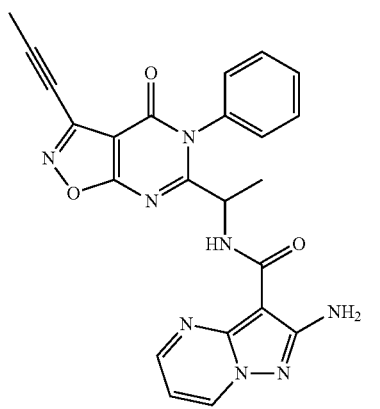 [SMILES: CC#Cc1noc2nc(C(C)NC(=O)c3c(N)nn4cccnc34)n(-c3ccccc3)c(=O)c12]
144
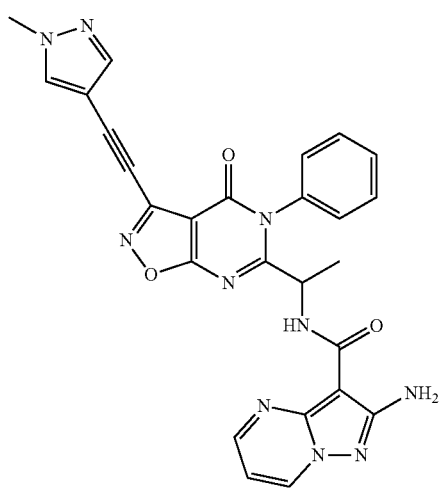
145
TABLE 1-continued
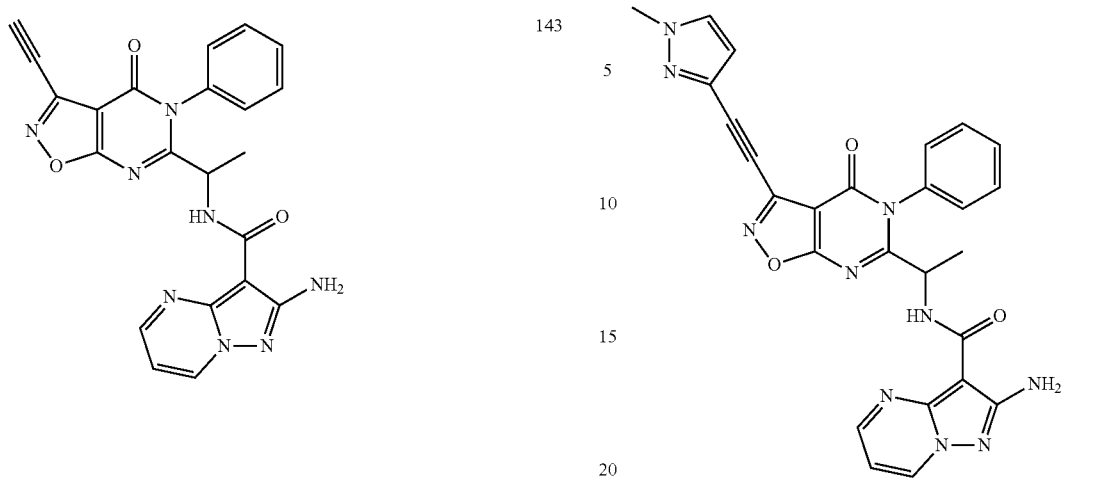
146
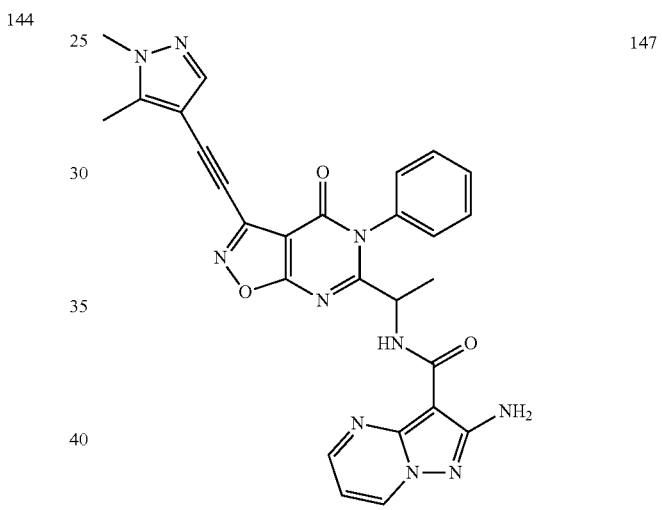
147
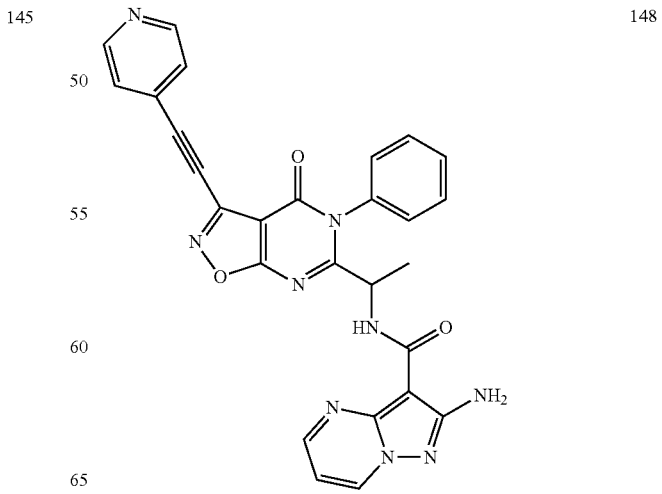
148

TABLE 1-continued
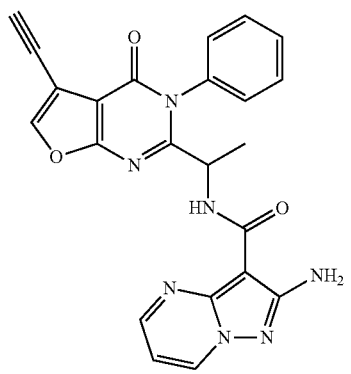 [SMILES: C#Cc1coc2nc(C(C)NC(=O)c3c(N)nn4cccnc34)n(-c3ccccc3)c(=O)c12] 149
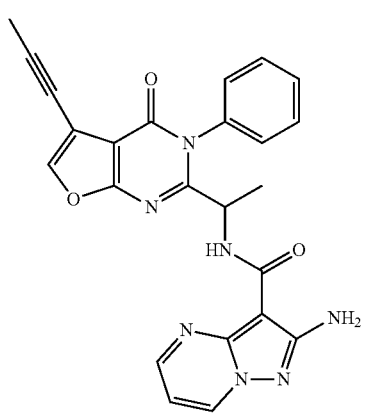 150
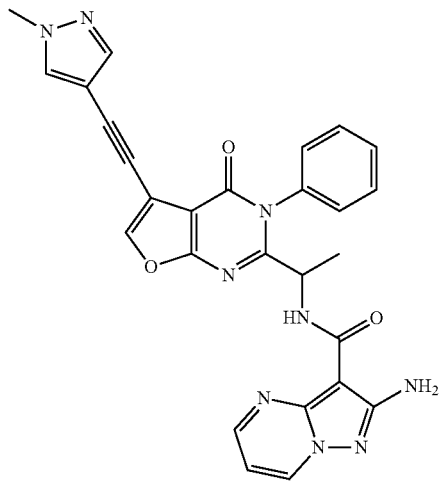 [SMILES: CC(NC(=O)c1c(N)nn2cccnc12)c1nc2occ(C#Cc3cnn(C)c3)c2c(=O)n1-c1ccccc1] 151
TABLE 1-continued
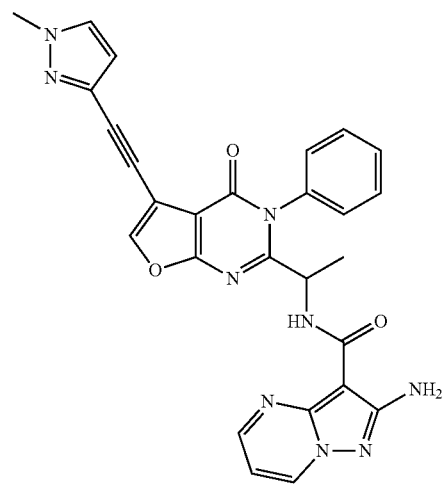 152
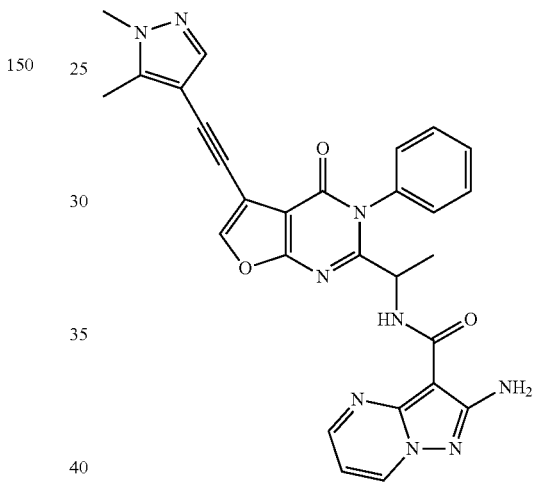 153
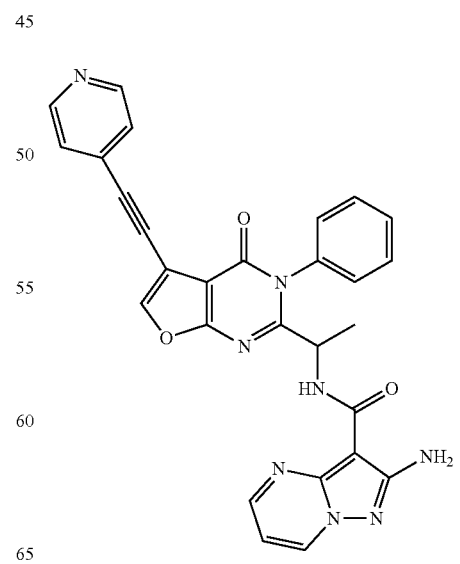 154

TABLE 1-continued
155
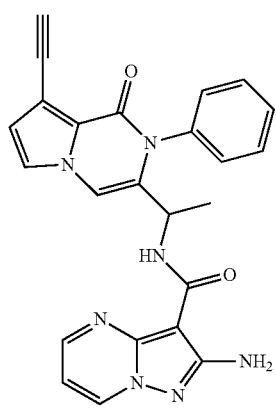
156
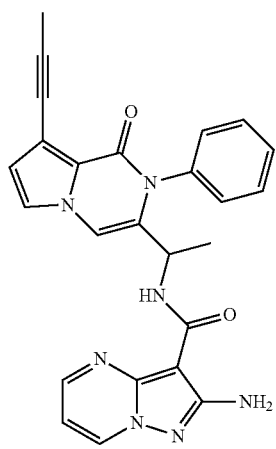
157
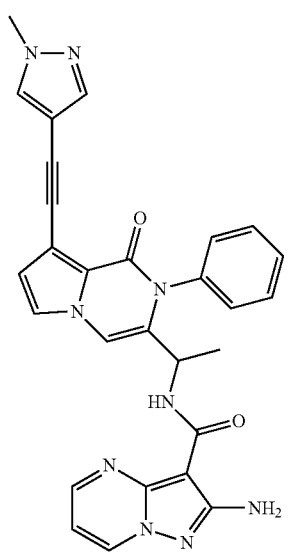
TABLE 1-continued
158
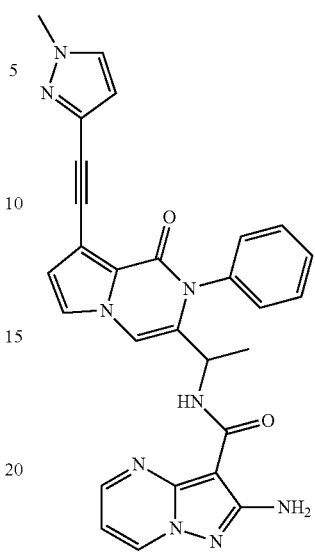
159
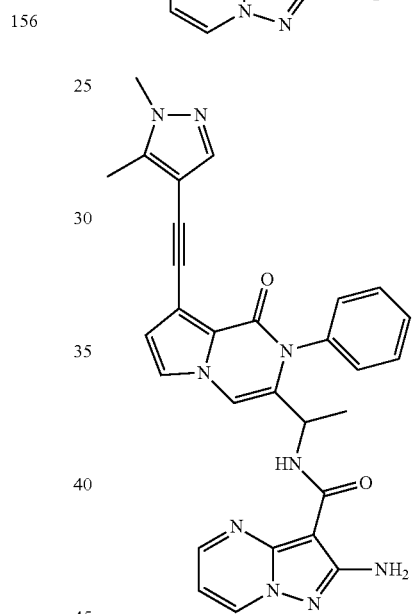
160
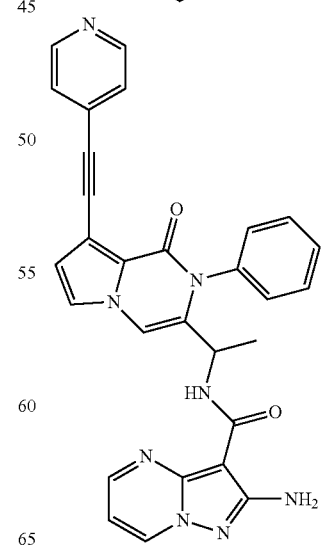

TABLE 1-continued
161
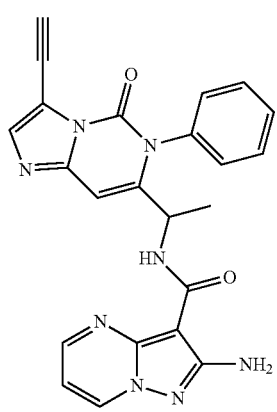 [SMILES: C#Cc1cnc2cc(C(C)NC(=O)c3c(N)nn4cccnc34)n(-c3ccccc3)c(=O)n12]
162
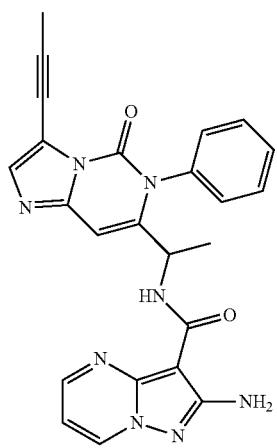
163
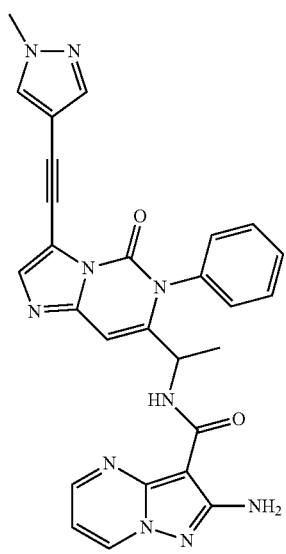
TABLE 1-continued
164
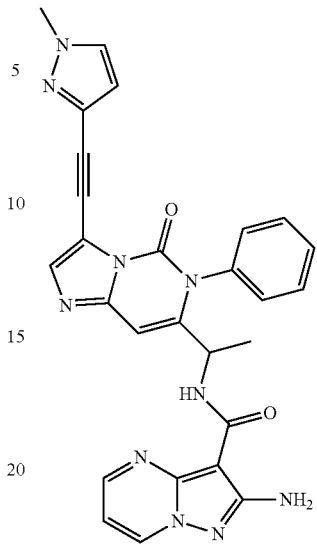
165
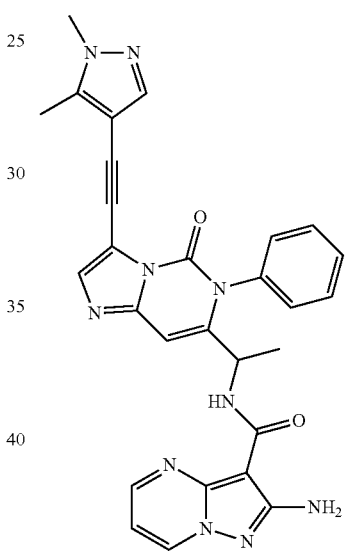
166
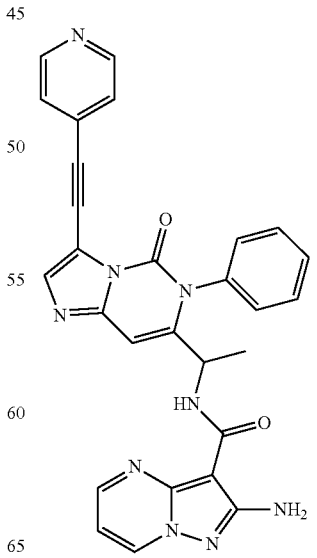

TABLE 1-continued
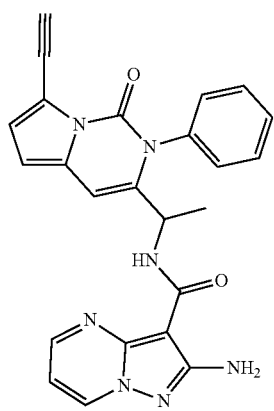 [SMILES: C#Cc1ccc2cc(C(C)NC(=O)c3c(N)nn4cccnc34)n(-c3ccccc3)c(=O)n12]
167
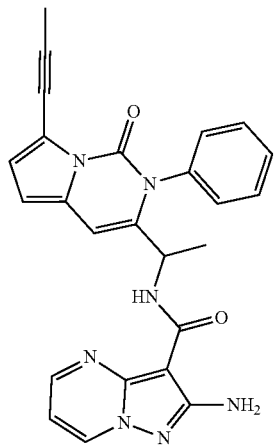 [SMILES: CC#Cc1ccc2cc(C(C)NC(=O)c3c(N)nn4cccnc34)n(-c3ccccc3)c(=O)n12]
168
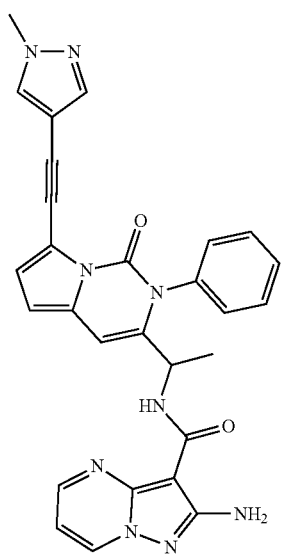 [SMILES: CC(NC(=O)c1c(N)nn2cccnc12)c1cc2ccc(C#Cc3cnn(C)c3)n2c(=O)n1-c1ccccc1]
169
TABLE 1-continued
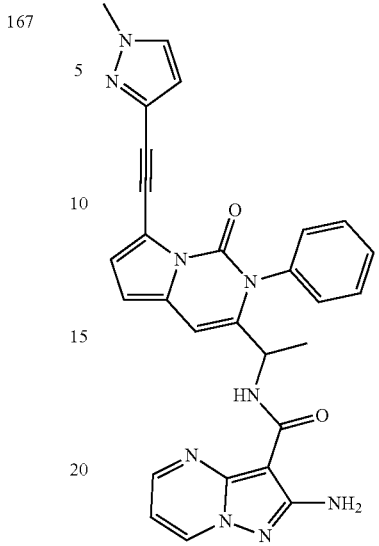
170
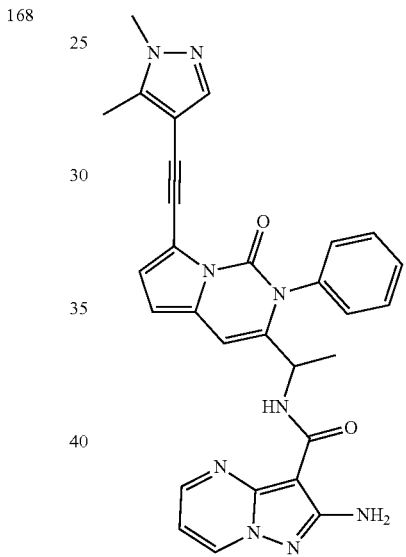
171
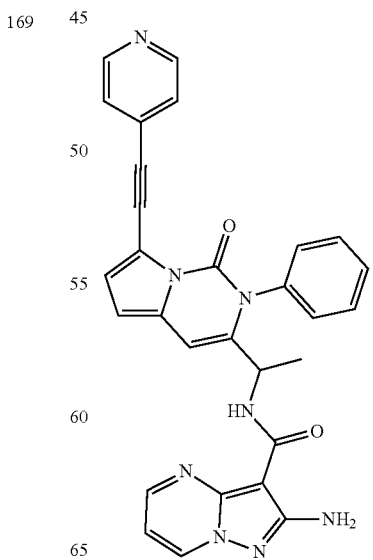
172

TABLE 1-continued
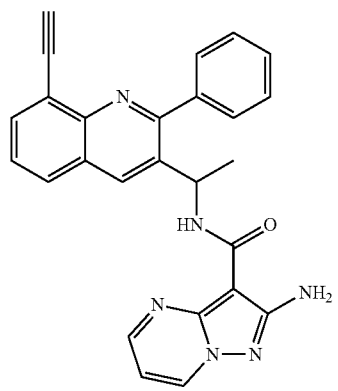 [SMILES: C#Cc1cccc2cc(C(C)NC(=O)c3c(N)nn4cccnc34)c(-c3ccccc3)nc12]
173
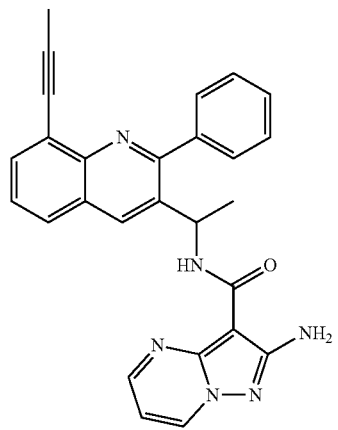 [SMILES: CC#Cc1cccc2cc(C(C)NC(=O)c3c(N)nn4cccnc34)c(-c3ccccc3)nc12]
174
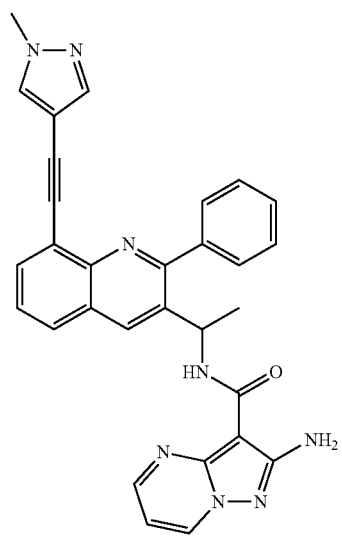 [SMILES: CC(NC(=O)c1c(N)nn2cccnc12)c1cc2cccc(C#Cc3cnn(C)c3)c2nc1-c1ccccc1]
175
TABLE 1-continued
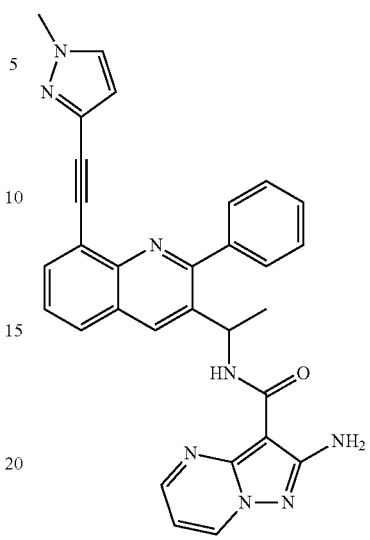
176
177
178

TABLE 1-continued
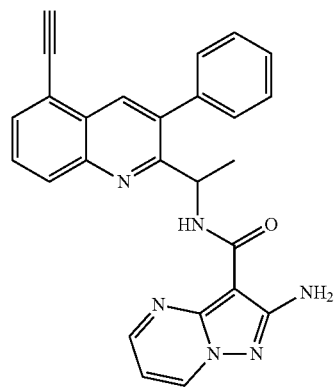 [SMILES: C#Cc1cccc2nc(C(C)NC(=O)c3c(N)nn4cccnc34)c(-c3ccccc3)cc12]
179
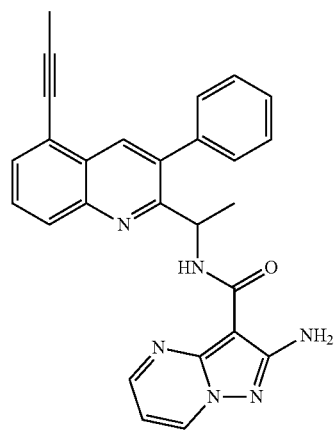 [SMILES: CC#Cc1cccc2nc(C(C)NC(=O)c3c(N)nn4cccnc34)c(-c3ccccc3)cc12]
180
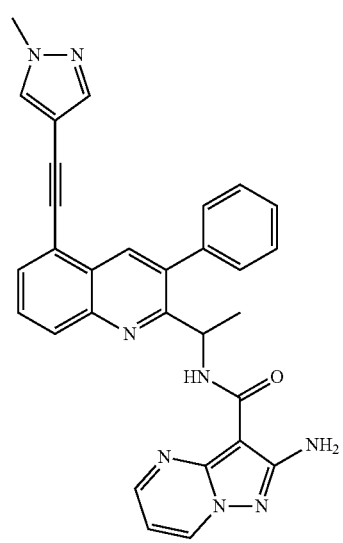 [SMILES: CC(NC(=O)c1c(N)nn2cccnc12)c1nc2cccc(C#Cc3cnn(C)c3)c2cc1-c1ccccc1]
181
TABLE 1-continued
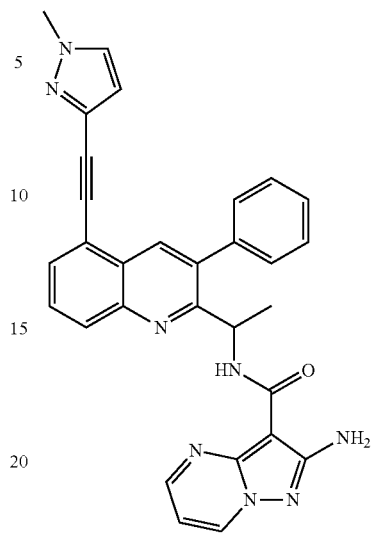
182
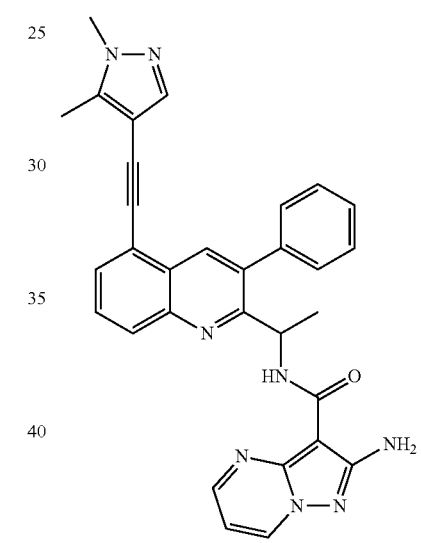
183
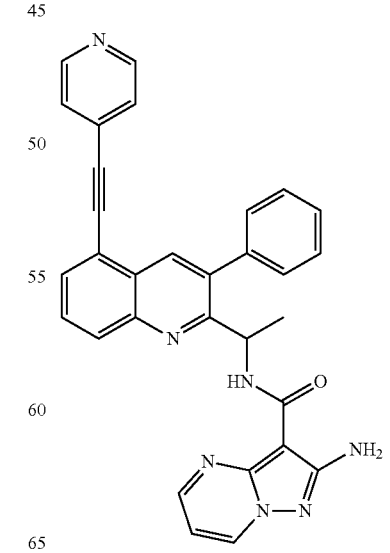
184

TABLE 1-continued
185
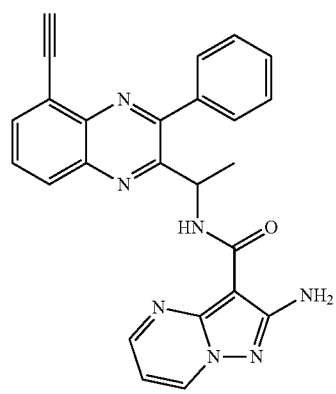
186
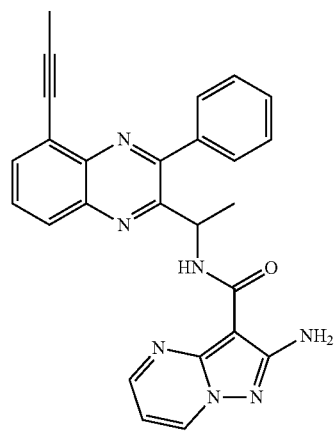 [SMILES: CC#Cc1cccc2nc(C(C)NC(=O)c3c(N)nn4cccnc34)c(-c3ccccc3)nc12]
187
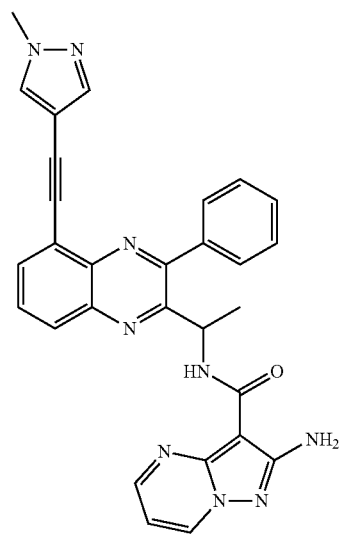 [SMILES: CC(NC(=O)c1c(N)nn2cccnc12)c1nc2cccc(C#Cc3cnn(C)c3)c2nc1-c1ccccc1]
188
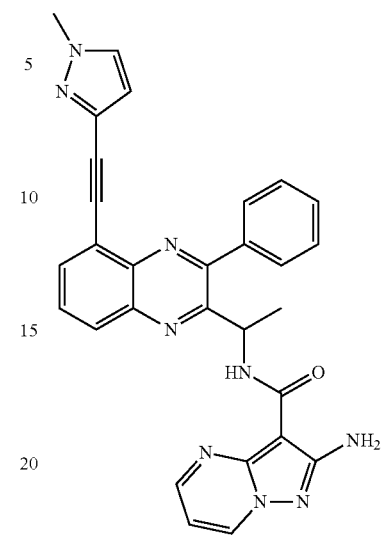
189
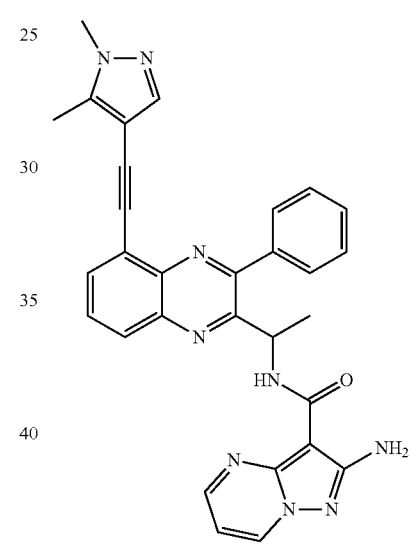
190
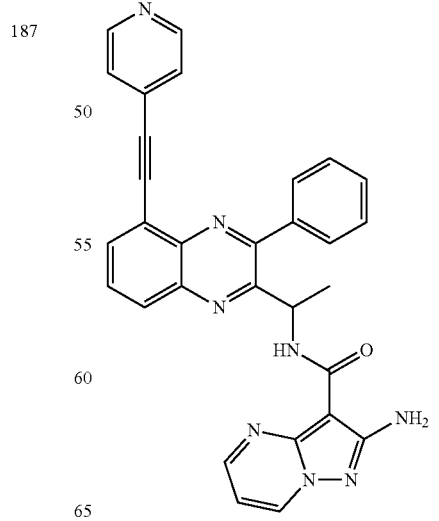

TABLE 1-continued
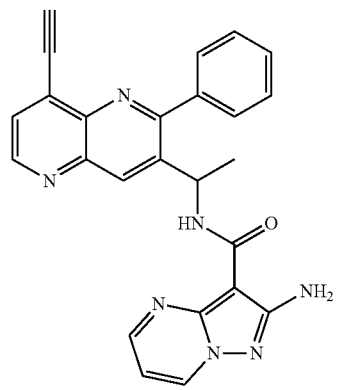 [SMILES: C#Cc1ccnc2cc(C(C)NC(=O)c3c(N)nn4cccnc34)c(-c3ccccc3)nc12]
191
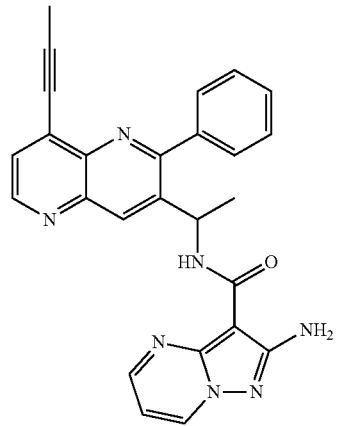 [SMILES: CC#Cc1ccnc2cc(C(C)NC(=O)c3c(N)nn4cccnc34)c(-c3ccccc3)nc12]
192
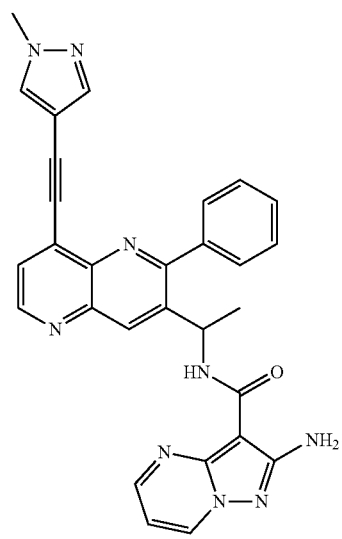 [SMILES: CC(NC(=O)c1c(N)nn2cccnc12)c1cc2nncc(C#Cc3ccn(C)n3)c2cc1-c1ccccc1]
193
TABLE 1-continued
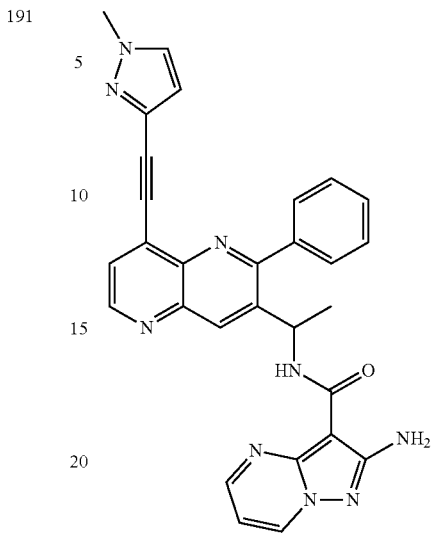
194
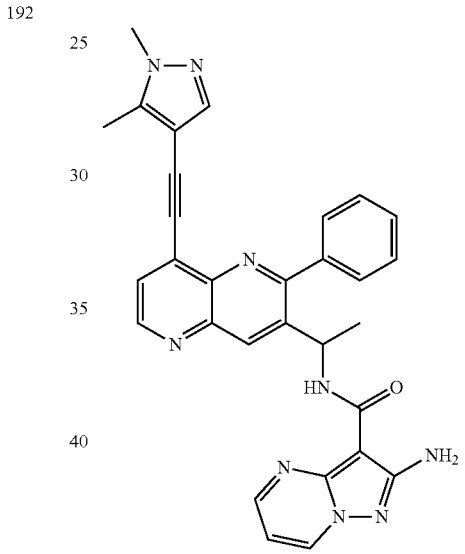
195
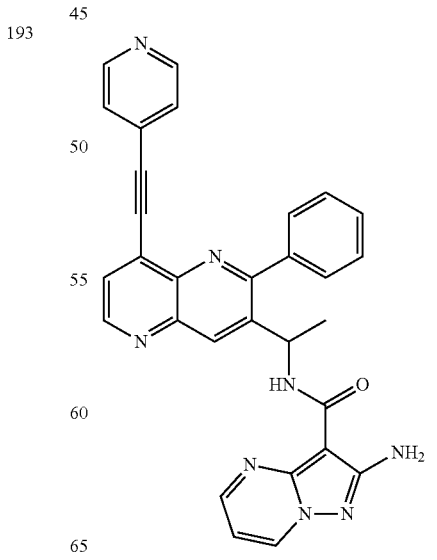
196

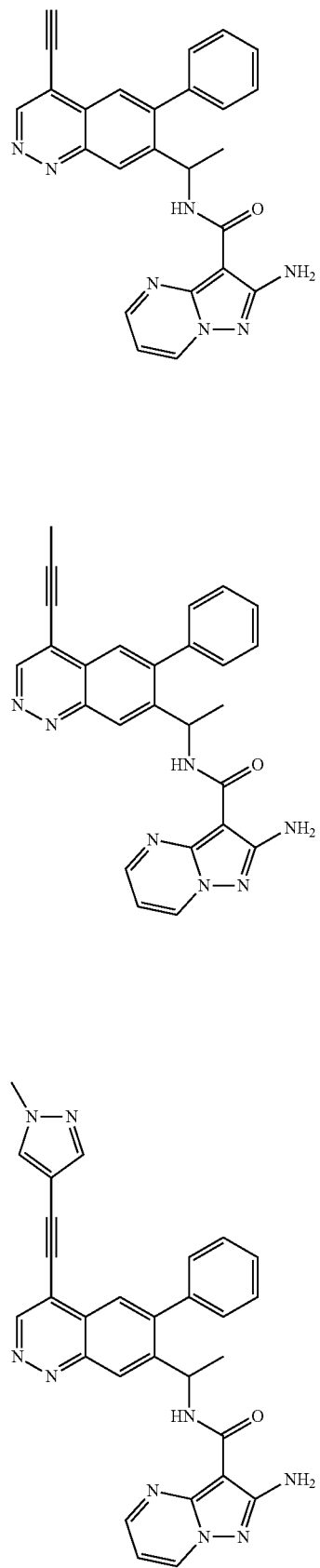
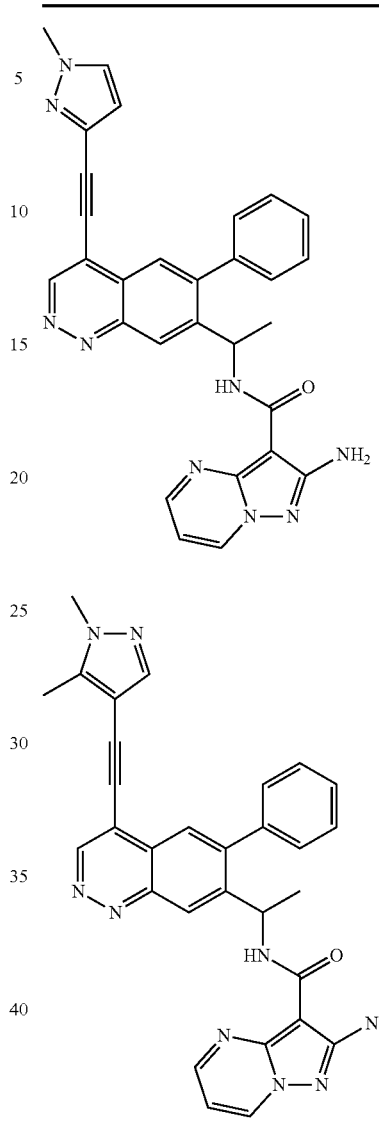
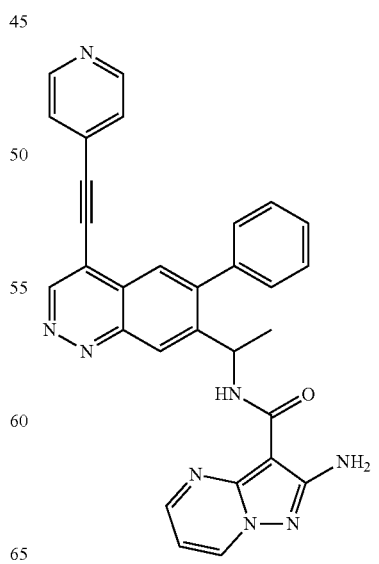

TABLE 1-continued
203
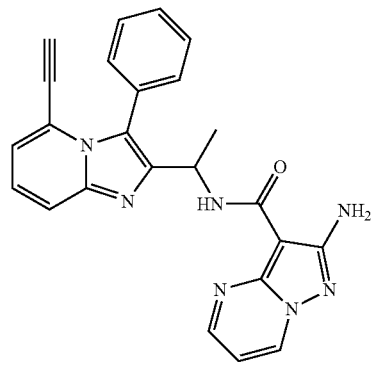 [SMILES: C#Cc1cccc2nc(C(C)NC(=O)c3c(N)nn4cccnc34)c(-c3ccccc3)n12]
204
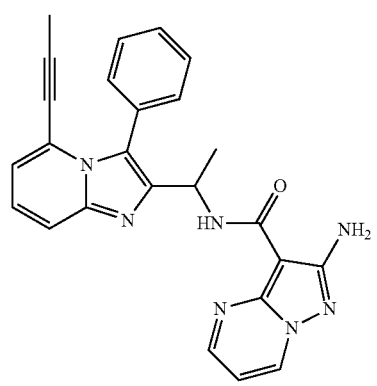 [SMILES: CC#Cc1cccc2nc(C(C)NC(=O)c3c(N)nn4cccnc34)c(-c3ccccc3)n12]
205
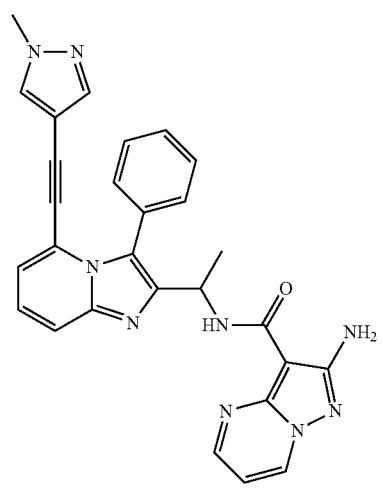 [SMILES: CC(NC(=O)c1c(N)nn2cccnc12)c1nc2cccc(C#Cc3cnn(C)c3)n2c1-c1ccccc1]
TABLE 1-continued
206
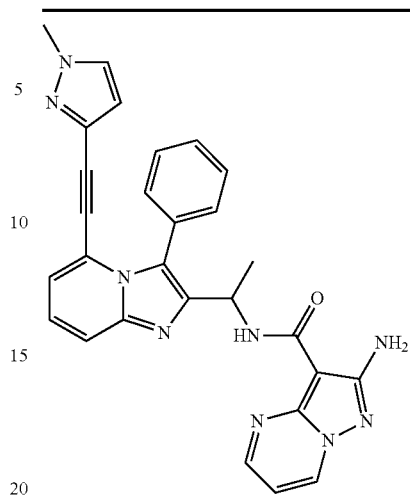
207
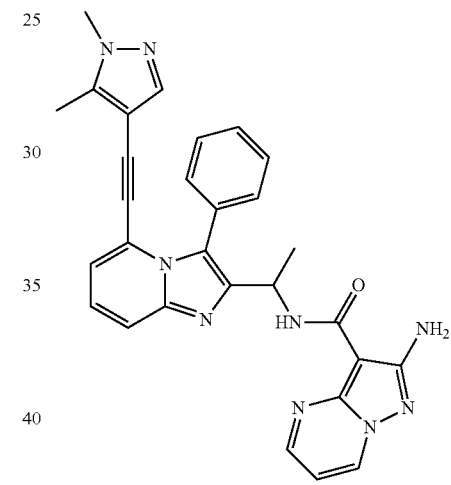
208
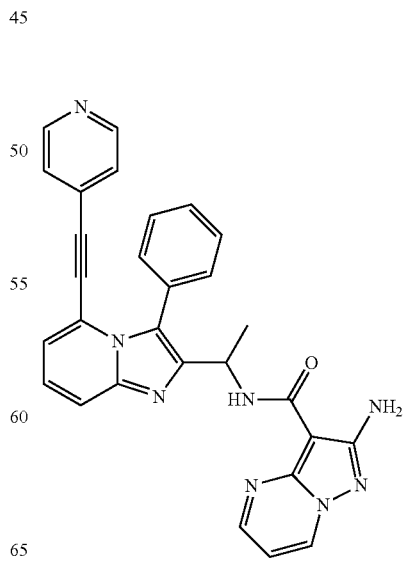

TABLE 1-continued
209
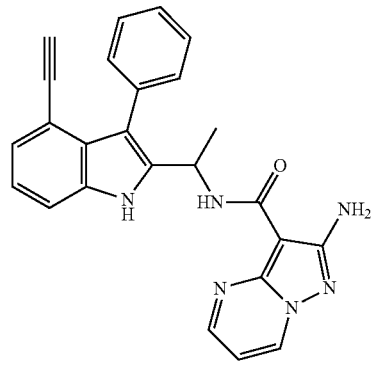 [SMILES: C#Cc1cccc2[nH]c(C(C)NC(=O)c3c(N)nn4cccnc34)c(-c3ccccc3)c12]
210
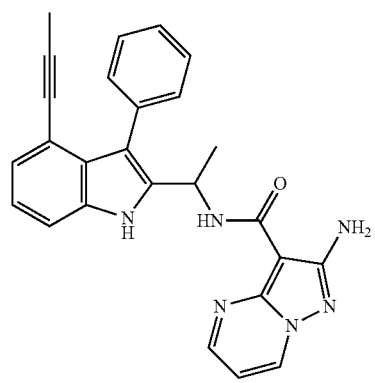 [SMILES: CC#Cc1cccc2[nH]c(C(C)NC(=O)c3c(N)nn4cccnc34)c(-c3ccccc3)c12]
211
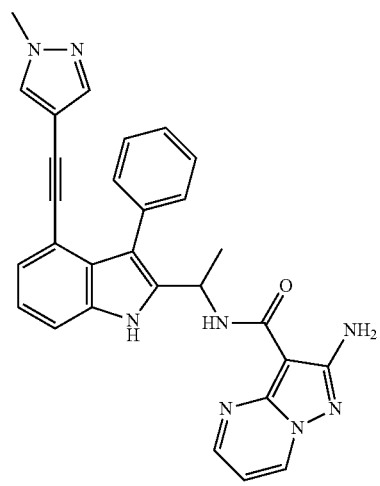 [SMILES: CC(NC(=O)c1c(N)nn2cccnc12)c1[nH]c2cccc(C#Cc3ccn(C)n3)c2c1-c1ccccc1]
TABLE 1-continued
212
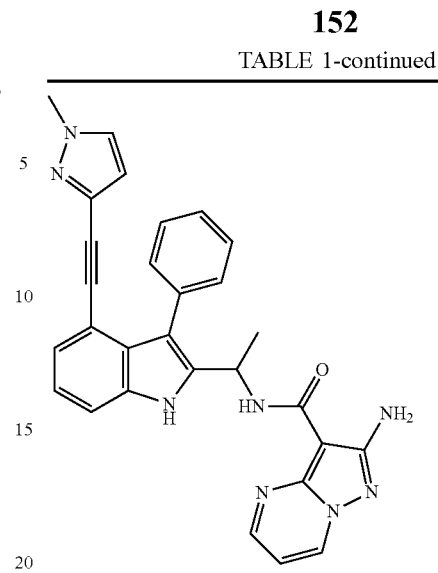
213
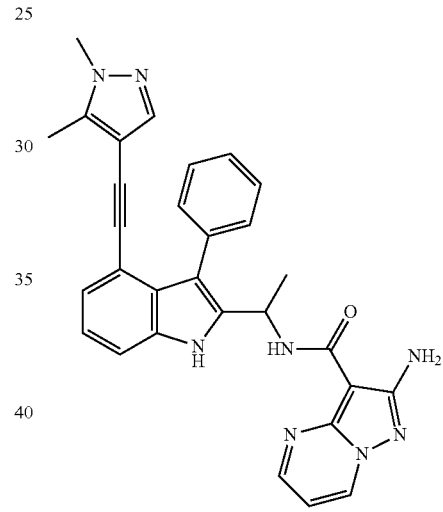
214
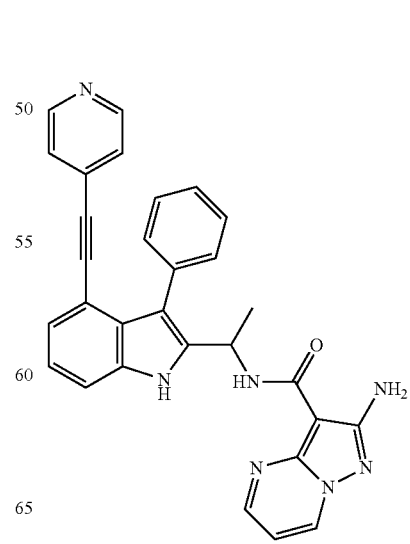

TABLE 1-continued
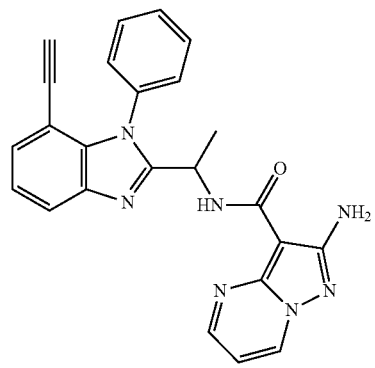 [SMILES: C#Cc1cccc2nc(C(C)NC(=O)c3c(N)nn4cccnc34)n(-c3ccccc3)c12]
215
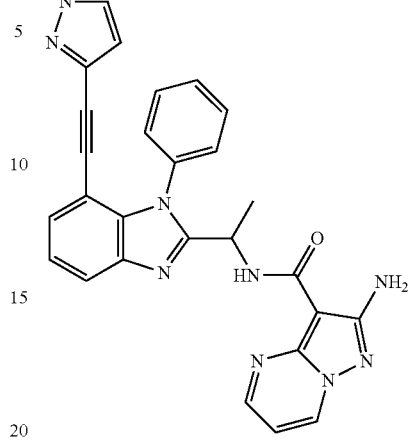
218
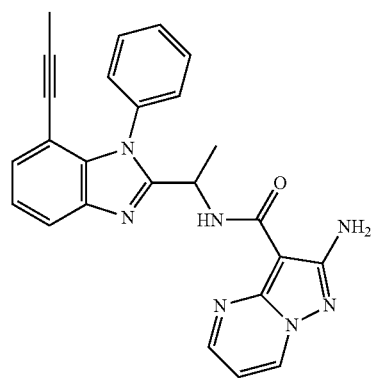 [SMILES: CC#Cc1cccc2nc(C(C)NC(=O)c3c(N)nn4cccnc34)n(-c3ccccc3)c12]
216
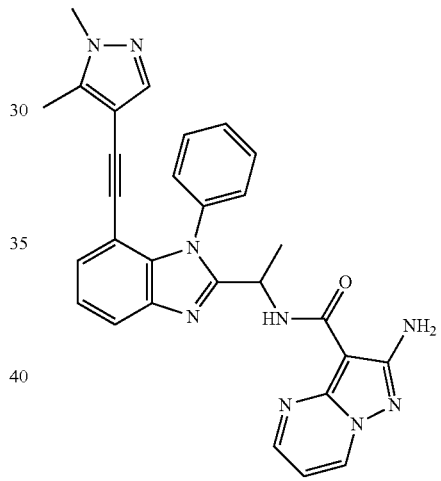
219
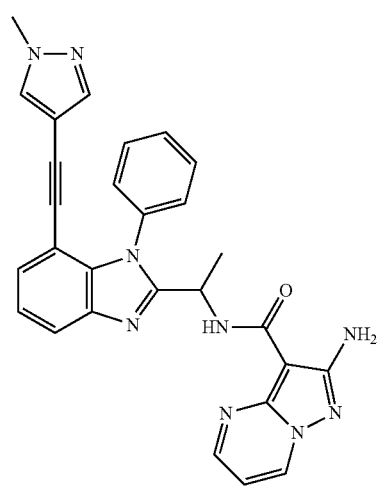
217
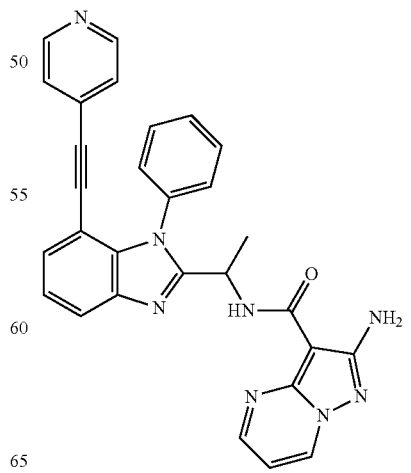
220

TABLE 1-continued
| | |
|---|---|
| 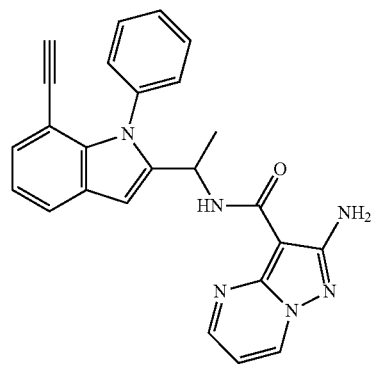 [SMILES: C#Cc1cccc2cc(C(C)NC(=O)c3c(N)nn4cccnc34)n(-c3ccccc3)c12] | 221 |
| 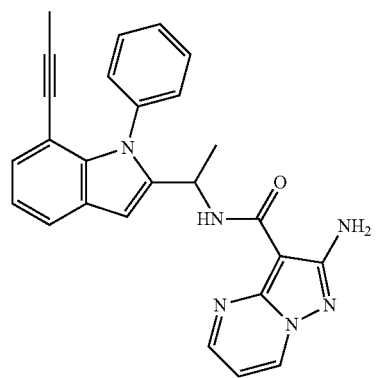 [SMILES: CC#Cc1cccc2cc(C(C)NC(=O)c3c(N)nn4cccnc34)n(-c3ccccc3)c12] | 222 |
| 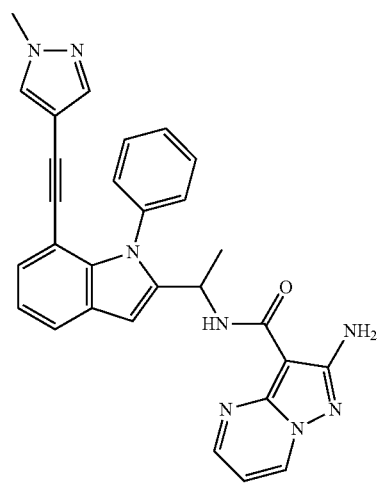 [SMILES: CC(NC(=O)c1c(N)nn2cccnc12)c1cc2cccc(C#Cc3cnn(C)c3)c2n1-c1ccccc1] | 223 |
| 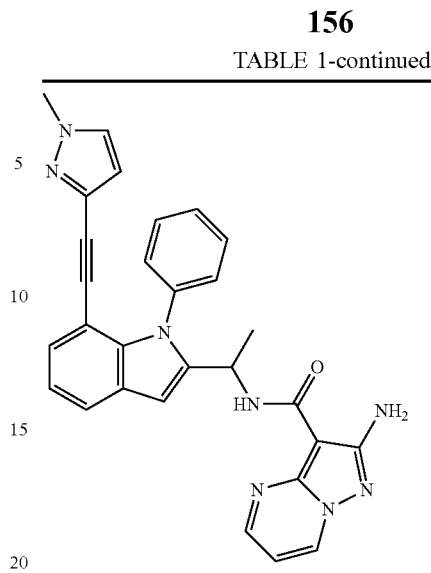 | 224 |
| 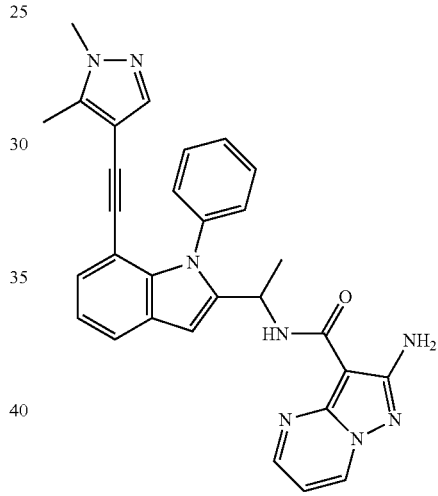 | 225 |
| 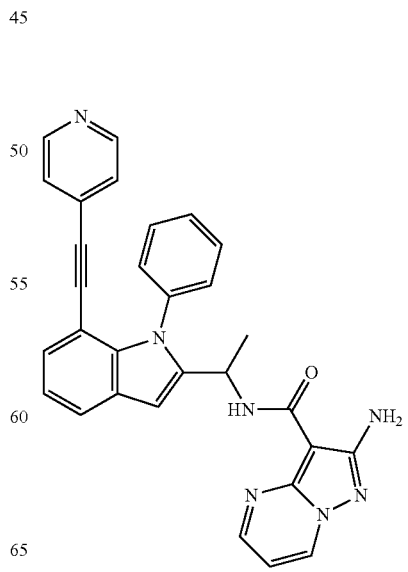 | 226 |

TABLE 1-continued
227
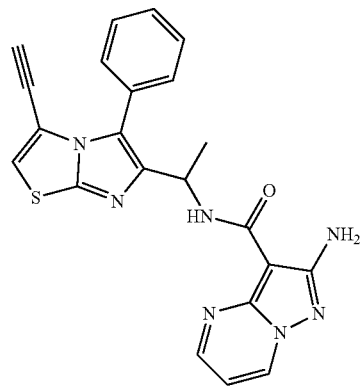 [SMILES: C#Cc1csc2nc(C(C)NC(=O)c3c(N)nn4cccnc34)c(-c3ccccc3)n12]
228
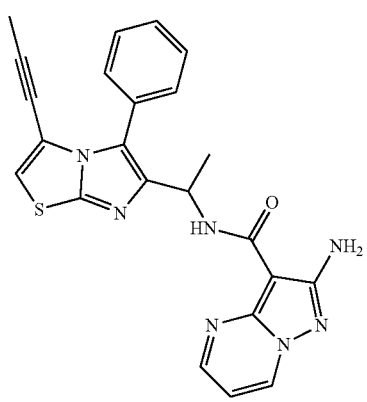 [SMILES: CC#Cc1csc2nc(C(C)NC(=O)c3c(N)nn4cccnc34)c(-c3ccccc3)n12]
229
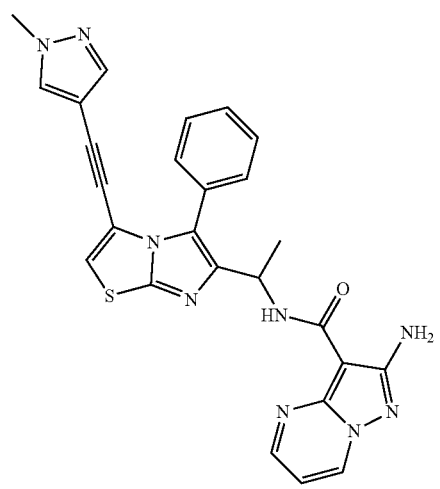 [SMILES: CC(NC(=O)c1c(N)nn2cccnc12)c1nc2scc(C#Cc3cnn(C)c3)n2c1-c1ccccc1]
TABLE 1-continued
230
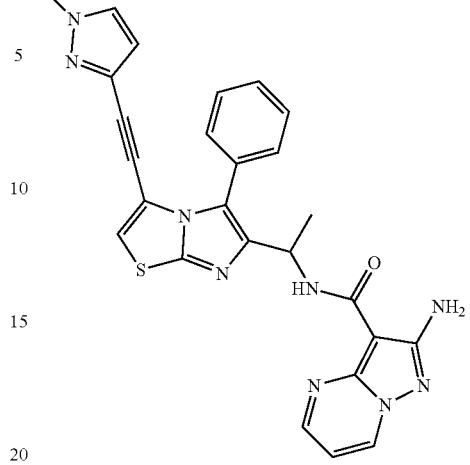
231
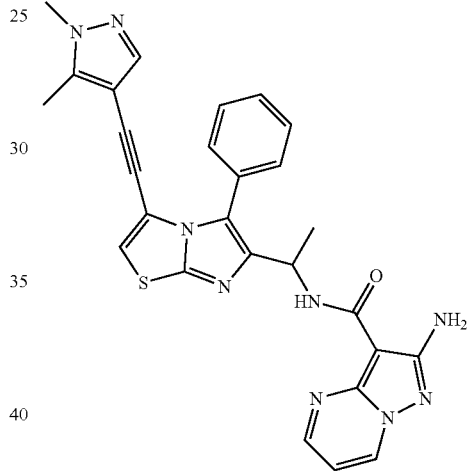
232
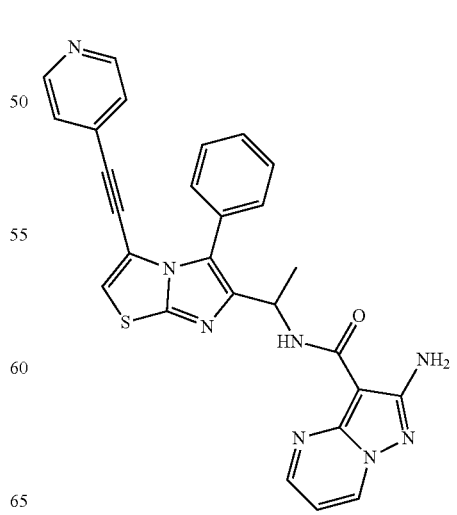

TABLE 1-continued
233
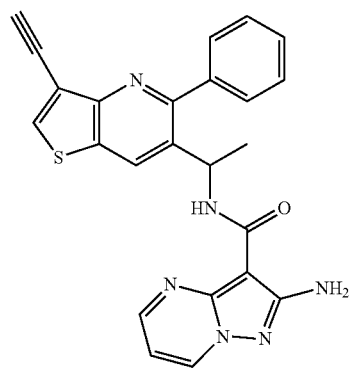 [SMILES: C#Cc1csc2cc(C(C)NC(=O)c3c(N)nn4cccnc34)c(-c3ccccc3)nc12]
236
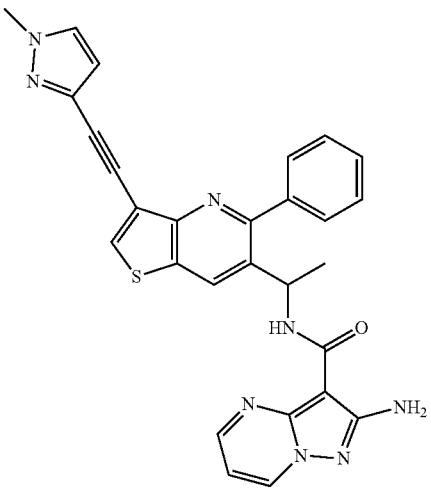
234
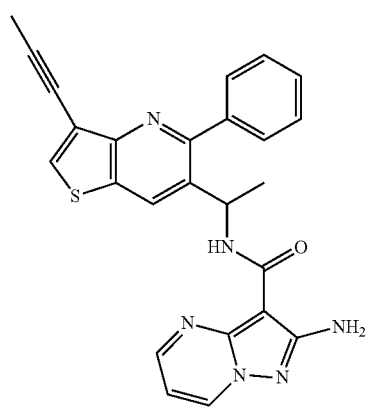 [SMILES: CC#Cc1csc2cc(C(C)NC(=O)c3c(N)nn4cccnc34)c(-c3ccccc3)nc12]
237
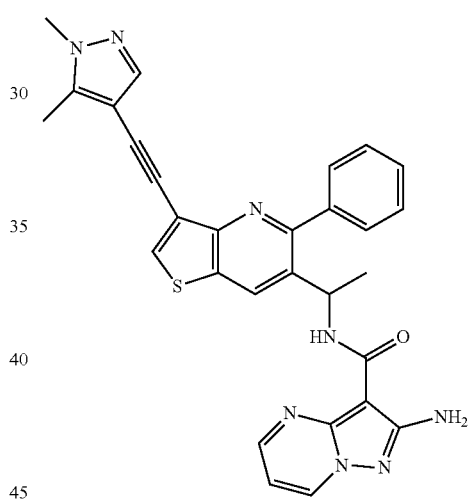
235
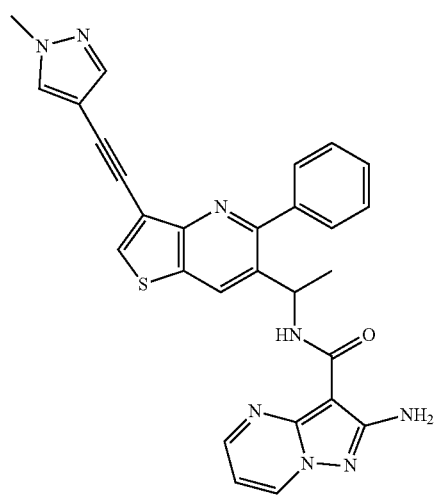 [SMILES: CC(NC(=O)c1c(N)nn2cccnc12)c1cc2scc(C#Cc3cnn(C)c3)c2nc1-c1ccccc1]
238
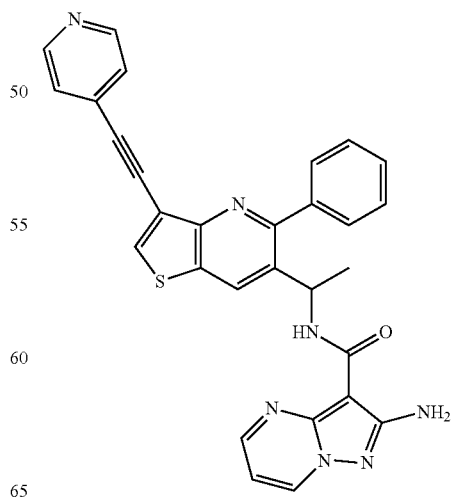

TABLE 1-continued
| | |
|---|---|
| 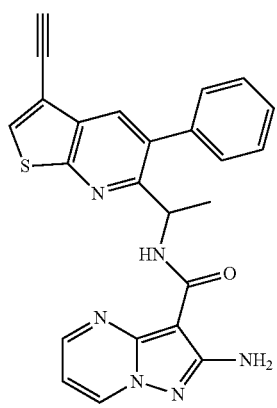 239 | 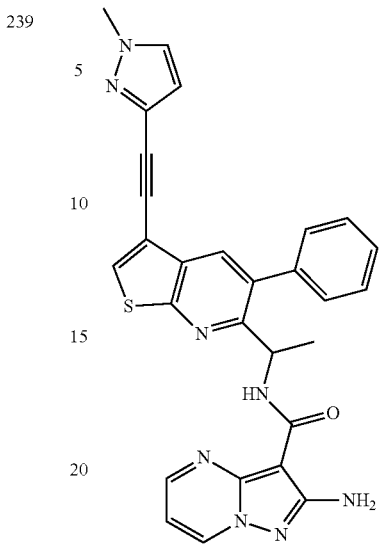 242 |
| 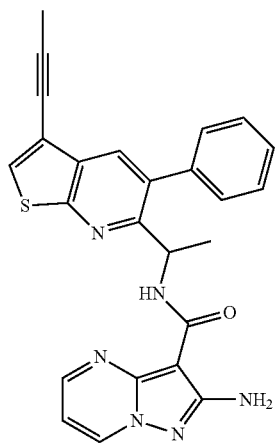 240 | 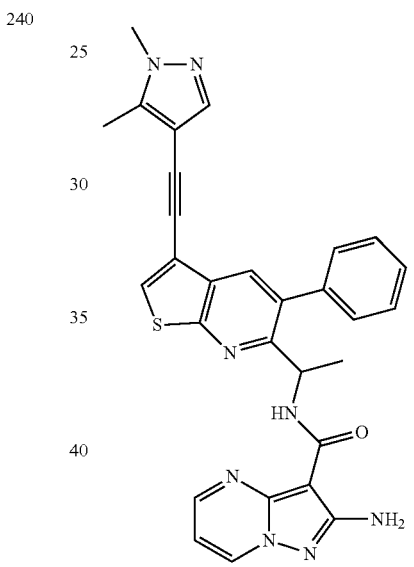 243 |
| 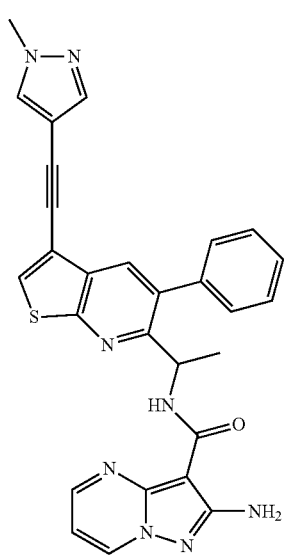 241 | 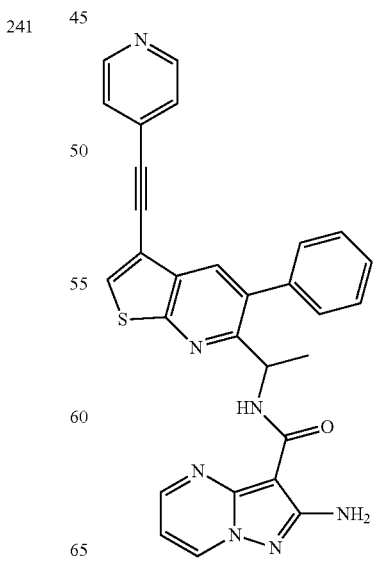 244 |

TABLE 1-continued
245 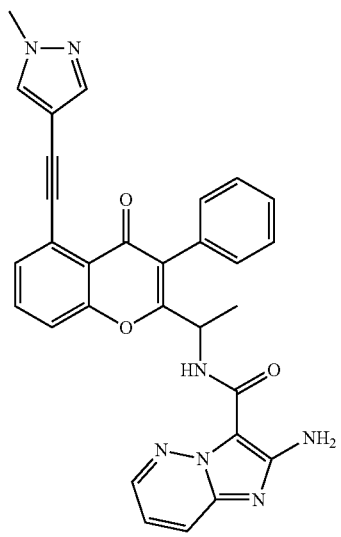 [SMILES: CC(NC(=O)c1c(N)nc2cccnn12)c1oc2cccc(C#Cc3cnn(C)c3)c2c(=O)c1-c1ccccc1]
246 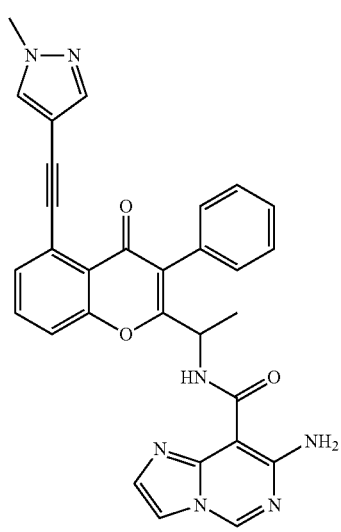
247 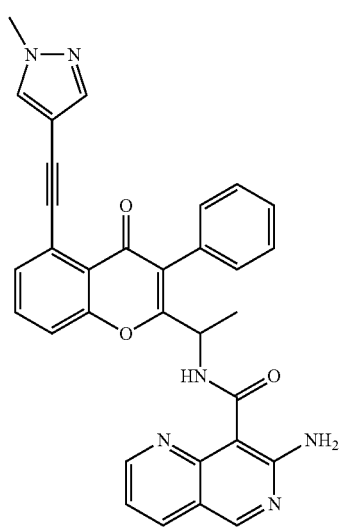 [SMILES: CC(NC(=O)c1c(N)ncc2cccnc12)c1oc2cccc(C#Cc3cnn(C)c3)c2c(=O)c1-c1ccccc1]
TABLE 1-continued
248 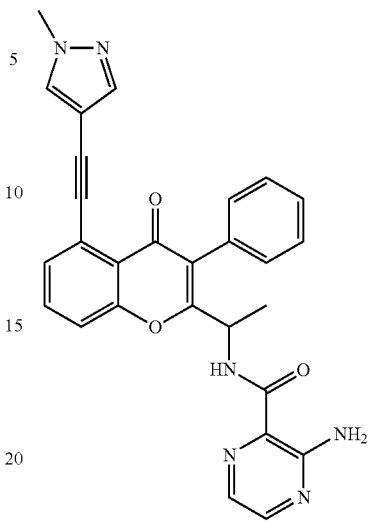
249 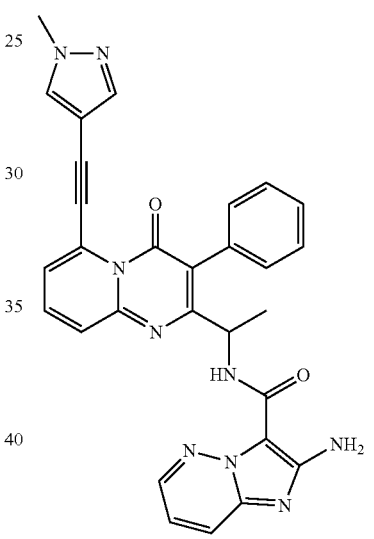
250 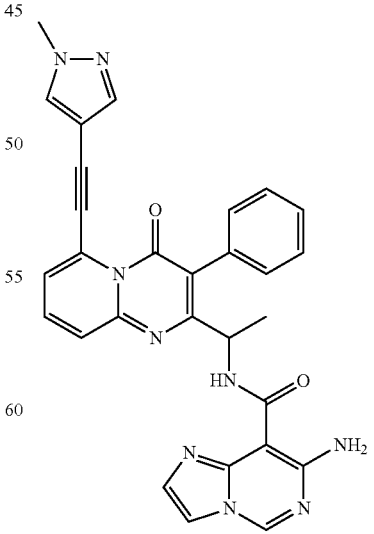

TABLE 1-continued
251
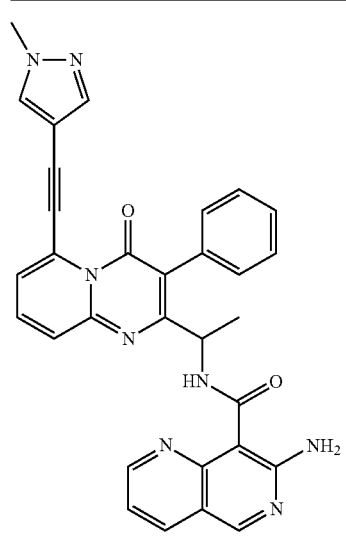
252
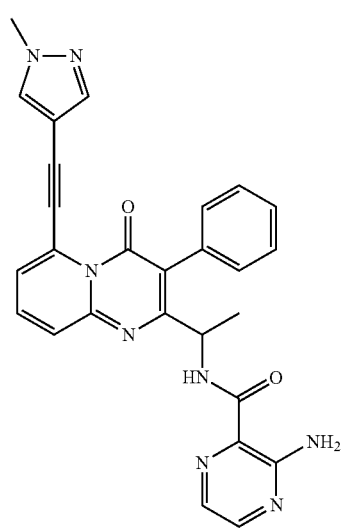
253
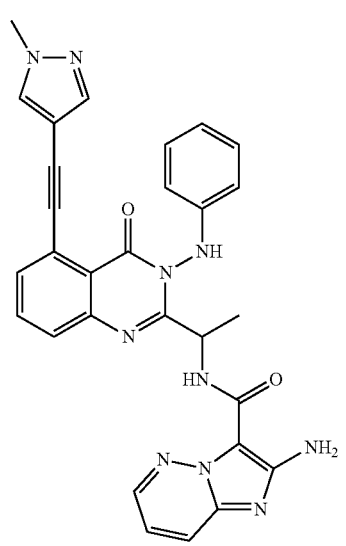 [SMILES: CC(NC(=O)c1c(N)nc2cccnn12)c1nc2cccc(C#Cc3cnn(C)c3)c2c(=O)n1Nc1ccccc1]
TABLE 1-continued
254
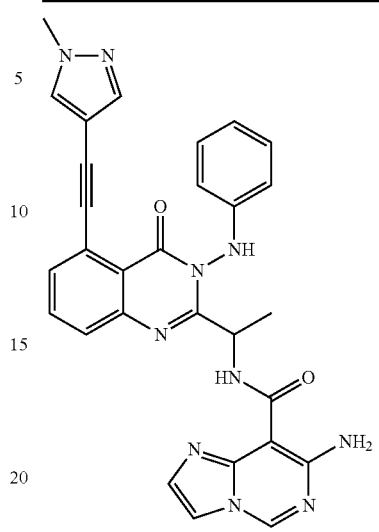
255
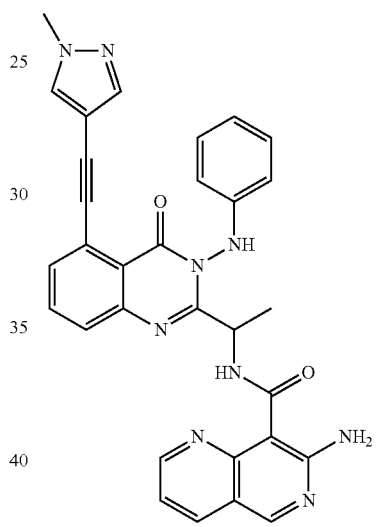
256
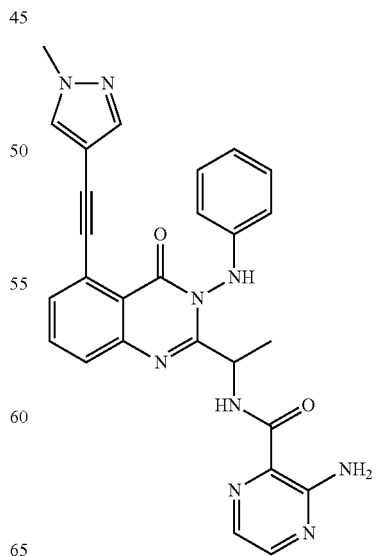

TABLE 1-continued
257
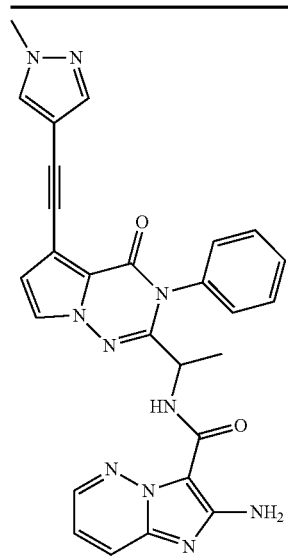
258
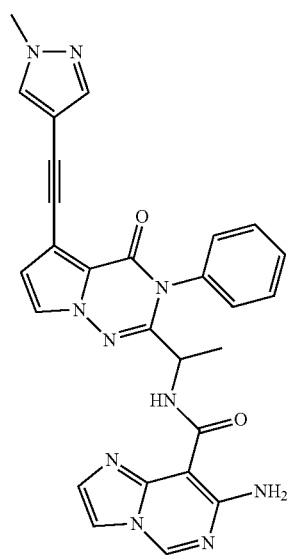 [SMILES: CC(NC(=O)c1c(N)ncn2ccnc12)c1nn2ccc(C#Cc3cnn(C)c3)c2c(=O)n1-c1ccccc1]
259
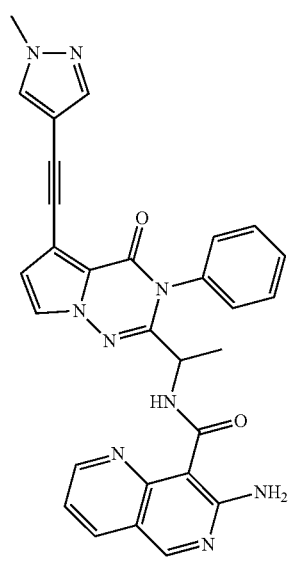 [SMILES: CC(NC(=O)c1c(N)ncc2cccnc12)c1nn2ccc(C#Cc3cnn(C)c3)c2c(=O)n1-c1ccccc1]
TABLE 1-continued
260
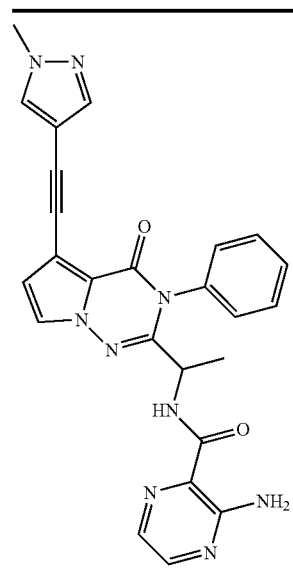
261
262
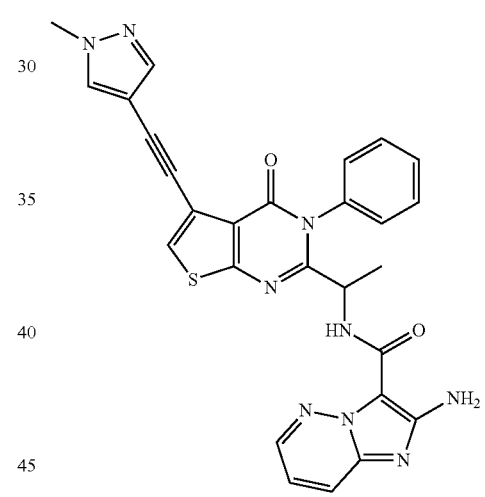
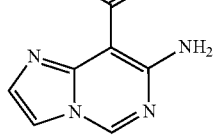

TABLE 1-continued
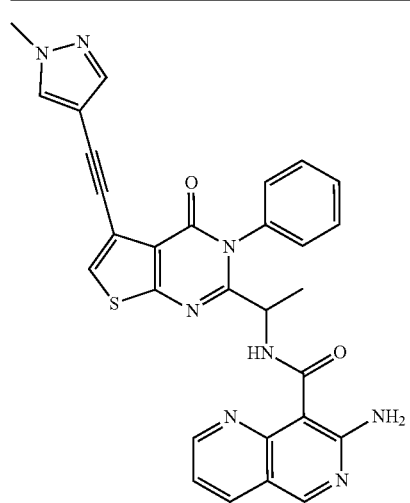
263
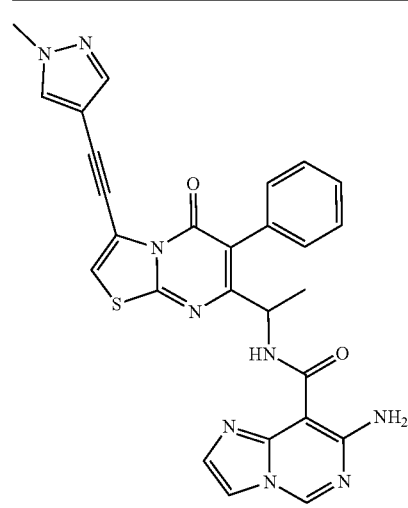
266
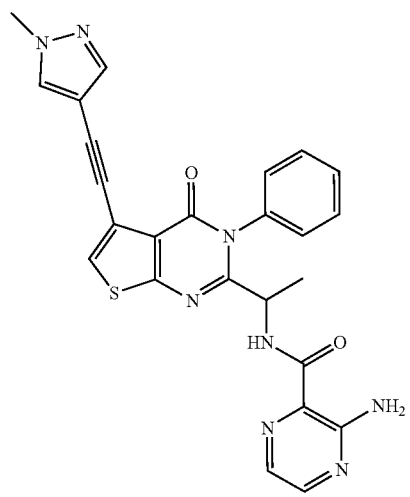
264
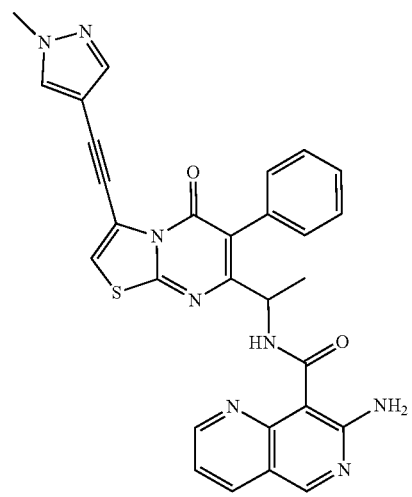
267
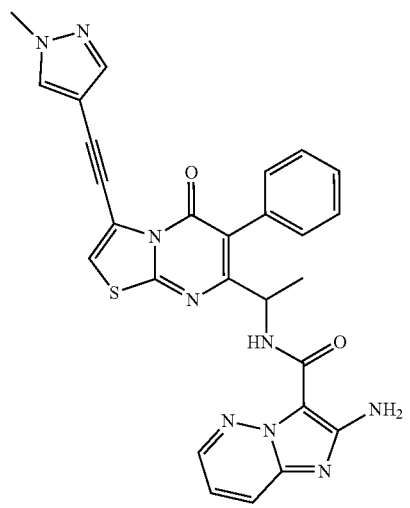 [SMILES: CC(NC(=O)c1c(N)nc2cccnn12)c1nc2scc(C#Cc3cnn(C)c3)n2c(=O)c1-c1ccccc1]
265
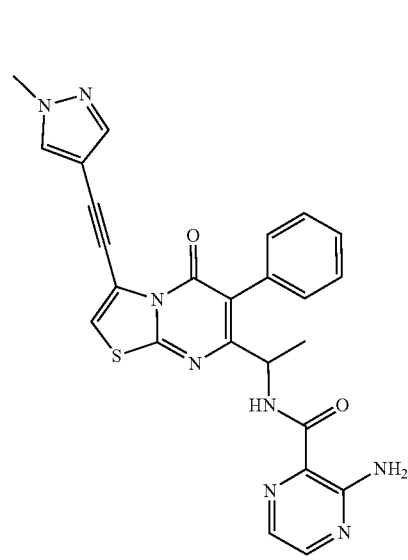 [SMILES: CC(NC(=O)c1nccnc1N)c1nc2scc(C#Cc3cnn(C)c3)n2c(=O)c1-c1ccccc1]
268

TABLE 1-continued
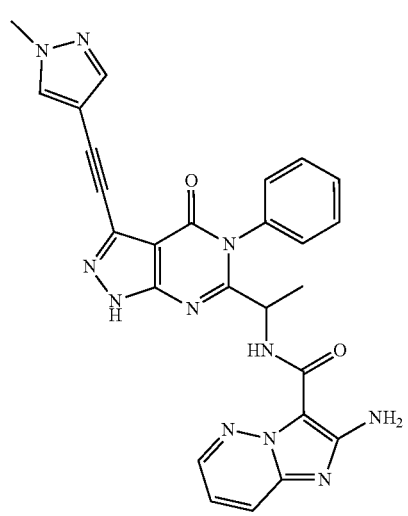 [SMILES: CC(NC(=O)c1c(N)nc2cccnn12)c1nc2[nH]nc(C#Cc3cnn(C)c3)c2c(=O)n1-c1ccccc1]
269
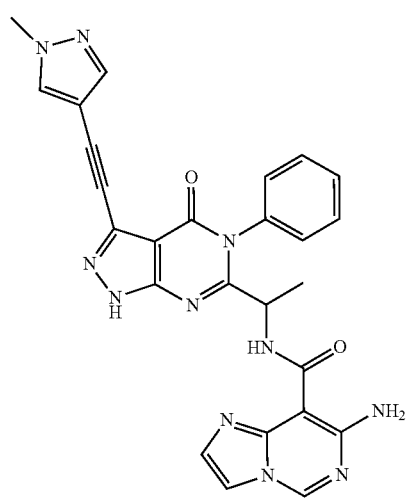 [SMILES: CC(NC(=O)c1c(N)ncn2ccnc12)c1nc2[nH]nc(C#Cc3cnn(C)c3)c2c(=O)n1-c1ccccc1]
270
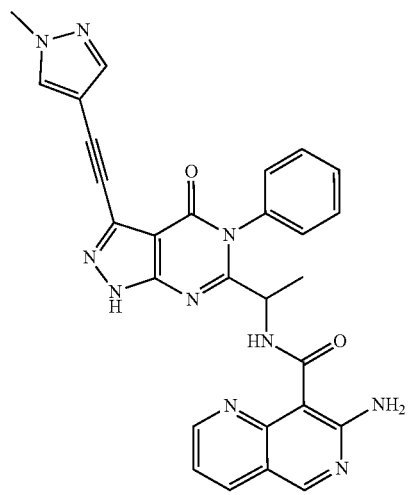 [SMILES: CC(NC(=O)c1c(N)ncc2cccnc12)c1nc2[nH]nc(C#Cc3cnn(C)c3)c2c(=O)n1-c1ccccc1]
271
TABLE 1-continued
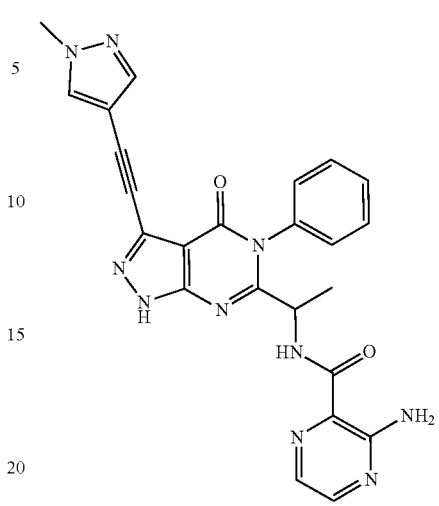
272
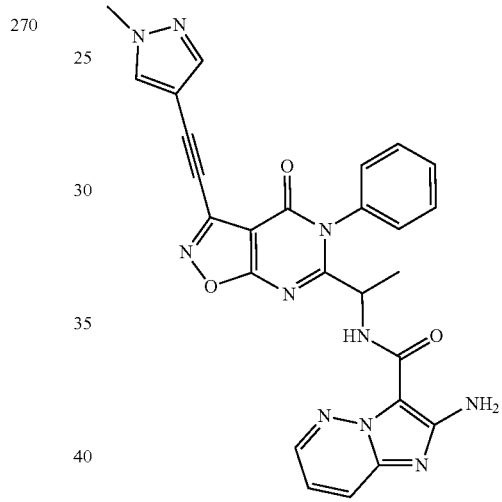
273
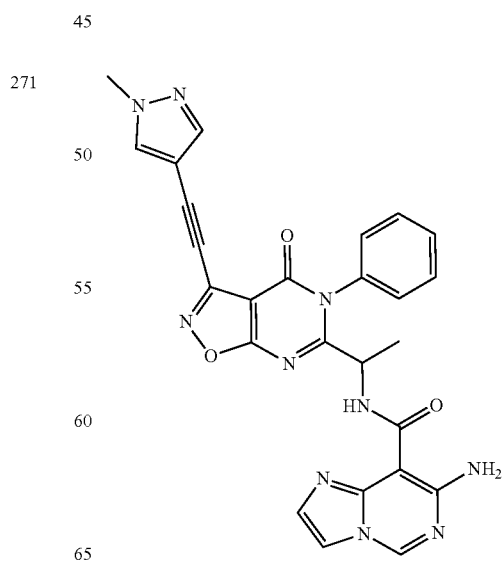
274

TABLE 1-continued
275
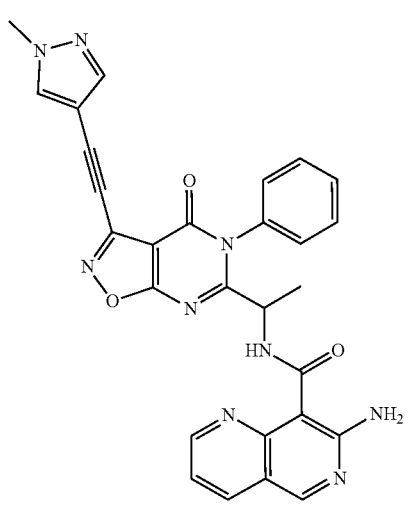 [SMILES: CC(NC(=O)c1c(N)ncc2cccnc12)c1nc2onc(C#Cc3cnn(C)c3)c2c(=O)n1-c1ccccc1]
276
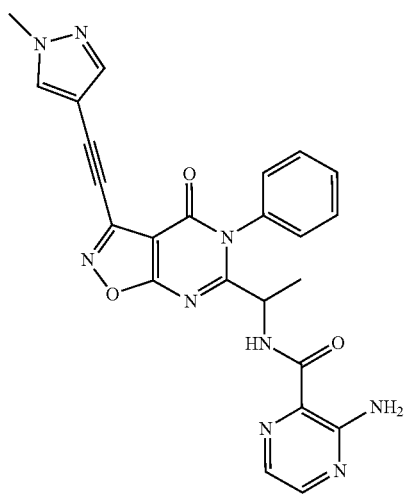 [SMILES: CC(NC(=O)c1nccnc1N)c1nc2onc(C#Cc3cnn(C)c3)c2c(=O)n1-c1ccccc1]
277
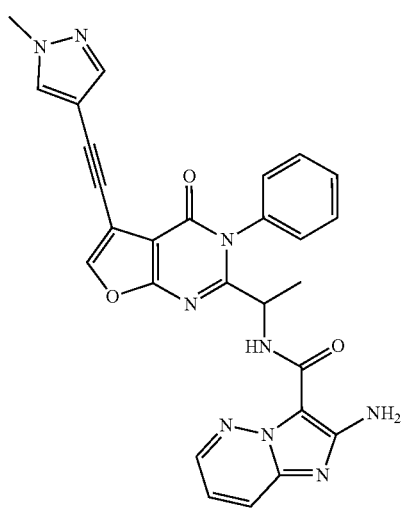 [SMILES: CC(NC(=O)c1c(N)nc2cccnn12)c1nc2occ(C#Cc3cnn(C)c3)c2c(=O)n1-c1ccccc1]
TABLE 1-continued
278
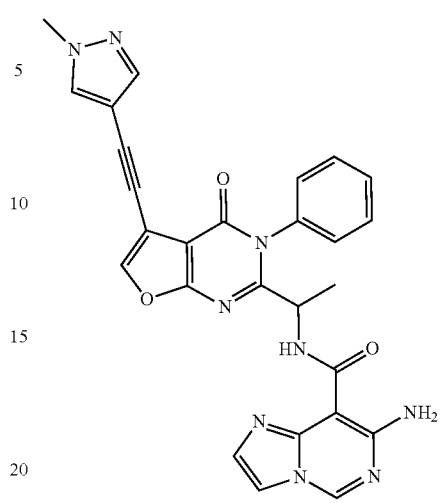
279
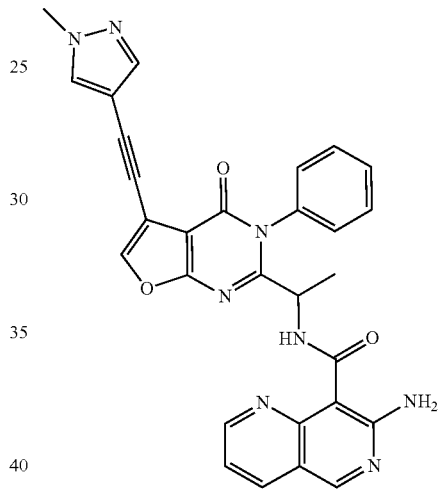
280
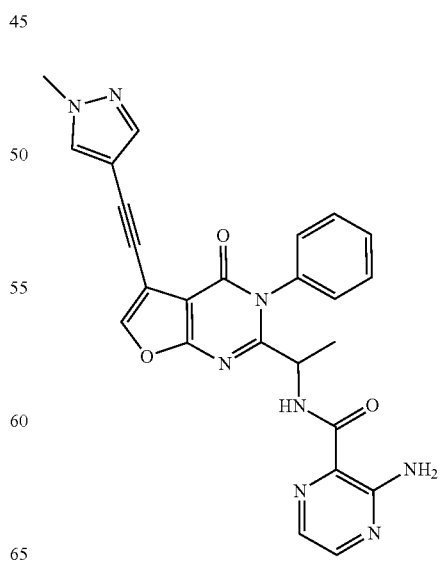

TABLE 1-continued
281
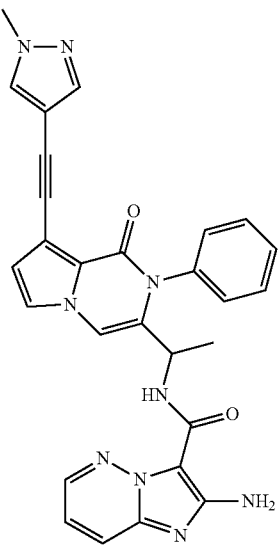
282
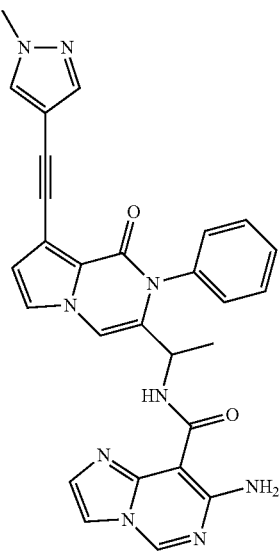 [SMILES: CC(NC(=O)c1c(N)ncn2ccnc12)c1cn2ccc(C#Cc3cnn(C)c3)c2c(=O)n1-c1ccccc1]
283
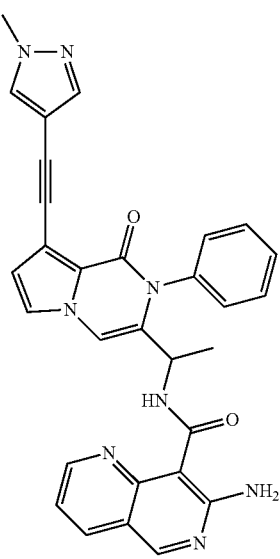 [SMILES: CC(NC(=O)c1c(N)ncc2cccnc12)c1cn2ccc(C#Cc3cnn(C)c3)c2c(=O)n1-c1ccccc1]
TABLE 1-continued
284
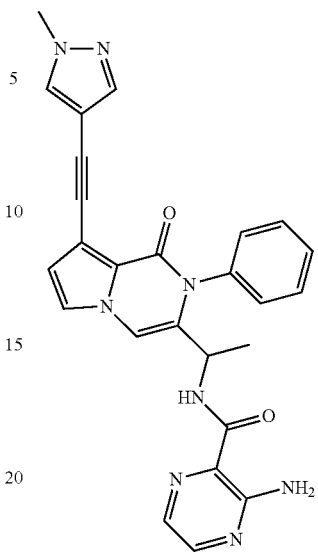
285
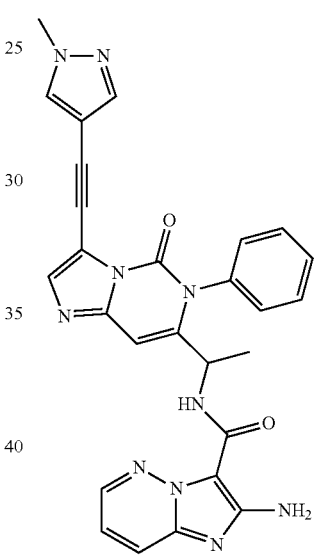
286
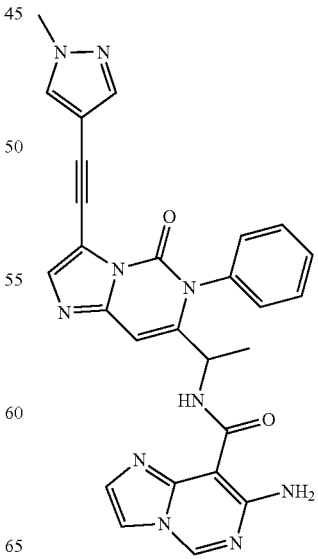

TABLE 1-continued
287
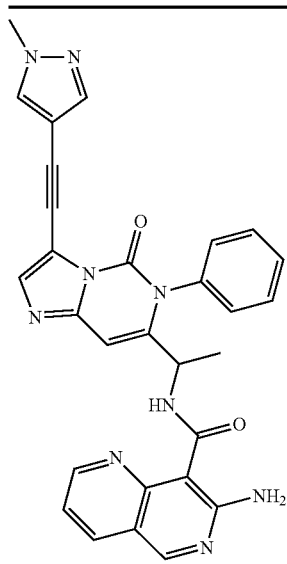
288
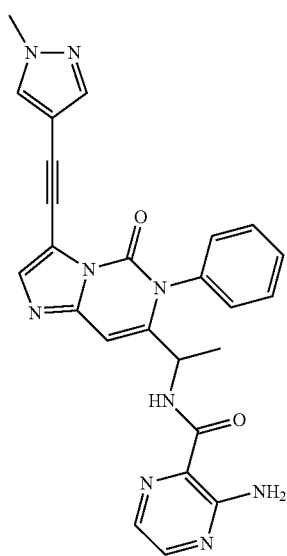
289
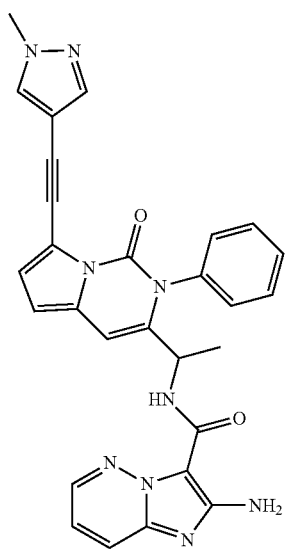 [SMILES: CC(NC(=O)c1c(N)nc2cccnn12)c1cc2ncc(C#Cc3cnn(C)c3)n2c(=O)n1-c1ccccc1]
TABLE 1-continued
290
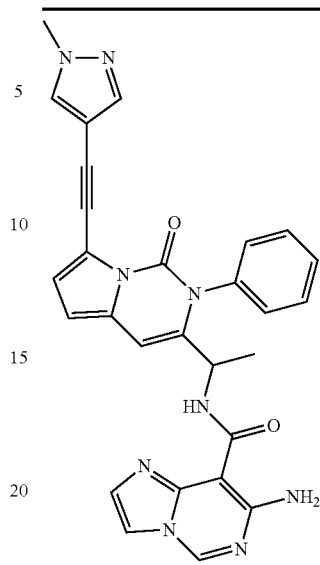
291
292
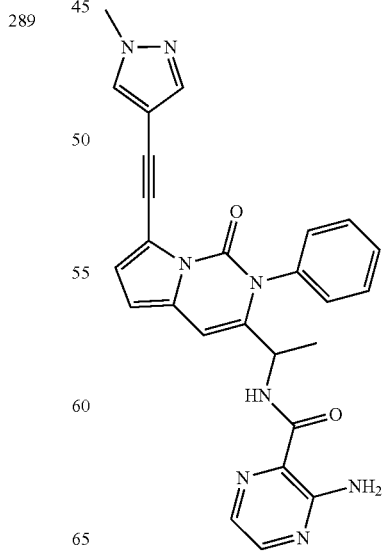

TABLE 1-continued
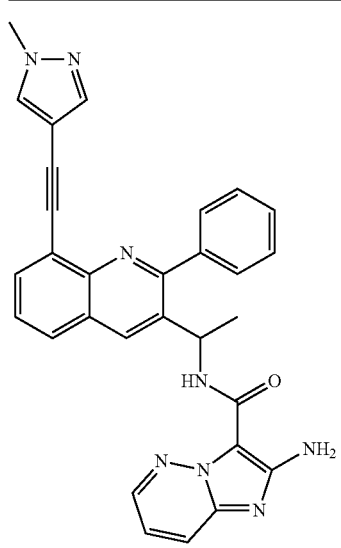
293
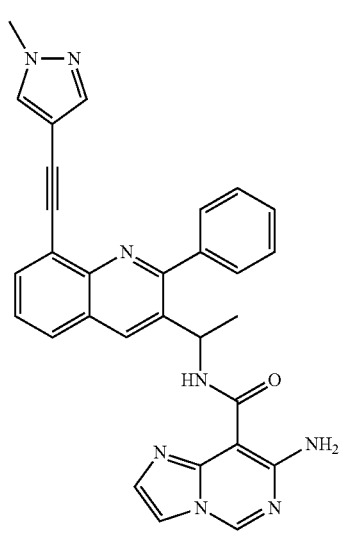
294
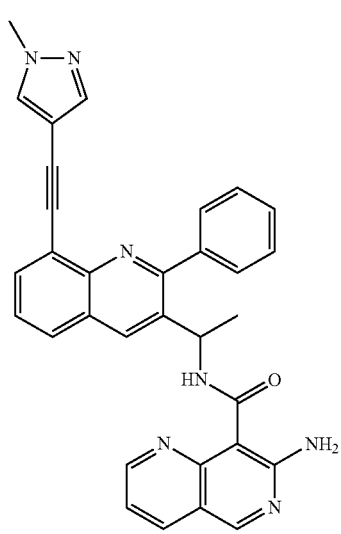
295
TABLE 1-continued
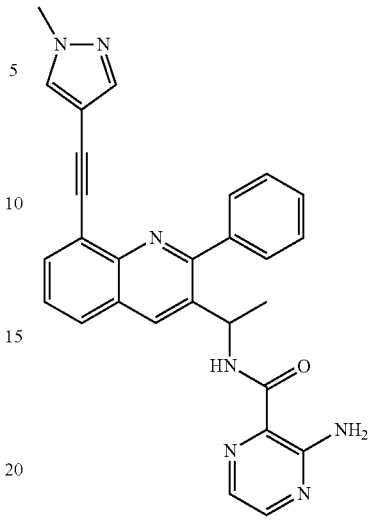
296
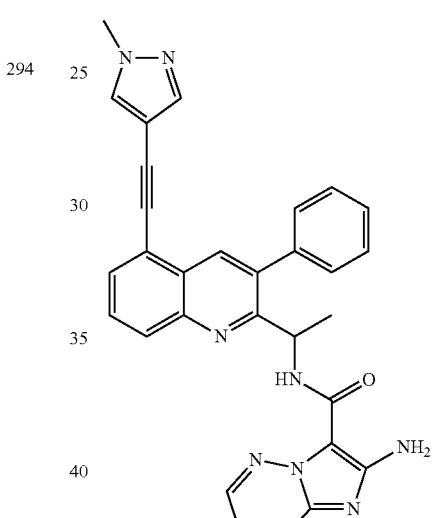
297
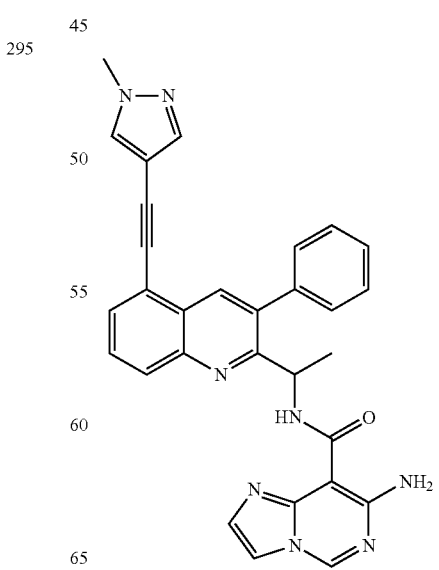
298

TABLE 1-continued
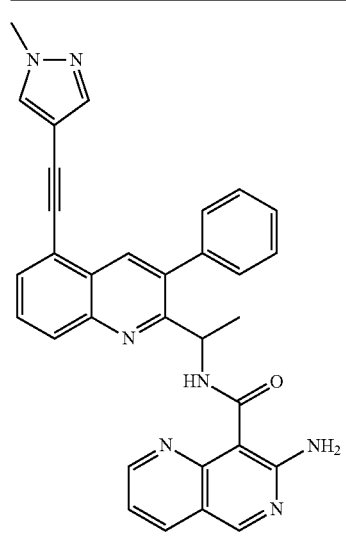
299
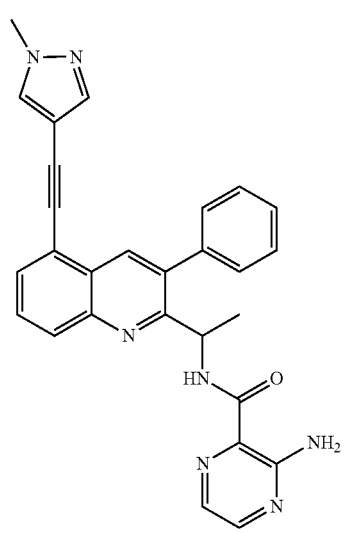
300
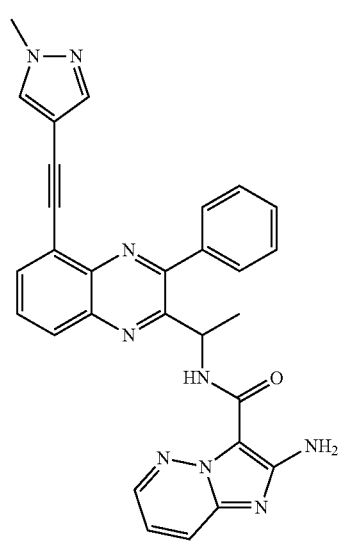 [SMILES: CC(NC(=O)c1c(N)nc2cccnn12)c1nc2cccc(C#Cc3cnn(C)c3)c2nc1-c1ccccc1]
301
TABLE 1-continued
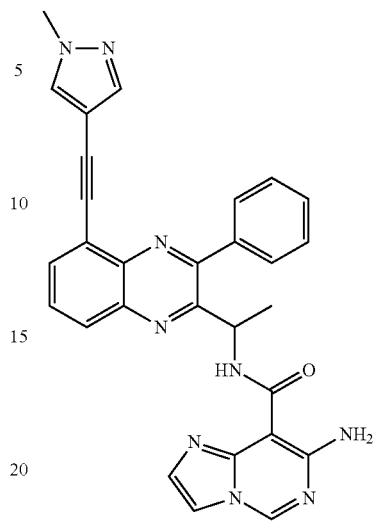
302
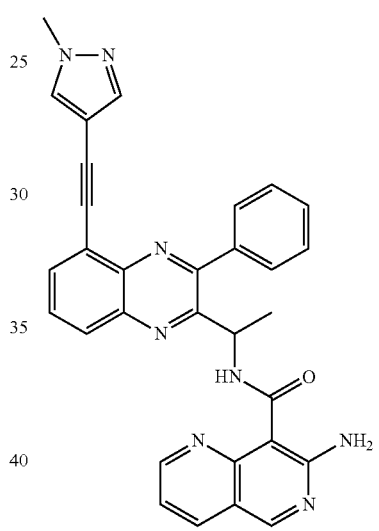
303
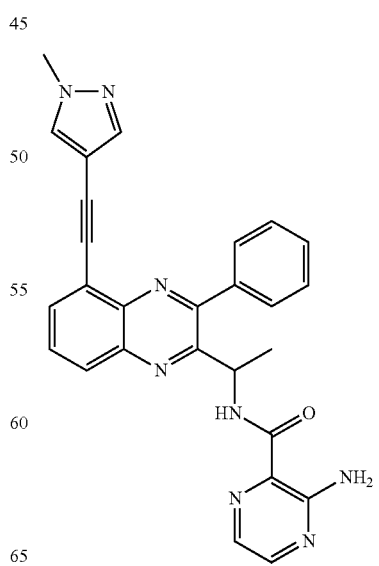
304

TABLE 1-continued
305
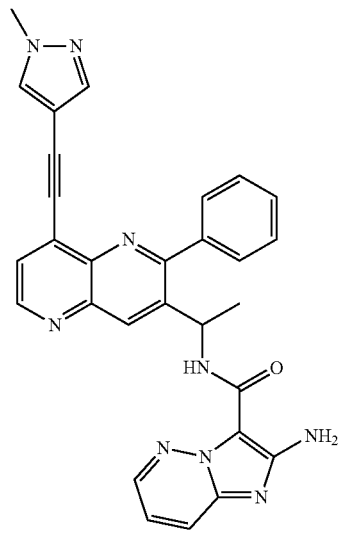 [SMILES: CC(NC(=O)c1c(N)nc2cccnn12)c1cc2nccc(C#Cc3cnn(C)c3)c2nc1-c1ccccc1]
306
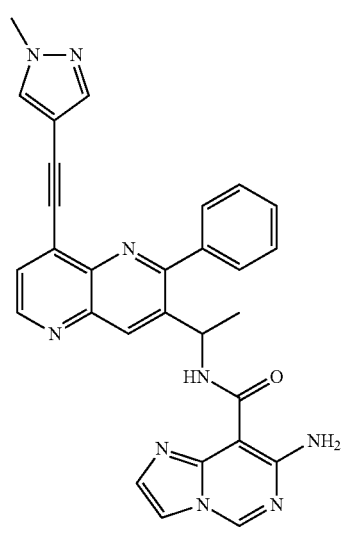 [SMILES: CC(NC(=O)c1c(N)ncn2ccnc12)c1cc2nccc(C#Cc3cnn(C)c3)c2nc1-c1ccccc1]
307
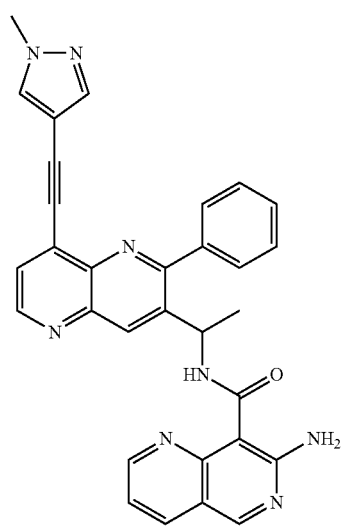
TABLE 1-continued
308
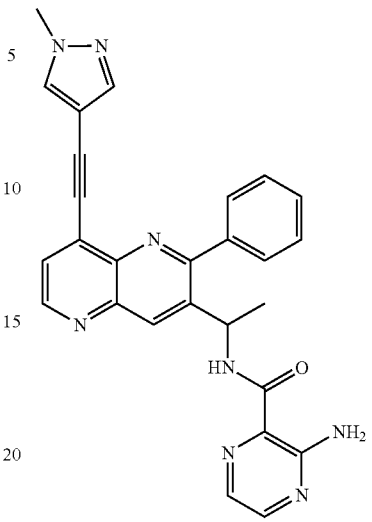
309
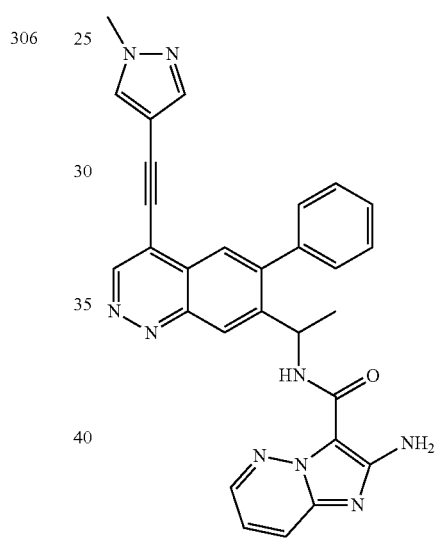
310
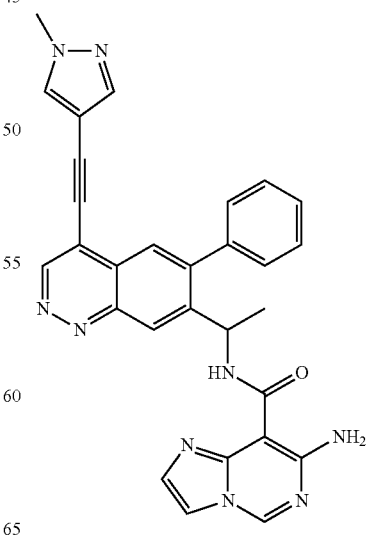

TABLE 1-continued
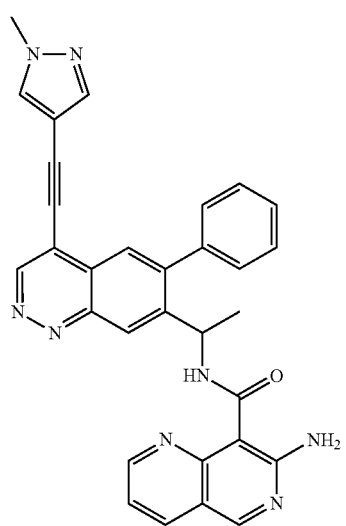
311
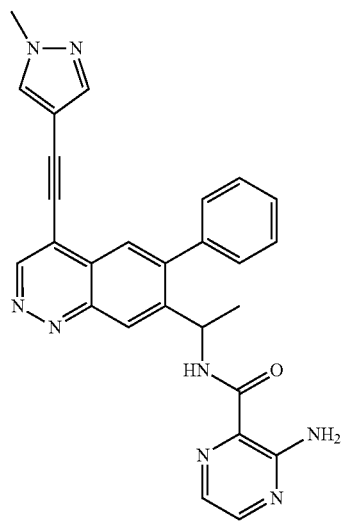
312
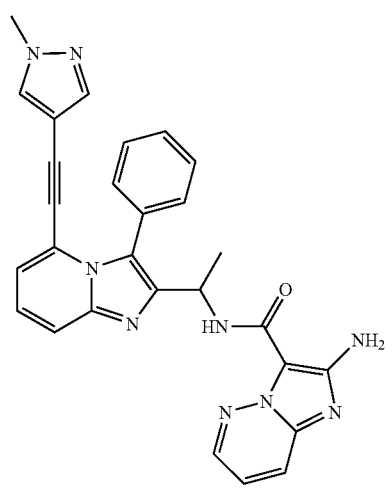 [SMILES: CC(NC(=O)c1c(N)nc2cccnn12)c1nc2cccc(C#Cc3cnn(C)c3)n2c1-c1ccccc1]
313
TABLE 1-continued
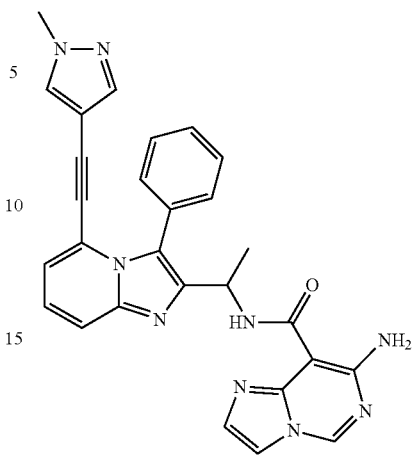
314
315
316

TABLE 1-continued
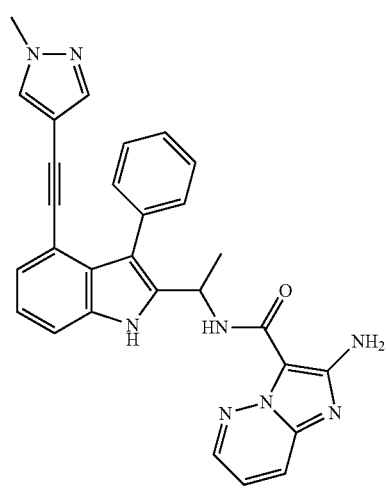 [SMILES: CC(NC(=O)c1c(N)nc2cccnn12)c1[nH]c2cccc(C#Cc3cnn(C)c3)c2c1-c1ccccc1]
317
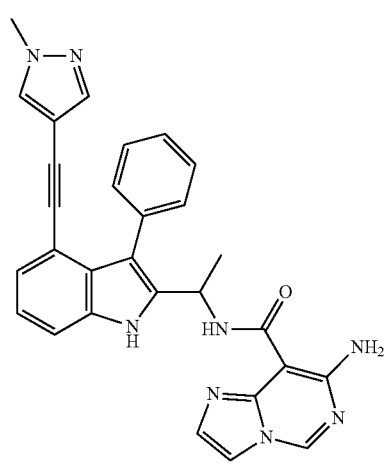 [SMILES: CC(NC(=O)c1c(N)ncn2ccnc12)c1[nH]c2cccc(C#Cc3cnn(C)c3)c2c1-c1ccccc1]
318
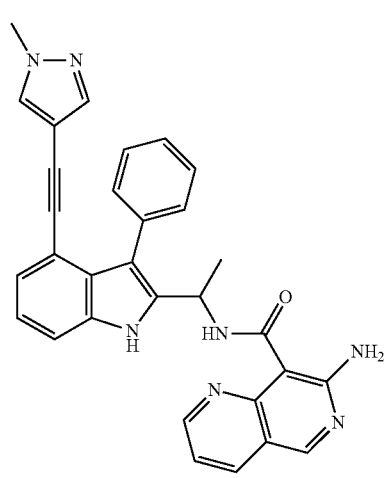 [SMILES: CC(NC(=O)c1c(N)ncc2cccnc12)c1[nH]c2cccc(C#Cc3cnn(C)c3)c2c1-c1ccccc1]
319
TABLE 1-continued
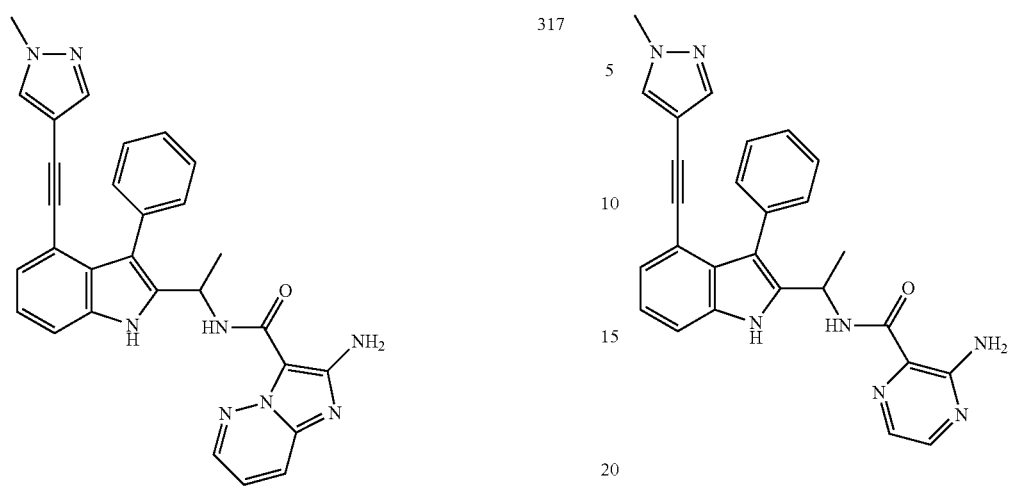
320
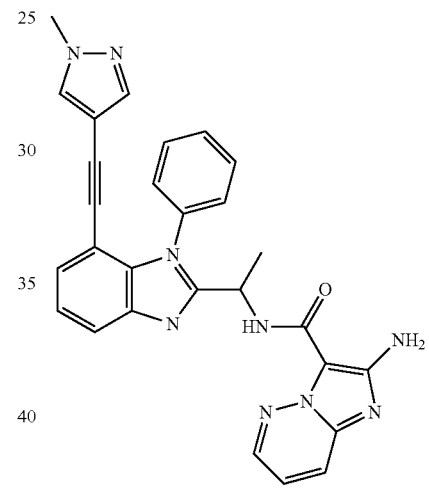
321
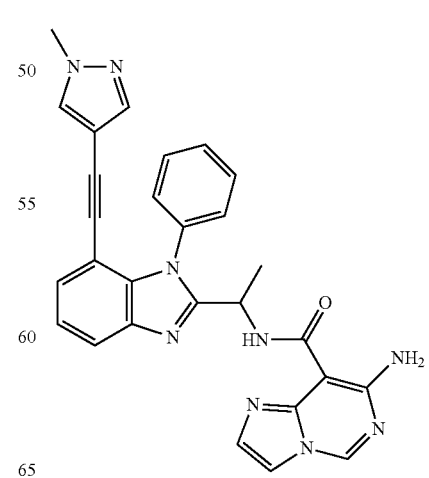
322

TABLE 1-continued
323
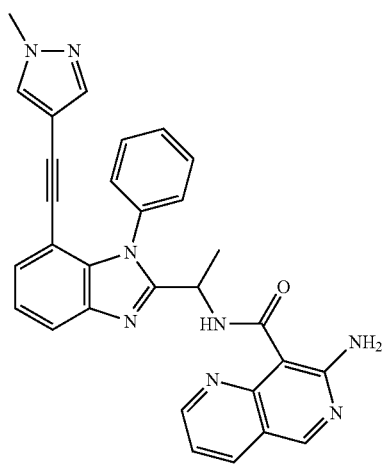 [SMILES: CC(NC(=O)c1c(N)ncc2cccnc12)c1nc2cccc(C#Cc3cnn(C)c3)c2n1-c1ccccc1]
324
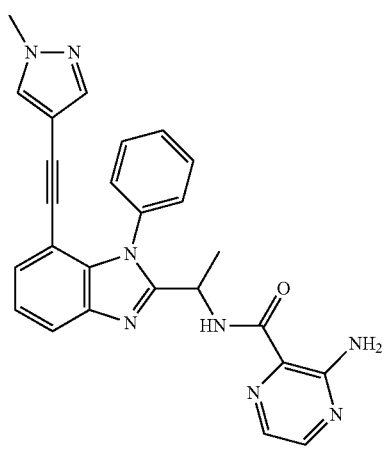 [SMILES: CC(NC(=O)c1nccnc1N)c1nc2cccc(C#Cc3cnn(C)c3)c2n1-c1ccccc1]
325
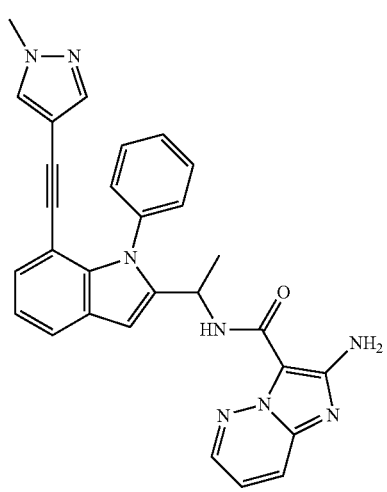 [SMILES: CC(NC(=O)c1c(N)nc2cccnn12)c1cc2cccc(C#Cc3cnn(C)c3)c2n1-c1ccccc1]
TABLE 1-continued
326
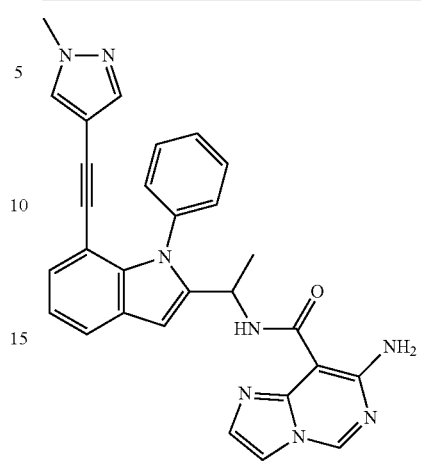
327
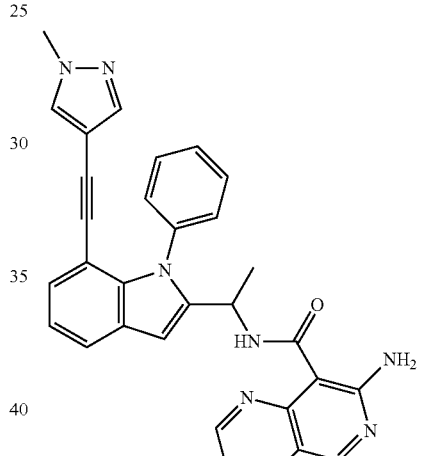
328
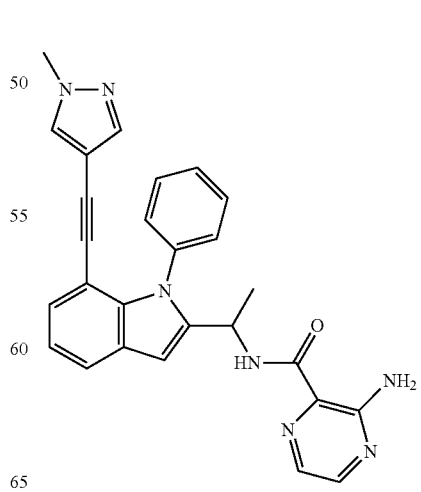

TABLE 1-continued
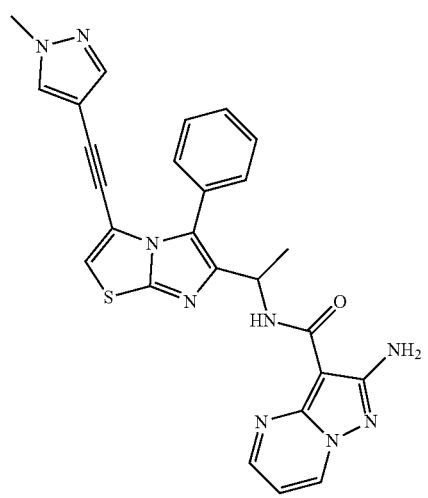 [SMILES: CC(NC(=O)c1c(N)nn2cccnc12)c1nc2scc(C#Cc3cnn(C)c3)n2c1-c1ccccc1]
329
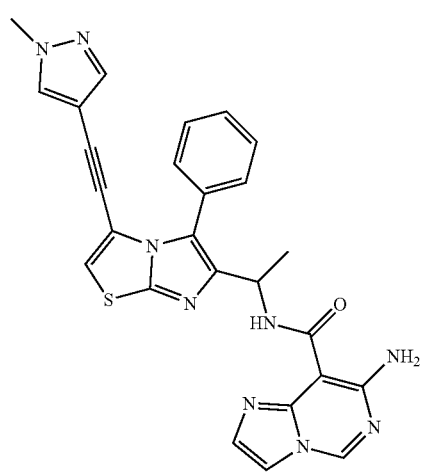 [SMILES: CC(NC(=O)c1c(N)ncn2ccnc12)c1nc2scc(C#Cc3cnn(C)c3)n2c1-c1ccccc1]
330
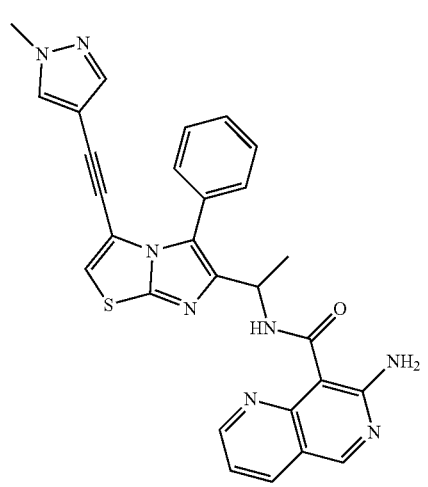 [SMILES: CC(NC(=O)c1c(N)ncc2cccnc12)c1nc2scc(C#Cc3cnn(C)c3)n2c1-c1ccccc1]
331
TABLE 1-continued
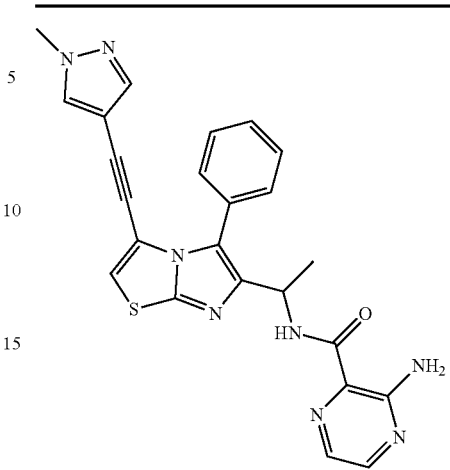
332
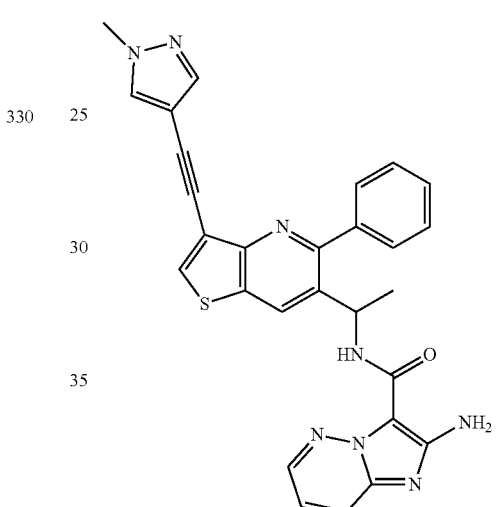
333
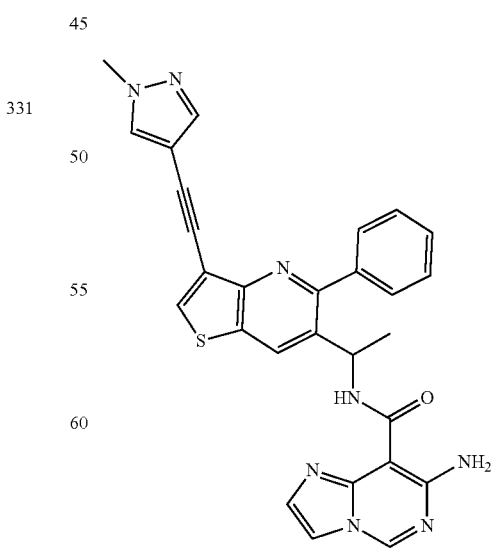
334

TABLE 1-continued
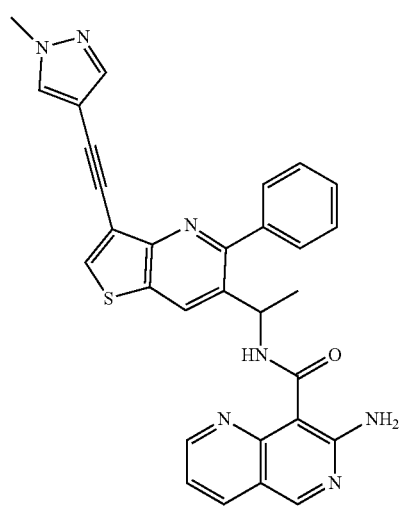 [SMILES: CC(NC(=O)c1c(N)ncc2cccnc12)c1cc2scc(C#Cc3cnn(C)c3)c2nc1-c1ccccc1]
335
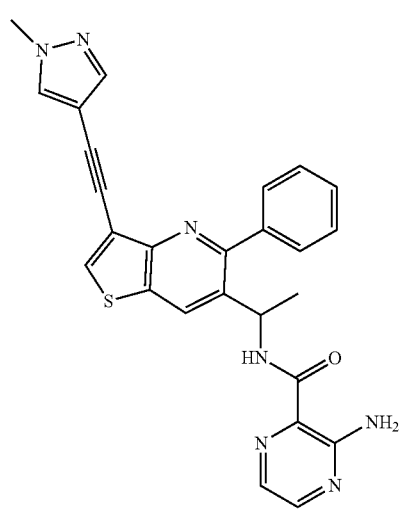 [SMILES: CC(NC(=O)c1nccnc1N)c1cc2scc(C#Cc3cnn(C)c3)c2nc1-c1ccccc1]
336
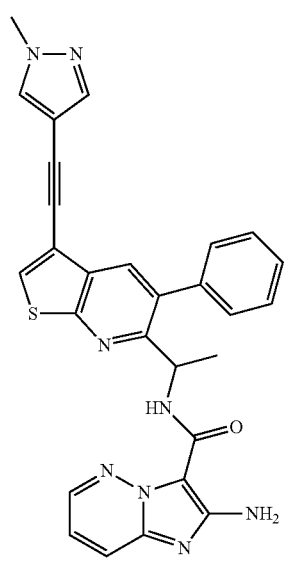 [SMILES: CC(NC(=O)c1c(N)nc2cccnn12)c1nc2scc(C#Cc3cnn(C)c3)c2cc1-c1ccccc1]
337
TABLE 1-continued
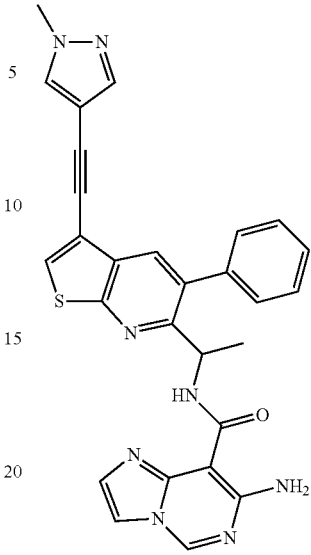
338
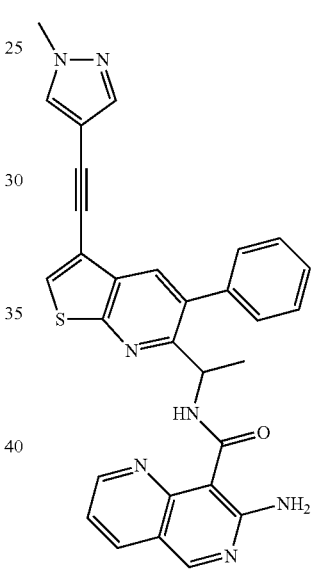
339
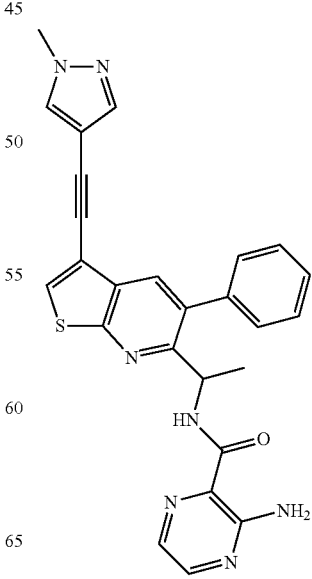
340

TABLE 1-continued
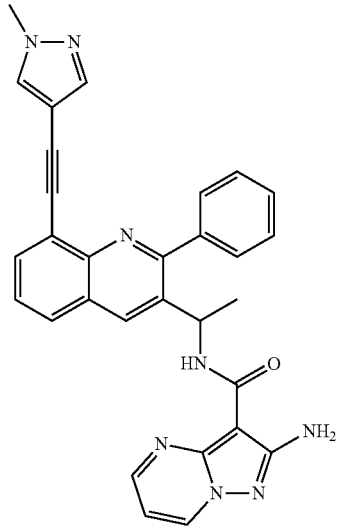 [SMILES: CC(NC(=O)c1c(N)nn2cccnc12)c1cc2cccc(C#Cc3cnn(C)c3)c2nc1-c1ccccc1]
341
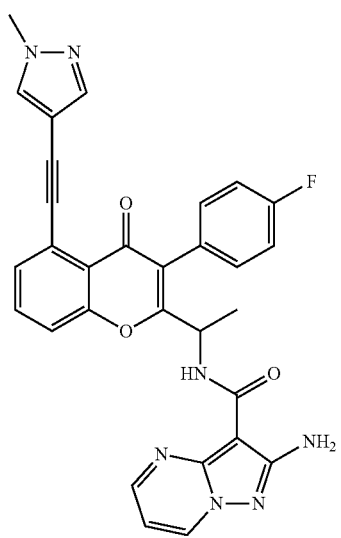 [SMILES: CC(NC(=O)c1c(N)nn2cccnc12)c1oc2cccc(C#Cc3cnn(C)c3)c2c(=O)c1-c1ccc(F)cc1]
342
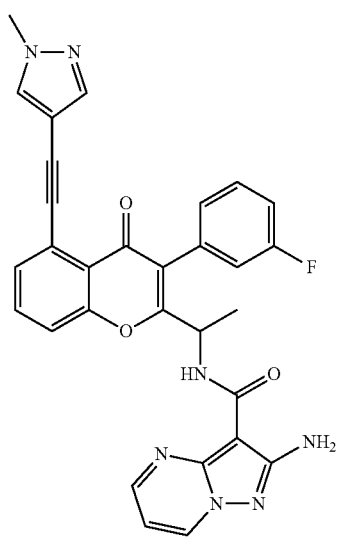 [SMILES: CC(NC(=O)c1c(N)nn2cccnc12)c1oc2cccc(C#Cc3cnn(C)c3)c2c(=O)c1-c1cccc(F)c1]
343
TABLE 1-continued
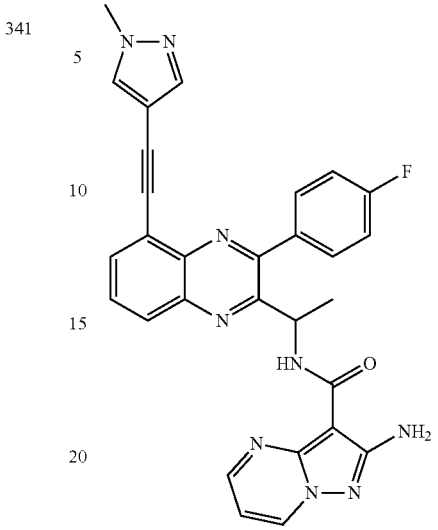
344
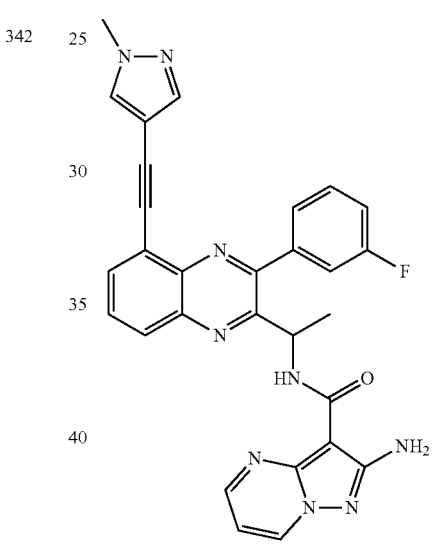
345
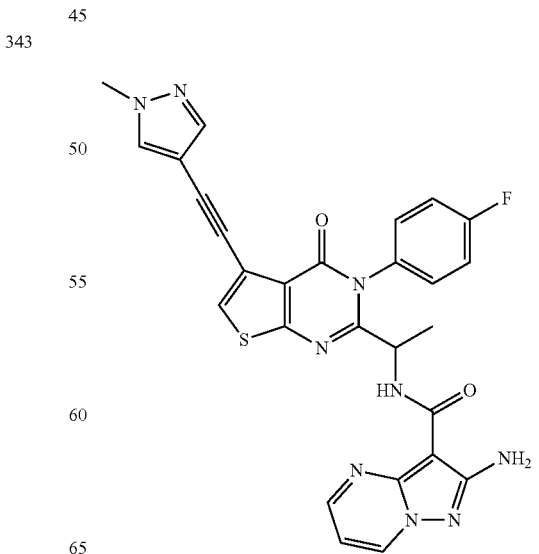
346

TABLE 1-continued
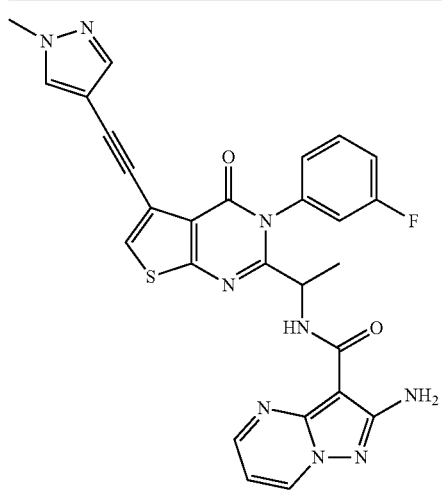 [SMILES: CC(NC(=O)c1c(N)nn2cccnc12)c1nc2scc(C#Cc3cnn(C)c3)c2c(=O)n1-c1cccc(F)c1]
347
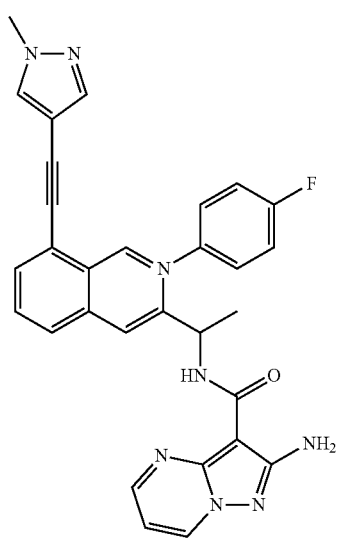
348
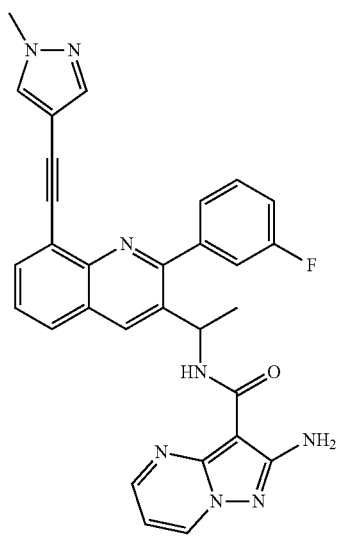 [SMILES: CC(NC(=O)c1c(N)nn2cccnc12)c1cc2cccc(C#Cc3cnn(C)c3)c2nc1-c1cccc(F)c1]
349
TABLE 1-continued
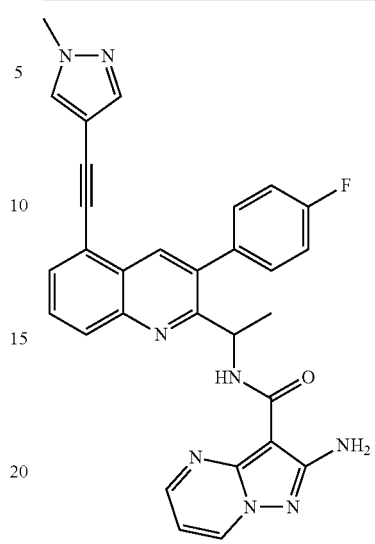
350
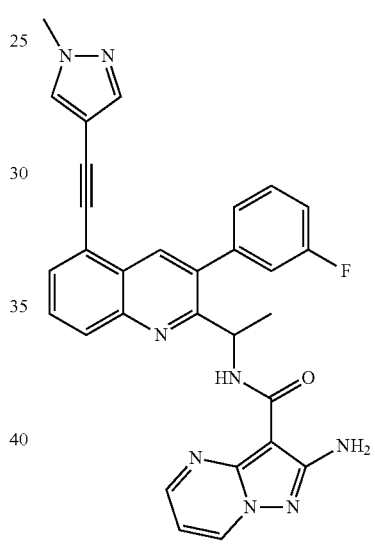
351
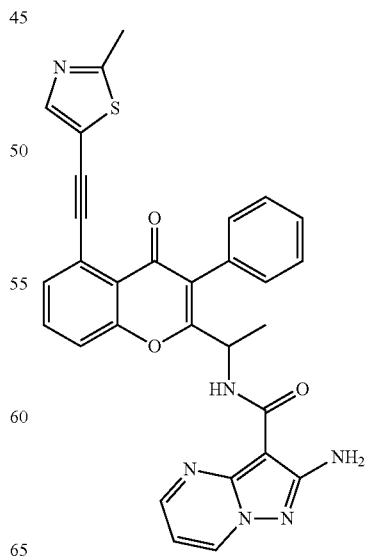
352

TABLE 1-continued
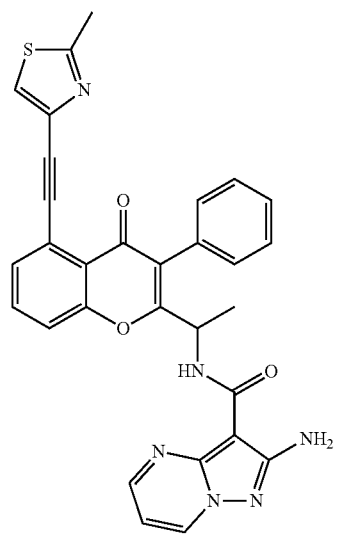 [SMILES: Cc1nc(C#Cc2cccc3oc(C(C)NC(=O)c4c(N)nn5cccnc45)c(-c4ccccc4)c(=O)c23)cs1] 353
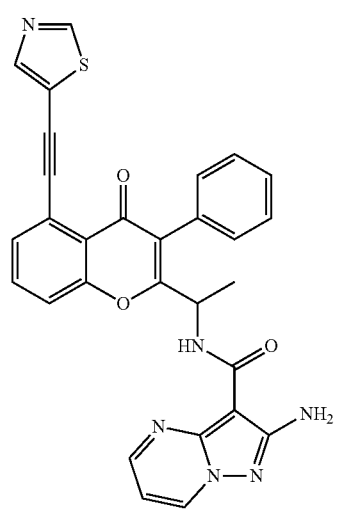 [SMILES: CC(NC(=O)c1c(N)nn2cccnc12)c1oc2cccc(C#Cc3cncs3)c2c(=O)c1-c1ccccc1] 354
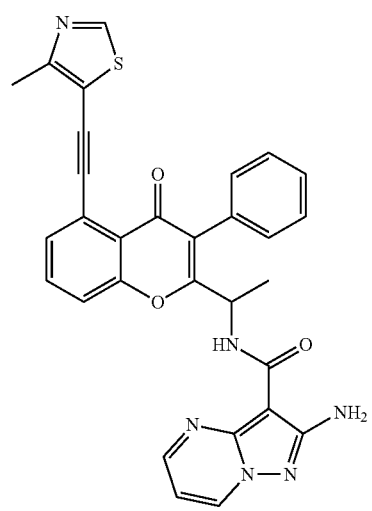 [SMILES: Cc1ncsc1C#Cc1cccc2oc(C(C)NC(=O)c3c(N)nn4cccnc34)c(-c3ccccc3)c(=O)c12] 355
TABLE 1-continued
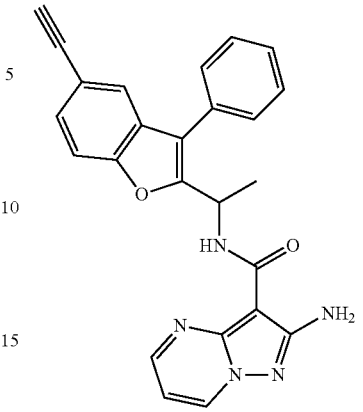 356
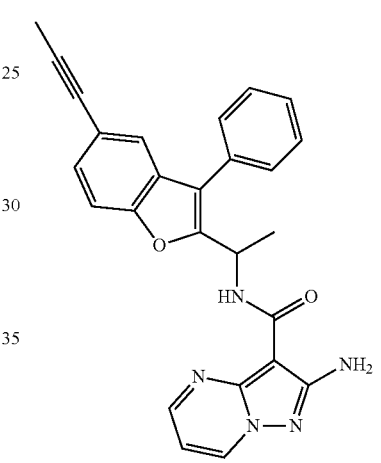 357
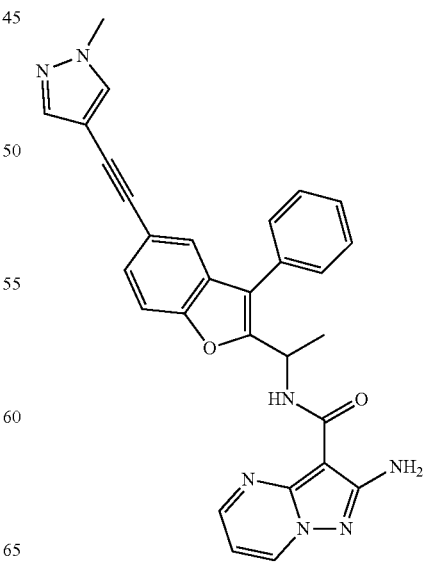 358

TABLE 1-continued
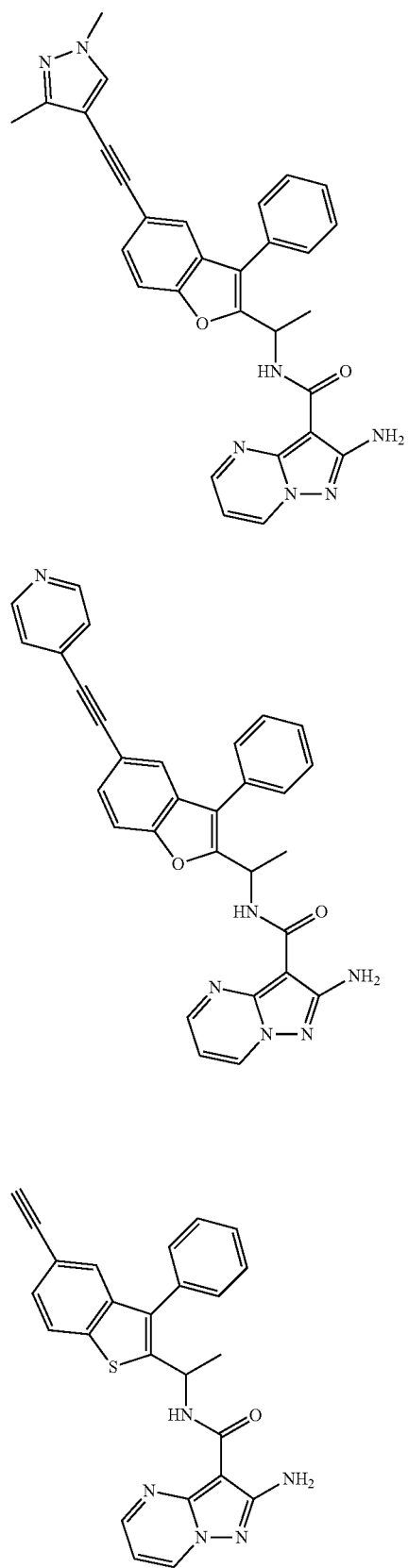
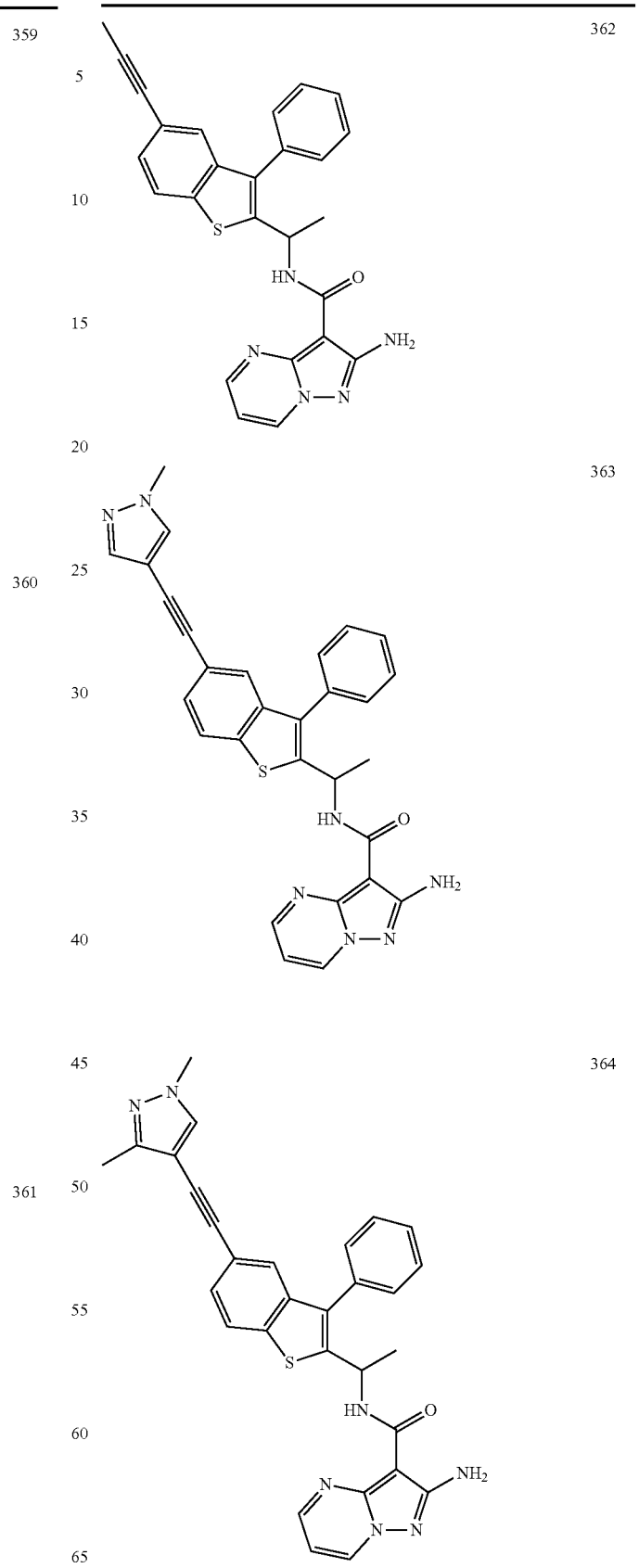

TABLE 1-continued
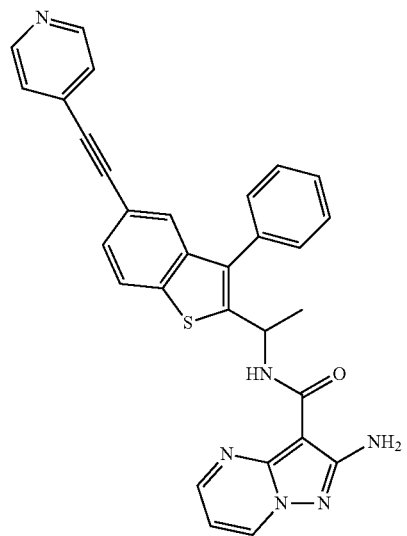 [SMILES: CC(NC(=O)c1c(N)nn2cccnc12)c1sc2ccc(C#Cc3ccncc3)cc2c1-c1ccccc1]
365
TABLE 2
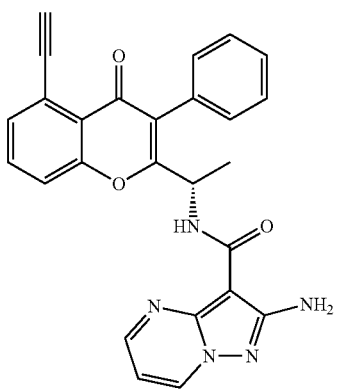 [SMILES: C#Cc1cccc2oc([C@H](C)NC(=O)c3c(N)nn4cccnc34)c(-c3ccccc3)c(=O)c12]
101S
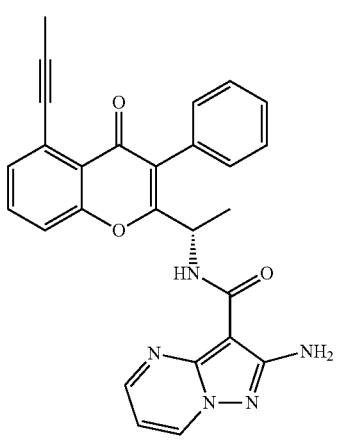 [SMILES: CC#Cc1cccc2oc([C@H](C)NC(=O)c3c(N)nn4cccnc34)c(-c3ccccc3)c(=O)c12]
102S
TABLE 2-continued
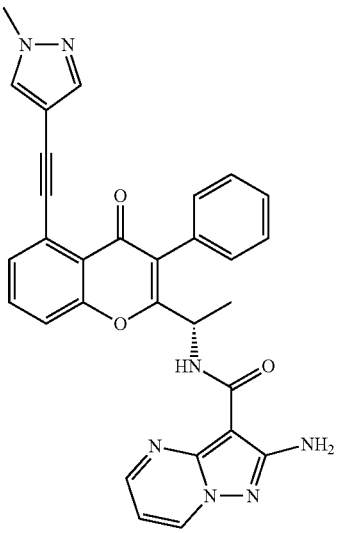 [SMILES: C[C@H](NC(=O)c1c(N)nn2cccnc12)c1oc2cccc(C#Cc3cnn(C)c3)c2c(=O)c1-c1ccccc1]
103S
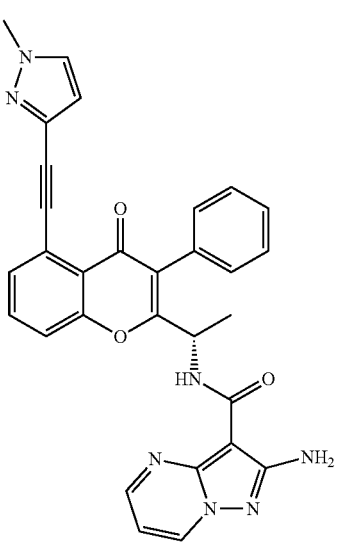 [SMILES: C[C@H](NC(=O)c1c(N)nn2cccnc12)c1oc2cccc(C#Cc3ccn(C)n3)c2c(=O)c1-c1ccccc1]
104S
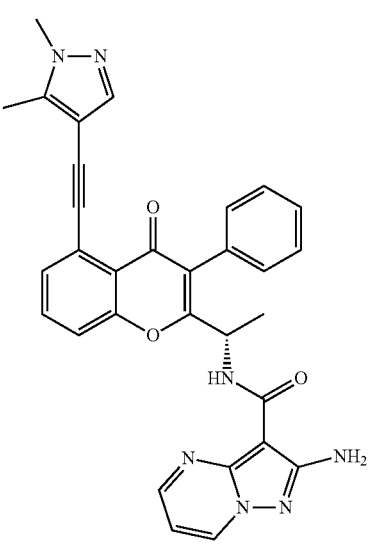 [SMILES: Cc1c(C#Cc2cccc3oc([C@H](C)NC(=O)c4c(N)nn5cccnc45)c(-c4ccccc4)c(=O)c23)cnn1C]
105S TABLE 2-continued
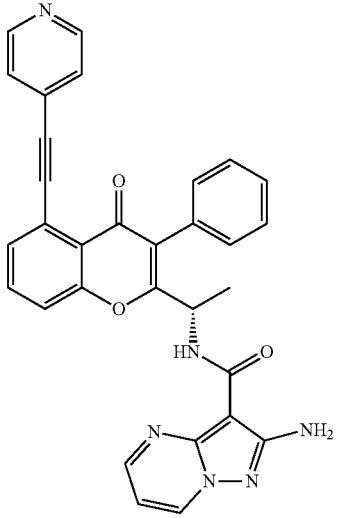 [SMILES: C[C@H](NC(=O)c1c(N)nn2cccnc12)c1oc2cccc(C#Cc3ccncc3)c2c(=O)c1-c1ccccc1]
106S
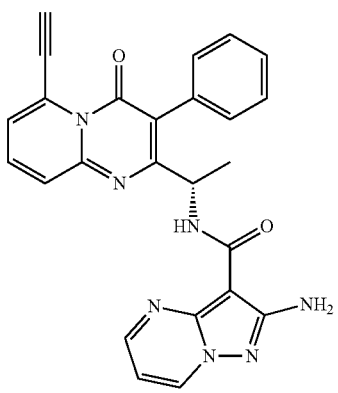 [SMILES: C#Cc1cccc2nc([C@H](C)NC(=O)c3c(N)nn4cccnc34)c(-c3ccccc3)c(=O)n12]
107Ss
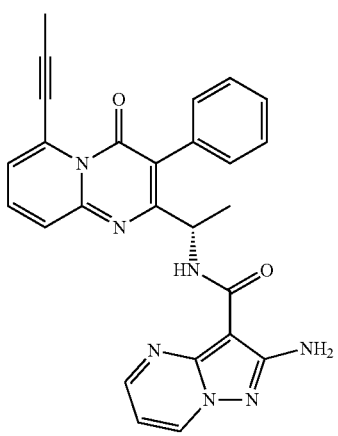 [SMILES: CC#Cc1cccc2nc([C@H](C)NC(=O)c3c(N)nn4cccnc34)c(-c3ccccc3)c(=O)n12]
108S
TABLE 2-continued
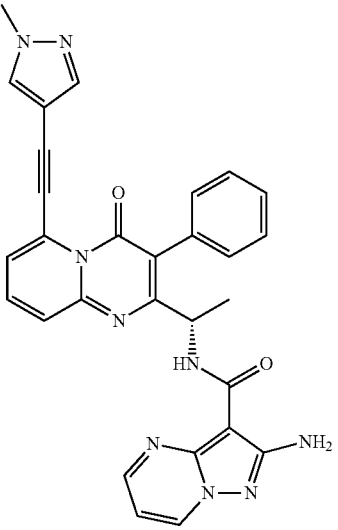 [SMILES: C[C@H](NC(=O)c1c(N)nn2cccnc12)c1nc2cccc(C#Cc3cnn(C)c3)n2c(=O)c1-c1ccccc1]
109Ss
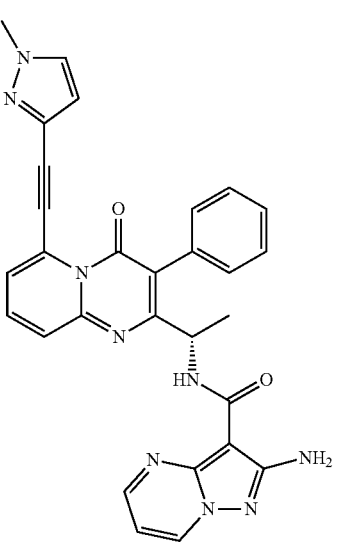 [SMILES: C[C@H](NC(=O)c1c(N)nn2cccnc12)c1nc2cccc(C#Cc3ccn(C)n3)n2c(=O)c1-c1ccccc1]
110S
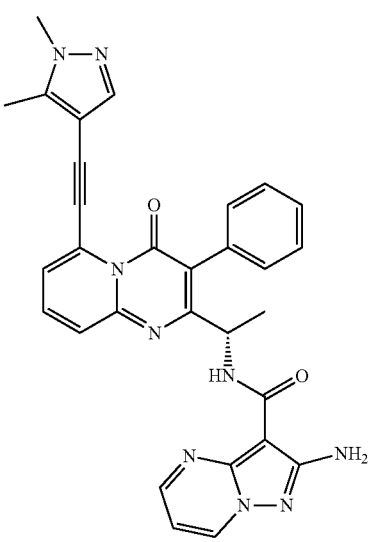 [SMILES: Cc1c(C#Cc2cccc3nc([C@H](C)NC(=O)c4c(N)nn5cccnc45)c(-c4ccccc4)c(=O)n23)cnn1C]
111S TABLE 2-continued
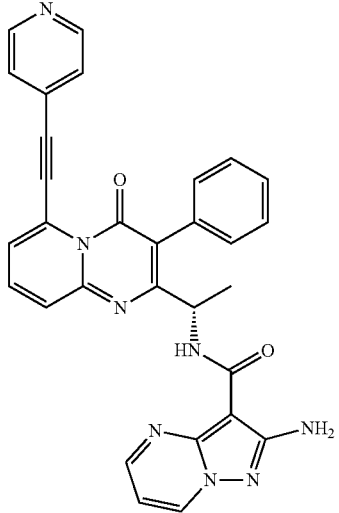 [SMILES: C[C@H](NC(=O)c1c(N)nn2cccnc12)c1nc2cccc(C#Cc3ccncc3)n2c(=O)c1-c1ccccc1]
112S
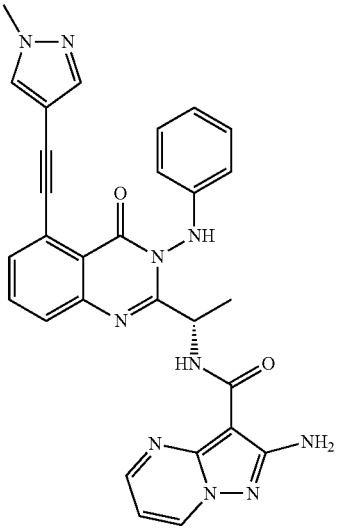
115S
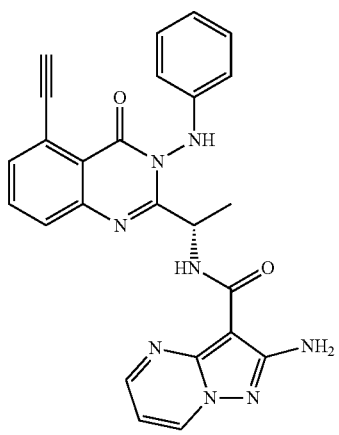 [SMILES: C#Cc1cccc2nc([C@H](C)NC(=O)c3c(N)nn4cccnc34)n(Nc3ccccc3)c(=O)c12]
113S
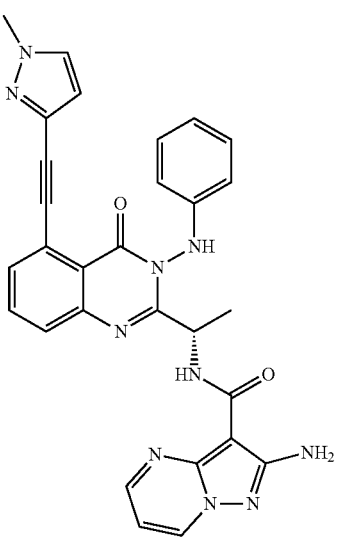
116S
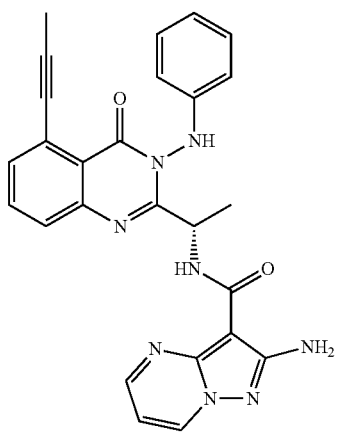 [SMILES: CC#Cc1cccc2nc([C@H](C)NC(=O)c3c(N)nn4cccnc34)n(Nc3ccccc3)c(=O)c12]
114S
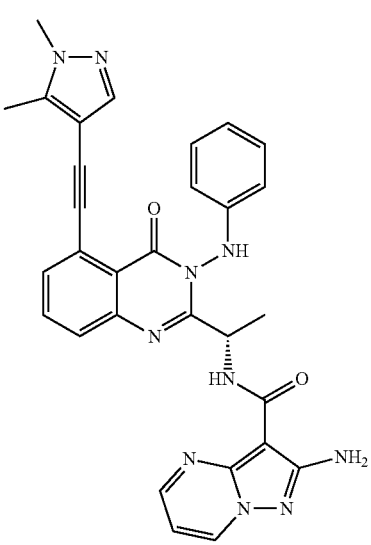 [SMILES: Cc1c(C#Cc2cccc3nc([C@H](C)NC(=O)c4c(N)nn5cccnc45)n(Nc4ccccc4)c(=O)c23)cnn1C]
117S TABLE 2-continued
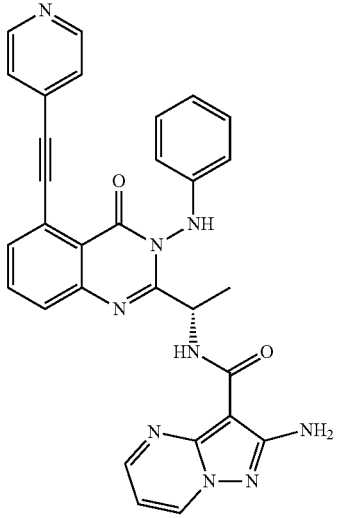 [SMILES: C[C@H](NC(=O)c1c(N)nn2cccnc12)c1nc2cccc(C#Cc3ccncc3)c2c(=O)n1Nc1ccccc1]
118S
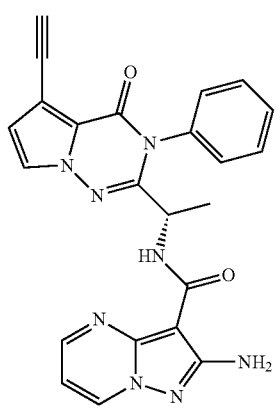 [SMILES: C#Cc1ccn2nc([C@H](C)NC(=O)c3c(N)nn4cccnc34)n(-c3ccccc3)c(=O)c12]
119S
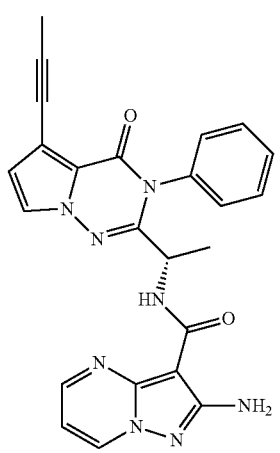
120S
TABLE 2-continued
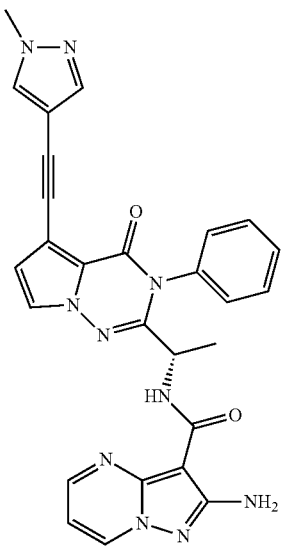
121S
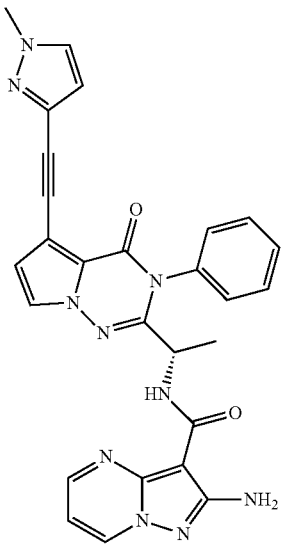 [SMILES: C[C@H](NC(=O)c1c(N)nn2cccnc12)c1nn2ccc(C#Cc3ccn(C)n3)c2c(=O)n1-c1ccccc1]
122S
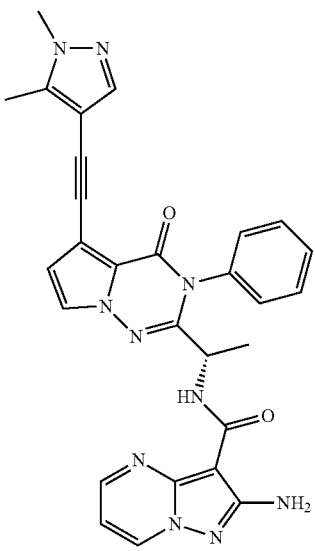 [SMILES: Cc1c(C#Cc2ccn3nc([C@H](C)NC(=O)c4c(N)nn5cccnc45)n(-c4ccccc4)c(=O)c23)cnn1C]
123S TABLE 2-continued
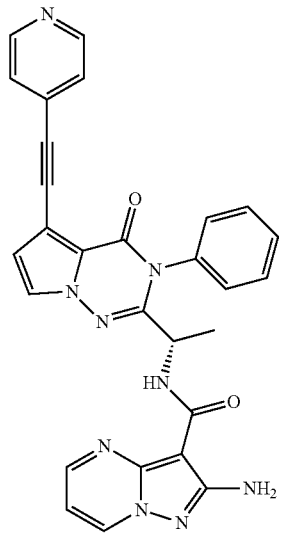
124S
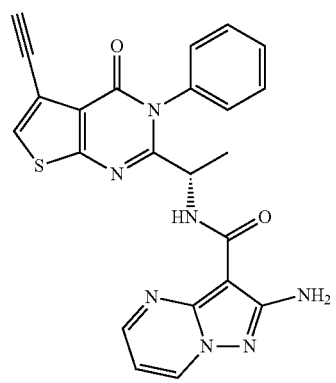 [SMILES: C#Cc1csc2nc([C@H](C)NC(=O)c3c(N)nn4cccnc34)n(-c3ccccc3)c(=O)c12]
125S
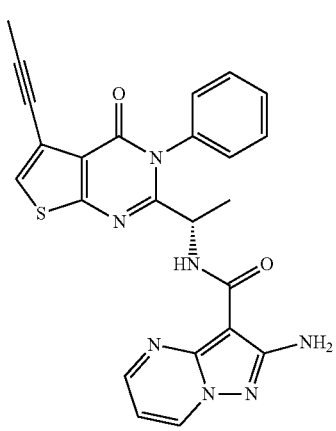 [SMILES: CC#Cc1csc2nc([C@H](C)NC(=O)c3c(N)nn4cccnc34)n(-c3ccccc3)c(=O)c12]
126S
TABLE 2-continued
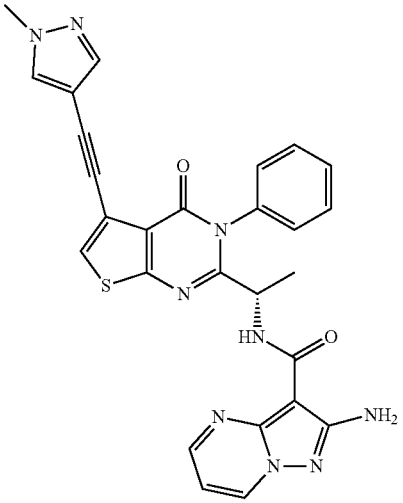 [SMILES: C[C@H](NC(=O)c1c(N)nn2cccnc12)c1nc2scc(C#Cc3cnn(C)c3)c2c(=O)n1-c1ccccc1]
127S
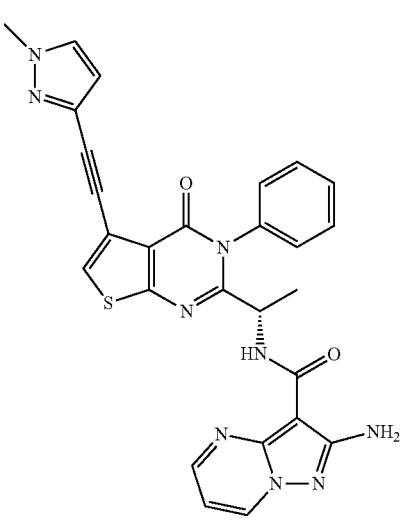 [SMILES: C[C@H](NC(=O)c1c(N)nn2cccnc12)c1nc2scc(C#Cc3ccn(C)n3)c2c(=O)n1-c1ccccc1]
128S
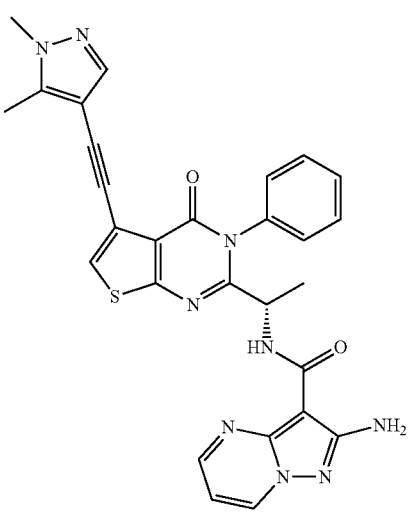
129S TABLE 2-continued
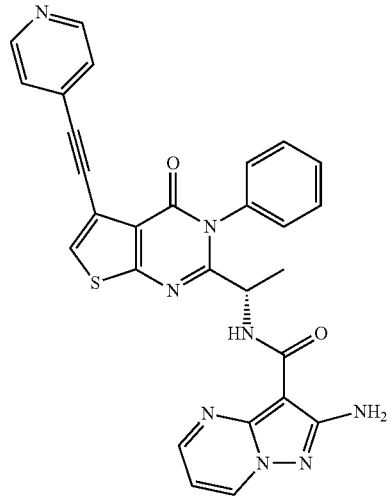
130S
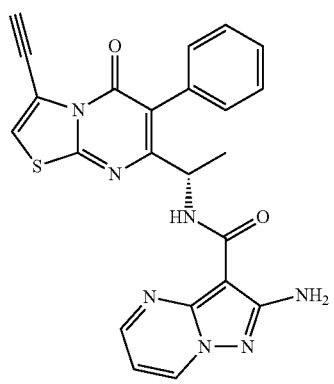 [SMILES: C#Cc1csc2nc([C@H](C)NC(=O)c3c(N)nn4cccnc34)c(-c3ccccc3)c(=O)n12]
131S
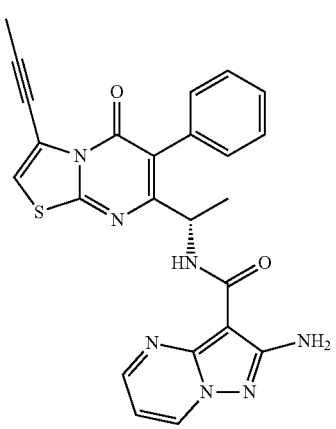 [SMILES: CC#Cc1csc2nc([C@H](C)NC(=O)c3c(N)nn4cccnc34)c(-c3ccccc3)c(=O)n12]
132S
TABLE 2-continued
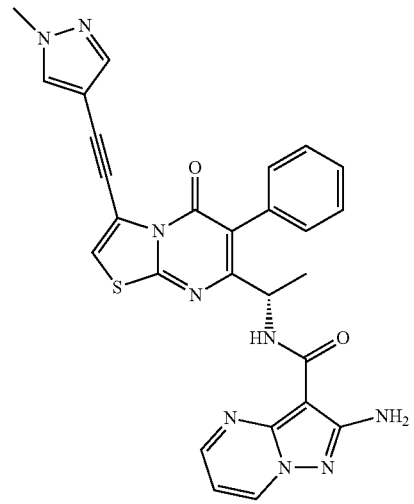 [SMILES: C[C@H](NC(=O)c1c(N)nn2cccnc12)c1nc2scc(C#Cc3cnn(C)c3)n2c(=O)c1-c1ccccc1]
133S
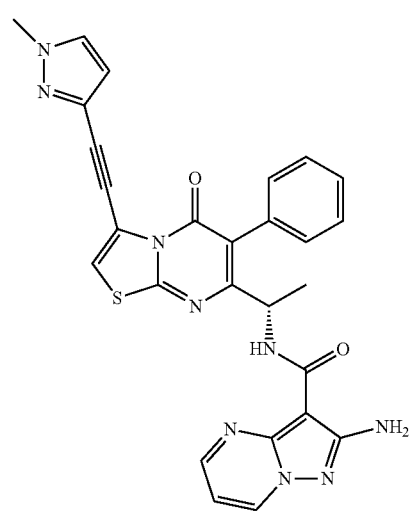 [SMILES: C[C@H](NC(=O)c1c(N)nn2cccnc12)c1nc2scc(C#Cc3ccn(C)n3)n2c(=O)c1-c1ccccc1]
134S
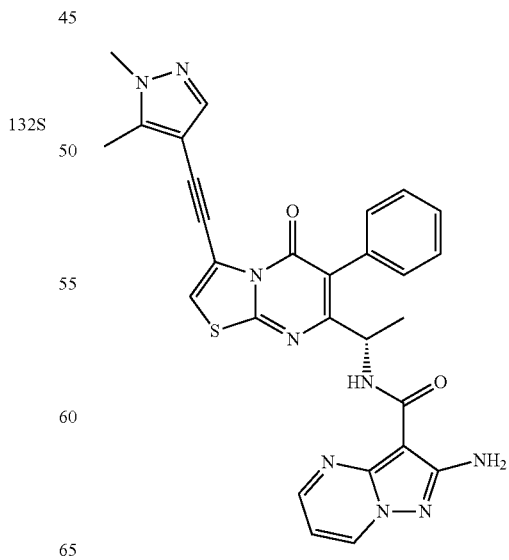
135S TABLE 2-continued
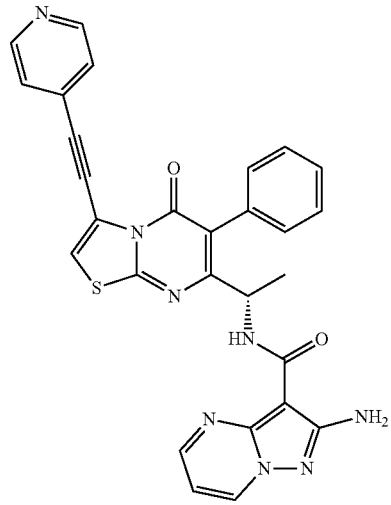 [SMILES: C[C@H](NC(=O)c1c(N)nn2cccnc12)c1nc2scc(C#Cc3ccncc3)n2c(=O)c1-c1ccccc1]
136S
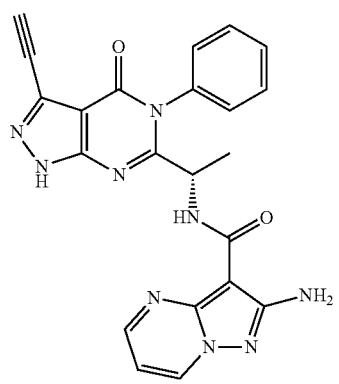 [SMILES: C#Cc1n[nH]c2nc([C@H](C)NC(=O)c3c(N)nn4cccnc34)n(-c3ccccc3)c(=O)c12]
137S
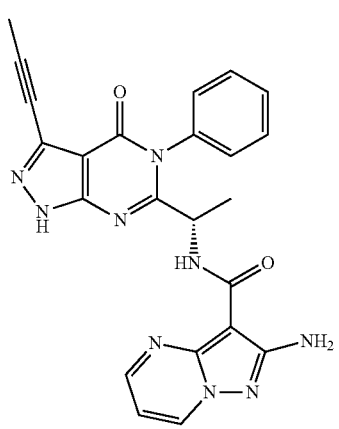 [SMILES: CC#Cc1n[nH]c2nc([C@H](C)NC(=O)c3c(N)nn4cccnc34)n(-c3ccccc3)c(=O)c12]
138S
TABLE 2-continued
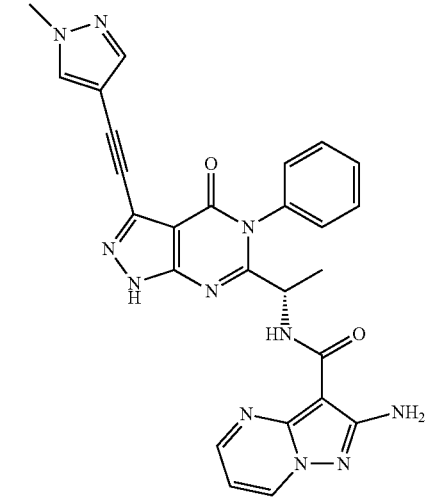 [SMILES: C[C@H](NC(=O)c1c(N)nn2cccnc12)c1nc2[nH]nc(C#Cc3cnn(C)c3)c2c(=O)n1-c1ccccc1]
139S
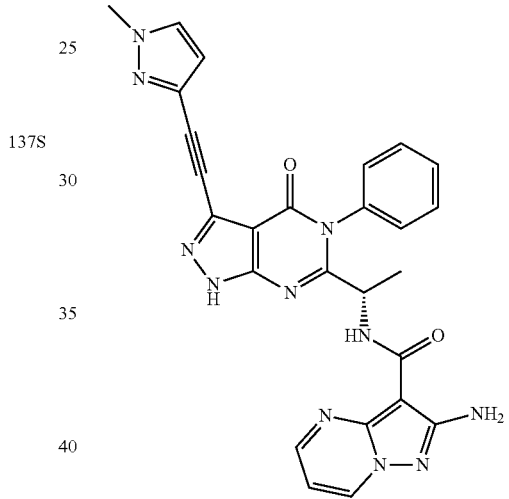
140S
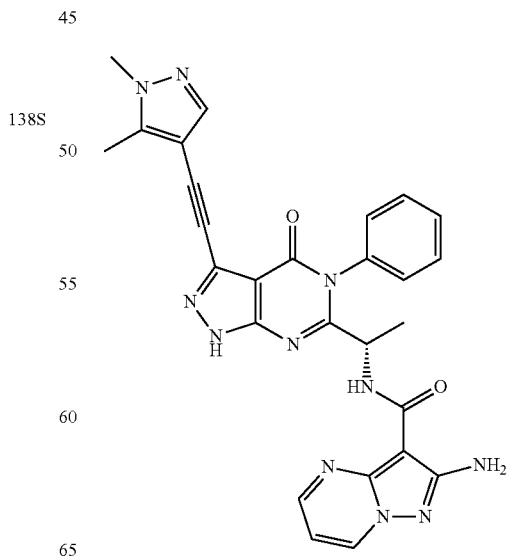
141S TABLE 2-continued
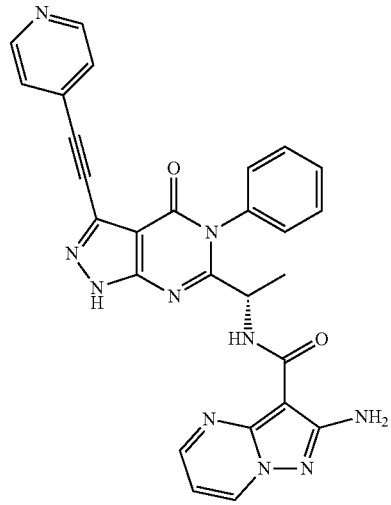 [SMILES: C[C@H](NC(=O)c1c(N)nn2cccnc12)c1nc2[nH]nc(C#Cc3ccncc3)c2c(=O)n1-c1ccccc1]
142S
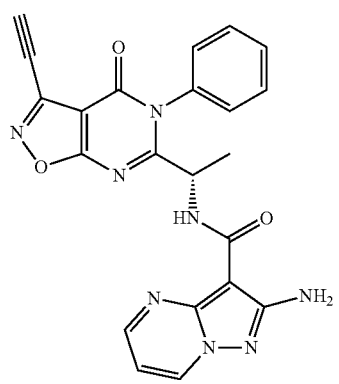 [SMILES: C#Cc1noc2nc([C@H](C)NC(=O)c3c(N)nn4cccnc34)n(-c3ccccc3)c(=O)c12]
143S
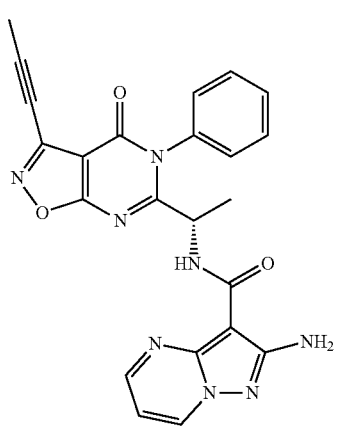 [SMILES: CC#Cc1noc2nc([C@H](C)NC(=O)c3c(N)nn4cccnc34)n(-c3ccccc3)c(=O)c12]
144S
TABLE 2-continued
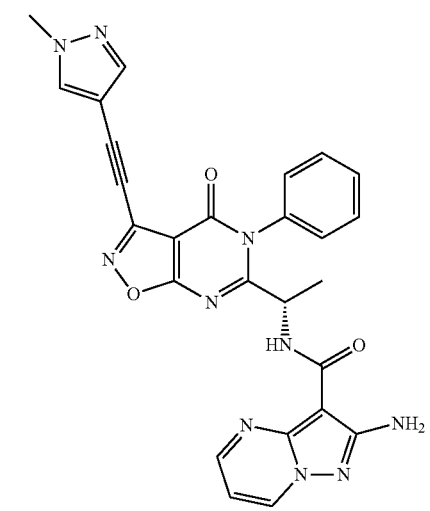 [SMILES: C[C@H](NC(=O)c1c(N)nn2cccnc12)c1nc2onc(C#Cc3cnn(C)c3)c2c(=O)n1-c1ccccc1]
145S
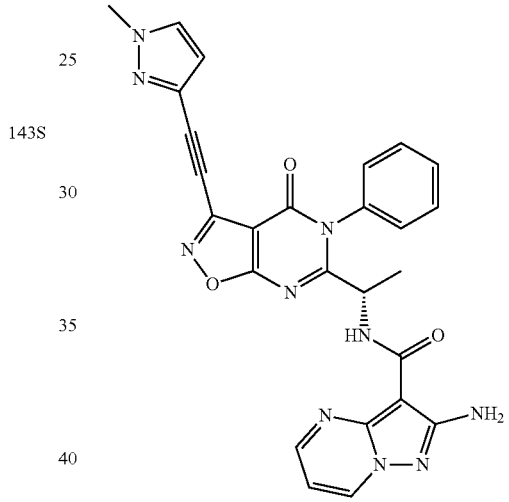
146S
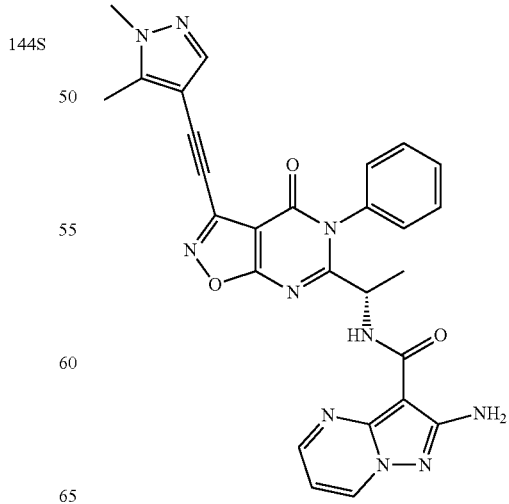
147S TABLE 2-continued
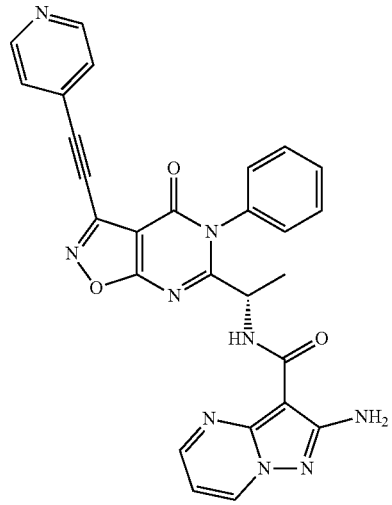
148S
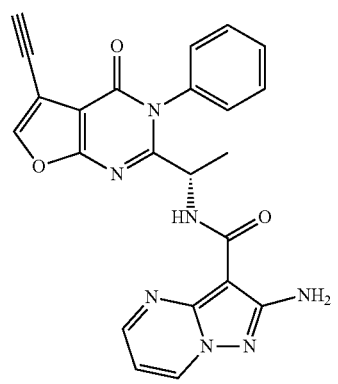
149S
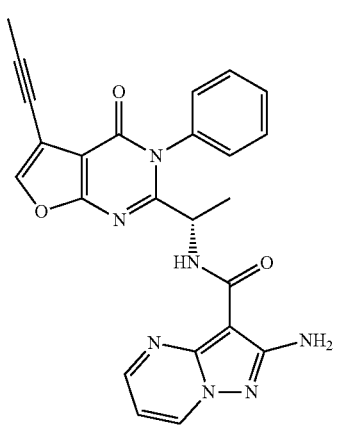
150S
TABLE 2-continued
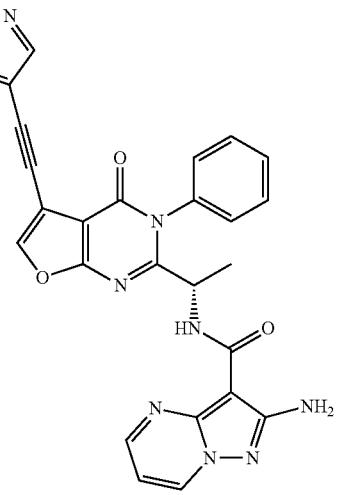
151S
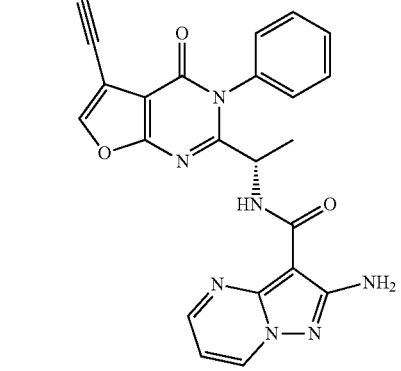 [SMILES: C#Cc1coc2nc([C@H](C)NC(=O)c3c(N)nn4cccnc34)n(-c3ccccc3)c(=O)c12]
152S
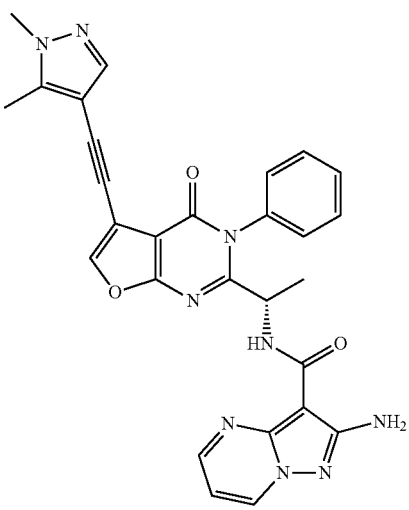 [SMILES: Cc1c(C#Cc2coc3nc([C@H](C)NC(=O)c4c(N)nn5cccnc45)n(-c4ccccc4)c(=O)c23)cnn1C]
153S TABLE 2-continued
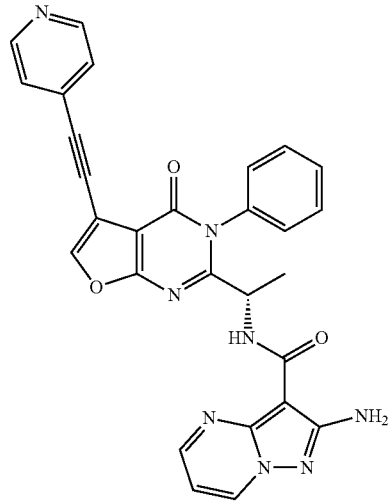 [SMILES: C[C@H](NC(=O)c1c(N)nn2cccnc12)c1nc2occ(C#Cc3ccncc3)c2c(=O)n1-c1ccccc1]
154S
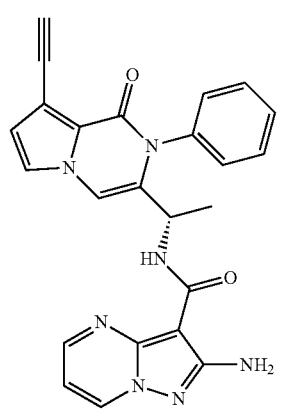 [SMILES: C#Cc1ccn2cc([C@H](C)NC(=O)c3c(N)nn4cccnc34)n(-c3ccccc3)c(=O)c12]
155S
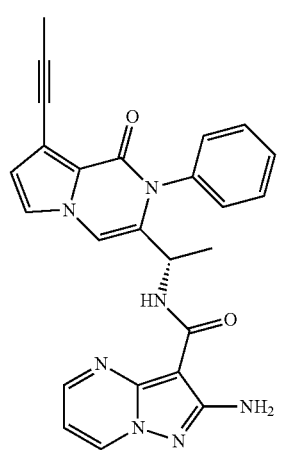 [SMILES: CC#Cc1ccn2cc([C@H](C)NC(=O)c3c(N)nn4cccnc34)n(-c3ccccc3)c(=O)c12]
156S
TABLE 2-continued
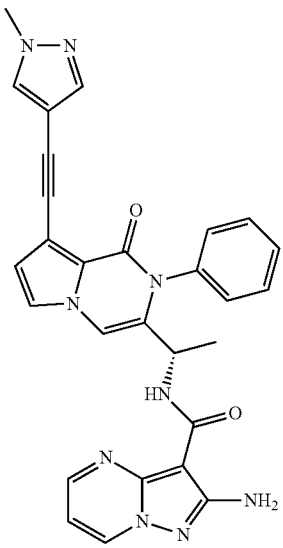
157S
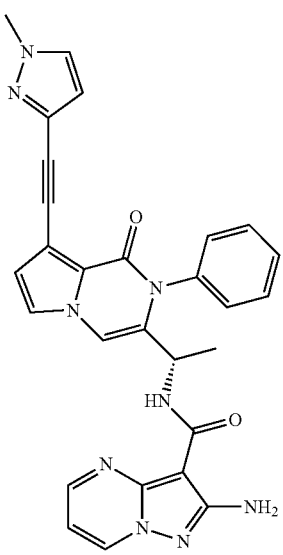
158S
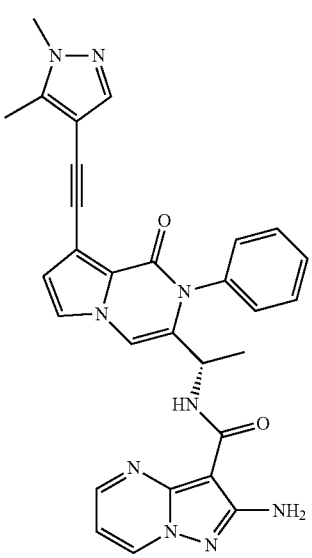 [SMILES: Cc1c(C#Cc2ccn3cc([C@H](C)NC(=O)c4c(N)nn5cccnc45)n(-c4ccccc4)c(=O)c23)cnn1C]
159S TABLE 2-continued
160S 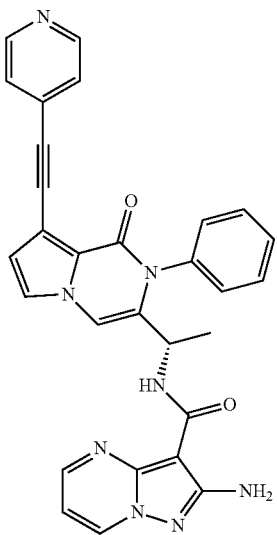
161S 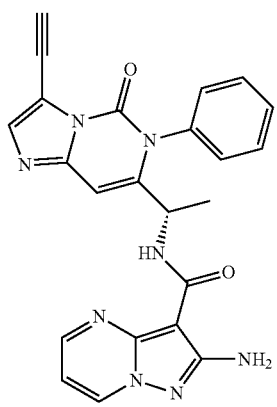
162S 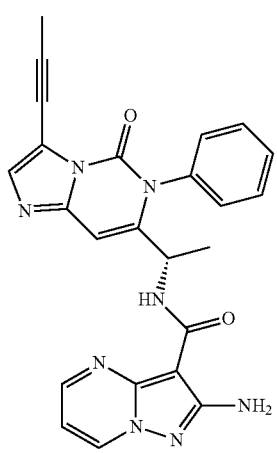 [SMILES: CC#Cc1cnc2cc([C@H](C)NC(=O)c3c(N)nn4cccnc34)n(-c3ccccc3)c(=O)n12]
TABLE 2-continued
163S 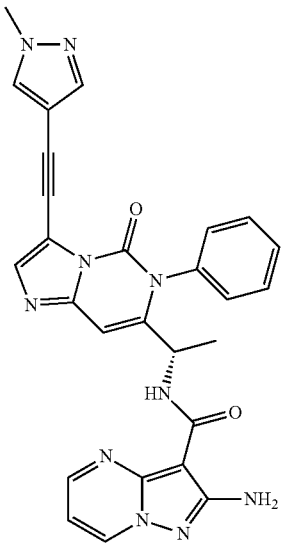
164S 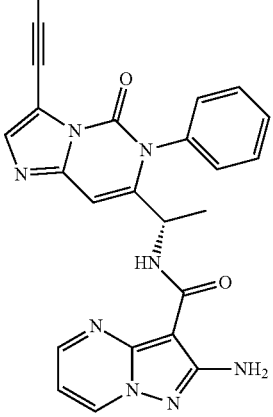
165S 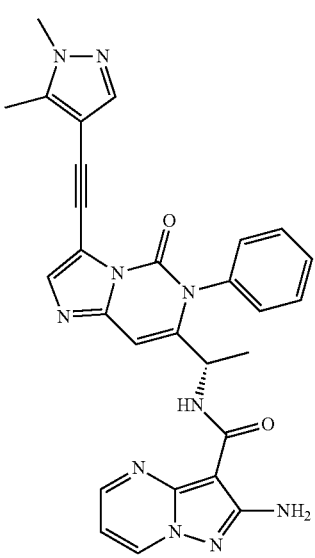 [SMILES: Cc1c(C#Cc2cnc3cc([C@H](C)NC(=O)c4c(N)nn5cccnc45)n(-c4ccccc4)c(=O)n23)cnn1C]

TABLE 2-continued
| | |
|---|---|
| 166S 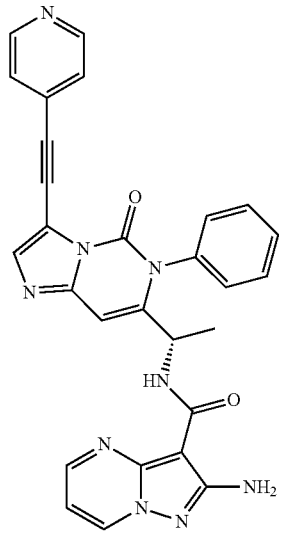 | 169S 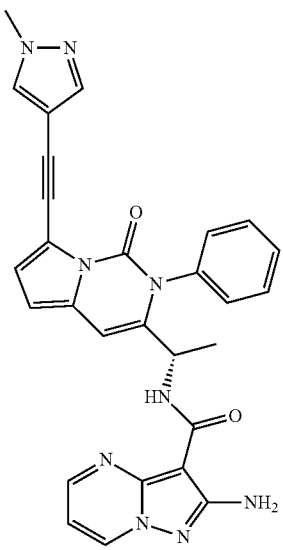 |
| 167S 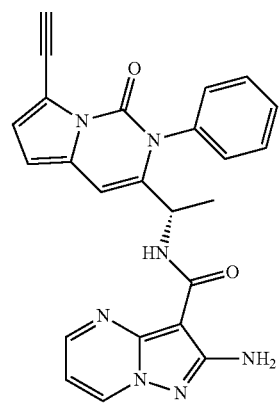 [SMILES: C#Cc1ccc2cc([C@H](C)NC(=O)c3c(N)nn4cccnc34)n(-c3ccccc3)c(=O)n12] | 170S 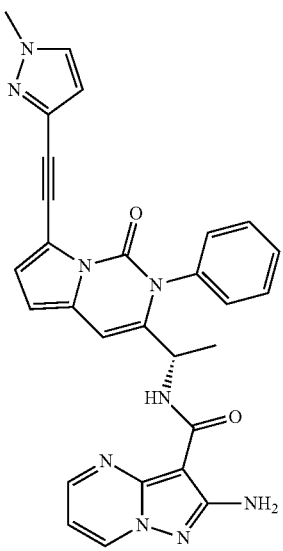 |
| 168S 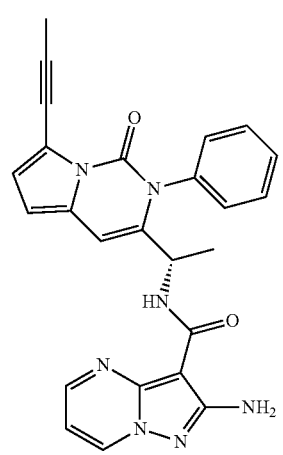 [SMILES: CC#Cc1ccc2cc([C@H](C)NC(=O)c3c(N)nn4cccnc34)n(-c3ccccc3)c(=O)n12] | 171S 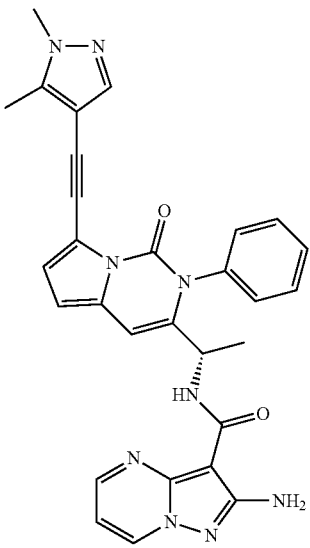 [SMILES: Cc1c(C#Cc2ccc3cc([C@H](C)NC(=O)c4c(N)nn5cccnc45)n(-c4ccccc4)c(=O)n23)cnn1C] |

TABLE 2-continued
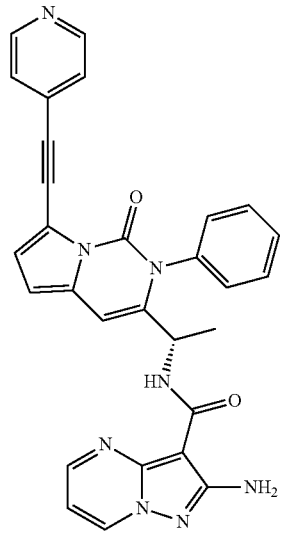
172S
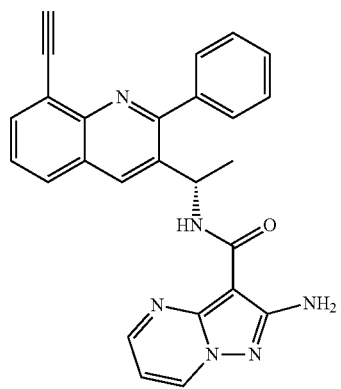 [SMILES: C#Cc1cccc2cc([C@H](C)NC(=O)c3c(N)nn4cccnc34)c(-c3ccccc3)nc12]
173S
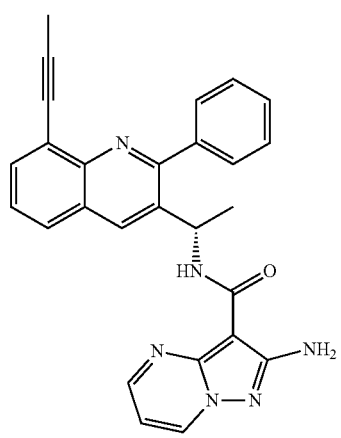 [SMILES: CC#Cc1cccc2cc([C@H](C)NC(=O)c3c(N)nn4cccnc34)c(-c3ccccc3)nc12]
174S
TABLE 2-continued
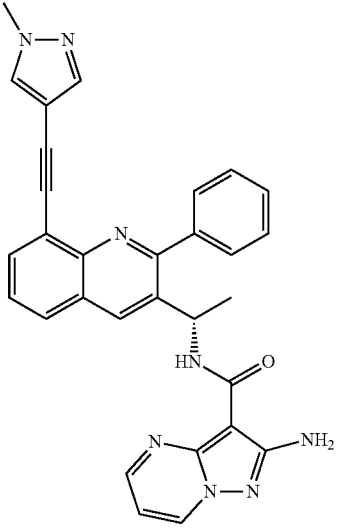 [SMILES: C[C@H](NC(=O)c1c(N)nn2cccnc12)c1cc2cccc(C#Cc3cnn(C)c3)c2nc1-c1ccccc1]
175S
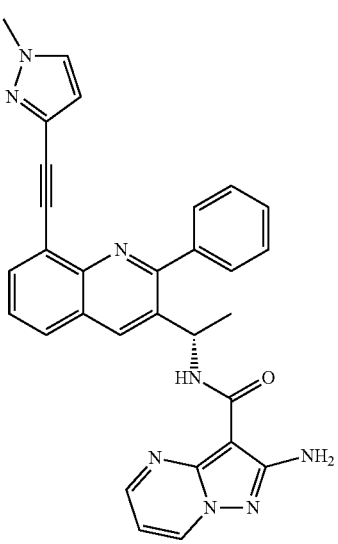 [SMILES: C[C@H](NC(=O)c1c(N)nn2cccnc12)c1cc2cccc(C#Cc3ccn(C)n3)c2nc1-c1ccccc1]
176S
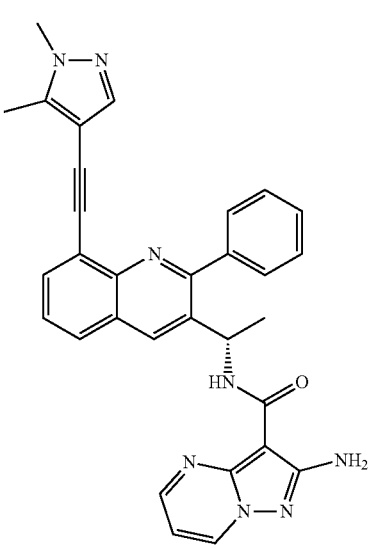 [SMILES: Cc1c(C#Cc2cccc3cc([C@H](C)NC(=O)c4c(N)nn5cccnc45)c(-c4ccccc4)nc23)cnn1C]
177S TABLE 2-continued
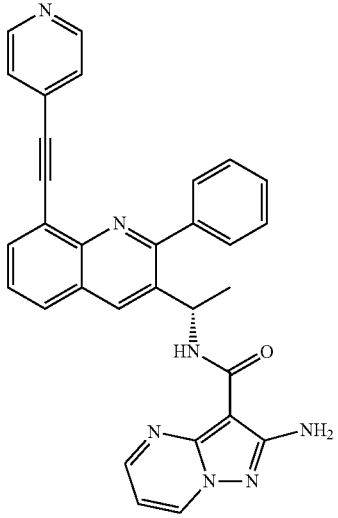 [SMILES: C[C@H](NC(=O)c1c(N)nn2cccnc12)c1cc2cccc(C#Cc3ccncc3)c2nc1-c1ccccc1]
178S
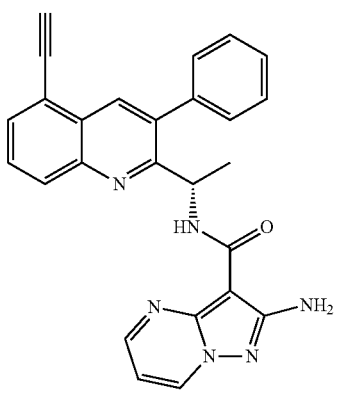 [SMILES: C#Cc1cccc2nc([C@H](C)NC(=O)c3c(N)nn4cccnc34)c(-c3ccccc3)cc12]
179S
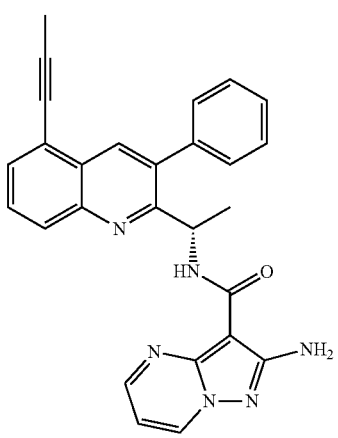 [SMILES: CC#Cc1cccc2nc([C@H](C)NC(=O)c3c(N)nn4cccnc34)c(-c3ccccc3)cc12]
180S
TABLE 2-continued
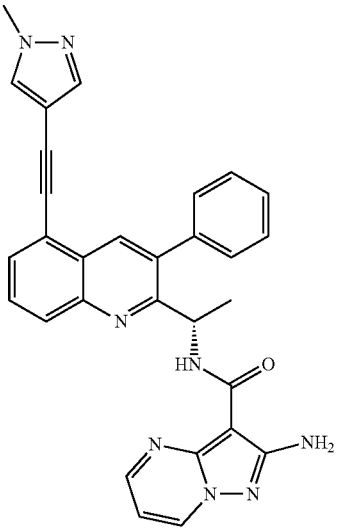 [SMILES: C[C@H](NC(=O)c1c(N)nn2cccnc12)c1nc2cccc(C#Cc3cnn(C)c3)c2cc1-c1ccccc1]
181S
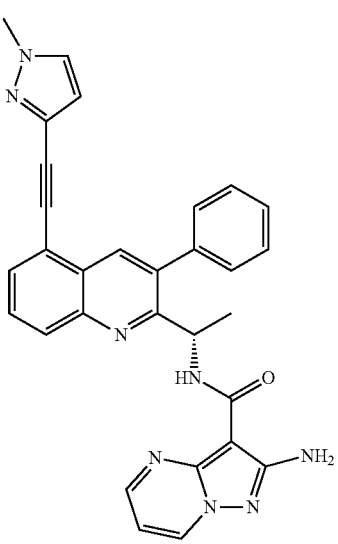 [SMILES: C[C@H](NC(=O)c1c(N)nn2cccnc12)c1nc2cccc(C#Cc3ccn(C)n3)c2cc1-c1ccccc1]
182S
183S TABLE 2-continued
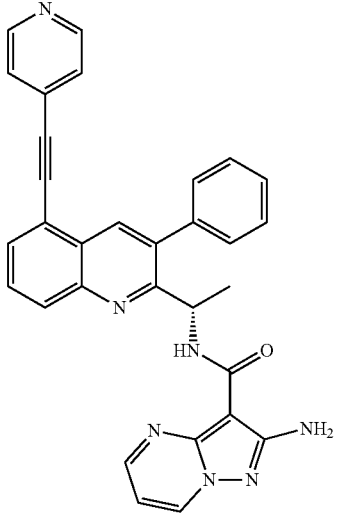 [SMILES: C[C@H](NC(=O)c1c(N)nn2cccnc12)c1nc2cccc(C#Cc3ccncc3)c2cc1-c1ccccc1]
184S
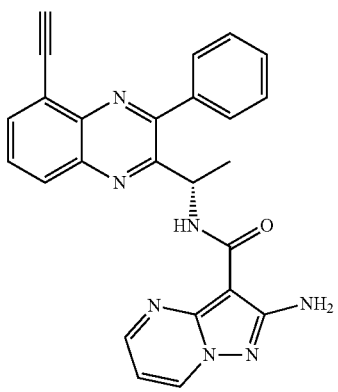 [SMILES: C#Cc1cccc2nc([C@H](C)NC(=O)c3c(N)nn4cccnc34)c(-c3ccccc3)nc12]
185S
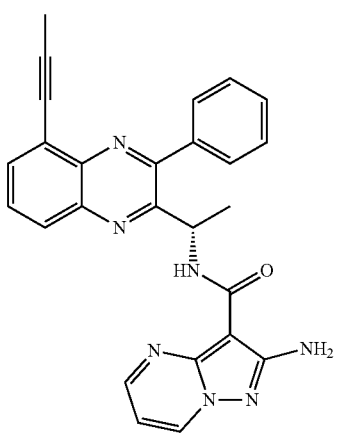 [SMILES: CC#Cc1cccc2nc([C@H](C)NC(=O)c3c(N)nn4cccnc34)c(-c3ccccc3)nc12]
186S
TABLE 2-continued
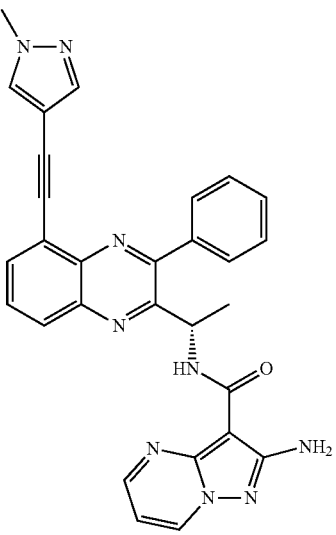 [SMILES: C[C@H](NC(=O)c1c(N)nn2cccnc12)c1nc2cccc(C#Cc3cnn(C)c3)c2nc1-c1ccccc1]
187S
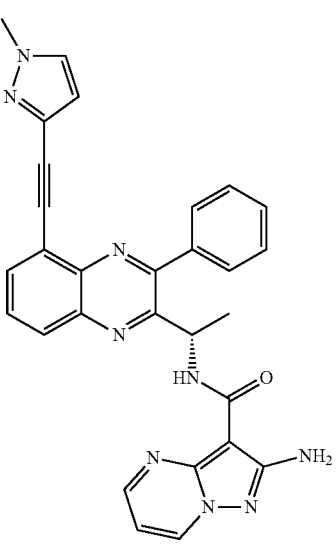 [SMILES: C[C@H](NC(=O)c1c(N)nn2cccnc12)c1nc2cccc(C#Cc3ccn(C)n3)c2nc1-c1ccccc1]
188S
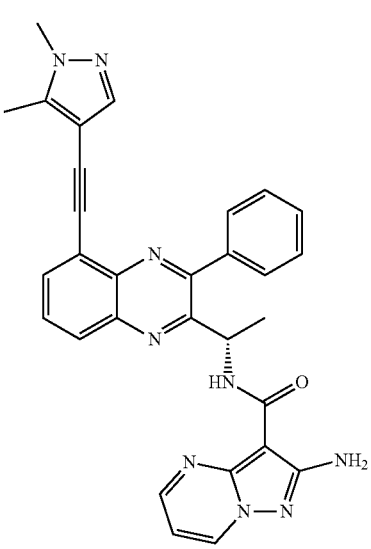 [SMILES: Cc1c(C#Cc2cccc3nc([C@H](C)NC(=O)c4c(N)nn5cccnc45)c(-c4ccccc4)nc23)cnn1C]
189S TABLE 2-continued
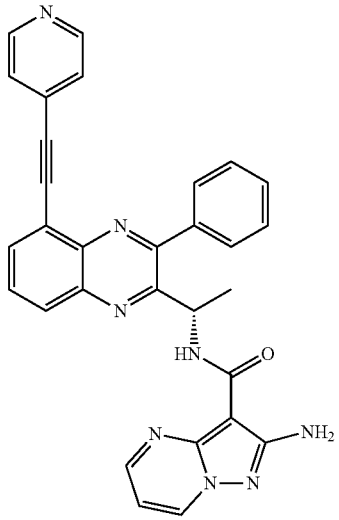 [SMILES: C[C@H](NC(=O)c1c(N)nn2cccnc12)c1nc2cccc(C#Cc3ccncc3)c2nc1-c1ccccc1]
190S
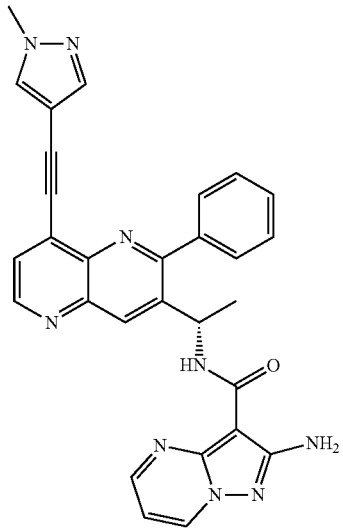
193S
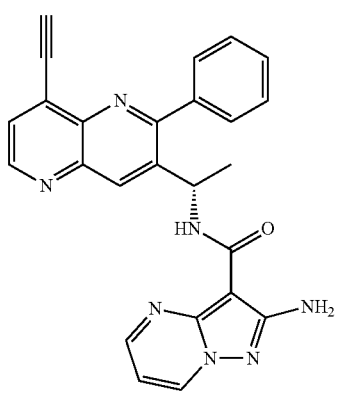 [SMILES: C#Cc1ccnc2cc([C@H](C)NC(=O)c3c(N)nn4cccnc34)c(-c3ccccc3)nc12]
191S
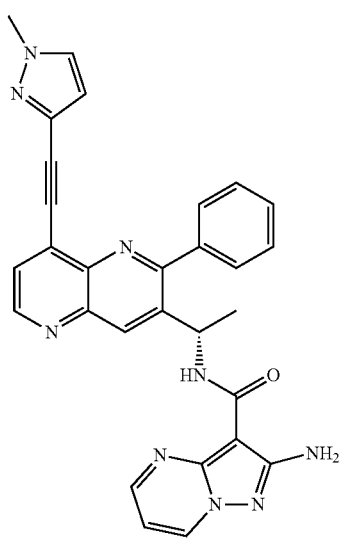 [SMILES: C[C@H](NC(=O)c1c(N)nn2cccnc12)c1cc2nccc(C#Cc3ccn(C)n3)c2nc1-c1ccccc1]
194S
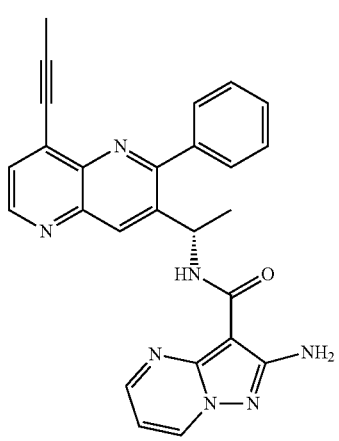
192S
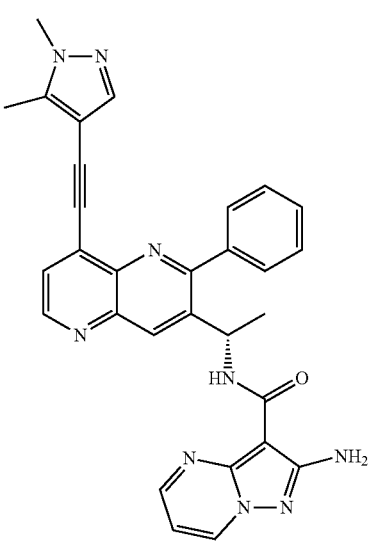 [SMILES: Cc1c(C#Cc2ccnc3cc([C@H](C)NC(=O)c4c(N)nn5cccnc45)c(-c4ccccc4)nc23)cnn1C]
195S TABLE 2-continued
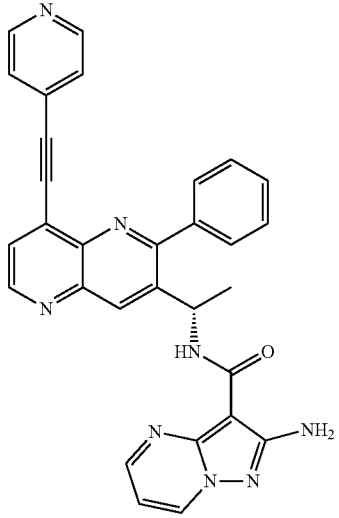 [SMILES: C[C@H](NC(=O)c1c(N)nn2cccnc12)c1cc2nccc(C#Cc3ccncc3)c2nc1-c1ccccc1]
196S
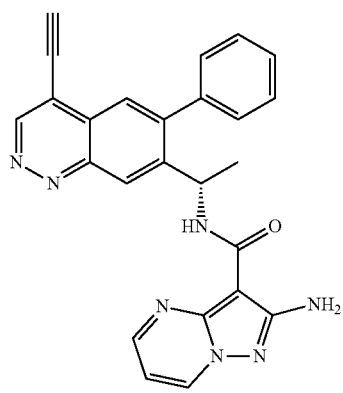 [SMILES: C#Cc1cnnc2cc([C@H](C)NC(=O)c3c(N)nn4cccnc34)c(-c3ccccc3)cc12]
197S
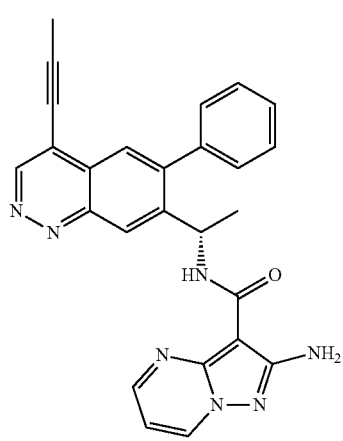 [SMILES: CC#Cc1cnnc2cc([C@H](C)NC(=O)c3c(N)nn4cccnc34)c(-c3ccccc3)cc12]
198S
TABLE 2-continued
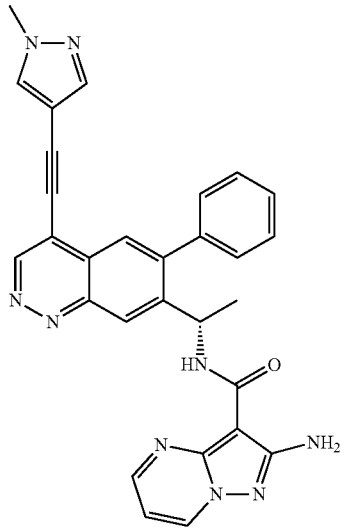 [SMILES: C[C@H](NC(=O)c1c(N)nn2cccnc12)c1cc2nncc(C#Cc3cnn(C)c3)c2cc1-c1ccccc1]
199S
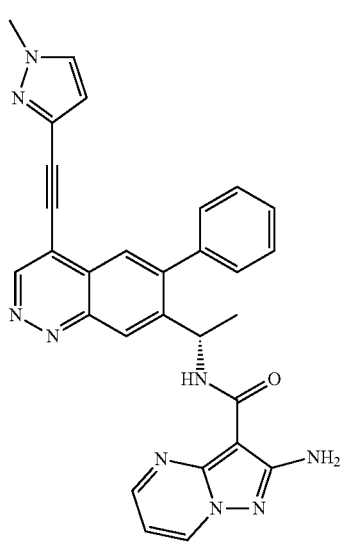 [SMILES: C[C@H](NC(=O)c1c(N)nn2cccnc12)c1cc2nncc(C#Cc3ccn(C)n3)c2cc1-c1ccccc1]
200S
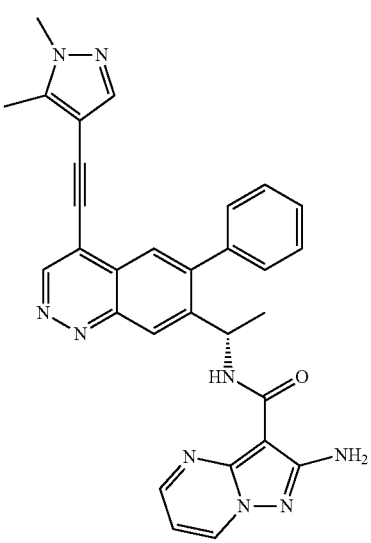 [SMILES: Cc1c(C#Cc2cnnc3cc([C@H](C)NC(=O)c4c(N)nn5cccnc45)c(-c4ccccc4)cc23)cnn1C]
201S TABLE 2-continued
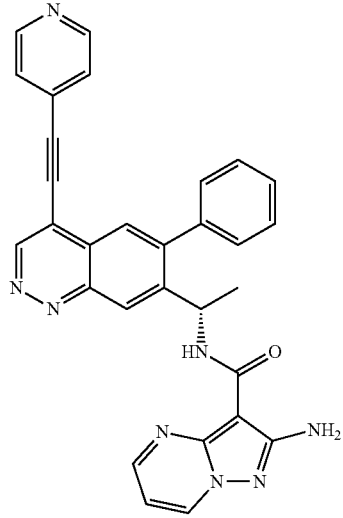 [SMILES: C[C@H](NC(=O)c1c(N)nn2cccnc12)c1cc2nncc(C#Cc3ccncc3)c2cc1-c1ccccc1]
202S
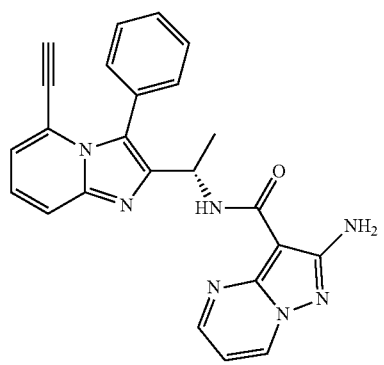 [SMILES: C#Cc1cccc2nc([C@H](C)NC(=O)c3c(N)nn4cccnc34)c(-c3ccccc3)n12]
203S
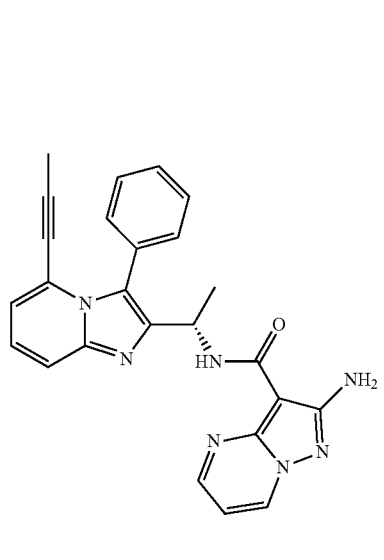 [SMILES: CC#Cc1cccc2nc([C@H](C)NC(=O)c3c(N)nn4cccnc34)c(-c3ccccc3)n12]
204S
TABLE 2-continued
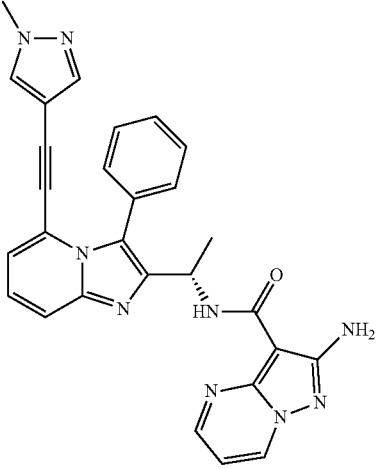 [SMILES: C[C@H](NC(=O)c1c(N)nn2cccnc12)c1nc2cccc(C#Cc3cnn(C)c3)n2c1-c1ccccc1]
205S
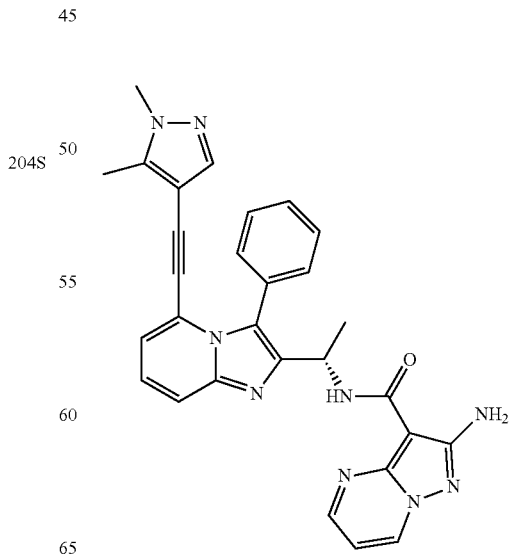
206S
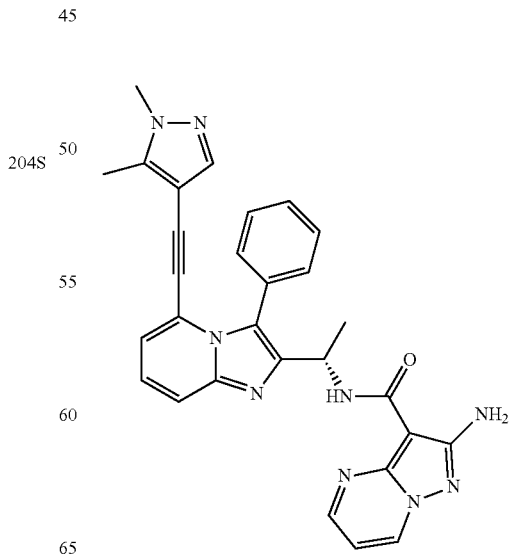
207S TABLE 2-continued
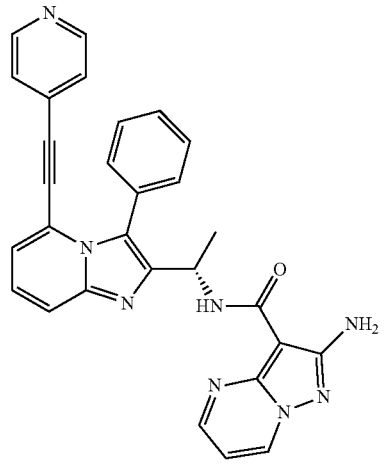 [SMILES: C[C@H](NC(=O)c1c(N)nn2cccnc12)c1nc2cccc(C#Cc3ccncc3)n2c1-c1ccccc1]
208S
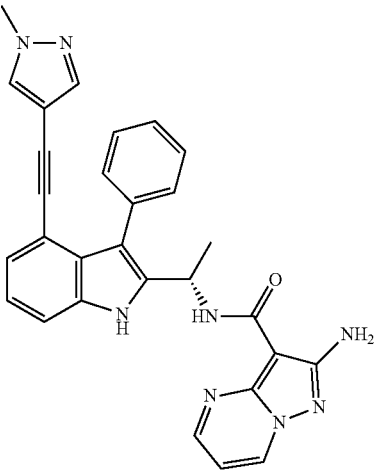
211S
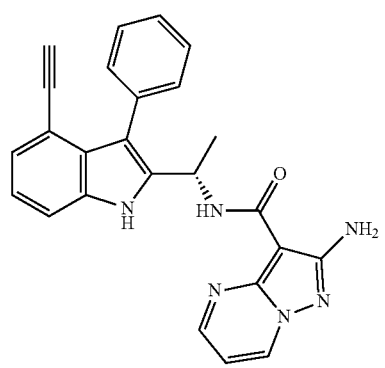 [SMILES: C#Cc1cccc2[nH]c([C@H](C)NC(=O)c3c(N)nn4cccnc34)c(-c3ccccc3)c12]
209S
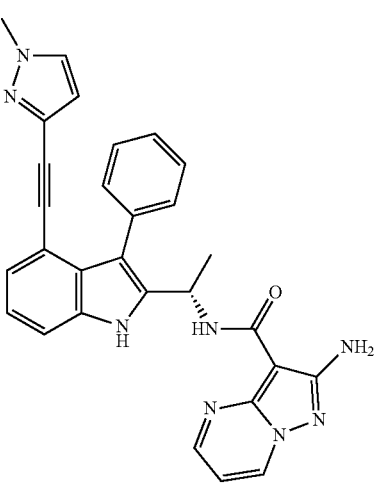
212S
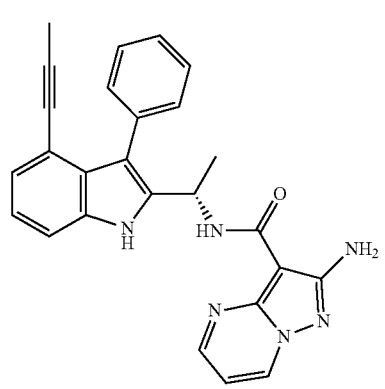 [SMILES: CC#Cc1cccc2[nH]c([C@H](C)NC(=O)c3c(N)nn4cccnc34)c(-c3ccccc3)c12]
210S
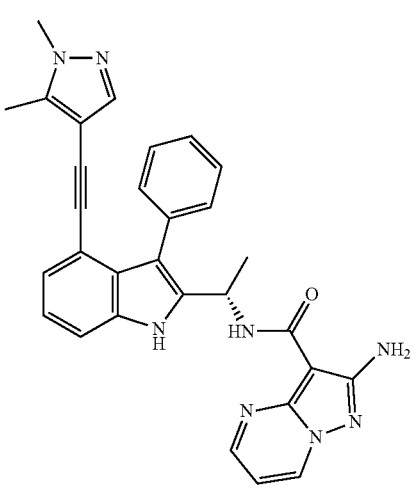 [SMILES: Cc1c(C#Cc2cccc3[nH]c([C@H](C)NC(=O)c4c(N)nn5cccnc45)c(-c4ccccc4)c23)cnn1C]
213S TABLE 2-continued
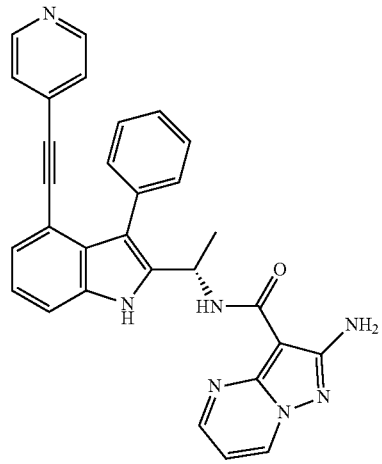 [SMILES: C[C@H](NC(=O)c1c(N)nn2cccnc12)c1[nH]c2cccc(C#Cc3ccncc3)c2c1-c1ccccc1] 214S
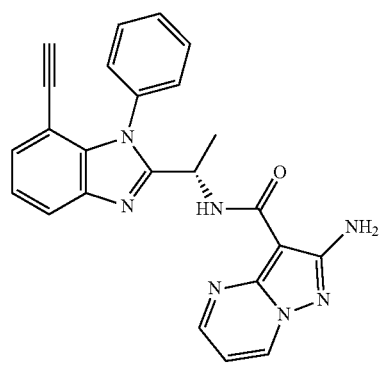 [SMILES: C#Cc1cccc2nc([C@H](C)NC(=O)c3c(N)nn4cccnc34)n(-c3ccccc3)c12] 215S
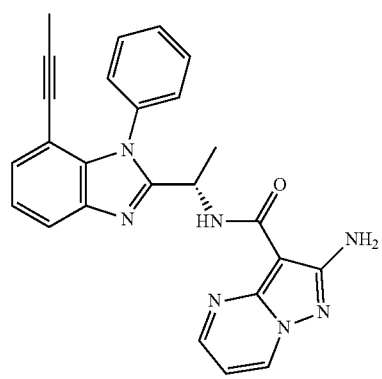 [SMILES: CC#Cc1cccc2nc([C@H](C)NC(=O)c3c(N)nn4cccnc34)n(-c3ccccc3)c12] 216S
TABLE 2-continued
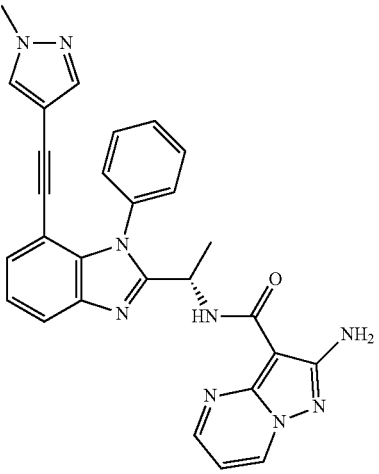 [SMILES: C[C@H](NC(=O)c1c(N)nn2cccnc12)c1nc2cccc(C#Cc3cnn(C)c3)c2n1-c1ccccc1] 217S
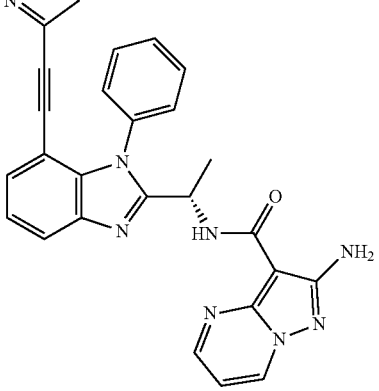 218S
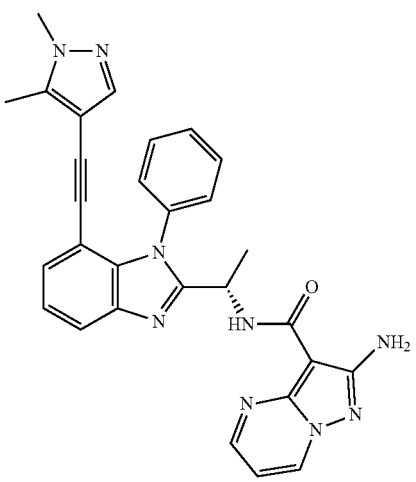 [SMILES: Cc1c(C#Cc2cccc3nc([C@H](C)NC(=O)c4c(N)nn5cccnc45)n(-c4ccccc4)c23)cnn1C] 219S TABLE 2-continued
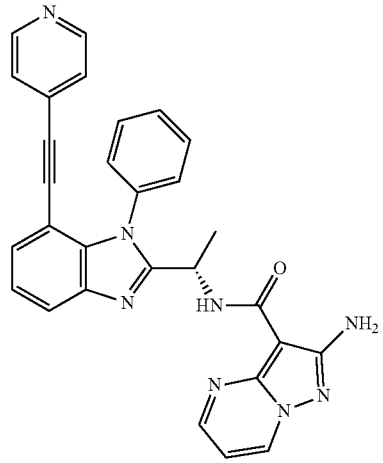 [SMILES: C[C@H](NC(=O)c1c(N)nn2cccnc12)c1nc2cccc(C#Cc3ccncc3)c2n1-c1ccccc1]
220S
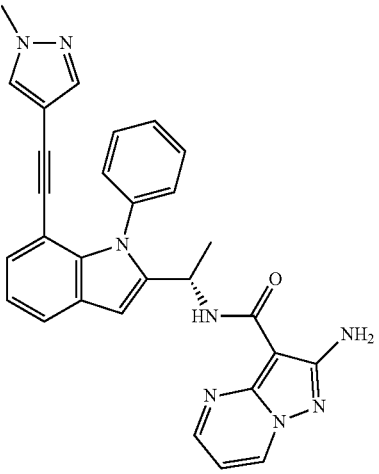
223S
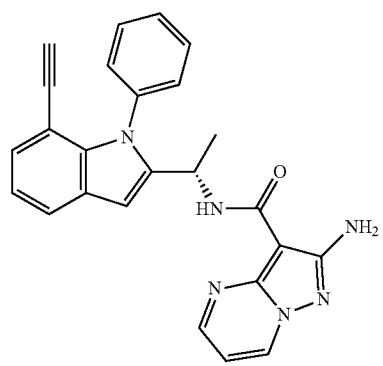 [SMILES: C#Cc1cccc2cc([C@H](C)NC(=O)c3c(N)nn4cccnc34)n(-c3ccccc3)c12]
221S
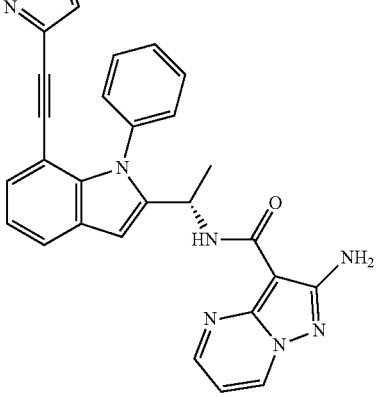
224S
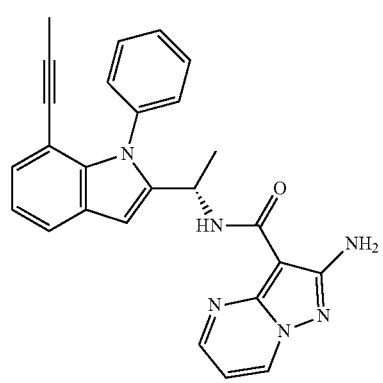 [SMILES: CC#Cc1cccc2cc([C@H](C)NC(=O)c3c(N)nn4cccnc34)n(-c3ccccc3)c12]
222S
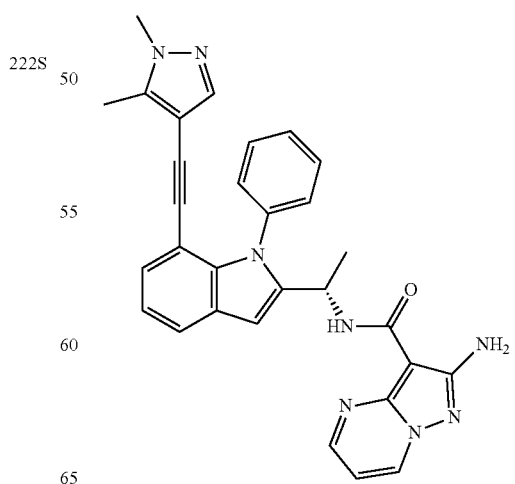
225S TABLE 2-continued
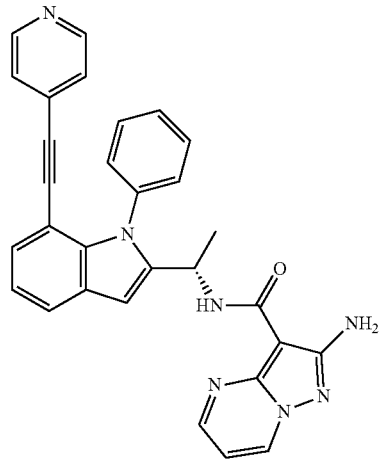 [SMILES: C[C@H](NC(=O)c1c(N)nn2cccnc12)c1cc2cccc(C#Cc3ccncc3)c2n1-c1ccccc1]
226S
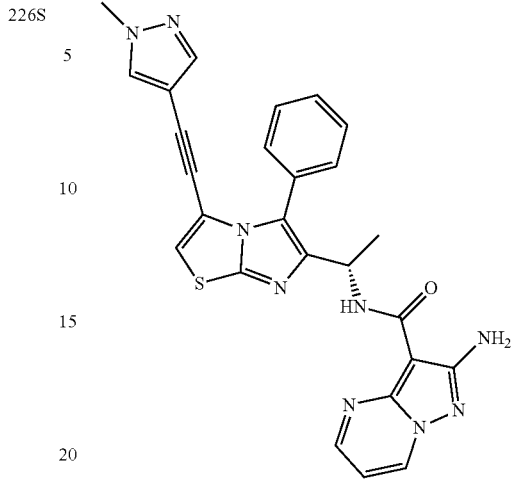
229S
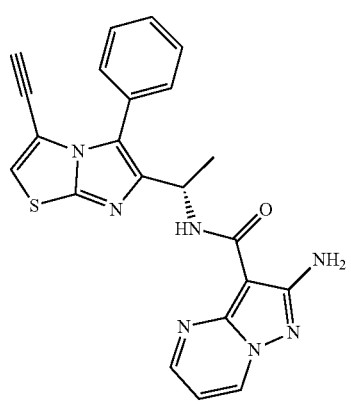 [SMILES: C#Cc1csc2nc([C@H](C)NC(=O)c3c(N)nn4cccnc34)c(-c3ccccc3)n12]
227S
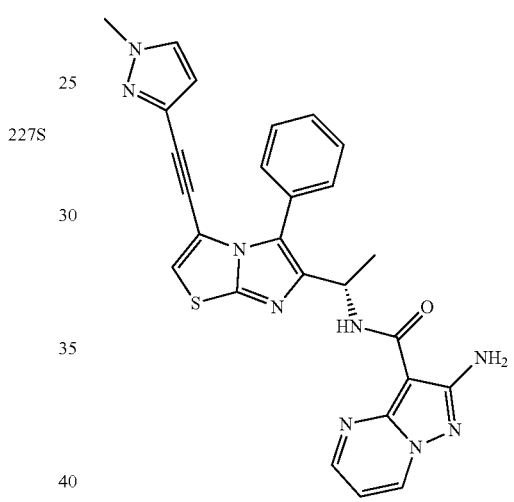
230S
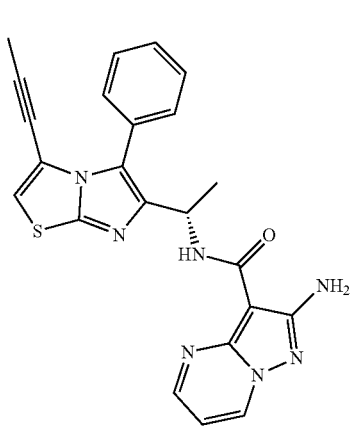 [SMILES: CC#Cc1csc2nc([C@H](C)NC(=O)c3c(N)nn4cccnc34)c(-c3ccccc3)n12]
228S
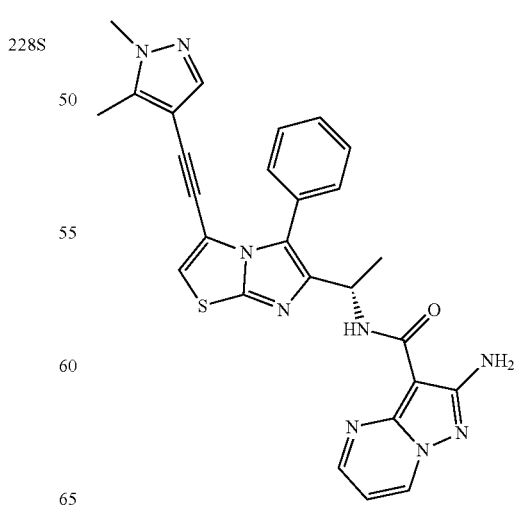
231S TABLE 2-continued
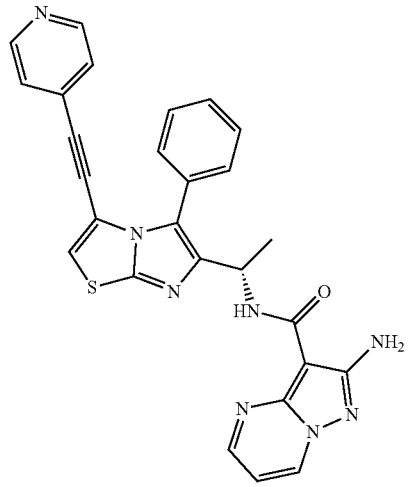 [SMILES: C[C@H](NC(=O)c1c(N)nn2cccnc12)c1nc2scc(C#Cc3ccncc3)n2c1-c1ccccc1]
232S
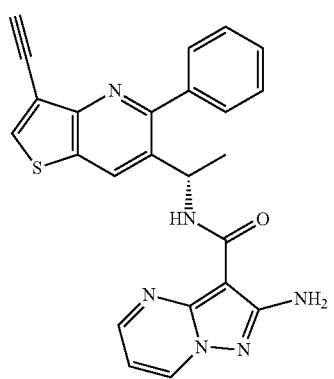 [SMILES: C#Cc1csc2cc([C@H](C)NC(=O)c3c(N)nn4cccnc34)c(-c3ccccc3)nc12]
233S
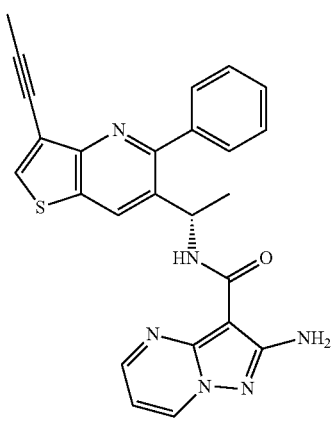 [SMILES: CC#Cc1csc2cc([C@H](C)NC(=O)c3c(N)nn4cccnc34)c(-c3ccccc3)nc12]
234S
TABLE 2-continued
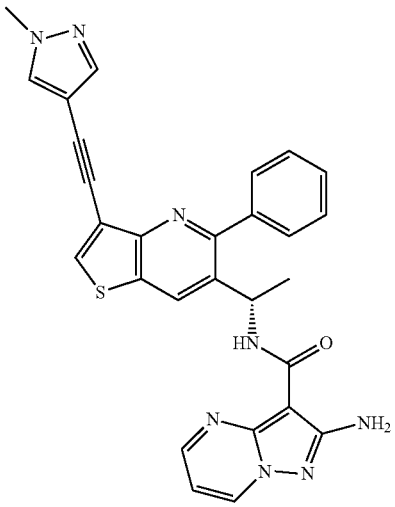 [SMILES: C[C@H](NC(=O)c1c(N)nn2cccnc12)c1cc2scc(C#Cc3cnn(C)c3)c2nc1-c1ccccc1]
235S
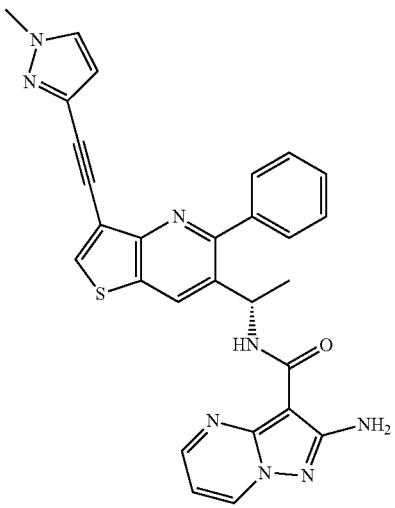 [SMILES: C[C@H](NC(=O)c1c(N)nn2cccnc12)c1cc2scc(C#Cc3ccn(C)n3)c2nc1-c1ccccc1]
236S
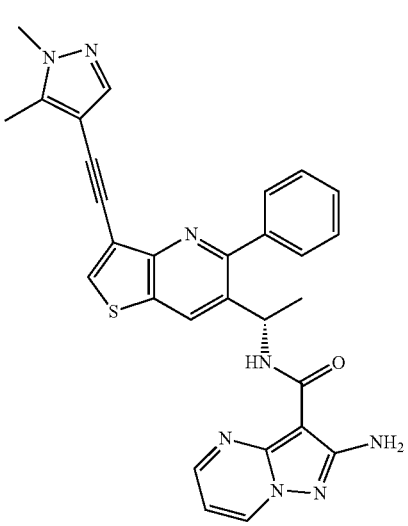 [SMILES: Cc1c(C#Cc2csc3cc([C@H](C)NC(=O)c4c(N)nn5cccnc45)c(-c4ccccc4)nc23)cnn1C]
237S TABLE 2-continued
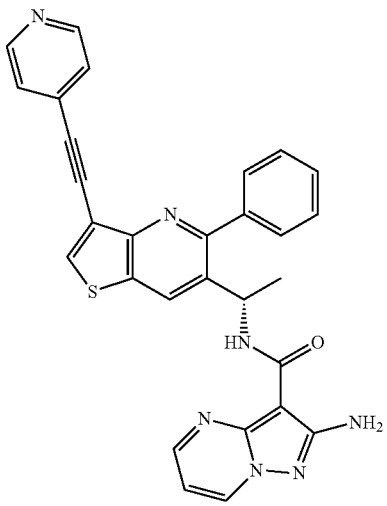 [SMILES: C[C@H](NC(=O)c1c(N)nn2cccnc12)c1cc2scc(C#Cc3ccncc3)c2nc1-c1ccccc1]
238S
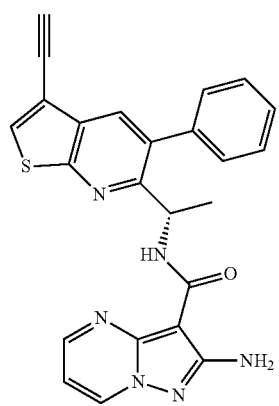 [SMILES: C#Cc1csc2nc([C@H](C)NC(=O)c3c(N)nn4cccnc34)c(-c3ccccc3)cc12]
239S
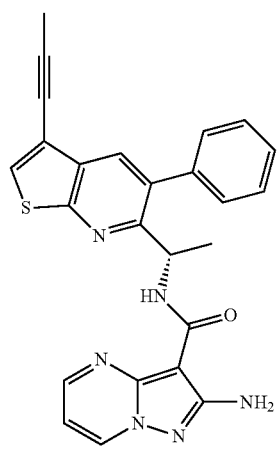 [SMILES: CC#Cc1csc2nc([C@H](C)NC(=O)c3c(N)nn4cccnc34)c(-c3ccccc3)cc12]
240S
TABLE 2-continued
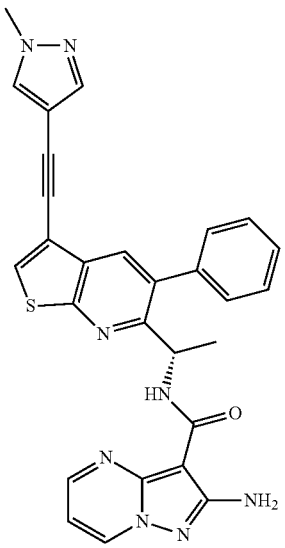
241S
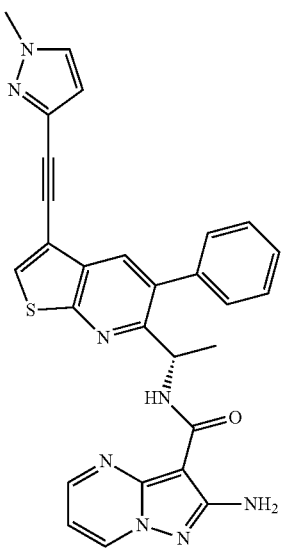 [SMILES: C[C@H](NC(=O)c1c(N)nn2cccnc12)c1nc2scc(C#Cc3ccn(C)n3)c2cc1-c1ccccc1]
242S
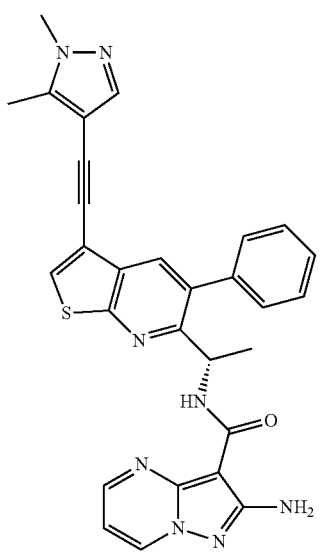 [SMILES: Cc1c(C#Cc2csc3nc([C@H](C)NC(=O)c4c(N)nn5cccnc45)c(-c4ccccc4)cc23)cnn1C]
243S TABLE 2-continued
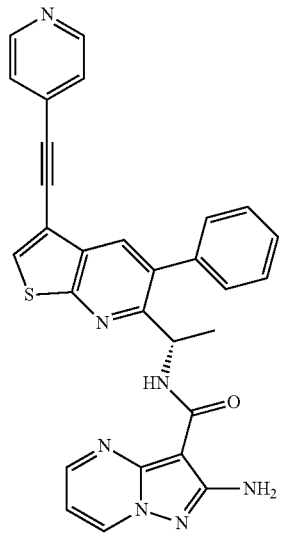
244S
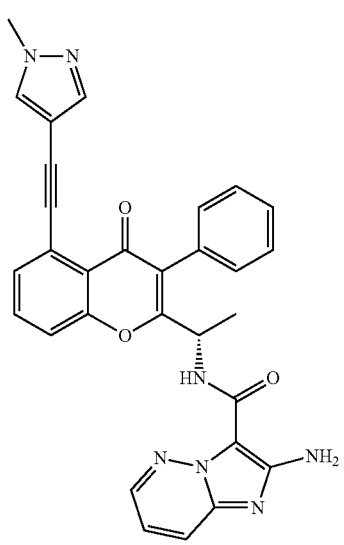 [SMILES: C[C@H](NC(=O)c1c(N)nc2cccnn12)c1oc2cccc(C#Cc3cnn(C)c3)c2c(=O)c1-c1ccccc1]
245S
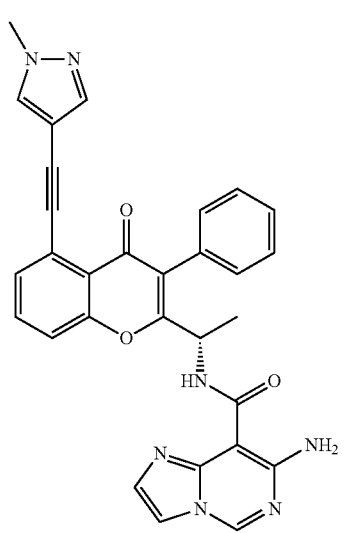 [SMILES: C[C@H](NC(=O)c1c(N)ncn2ccnc12)c1oc2cccc(C#Cc3cnn(C)c3)c2c(=O)c1-c1ccccc1]
246S
TABLE 2-continued
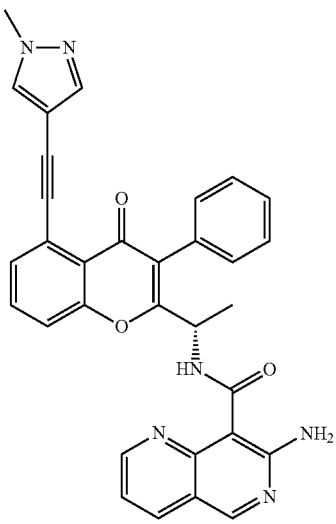 [SMILES: C[C@H](NC(=O)c1c(N)ncc2cccnc12)c1oc2cccc(C#Cc3cnn(C)c3)c2c(=O)c1-c1ccccc1]
247S
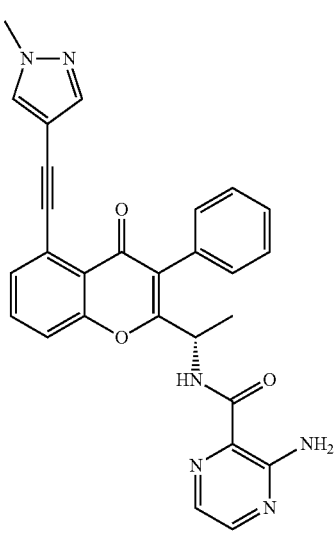 [SMILES: C[C@H](NC(=O)c1nccnc1N)c1oc2cccc(C#Cc3cnn(C)c3)c2c(=O)c1-c1ccccc1]
248S
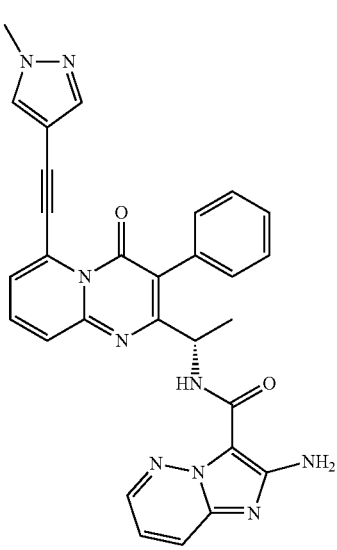 [SMILES: C[C@H](NC(=O)c1c(N)nc2cccnn12)c1nc2cccc(C#Cc3cnn(C)c3)n2c(=O)c1-c1ccccc1]
249S TABLE 2-continued
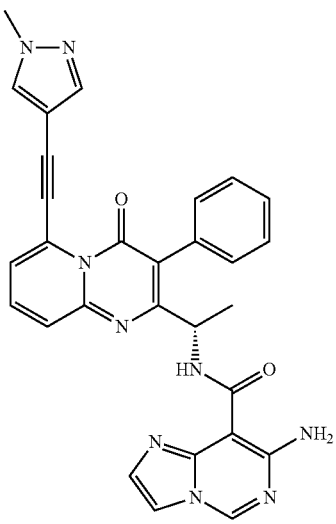 [SMILES: C[C@H](NC(=O)c1c(N)ncn2ccnc12)c1nc2cccc(C#Cc3cnn(C)c3)n2c(=O)c1-c1ccccc1]
250S
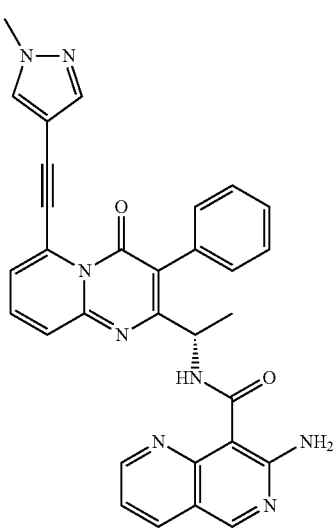 [SMILES: C[C@H](NC(=O)c1c(N)ncc2cccnc12)c1nc2cccc(C#Cc3cnn(C)c3)n2c(=O)c1-c1ccccc1]
251S
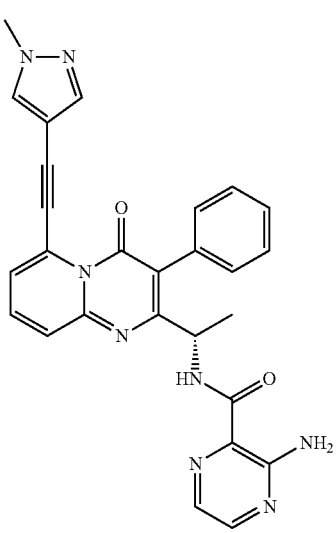 [SMILES: C[C@H](NC(=O)c1nccnc1N)c1nc2cccc(C#Cc3cnn(C)c3)n2c(=O)c1-c1ccccc1]
252S
TABLE 2-continued
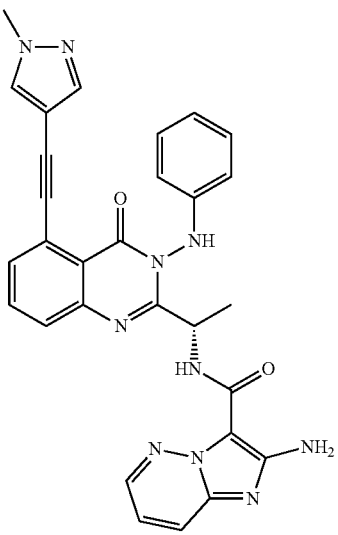 [SMILES: C[C@H](NC(=O)c1c(N)nc2cccnn12)c1nc2cccc(C#Cc3cnn(C)c3)c2c(=O)n1Nc1ccccc1]
253S
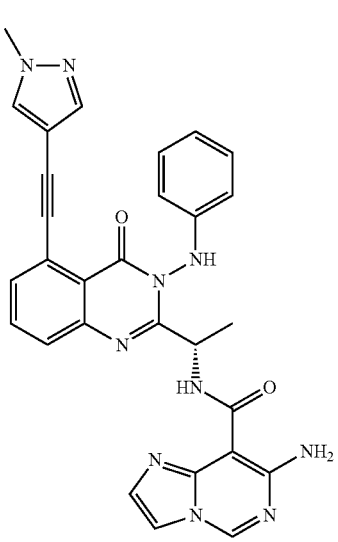 [SMILES: C[C@H](NC(=O)c1c(N)ncn2ccnc12)c1nc2cccc(C#Cc3cnn(C)c3)c2c(=O)n1Nc1ccccc1]
254S
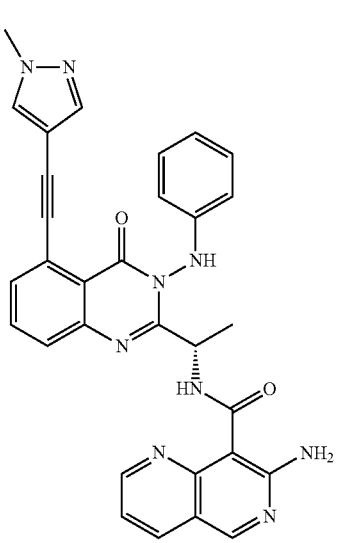 [SMILES: C[C@H](NC(=O)c1c(N)ncc2cccnc12)c1nc2cccc(C#Cc3cnn(C)c3)c2c(=O)n1Nc1ccccc1]
255S TABLE 2-continued
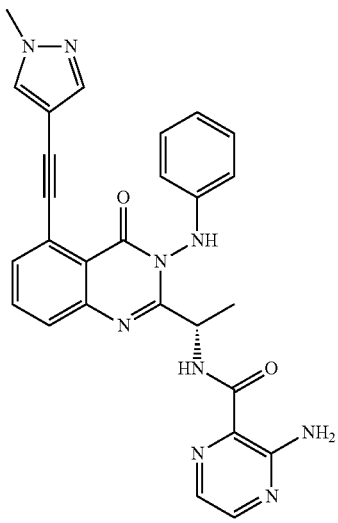 [SMILES: C[C@H](NC(=O)c1nccnc1N)c1nc2cccc(C#Cc3cnn(C)c3)c2c(=O)n1Nc1ccccc1]
256S
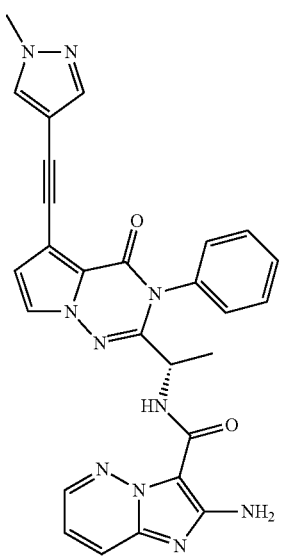 [SMILES: C[C@H](NC(=O)c1c(N)nc2cccnn12)c1nn2ccc(C#Cc3cnn(C)c3)c2c(=O)n1-c1ccccc1]
257S
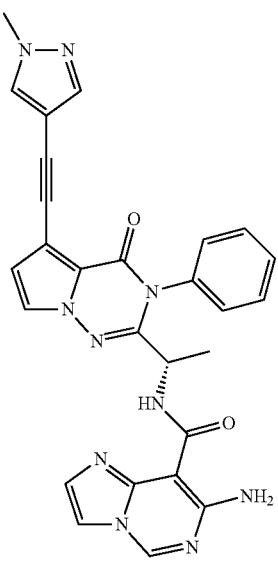 [SMILES: C[C@H](NC(=O)c1c(N)ncn2ccnc12)c1nn2ccc(C#Cc3cnn(C)c3)c2c(=O)n1-c1ccccc1]
258S
TABLE 2-continued
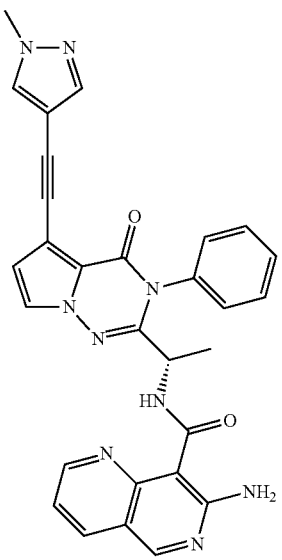 [SMILES: C[C@H](NC(=O)c1c(N)ncc2cccnc12)c1nn2ccc(C#Cc3cnn(C)c3)c2c(=O)n1-c1ccccc1]
259S
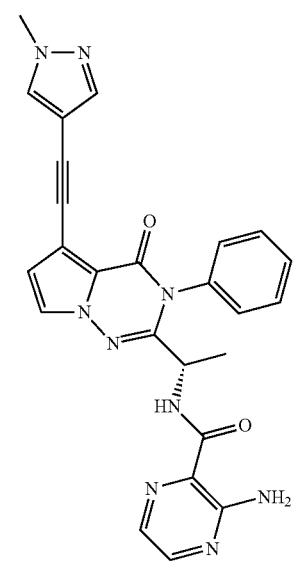 [SMILES: C[C@H](NC(=O)c1nccnc1N)c1nn2ccc(C#Cc3cnn(C)c3)c2c(=O)n1-c1ccccc1]
260S
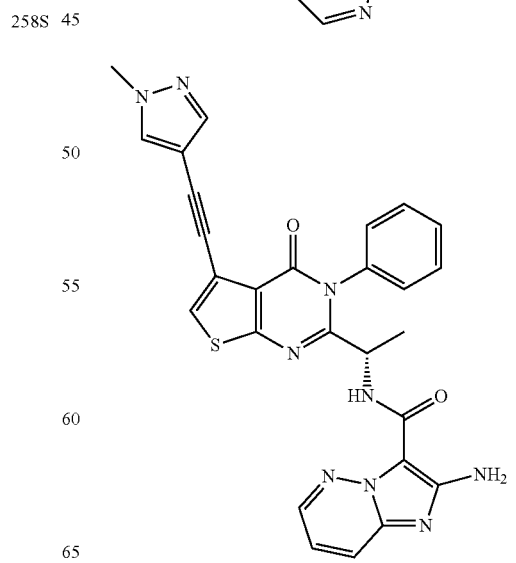
261S TABLE 2-continued
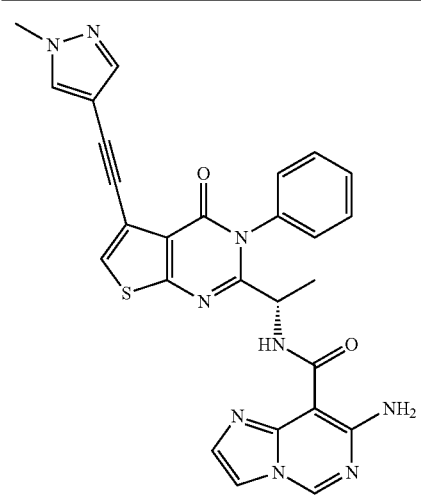
262S
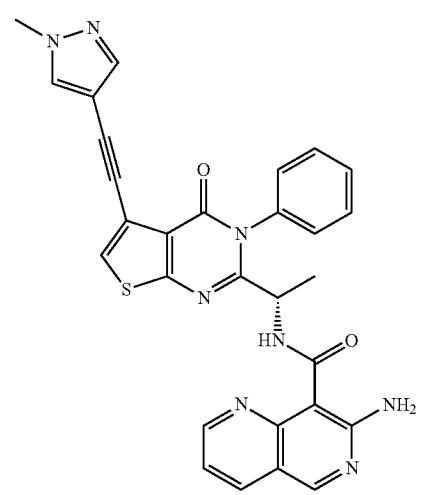 [SMILES: C[C@H](NC(=O)c1c(N)ncc2cccnc12)c1nc2scc(C#Cc3cnn(C)c3)c2c(=O)n1-c1ccccc1]
263S
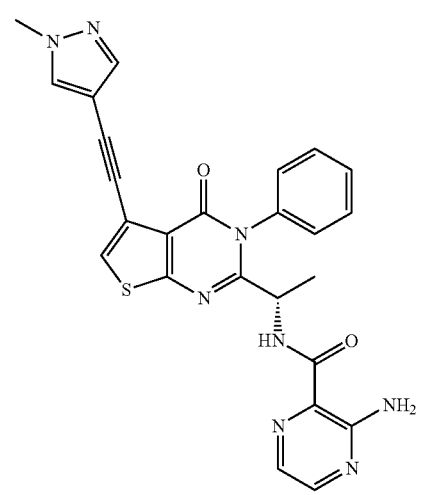 [SMILES: C[C@H](NC(=O)c1nccnc1N)c1nc2scc(C#Cc3cnn(C)c3)c2c(=O)n1-c1ccccc1]
264S
TABLE 2-continued
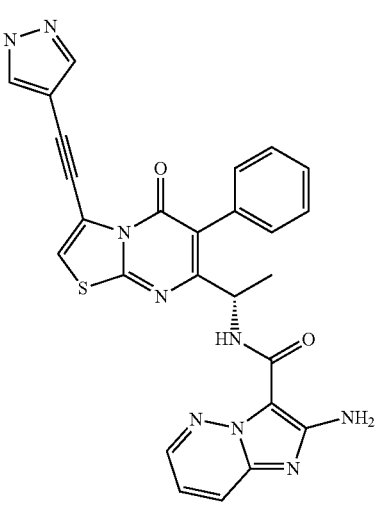
265S
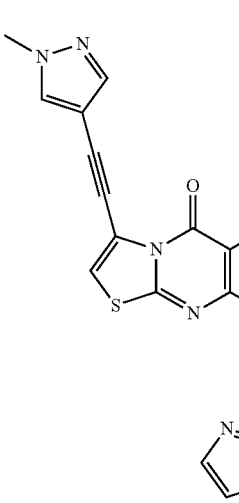
266S
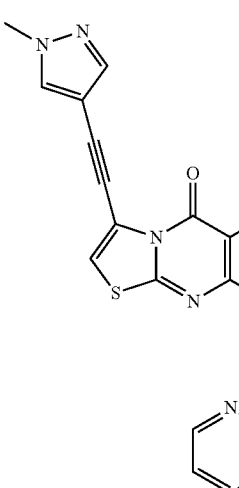
267S TABLE 2-continued
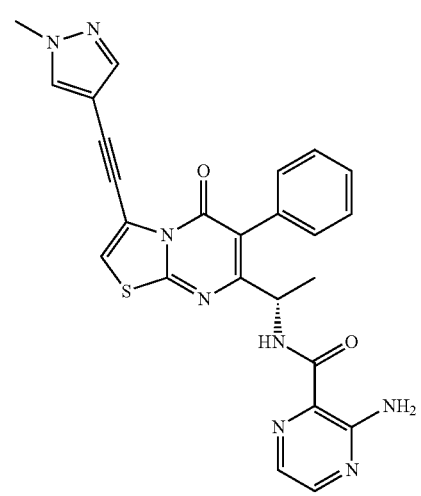 [SMILES: C[C@H](NC(=O)c1nccnc1N)c1nc2scc(C#Cc3cnn(C)c3)n2c(=O)c1-c1ccccc1] 268S
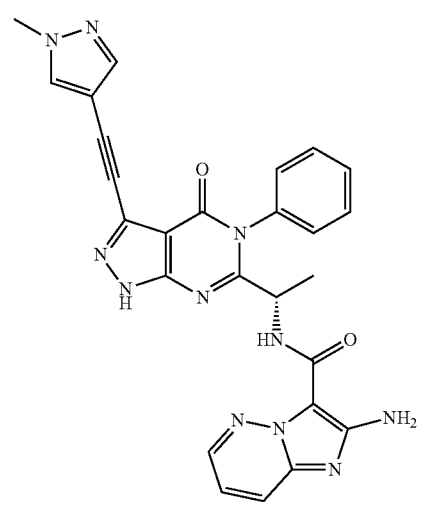 [SMILES: C[C@H](NC(=O)c1c(N)nc2cccnn12)c1nc2[nH]nc(C#Cc3cnn(C)c3)c2c(=O)n1-c1ccccc1] 269S
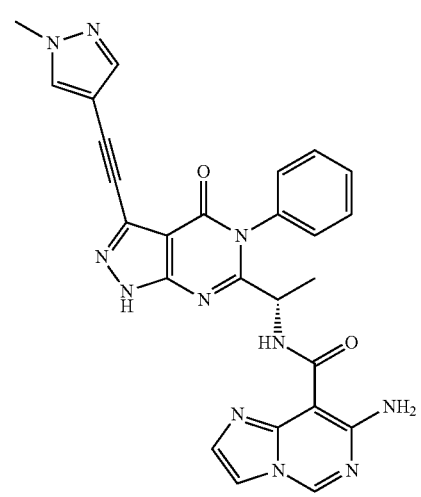 [SMILES: C[C@H](NC(=O)c1c(N)ncn2ccnc12)c1nc2[nH]nc(C#Cc3cnn(C)c3)c2c(=O)n1-c1ccccc1] 270S
TABLE 2-continued
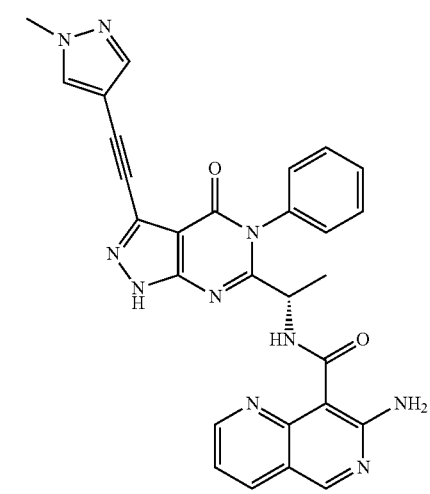 [SMILES: C[C@H](NC(=O)c1c(N)ncc2cccnc12)c1nc2[nH]nc(C#Cc3cnn(C)c3)c2c(=O)n1-c1ccccc1] 271S
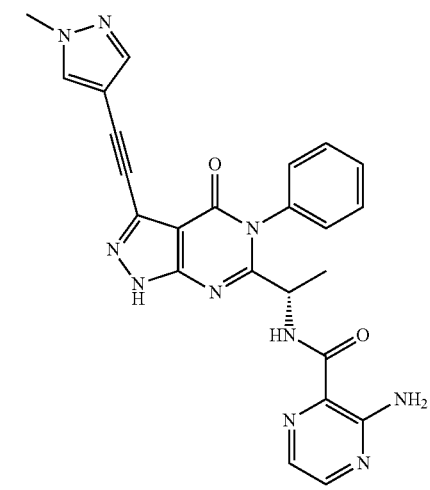 [SMILES: C[C@H](NC(=O)c1nccnc1N)c1nc2[nH]nc(C#Cc3cnn(C)c3)c2c(=O)n1-c1ccccc1] 272S
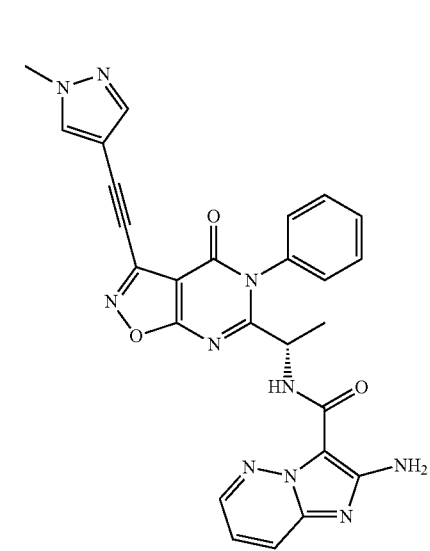 [SMILES: C[C@H](NC(=O)c1c(N)nc2cccnn12)c1nc2onc(C#Cc3cnn(C)c3)c2c(=O)n1-c1ccccc1] 273S TABLE 2-continued
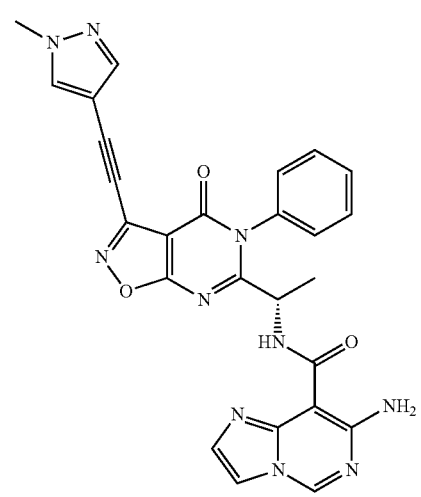 [SMILES: C[C@H](NC(=O)c1c(N)ncn2ccnc12)c1nc2onc(C#Cc3cnn(C)c3)c2c(=O)n1-c1ccccc1] 274S
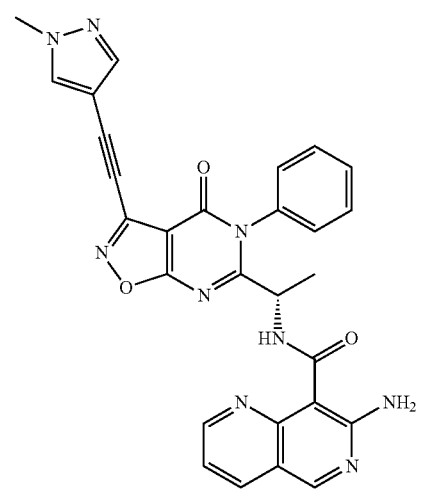 [SMILES: C[C@H](NC(=O)c1c(N)ncc2cccnc12)c1nc2onc(C#Cc3cnn(C)c3)c2c(=O)n1-c1ccccc1] 275S
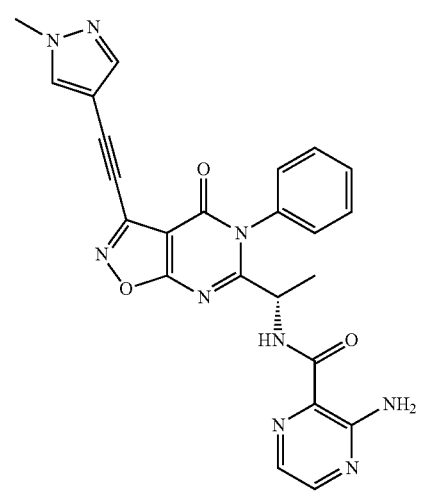 [SMILES: C[C@H](NC(=O)c1nccnc1N)c1nc2onc(C#Cc3cnn(C)c3)c2c(=O)n1-c1ccccc1] 276S
TABLE 2-continued
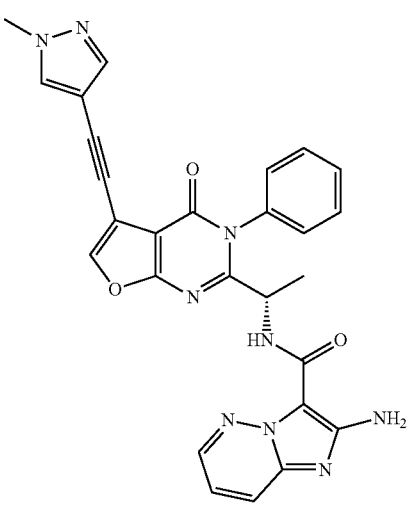 [SMILES: C[C@H](NC(=O)c1c(N)nc2cccnn12)c1nc2occ(C#Cc3cnn(C)c3)c2c(=O)n1-c1ccccc1] 277S
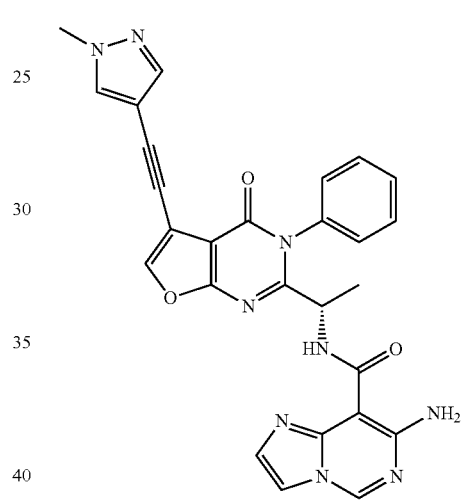 278S
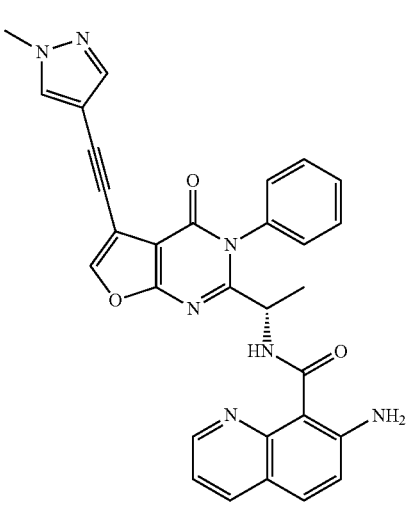 [SMILES: C[C@H](NC(=O)c1c(N)ccc2cccnc12)c1nc2occ(C#Cc3cnn(C)c3)c2c(=O)n1-c1ccccc1] 279S TABLE 2-continued
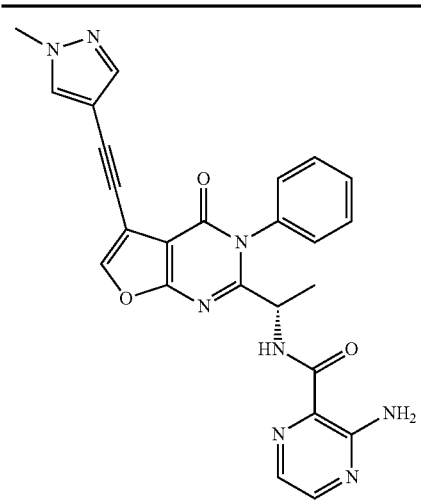
280S
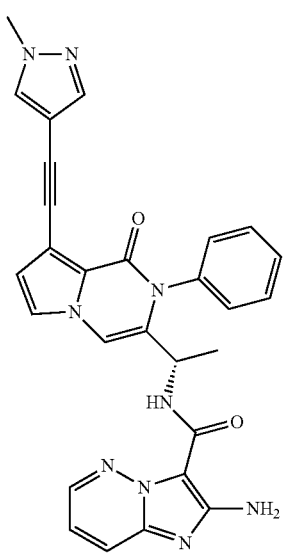 [SMILES: C[C@H](NC(=O)c1c(N)nc2cccnn12)c1cn2ccc(C#Cc3cnn(C)c3)c2c(=O)n1-c1ccccc1]
281S
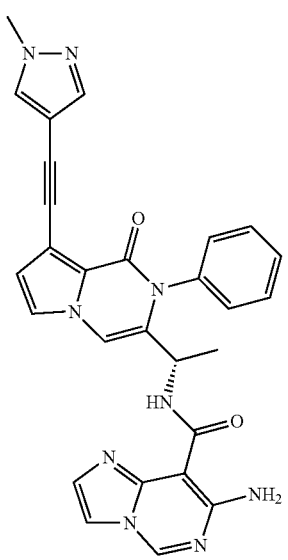 [SMILES: C[C@H](NC(=O)c1c(N)ncn2ccnc12)c1cn2ccc(C#Cc3cnn(C)c3)c2c(=O)n1-c1ccccc1]
282S
TABLE 2-continued
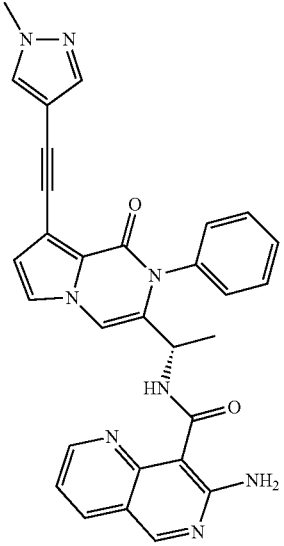 [SMILES: C[C@H](NC(=O)c1c(N)ncc2cccnc12)c1cn2ccc(C#Cc3cnn(C)c3)c2c(=O)n1-c1ccccc1]
283S
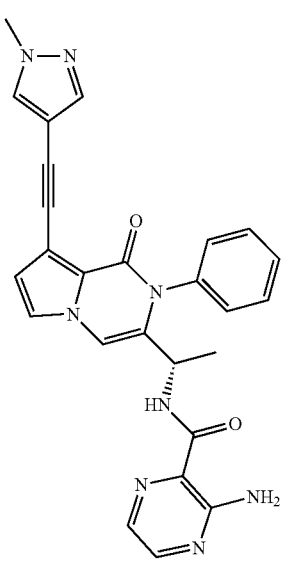 [SMILES: C[C@H](NC(=O)c1nccnc1N)c1cn2ccc(C#Cc3cnn(C)c3)c2c(=O)n1-c1ccccc1]
284S
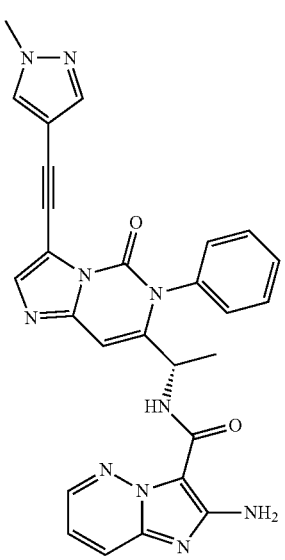 [SMILES: C[C@H](NC(=O)c1c(N)nc2cccnn12)c1cc2ncc(C#Cc3cnn(C)c3)n2c(=O)n1-c1ccccc1]
285S TABLE 2-continued
| | |
|---|---|
| 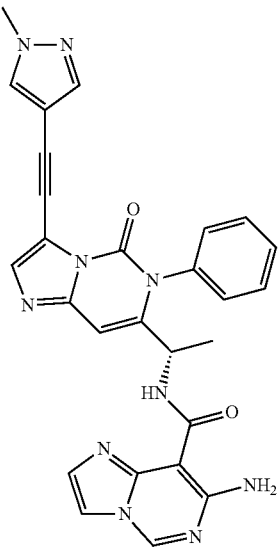 [SMILES: C[C@H](NC(=O)c1c(N)ncn2ccnc12)c1cc2ncc(C#Cc3cnn(C)c3)n2c(=O)n1-c1ccccc1] 286S | 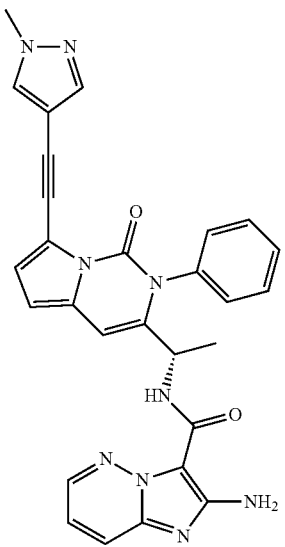 289S |
| 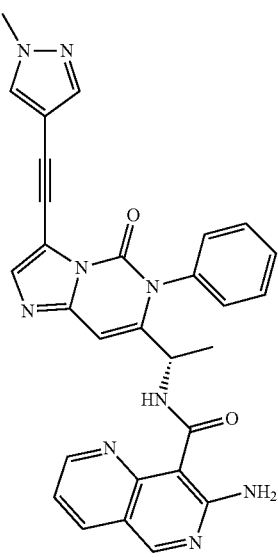 [SMILES: C[C@H](NC(=O)c1c(N)ncc2cccnc12)c1cc2ncc(C#Cc3cnn(C)c3)n2c(=O)n1-c1ccccc1] 287S | 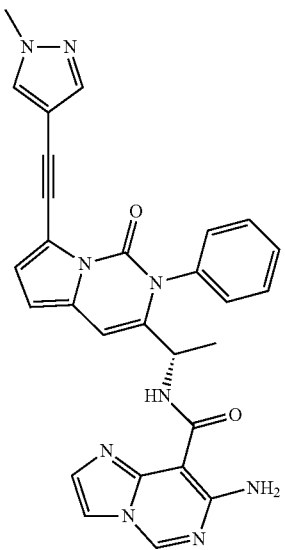 290S |
| 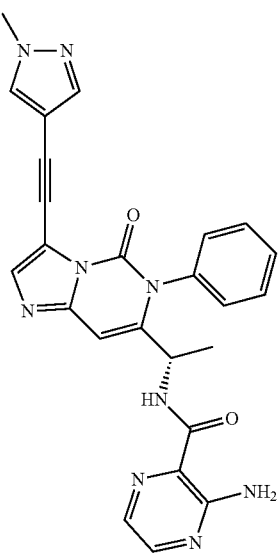 [SMILES: C[C@H](NC(=O)c1nccnc1N)c1cc2ncc(C#Cc3cnn(C)c3)n2c(=O)n1-c1ccccc1] 288S | 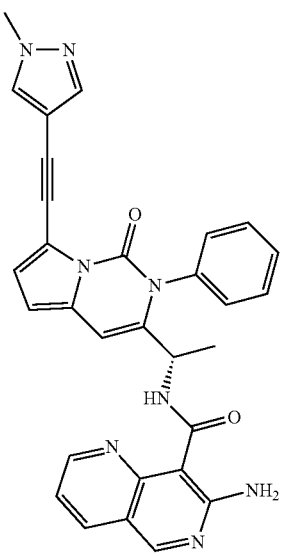 [SMILES: C[C@H](NC(=O)c1c(N)ncc2cccnc12)c1cc2ccc(C#Cc3cnn(C)c3)n2c(=O)n1-c1ccccc1] 291S |

TABLE 2-continued
292S
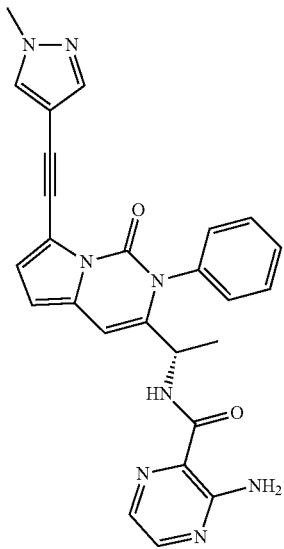 [SMILES: C[C@H](NC(=O)c1nccnc1N)c1cc2ccc(C#Cc3cnn(C)c3)n2c(=O)n1-c1ccccc1]
293S
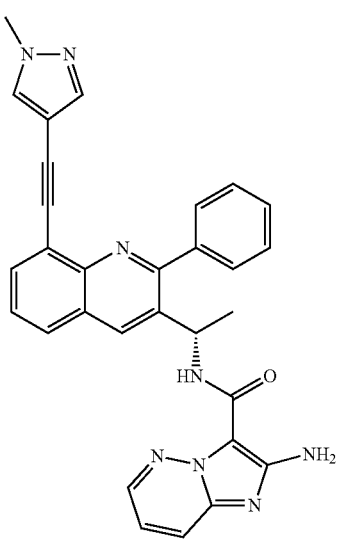
294S
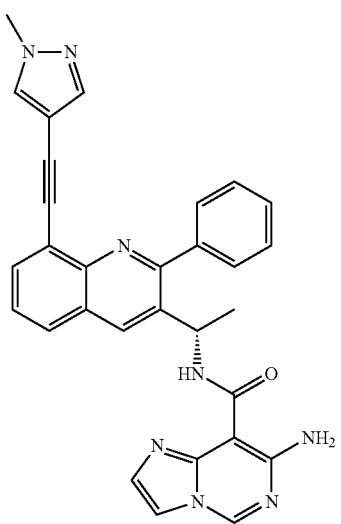
TABLE 2-continued
295S
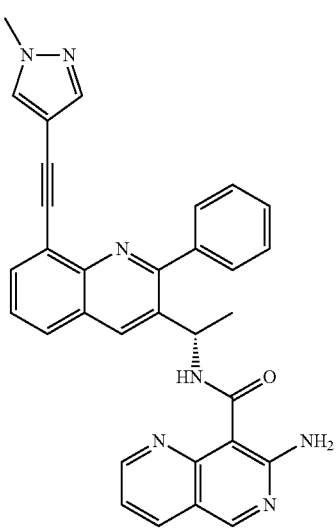 [SMILES: C[C@H](NC(=O)c1c(N)ncc2cccnc12)c1cc2cccc(C#Cc3cnn(C)c3)c2nc1-c1ccccc1]
296S
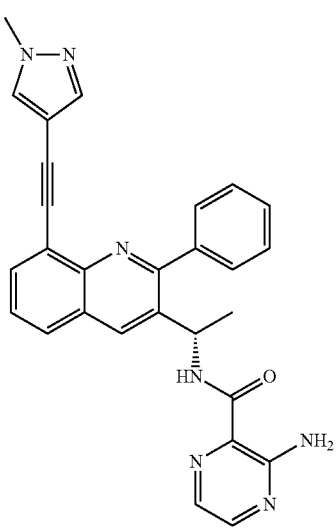 [SMILES: C[C@H](NC(=O)c1nccnc1N)c1cc2cccc(C#Cc3cnn(C)c3)c2nc1-c1ccccc1]
297S
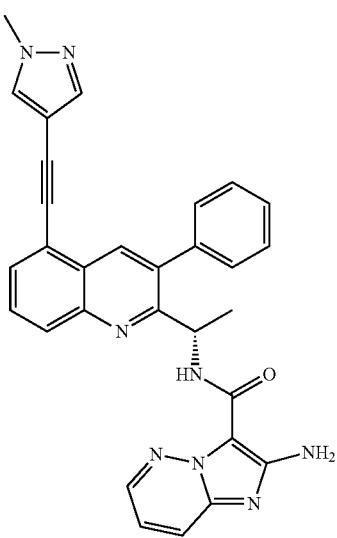 [SMILES: C[C@H](NC(=O)c1c(N)nc2cccnn12)c1nc2cccc(C#Cc3cnn(C)c3)c2cc1-c1ccccc1]

269
TABLE 2-continued
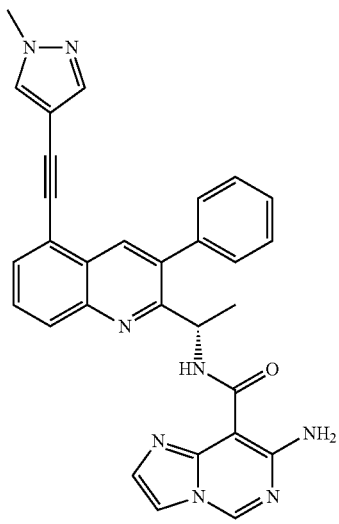
298S
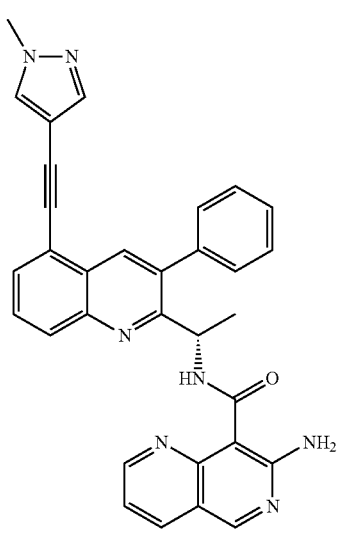
299S
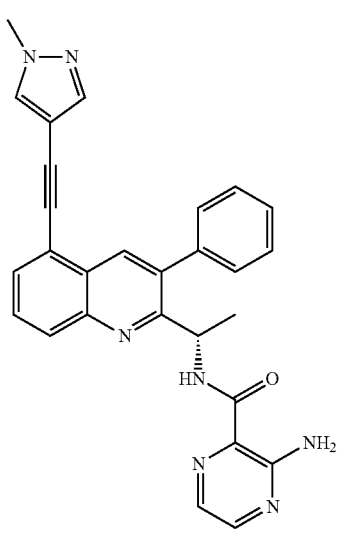
300S
270
TABLE 2-continued
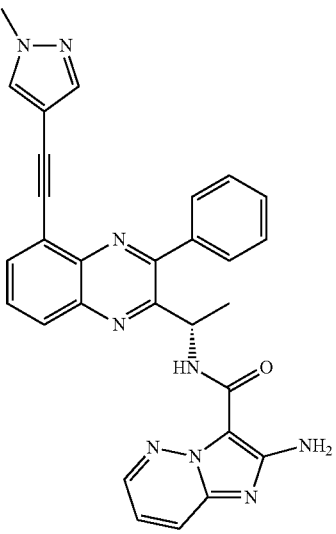
301S
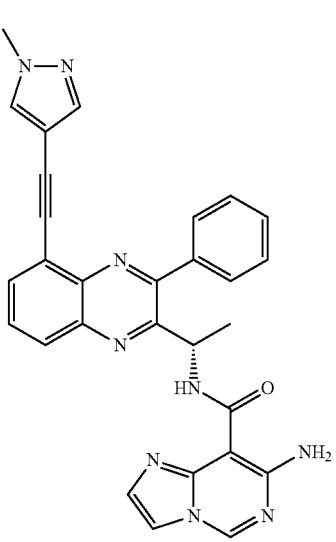 [SMILES: C[C@H](NC(=O)c1c(N)ncn2ccnc12)c1nc2cccc(C#Cc3cnn(C)c3)c2nc1-c1ccccc1]
302S
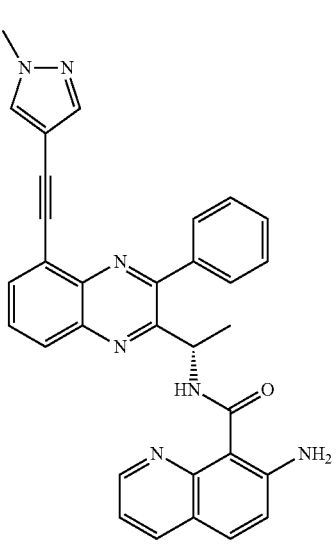 [SMILES: C[C@H](NC(=O)c1c(N)ccc2cccnc12)c1nc2cccc(C#Cc3cnn(C)c3)c2nc1-c1ccccc1]
303S 271
TABLE 2-continued
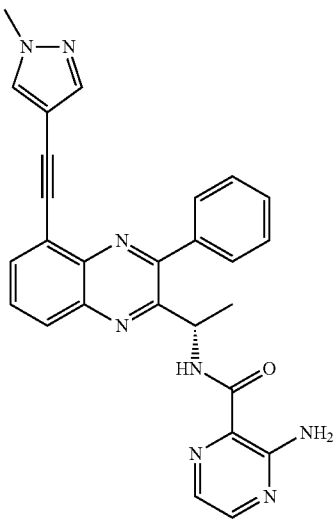 [SMILES: C[C@H](NC(=O)c1nccnc1N)c1nc2cccc(C#Cc3cnn(C)c3)c2nc1-c1ccccc1]
304S
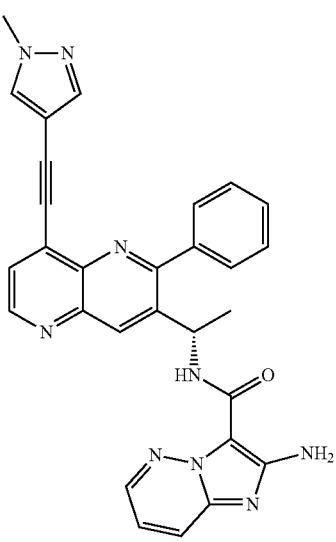
305S
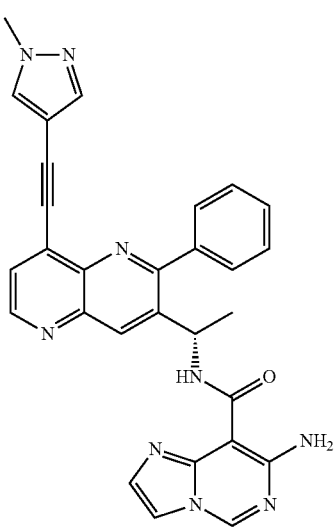
306S
272
TABLE 2-continued
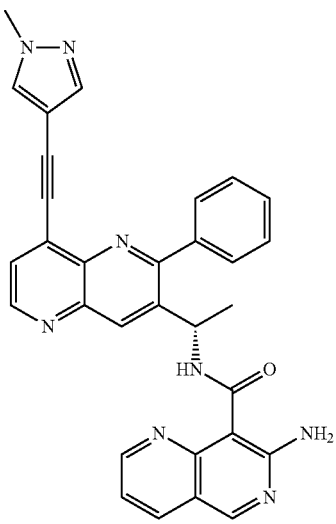 [SMILES: C[C@H](NC(=O)c1c(N)ncc2cccnc12)c1cc2nccc(C#Cc3cnn(C)c3)c2nc1-c1ccccc1]
307S
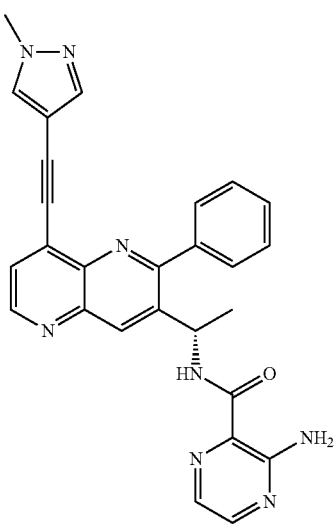 [SMILES: C[C@H](NC(=O)c1nccnc1N)c1cc2nccc(C#Cc3cnn(C)c3)c2nc1-c1ccccc1]
308S
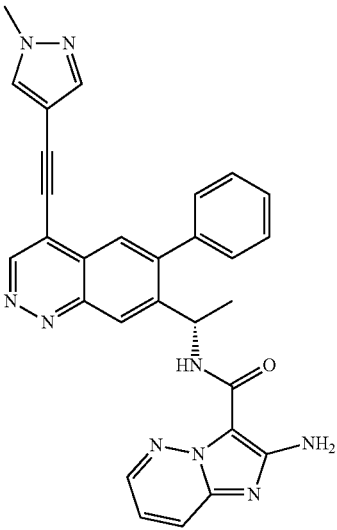 [SMILES: C[C@H](NC(=O)c1c(N)nc2cccnn12)c1cc2nncc(C#Cc3cnn(C)c3)c2cc1-c1ccccc1]
309S TABLE 2-continued
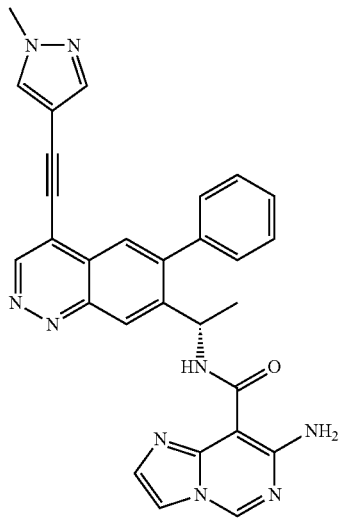 [SMILES: C[C@H](NC(=O)c1c(N)ncn2ccnc12)c1cc2nncc(C#Cc3cnn(C)c3)c2cc1-c1ccccc1] 310S
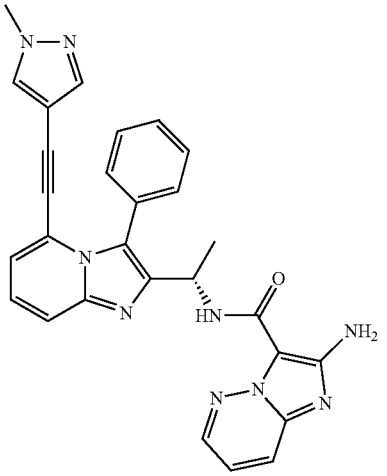 313S
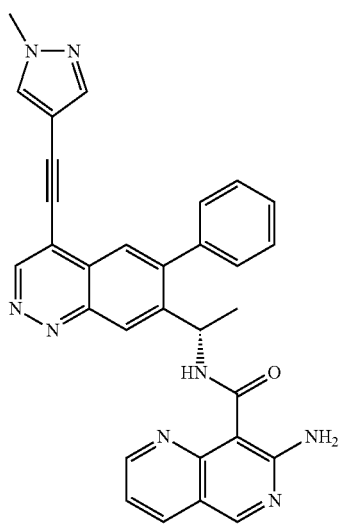 [SMILES: C[C@H](NC(=O)c1c(N)ncc2cccnc12)c1cc2nncc(C#Cc3cnn(C)c3)c2cc1-c1ccccc1] 311S
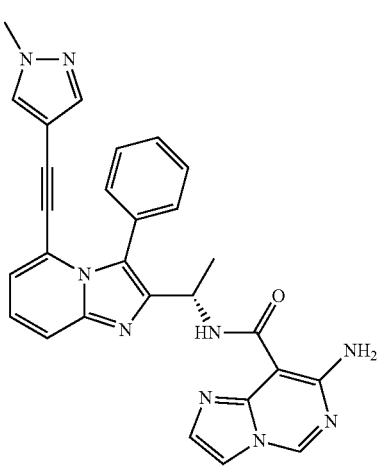 314S
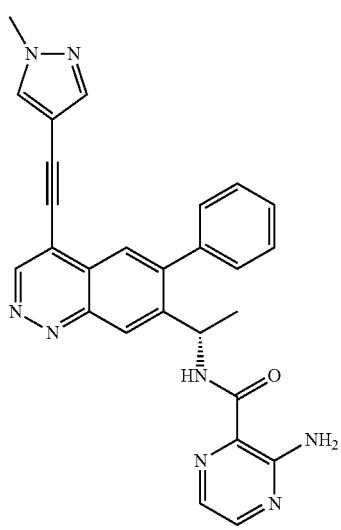 [SMILES: C[C@H](NC(=O)c1nccnc1N)c1cc2nncc(C#Cc3cnn(C)c3)c2cc1-c1ccccc1] 312S
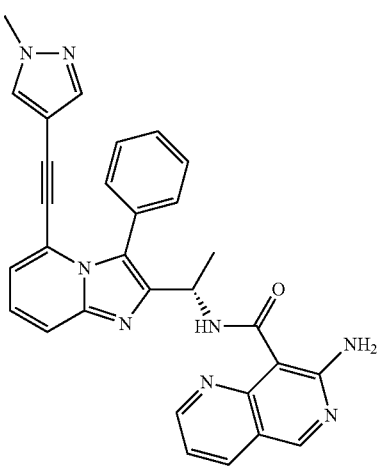 [SMILES: C[C@H](NC(=O)c1c(N)ncc2cccnc12)c1nc2cccc(C#Cc3cnn(C)c3)n2c1-c1ccccc1] 315S TABLE 2-continued
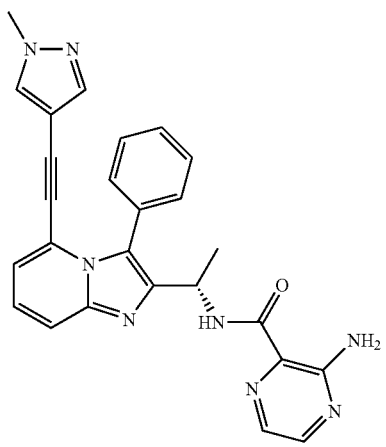
316S
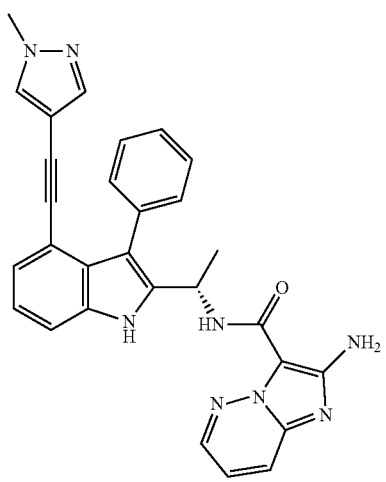 [SMILES: C[C@H](NC(=O)c1c(N)nc2cccnn12)c1[nH]c2cccc(C#Cc3cnn(C)c3)c2c1-c1ccccc1]
317S
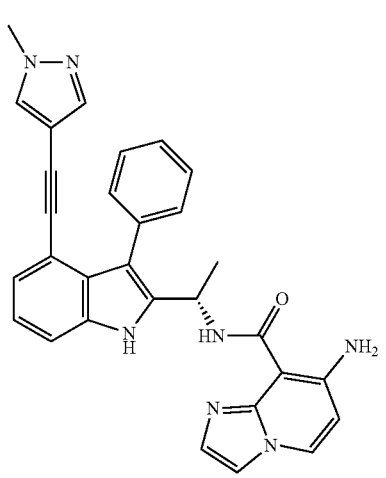 [SMILES: C[C@H](NC(=O)c1c(N)ccn2ccnc12)c1[nH]c2cccc(C#Cc3cnn(C)c3)c2c1-c1ccccc1]
318S
TABLE 2-continued
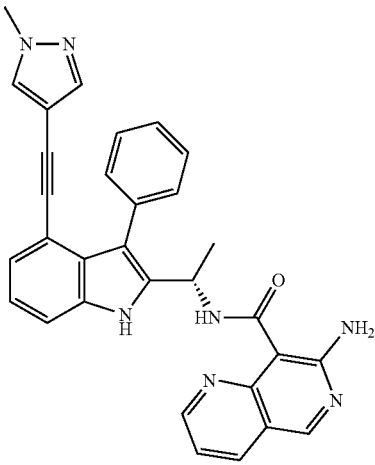 [SMILES: C[C@H](NC(=O)c1c(N)ncc2cccnc12)c1[nH]c2cccc(C#Cc3cnn(C)c3)c2c1-c1ccccc1]
319S
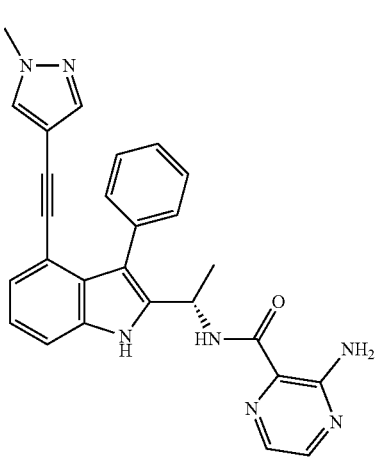 [SMILES: C[C@H](NC(=O)c1nccnc1N)c1[nH]c2cccc(C#Cc3cnn(C)c3)c2c1-c1ccccc1]
320S
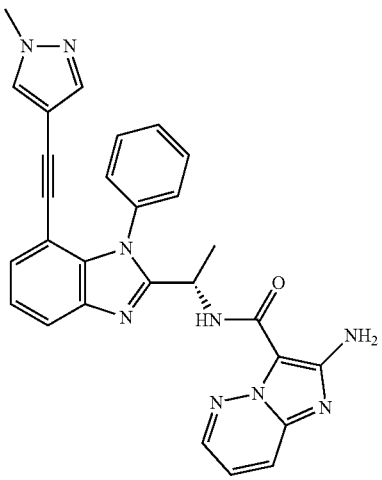 [SMILES: C[C@H](NC(=O)c1c(N)nc2cccnn12)c1nc2cccc(C#Cc3cnn(C)c3)c2n1-c1ccccc1]
321S TABLE 2-continued
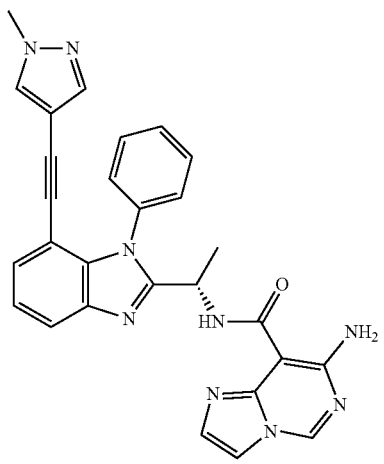 [SMILES: C[C@H](NC(=O)c1c(N)ncn2ccnc12)c1nc2cccc(C#Cc3cnn(C)c3)c2n1-c1ccccc1]
322S
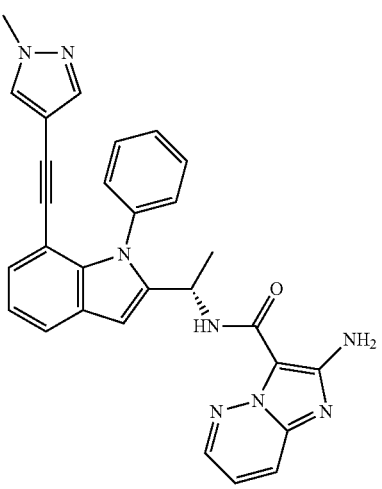
325S
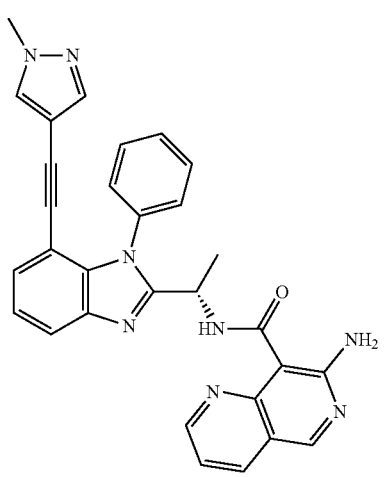 [SMILES: C[C@H](NC(=O)c1c(N)ncc2cccnc12)c1nc2cccc(C#Cc3cnn(C)c3)c2n1-c1ccccc1]
323S
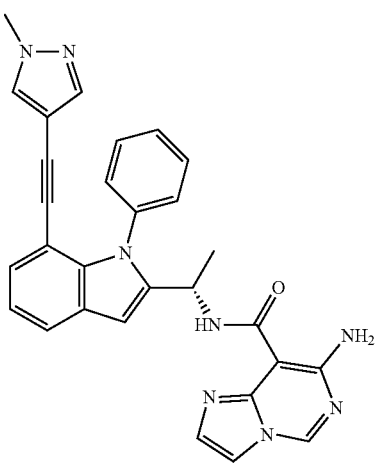
326S
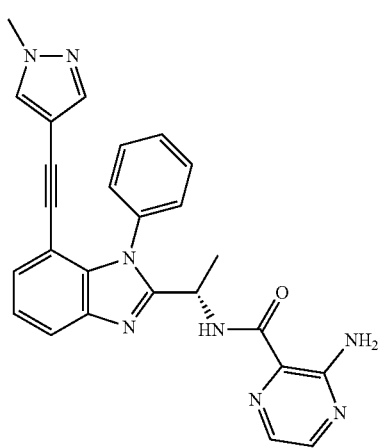 [SMILES: C[C@H](NC(=O)c1nccnc1N)c1nc2cccc(C#Cc3cnn(C)c3)c2n1-c1ccccc1]
324S
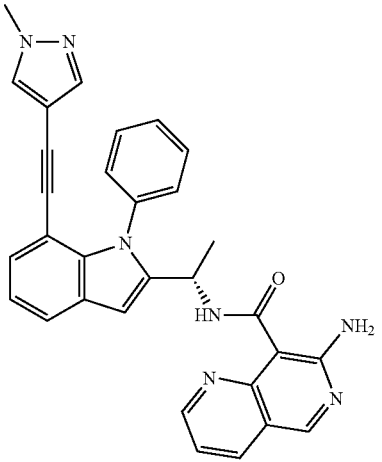 [SMILES: C[C@H](NC(=O)c1c(N)ncc2cccnc12)c1cc2cccc(C#Cc3cnn(C)c3)c2n1-c1ccccc1]
327S TABLE 2-continued
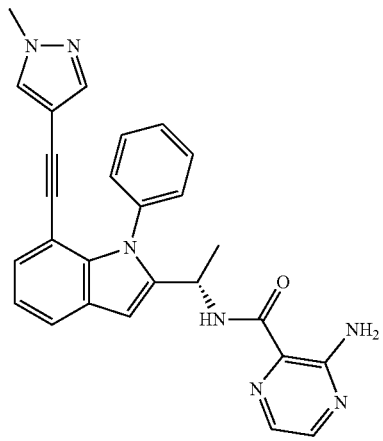 [SMILES: C[C@H](NC(=O)c1nccnc1N)c1cc2cccc(C#Cc3cnn(C)c3)c2n1-c1ccccc1]
328S
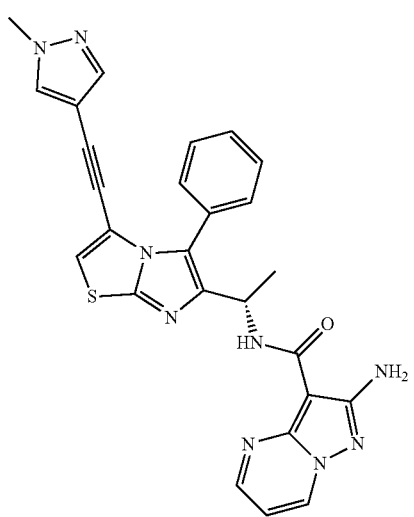 [SMILES: C[C@H](NC(=O)c1c(N)nn2cccnc12)c1nc2scc(C#Cc3cnn(C)c3)n2c1-c1ccccc1]
329S
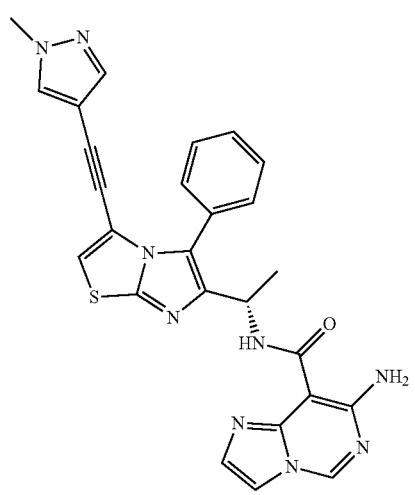 [SMILES: C[C@H](NC(=O)c1c(N)ncn2ccnc12)c1nc2scc(C#Cc3cnn(C)c3)n2c1-c1ccccc1]
330S
TABLE 2-continued
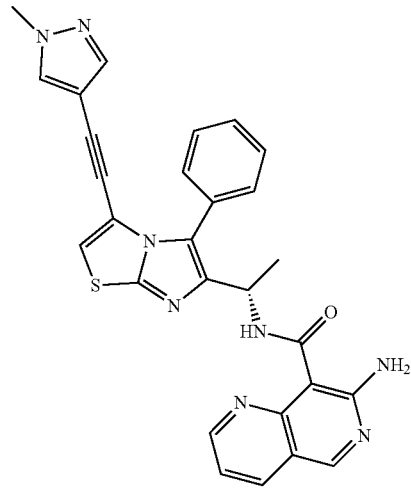 [SMILES: C[C@H](NC(=O)c1c(N)ncc2cccnc12)c1nc2scc(C#Cc3cnn(C)c3)n2c1-c1ccccc1]
331S
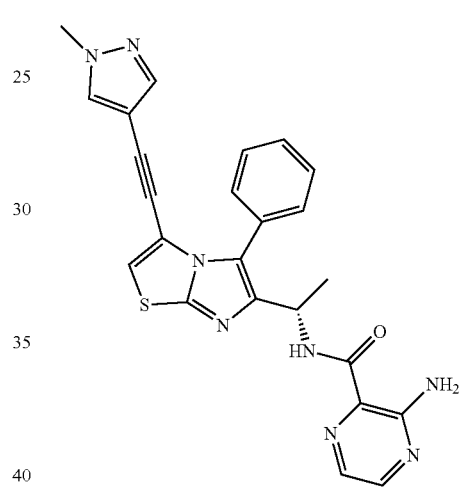
332S
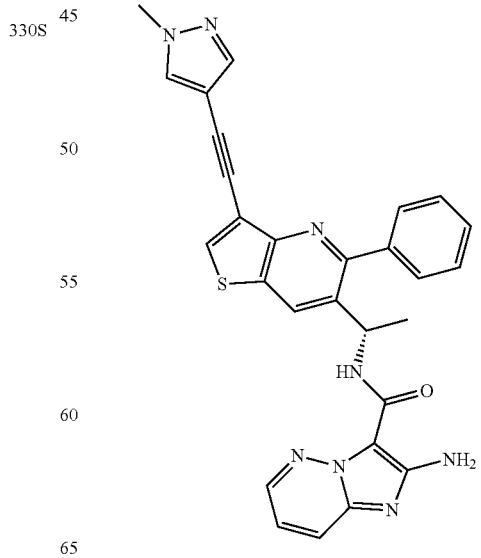
333S TABLE 2-continued
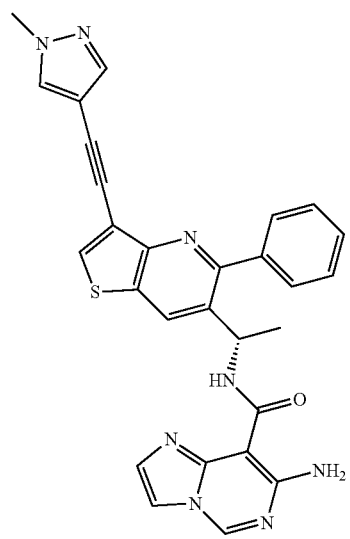 [SMILES: C[C@H](NC(=O)c1c(N)ncn2ccnc12)c1cc2scc(C#Cc3cnn(C)c3)c2nc1-c1ccccc1]
334S
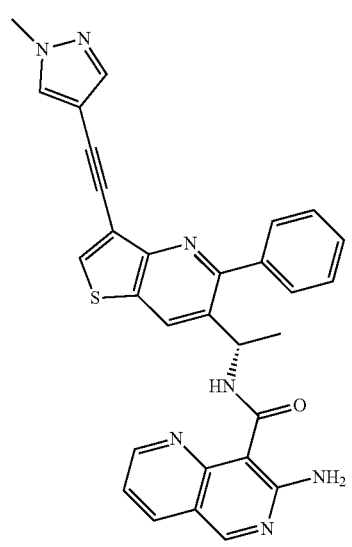 [SMILES: C[C@H](NC(=O)c1c(N)ncc2cccnc12)c1cc2scc(C#Cc3cnn(C)c3)c2nc1-c1ccccc1]
335S
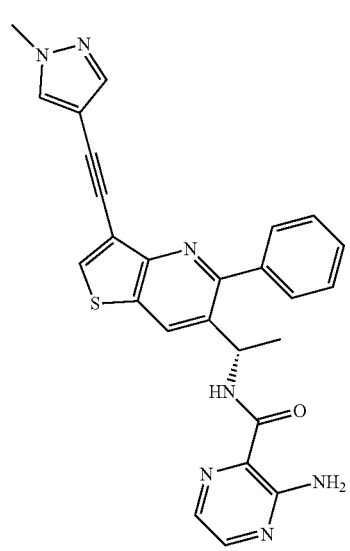 [SMILES: C[C@H](NC(=O)c1nccnc1N)c1cc2scc(C#Cc3cnn(C)c3)c2nc1-c1ccccc1]
336S
TABLE 2-continued
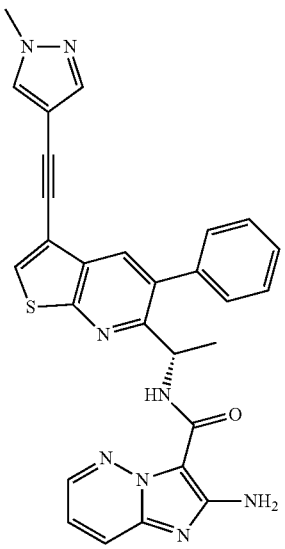 [SMILES: C[C@H](NC(=O)c1c(N)nc2cccnn12)c1nc2scc(C#Cc3cnn(C)c3)c2cc1-c1ccccc1]
337S
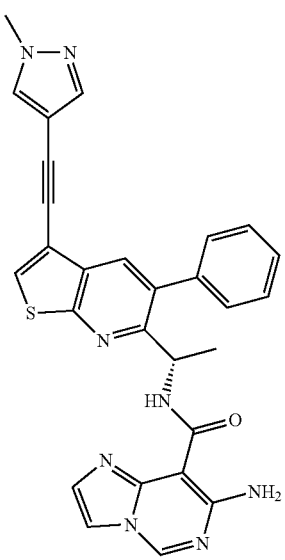 [SMILES: C[C@H](NC(=O)c1c(N)ncn2ccnc12)c1nc2scc(C#Cc3cnn(C)c3)c2cc1-c1ccccc1]
338S
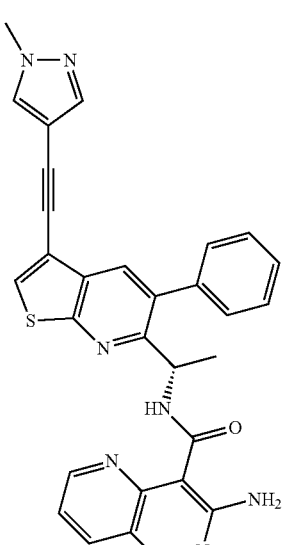
339S TABLE 2-continued
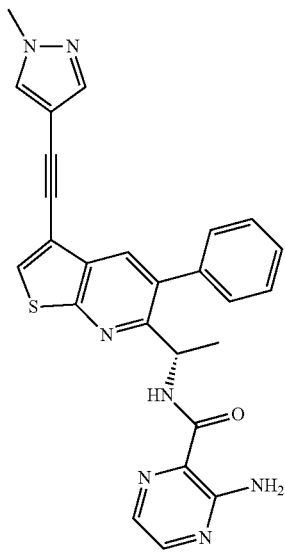 [SMILES: C[C@H](NC(=O)c1nccnc1N)c1nc2scc(C#Cc3cnn(C)c3)c2cc1-c1ccccc1]
340S
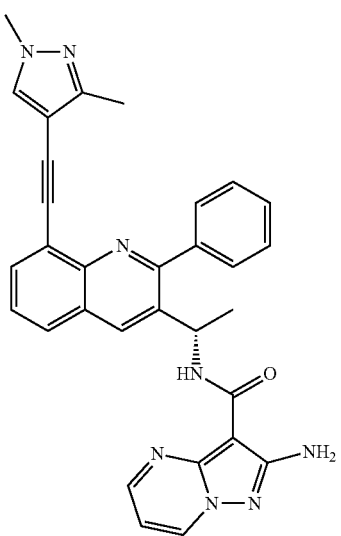 [SMILES: Cc1nn(C)cc1C#Cc1cccc2cc([C@H](C)NC(=O)c3c(N)nn4cccnc34)c(-c3ccccc3)nc12]
341S
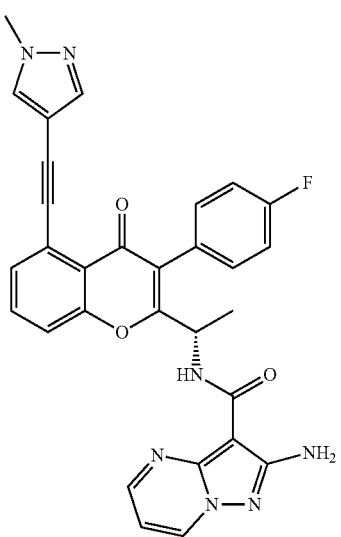 [SMILES: C[C@H](NC(=O)c1c(N)nn2cccnc12)c1oc2cccc(C#Cc3cnn(C)c3)c2c(=O)c1-c1ccc(F)cc1]
342S
TABLE 2-continued
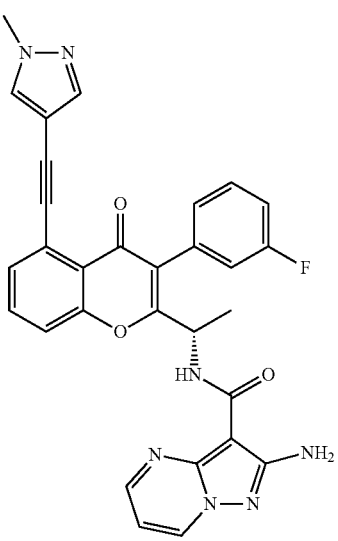 [SMILES: C[C@H](NC(=O)c1c(N)nn2cccnc12)c1oc2cccc(C#Cc3cnn(C)c3)c2c(=O)c1-c1cccc(F)c1]
343S
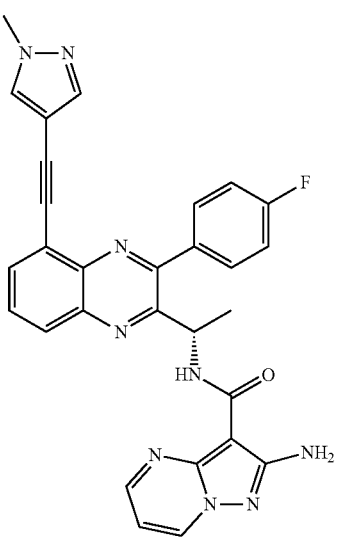 [SMILES: C[C@H](NC(=O)c1c(N)nn2cccnc12)c1nc2cccc(C#Cc3cnn(C)c3)c2nc1-c1ccc(F)cc1]
344S
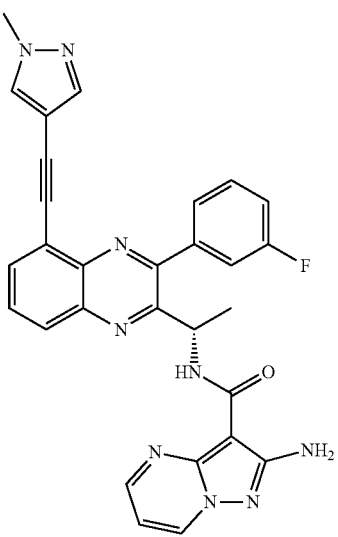 [SMILES: C[C@H](NC(=O)c1c(N)nn2cccnc12)c1nc2cccc(C#Cc3cnn(C)c3)c2nc1-c1cccc(F)c1]
345S TABLE 2-continued
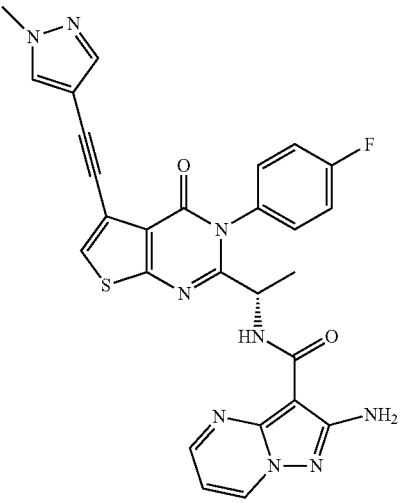 [SMILES: C[C@H](NC(=O)c1c(N)nn2cccnc12)c1nc2scc(C#Cc3cnn(C)c3)c2c(=O)n1-c1ccc(F)cc1]
346S
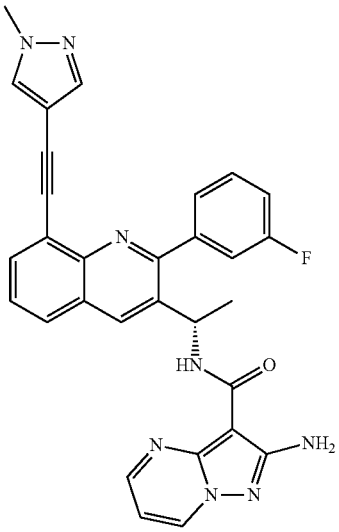
349S
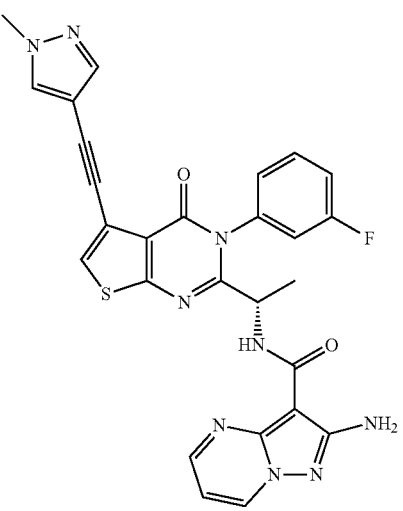 [SMILES: C[C@H](NC(=O)c1c(N)nn2cccnc12)c1nc2scc(C#Cc3cnn(C)c3)c2c(=O)n1-c1cccc(F)c1]
347S
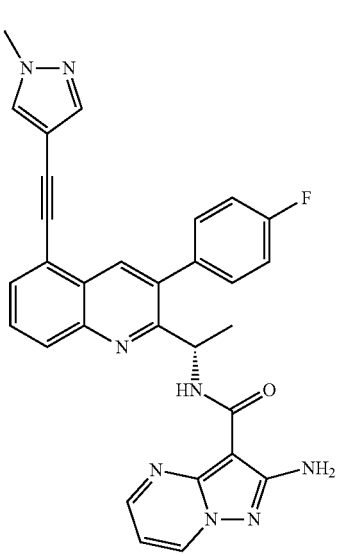 [SMILES: C[C@H](NC(=O)c1c(N)nn2cccnc12)c1nc2cccc(C#Cc3cnn(C)c3)c2cc1-c1ccc(F)cc1]
350S
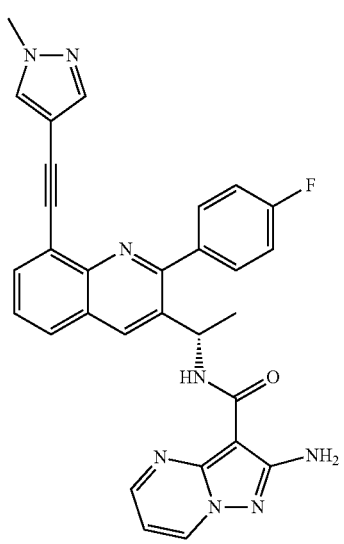
348S
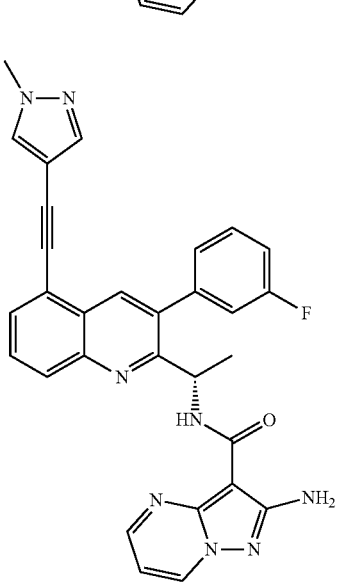
351S TABLE 2-continued
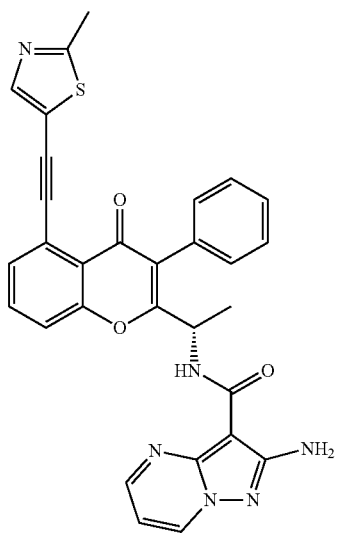 [SMILES: Cc1ncc(C#Cc2cccc3oc([C@H](C)NC(=O)c4c(N)nn5cccnc45)c(-c4ccccc4)c(=O)c23)s1]
352S
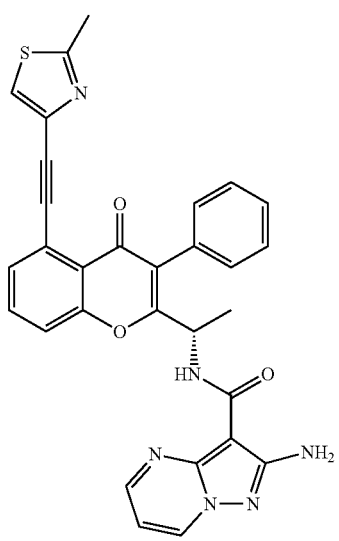 [SMILES: Cc1nc(C#Cc2cccc3oc([C@H](C)NC(=O)c4c(N)nn5cccnc45)c(-c4ccccc4)c(=O)c23)cs1]
353S
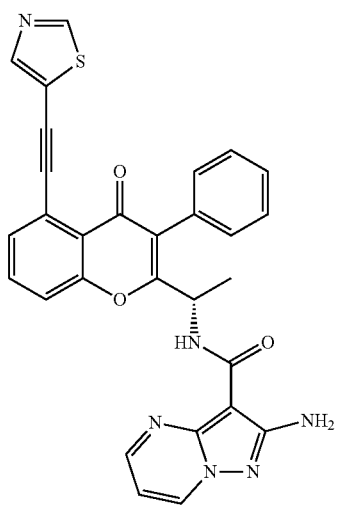 [SMILES: C[C@H](NC(=O)c1c(N)nn2cccnc12)c1oc2cccc(C#Cc3cncs3)c2c(=O)c1-c1ccccc1]
354S
TABLE 2-continued
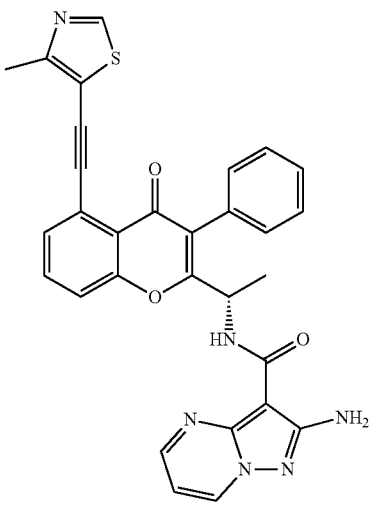 [SMILES: Cc1ncsc1C#Cc1cccc2oc([C@H](C)NC(=O)c3c(N)nn4cccnc34)c(-c3ccccc3)c(=O)c12]
355S
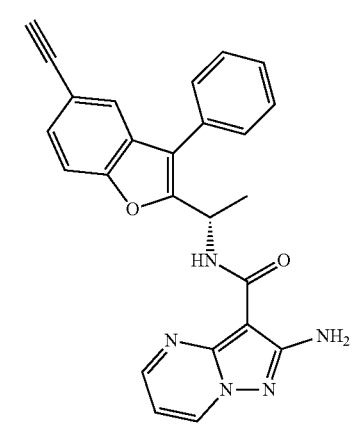
356S
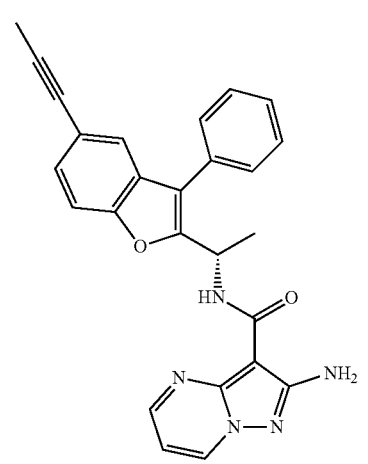 [SMILES: CC#Cc1ccc2oc([C@H](C)NC(=O)c3c(N)nn4cccnc34)c(-c3ccccc3)c2c1]
357S TABLE 2-continued
358S 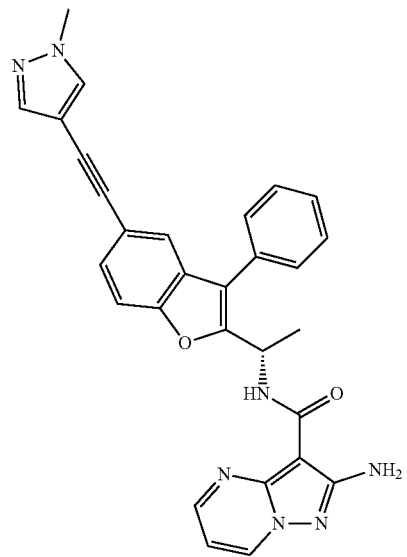 [SMILES: C[C@H](NC(=O)c1c(N)nn2cccnc12)c1oc2ccc(C#Cc3cnn(C)c3)cc2c1-c1ccccc1]
359S 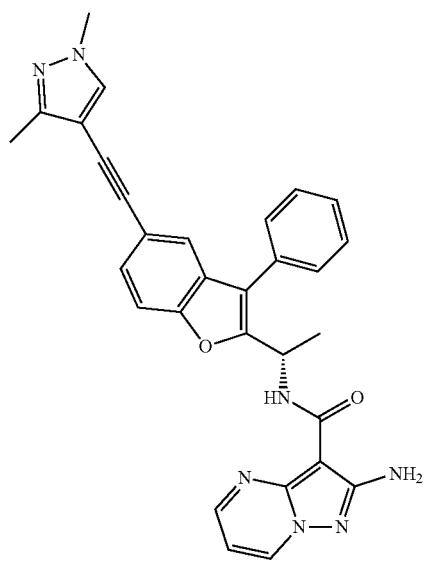
360S 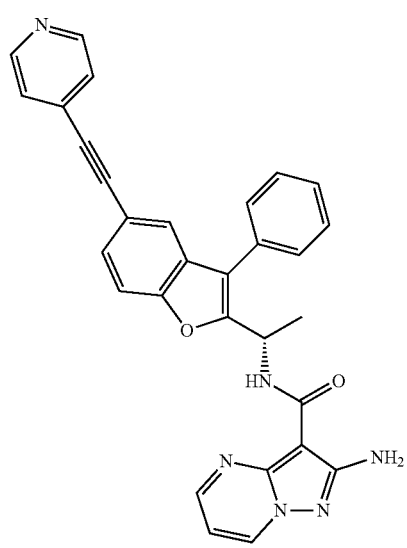
TABLE 2-continued
361S 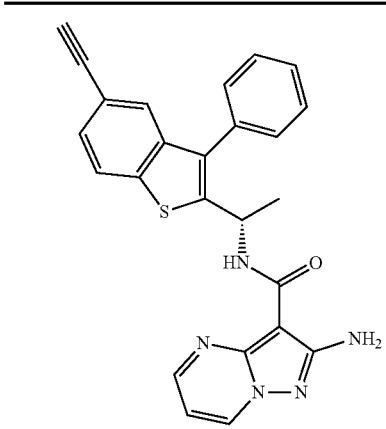
362S 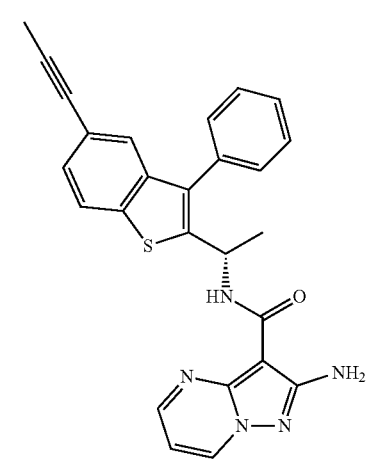 [SMILES: CC#Cc1ccc2sc([C@H](C)NC(=O)c3c(N)nn4cccnc34)c(-c3ccccc3)c2c1]
363S 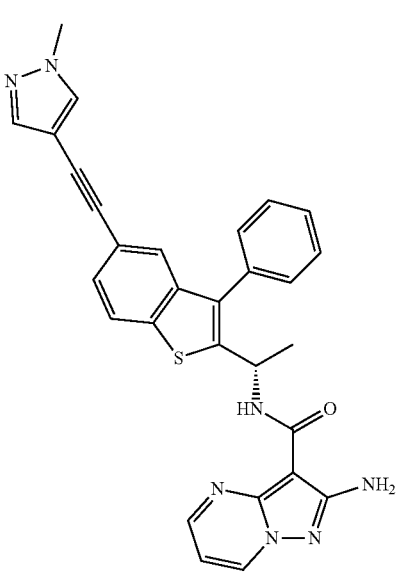 [SMILES: C[C@H](NC(=O)c1c(N)nn2cccnc12)c1sc2ccc(C#Cc3cnn(C)c3)cc2c1-c1ccccc1]

TABLE 2-continued
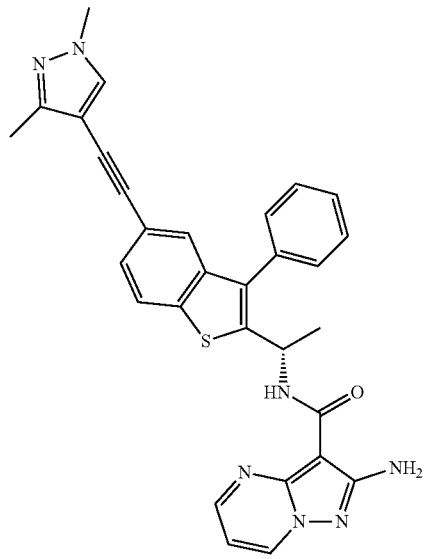
364S
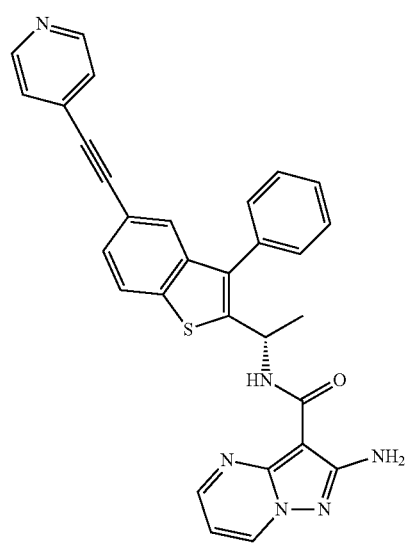 [SMILES: C[C@H](NC(=O)c1c(N)nn2cccnc12)c1sc2ccc(C#Cc3ccncc3)cc2c1-c1ccccc1]
365S
TABLE 3
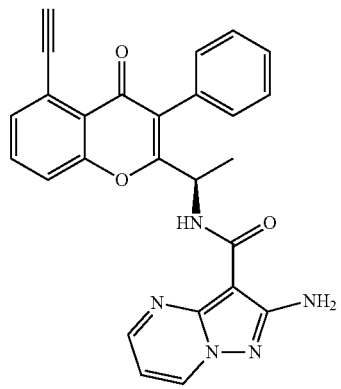 [SMILES: C#Cc1cccc2oc([C@@H](C)NC(=O)c3c(N)nn4cccnc34)c(-c3ccccc3)c(=O)c12]
101R
TABLE 3-continued
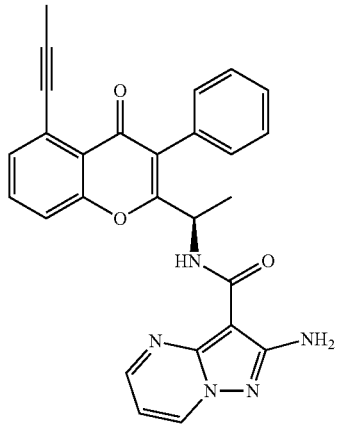 [SMILES: CC#Cc1cccc2oc([C@@H](C)NC(=O)c3c(N)nn4cccnc34)c(-c3ccccc3)c(=O)c12]
102R
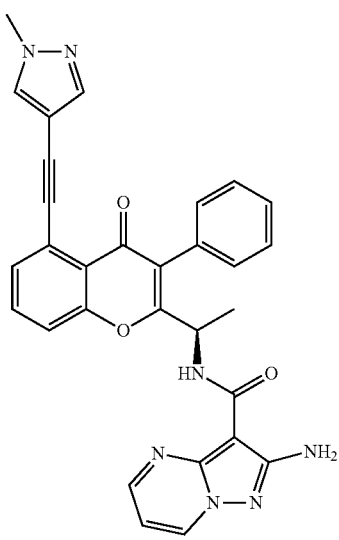 [SMILES: C[C@@H](NC(=O)c1c(N)nn2cccnc12)c1oc2cccc(C#Cc3cnn(C)c3)c2c(=O)c1-c1ccccc1]
103R
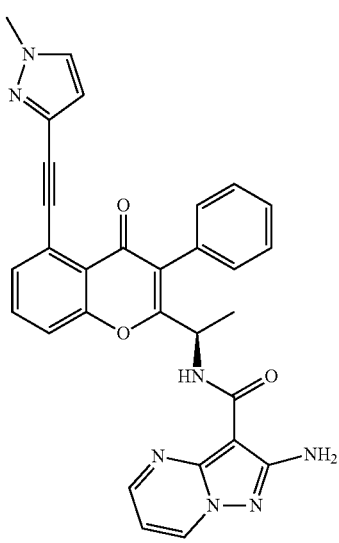
104R TABLE 3-continued
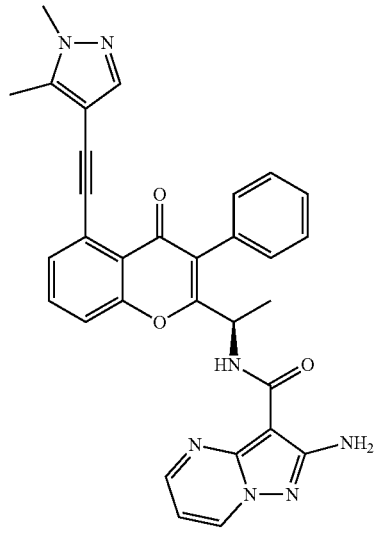 [SMILES: Cc1c(C#Cc2cccc3oc([C@@H](C)NC(=O)c4c(N)nn5cccnc45)c(-c4ccccc4)c(=O)c23)cnn1C]
105R
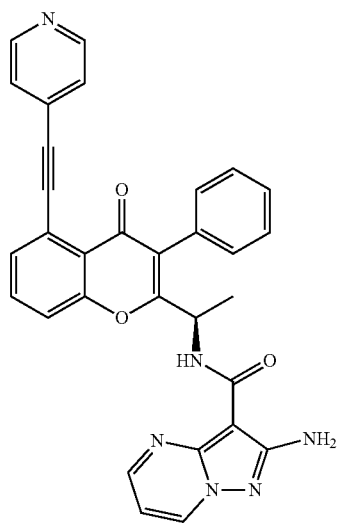 [SMILES: C[C@@H](NC(=O)c1c(N)nn2cccnc12)c1oc2cccc(C#Cc3ccncc3)c2c(=O)c1-c1ccccc1]
106R
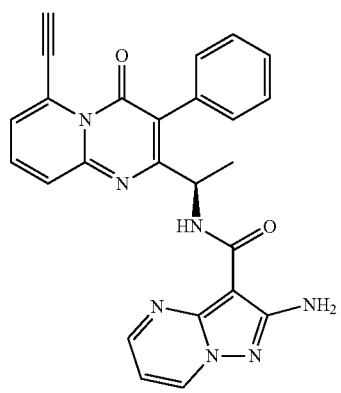 [SMILES: C#Cc1cccc2nc([C@@H](C)NC(=O)c3c(N)nn4cccnc34)c(-c3ccccc3)c(=O)n12]
107R
TABLE 3-continued
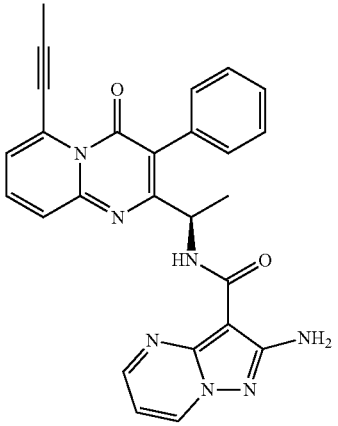 [SMILES: CC#Cc1cccc2nc([C@@H](C)NC(=O)c3c(N)nn4cccnc34)c(-c3ccccc3)c(=O)n12]
108R
109R
110R TABLE 3-continued
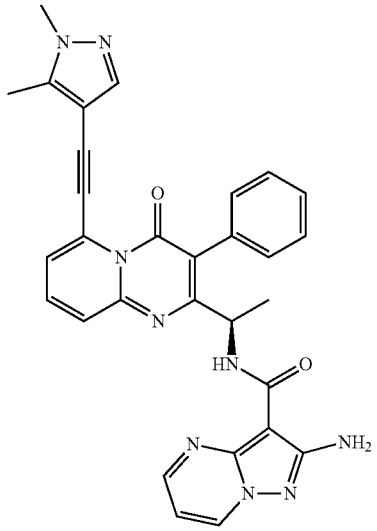 [SMILES: Cc1c(C#Cc2cccc3nc([C@@H](C)NC(=O)c4c(N)nn5cccnc45)c(-c4ccccc4)c(=O)n23)cnn1C]
111R
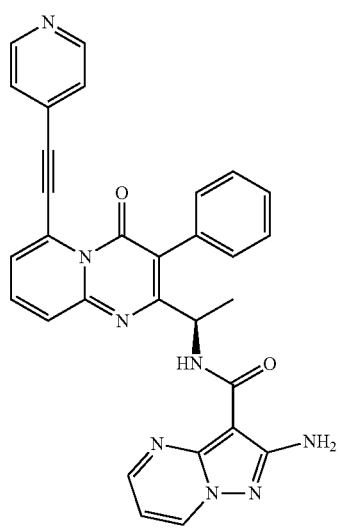 [SMILES: C[C@@H](NC(=O)c1c(N)nn2cccnc12)c1nc2cccc(C#Cc3ccncc3)n2c(=O)c1-c1ccccc1]
112R
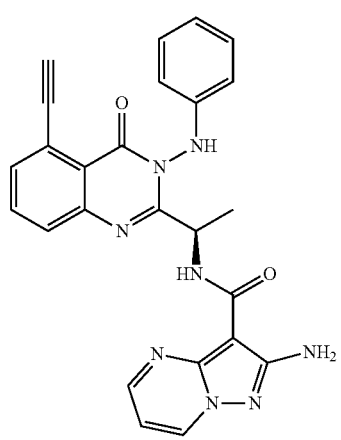 [SMILES: C#Cc1cccc2nc([C@@H](C)NC(=O)c3c(N)nn4cccnc34)n(Nc3ccccc3)c(=O)c12]
113R
TABLE 3-continued
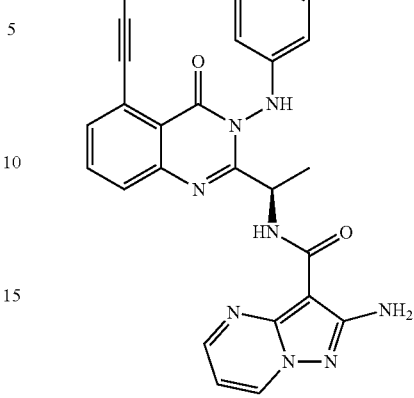
114R
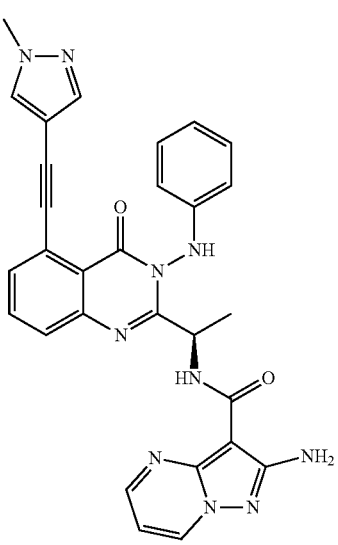 [SMILES: C[C@@H](NC(=O)c1c(N)nn2cccnc12)c1nc2cccc(C#Cc3cnn(C)c3)c2c(=O)n1Nc1ccccc1]
115R
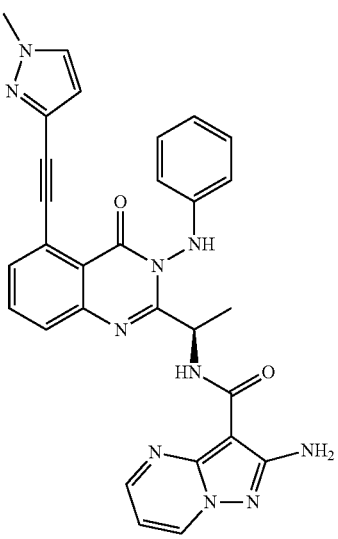 [SMILES: C[C@@H](NC(=O)c1c(N)nn2cccnc12)c1nc2cccc(C#Cc3ccn(C)n3)c2c(=O)n1Nc1ccccc1]
116R TABLE 3-continued
117R
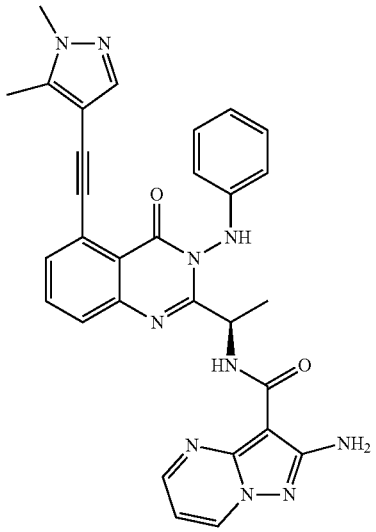 [SMILES: Cc1c(C#Cc2cccc3nc([C@@H](C)NC(=O)c4c(N)nn5cccnc45)n(Nc4ccccc4)c(=O)c23)cnn1C]
118R
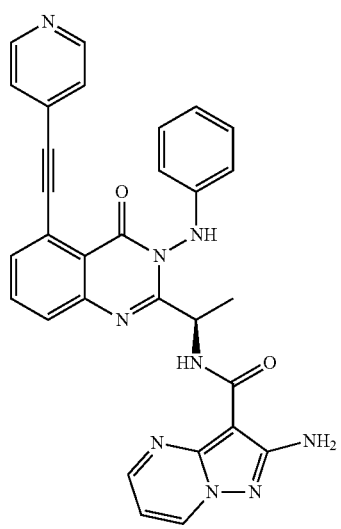 [SMILES: C[C@@H](NC(=O)c1c(N)nn2cccnc12)c1nc2cccc(C#Cc3ccncc3)c2c(=O)n1Nc1ccccc1]
119R
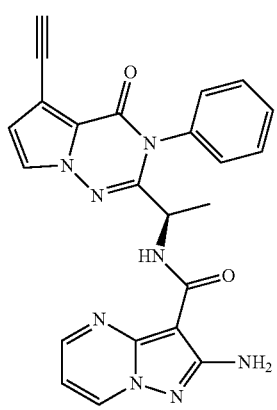
TABLE 3-continued
120R
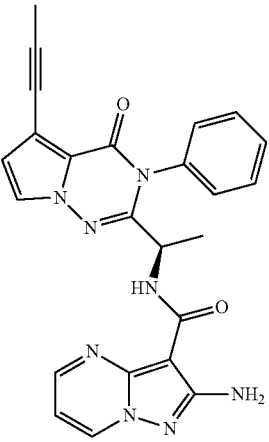
121R
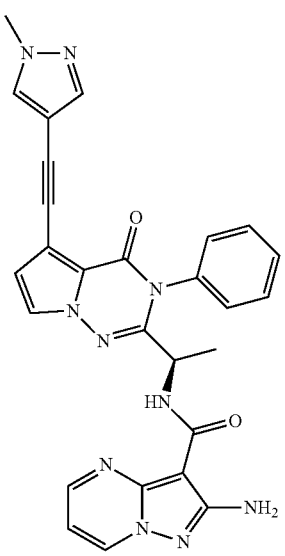 [SMILES: C[C@@H](NC(=O)c1c(N)nn2cccnc12)c1nn2ccc(C#Cc3cnn(C)c3)c2c(=O)n1-c1ccccc1]
122R
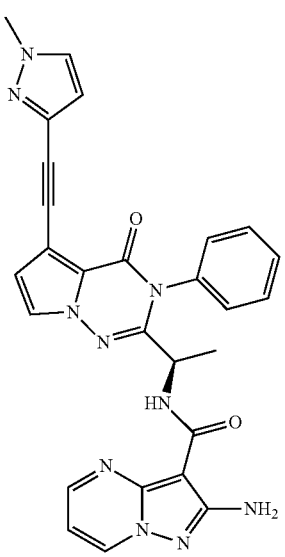 [SMILES: C[C@@H](NC(=O)c1c(N)nn2cccnc12)c1nn2ccc(C#Cc3ccn(C)n3)c2c(=O)n1-c1ccccc1]

TABLE 3-continued
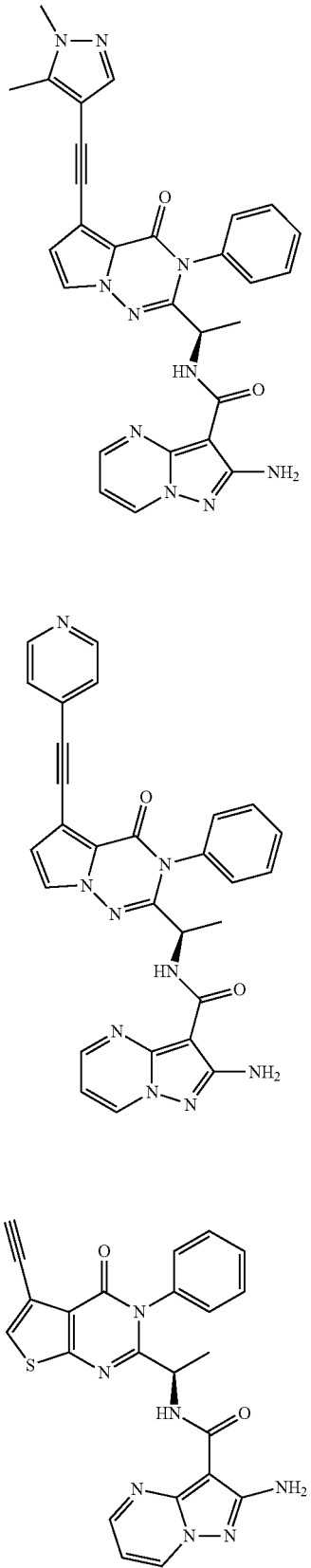
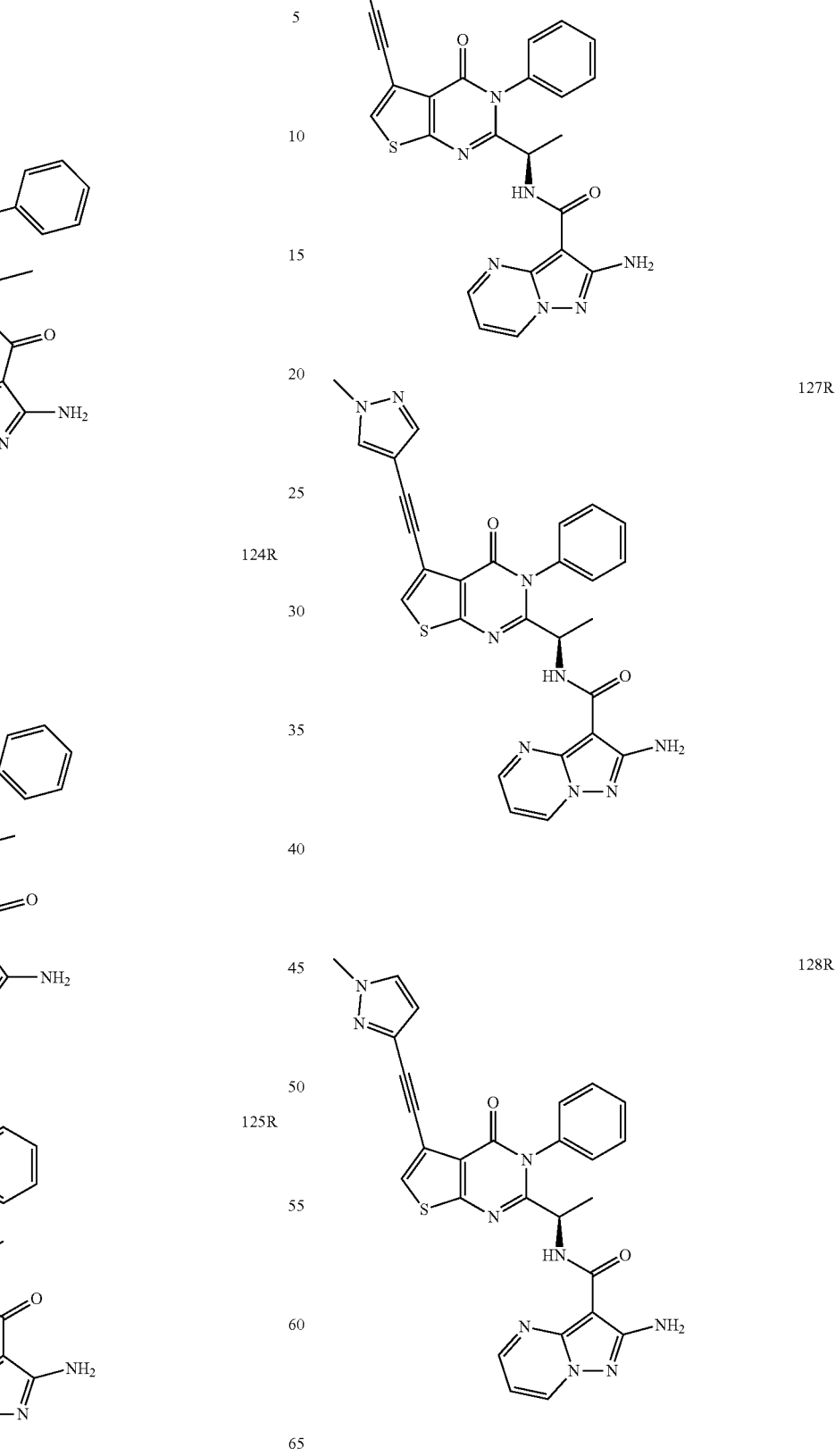

TABLE 3-continued
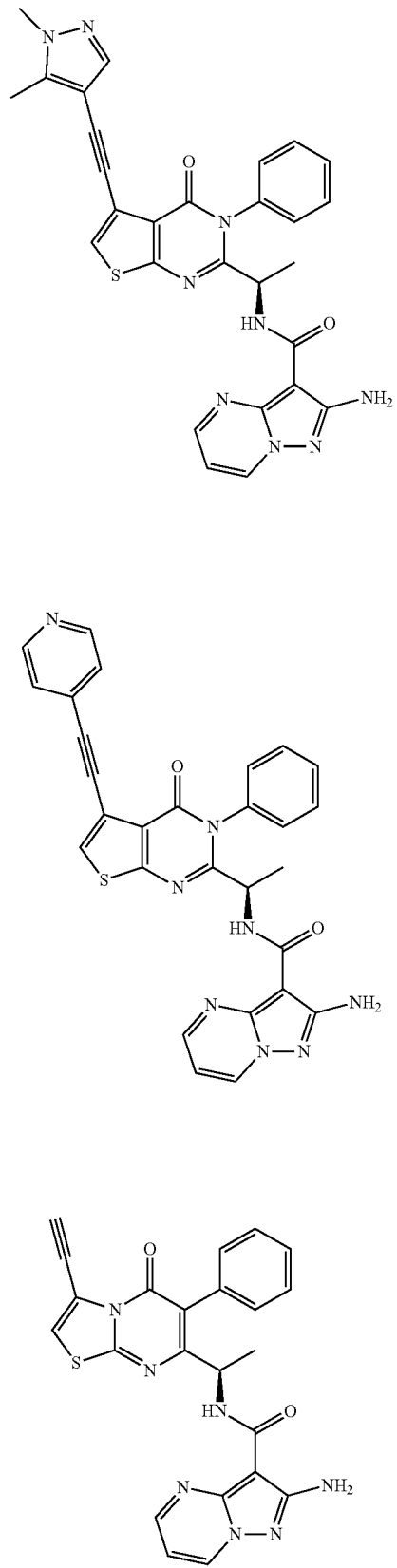
129R
130R
131R
TABLE 3-continued
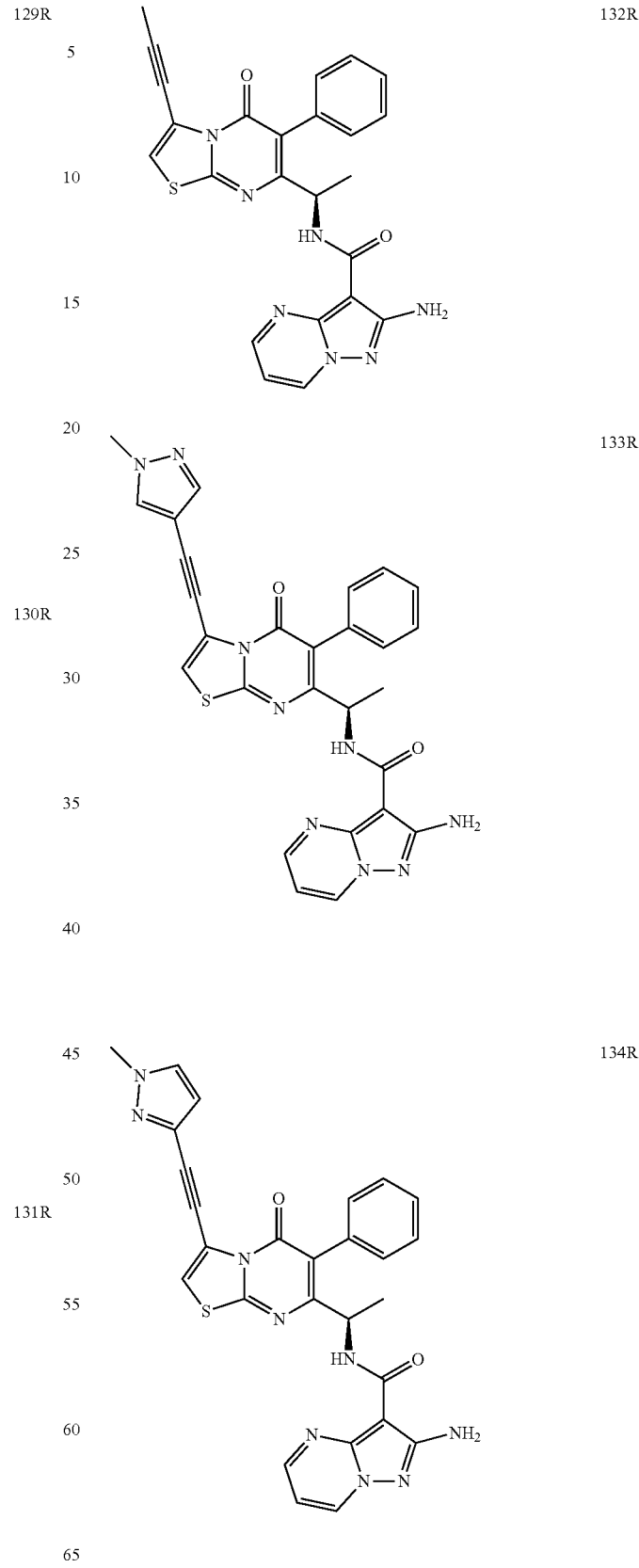
132R
133R
134R TABLE 3-continued
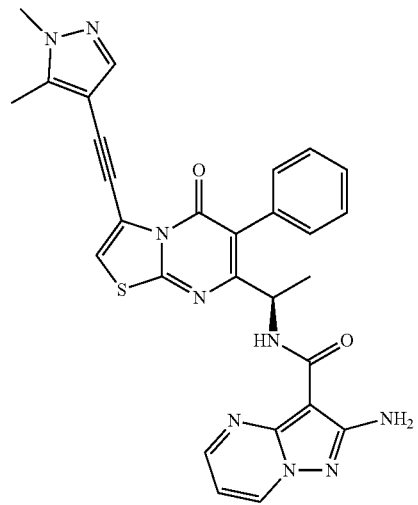 [SMILES: Cc1c(C#Cc2csc3nc([C@@H](C)NC(=O)c4c(N)nn5cccnc45)c(-c4ccccc4)c(=O)n23)cnn1C]
135R
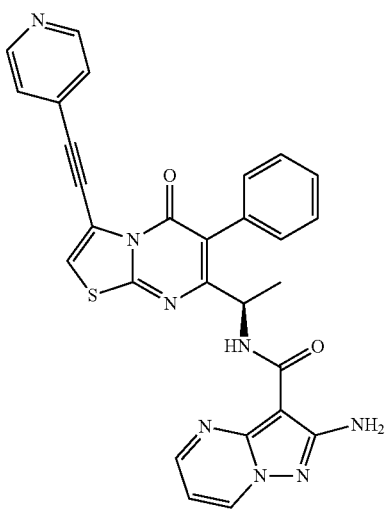 [SMILES: C[C@@H](NC(=O)c1c(N)nn2cccnc12)c1nc2scc(C#Cc3ccncc3)n2c(=O)c1-c1ccccc1]
136R
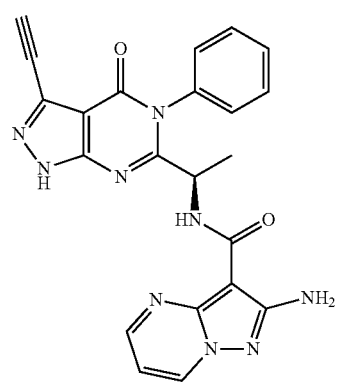 [SMILES: C#Cc1n[nH]c2nc([C@@H](C)NC(=O)c3c(N)nn4cccnc34)n(-c3ccccc3)c(=O)c12]
137R
TABLE 3-continued
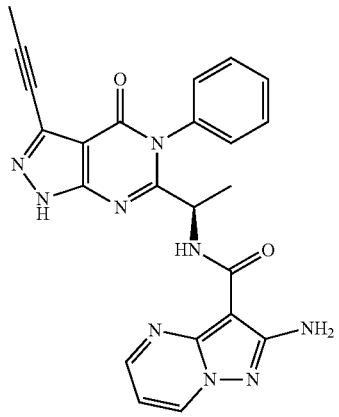 [SMILES: CC#Cc1n[nH]c2nc([C@@H](C)NC(=O)c3c(N)nn4cccnc34)n(-c3ccccc3)c(=O)c12]
138R
139R
140R TABLE 3-continued
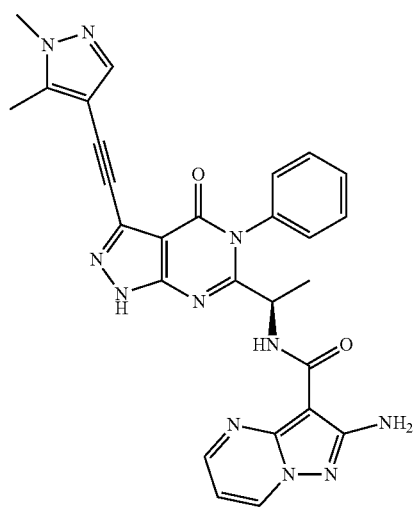 [SMILES: Cc1c(C#Cc2n[nH]c3nc([C@@H](C)NC(=O)c4c(N)nn5cccnc45)n(-c4ccccc4)c(=O)c23)cnn1C]
141R
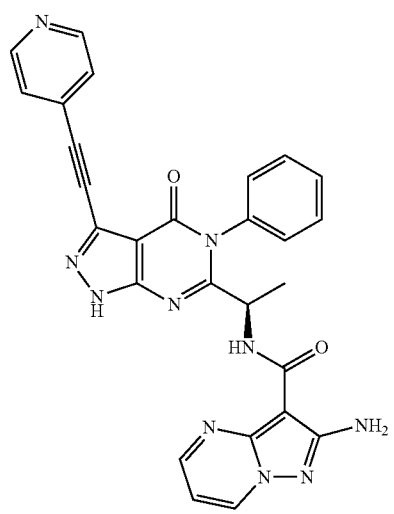 [SMILES: C[C@@H](NC(=O)c1c(N)nn2cccnc12)c1nc2[nH]nc(C#Cc3ccncc3)c2c(=O)n1-c1ccccc1]
142R
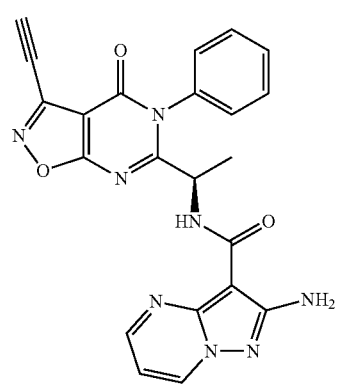 [SMILES: C#Cc1noc2nc([C@@H](C)NC(=O)c3c(N)nn4cccnc34)n(-c3ccccc3)c(=O)c12]
143R
TABLE 3-continued
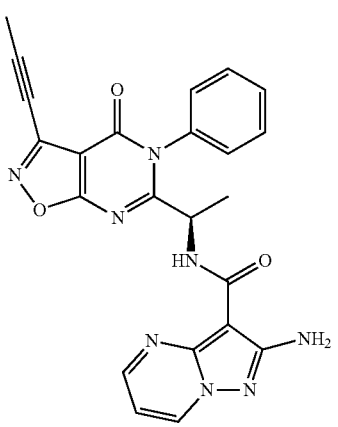 [SMILES: CC#Cc1noc2nc([C@@H](C)NC(=O)c3c(N)nn4cccnc34)n(-c3ccccc3)c(=O)c12]
144R
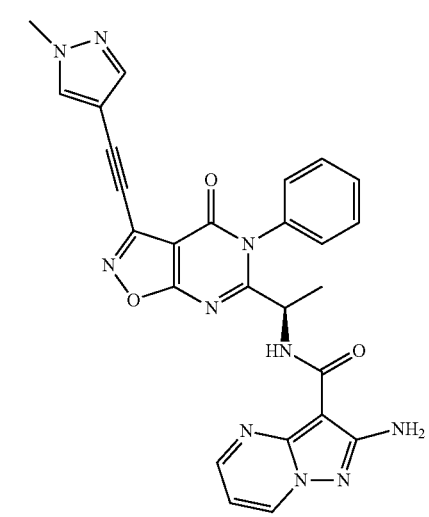 [SMILES: C[C@@H](NC(=O)c1c(N)nn2cccnc12)c1nc2onc(C#Cc3cnn(C)c3)c2c(=O)n1-c1ccccc1]
145R
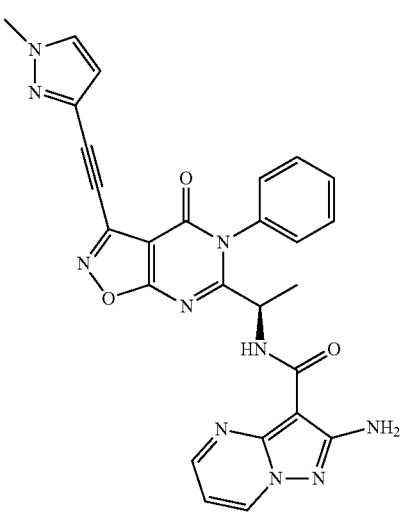 [SMILES: C[C@@H](NC(=O)c1c(N)nn2cccnc12)c1nc2onc(C#Cc3ccn(C)n3)c2c(=O)n1-c1ccccc1]
146R TABLE 3-continued
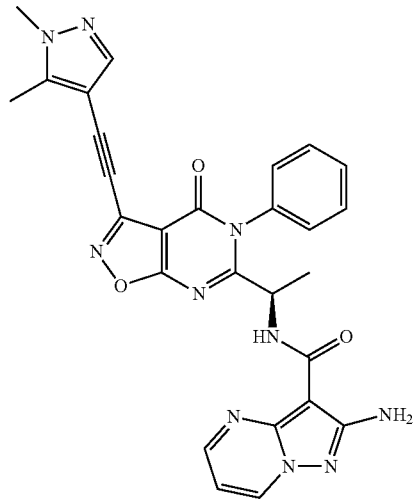 [SMILES: Cc1c(C#Cc2noc3nc([C@@H](C)NC(=O)c4c(N)nn5cccnc45)n(-c4ccccc4)c(=O)c23)cnn1C]
147R
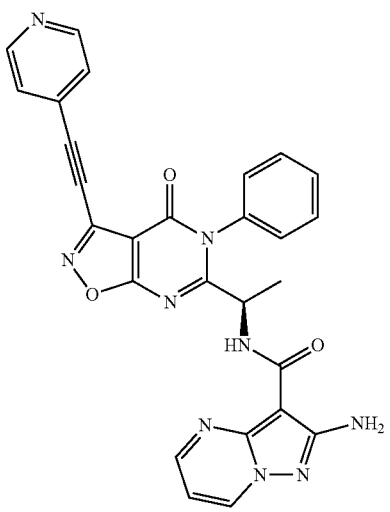 [SMILES: C[C@@H](NC(=O)c1c(N)nn2cccnc12)c1nc2onc(C#Cc3ccncc3)c2c(=O)n1-c1ccccc1]
148R
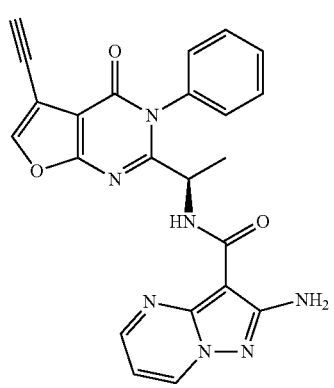 [SMILES: C#Cc1coc2nc([C@@H](C)NC(=O)c3c(N)nn4cccnc34)n(-c3ccccc3)c(=O)c12]
149R
TABLE 3-continued
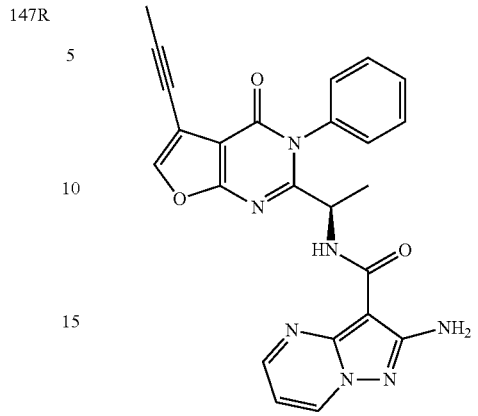
150R
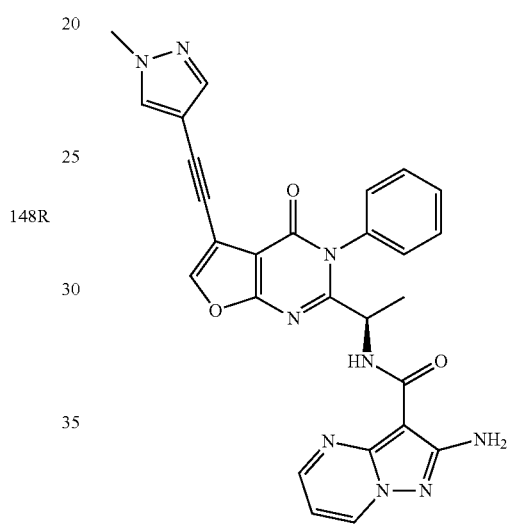
151R
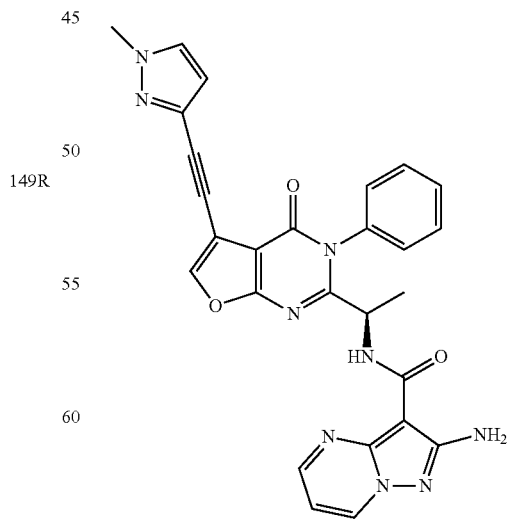
152R TABLE 3-continued
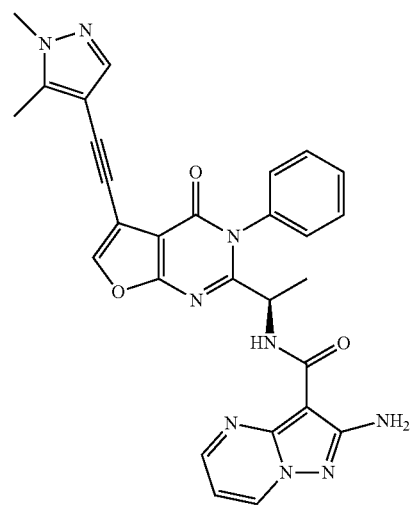 [SMILES: Cc1c(C#Cc2coc3nc([C@@H](C)NC(=O)c4c(N)nn5cccnc45)n(-c4ccccc4)c(=O)c23)cnn1C]
153R
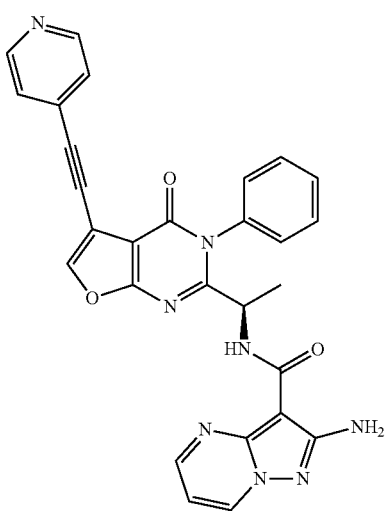
154R
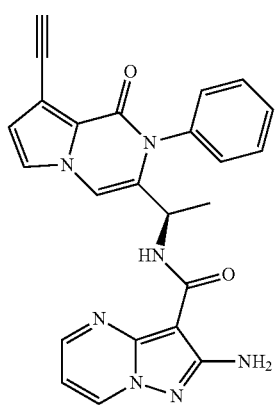 [SMILES: C#Cc1ccn2cc([C@@H](C)NC(=O)c3c(N)nn4cccnc34)n(-c3ccccc3)c(=O)c12]
155R
TABLE 3-continued
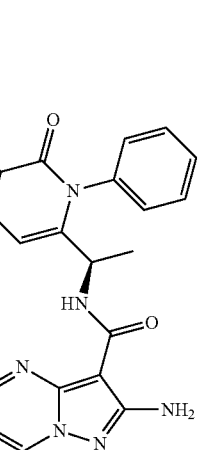
156R
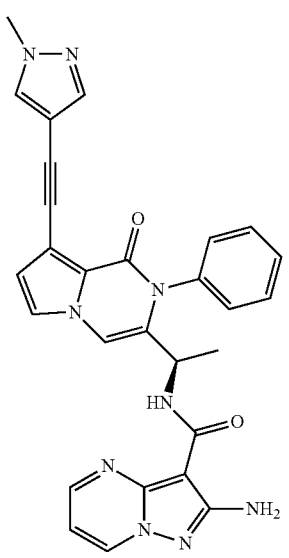 [SMILES: C[C@@H](NC(=O)c1c(N)nn2cccnc12)c1cn2ccc(C#Cc3cnn(C)c3)c2c(=O)n1-c1ccccc1]
157R
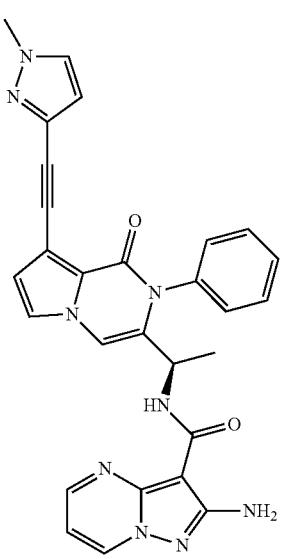 [SMILES: C[C@@H](NC(=O)c1c(N)nn2cccnc12)c1cn2ccc(C#Cc3ccn(C)n3)c2c(=O)n1-c1ccccc1]
158R TABLE 3-continued
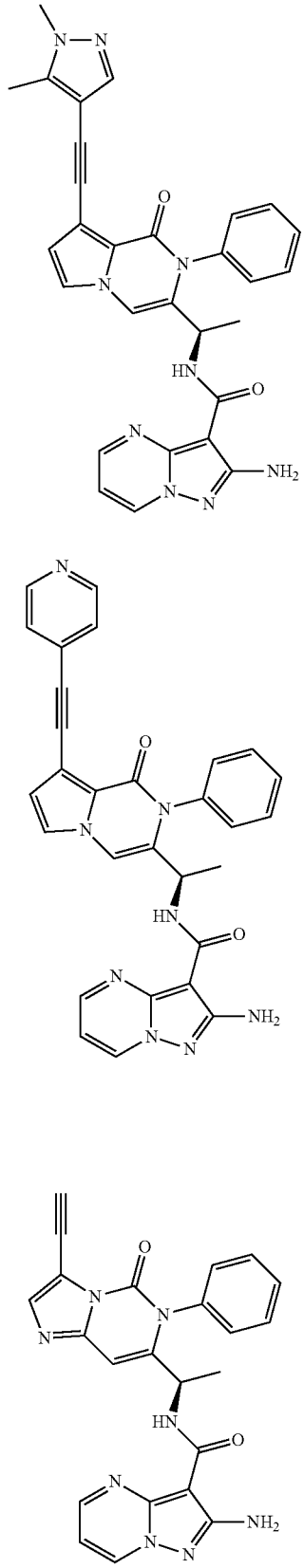
159R
160R
161R
TABLE 3-continued
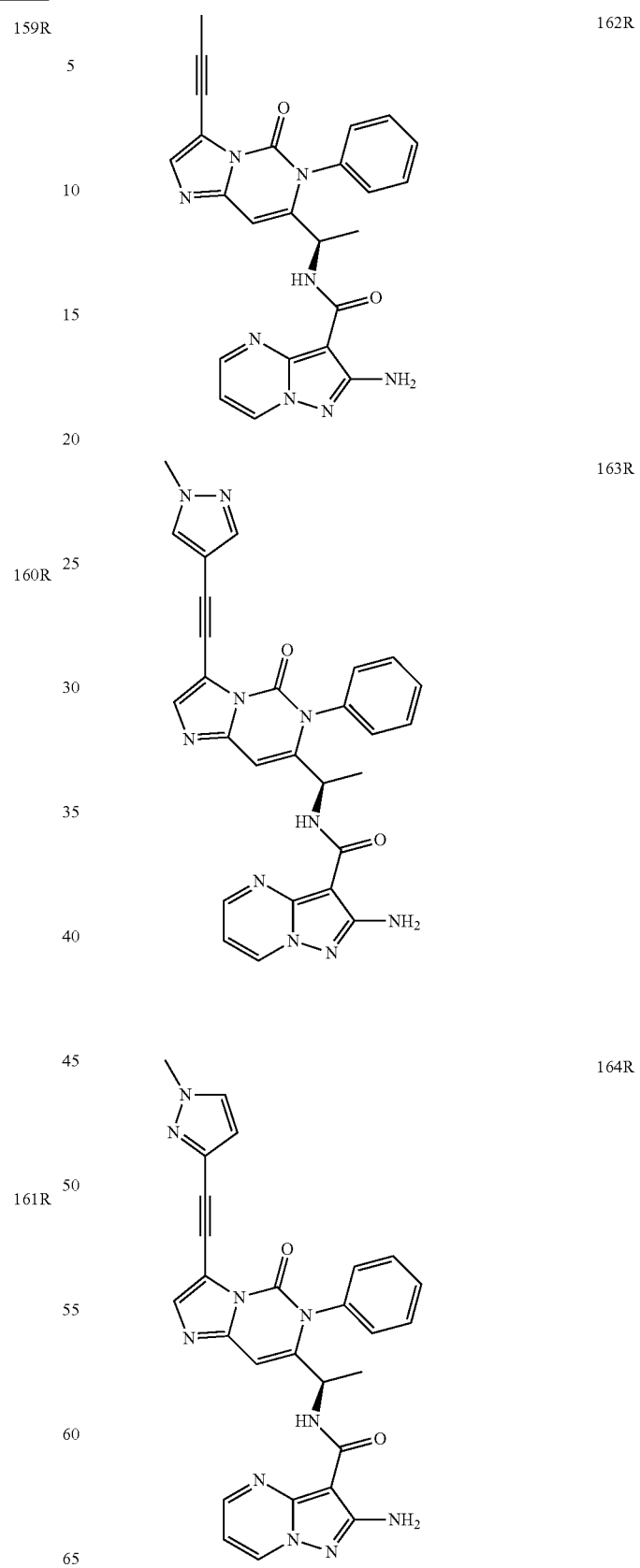
162R
163R
164R TABLE 3-continued
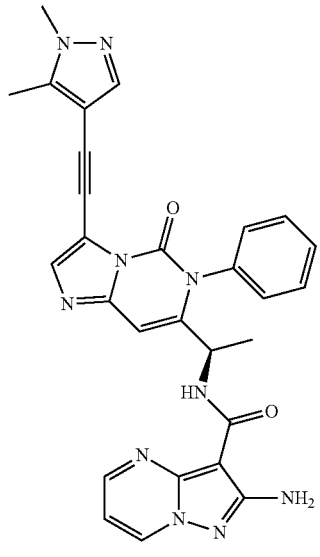 [SMILES: Cc1c(C#Cc2cnc3cc([C@@H](C)NC(=O)c4c(N)nn5cccnc45)n(-c4ccccc4)c(=O)n23)cnn1C]
165R
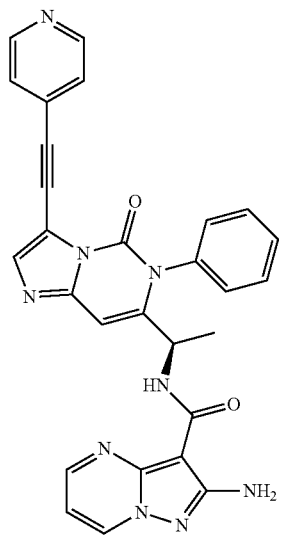
166R
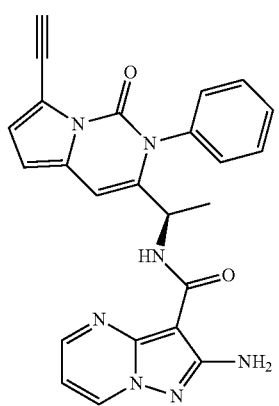 [SMILES: C#Cc1ccc2cc([C@@H](C)NC(=O)c3c(N)nn4cccnc34)n(-c3ccccc3)c(=O)n12]
167R
TABLE 3-continued
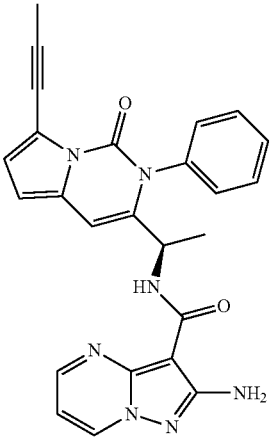 [SMILES: CC#Cc1ccc2cc([C@@H](C)NC(=O)c3c(N)nn4cccnc34)n(-c3ccccc3)c(=O)n12]
168R
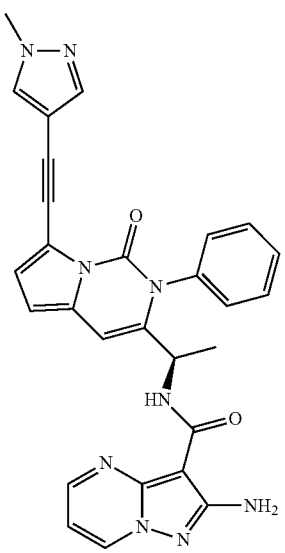 [SMILES: C[C@@H](NC(=O)c1c(N)nn2cccnc12)c1cc2ccc(C#Cc3cnn(C)c3)n2c(=O)n1-c1ccccc1]
169R
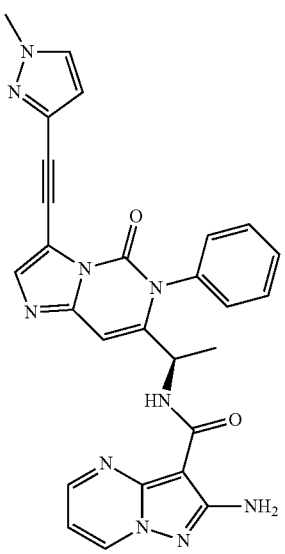 [SMILES: C[C@@H](NC(=O)c1c(N)nn2cccnc12)c1cc2ncc(C#Cc3ccn(C)n3)n2c(=O)n1-c1ccccc1]
170R TABLE 3-continued
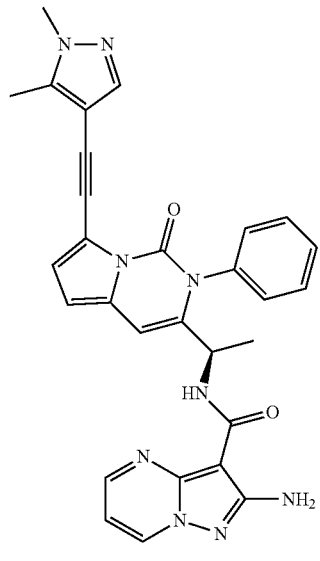 [SMILES: Cc1c(C#Cc2ccc3cc([C@@H](C)NC(=O)c4c(N)nn5cccnc45)n(-c4ccccc4)c(=O)n23)cnn1C]
171R
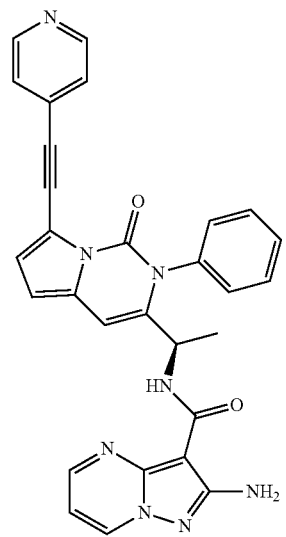 [SMILES: C[C@@H](NC(=O)c1c(N)nn2cccnc12)c1cc2ccc(C#Cc3ccncc3)n2c(=O)n1-c1ccccc1]
172R
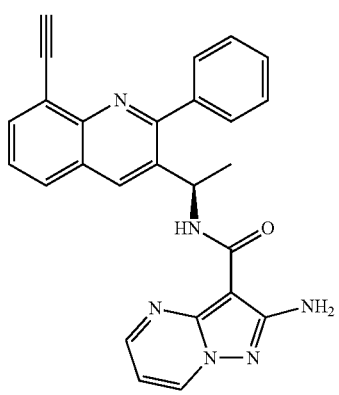 [SMILES: C#Cc1cccc2cc([C@@H](C)NC(=O)c3c(N)nn4cccnc34)c(-c3ccccc3)nc12]
173R
TABLE 3-continued
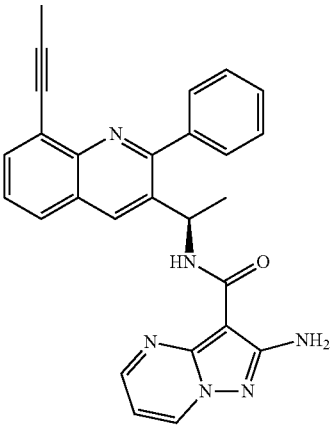 [SMILES: CC#Cc1cccc2cc([C@@H](C)NC(=O)c3c(N)nn4cccnc34)c(-c3ccccc3)nc12]
174R
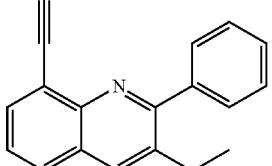
175R
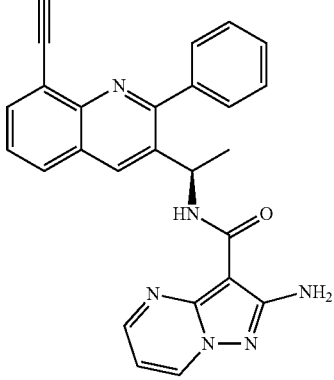
176R TABLE 3-continued
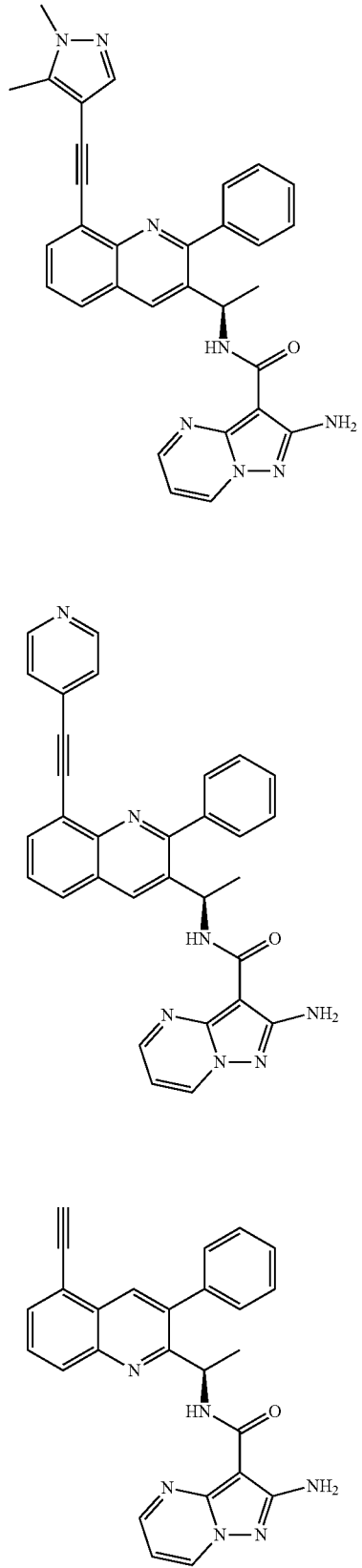

TABLE 3-continued
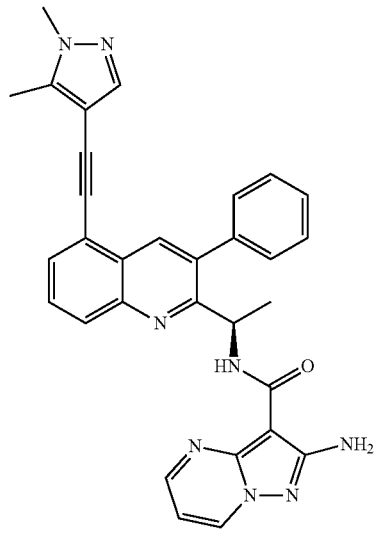 [SMILES: Cc1c(C#Cc2cccc3nc([C@@H](C)NC(=O)c4c(N)nn5cccnc45)c(-c4ccccc4)cc23)cnn1C]
183R
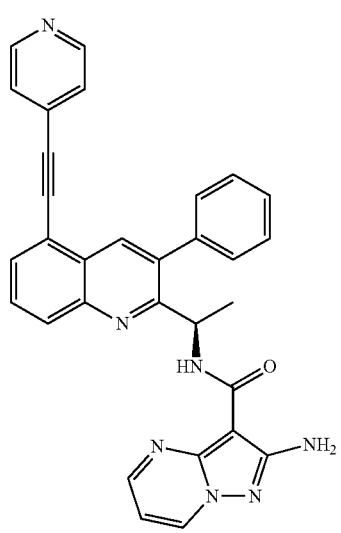
184R
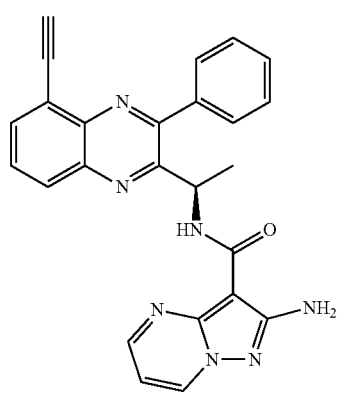 [SMILES: C#Cc1cccc2nc([C@@H](C)NC(=O)c3c(N)nn4cccnc34)c(-c3ccccc3)nc12]
185R
TABLE 3-continued
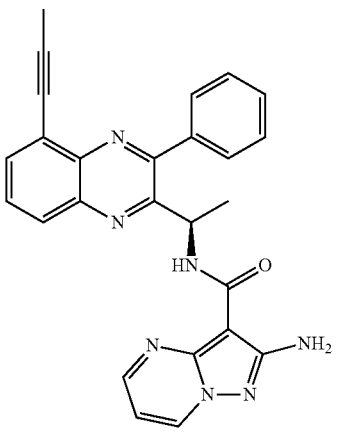 [SMILES: CC#Cc1cccc2nc([C@@H](C)NC(=O)c3c(N)nn4cccnc34)c(-c3ccccc3)nc12]
186R
187R
188R TABLE 3-continued
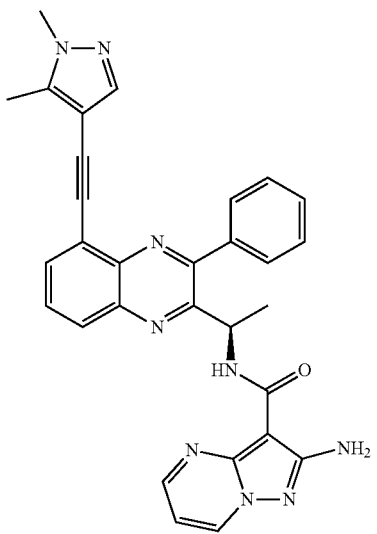 [SMILES: Cc1c(C#Cc2cccc3nc([C@@H](C)NC(=O)c4c(N)nn5cccnc45)c(-c4ccccc4)nc23)cnn1C]
189R
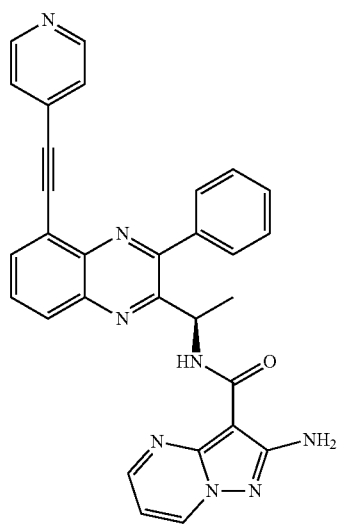 [SMILES: C[C@@H](NC(=O)c1c(N)nn2cccnc12)c1nc2cccc(C#Cc3ccncc3)c2nc1-c1ccccc1]
190R
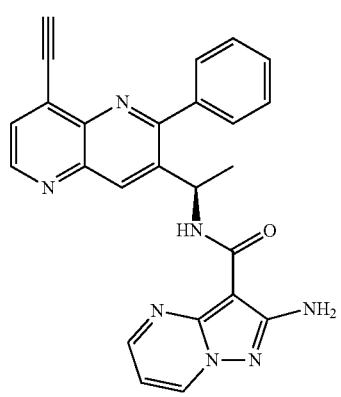 [SMILES: C#Cc1ccnc2cc([C@@H](C)NC(=O)c3c(N)nn4cccnc34)c(-c3ccccc3)nc12]
191R
TABLE 3-continued
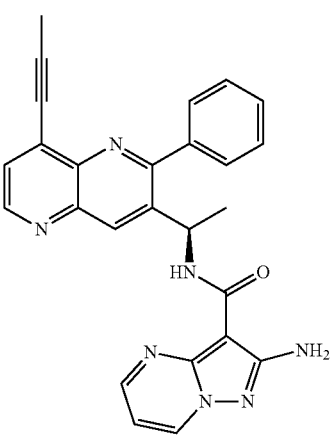 [SMILES: CC#Cc1ccnc2cc([C@@H](C)NC(=O)c3c(N)nn4cccnc34)c(-c3ccccc3)nc12]
192R
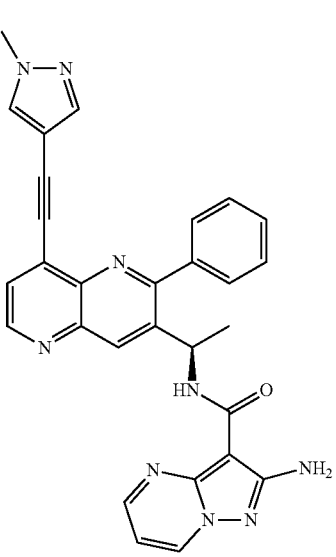 [SMILES: C[C@@H](NC(=O)c1c(N)nn2cccnc12)c1cc2nccc(C#Cc3cnn(C)c3)c2nc1-c1ccccc1]
193R
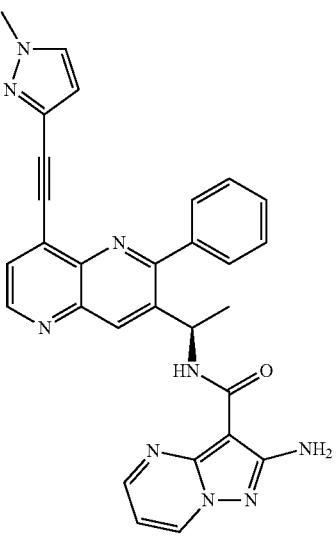 [SMILES: C[C@@H](NC(=O)c1c(N)nn2cccnc12)c1cc2nccc(C#Cc3ccn(C)n3)c2nc1-c1ccccc1]
194R TABLE 3-continued
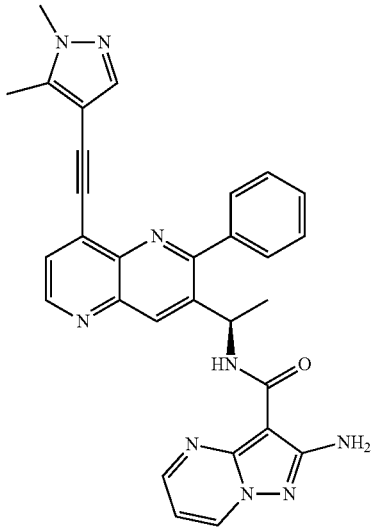
195R
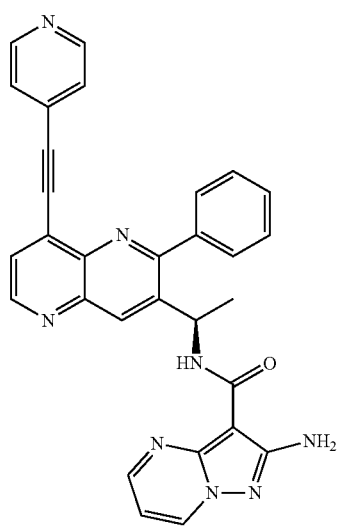 [SMILES: C[C@@H](NC(=O)c1c(N)nn2cccnc12)c1cc2nccc(C#Cc3ccncc3)c2nc1-c1ccccc1]
196R
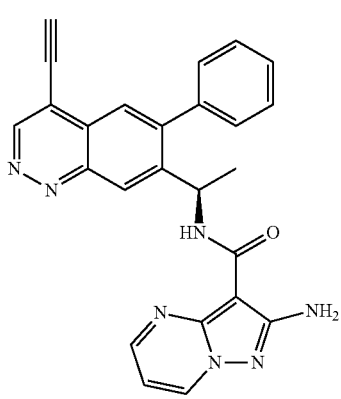 [SMILES: C#Cc1cnnc2cc([C@@H](C)NC(=O)c3c(N)nn4cccnc34)c(-c3ccccc3)cc12]
197R
TABLE 3-continued
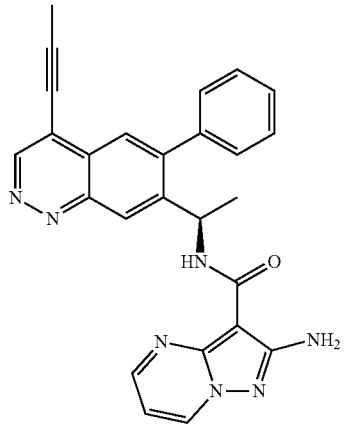 [SMILES: CC#Cc1cnnc2cc([C@@H](C)NC(=O)c3c(N)nn4cccnc34)c(-c3ccccc3)cc12]
198R
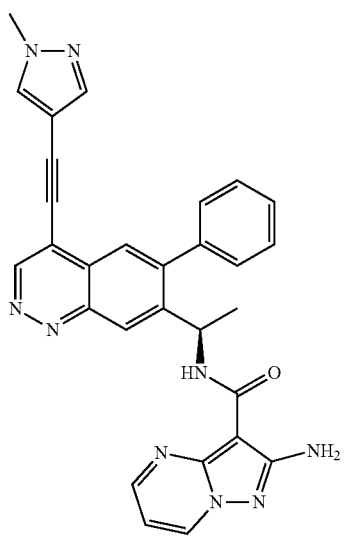 [SMILES: C[C@@H](NC(=O)c1c(N)nn2cccnc12)c1cc2nncc(C#Cc3cnn(C)c3)c2cc1-c1ccccc1]
199R
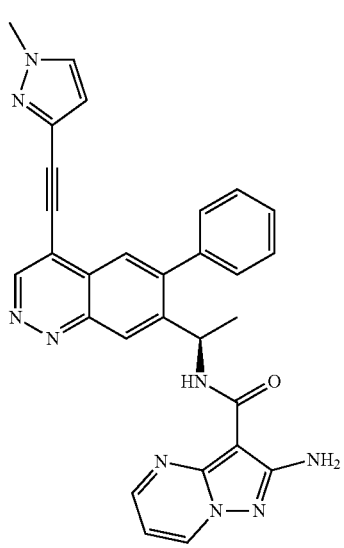 [SMILES: C[C@@H](NC(=O)c1c(N)nn2cccnc12)c1cc2nncc(C#Cc3ccn(C)n3)c2cc1-c1ccccc1]
200R TABLE 3-continued
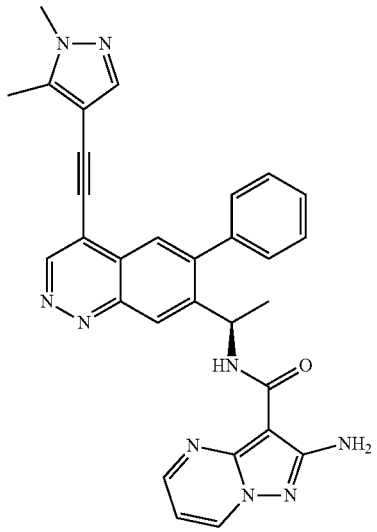 [SMILES: Cc1c(C#Cc2cnnc3cc([C@@H](C)NC(=O)c4c(N)nn5cccnc45)c(-c4ccccc4)cc23)cnn1C]
201R
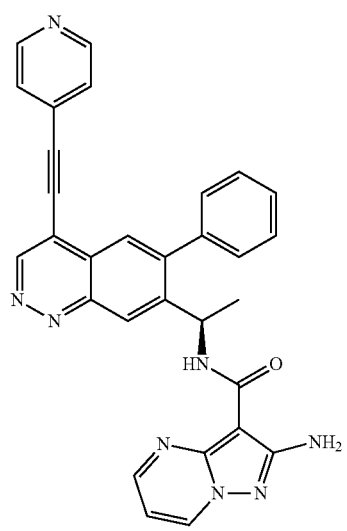 [SMILES: C[C@@H](NC(=O)c1c(N)nn2cccnc12)c1cc2nncc(C#Cc3ccncc3)c2cc1-c1ccccc1]
202R
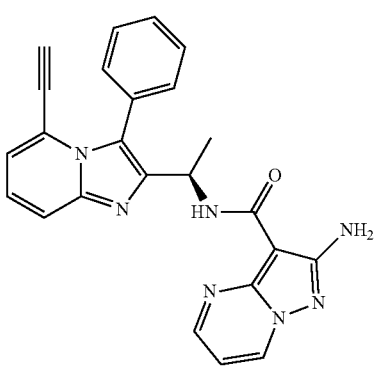 [SMILES: C#Cc1cccc2nc([C@@H](C)NC(=O)c3c(N)nn4cccnc34)c(-c3ccccc3)n12]
203R
TABLE 3-continued
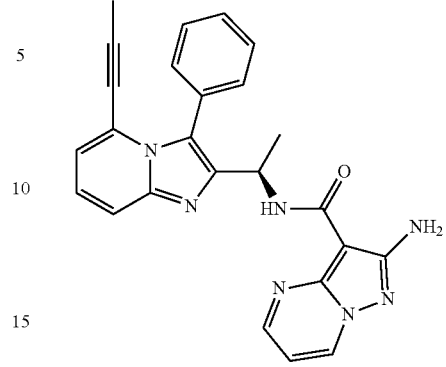
204R
205R
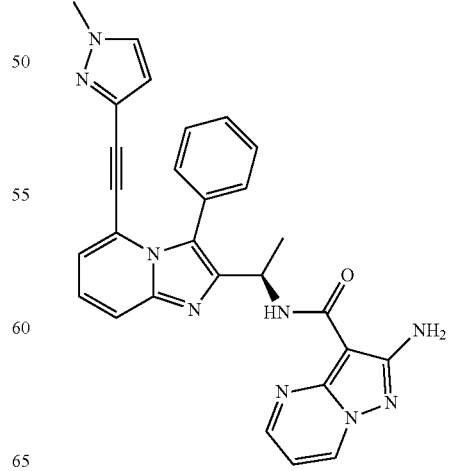
206R TABLE 3-continued
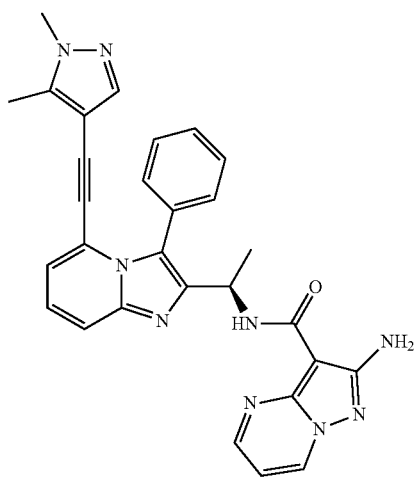 [SMILES: Cc1c(C#Cc2cccc3nc([C@@H](C)NC(=O)c4c(N)nn5cccnc45)c(-c4ccccc4)n23)cnn1C]
207R
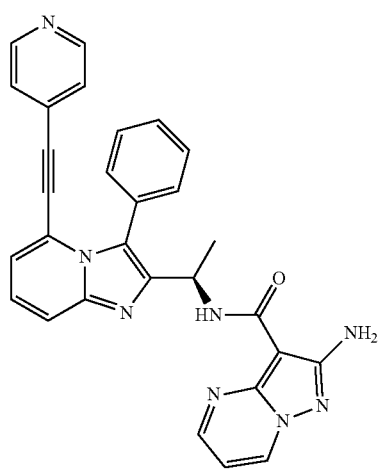 [SMILES: C[C@@H](NC(=O)c1c(N)nn2cccnc12)c1nc2cccc(C#Cc3ccncc3)n2c1-c1ccccc1]
208R
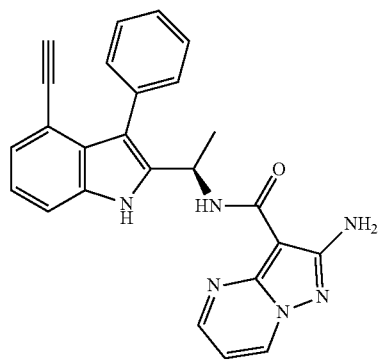 [SMILES: C#Cc1cccc2[nH]c([C@@H](C)NC(=O)c3c(N)nn4cccnc34)c(-c3ccccc3)c12]
209R
TABLE 3-continued
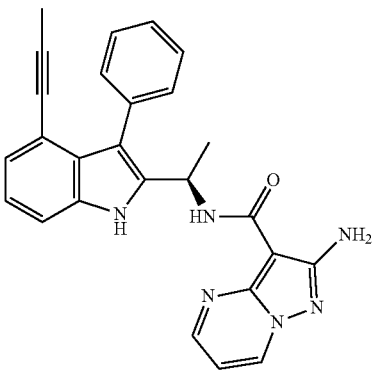 [SMILES: CC#Cc1cccc2[nH]c([C@@H](C)NC(=O)c3c(N)nn4cccnc34)c(-c3ccccc3)c12]
210R
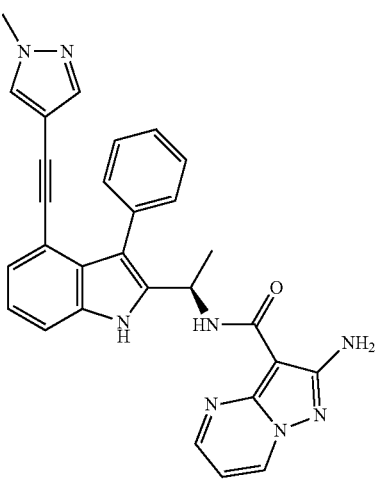 [SMILES: C[C@@H](NC(=O)c1c(N)nn2cccnc12)c1[nH]c2cccc(C#Cc3cnn(C)c3)c2c1-c1ccccc1]
211R
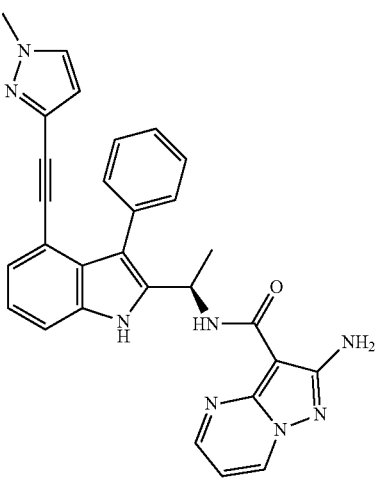 [SMILES: C[C@@H](NC(=O)c1c(N)nn2cccnc12)c1[nH]c2cccc(C#Cc3ccn(C)n3)c2c1-c1ccccc1]
212R TABLE 3-continued
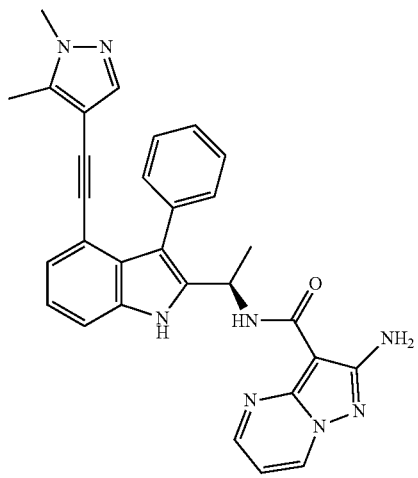 [SMILES: Cc1c(C#Cc2cccc3[nH]c([C@@H](C)NC(=O)c4c(N)nn5cccnc45)c(-c4ccccc4)c23)cnn1C]
213R
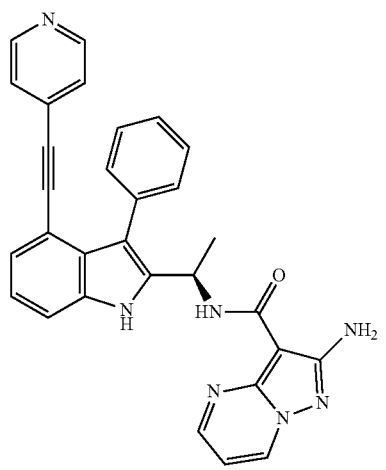 [SMILES: C[C@@H](NC(=O)c1c(N)nn2cccnc12)c1[nH]c2cccc(C#Cc3ccncc3)c2c1-c1ccccc1]
214R
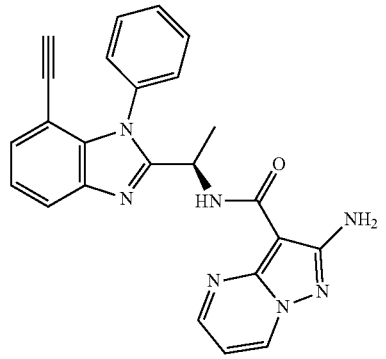 [SMILES: C#Cc1cccc2nc([C@@H](C)NC(=O)c3c(N)nn4cccnc34)n(-c3ccccc3)c12]
215R
TABLE 3-continued
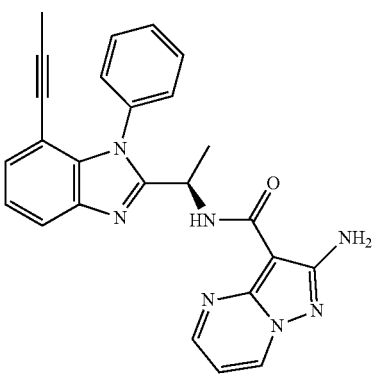
216R
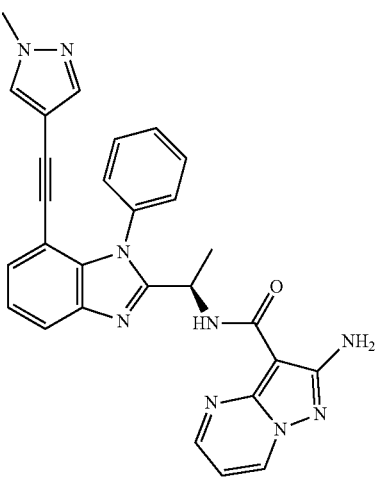 [SMILES: C[C@@H](NC(=O)c1c(N)nn2cccnc12)c1nc2cccc(C#Cc3cnn(C)c3)c2n1-c1ccccc1]
217R
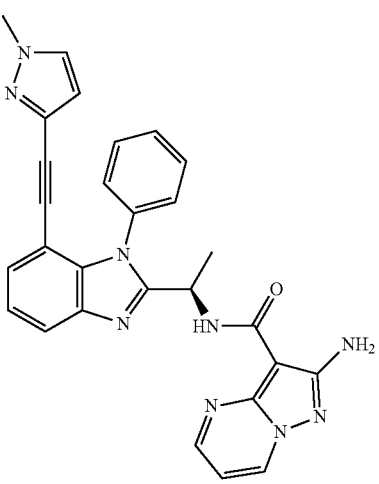 [SMILES: C[C@@H](NC(=O)c1c(N)nn2cccnc12)c1nc2cccc(C#Cc3ccn(C)n3)c2n1-c1ccccc1]
218R TABLE 3-continued
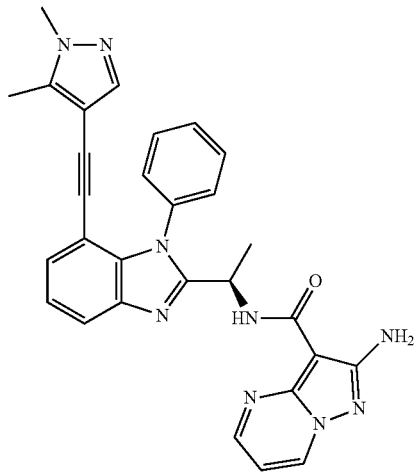 [SMILES: Cc1c(C#Cc2cccc3nc([C@@H](C)NC(=O)c4c(N)nn5cccnc45)n(-c4ccccc4)c23)cnn1C]
219R
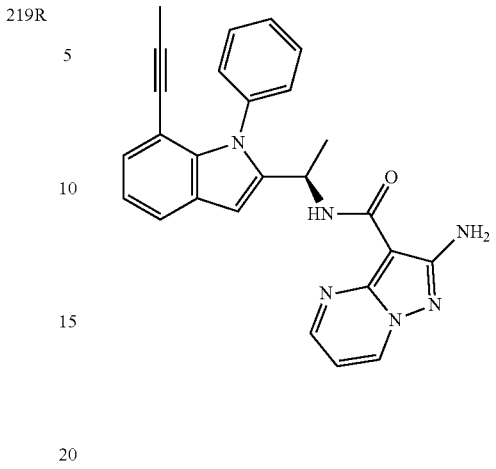
222R
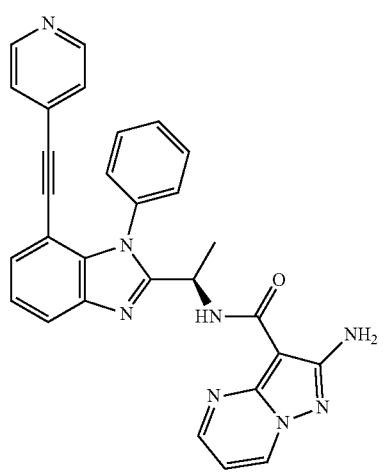 [SMILES: C[C@@H](NC(=O)c1c(N)nn2cccnc12)c1nc2cccc(C#Cc3ccncc3)c2n1-c1ccccc1]
220R
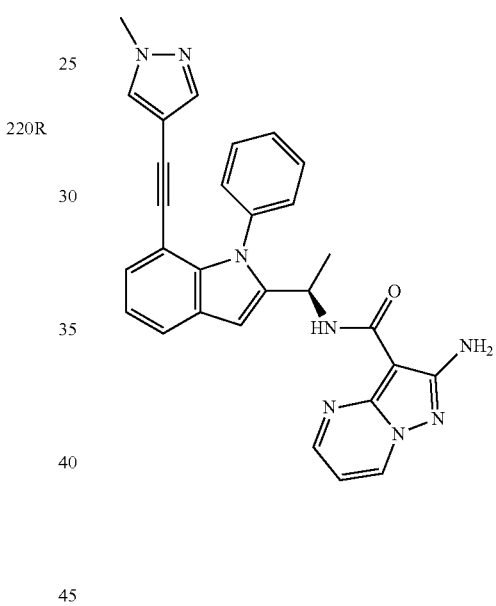
223R
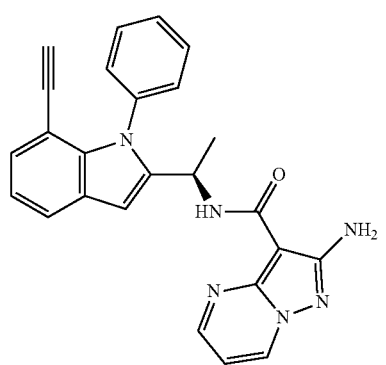 [SMILES: C#Cc1cccc2cc([C@@H](C)NC(=O)c3c(N)nn4cccnc34)n(-c3ccccc3)c12]
221R
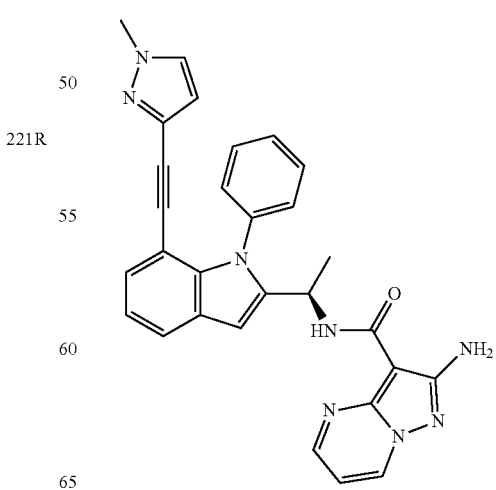
224R TABLE 3-continued
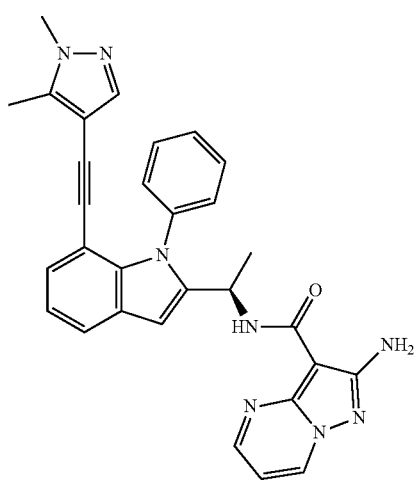 [SMILES: Cc1c(C#Cc2cccc3cc([C@@H](C)NC(=O)c4c(N)nn5cccnc45)n(-c4ccccc4)c23)cnn1C]
225R
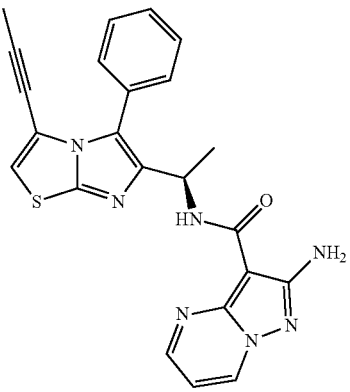
228R
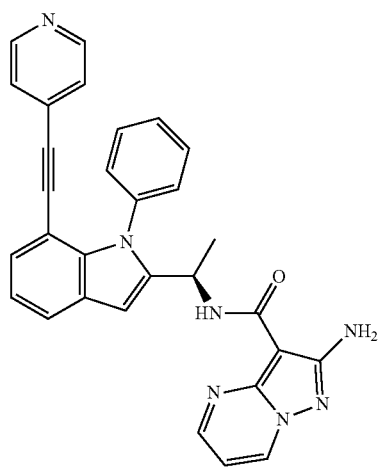 [SMILES: C[C@@H](NC(=O)c1c(N)nn2cccnc12)c1cc2cccc(C#Cc3ccncc3)c2n1-c1ccccc1]
226R
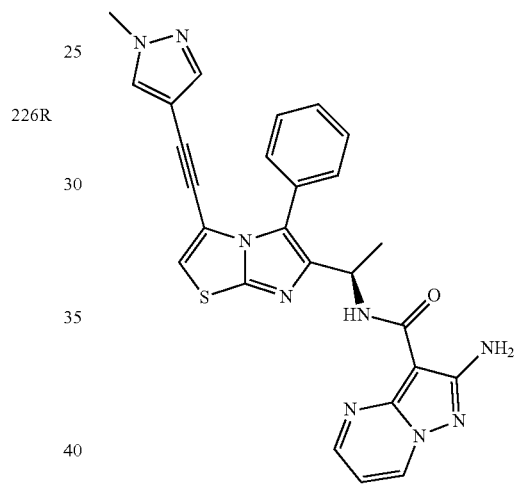
229R
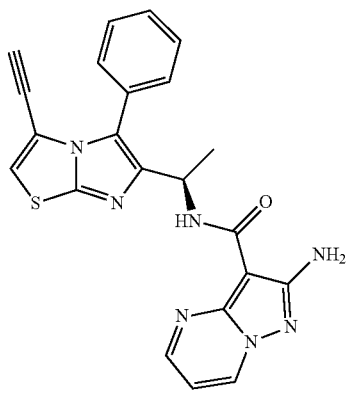 [SMILES: C#Cc1csc2nc([C@@H](C)NC(=O)c3c(N)nn4cccnc34)c(-c3ccccc3)n12]
227R
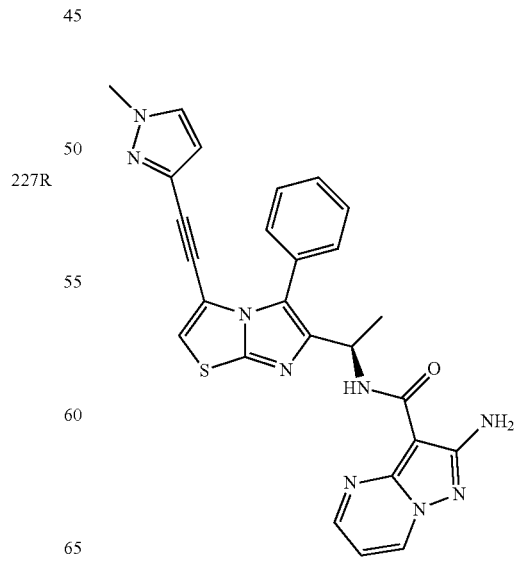
230R TABLE 3-continued
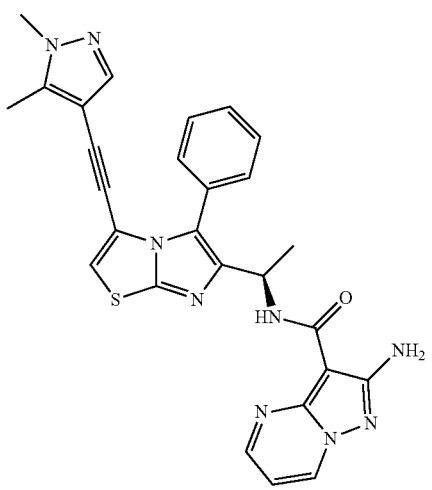 [SMILES: Cc1c(C#Cc2csc3nc([C@@H](C)NC(=O)c4c(N)nn5cccnc45)c(-c4ccccc4)n23)cnn1C]
231R
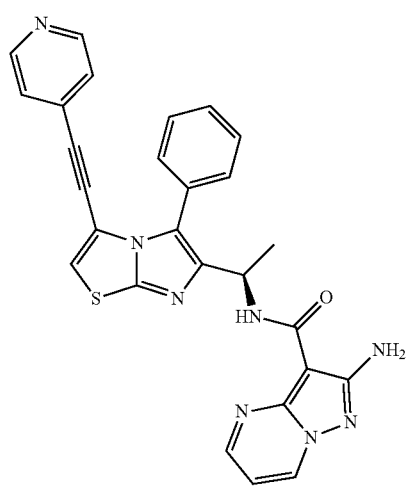 [SMILES: C[C@@H](NC(=O)c1c(N)nn2cccnc12)c1nc2scc(C#Cc3ccncc3)n2c1-c1ccccc1]
232R
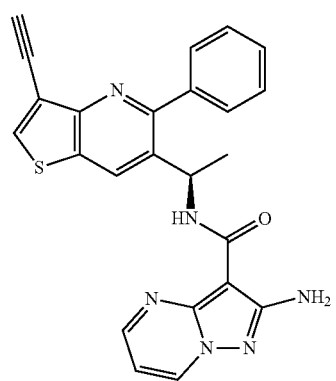 [SMILES: C#Cc1csc2cc([C@@H](C)NC(=O)c3c(N)nn4cccnc34)c(-c3ccccc3)nc12]
233R
TABLE 3-continued
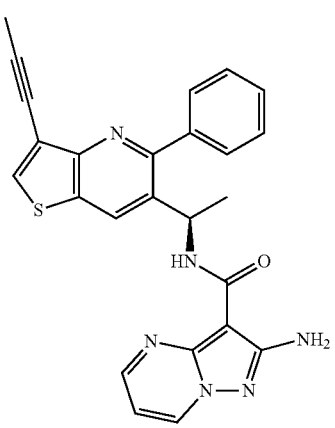 [SMILES: CC#Cc1csc2cc([C@@H](C)NC(=O)c3c(N)nn4cccnc34)c(-c3ccccc3)nc12]
234R
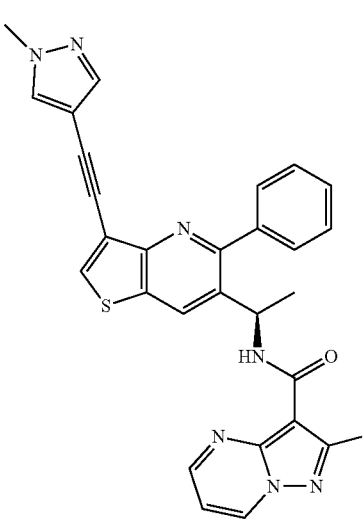
235R
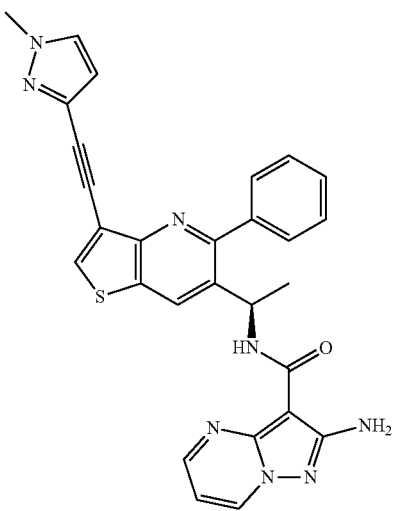 [SMILES: C[C@@H](NC(=O)c1c(N)nn2cccnc12)c1cc2scc(C#Cc3ccn(C)n3)c2nc1-c1ccccc1]
236R TABLE 3-continued
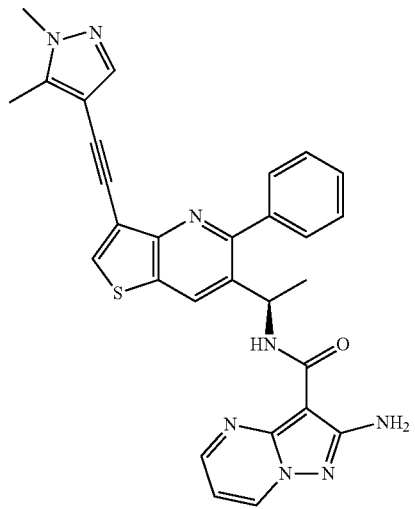 [SMILES: Cc1c(C#Cc2csc3cc([C@@H](C)NC(=O)c4c(N)nn5cccnc45)c(-c4ccccc4)nc23)cnn1C]
237R
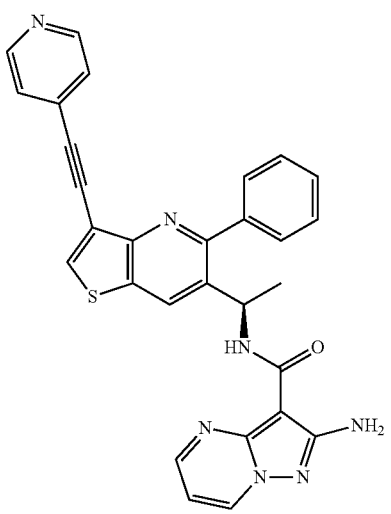 [SMILES: C[C@@H](NC(=O)c1c(N)nn2cccnc12)c1cc2scc(C#Cc3ccncc3)c2nc1-c1ccccc1]
238R
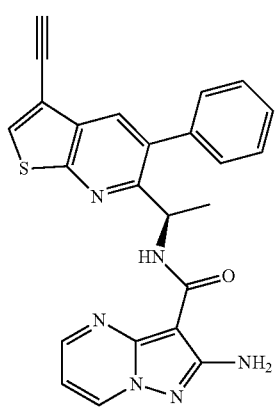 [SMILES: C#Cc1csc2nc([C@@H](C)NC(=O)c3c(N)nn4cccnc34)c(-c3ccccc3)cc12]
239R
TABLE 3-continued
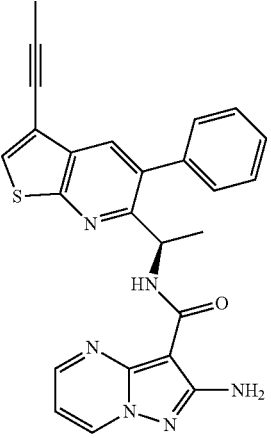 [SMILES: CC#Cc1csc2nc([C@@H](C)NC(=O)c3c(N)nn4cccnc34)c(-c3ccccc3)cc12]
240R
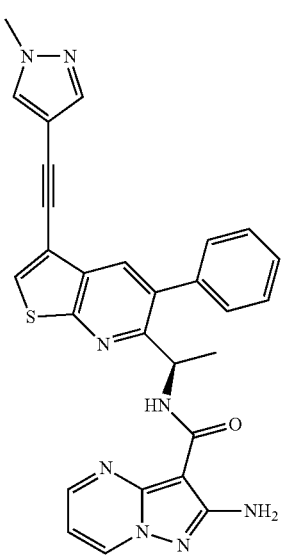 [SMILES: C[C@@H](NC(=O)c1c(N)nn2cccnc12)c1nc2scc(C#Cc3cnn(C)c3)c2cc1-c1ccccc1]
241R
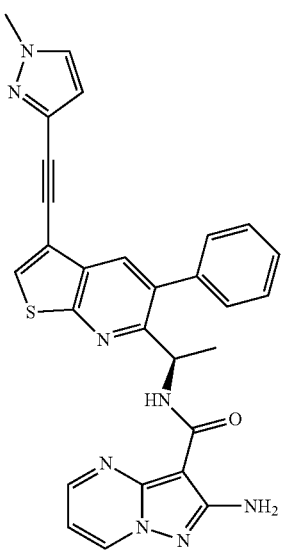 [SMILES: C[C@@H](NC(=O)c1c(N)nn2cccnc12)c1nc2scc(C#Cc3ccn(C)n3)c2cc1-c1ccccc1]
242R TABLE 3-continued
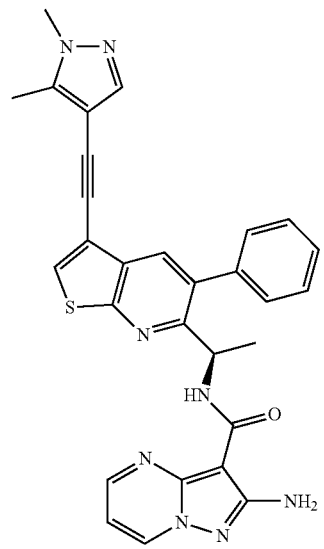 [SMILES: Cc1c(C#Cc2csc3nc([C@@H](C)NC(=O)c4c(N)nn5cccnc45)c(-c4ccccc4)cc23)cnn1C]
243R
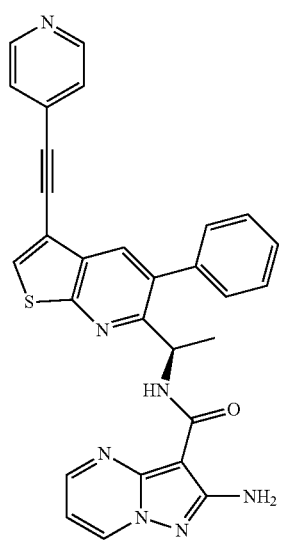
244R
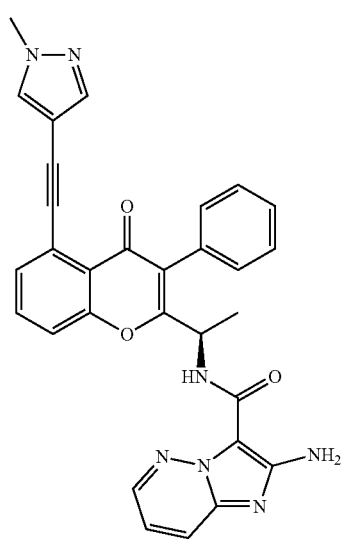 [SMILES: C[C@@H](NC(=O)c1c(N)nc2cccnn12)c1oc2cccc(C#Cc3cnn(C)c3)c2c(=O)c1-c1ccccc1]
245R
TABLE 3-continued
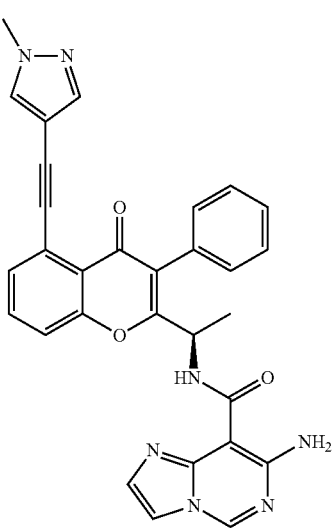 [SMILES: C[C@@H](NC(=O)c1c(N)ncn2ccnc12)c1oc2cccc(C#Cc3cnn(C)c3)c2c(=O)c1-c1ccccc1]
246R
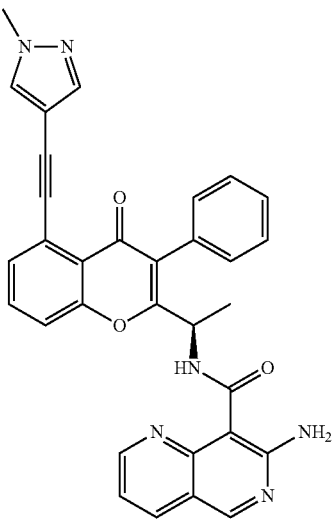 [SMILES: C[C@@H](NC(=O)c1c(N)ncc2cccnc12)c1oc2cccc(C#Cc3cnn(C)c3)c2c(=O)c1-c1ccccc1]
247R
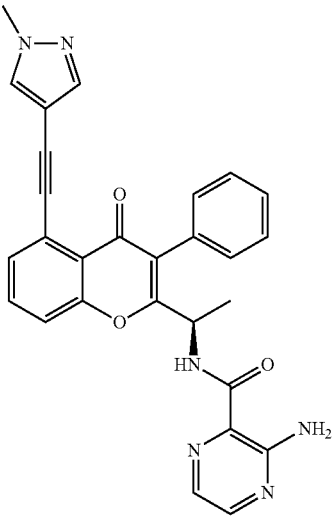 [SMILES: C[C@@H](NC(=O)c1nccnc1N)c1oc2cccc(C#Cc3cnn(C)c3)c2c(=O)c1-c1ccccc1]
248R TABLE 3-continued
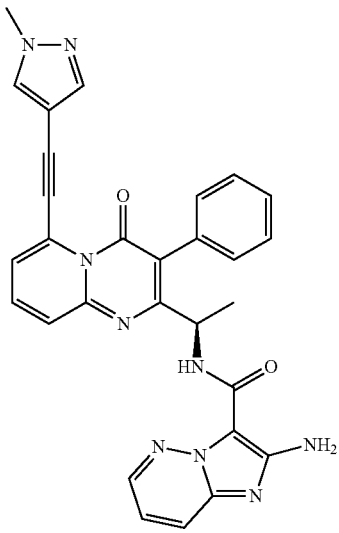 [SMILES: C[C@@H](NC(=O)c1c(N)nc2cccnn12)c1nc2cccc(C#Cc3cnn(C)c3)n2c(=O)c1-c1ccccc1]
249R
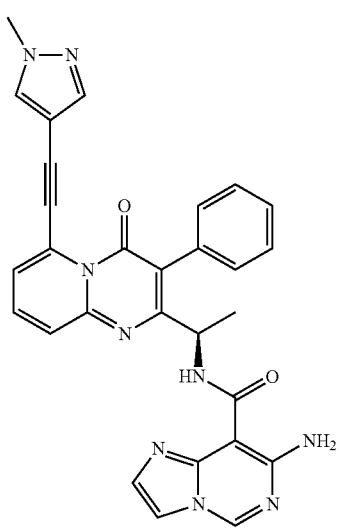 [SMILES: C[C@@H](NC(=O)c1c(N)ncn2ccnc12)c1nc2cccc(C#Cc3cnn(C)c3)n2c(=O)c1-c1ccccc1]
250R
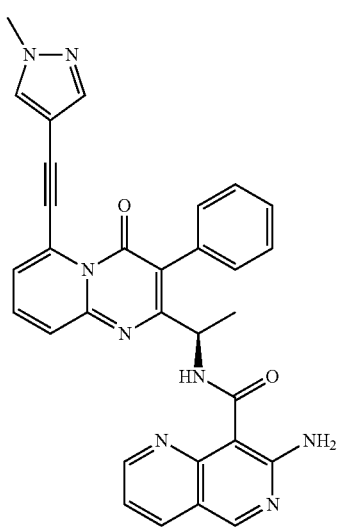 [SMILES: C[C@@H](NC(=O)c1c(N)ncc2cccnc12)c1nc2cccc(C#Cc3cnn(C)c3)n2c(=O)c1-c1ccccc1]
251R
TABLE 3-continued
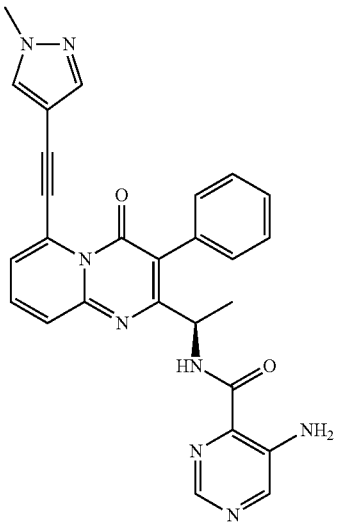 [SMILES: C[C@@H](NC(=O)c1ncncc1N)c1nc2cccc(C#Cc3cnn(C)c3)n2c(=O)c1-c1ccccc1]
252R
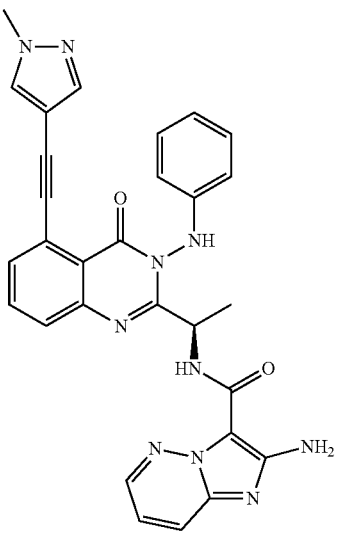 [SMILES: C[C@@H](NC(=O)c1c(N)nc2cccnn12)c1nc2cccc(C#Cc3cnn(C)c3)c2c(=O)n1Nc1ccccc1]
253R
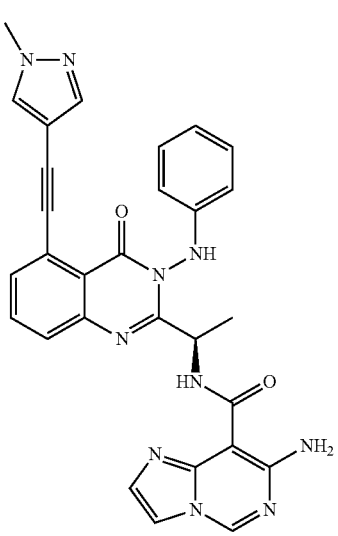 [SMILES: C[C@@H](NC(=O)c1c(N)ncn2ccnc12)c1nc2cccc(C#Cc3cnn(C)c3)c2c(=O)n1Nc1ccccc1]
254R 343
TABLE 3-continued
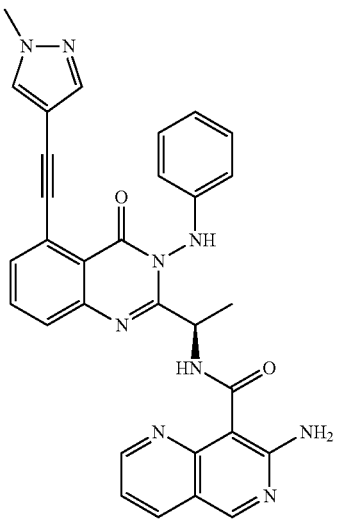 [SMILES: C[C@@H](NC(=O)c1c(N)ncc2cccnc12)c1nc2cccc(C#Cc3cnn(C)c3)c2c(=O)n1Nc1ccccc1]
255R
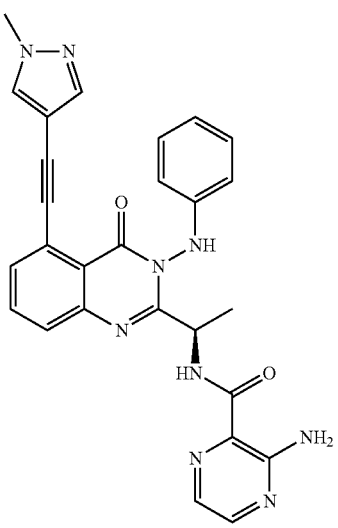 [SMILES: C[C@@H](NC(=O)c1nccnc1N)c1nc2cccc(C#Cc3cnn(C)c3)c2c(=O)n1Nc1ccccc1]
256R
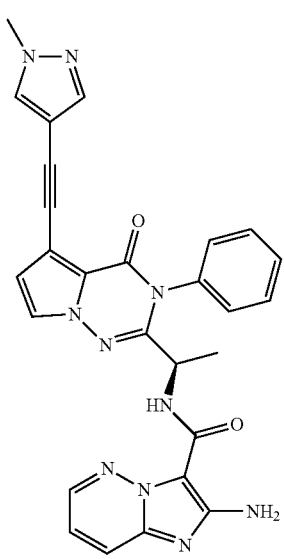 [SMILES: C[C@@H](NC(=O)c1c(N)nc2cccnn12)c1nn2ccc(C#Cc3cnn(C)c3)c2c(=O)n1-c1ccccc1]
257R
344
TABLE 3-continued
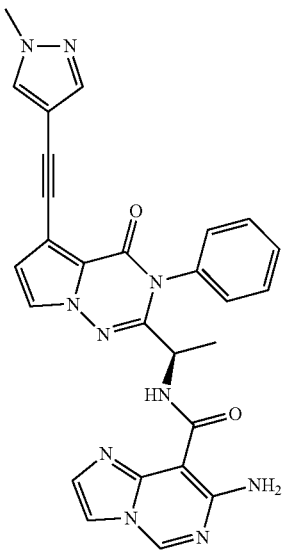 [SMILES: C[C@@H](NC(=O)c1c(N)ncn2ccnc12)c1nn2ccc(C#Cc3cnn(C)c3)c2c(=O)n1-c1ccccc1]
258R
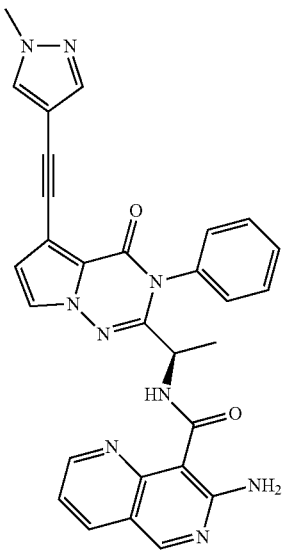 [SMILES: C[C@@H](NC(=O)c1c(N)ncc2cccnc12)c1nn2ccc(C#Cc3cnn(C)c3)c2c(=O)n1-c1ccccc1]
259R
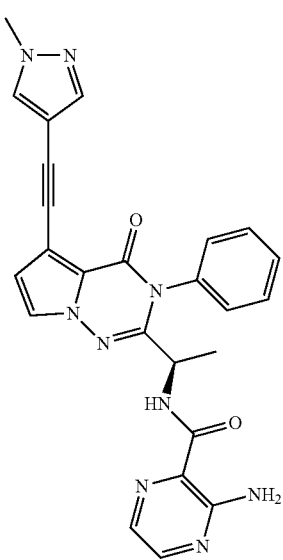 [SMILES: C[C@@H](NC(=O)c1nccnc1N)c1nn2ccc(C#Cc3cnn(C)c3)c2c(=O)n1-c1ccccc1]
260R TABLE 3-continued
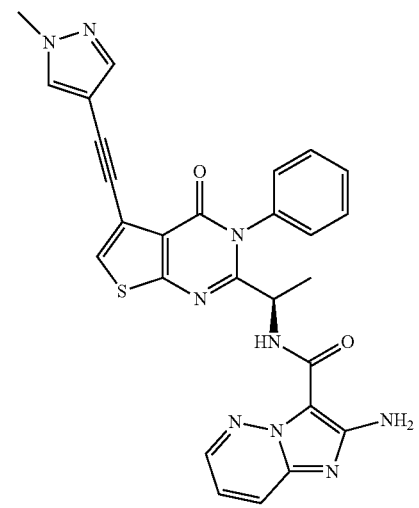 [SMILES: C[C@@H](NC(=O)c1c(N)nc2cccnn12)c1nc2scc(C#Cc3cnn(C)c3)c2c(=O)n1-c1ccccc1]
261R
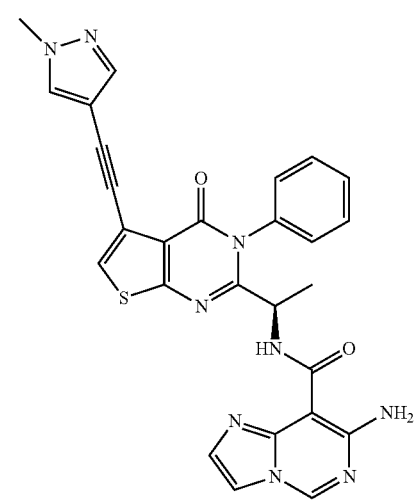 [SMILES: C[C@@H](NC(=O)c1c(N)ncn2ccnc12)c1nc2scc(C#Cc3cnn(C)c3)c2c(=O)n1-c1ccccc1]
262R
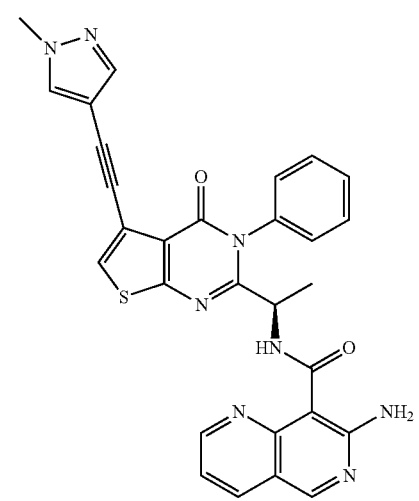
263R
TABLE 3-continued
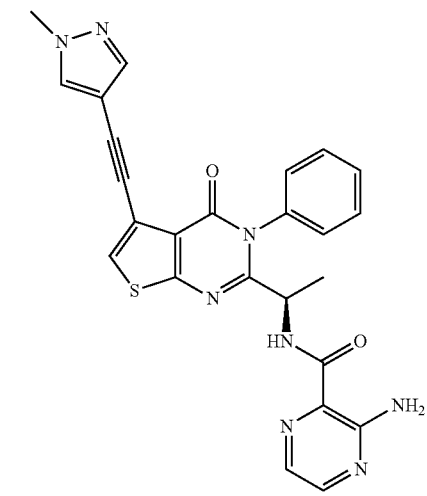 [SMILES: C[C@@H](NC(=O)c1nccnc1N)c1nc2scc(C#Cc3cnn(C)c3)c2c(=O)n1-c1ccccc1]
264R
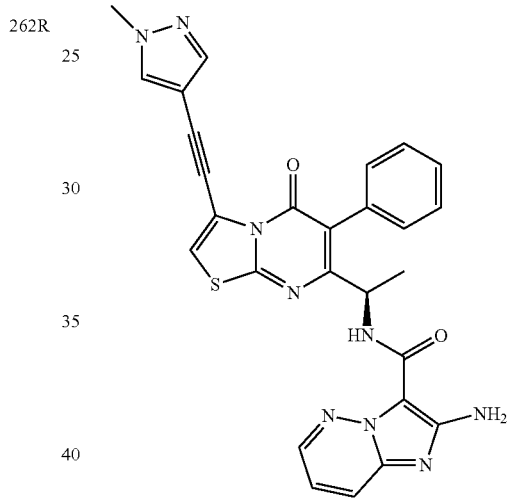
265R
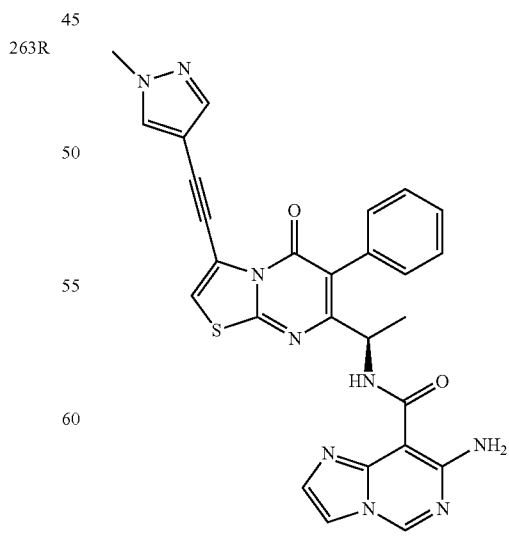
266R TABLE 3-continued
267R 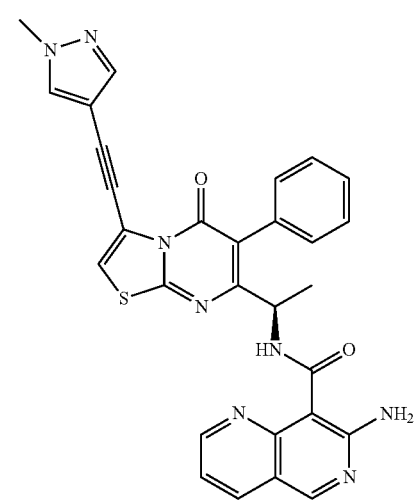 [SMILES: C[C@@H](NC(=O)c1c(N)ncc2cccnc12)c1nc2scc(C#Cc3cnn(C)c3)n2c(=O)c1-c1ccccc1]
268R 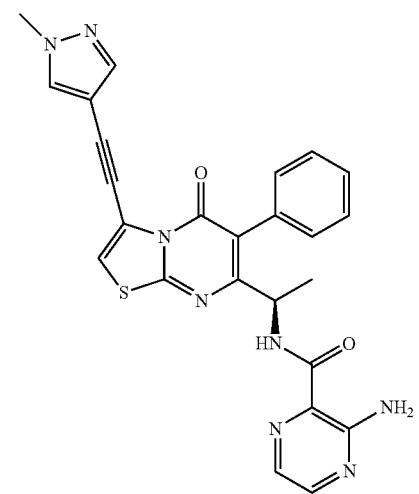 [SMILES: C[C@@H](NC(=O)c1nccnc1N)c1nc2scc(C#Cc3cnn(C)c3)n2c(=O)c1-c1ccccc1]
269R 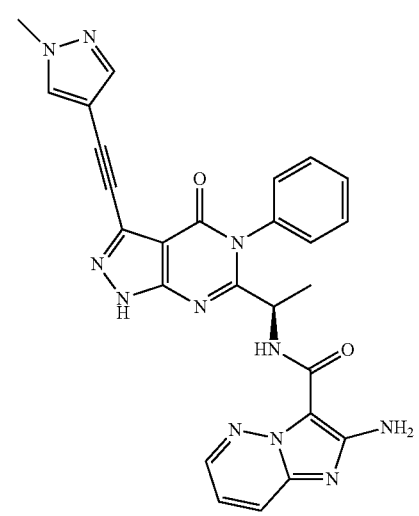 [SMILES: C[C@@H](NC(=O)c1c(N)nc2cccnn12)c1nc2[nH]nc(C#Cc3cnn(C)c3)c2c(=O)n1-c1ccccc1]
TABLE 3-continued
270R 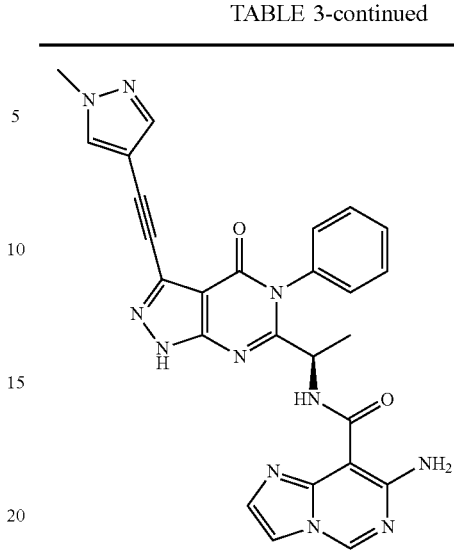
271R 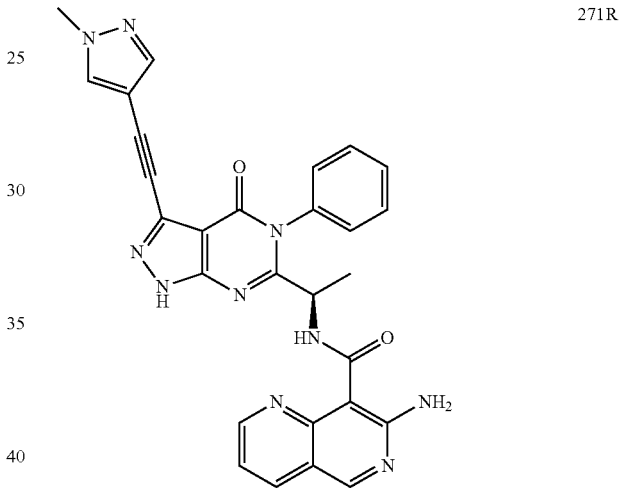
272R 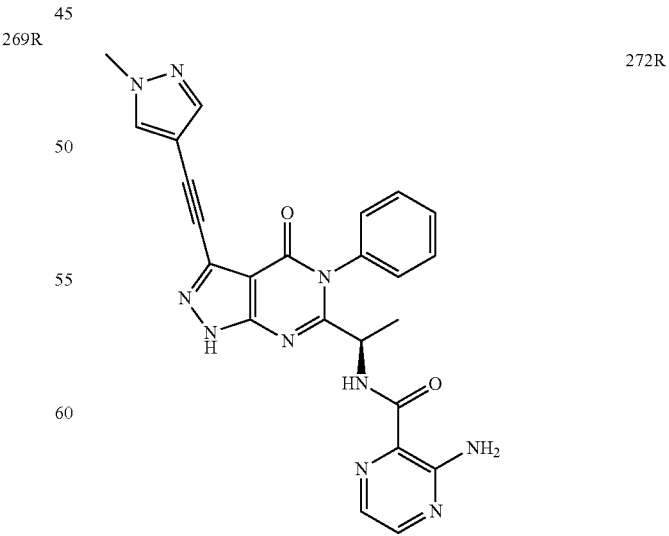

TABLE 3-continued
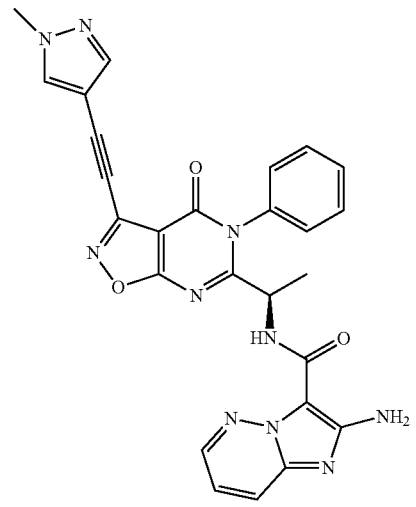 [SMILES: C[C@@H](NC(=O)c1c(N)nc2cccnn12)c1nc2onc(C#Cc3cnn(C)c3)c2c(=O)n1-c1ccccc1]
273R
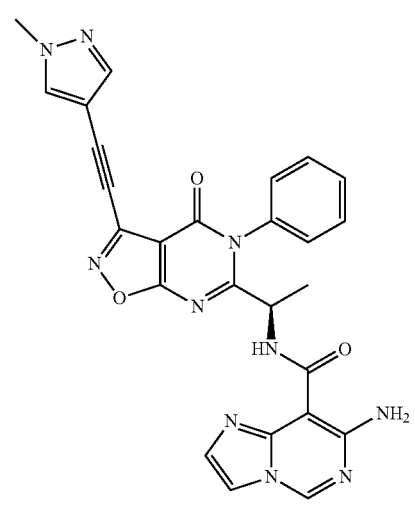 [SMILES: C[C@@H](NC(=O)c1c(N)ncn2ccnc12)c1nc2onc(C#Cc3cnn(C)c3)c2c(=O)n1-c1ccccc1]
274R
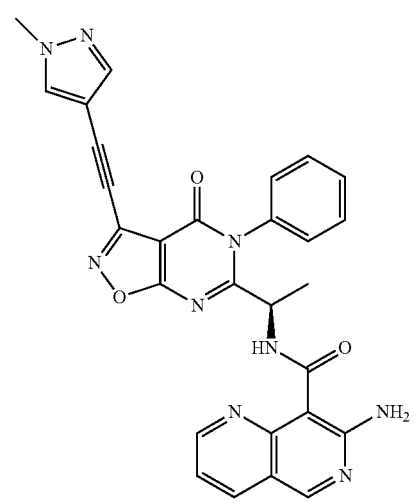 [SMILES: C[C@@H](NC(=O)c1c(N)ncc2cccnc12)c1nc2onc(C#Cc3cnn(C)c3)c2c(=O)n1-c1ccccc1]
275R
TABLE 3-continued
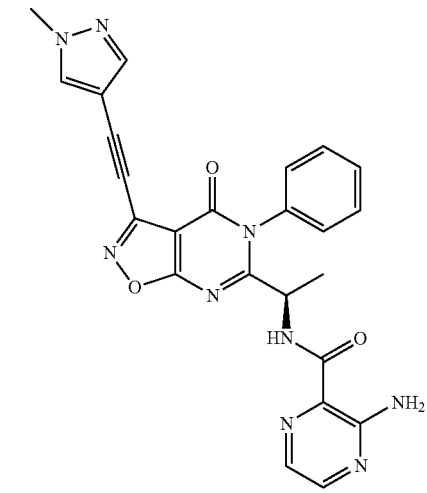 [SMILES: C[C@@H](NC(=O)c1nccnc1N)c1nc2onc(C#Cc3cnn(C)c3)c2c(=O)n1-c1ccccc1]
276R
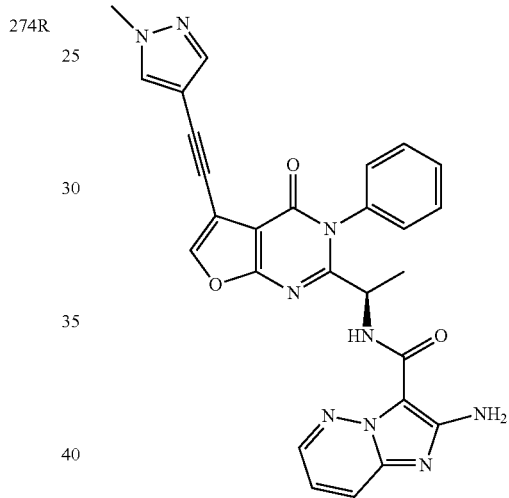
277R
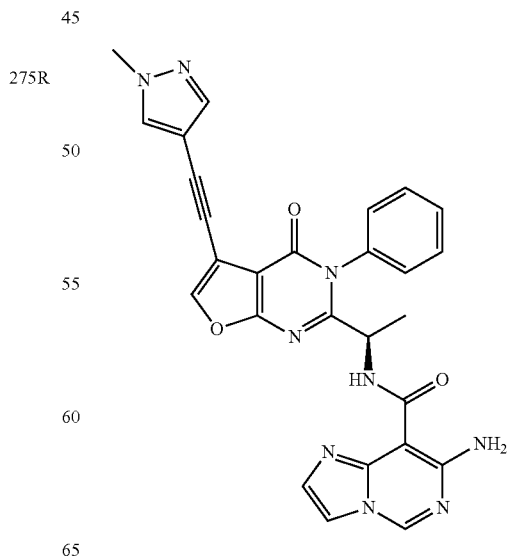
278R TABLE 3-continued
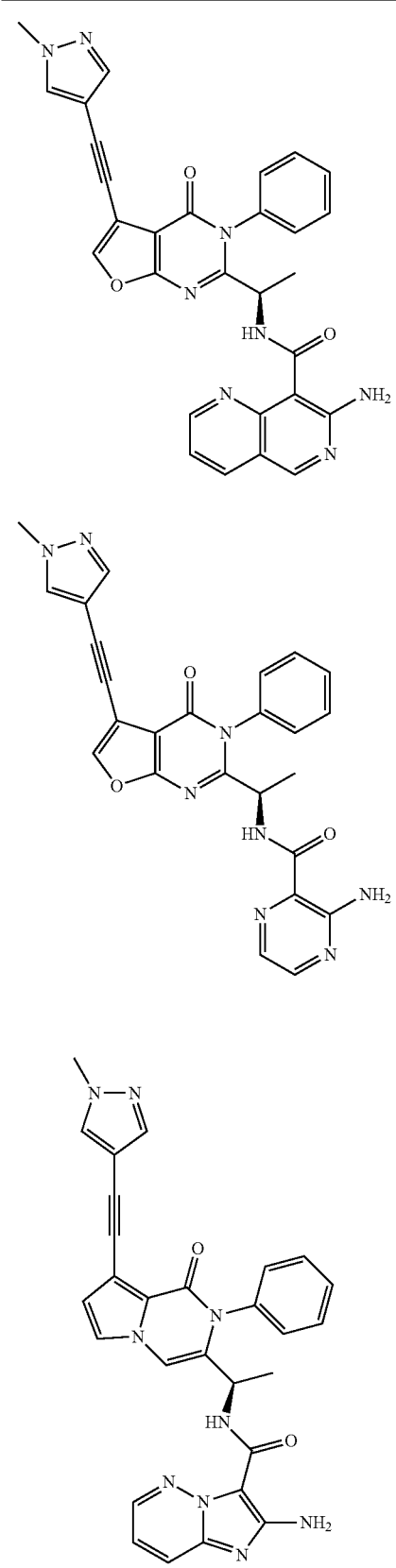
279R
280R
281R
TABLE 3-continued
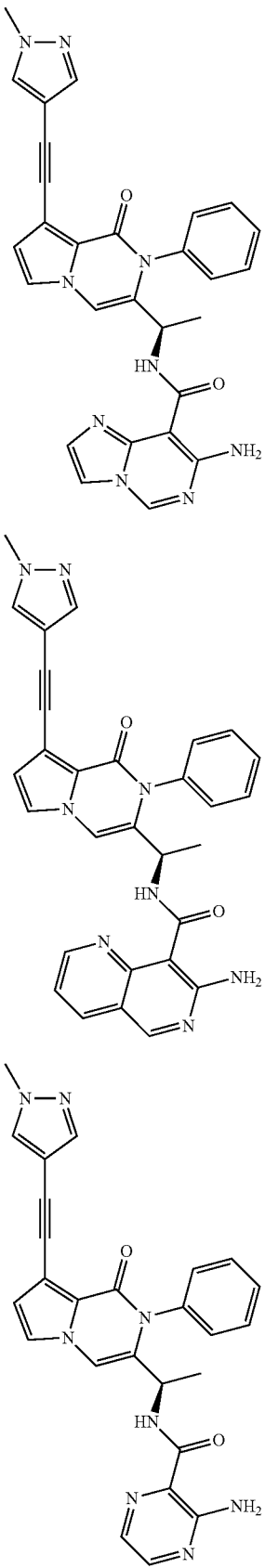
282R
283R
284R TABLE 3-continued
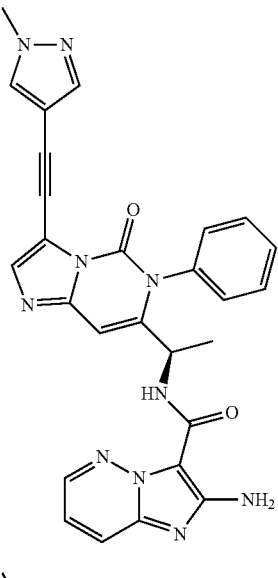
285R
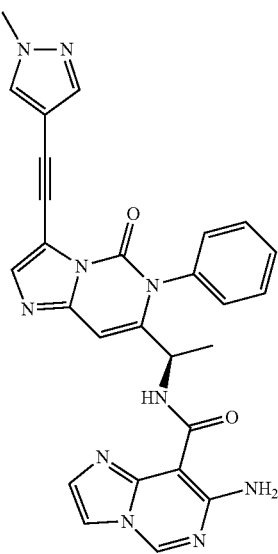 [SMILES: C[C@@H](NC(=O)c1c(N)ncn2ccnc12)c1cc2ncc(C#Cc3cnn(C)c3)n2c(=O)n1-c1ccccc1]
286R
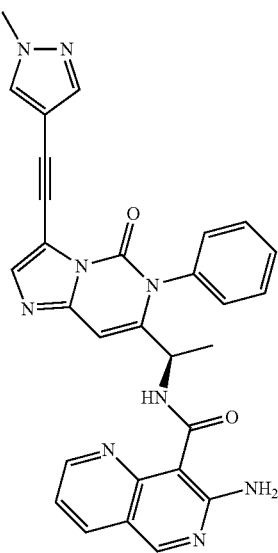 [SMILES: C[C@@H](NC(=O)c1c(N)ncc2cccnc12)c1cc2ncc(C#Cc3cnn(C)c3)n2c(=O)n1-c1ccccc1]
287R
TABLE 3-continued
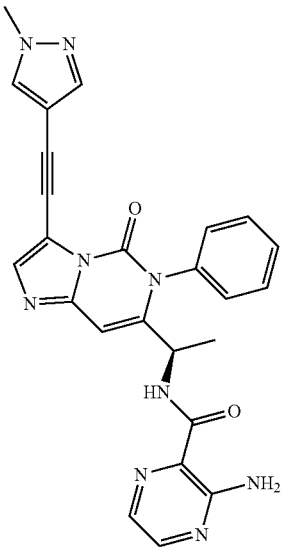 [SMILES: C[C@@H](NC(=O)c1nccnc1N)c1cc2ncc(C#Cc3cnn(C)c3)n2c(=O)n1-c1ccccc1]
288R
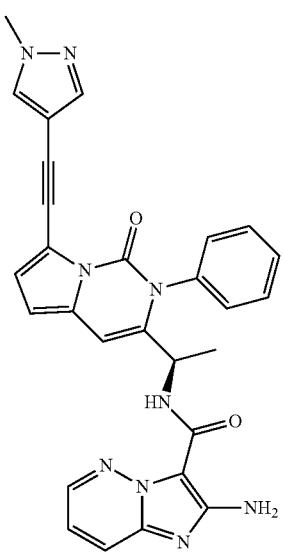 [SMILES: C[C@@H](NC(=O)c1c(N)nc2cccnn12)c1cc2ccc(C#Cc3cnn(C)c3)n2c(=O)n1-c1ccccc1]
289R
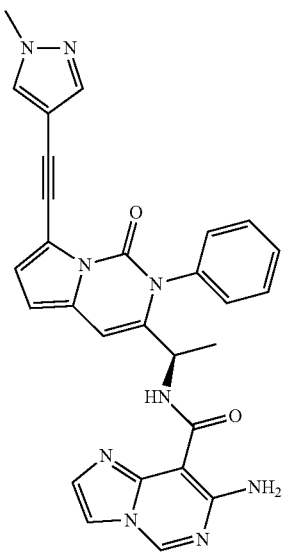 [SMILES: C[C@@H](NC(=O)c1c(N)ncn2ccnc12)c1cc2ccc(C#Cc3cnn(C)c3)n2c(=O)n1-c1ccccc1]
290R TABLE 3-continued
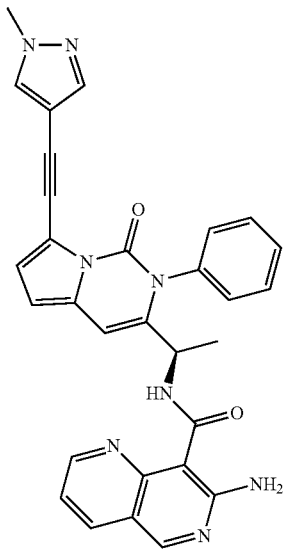 [SMILES: C[C@@H](NC(=O)c1c(N)ncc2cccnc12)c1cc2ccc(C#Cc3cnn(C)c3)n2c(=O)n1-c1ccccc1]
291R
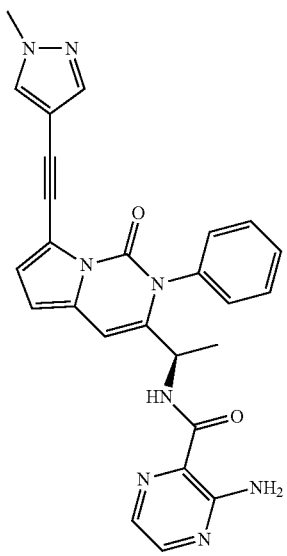
292R
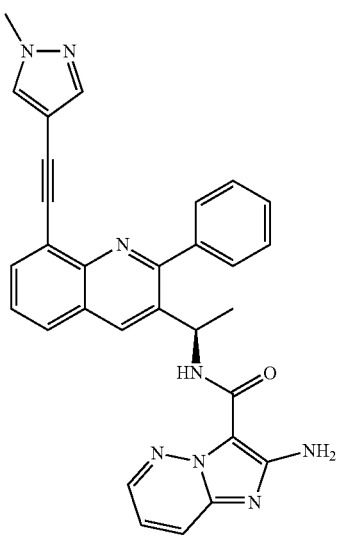
293R
TABLE 3-continued
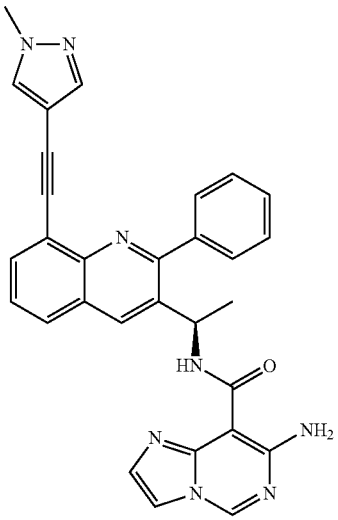 [SMILES: C[C@@H](NC(=O)c1c(N)ncn2ccnc12)c1cc2cccc(C#Cc3cnn(C)c3)c2nc1-c1ccccc1]
294R
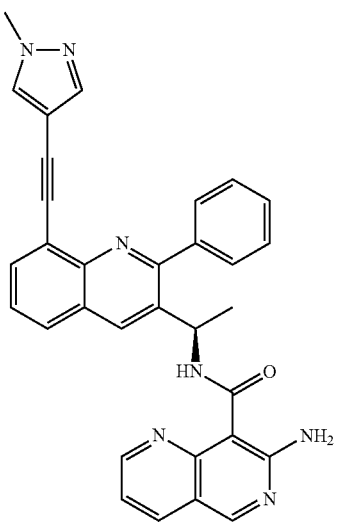 [SMILES: C[C@@H](NC(=O)c1c(N)ncc2cccnc12)c1cc2cccc(C#Cc3cnn(C)c3)c2nc1-c1ccccc1]
295R
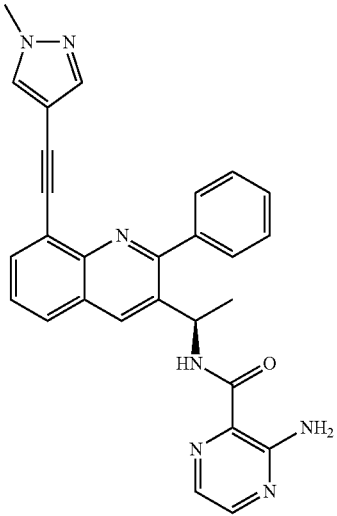 [SMILES: C[C@@H](NC(=O)c1nccnc1N)c1cc2cccc(C#Cc3cnn(C)c3)c2nc1-c1ccccc1]
296R TABLE 3-continued
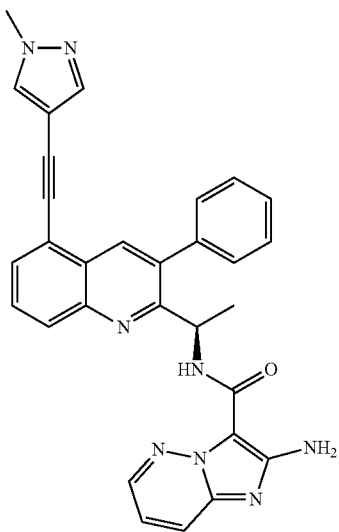
297R
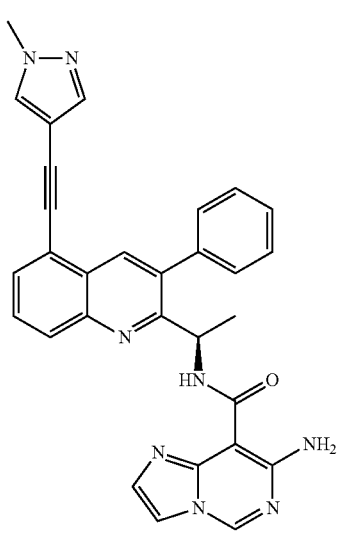
298R
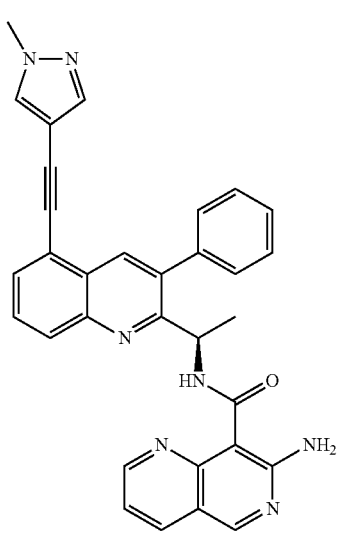
299R
TABLE 3-continued
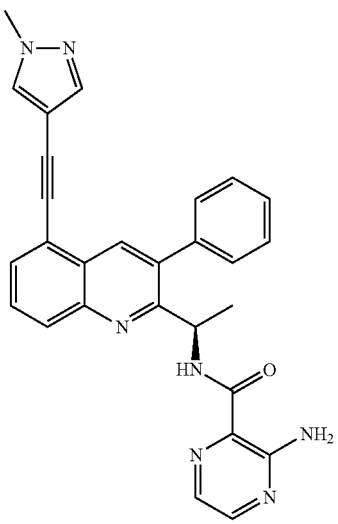 [SMILES: C[C@@H](NC(=O)c1nccnc1N)c1nc2cccc(C#Cc3cnn(C)c3)c2cc1-c1ccccc1]
300R
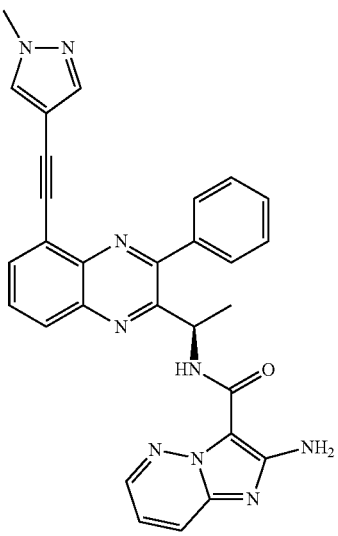 [SMILES: C[C@@H](NC(=O)c1c(N)nc2cccnn12)c1nc2cccc(C#Cc3cnn(C)c3)c2nc1-c1ccccc1]
301R
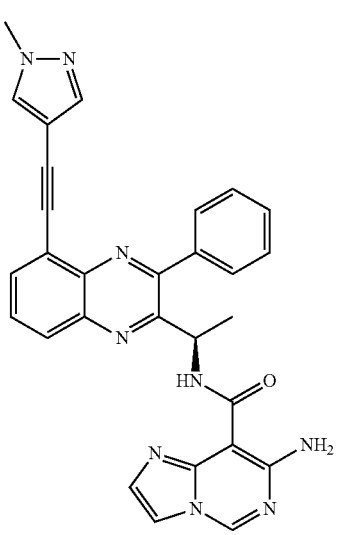 [SMILES: C[C@@H](NC(=O)c1c(N)ncn2ccnc12)c1nc2cccc(C#Cc3cnn(C)c3)c2nc1-c1ccccc1]
302R TABLE 3-continued
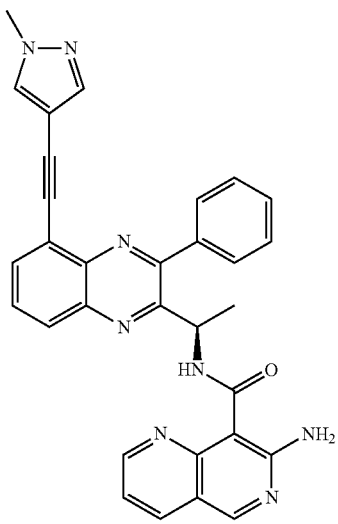 [SMILES: C[C@@H](NC(=O)c1c(N)ncc2cccnc12)c1nc2cccc(C#Cc3cnn(C)c3)c2nc1-c1ccccc1]
303R
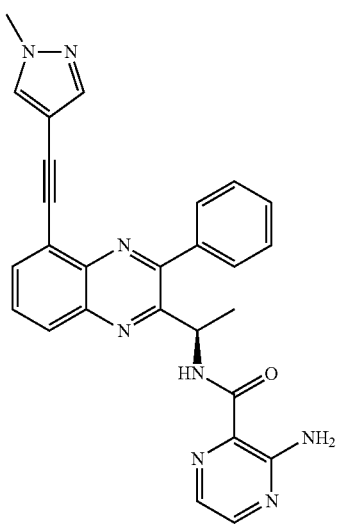 [SMILES: C[C@@H](NC(=O)c1nccnc1N)c1nc2cccc(C#Cc3cnn(C)c3)c2nc1-c1ccccc1]
304R
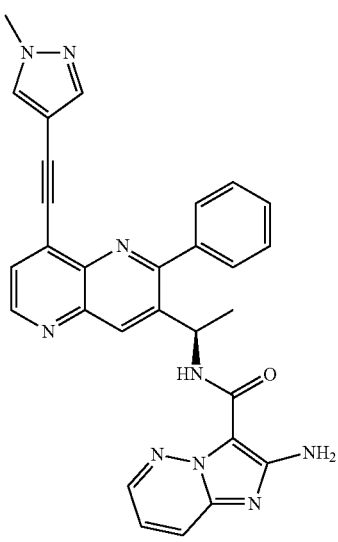 [SMILES: C[C@@H](NC(=O)c1c(N)nc2cccnn12)c1cc2nccc(C#Cc3cnn(C)c3)c2nc1-c1ccccc1]
305R
TABLE 3-continued
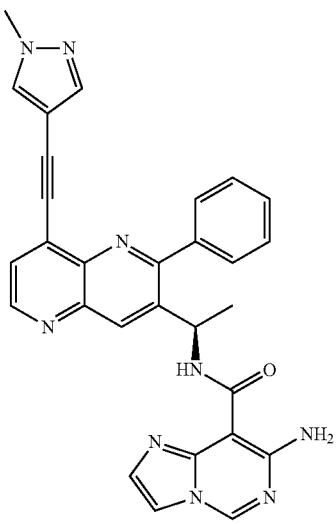
306R
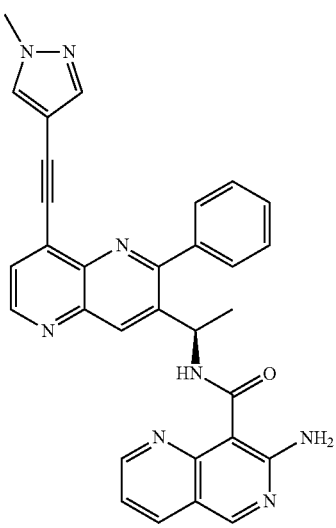 [SMILES: C[C@@H](NC(=O)c1c(N)ncc2cccnc12)c1cc2nccc(C#Cc3cnn(C)c3)c2nc1-c1ccccc1]
307R
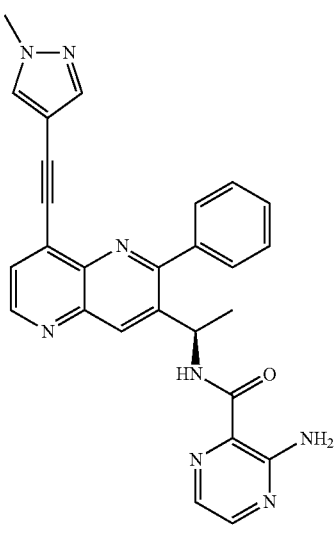 [SMILES: C[C@@H](NC(=O)c1nccnc1N)c1cc2nccc(C#Cc3cnn(C)c3)c2nc1-c1ccccc1]
308R TABLE 3-continued
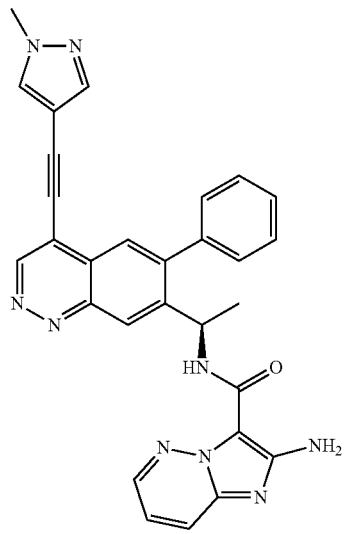 [SMILES: C[C@@H](NC(=O)c1c(N)nc2cccnn12)c1cc2nncc(C#Cc3cnn(C)c3)c2cc1-c1ccccc1]
309R
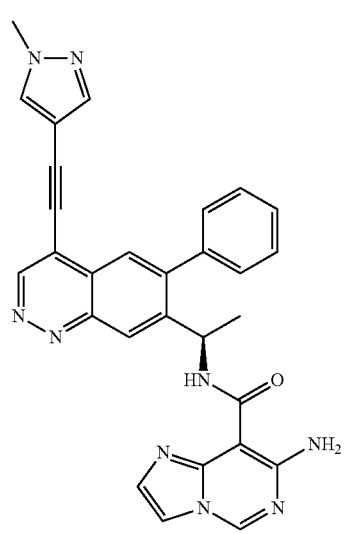 [SMILES: C[C@@H](NC(=O)c1c(N)ncn2ccnc12)c1cc2nncc(C#Cc3cnn(C)c3)c2cc1-c1ccccc1]
310R
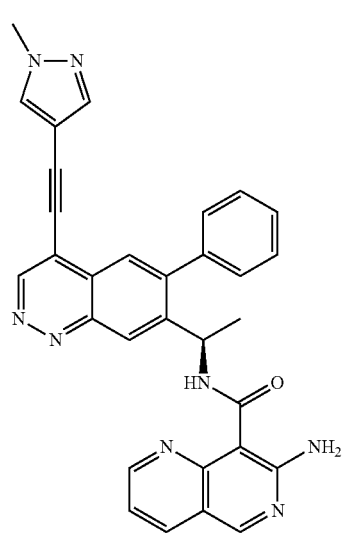 [SMILES: C[C@@H](NC(=O)c1c(N)ncc2cccnc12)c1cc2nncc(C#Cc3cnn(C)c3)c2cc1-c1ccccc1]
311R
TABLE 3-continued
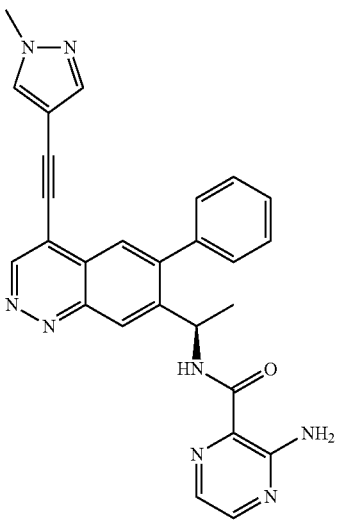 [SMILES: C[C@@H](NC(=O)c1nccnc1N)c1cc2nncc(C#Cc3cnn(C)c3)c2cc1-c1ccccc1]
312R
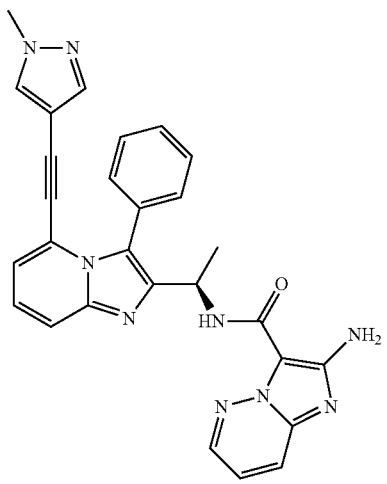 [SMILES: C[C@@H](NC(=O)c1c(N)nc2cccnn12)c1nc2cccc(C#Cc3cnn(C)c3)n2c1-c1ccccc1]
313R
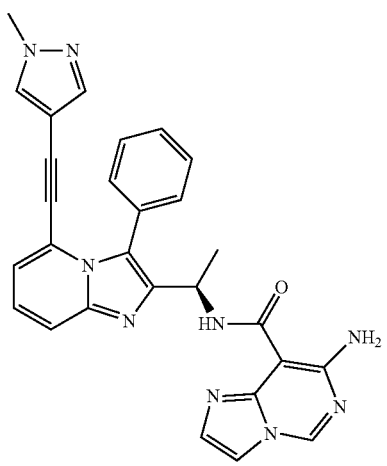 [SMILES: C[C@@H](NC(=O)c1c(N)ncn2ccnc12)c1nc2cccc(C#Cc3cnn(C)c3)n2c1-c1ccccc1]
314R TABLE 3-continued
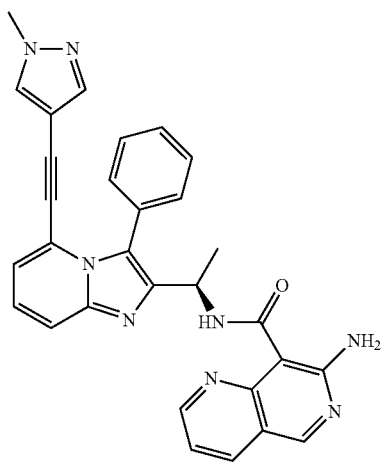 [SMILES: C[C@@H](NC(=O)c1c(N)ncc2cccnc12)c1nc2cccc(C#Cc3cnn(C)c3)n2c1-c1ccccc1]
315R
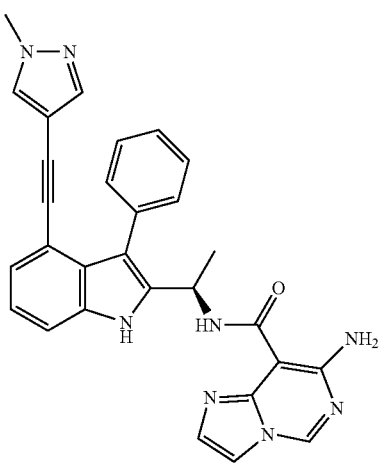
318R
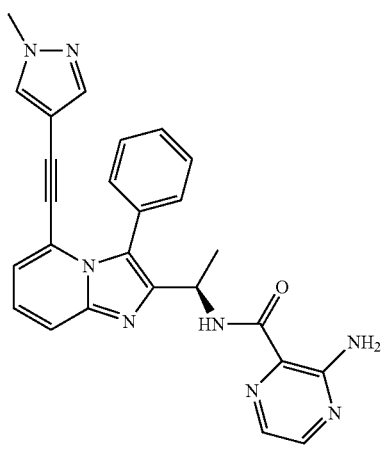 [SMILES: C[C@@H](NC(=O)c1nccnc1N)c1nc2cccc(C#Cc3cnn(C)c3)n2c1-c1ccccc1]
316R
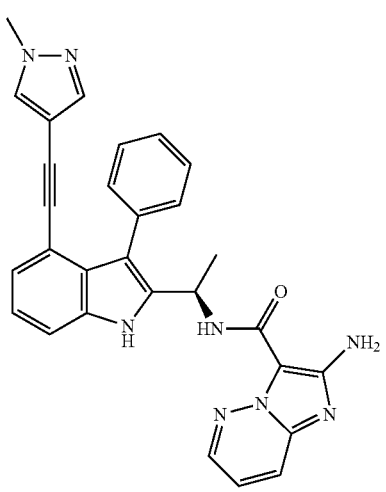
317R
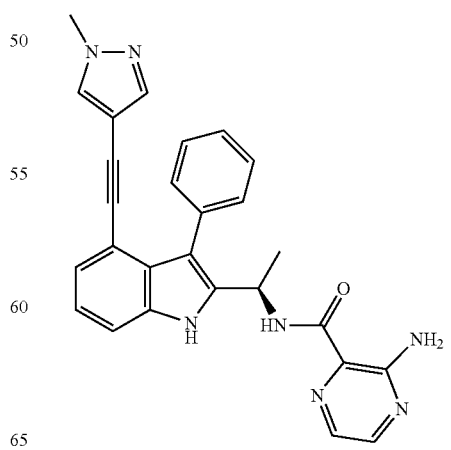
320R TABLE 3-continued
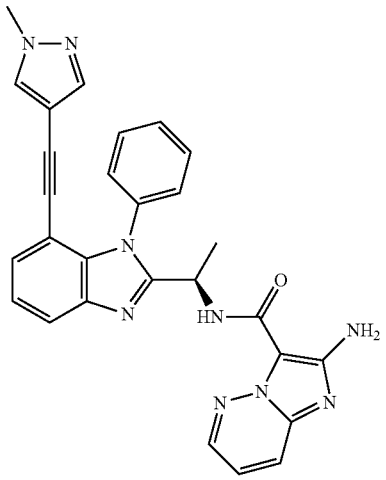
321R
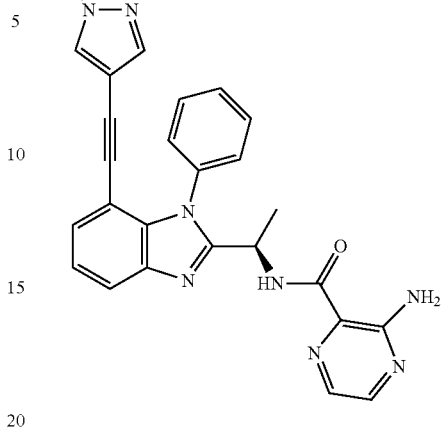
324R
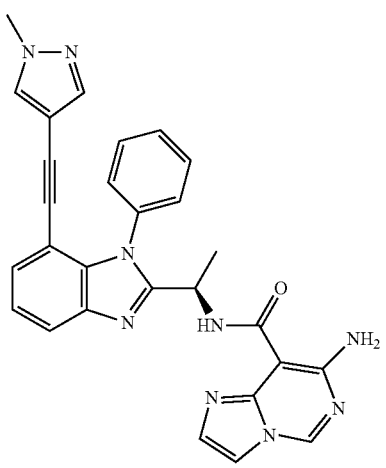 [SMILES: C[C@@H](NC(=O)c1c(N)ncn2ccnc12)c1nc2cccc(C#Cc3cnn(C)c3)c2n1-c1ccccc1]
322R
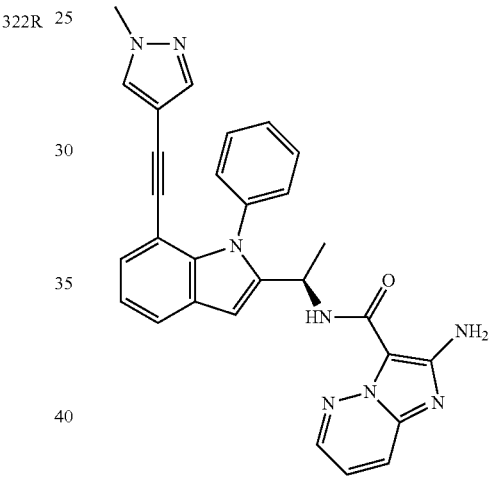
325R
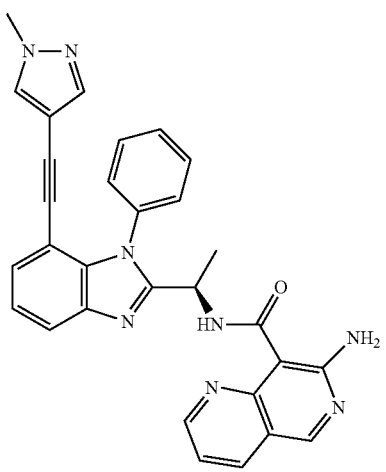 [SMILES: C[C@@H](NC(=O)c1c(N)ncc2cccnc12)c1nc2cccc(C#Cc3cnn(C)c3)c2n1-c1ccccc1]
323R
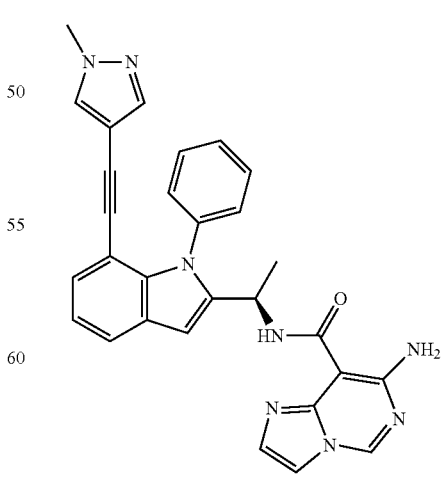
326R TABLE 3-continued
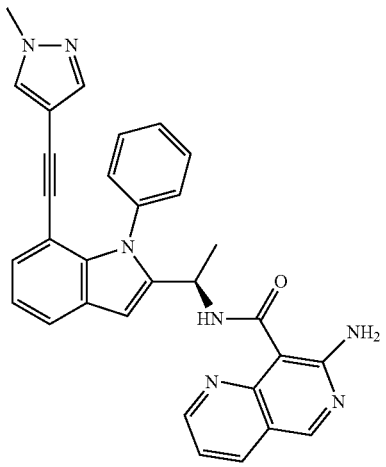 [SMILES: C[C@@H](NC(=O)c1c(N)ncc2cccnc12)c1cc2cccc(C#Cc3cnn(C)c3)c2n1-c1ccccc1]
327R
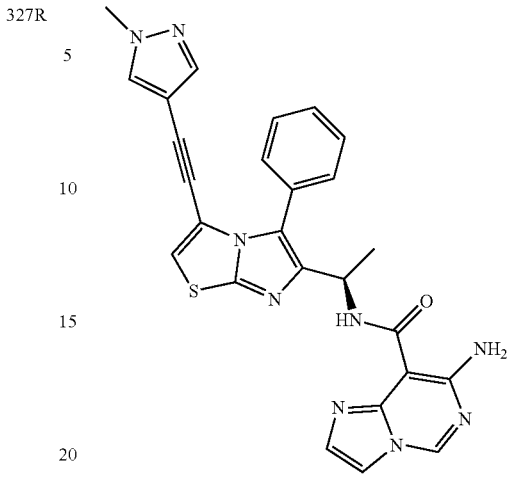
330R
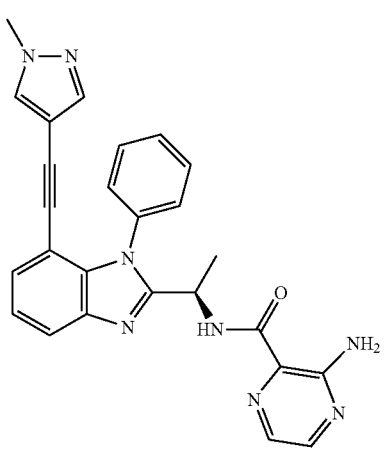 [SMILES: C[C@@H](NC(=O)c1nccnc1N)c1nc2cccc(C#Cc3cnn(C)c3)c2n1-c1ccccc1]
328R
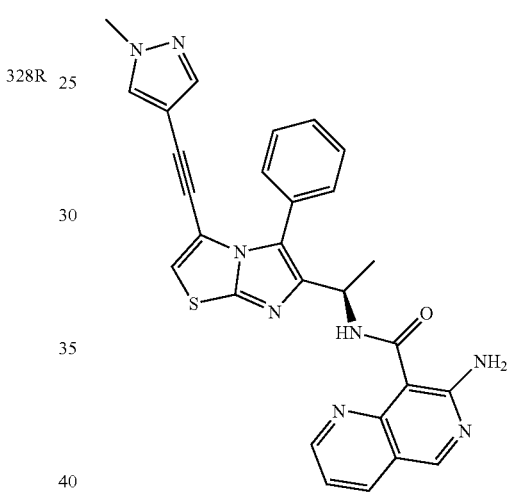
331R
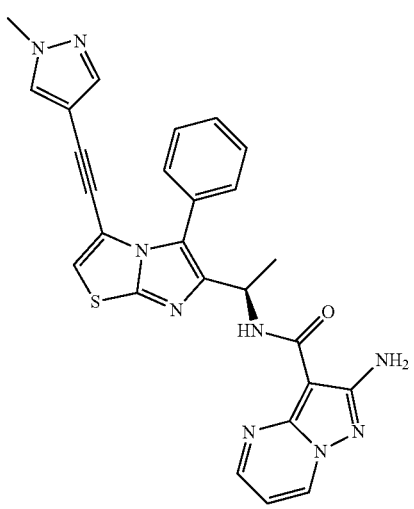 [SMILES: C[C@@H](NC(=O)c1c(N)nn2cccnc12)c1nc2scc(C#Cc3cnn(C)c3)n2c1-c1ccccc1]
329R
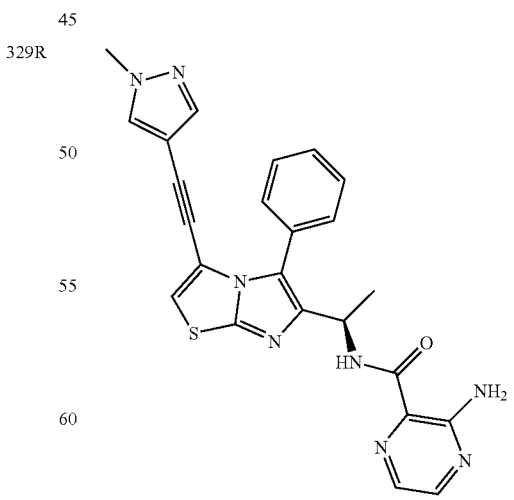
332R TABLE 3-continued
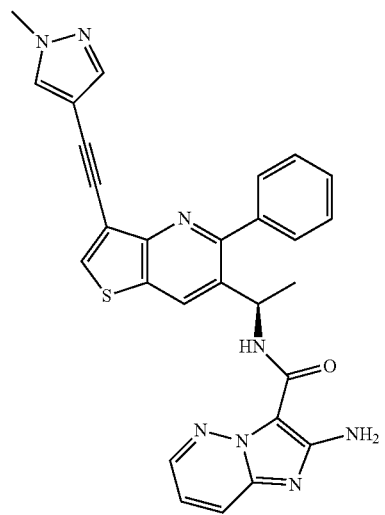 [SMILES: C[C@@H](NC(=O)c1c(N)nc2cccnn12)c1cc2scc(C#Cc3cnn(C)c3)c2nc1-c1ccccc1] 333R
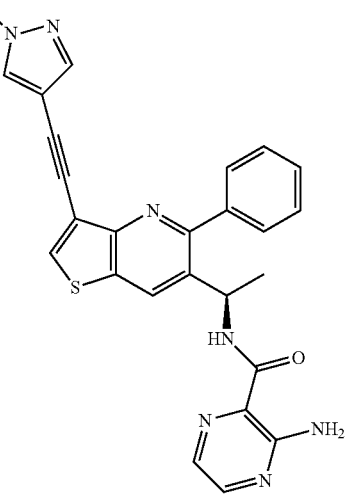 336R
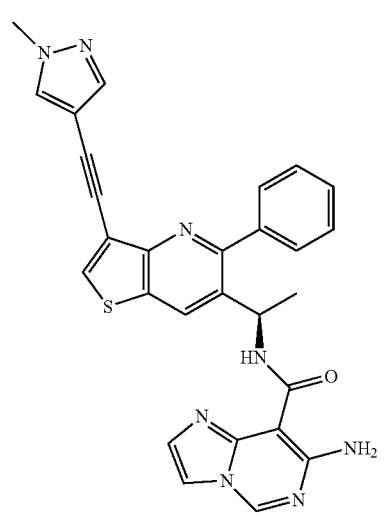 [SMILES: C[C@@H](NC(=O)c1c(N)ncn2ccnc12)c1cc2scc(C#Cc3cnn(C)c3)c2nc1-c1ccccc1] 334R
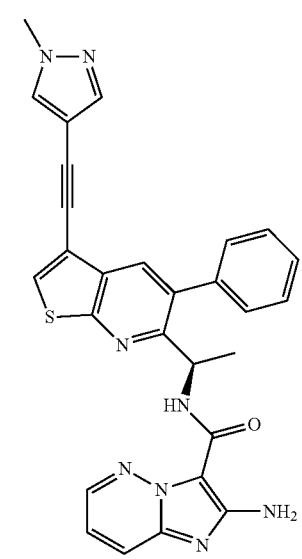 337R
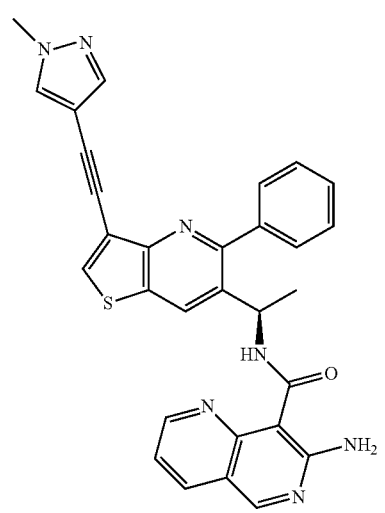 [SMILES: C[C@@H](NC(=O)c1c(N)ncc2cccnc12)c1cc2scc(C#Cc3cnn(C)c3)c2nc1-c1ccccc1] 335R
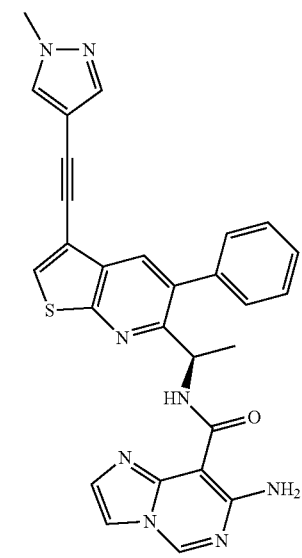 [SMILES: C[C@@H](NC(=O)c1c(N)ncn2ccnc12)c1nc2scc(C#Cc3cnn(C)c3)c2cc1-c1ccccc1] 338R TABLE 3-continued
339R
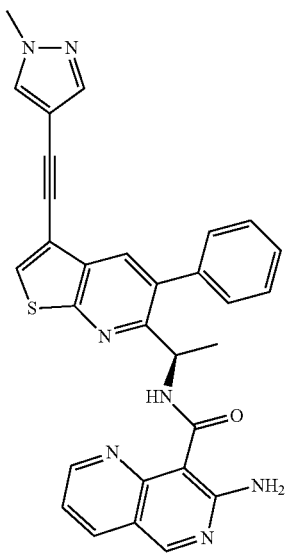 [SMILES: C[C@@H](NC(=O)c1c(N)ncc2cccnc12)c1nc2scc(C#Cc3cnn(C)c3)c2cc1-c1ccccc1]
340R
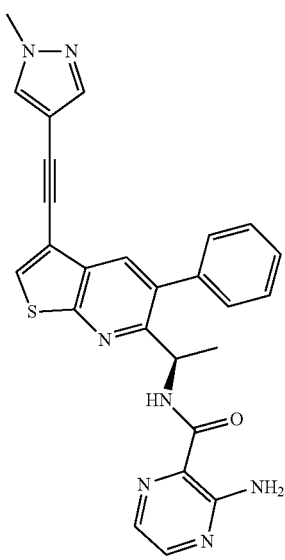 [SMILES: C[C@@H](NC(=O)c1nccnc1N)c1nc2scc(C#Cc3cnn(C)c3)c2cc1-c1ccccc1]
341R
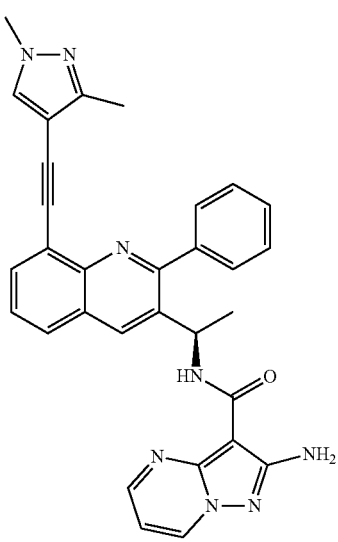 [SMILES: Cc1nn(C)cc1C#Cc1cccc2cc([C@@H](C)NC(=O)c3c(N)nn4cccnc34)c(-c3ccccc3)nc12]
TABLE 3-continued
342R
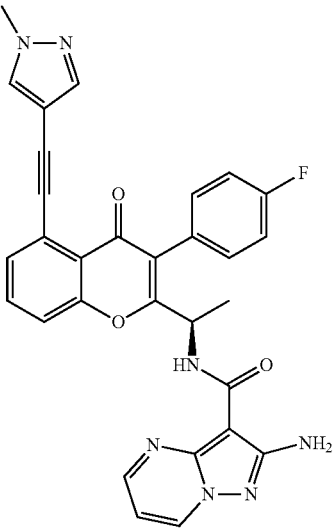 [SMILES: C[C@@H](NC(=O)c1c(N)nn2cccnc12)c1oc2cccc(C#Cc3cnn(C)c3)c2c(=O)c1-c1ccc(F)cc1]
343R
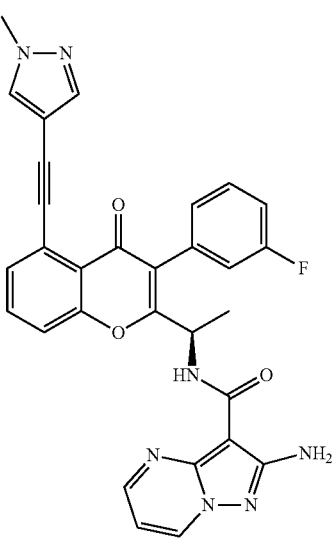 [SMILES: C[C@@H](NC(=O)c1c(N)nn2cccnc12)c1oc2cccc(C#Cc3cnn(C)c3)c2c(=O)c1-c1cccc(F)c1]
344R
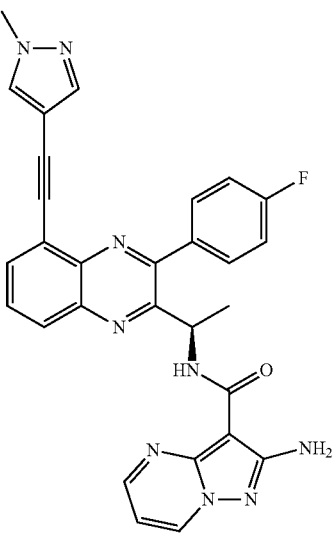 [SMILES: C[C@@H](NC(=O)c1c(N)nn2cccnc12)c1nc2cccc(C#Cc3cnn(C)c3)c2nc1-c1ccc(F)cc1]

TABLE 3-continued
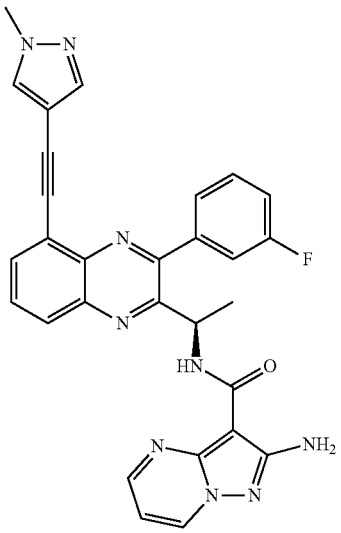 [SMILES: C[C@@H](NC(=O)c1c(N)nn2cccnc12)c1nc2cccc(C#Cc3cnn(C)c3)c2nc1-c1cccc(F)c1]
345R
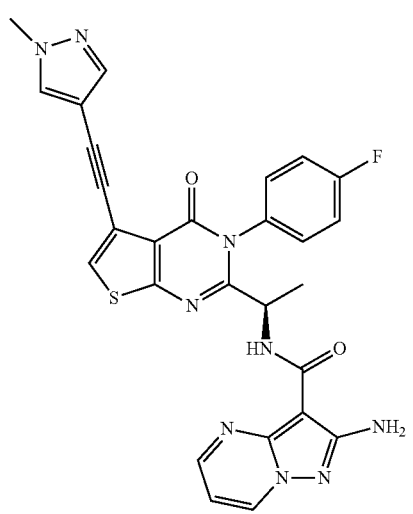 [SMILES: C[C@@H](NC(=O)c1c(N)nn2cccnc12)c1nc2scc(C#Cc3cnn(C)c3)c2c(=O)n1-c1ccc(F)cc1]
346R
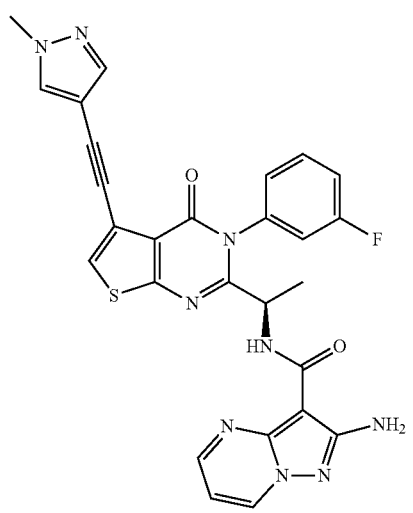 [SMILES: C[C@@H](NC(=O)c1c(N)nn2cccnc12)c1nc2scc(C#Cc3cnn(C)c3)c2c(=O)n1-c1cccc(F)c1]
347R
TABLE 3-continued
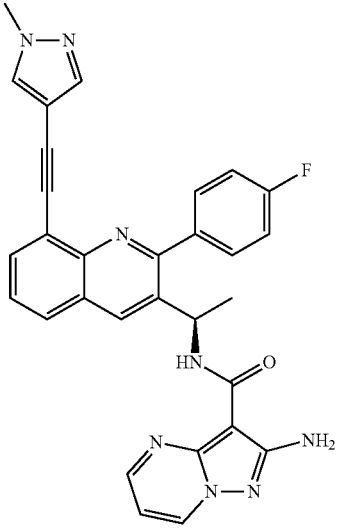
348R
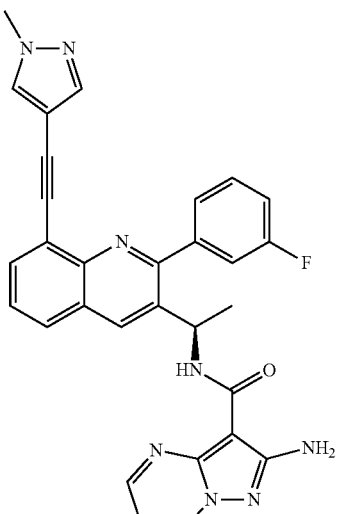
349R
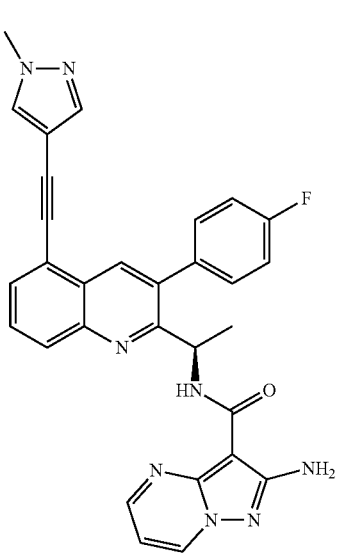 [SMILES: C[C@@H](NC(=O)c1c(N)nn2cccnc12)c1nc2cccc(C#Cc3cnn(C)c3)c2cc1-c1ccc(F)cc1]
350R TABLE 3-continued
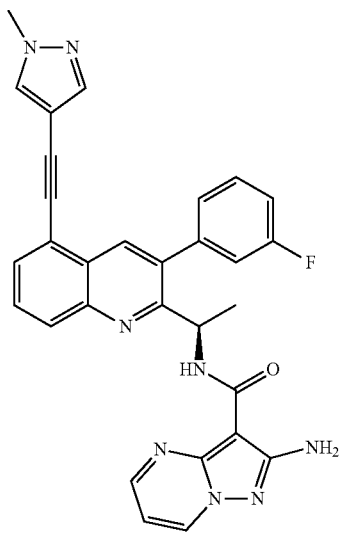 [SMILES: C[C@@H](NC(=O)c1c(N)nn2cccnc12)c1nc2cccc(C#Cc3cnn(C)c3)c2cc1-c1cccc(F)c1]
351R
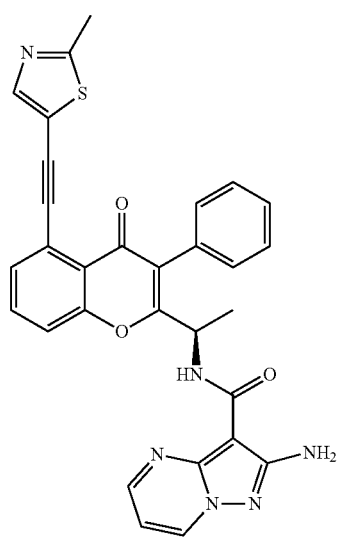 [SMILES: Cc1ncc(C#Cc2cccc3oc([C@@H](C)NC(=O)c4c(N)nn5cccnc45)c(-c4ccccc4)c(=O)c23)s1]
352R
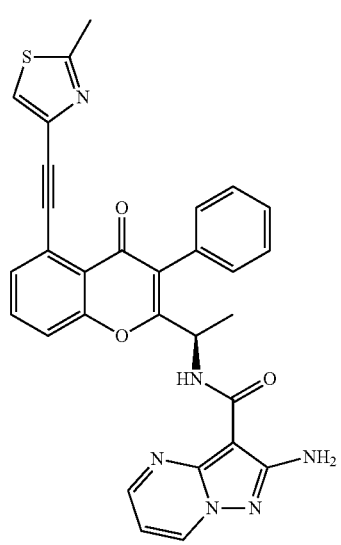 [SMILES: Cc1nc(C#Cc2cccc3oc([C@@H](C)NC(=O)c4c(N)nn5cccnc45)c(-c4ccccc4)c(=O)c23)cs1]
353R
TABLE 3-continued
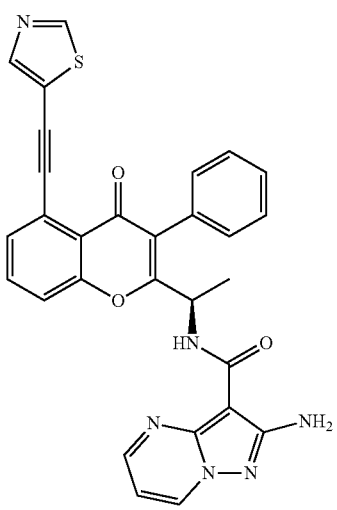
354R
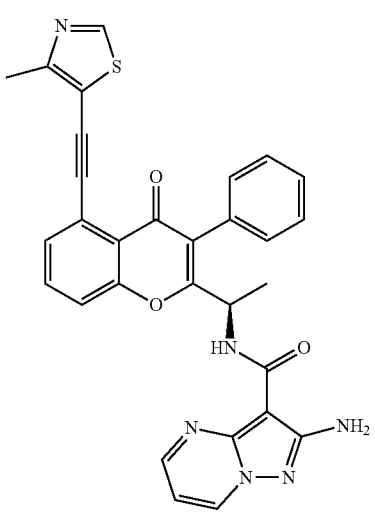 [SMILES: Cc1ncsc1C#Cc1cccc2oc([C@@H](C)NC(=O)c3c(N)nn4cccnc34)c(-c3ccccc3)c(=O)c12]
355R
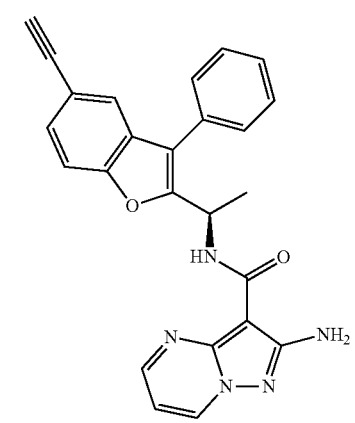
356R TABLE 3-continued
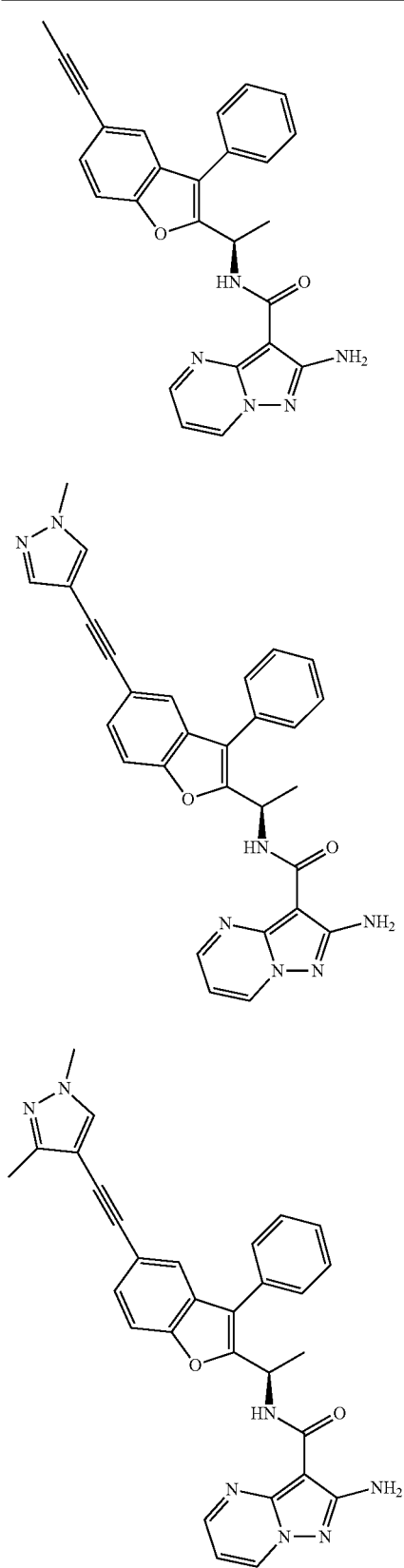
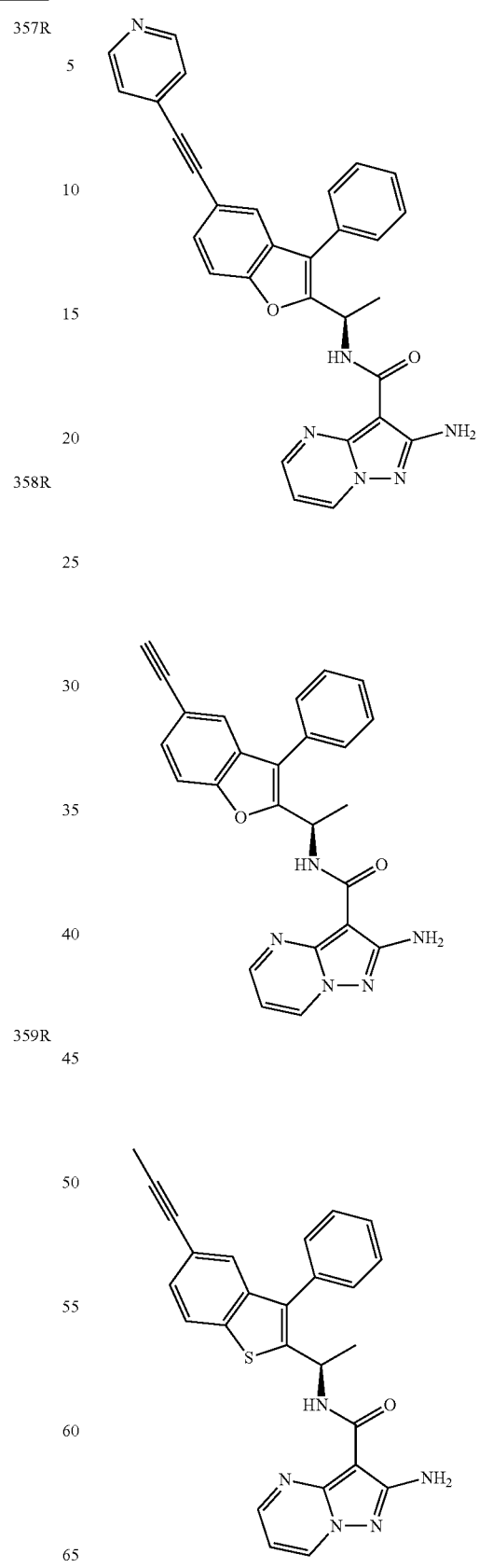

TABLE 3-continued

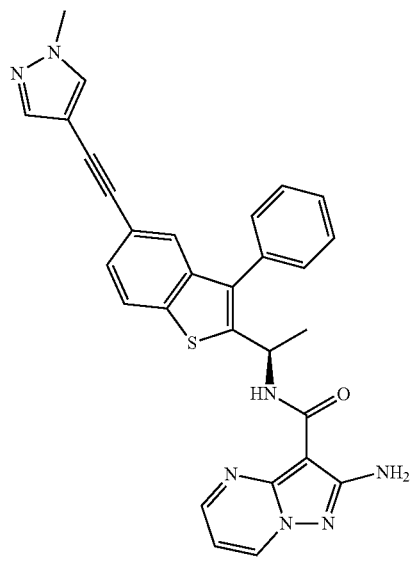 [SMILES: C[C@@H](NC(=O)c1c(N)nn2cccnc12)c1sc2ccc(C#Cc3cnn(C)c3)cc2c1-c1ccccc1]

363R

364R

365R

In one embodiment, for each compound in Table 1, Table 2, and Table 3, the alkynyl moiety of the structure

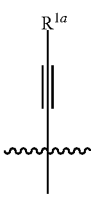

is replaced by an alkenyl moiety of the structure

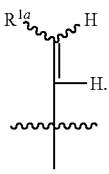

All of the resulted alkenyl compounds are provided herein. In one embodiment, the alkenyl moiety has a Z-configuration. In one embodiment, the alkenyl moiety has a E-configuration. Exemplary alkenyl compounds include:

TABLE 4

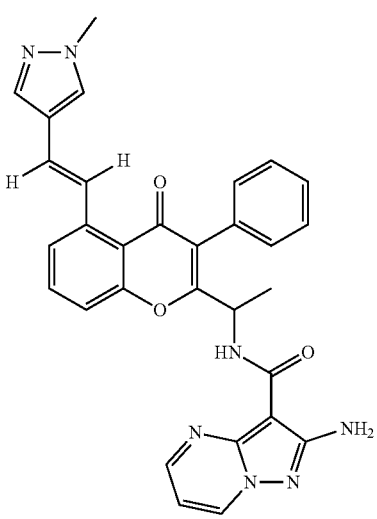 [SMILES: CC(NC(=O)c1c(N)nn2cccnc12)c1oc2cccc(/C=C/c3cnn(C)c3)c2c(=O)c1-c1ccccc1]

TABLE 4-continued
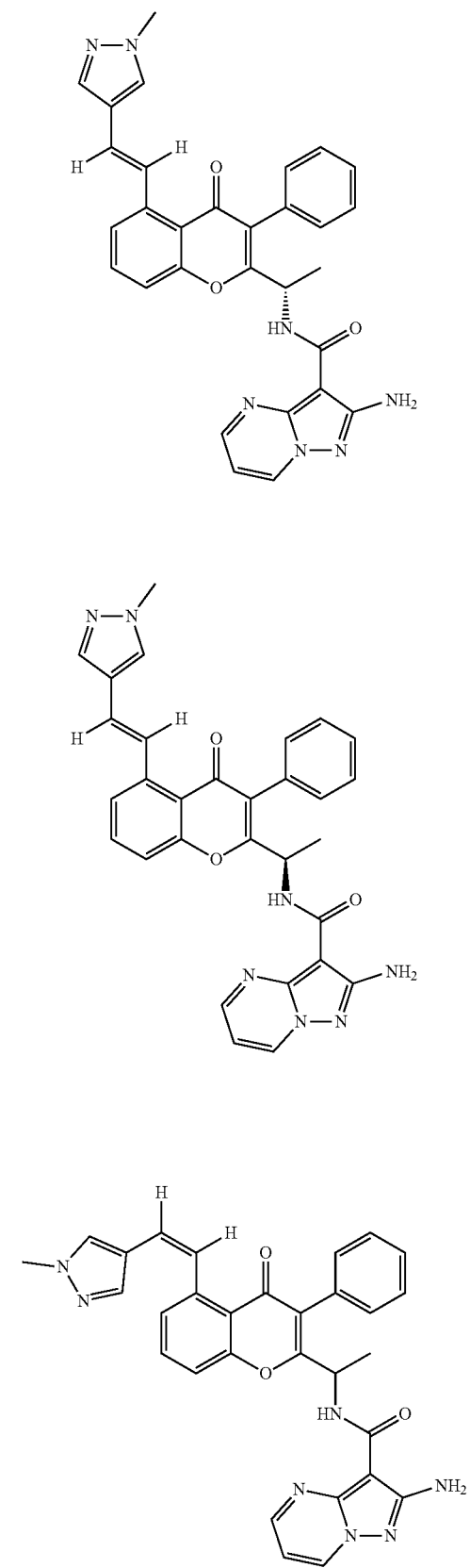
TABLE 4-continued
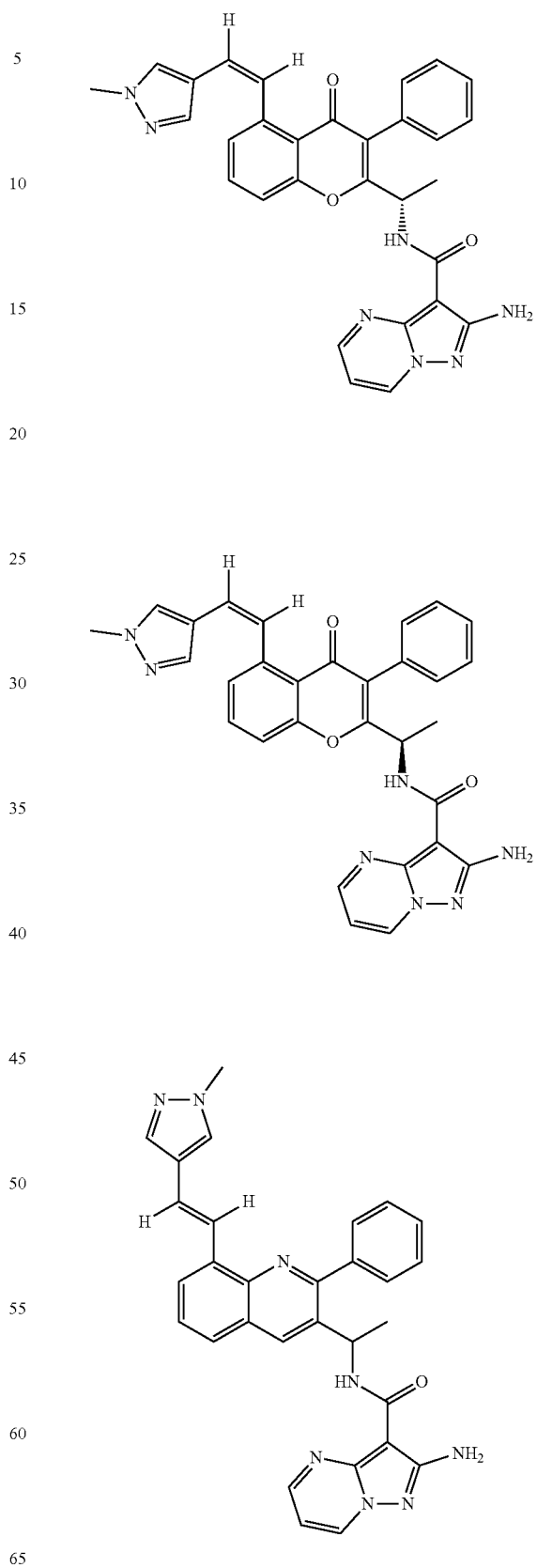

TABLE 4-continued
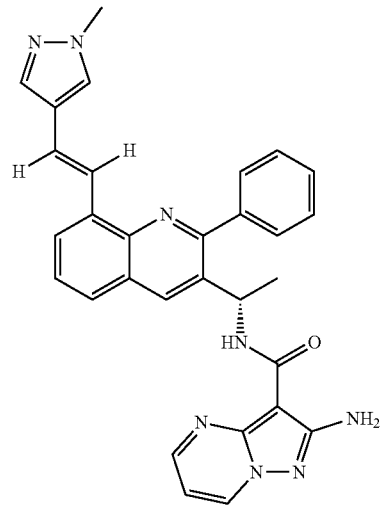 [SMILES: C[C@H](NC(=O)c1c(N)nn2cccnc12)c1cc2cccc(/C=C/c3cnn(C)c3)c2nc1-c1ccccc1]
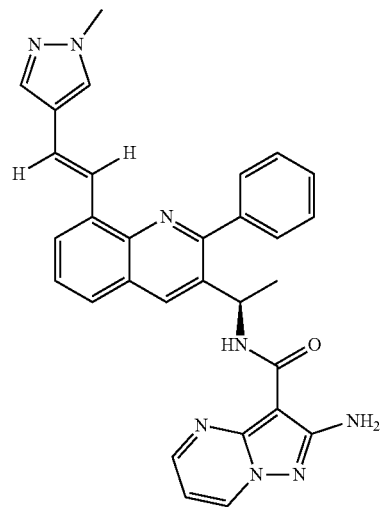 [SMILES: C[C@@H](NC(=O)c1c(N)nn2cccnc12)c1cc2cccc(/C=C/c3cnn(C)c3)c2nc1-c1ccccc1]
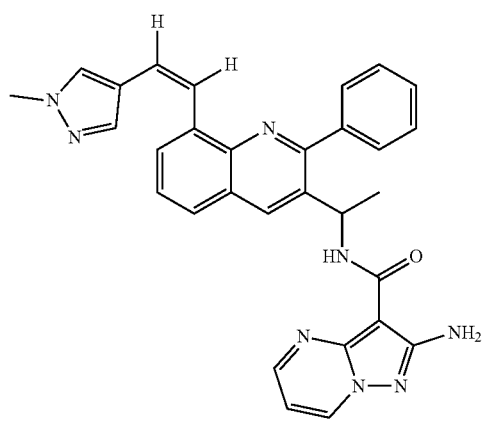 [SMILES: C[C@H](NC(=O)c1c(N)nn2cccnc12)c1cc2cccc(/C=C\c3cnn(C)c3)c2nc1-c1ccccc1]
TABLE 4-continued
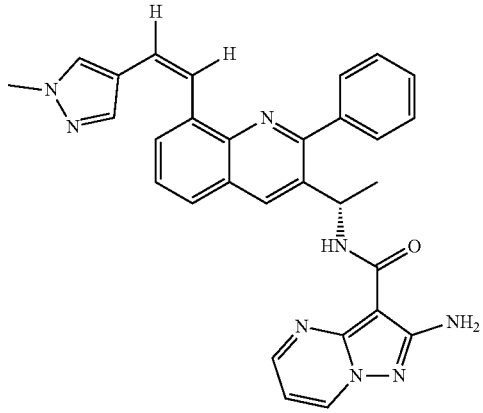
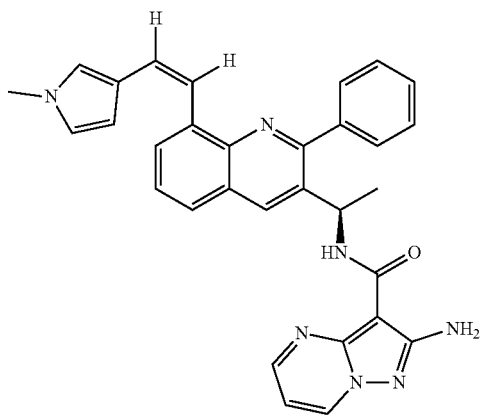
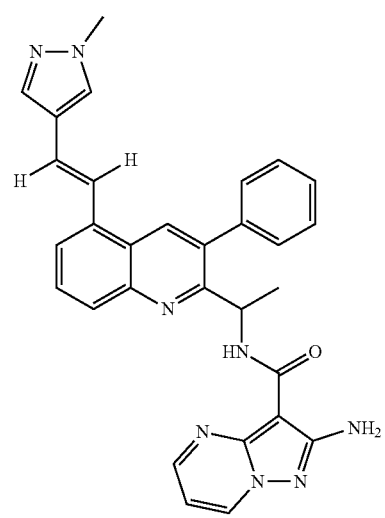 [SMILES: CC(NC(=O)c1c(N)nn2cccnc12)c1nc2cccc(/C=C/c3cnn(C)c3)c2cc1-c1ccccc1]

385
TABLE 4-continued
386
TABLE 4-continued
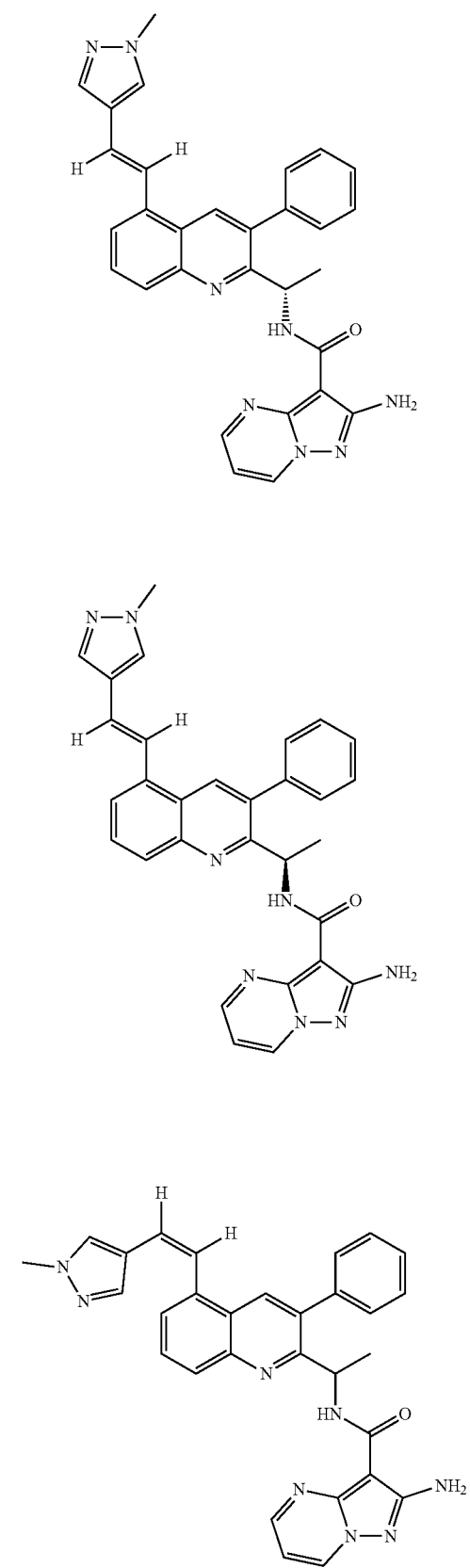
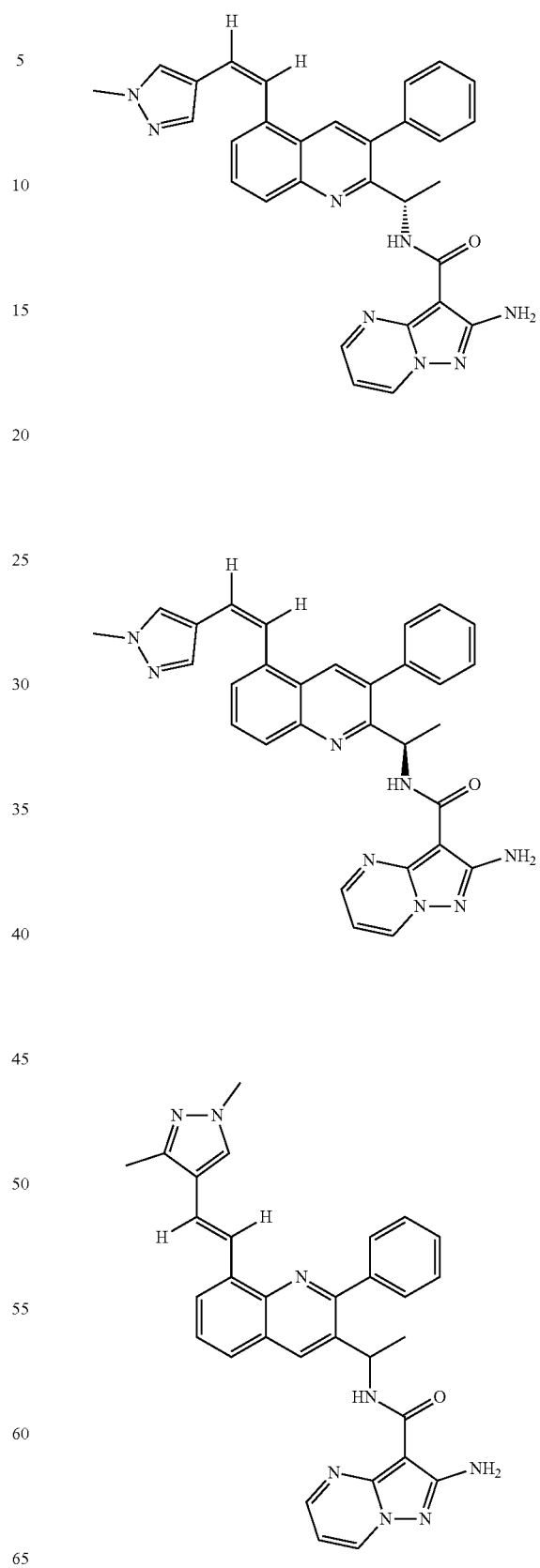

TABLE 4-continued

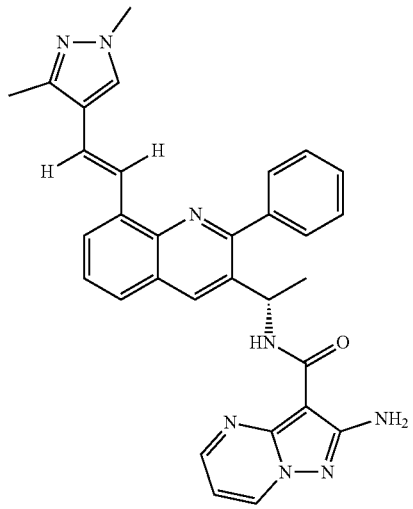 [SMILES: Cc1nn(C)cc1/C=C/c1cccc2cc([C@H](C)NC(=O)c3c(N)nn4cccnc34)c(-c3ccccc3)nc12]

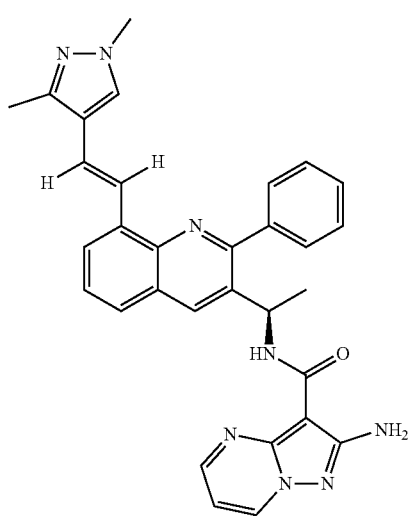 [SMILES: Cc1nn(C)cc1/C=C/c1cccc2cc([C@@H](C)NC(=O)c3c(N)nn4cccnc34)c(-c3ccccc3)nc12]

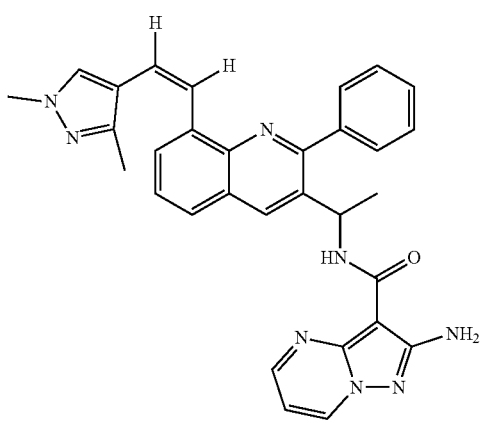 [SMILES: Cc1nn(C)cc1/C=C\c1cccc2cc(C(C)NC(=O)c3c(N)nn4cccnc34)c(-c3ccccc3)nc12]

TABLE 4-continued

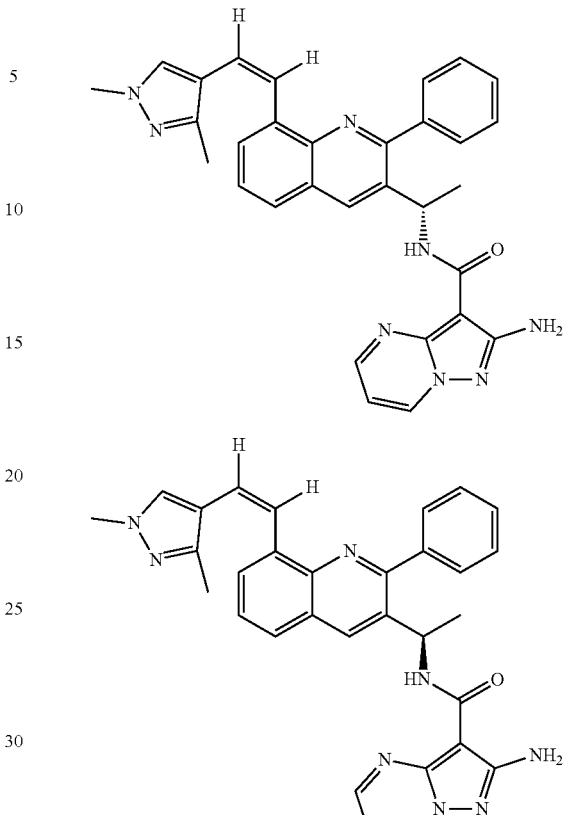

In some embodiments, one or more compounds described herein bind to a PI3 kinase (e.g., bind selectively). In some embodiments, one or more compounds described herein bind selectively to a γ- or δ-subtype of a PI3 kinase. In some embodiments, one or more compounds described herein bind selectively to a γ-subtype of a PI3 kinase. In some embodiments, one or more compounds described herein bind selectively to a δ-subtype of a PI3 kinase.

In some embodiments, non-limiting exemplary compounds exhibit one or more functional characteristics disclosed herein. For example, one or more compounds provided herein bind specifically to a PI3 kinase. In some embodiments, the $IC_{50}$ of a compound provided herein for p110α, p110β, p110γ, or p110δ is less than about 1 µM, less than about 100 nM, less than about 50 nM, less than about 10 nM, less than about 1 nM, less than about 0.5 nM, less than about 100 pM, or less than about 50 pM.

In some embodiments, one or more of the compounds provided herein can selectively inhibit one or more members of type 1 or class I phosphatidylinositol 3-kinases (PI3-kinase) with an $IC_{50}$ value of about 100 nM, about 50 nM, about 10 nM, about 5 nM, about 100 pM, about 10 pM, or about 1 pM, or less, as measured in an in vitro kinase assay.

In some embodiments, one or more of the compounds provided herein can selectively inhibit one or two members of type I or class I phosphatidylinositol 3-kinases (PI3-kinase), such as, PI3-kinase α, PI3-kinase β. PI3-kinase γ, and PI3-kinase δ. In some aspects, some of the compounds provided herein selectively inhibit PI3-kinase δ as compared to all other type I PI3-kinases. In other aspects, some of the compounds provided herein selectively inhibit PI3-kinase δ and PI3-kinase γ as compared to the rest of the type I PI3-kinases. In other aspects, some of the compounds provided herein selectively inhibit PI3-kinase γ as compared to all other type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration ($IC_{50}$) with respect to a given type I PI3-kinase, that is at least about 10-fold, at least about 20-fold, at least about 50-fold, at least about 100-fold, at least about 200-fold, at least about 500-fold, at least about 1000-fold, at least about 2000-fold, at least about 5000-fold, or at least about 10,000-fold, lower than the inhibitor's $IC_{50}$ with respect to the rest of the other type I PI3-kinases. In one embodiment, an inhibitor selectively inhibits PI3-kinase δ as compared to PI3-kinase p with at least about 10-fold lower $IC_{50}$ for PI3-kinase δ. In certain embodiments, the $IC_{50}$ for PI3-kinase δ is below about 100 nM, while the $IC_{50}$ for PI3-kinase β is above about 1000 nM. In certain embodiments, the $IC_{50}$ for PI3-kinase δ is below about 50 nM, while the $IC_{50}$ for PI3-kinase β is above about 5000 nM. In certain embodiments, the $IC_{50}$ for PI3-kinase δ is below about 10 nM, while the $IC_{50}$ for PI3-kinase β is above about 1000 nM, above about 5,000 nM, or above about 10,000 nM. In one embodiment, an inhibitor selectively inhibits PI3-kinase γ as compared to PI3-kinase β with at least about 10-fold lower $IC_{50}$ for PI3-kinase γ. In certain embodiments, the $IC_{50}$ for PI3-kinase γ is below about 100 nM, while the $IC_5$, for PI3-kinase β is above about 1000 nM. In certain embodiments, the $IC_{50}$ for PI3-kinase γ is below about 50 nM, while the $IC_5$ for PI3-kinase β is above about 5000 nM. In certain embodiments, the $IC_{50}$ for PI3-kinase γ is below about 10 nM, while the $IC_{50}$ for PI3-kinase β is above about 1000 nM, above about 5,000 nM, or above about 10,000 nM.

Pharmaceutical Compositions

In some embodiments, provided herein are pharmaceutical compositions comprising a compound as disclosed herein, or an enantiomer, a mixture of enantiomers, or a mixture of two or more diastereomers thereof, or a pharmaceutically acceptable form thereof (e.g., pharmaceutically acceptable salts, hydrates, solvates, isomers, prodrugs, and isotopically labeled derivatives), and a pharmaceutically acceptable excipient, diluent, or carrier, including inert solid diluents and fillers, sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic).

1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. Se, e.g., Anderson, Philip O.; Knoben. James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Twelfth Edition, McGraw Hill, 20111 Goodman and Gilman, eds., *The Pharmacological Basis of Therapeutics*, Tenth Edition McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the disclosed pharmaceutical compositions is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v or v/v.

In some embodiments, the concentration of one or more of the compounds as disclosed herein is greater than about 90%, about 80%, about 70%, about 60%, about 50°, about 40%, about 30%, about 20%, about 19.75%, about 19.50%, about 19.25%, about 19% about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%1, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.00066, about 0.0005/6, about 0.0004%, about 0.0003%, about 0.0002%, or about 0.0001%, w/w, w/v, or v/v.

In some embodiments, the concentration of one or more of the compounds as disclosed herein is in the range from approximately 0.0001% to approximately 50%, approximately 0.001%, to approximately 40%, approximately 0.01% to approximately 30%, approximately 0.02%0 to approximately 29%, approximately 0.03% to approximately 28% approximately 0.04% to approximately 27%, approximately 0.05% to approximately 260%, approximately 0.06% to approximately 25%, approximately 0.07% to approximately 24%, approximately 0.08% to approximately 23%, approximately 0.09%, to approximately 22%, approximately 0.1% to approximately 21%, approximately 0.2% to approximately 20%, approximately 0.3% to approximately 19, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10%, w/w, w/v or v/v.

In some embodiments, the concentration of one or more of the compounds as disclosed herein is in the range from approximately 0.001% to approximately 10%, approximately 0.01% to approximately 5%, approximately 0.02%, to approximately 4.5%, approximately 0.03% to approximately 4%, approximately 0.04% to approximately 3.5%, approximately 0.05% to approximately 3% approximately 0.06% to approximately 2.5%, approximately 0.07% to approximately 2%, approximately, 0.08% to approximately 1.5%, approximately 0.09% to approximately 1%, or approximately 0.1% to approximately 0.9%, w/w, w/v or v/v.

In some embodiments, the amount of one or more of the compounds as disclosed herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of the compounds as disclosed herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g about 0.4 g, about 0.45 g, about 0.5 g, about 0.55 g about 0.6 g about 0.65 g, about 0.7 g, about 0.75 g, about 0.8 g about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as disclosed herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

1A. Formulations for Oral Administration

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters: hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythrtol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives, ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam. N-alkylpyrrolidone. N-hydroxyalkylpyrrolidone, N-alkylpiperidone, N-alkylcaprolactanm, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as disclosed herein, and a pharmaceutical excipient suitable for parenteral administration. In some embodiments, provided herein are pharmaceutical compositions for parenteral administration containing: (i) an effective amount of a disclosed compound, optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

1C. Formulations for Topical Administration

In some embodiments, provided herein are pharmaceutical compositions for topical (e.g., transdermal) administration containing a compound as disclosed herein, and a pharmaceutical excipient suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable excipients described herein.

1D. Formulations for Inhalation Administration

In some embodiments, provided herein are pharmaceutical compositions for inhalation administration containing a compound as disclosed herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients as described herein. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

1E. Formulations for Ocular Administration

In some embodiments, the disclosure provides a pharmaceutical composition for treating ophthalmic disorders. The pharmaceutical composition can contain an effective amount of a compound as disclosed herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethlammonium halide, dodecyltrimethylammonium halide, cetrimonium halide, benzethonium halide, behenalkonium halide, cetalkomum halide, cetethyldimonium halide, cetylpyridinium halide, benzododecmium halide, chlorallyl methenamine halide, myristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethlammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

1F. Formulations for Controlled Release Administration

In some embodiments, provided herein are pharmaceutical compositions for controlled release administration containing a compound as disclosed herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as disclosed herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see. Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, e.g., thus requiring only a fraction of the systemic dose (see, e.g., Goodson, *Medical Applications of Controlled Release,* 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

2. Dosage

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described herein. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg per day. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as disclosed herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as disclosed herein can continue as long as necessary. In some embodiments, an agent as disclosed herein is administered for more than about 1, about 2, about 3, about 4, about 5, about 6, about 7, about 14, or about 28 days. In some embodiments, an agent as disclosed herein is administered for less than about 28, about 14, about 7, about 6, about 5, about 4, about 3, about 2, or about 1 day. In some embodiments, an agent as disclosed herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day. In some embodiments, the dose is about 1 mg/kg, about 5 mg/kg, about 7.5 mg/kg, about 10 mg/kg, about 15 mg/kg, about 20 mg/kg, about 25 mg/kg, about 50 mg/kg, about 75 mg/kg, or about 100 mg/kg per day. In some embodiments, the dose is about 1 mg/kg, about 7.5 mg/kg, about 20 mg/kg, or about 50 mg/kg per day.

When a compound provided herein, is administered in a pharmaceutical composition that comprises one or more agents, and the agent has a shorter half-life than the compound provided herein unit dose forms of the agent and the compound provided herein can be adjusted accordingly.

3. Kits

In some embodiments, provided herein are kits. In one embodiment, provided herein is a kit comprising a compound provided herein or a pharmaceutical composition provided herein. The kits can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as disclosed herein and the agent are provided as separate pharmaceutical compositions in separate containers within the kit. In some embodiments, the compound as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection. Dextrose Injection. Dextrose and Sodium Chloride Injection, and Lactated Ringer's Injection water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

Therapeutic Methods

In one embodiment, provided herein is a method of treating or preventing a PI3K mediated disorder in a subject comprising administering an effective amount of a compound of provided herein or a pharmaceutical composition provided herein to the subject.

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-α, β, δ), which are generally activated by receptor tyrosine kinases (RTKs); Class IB (e.g., PI3K-γ), which is activated by G-protein coupled receptors (GPCRs), among others. PI3Ks exert their biological activities via a "PI3K-mediated signaling pathway" that includes several components that directly and/or indirectly transduce a signal triggered by a PI3K, including the generation of second messenger phosphotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B, et al. (2001) *Annu Rev Biochem.* 70:535-602). For example, PI3K-δ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]), (Fung-Leung W P. (2011) *Cell Signal,* 23(4):603-8). Unlike PI3K-δ, PI3K-γ is not associated with a regulatory subunit of the p85 family, but rather with a regulatory subunit in the p101 family. PI3K-γ is associated with GPCRs, and is responsible for the very rapid induction of PIP3. PI3K-γ can be also activated by RAS.

In some embodiments, provided herein are methods of modulating a PI3 kinase activity (e.g., selectively modulating) by contacting the kinase with an effective amount of a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Modulation can be inhibition (e.g., reduction) or activation (e.g., enhancement) of kinase activity. In some embodiments, provided herein are methods of inhibiting kinase activity by contacting the kinase with an effective amount of a compound as provided herein in solution. In some embodiments, provided herein are methods of inhibiting the kinase activity by contacting a cell, tissue, organ that express the kinase of interest, with a compound provided herein. In some embodiments, provided herein are methods of inhibiting kinase activity in a subject by administering into the subject an effective amount of a compound as provided herein, or a pharmaceutically acceptable form thereof. In some embodiments, the kinase activity is inhibited (e.g., reduced) by more than about 25%, 30%, 40%, 50%, 60%, 70%, 80%, or 90%, when contacted with a compound provided herein as compared to the kinase activity without such contact. In some embodiments, provided herein are methods of inhibiting PI3 kinase activity in a subject (including mammals such as humans) by contacting said subject with an amount of a compound as provided herein sufficient to inhibit or reduce the activity of the PI3 kinase in said subject.

In some embodiments, the kinase is a lipid kinase or a protein kinase. In some embodiments, the kinase is selected from a PI3 kinase including different isoforms, such as PI3 kinase α, PI3 kinase β, PI3 kinase γ, PI3 kinase δ; DNA-PK; mTOR; Abl, VEGFR. Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR); and IGFR.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound as provided herein, or a pharmaceutically acceptable form thereof, or a pharmaceutical composition as provided herein. In some embodiments, provided herein is a method of treating a PI3K-δ or PI3K-γ mediated disorder in a subject, the method comprising administering a therapeutically effective amount of a compound as provided herein, or a pharmaceutically acceptable form thereof, or a pharmaceutical composition as provided herein. In some embodiments, provided herein is a method for inhibiting at least one of PI3K-δ and PI3K-γ, the method comprising contacting a cell expressing PI3K in vitro or in vivo with an effective amount of a compound or composition provided herein. PI3Ks have been associated with a wide range of conditions, including immunity, cancer and thrombosis (reviewed in Vanhaesebroeck, B, et al. (2010) *Current Topics in Microbiology and Immunology*, DOI 10.1007/82_2010_65). For example, Class I PI3Ks, particularly PI3K-γ and PI3K-δ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11):1151-62); Rommel C, et al. (2007) *Nat Rev Immunol* 7(3):191-201; Durand C A et al. (2009) *J Immunol.* 183(9):5673-84; Dil N, Marshall A J. (2009) *Mol Immunol.* 46(10):1970-8; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86).

PI3K-γ is a Class 1B PI3K that associates with the p101 and p84 (p87PIKAP) adaptor proteins, and canonically signals through GPCRs. Non-cononical activation through tyrosine kinase receptors and RAS can occur. Activated PI3K-γ leads to production of PIP3, which serves as a docking site for downstream effector proteins including AKT and BTK, bringing these enzymes to the cell membrane where they may be activated. A scaffolding role for PI3k-γ has been proposed and may contribute to the activation of the RAS/MEK/ERK pathway. The interaction with the RAS pathway explains activities attributed to kinase dead PI3K-γ in cells or in animals. PI3K-γ is essential for function of a variety of immune cells and pathways. Chemokine responses (including IL-8, fMLP, and C5a), leading to neutrophil or monocyte cell migration is dependent on PI3K-γ (HIRSCH et al., "Central Role for G Protein-Coupled Phosphoinositide 3-Kinase γ in Inflammation," *Science* 287:1049-1053 (2000); SASAKI et al., "Function of PI3Kγ in Thymocyte Development, T Cell Activation, and Neutrophil Migration," *Science* 287:1040-1046 (2000); LI et al., "Roles of PLC-β2 and -β3 and PI3Kγ in Chemoattractant-Mediated Signal Transduction," *Science* 287:1046-1049 (2000)). The requirement for PI3K-γ-dependent neutrophil migration is demonstrated by failure of arthritis development in the K/BXN serum transfer arthritis model in PI3K-γ knockout mice (Randis et al., *Eur. J. Immunol.*, 2008, 38(5), 1215-24). Similarly, the mice fail to develop cellular inflammation and airway hyper-responsiveness in the ovalbumin induced asthma model (Takeda et al., *J. Allergy Clin. Immunol.*, 2009; 123, 805-12). PI3K-γ deficient mice also have defects in T-helper cell function. T-cell cytokine production and proliferation in response to activation is reduced, and T helper dependent viral clearance is defective (Sasaki et al., *Science,* 2000, 287, 1040-46). T cell dependent inflammatory disease models including EAE also do not develop in PI3K-γ deficient mice, and both the T-cell activation defect and cellular migration defects may contribute to efficacy in this model (Comerfold, *PLOS One,* 2012, 7, e45095). The imiquimod psoriasis model has also been used to demonstrate the importance of PI3K-γ in the inflammatory response. Using PI3K-γ deficient mice in this model, the accumulation of γδ T cells in the skin is blocked, as well as dendritic cell maturation and migration (ROLLER et al., "Blockade of Phosphatidylinositol 3-Kinase (PI3K)δ or PI3Kγ Reduces IL-17 and Ameliorates Imiquimod-Induced Psoriasis-like Dermatitis." *J. Immunol.* 189:4612-4620 (2012)). The role of PI3K-γ in cellular trafficking can also be demonstrated in oncology models where tumor inflammation is important for growth and metastasis of cancers. In the Lewis Lung Carcinoma model, monocyte activation, migration, and differentiation in tumors are defective. This defect results in a reduction in tumor growth and extended survival in PI3K-γ deficient mice (Schmid et al., *Cancer Cell,* 2011, 19, 715-27) or upon treatment with inhibitors that target PI3K-γ. In pancreatic cancer, PI3K-γ can be inappropriately expressed, and in this solid tumor cancer or others where PI3K-γ plays a functional role, inhibition of PI3K-γ can be beneficial. Inhibition of PI3K-γ shows promise for the treatment of hematologic malignancies. In a T-ALL model employing a T cell directed knockout of P-Ten, PI3K-δ and PI3K-γ are both essential for the appropriate development of disease, as shown with genetic deletion of both genes (Subramaniam et al. *Cancer Cell* 21, 459-472, 2012). In addition, in this TALL model, treatment with a small molecule inhibitor of both kinases leads to extended survival of these mice. In CLL, chemokine networks support a pseudo-follicular microenvironment that includes Nurse like cells, stromal cells and T-helper cells. The roles of PI3K-γ in the normal chemokine signaling and T cell biology suggest the value of inhibiting this target in CLL (BURGER, "Inhibiting B-Cell Receptor Signaling Pathways in Chronic Lymphocytic Leukemia," *Curr. Mematol. Malig. Rep.* 7:26-33 (2012)). Accordingly, PI3K-γ inhibitors are therapeutically interesting for diseases of the immune system where cell trafficking and T cell or myeloid cell function is important. In oncology, solid tumors that are dependent on tumor inflammation, or tumors with high levels of PI3K-γ expression, may be targeted. For hematological cancers a special role for PI3K-γ and PI3K-δ isoforms in TALL and potentially in CLL suggests targeting these PI3Ks in these diseases.

Without being limited by a particular theory, PI3K-γ has been shown to play roles in inflammation, arthritis, asthma, allergy, multiple sclerosis (MS), and cancer, among others (e.g., Ruckle et al., *Nature Rev., Drug Discovery,* 2006, 5, 903-18; Schmid et al., "Myeloid cells in tumor inflammation," *Vascular Cell,* 2012, doi: 10.1186/2045-824X-4-14). For example, PI3K-γ functions in multiple signaling pathways involved in leukocyte activation and migration. PI3K-γ has been shown to drive priming and survival of autoreactive CD4$^+$ T cells during experimental autoimmune encephalomyelitis (EAE), a model for MS. When administered from onset of EAE, a PI3K-γ inhibitor has been shown to cause inhibition and reversal of clinical disease, and reduction of demyelination and cellular pathology in the CNS (Comerford et al., *PLOS One,* 2012, 7, e45095). PI3K-γ also regulates thymocyte development, T cell activation, neutrophil migration, and the oxidative burst (Sasaki et al., *Science,* 2000, 287, 1040-46). In addition, it is shown that allergic airway hyper-responsiveness, inflammation, and remodeling do not develop it PI3K-γ deficient mice (Takeda et al., *J. Allergy Clin. Immunol.,* 2009, 123, 805-12). PI3K-γ is shown to be required for chemoattractant-induced production of phosphatidylinositol 3,4,5-trisphosphate and has an important role in chemoattractant-induced superoxide production and chemotaxis in mouse neutrophils and in production of T cell-independent antigen-specific antibodies composed of the immunoglobulin λ light chain (Li et al., *Science,* 2000, 287, 1046-49). PI3K-γ is reported to be a crucial signaling molecule required for macrophage accumulation in inflammation (Hirsch et al., *Science,* 2000, 287, 1049-53). In cancers, pharmacological or genetic blockade of p110γ suppresses inflammation, growth, and metastasis of implanted and spontaneous tumors, suggesting that PI3K-γ can be an important therapeutic target in oncology (Schmid et al., *Cancer Cell,* 2011, 19, 715-27). For example, it is shown that PI3K-γ has a tumor-specific high accumulation in pancreatic ductal adenocarcinoma (PDAC) in human, signifying a role of PI3K-γ in pancreatic cancer (Edling et al., *Human Cancer Biology,* 2010, 16(2), 4928-37).

PI3K-δ has roles in impairments of B-cell signaling and development, antibody production, T-cell function. Th1 and Th2 differentiation, and mast and basophil degranulation. Without being limited by a particular theory, PI3K-γ has roles in T-cell function, neutrophil and macrophage recruitment, macrophage activation, neutrophil oxidative burst, and dendritic cell migration. Inhibition of PI3K-δ and/or PI3K-γ isoforms can result in efficacy against inflammation and cancer, e.g., in arthritis, asthma, multiple sclerosis (MS), and tumor models. For example, deficiency in PI3K-δ and/or PI3K-γ can result in efficacy in K/BxN arthritis model (Kyburz et al., *Springer Semin. Immunopathology,* 2003, 25, 79-90) or K/BxN serum transfer model of arthritis (Randis et al., *Eur. J. Immunol.,* 2008, 38(5), 1215-24), where it is shown that recognition of the immune complexes depends on both PI3K-δ and PI3K-γ, whereas cell migration is dependent on PI3K-γ. Deficiency in PI3K-δ or PI3K-γ can also result in efficacy in murine ovalbumin (OVA) induced allergic asthma model (Lee et al., *FASEB J.,* 2006, 20, 455-65; Takeda et al., *J. Allergy Clin. Immunol.,* 2009; 123, 805-12), where it is shown that inhibition of either PI3K-δ or PI3K-γ inhibits ovalbumin induced lung infiltration and improves airway responsiveness. Deficiency in PI3K-δ or PI3K-γ can also result in efficacy in murine experimental autoimmune encephalomyelitis (model for MS), where it is shown that PI3K-γ deletion may provide better efficacy as compared to PI3K-δ deletion (Haylock-Jacob et al., *J. Autoimmunity,* 2011, 36, 278-87; Comerford et al., *PLOS One,* 2012, 7, e45095), including reduction in T-cell receptor induced CD4$^+$ T cell activation, leukocyte infiltration and Th1/Th17 responses, and dendritic cell migration (Comerfold, *PLOS One,* 2012, 7, e45095). Furthermore, inhibition of PI3K-γ can also result in decreased tumor inflammation and growth (e.g., Lewis lung carcinoma model, Schmid et al., *Cancer Cell,* 2011, 19(6), 715-27). PI3K-γ deletion combined with PI3K-δ deletion results in increased survival in T-cell acute lymphoblastic leukemia (T-ALL) (Subramaniam et al., *Cancer Cell,* 2012, 21, 459-72). Inhibitors of both PI3K-δ and PI3K-γ are also shown to be efficacious in PTEN-deleted T-ALL cell line (MOLT-4). In the absence of PTEN phosphatase tumor suppressor function, PI3K-δ or PI3K-γ alone can support the development of leukemia, whereas inactivation of both isoforms suppresses tumor formation. Thus, inhibitors of PI3K-δ and/or PI3K-γ can be useful in treating inflammation, such as arthritis, allergic asthma, and MS; and in treating cancer, for example, due to effects such as reductions in solid tumor associated inflammation, angiogenesis and tumor progression.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, SIP, and CXCR5 signaling, and has been shown to modulate responses to toll-like receptors 4 and 9. Inhibitors of PI3K-δ have shown the importance of PI3K-δ in B-cell development (Marginal zone and BI cells), B-cell activation, chemotaxis, migration and homing to lymphoid tissue, and in the control of immunoglobulin class switching leading to the production of IgE. Clayton E et al. (2002) *J Exp Med.* 196(6):753-63; Bilancio A, et al. (2006) *Blood* 107(2):642-50; Okkenhaug K, et al. (2002) *Science* 297(5583):1031-4; Al-Alwan M M et al. (2007) *J Immunol.* 178(4):2328-35; Zhang T T, et al. (2008) *J. Allergy Clin Immunol.* 2008; 122(4):811-819.e2; Srinivasan L, et al. (2009) *Cell* 139(3):573-86).

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., SIP, CCR7, CD62L). (Garçon F, et al. (2008) *Blood* 111(3):1464-71; Okkenhaug K et al. (2006). *J Immunol.* 177(8):5122-8; Soond D R, et al. (2010) *Blood* 115(11):2203-13; Reif K, (2004). *J Immunol.* 2004; 173(4):2236-40; Ji H, et al. (2007) *Blood* 110(8): 2940-7; Webb L M, et al. (2005) *J Immunol.* 175(5):2783-7; Liu D, et al. (2010) *J Immunol.* 184(6):3098-105; Haylock-Jacobs S, et al. (2011) *J Autoimmun.* 2011; 36(3-4):278-87; Jarmin S J, et al. (2008) *J Clin Invest.* 118(3):1154-64).

Numerous publications support roles of PI3K-δ and PI3K-γ in the differentiation, maintenance, and activation of immune and malignant cells, as described in more detail herein.

PI3K-δ and PI3K-γ isoforms are preferentially expressed in leukocytes where they have distinct and non-overlapping roles in immune cell development and function. See, e.g., PURI and GOLD, "Selective inhibitors of phosphoinositide 3-kinase delta: modulators of B-cell function with potential for treating autoimmune inflammatory disease and B-cell malignancies." *Front. Immunol.* 3:256 (2012); BUITEN-HUIS et al, "The role of the PI3k-PKB signaling module in regulation of hematopoiesis." *Cell Cycle* 8(4):560-566 (2009); HOELLENRIEGEL and BURGER. "Phosphoinositide 3'-kinase delta: turning off BCR signaling in Chronic Lymphocytic Leukemia," *Oncotarget* 2(10):737-738 (2011); HIRSCH et al., "Central Role for G Protein-Coupled Phosphoinositide 3-Kinase γ in Inflammation," *Science* 287: 1049-1053 (2000); LI et al., "Roles of PLC-γ2 and -β3 and PI3Kγ in Chemoattractant-Mediated Signal Transduction," *Science* 287:1046-1049 (2000); SASAKI et al., "Function of PI3Kγ in Thymocyte Development. T Cell Activation, and Neutrophil Migration." *Science* 287:1040-1046 (2000); CUSHING et al., "PI3Kδ and PI3Kγ as Targets for Autoimmune and Inflammatory Diseases." *J. Med. Chem.* 55:8559-8581 (2012); MAXWELL et al., "Attenuation of phosphoinositide 3-kinase δ signaling restrains autoimmune disease." *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation." *J. Autoimmun.* 36:278-287 (2011); SOOND et al., "PI3K p110δ regulates T-cell cytokine production during primary and secondary immune responses in mice and humans," *Blood* 115(11):2203-2213 (2010); ROLLER et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9):936-943 (2005). As key enzymes in leukocyte signaling, PI3K-δ and PI3K-γ facilitate normal B-cell, T-cell and myeloid cell functions including differentiation, activation, and migration. See, e.g., HOELLENRIEGEL and BURGER, "Phosphoinositide 3'-kinase delta: turning off BCR signaling in Chronic Lymphocytic Leukemia." *Oncotarget* 2(10):737-738 (2011); CUSHING et al., "PI3Kδ and PI3Kγ as Targets for Autoimmune and Inflammatory Diseases," *J. Med. Chem.* 55:8559-8581 (2012). PI3K-δ or PI3K-γ activity is critical for preclinical models of autoimmune and inflammatory diseases. See, e.g., HIRSCH et al., "Central Role for G Protein-Coupled Phosphoinositide 3-Kinase γ in Inflammation," *Science* 287:1049-1053 (2000); LI et al., "Roles of PLC-β2 and -β3 and PI3Kγ in Chemoattractant-Mediated Signal Transduction," *Science* 287:1046-1049 (2000); SASAKI et al., "Function of PI3Kγ in Thymocyte Development. T Cell Activation, and Neutrophil Migration," *Science* 287:1040-1046 (2000); CUSHING et al., "PI3Kδ and PI3Kγ as Targets for Autoimmune and Inflammatory Diseases," *J. Med. Chem.* 55:8559-8581 (2012); MAXWELL et al., "Attenuation of phosphoinositide 3-kinase δ signaling restrains autoimmune disease," *J. Autoimmun.* 38:381-391 (2012); HAYLOCK-JACOBS et al., "PI3Kδ drives the pathogenesis of experimental autoimmune encephalomyelitis by inhibiting effector T cell apoptosis and promoting Th17 differentiation." *J. Autoimmun.* 36:278-287 (2011); SOOND et al., "PI3K p110δ regulates T-cell cytokine production during primary and secondary immune responses in mice and humans." *Blood* 115(11): 2203-2213 (2010); ROLLER et al., "Blockade of Phosphatidylinositol 3-Kinase (PI3K) or PI3Kγ Reduces IL-17 and Ameliorates Imiquimod-Induced Psoriasis-like Dermatitis," *J. Immunol.* 189:4612-4620 (2012); CAMPS et al., "Blockade of PI3Kγ suppresses joint inflammation and damage in mouse models of rheumatoid arthritis," *Nat. Med.* 11(9): 936-943 (2005). Given the key role for PI3K-δ and PI3K-γ in immune function, inhibitors of the PI3K-δ and/or γ have therapeutic potential in immune-related inflammatory or neoplastic diseases.

PI3K-δ and PI3K-γ are central to the growth and survival of B- and T-cell malignancies and inhibition of these isoforms may effectively limit these diseases. See, e.g., SUBRAMANIAM et al., "Targeting Nonclassical Oncogenes for Therapy in T-ALL," *Cancer Cell* 21:459-472 (2012); LANNUTTI et al., "CAL-101 a p110δ selective phosphatidylinositol-3-kinase inhibitor for the treatment of B-cell malignancies, inhibits PI3K signaling and cellular viability," *Blood* 117(2):591-594 (2011). PI3K-δ and PI3K-γ support the growth and survival of certain B-cell malignancies by mediating intracellular BCR signaling and interactions between the tumor cells and their microenvironment. See, e.g., PURI and GOLD. "Selective inhibitors of phosphoinositide 3-kinase delta: modulators of B-cell function with potential for treating autoimmune inflammatory disease and B-cell malignancies." *Front. Immunol.* 3:256 (2012); HOELLENRIEGEL et al., "The phosphoinositide 3'-kinase delta inhibitor, CAL-101, inhibits B-cell receptor signaling and chemokine networks in chronic lymphocytic leukemia," *Blood* 118(13):3603-3612 (2011); BURGER, "Inhibiting B-Cell Receptor Signaling Pathways in Chronic Lymphocytic Leukemia," *Curr. Mematol. Malig. Rep.* 7:26-33 (2012). Increased BCR signaling is a central pathologic mechanism of B-cell malignancies and PI3K activation is a direct consequence of BCR pathway activation. See, e.g., BURGER, "Inhibiting B-Cell Receptor Signaling Pathways in Chronic Lymphocytic Leukemia," *Cur. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia." *Blood* 117(2):563-574 (2011); DAVIS et al., "Chronic active B-cell-receptor signaling in diffuse large B-cell lymphoma," *Nature* 463:88-92 (2010); PIGHI et al., "Phospho-proteomic analysis of mantle cell lymphoma cells suggests a pro-survival role of B-cell receptor signaling," *Cell Oncl.* (*Dordr*) 34(2):141-153 (2011); RIZZATTI et al., "Gene expression profiling of mantle cell lymphoma cells reveals aberrant expression of genes from the PI3K-AKT, WNT and TGFβ signaling pathways," *Brit. J. Haematol.* 130:516-526 (2005); MARTINEZ et al., "The Molecular Signature of Mantle Cell Lymphoma Reveals Multiple Signals Favoring Cell Survival," *Cancer Res.* 63:8226-8232 (2003). Interactions between malignant B-cells and supporting cells (eg, stromal cells, nurse-like cells) in the tumor microenvironment are important for tumor cell survival, proliferation, homing, and tissue retention. See, e.g., BURGER, "Inhibiting B-Cell Receptor Signaling Pathways in Chronic Lymphocytic Leukemia," *Curr. Mematol. Malig. Rep.* 7:26-33 (2012); HERISHANU et al., "The lymph node microenvironment promotes B-cell receptor signaling, NF-κB activation, and tumor proliferation in chronic lymphocytic leukemia." *Blood* 117(2):563-574 (2011); KURTOVA et al., "Diverse marrow stromal cells protect CLL cells from spontaneous and drug-induced apoptosis: development of a reliable and reproducible system to assess stromal cell adhesion-mediated drug resistance." *Blood* 114(20): 4441-4450 (2009); BURGER et al., "High-level expression of the T-cell chemokines CCL3 and CCL4 by chronic lymphocytic leukemia B cells in nurselike cell cocultures and after BCR stimulation." *Blood* 113(13) 3050-3058 (2009); QUIROGA et al., "B-cell antigen receptor signaling enhances chronic lymphocytic leukemia cell migration and survival: specific targeting with a novel spleen tyrosine kinase inhibitor, R406," *Blood* 114(5):1029-

1037 (2009). Inhibiting PI3K-δ,γ with an inhibitor in certain malignant B-cells can block the BCR-mediated intracellular survival signaling as well as key interactions with their microenvironment that are critical for their growth.

PI3K-δ and PI3K-γ also play a direct role in the survival and proliferation of certain T-cell malignancies. See, e.g., SUBRAMANIAM et al., "Targeting Nonclassical Oncogenes for Therapy in T-ALL," *Cancer Cell* 21:459-472 (2012). Aberrant PI3K-δ and PI3K-γ activity provides the signals necessary for the development and growth of certain T-cell malignancies. While BTK is expressed in B-cells, it is not expressed in T-cells, and therefore BTK is not a viable target for the treatment of T-cell malignancies. See, e.g., NISITANI et al., "Posttranscriptional regulation of Bruton's tyrosine kinase expression in antigen receptor-stimulated splenic B cells," *PNAS* 97(6):2737-2742 (2000); DE WEERS et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993); SMITH et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994). PI3K-δ and/or γ inhibitors may have unique therapeutic potential in T-cell malignancies.

In neutrophils, PI3K-δ, along with PI3K-γ, contribute to the responses to immune complexes. FCγRII signaling, including migration and neutrophil respiratory burst. Human neutrophils undergo rapid induction of PIP3 in response to fornyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis™ et al. (2008) *Eur Immunol.* 38(5):1215-24; Pinho V, (2007) *J Immunol.* 179(11):7891-8; Sadhu C, et al. (2003) *J Immunol.* 170(5):2647-54; Condliffe A M et al. (2005) *Blood* 106(4):1432-40). It has been reported that in certain autoimmune diseases, preferential activation of PI3K-β may be involved (Kulkarni et al., *Immunology* (2011) 4(168) ra23: 1-11). It was also reported that PI3K-β-deficient mice were highly protected in an FcγR-dependent model of autoantibody-induced skin blistering and partially protected in an FcγR-dependent model of inflammatory arthritis, whereas combined deficiency of PI3K-β and PI3K-δ resulted in near complete protection in inflammatory arthritis (Id.).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCγR and C5a signaling) (Randis T M, et al. (2008) *Eur J Immunol.* 38(5):1215-24; Mawnick J A et al. (2009) *Am J Respir Crit Care Med.* 179(7):542-8; Konrad S, et al. (2008). *Biol Chem.* 283(48):33296-303).

In mast cells, stem cell factor—(SCF) and IL3-dependent proliferation, differentiation and function are PI3K-δ dependent, as is chemotaxis. The allergen/IgE crosslinking of FCγRI resulting in cytokine release and degranulation of the mast cells is severely inhibited by treatment with PI3K-δ inhibitors, suggesting a role for PI3K-δ in allergic disease (Ali K et al. (2004) *Nature* 431(7011):1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, SIP and CXCL12, or in response to LPS in the peritoneum (Guo H, et al. (2008) *J Exp Med.* 205(10):2419-35; Tassi I, et al. (2007) *Immunity* 27(2):214-27; Saudemont A, (2009) *Proc Natl Acad Sc, USA.* 106(14): 5795-800; Kim N, et al. (2007) *Blood* 110(9):3202-8).

The roles of PI3K-δ and PI3K-γ in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma, and inflammatory respiratory disease, such as COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3K-δ and/or -γ have been shown to have anti-inflammatory activity in several autoimmune animal models for rheumatoid arthritis (Williams, O, et al. (2010) *Chem Biol*, 17(2):123-34; WO 2009/088986; WO2009/088880; WO 2011/008302; each incorporated herein by reference). PI3K-δ is expressed in the RA synovial tissue (especially in the synovial lining which contains fibroblast-like synoviocytes (FLS), and selective PI3K-δ inhibitors have been shown to be effective in inhibiting synoviocyte growth and survival (Bartok et al. (2010) *Arthritis Rheum* 62 Suppl 10:362). Several PI3K-δ and -γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302; each incorporated herein by reference).

The role of PI3K-δ has also been shown in models of T-cell dependent response, including the DTH model. In the murine experimental autoimmune encephalomyelitis (EAE) model of multiple sclerosis, the PI3K-γ/δ-double mutant mice are resistant. PI3K-δ inhibitors have also been shown to block EAE disease induction and development of TH-17 cells both in vitro and in vivo (Haylock-Jacobs, S, et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_C$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class IA PI3Ks, which includes PI3K-δ. The deletion of PI3K-γ in the transgenically activated class IA lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphylaxis assay (Ali K et al. (2008) *J Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2):403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

Class I PI3Ks, particularly PI3K-δ and PI3K-γ isoforms, are also associated with cancers (reviewed, e.g., in Vogt, P K et al. (2010) *Curr Top Microbiol Immunol.* 347:79-104; Fresno Vara, J A et al. (2004) *Cancer Treat Rev.* 30(2):193-204; Zhao, L and Vogt, P K. (2008) *Oncogene* 27(41):5486-96). Inhibitors of PI3K, e.g., PI3K-δ and/or PI3K-γ, have been shown to have anti-cancer activity (e.g., Courtney, K D et al. (2010) *J Clin Oncol.* 28(6):1075-1083); Markman, B et al. (2010) *Ann Oncol.* 21(4):683-91; Kong. D and Yamori, T (2009) *Curr Med Chem.* 16(22):2839-54; Jimeno, A et al. (2009) *J Clin Oncol.* 27:156s (suppl; abstr 3542); Flinn, I W et al. (2009) *J Clin Oncol.* 27:156s (suppl; abstr 3543); Shapiro. G et al. (2009) *J Clin Oncol.* 27:146s (suppl; abstr 3500); Wagner, A J et al. (2009) *J Chin Oncol.* 27:146s (suppl: abstr 3501); Vogt, P K et al. (2006) *Virology* 344(1):131-8; Ward. S et al. (2003) *Chem Biol.* 10(3):207-13; WO 2011/041399; US 2010/0029693; US 2010/0305096; US 2010/0305084; each incorporated herein by reference).

In one embodiment, described herein is a method of treating cancer. Types of cancer that can be treated with an inhibitor of PI3K (particularly, PI3K-δ and/or PI3K-γ) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena. L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) *Mol Cancer Ther.* 7:841-850); endometrial cancer (e.g., Bansal, N et al. (2009) *Cancer Control.* 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6):2569-77); colorectal cancer (e.g., Saif, M W and Chu, E (2010) *Cancer J.* 16(3):196-201); breast cancer (e.g., Torbett, N E et al. (2008) *Biochemn J.* 415:97-100); thyroid cancer (e.g., Brzezianska, E and Pastuszak-Lewandoska, D (2011) *Front Brosci.* 16:422-39); and ovarian cancer (e.g., Mazzoletti, M and Broggini, M (2010) *Curr Med Chem.* 17(36):4433-47).

Numerous publications support a role of PI3K-δ and PI3K-γ in treating hematological cancers. PI3K-δ and PI3K-γ are highly expressed in the heme compartment, and solid tumors, including prostate, breast and glioblastomas (Chen J. S. et al. (2008) *Mol Cancer Ther.* 7(4):841-50; Ikeda H, et al. (2010) *Blood* 116(9):1460-8).

In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3):1027-36; Meadows, S A, $52^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16):4323-7.

In one embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. $52^{nd}$ Annual ASH Meeting and Exposition; 2010 Dec. 4-7; Orlando, Fla.; Hoellenriegel, J, et al. $52^{nd}$ Annual ASH Meeting and Exposition 2010 Dec. 4-7; Orlando, Fla.; Webb, H K, et al. $52^{nd}$ Annual ASH Meeting and Exposition; 2010 Dec. 4-7; Orlando, Fla.; Meadows, et al. $52^{nd}$ Annual ASH Meeting and Exposition; 2010 Dec. 4-7; Orlando, Fla.; Kahl, B, et al. $52^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research $102^{nd}$ Annual Meeting; 2011 Apr. 2-6; Orlando, Fla.). PI3K-δ is the PI3K isoform that is most commonly activated in tumors where the PTEN tumor suppressor is mutated (Ward S, et al. (2003) *Chem Biol.* 10(3):207-13). In this subset of tumors, treatment with the PI3K-δ inhibitor either alone or in combination with a cytotoxic agent can be effective.

Another mechanism for PI3K-δ inhibitors to have an effect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. 52$^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenvironment, including stromal cells, immune cells, and endothelial cells and be therapeutic either on its own or in conjunction with another therapy (Meadows, S A, et al. Paper presented at: 52$^{nd}$ Annual ASH Meeting and Exposition; 2010 Dec. 4-7; Orlando, Fla.; Geng L, et al. (2004) *Cancer Res.* 64(14):4893-9).

In one embodiment, provided herein is a method of treating or preventing a cancer or disease, such as hematologic malignancy, or a specific type or sub-type of cancer or disease, such as a specific type or sub-type of hematologic malignancy, with a PI3K-γ selective inhibitor, wherein the adverse effects associated with administration of inhibitors for other isoform(s) of PI3K (e.g., PI3K-α and/or PI3K-β) are reduced. In one embodiment, provided herein is a method of treating or preventing a cancer or disease, such as hematologic malignancy, or a specific type or sub-type of cancer or disease, such as a specific type or sub-type of hematologic malignancy, with a PI3K-γ selective inhibitor, at a lower (e.g., by about 10%, by about 20%, by about 30%, by about 40%, by about 50%, by about 60%, by about 70%, or by about 80%) dose as compared to treatment with a PI3K-γ non-selective or less selective PI3K-γ inhibitor (e.g., a PI3Kpan inhibitors, e.g., inhibiting PI3K-α, β, δ, and γ).

The role of PI3K-γ pathway in promoting myeloid cell trafficking to tumors and the role of blockade of p100γ in suppression of tumor inflammation and growth in breast cancer, pancreatic cancer, and lung cancer are reported, for example, in Schmid et al. (2011) *Cancer Cell* 19, 715-727, the entirety of which is incorporated herein by reference. In one embodiment, provided herein is a method of treating or preventing pancreatic cancer with a PI3K inhibitor. In another embodiment, provided herein is a method of treating or preventing breast cancer with a PI3K inhibitor. In yet another embodiment, provided herein is a method of treating or preventing lung cancer with a PI3K inhibitor. In one embodiment, the PI3K inhibitor is a PI3K-γ inhibitor, selective or non-selective over one or more other PI3K isoform (s). In one embodiment, the PI3K inhibitor is a PI3K-γ selective inhibitor.

In certain embodiments, provided herein is a method of treating a disorder or disease provided herein, comprising administering a compound provided herein, e.g., a PI3K γ selective inhibitor, a PI3K δ selective inhibitor, or a PI3K γ/δ dual inhibitor. Without being limited by a particular theory, in some embodiments, selectively inhibiting PI3K-γ isoform can provide a treatment regimen where adverse effects associated with administration of a non-selective PI3K inhibitor are minimized or reduced. Without being limited by a particular theory, in some embodiments, selectively inhibiting PI3K-δ isoform can provide a treatment regimen where adverse effects associated with administration of a non-selective PI3K inhibitor are minimized or reduced. Without being limited by a particular theory, in some embodiments, selectively inhibiting PI3K-δ and γ isoform can provide a treatment regimen where adverse effects associated with administration of a non-selective PI3K inhibitor are minimized or reduced. Without being limited by a particular theory, it is believed that the adverse effects can be reduced by avoiding the inhibition of other isoforms (e.g., α or β) of PI3K.

In one embodiment, the adverse effect is hyperglycemia. In another embodiment, the adverse effect is rash. In another embodiment, the adverse effect is impaired male fertility that may result from inhibition of β isoform of PI3K (see, e.g., Ciraolo et al., *Molecular Biology of the Cell*, 21: 704-711 (2010)). In another embodiment, the adverse effect is testicular toxicity that may result from inhibition of PI3K-β (see, e.g., Wisler et al., Amgen SOT. Abstract ID #2334 (2012)). In another embodiment, the adverse effect is embryonic lethality (see, e.g., Bi et al., *J Biol Chem*, 274: 10963-10968 (1999)). In another embodiment, the adverse effect is defective platelet aggregation (see, e.g., Kulkarni et al., *Science*, 287: 1049-1053 (2000)). In another embodiment, the adverse effect is functionally defective neutrophil (id.).

In certain embodiments, the PI3K-γ inhibitor selectively modulates phosphatidyl inositol-3 kinase (PI3 kinase) gamma isoform. In one embodiment, the PI3K-γ inhibitor selectively inhibits the gamma isoform over the alpha, beta, or delta isoform. In one embodiment, the PI3K-γ inhibitor selectively inhibits the gamma isoform over the alpha or beta isoform. In one embodiment, the PI3K-γ inhibitor selectively inhibits the gamma isoform over the alpha, beta, and delta isoforms. In one embodiment, the PI3K-γ inhibitor selectively inhibits the gamma isoform over the alpha and beta isoforms. In one embodiment, the PI3K-γ inhibitor selectively inhibits the gamma isoform over the alpha and beta isoforms, but not the delta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_0$ values, among other means. In one embodiment, the selectivity of PI3K gamma isoform over an other PI3K isoform is measured by the ratio of the $IC_{50}$ value against the other PI3K isoform to the $IC_{50}$ value against PI3K gamma isoform. In certain embodiments, the PI3 kinase gamma isoform $IC_{50}$ activity of a compound as disclosed herein can be less than about 1000 nM, less than about 100 nM, less than about 10 nM, or less than about 1 nM. For example, a compound that selectively inhibits one isoform of PI3K over another isoform of PI3K has an activity of at least 2× against a first isoform relative to the compound's activity against the second isoform (e.g., at least about 3×, 5×, 10×, 20×, 50×, 100×, 200×, 500×, or 1000×).

In other embodiments, inhibition of PI3K (such as PI3K-δ and/or PI3K-γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A, et al. (2005) *J. Child Neurol.* 20:424-429), Tourette's syndrome (TS), obsessive compulsive disorder (OCD) (Asbahr, F. R, et al. (1998) *Am. J. Psychiatry* 155:1122-1124), attention deficit/hyperactivity disorder (AD/HD) (Hirschtritt, M. E, et al. (2008) *Child Neuropsychol.* 1:1-16; Peterson, B. S, et al. (2000) *Arch. Gen. Psychiatry* 57:364-372), anorexia nervosa (Sokol, M. S. (2000) *J. Child Adolesc. Psychopharmacol.* 10:133-145; Sokol, M. S. et al. (2002) *Am. J. Psychiatry*

159:1430-1432), depression (Leslie, D. L, et al. (2008) *J. Am. Acad. Child Adolesc. Psychiatry* 47:1166-1172), and autism spectrum disorders (ASD) (Hollander. E, et al. (1999) *Am. J. Psychiatry* 156:317-320; Margutti, P, et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113:883-886; Garvey, M. A, et al. (1998) *J. Clin. Neurol.* 13:413-423). Many of the PANDAS disorders share a common mechanism of action resulting from antibody responses against streptococcal associated epitopes, such as GlcNAc, which produces neurological effects (Kirvan, C. A. et al. (2006) *J. Neuroimmunol.* 179: 173-179). Autoantibodies recognizing central nervous system (CNS) epitopes are also found in sera of most PANDAS subjects (Yaddanapudi, K, et al. (2010) *Mol. Psychiatry* 15:712-726). Thus, several neuropsychiatric disorders have been associated with immune and autoimmune components, making them suitable for therapies that include PI3K-δ and/or PI3K-γ inhibition.

In certain embodiments, a method of treating (e.g., reducing or ameliorating one or more symptoms of) a neuropsychiatric disorder, (e.g., an autoimmune brain disorder), using a PI3K-δ and/or PI3K-γ inhibitor is described, alone or in combination therapy. For example, one or more PI3K-δ and/or PI3K-γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or PI3K-γ inhibitors described herein include, but are not limited to, PANDAS disorders. Sydenham's chorea. Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder. Asperger's Disorder, Childhood Disintegrative Disorder (CDD), Rett's Disorder and PDD—Not Otherwise Specified (PDD-NOS). Animal models for evaluating the activity of the PI3K-δ and/or PI3K-γ inhibitor are known in the art. For example, a mouse model of PANDAS disorders is described in, e.g., Yaddanapudi. K, et al. (2010) supra; and Hoffman. K. I. et al. (2004) *J. Neurosci.* 24:1780-1791.

In some embodiments, provided herein is a method for treating rheumatoid arthritis or asthma in a subject or for reducing a rheumatoid arthritis-associated symptom or an asthma-associated symptom in a subject, comprising administering an effective amount of a PI3K-γ inhibitor to a subject in need thereof, wherein one or more of the adverse effects associated with administration of inhibitors for one or more other isoforms of PI3K are reduced. In one embodiment, the one or more other isoforms of PI3K is PI3K-α, PI3K-β, and/or PI3K-δ. In one embodiment, the one or more other isoforms of PI3K is PI3K-α and/or PI3K-β. In one embodiment, the method is for treating rheumatoid arthritis in a subject, or for reducing a rheumatoid arthritis-associated symptom in a subject. In another embodiment, the method is for treating asthma in a subject, or for reducing an asthma-associated symptom in a subject.

In some embodiments, provided herein are methods of using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, to treat disease conditions, including, but not limited to, diseases associated with malfunctioning of one or more types of PI3 kinase. In one embodiment, a detailed description of conditions and disorders mediated by p110δ kinase activity is set forth in Sadu et al., WO 01/81346, which is incorporated herein by reference in its entirety for all purposes.

In some embodiments, the disclosure relates to a method of treating a hyperproliferative disorder in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the disclosure relates to a method of treating a solid tumor. In some embodiments, the solid tumor is selected from ovarian cancer, colon cancer, fibrosarcoma, pancreatic cancer, lung cancer, breast cancer, lymphoma, melanoma, and glioblastoma.

As used herein "solid tumor" refers to an abnormal mass of tissue. Solid tumors may be benign or malignant. A solid tumor grows in an anatomical site outside the bloodstream and requires the formation of small blood vessels and capillaries to supply nutrients, etc. to the growing tumor mass. Solid tumors are named for the type of cells that form them. Non-limiting examples of solid tumors are sarcomas, carcinomas (epithelial tumors), melanomas, and glioblastomas.

In some embodiments, the disclosure relates to a method of inhibiting growth of a tumor. "Inhibiting growth of a tumor" refers to slowing tumor growth and/or reducing tumor size. "Inhibiting growth of a tumor" thus includes killing tumor cells as well as slowing or arresting tumor cell growth.

In some embodiments, the disclosure relates to a method of treating a solid tumor comprising administering to a subject a gamma selective compound.

In some embodiments, the disclosure relates to a method of treating an inflammatory disease comprising administering to a subject a gamma selective compound.

In some embodiment, the gamma selective compound has a delta/gamma selectivity ratio of >1 to <10, 10 to <50, or 50 to <350 can be combined with a compound that has a gamma/delta selectivity ratio of greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000.

Patients that can be treated with a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, according to the methods as provided herein include, for example, but not limited to, patients that have been diagnosed as having psoriasis; restenosis; atherosclerosis; BPH: breast cancer such as a ductal carcinoma, lobular carcinoma, medullary carcinomas, colloid carcinomas, tubular carcinomas, and inflammatory breast cancer, ovarian cancer, including epithelial ovarian tumors such as adenocarcinoma in the ovary and an adenocarcinoma that has migrated from the ovary into the abdominal cavity uterine cancer, cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer, lung cancer such as non-small cell lung cancer (NSCLC), which is divided into squamous cell carcinomas, adenocarcinomas, and large cell undifferentiated carcinomas, and small cell lung cancer, skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer, thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotrophic virus-type 1 (HTLV-1) and adult T-cell leukemia/lymphoma; and human papilloma virus (HPV) and cervical cancer, central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Müllierian tumor, oral cavity and oropharyngeal cancers such as, hypopharyngeal cancer, laryngeal cancer, nasopharyngeal cancer, and oropharyngeal cancer stomach cancers such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas carcinoids or carcinoid tumors; rectal cancer, and colon cancer.

Patients that can be treated with compounds provided herein, or pharmaceutically acceptable salt, ester, prodrug, solvate, hydrate or derivative of said compounds, according to the methods provided herein include, for example, patients that have been diagnosed as having conditions including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarcinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphoctic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Stemberg disease; acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a, myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic adenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenström's macroglobulinemia.

Without being limited by a particular theory, in one embodiment, the cancer or disease being treated or prevented, such as a blood disorder or hematologic malignancy, has a high expression level of one or more PI3K isoform(s) (e.g., PI3K-α, PI3K-β, PI3K-δ, or PI3K-γ, or a combination thereof). In one embodiment, the cancer or disease that can be treated or prevented by methods, compositions, or kits provided herein includes a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others. In one embodiment, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CML), blast phase CML, small lymphocytic lymphoma (SLL), CLL/SLL, blast phase CLL, Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sézary syndrome, anaplastic large-cell lymphoma (ALCL), follicular lymphoma (FL), Waldenström macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), angioimmunoblastic lymphoma, high-risk MDS, and low-risk MDS. In one embodiment, the hematologic malignancy is relapsed. In one embodiment, the hematologic malignancy is refractory. In one embodiment, the cancer or disease is in a pediatric patient (including an infantile patient). In one embodiment, the cancer or disease is in an adult patient. Additional embodiments of a cancer or disease being treated or prevented by methods, compositions, or kits provided herein are described herein elsewhere.

In exemplary embodiments, the cancer or hematologic malignancy is CLL. In exemplary embodiments, the cancer or hematologic malignancy is CLL/SLL. In exemplary embodiments, the cancer or hematologic malignancy is blast phase CLL. In exemplary embodiments, the cancer or hematologic malignancy is SLL.

In exemplary embodiments, the cancer or hematologic malignancy is iNHL. In exemplary embodiments, the cancer or hematologic malignancy is DLBCL. In exemplary embodiments, the cancer or hematologic malignancy is B-cell NHL (e.g., aggressive B-cell NHL). In exemplary embodiments, the cancer or hematologic malignancy is MCL. In exemplary embodiments, the cancer or hematologic malignancy is RS. In exemplary embodiments, the cancer or hematologic malignancy is AML. In exemplary embodiments, the cancer or hematologic malignancy is MM. In exemplary embodiments, the cancer or hematologic malignancy is ALL. In exemplary embodiments, the cancer or hematologic malignancy is T-ALL. In exemplary embodiments, the cancer or hematologic malignancy is B-ALL. In exemplary embodiments, the cancer or hematologic malignancy is TCL. In exemplary embodiments, the cancer or hematologic malignancy is ALCL. In exemplary embodiments, the cancer or hematologic malignancy is leukemia. In exemplary embodiments, the cancer or hematologic malignancy is lymphoma. In exemplary embodiments, the cancer or hematologic malignancy is T-cell lymphoma. In exemplary embodiments, the cancer or hematologic malignancy is MDS (e.g., low grade MDS). In exemplary embodiments, the cancer or hematologic malignancy is MPD. In exemplary embodiments, the cancer or hematologic malignancy is a mast cell disorder. In exemplary embodiments, the cancer or hematologic malignancy is Hodgkin lymphoma (HL). In exemplary embodiments, the cancer or hematologic malignancy is non-Hodgkin lymphoma. In exemplary embodiments, the cancer or hematologic malignancy is PTCL. In exemplary embodiments, the cancer or hematologic malignancy is CTCL (e.g., mycosis fungoides or Sézary syndrome). In exemplary embodiments, the cancer or hematologic malignancy is WM. In exemplary embodiments, the cancer or hematologic malignancy is CML. In exemplary embodiments, the cancer or hematologic malignancy is FL. In exemplary embodiments, the cancer or hematologic malignancy is transformed mycosis fungoides. In exemplary embodiments, the cancer or hematologic malignancy is Sézary syndrome. In exemplary embodiments, the cancer or hematologic malignancy is acute T-cell leukemia. In exemplary embodiments, the cancer or hematologic malignancy is acute B-cell leukemia. In exemplary embodiments, the cancer or hematologic malignancy is Burkitt lymphoma. In exemplary embodiments, the cancer or hematologic malignancy is myeloproliferative neoplasms. In exemplary embodiments, the cancer or hematologic malignancy is splenic marginal zone. In exemplary embodiments, the cancer or hematologic malignancy is nodal marginal zone. In exemplary embodiments, the cancer or hematologic malignancy is extranodal marginal zone.

In one embodiment, the cancer or hematologic malignancy is a B cell lymphoma. In a specific embodiment, provided herein is a method of treating or managing a B cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a B cell lymphoma comprising administering to a patient a therapeutically effective amount of a compound provided herein, or a pharmaceutically acceptable derivative (e.g., salt or solvate) thereof. In one embodiment, the B cell lymphoma is iNHL. In another embodiment, the B cell lymphoma is follicular lymphoma. In another embodiment, the B cell lymphoma is Waldenstrom macroglobulinemia (lymphoplasmacytic lymphoma). In another embodiment, the B cell lymphoma is marginal zone lymphoma (MZL). In another embodiment, the B cell lymphoma is MCL. In another embodiment, the B cell lymphoma is HL. In another embodiment, the B cell lymphoma is aNHL. In another embodiment, the B cell lymphoma is DLBCL. In another embodiment, the B cell lymphoma is Richters lymphoma.

In one embodiment, the cancer or hematologic malignancy is a T cell lymphoma. In a specific embodiment, provided herein is a method of treating or managing a T cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a T cell lymphoma comprising administering to a patient a therapeutically effective amount of a compound provided herein, or a pharmaceutically acceptable derivative (e.g., salt or solvate) thereof. In one embodiment, the T cell lymphoma is peripheral T cell lymphoma (PTCL). In another embodiment, the T cell lymphoma is cutaneous T cell lymphoma (CTCL).

In one embodiment, the cancer or hematologic malignancy is Sézary syndrome. In a specific embodiment, provided herein is a method of treating or managing Sézary syndrome comprising administering to a patient a therapeutically effective amount of a compound provided herein, or a pharmaceutically acceptable derivative (e.g., sat or solvate) thereof Also provided herein is a method of treating or lessening one or more of the symptoms associated with Sézary syndrome comprising administering to a patient a therapeutically effective amount of a compound provided herein, or a pharmaceutically acceptable derivative (e.g., salt or solvate) thereof. The symptoms associated with Sézary syndrome include, but are not limited to, epidermotropism by neoplastic CD4+ lymphocytes, Pautrier's microabscesses, erythroderma, lymphadenopathy, atypical T cells in the peripheral blood, and hepatosplenomegaly In one embodiment, the therapeutically effective amount for treating or managing Sézary syndrome is from about 25 mg to 75 mg, administered twice daily. In other embodiments, the therapeutically effective amount is from about 50 mg to about 75 rag, from about 30 mg to about 65 mg, from about 45 mg to about 60 rag, from about 30 mg to about 50 mg, or from about 55 mg to about 65 mg, each of which is administered twice daily. In one embodiment, the effective amount is about 60 mg, administered twice daily.

In one embodiment, the cancer or hematologic malignancy is relapsed. In one embodiment, the cancer or hematologic malignancy is refractory. In certain embodiments, the cancer being treated or prevented is a specific sub-type of cancer described herein. In certain embodiments, the hematologic malignancy being treated or prevented is a specific sub-type of hematologic malignancy described herein. Certain classifications of type or sub-type of a cancer or hematologic malignancy provided herein is known in the art. Without being limited by a particular theory, it is believed that many of the cancers that become relapsed or refractory develop resistance to the particular prior therapy administered to treat the cancers. Thus, without being limited by a particular theory, a compound provided herein can provide a second line therapy by providing an alternative mechanism to treat cancers different from those mechanisms utilized by certain prior therapies. Accordingly, in one embodiment, provided herein is a method of treating or managing cancer or hematologic malignancy comprising administering to a patient a therapeutically effective amount of a compound provided herein, or a pharmaceutically acceptable derivative (e.g., salt or solvate) thereof, wherein the cancer or hematologic malignancy is relapsed after, or refractory to, a prior therapy.

In exemplary embodiments, the cancer or hematologic malignancy is refractory iNHL. In exemplary embodiments, the cancer or hematologic malignancy is refractory CLL. In exemplary embodiments, the cancer or hematologic malignancy is refractory SLL. In exemplary embodiments, the cancer or hematologic malignancy is refractory to rituximab therapy. In exemplary embodiments, the cancer or hematologic malignancy is refractory to chemotherapy. In exemplary embodiments, the cancer or hematologic malignancy is refractory to radioimmunotherapy (RIT). In exemplary embodiments, the cancer or hematologic malignancy is iNHL, FL, splenic marginal zone, nodal marginal zone, extranodal marginal zone, or SLL, the cancer or hematologic malignancy is refractory to rituximab therapy, chemotherapy, and/or RIT.

In another exemplary embodiment, the cancer or hematologic malignancy is lymphoma, and the cancer is relapsed after, or refractory to, the treatment by a BTK inhibitor such as, but not limited to, ibrutinib. In another exemplary embodiment, the cancer or hematologic malignancy is CLL, and the cancer is relapsed after, or refractory to, the treatment by a BTK inhibitor such as, but not limited to, ibrutinib and AVL-292.

In one embodiment, provided herein is a method of treating an inflammation disorder, including autoimmune diseases in a subject. The method comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Examples of autoimmune diseases include but are not limited to acute disseminated encephalomyelitis (ADEM), Addison's disease, antiphospholipid antibody syndrome (APS), aplastic anemia, autoimmune hepatitis, autoimmune skin disease, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia. Wegener's granulomatosis, alopecia universalis (e.g., inflammatory alopecia). Chagas disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gout flare, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease. Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, polymyalgia rheumatic, reperfusion injury, regional enteritis, rheumatic fever, systemic lupus erythematosus, scleroderma, scleroderma, sarcoidosis, spondyloarthropathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammation disorder is selected from arthritis (e.g., rheumatoid arthritis), inflammatory bowel disease, inflammatory bowel syndrome, asthma, psoriasis, endometriosis, interstitial cystitis and prostatitis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthropathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), relapsing polychondritis (e.g., atrophic polychondritis and systemic polychondromalacia), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)). In certain embodiments, a method of treating inflammatory or autoimmune diseases is provided comprising administering to a subject (e.g., a mammal) a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, that selectively inhibit PI3K-δ and/or PI3K-γ as compared to all other type I PI3 kinases. Such selective inhibition of PI3K-δ and/or PI3K-γ can be advantageous for treating any of the diseases or conditions described herein. For example, selective inhibition of PI3K-δ and/or PI3K-γ can inhibit inflammatory responses associated with inflammatory diseases, autoimmune disease, or diseases related to an undesirable immune response including, but not limited to asthma, emphysema, allergy, dermatitis, rheumatoid arthritis, psoriasis, lupus erythematosus, anaphylaxis, or graft versus host disease. Selective inhibition of PI3K-δ and/or PI3K-γ can further provide for a reduction in the inflammatory or undesirable immune response without a concomitant reduction in the ability to reduce a bacterial, viral, and/or fungal infection. Selective inhibition of both PI3K-δ and PI3Kγ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including, but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, or 60%, or about 75% to 90%. In another aspect, the subject methods are effective in reducing knee inflammation by at least about 2%, 5%, 10%, 15%, 20%, 25%, 30%, 50%, or 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, or 87%, or about 90% or more. In another aspect, the subject methods are effective in reducing ankle histopathology scores by about 5%, 10% 15%, 20%, 25%, 30%, 40%, 50%, 60%, 75%, 80%, or 90%, or more. In still another aspect, the subject methods are effective in reducing knee histopathology scores by about 5%, 10%, 15%, 20%, 25%, 30%, 40%, 50%, 60%, 75%, 80%, or 90%, or more.

In some embodiments, provided herein are methods for treating disorders or conditions in which the δ isoform of PI3K is implicated to a greater extent than other PI3K isoforms such as PI3K-α and/or PI3K-α. In some embodiments, provided herein are methods for treating disorders or conditions in which the γ isoform of PI3K is implicated to a greater extent than other PI3K isoforms such as PI3K-α and/or PI3K-β. Selective inhibition of PI3K-δ and/or PI3K-γ can provide advantages over using less selective compounds which inhibit PI3K-α and/or PI3K-β, such as an improved side effects profile or lessened reduction in the ability to reduce a bacterial, viral, and/or fungal infection.

In other embodiments, provided herein are methods of using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, to treat respiratory diseases including, but not limited to, diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein is used for the treatment of asthma. Also, a compound provided herein, or a pharmaceutically acceptable form thereof, or a pharmaceutical composition described herein, can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In some embodiments, the disclosure provides a method of treating diseases related to vasculogenesis or angiogenesis in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. In some embodiments, said method is for treating a disease selected from tumor angiogenesis, chronic inflammatory disease such as rheumatoid arthritis and chronic inflammatory demyelinating polyneuropathy, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma. Kaposi's sarcoma and ovarian, breast, lung, pancreatic, prostate, colon and epidermoid cancer.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

In some embodiments, provided herein is a method of treating a cardiovascular disease in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein. Examples of cardiovascular conditions include, but are not limited to, atherosclerosis, restenosis, vascular occlusion and carotid obstructive disease.

In some embodiments, the disclosure relates to a method of treating diabetes in a subject that comprises administering to said subject a therapeutically effective amount of a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein.

In addition, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used to treat acne. In certain embodiments, the inflamatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritis.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

Further, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of multiorgan failure. Also provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the prevention of blastocyte implantation in a subject.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of disorders involving platelet aggregation or platelet adhesion, including, but not limited to, Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of a disease which is skeletal muscle atrophy, skeletal or muscle hypertrophy. In some embodiments, provided herein are compounds, or pharmaceutically acceptable forms (e.g., pharmaceutically acceptable salts, hydrates, solvates, isomers, prodrugs, and isotopically labeled derivatives) thereof, or pharmaceutical compositions as provided herein, for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease. Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

Additionally, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used for the treatment of bursitis, lupus, acute disseminated encephalomyelitis (ADEM), Addison's disease, antiphospholipid antibody syndrome (APS), amyloidosis (including systemic and localized amyloidosis; and primary and secondary amyloidosis), aplastic anemia, autoimmune hepatitis, coeliac disease, crohn's disease, diabetes mellitus (type 1), eosinophilic gastroenterides, goodpasture's syndrome, graves' disease, guillain-barré syndrome (GBS), hashimoto's disease, inflammatory bowel disease, lupus erythematosus (including cutaneous lupus erythematosus and systemic lupus erythematosus), myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonoumia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis (e.g., ocular uveitis), vaginitis, vasculitis, or vulvitis.

Further, the compounds provided herein may be used for the treatment of Perennial allergic rhinitis, Mesenteritis, Peritonitis, Acrodermatitis, Angiodermatitis, Atopic dermatitis, Contact dermatitis, Eczema, Erythema multiforme, Intertrigo, Stevens Johnson syndrome, Toxic epidermal necrolysis, Skin allergy, Severe allergic reaction/anaphylaxis, Allergic granulomatosis, Wegener granulomatosis, Allergic conjunctivitis, Chorioretinitis, Conjunctivitis, Infectious keratoconjunctivitis, Keratoconjunctivitis, Ophthalmia neonatorum, Trachoma, Uveitis, Ocular inflammation, Blepharoconjunctivitis, Mastitis, Gingivitis, Pericoronitis, Pharyngitis, Rhinopharyngitis, Sialadenitis, Musculoskeletal system inflammation, Adult onset Stills disease, Behcets disease, Bursitis, Chondrocalcinosis, Dactylitis, Felty syndrome, Gout, Infectious arthritis, Lyme disease, Inflammatory osteoarthritis, Periarthritis, Reiter syndrome, Ross River virus infection, Acute Respiratory, Distress Syndrome, Acute bronchitis, Acute sinusitis, Allergic rhinitis, Asthma, Severe refractory asthma, Pharyngitis, Pleurisy, Rhinopharyngitis, Seasonal allergic rhinitis, Sinusitis, Status asthmaticus, Tracheobronchitis, Rhinitis, Serositis, Meningitis, Neuromyelitis optica, Poliovirus infection, Alport syndrome, Balanitis, Epididymitis, Epididymo orchitis, Focal segmental, Glomerulosclerosis, Glomerulonephritis, IgA Nephropathy (Berger's Disease), Orchitis, Parametritis, Pelvic inflammatory disease, Prostatitis, Pyelitis, Pyelocystitis, Pyelonephritis, Wegener granulomatosis, Hyperuricemia, Aortitis, Arteritis, Chylopericarditis, Dressier syndrome, Endarteritis, Endocarditis, Extracranial temporal arteritis, HIV associated arteritis, Intracranial temporal arteritis, Kawasaki disease, Lymphangiophlebitis, Mondor disease, Periarteritis, or Pericarditis.

In other aspects, the compounds provided herein are used for the treatment of Autoimmune hepatitis, Jejunitis, Mesenteritis, Mucositis, Non alcoholic steatohepatitis, Non viral hepatitis, Autoimmune pancreatitis, Perihepatitis, Peritonitis, Pouchitis, Proctitis, Pseudomembranous colitis, Rectosigmoiditis, Salpingoperitonitis, Sigmoiditis, Steatohepatitis, Ulcerative colitis, Churg Strauss syndrome, Ulcerative proctitis, Irritable bowel syndrome, Gastrointestinal inflammation, Acute enterocolitis, Anusitis, Balser necrosis, Cholecystitis, Colitis, Crohns disease, Diverticulitis, Enteritis, Enterocolitis, Enterohepatitis, Eosinophilic esophagitis, Esophagitis, Gastritis, Hemorrhagic enteritis, Hepatitis, Hepatitis vinis infection, Hepatocholangitis, Hypertrophic gastritis, Ileitis, Ileocecitis, Sarcoidosis, Inflammatory bowel disease, Ankylosing spondylitis, Rheumatoid arthritis, Juvenile rheumatoid arthritis, Psoriasis, Psoriatic arthritis, Lupus (cutaneous/systemic/nephritis), AIDS, Agammaglobulinemia, AIDS related complex, Brutons disease, Chediak Higashi syndrome, Common variable immunodeficiency, DiGeorge syndrome, Dysgammaglobulinemia, Immunoglobulindeficiency, Job syndrome, Nezelof syndrome, Phagocyte bactericidal disorder, Wiskott Aldrich syndrome, Asplenia, Elephantiasis, Hypersplenism, Kawasaki disease, Lymphadenopathy, Lymphedema, Lymphocele, Nonne Milroy Meige syndrome, Spleen disease, Splenomegaly, Thymoma, Thymus disease, Perivasculitis, Phlebitis, Pleuropericarditis, Polvarteritis nodosa, Vasculitis, Takayasus arteritis, Temporal arteritis, Thromboangiitis, Thromboangiitis obliterans, Thromboendocarditis, Thrombophlebitis, or COPD.

In another aspect, provided herein are methods of disrupting the function of a leukocyte or disrupting a function of an osteoclast. The method includes contacting the leukocyte or the osteoclast with a function disrupting amount of a compound provided herein.

In another aspect, provided herein are methods for the treatment of an ophthalmic disease by administering one or more of compounds provided herein, or pharmaceutically acceptable forms thereof, or pharmaceutical compositions as provided herein, to the eye of a subject.

Methods are further provided for administering the compounds provided herein via eye drop, intraocular injection, intravitreal injection, topically, or through the use of a drug eluting device, microcapsule, implant, or microfluidic device. In some cases, the compounds provided herein are administered with a carrier or excipient that increases the intraocular penetrance of the compound such as an oil and water emulsion with colloid particles having an oily core surrounded by an interfacial film.

In certain embodiments, provided herein are methods of treating, preventing, and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: Crohn's disease; cutaneous lupus; multiple sclerosis; rheumatoid arthritis; and systemic lupus erythematosus.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: ankylosing spondylitis; chronic obstructive pulmonary disease; myasthenia gravis; ocular uveitis, psoriasis; and psoriatic arthritis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: adult-onset Still's disease; inflammatory alopecia; amyloidosis; antiphospholipid syndrome; autoimmune hepatitis; autoimmune skin disease. Behcet's disease; chronic inflammatory demyelinating polyneuropathy; eosinophilic gastroenteritis; inflammatory myopathies, pemphigus, polymyalgia rheumatica; relapsing polychondritis; Sjorgen's syndrome; temporal arthritis; ulcerative colitis; vasculis; vitiligo, and Wegner's granulomatosis.

In other embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: gout flare; sacoidosis; and systemic sclerosis.

In certain embodiments, provided herein are methods of treating, preventing and/or managing a disease or a disorder using a compound, or a pharmaceutically acceptable form (e.g., pharmaceutically acceptable salts, hydrates, solvates, isomers, prodrugs, and isotopically labeled derivatives) thereof, or pharmaceutical compositions as provided herein, wherein the disease or disorder is: asthma; arthritis (e.g., rheumatoid arthritis and psoriatic arthritis); psoriasis; scleroderma; myositis (e.g., dermatomyositis); lupus (e.g., cutaneous lupus erythematosus ("CLE") or systemic lupus erythematosus ("SLE")); or Sjögren's syndrome.

Efficacy of a compound provided herein in treating, preventing and/or managing the disease or disorder can be tested using various animal models known in the art. For example: efficacy in treating, preventing and/or managing asthma can be assessed using ova induced asthma model described, for example, in Lee et al. (2006) *J Allergy Clin Immunol* 118(2):403-9; efficacy in treating, preventing and/or managing arthritis (e.g., rheumatoid or psoriatic arthritis) can be assessed using autoimmune animal models described, for example, in Williams et al. (2010) *Chem Biol*, 17(2): 123-34, WO 2009/088986, WO2009/088880, and WO 2011/008302; efficacy in treating, preventing and/or managing psoriasis can be assessed using transgenic or knockout mouse model with targeted mutations in epidermis, vasculature or immune cells, mouse model resulting from spontaneous mutations, and immuno-deficient mouse model with xenotransplantation of human skin or immune cells, all of which are described, for example, in Boehncke et al. (2007) *Clinics in Dermatology*, 25: 596-605; efficacy in treating, preventing and/or managing fibrosis or fibrotic condition can be assessed using the unilateral ureteral obstruction model of renal fibrosis (see Chevalier et al., *Kidney International* (2009) 75:1145-1152), the bleomycin induced model of pulmonary fibrosis (see Moore and Hogaboam, *Am. J. Physiol. Lung. Cell. Mol. Physiol.* (2008) 294:L152-L160), a variety of liver/biliary fibrosis models (see Chuang et al., *Clin Liver Dis* (2008) 12:333-347 and Omenetti, A, et al. (2007) *Laboratory Investigation* 87:499-514 (biliary duct-ligated model)), or a number of myelofibrosis mouse models (see Varicchio, L, et al. (2009) *Expert Rev. Hematol.* 2(3): 315-334); efficacy in treating, preventing and/or managing scleroderma can be assessed using mouse model induced by repeated local injections of bleomycin ("BLM") described, for example, in Yamamoto et al. (1999) *J Invest Dermatol* 112: 456-462; efficacy in treating, preventing and/or managing dermatomyositis can be assessed using myositis mouse model induced by immunization with rabbit myosin described, for example, in Phyanagi et al. (2009) *Arthritis & Rheumatism*, 60(10): 3118-3127; efficacy in treating, preventing and/or managing lupus (e.g., CLE or SLE) can be assessed using various animal models described, for example, in Ghoreishi et al. (2009) *Lupus,* 19: 1029-1035, Ohl et al. (2011) *Journal of Biomedicine and Biotechnology,* Article ID 432595 (14 pages), Xia et al. (2011) *Rheumatology,* 50:2187-2196, Pau et al. (2012) *PLoS ONE,* 7(5): e36761 (15 pages), Mustafa et al. (2011) *Toxicology,* 290: 156-168, Ichikawa et al. (2012) *Arthritis and Rheumatism,* 62(2): 493-503, Ouyang et al. (2012) *J Mol Med,* DOI 10.1007/s00109-012-0866-3 (10 pages), Rankin et al. (2012) *Journal of Immunology,* 188:1656-1667; and efficacy in treating, preventing and/or managing Sjögren's syndrome can be assessed using various mouse models described, for example, in Chiorini et al. (2009) *Journal of Autoimmunity,* 33: 190-196.

In one embodiment, provided herein is a method of treating, preventing and/or managing asthma. As used herein, "asthma" encompasses airway constriction regardless of the cause. Common triggers of asthma include, but are not limited to, exposure to an environmental stimulants (e.g., allergens), cold air, warm air, perfume, moist air, exercise or exertion, and emotional stress. Also provided herein is a method of treating, preventing and/or managing one or more symptoms associated with asthma. Examples of the symptoms include, but are not limited to, severe coughing, airway constriction and mucus production.

In one embodiment, provided herein is a method of treating, preventing and/or managing arthritis. As used herein, "arthritis" encompasses all types and manifestations of arthritis. Examples include, but are not limited to, crystalline arthritis, osteoarthritis, psoriatic arthritis, gouty arthritis, reactive arthritis, rheumatoid arthritis and Reiter's arthritis. In one embodiment, the disease or disorder is rheumatoid arthritis. In another embodiment, the disease or disorder is psoriatic arthritis. Also provided herein is a method of treating, preventing and/or managing one or more symptoms associated with arthritis. Examples of the symptoms include, but are not limited to, joint pain, which progresses into joint deformation, or damages in body organs such as in blood vessels, heart, lungs, skin, and muscles.

In one embodiment, provided herein is a method of treating, preventing and/or managing psoriasis. As used herein, "psoriasis" encompasses all types and manifestations of psoriasis. Examples include, but are not limited to, plaque psoriasis (e.g., chronic plaque psoriasis, moderate plaque psoriasis and severe plaque psoriasis), guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Also provided herein is a method of treating, preventing and/or managing one or more symptoms associated with psoriasis. Examples of the symptoms include, but are not limited to: red patches of skin covered with silvery scales; small scaling spots; dry, cracked skin that may bleed; itching; burning; soreness; thickened, pitted or ridged nails; and swollen and stiff joints.

In one embodiment, provided herein is a method of treating, preventing and/or managing fibrosis and fibrotic condition. As used herein, "fibrosis" or "fibrotic condition" encompasses all types and manifestations of fibrosis or fibrotic condition. Examples include, but are not limited to, formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is associated with an autoimmune disease selected from scleroderma or lupus, e.g., systemic lupus erythematosus. In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs, host disease, or atherosclerosis.

In certain embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In other embodiment, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods provided herein is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, or focal segmental glomerulosclerosis (FSGS).

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogenous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In one embodiment, provided herein is a method of treating, preventing and/or managing scleroderma. Scleroderma is a group of diseases that involve hardening and tightening of the skin and/or other connective tissues. Scleroderma may be localized (e.g., affecting only the skin) or systemic (e.g., affecting other systems such as, e.g., blood vessels and/or internal organs). Common symptoms of scleroderma include Raynaud's phenomenon, gastroesophageal reflux disease, and skin changes (e.g., swollen fingers and hands, or thickened patches of skin). In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

Localized scleroderma (localized cutaneous fibrosis) includes morphea and linear scleroderma. Morphea is typically characterized by oval-shaped thickened patches of skin that are white in the middle, with a purple border. Linear scleroderma is more common in children Symptoms of linear scleroderma may appear mostly on one side of the body. In linear scleroderma, bands or streaks of hardened skin may develop on one or both arms or legs or on the forehead. En coup de sabre (frontal linear scleroderma or morphea en coup de sabre) is a type of localized scleroderma typically characterized by linear lesions of the scalp or face.

Systemic scleroderma (systemic sclerosis) includes, e.g., limited systemic sclerosis (also known as limited cutaneous systemic sclerosis, or CREST syndrome), diffuse systemic sclerosis (also known as diffuse cutaneous systemic sclerosis), and systemic sclerosis sine scleroderma. CREST stands for the following complications that may accompany limited scleroderma: calcinosis (e.g., of the digits), Raynaud's phenomenon, esophageal dysfunction, sclerodactyly, and telangiectasias. Typically, limited scleroderma involves cutaneous manifestations that mainly affect the hands, arms, and face. Limited and diffuse subtypes are distinguished based on the extent of skin involvement, with sparing of the proximal limbs and trunk in limited disease. See, e.g., Denton, C. P. et al. (2006), *Nature Clinical Practice Rheumatology*, 2(3):134-143. The limited subtype also typically involves a long previous history of Raynaud's phenomenon, whereas in the diffuse subtype, onset of Raynaud's phenomenon can be simultaneous with other manifestations or might occur later. Both limited and diffuse subtypes may involve internal organs. Typical visceral manifestations of limited systemic sclerosis include isolated pulmonary hypertension, severe bowel involvement, and pulmonary fibrosis. Typical visceral manifestations of diffuse systemic sclerosis include renal crisis, lung fibrosis, and cardiac disease. Diffuse systemic sclerosis typically progresses rapidly and affects a large area of the skin and one or more internal organs (e.g., kidneys, esophagus, heart, or lungs). Systemic sclerosis sine scleroderma is a rare disorder in which patients develop vascular and fibrotic damage to internal organs in the absence of cutaneous sclerosis.

In one embodiment, provided herein is a method of treating, preventing and/or managing inflammatory myopathies. As used herein, "inflammatory myopathies" encompass all types and manifestations of inflammatory myopathies. Examples include, but are not limited to, muscle weakness (e.g., proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, as well as biological concomitants of inflammatory myopathies as disclosed herein or as known in the art. Biological concomitants of inflammatory myopathies (e.g., dermatomyositis) include, e.g., altered (e.g., increased) levels of cytokines (e.g., Type I interferons (e.g., IFN-α and/or IFN-β), interleukins (e.g., IL-6, IL-10, IL-15, IL-17 and IL-18), and TNF-α), TGF-β, B-cell activating factor (BAFF), overexpression of IFN inducible genes (e.g., Type I IFN inducible genes). Other biological concomitants of inflammatory myopathies can include, e.g., an increased erythrocyte sedimentation rate (ESR) and/or elevated level of creatine kinase. Further biological concomitants of inflammatory myopathies can include autoantibodies, e.g., anti-synthetase autoantibodies (e.g., anti-Jo1 antibodies), anti-signal recognition particle antibodies (anti-SRP), anti-Mi-2 antibodies, anti-p155 antibodies, anti-PM/Sci antibodies, and anti-RNP antibodies.

The inflammatory myopathy can be an acute inflammatory myopathy or a chronic inflammatory myopathy. In some embodiments, the inflammatory myopathy is a chronic inflammatory myopathy (e.g., dermatomyositis, polymyositis, or inclusion body myositis). In some embodiments, the inflammatory myopathy is caused by an allergic reaction another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic. In some embodiments, the inflammatory myopathy is selected from polymyositis, dermatomyositis, inclusion body myositis, and immune-mediated necrotizing myopathy. In some embodiments, the inflammatory myopathy is dermatomyositis.

In another embodiment, provided herein is a method of treating, preventing and/or managing a skin condition (e.g., a dermatitis). In some embodiments, the methods provided herein can reduce symptoms associated with a skin condition (e.g., itchiness and/or inflammation). In some such embodiments, the compound provided herein is administered topically (e.g., as a topical cream, eye-drop, nose drop or nasal spray). In some such embodiments, the compound is a PI3K delta inhibitor (e.g., a PI3K inhibitor that demonstrates greater inhibition of PI3K delta than of other PI3K isoforms). In some embodiments, the PI3K delta inhibitor prevents mast cell degranulation.

As used herein, "skin condition" includes any inflammatory condition of the skin (e.g., eczema or dermatitis, e.g., contact dermatitis, atopic dermatitis, dermatitis herpetiformis, seborrheic dermatitis, nummular dermatitis, stasis dermatitis, perioral dermatitis), as well as accompanying symptoms (e.g., skin rash, itchiness (pruritis), swelling (edema), hay fever, anaphylaxis). Frequently, such skin conditions are caused by an allergen. As used herein, a "skin condition" also includes, e.g., skin rashes (e.g., allergic rashes, e.g., rashes resulting from exposure to allergens such as poison ivy, poison oak, or poison sumac, or rashes caused by other diseases or conditions), insect bites, minor burns, sunburn, minor cuts, and scrapes. In some embodiments, the symptom associated with inflammatory myopathy, or the skin condition or symptom associated with the skin condition, is a skin rash or itchiness (pruritis) caused by a skin rash.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., urticaria). In some embodiments, the skin condition is an insect bite. In some embodiments, the skin condition is associated with another disease (e.g., an inflammatory myopathy, e.g., dermatomyositis).

In some embodiments, the subject (e.g., the subject in need of treatment for an inflammatory myopathy and/or a skin condition) exhibits an elevated level or elevated activity of IFN-α, TNF-α, IL-6, IL-8, IL-1, or a combination thereof. In certain embodiments, the subject exhibits an elevated level of IFN-α. In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, or IL-1 in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

In one embodiment, provided herein is a method of treating, preventing and/or managing myositis. As used herein, "myositis" encompasses all types and manifestations of myositis. Examples include, but are not limited to, myositis ossificans, fibromyositis, idiopathic inflammatory myopathies, dermatomyositis, juvenile dermatomyositis, polymyositis, inclusion body myositis and pyomyositis. In one embodiment, the disease or disorder is dermatomyositis. Also provided herein is a method of treating, preventing and/or managing one or more symptoms associated with myositis. Examples of the symptoms include, but are not limited to: muscle weakness; trouble lifting anus; trouble swallowing or breathing; muscle pain; muscle tenderness; fatigue; fever, lung problems; gastrointestinal ulcers; intestinal perforations; calcinosis under the skin; soreness; arthritis; weight loss; and rashes.

In one embodiment, provided herein is a method of treating, preventing and/or managing lupus. As used herein, "lupus" refers to all types and manifestations of lupus. Examples include, but are not limited to, systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, hematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations. In one embodiment, the lupus is systemic lupus erythematosus (SLE), cutaneous lupus erythematosus (CLE), drug-induced lupus, or neonatal lupus. In another embodiment, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is chronic discloid lupus erythematosus (CDLE) or lupus erythematosus profundus (LEP) (also known as lupus erythematosus panniculitis). Types, symptoms, and pathogenesis of CLE are described, for example, in Wenzel et al. (2010), *Lupus,* 19, 1020-1028.

In one embodiment, provided herein is a method of treating, preventing and/or managing Sjögren's syndrome. As used herein, "Sjögren's syndrome" refers to all types and manifestations of Sjögren's syndrome. Examples include, but are not limited to, primary and secondary Sjögren's syndrome. Also provided herein is a method of treating, preventing and/or managing one or more symptoms associated with Sjögren's syndrome. Examples of the symptoms include, but are not limited to: dry eyes; dry mouth; joint pain; swelling; stiffness; swollen salivary glands; skin rashes; dry skin; vaginal dryness; persistent dry cough; and prolonged fatigue.

In some embodiments, a symptom associated with the disease or disorder provided herein is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease is statistically significant, for example, as assessed using an appropriate parametric or non-parametric statistical comparison.

Combination Therapy

In some embodiments, provided herein are methods for combination therapies in which an agent known to modulate other pathways, or other components of the same pathway, or even overlapping sets of target enzymes are used in combination with a compound provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and radiation treatment, to provide a synergistic or additive therapeutic effect.

By "in combination with," it is not intended to imply that the other therapy and the PI3K modulator must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies (e.g., one or more other additional agents). In general, each therapeutic agent will be administered at a dose and/or on a time schedule determined for that particular agent. The other therapeutic agent can be administered with the compound provided herein in a single composition or separately in a different composition. Triple therapy is also contemplated herein.

In general, it is expected that additional therapeutic agents employed in combination be utilized at levels that do not exceed the levels at which they are utilized individually. In some embodiments, the levels utilized in combination will be lower than those utilized individually.

In some embodiments, the compound provided herein is a first line treatment for cancer or hematologic malignancy, i.e., it is used in a subject who has not been previously administered another drug or therapy intended to treat cancer or hematologic malignancy or one or more symptoms thereof.

In other embodiments, the compound provided herein is a second line treatment for cancer or hematologic malignancy, i.e., it is used in a subject who has been previously administered another drug or therapy intended to treat cancer or hematologic malignancy or one or more symptoms thereof.

In other embodiments, the compound provided herein is a third or fourth line treatment for cancer or hematologic malignancy, i.e., it is used in a subject who has been previously administered two or three other drugs or therapies intended to treat cancer or hematologic malignancy or one or more symptoms thereof.

In embodiments where two agents are administered, the agents can be administered in am order. For example, the two agents can be administered concurrently (i.e., essentially at the same time, or within the same treatment) or sequentially (i.e., one immediately following the other, or alternatively, with a gap in between administration of the two). In some embodiments, the compound provided herein is administered sequentially (i.e., after the first therapeutic).

In one aspect, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can present synergistic or additive efficacy when administered in combination with agents that inhibit IgE production or activity. Such combination can reduce the undesired effect of high level of IgE associated with the use of one or more PI3K-δ inhibitors, if such effect occurs. This can be particularly useful in treatment of autoimmune and inflammatory disorders (AIID) such as rheumatoid arthritis. Additionally, the administration of PI3K-δ, PI3K-γ, or PI3K-δ/γ inhibitors as provided herein in combination with inhibitors of mTOR can also exhibit synergy through enhanced inhibition of the PI3K pathway.

In a separate but related aspect, provided herein is a combination treatment of a disease associated with PI3K-δ comprising administering to a subject in need thereof a PI3K-δ inhibitor and an agent that inhibits IgE production or activity. Other exemplary PI3K-δ inhibitors are applicable for this combination and they are described in, e.g., U.S. Pat. No. 6,800,620, incorporated herein by reference. Such combination treatment is particularly useful for treating autoimmune and inflammatory diseases (AIID) including, but not limited to rheumatoid arthritis.

Agents that inhibit IgE production are known in the art and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with commonly prescribed drugs including, but not limited to, Enbrel®, Remicade®, Humira®, Avonex®, and Rebif®. For treatment of respiratory diseases, the subject compounds, or pharmaceutically acceptable forms thereof, or pharmaceutical compositions, can be administered in combination with commonly prescribed drugs including, but not limited to, Xolair®, Advair®, Singulair®, and Spiriva®.

The compounds as provided herein, or pharmaceutically acceptable forms (e.g., pharmaceutically acceptable salts, hydrates, solvates, isomers, prodrugs, and isotopically labeled derivatives) thereof, or pharmaceutical compositions as provided herein, can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. An exemplary drug of this type is Prednisone. Chloroquine (Aralen) or hydroxychloroquine (Plaquenil) can also be used in some individuals with lupus. They can be prescribed for skin and joint symptoms of lupus. Azathioprine (Imuran) and cyclophosphamide (Cytoxan) suppress inflammation and tend to suppress the immune system. Other agents, e.g., methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another aspect, provided herein is a pharmaceutical composition for inhibiting abnormal cell growth in a subject which comprises an amount of a compound provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent). Many chemotherapeutics are presently known in the art and can be used in combination with a compound provided herein.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (imatinib mesylate), Velcade® (bortezomib), Casodex™ (bicalutamide), Iressa® (gefitinib), Tarceva® (erlotinib), and Adriamycin® (doxorubicin) as well as a host of chemotherapeutic agents. Non-limiting examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; BTK inhibitors such as ibrutinib (PCI-32765), AVL-292, Dasatinib, LFM-AI3, ONO-WG-307, and GDC-0834; HDAC inhibitors such as vorinostat, romidepsin, panobinostat, valproic acid, belinostat, mocetinostat, abrexinostat, entinostat, SB939, resmiunostat, givinostat, CUDC-101, AR-42, CHR-2845, CHR-3996, 4SC-202, CG200745, ACY-1215 and kevetrin; EZH2 inhibitors such as, but not limited to, EPZ-6438 (N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide), GSK-126 ((S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide), GSK-343 (1-Isopropyl-N-((6-methyl-2-oxo-4-propyl-1,2-dihydropyridin-3-yl)methyl)-6-(2-(4-methylpiperazin-1-yl)pyridine-4-yl)-1H-indazole-4-carboxamide). Ell, 3-deazaneplanocin A (DNNep, 5R-(4-amino-1H-imidazo[4,5-c]pyridin-1-yl)-3-(hydroxy methyl)-3-cyclopentene-1S,2R-diol), small interfering RNA (siRNA) duplexes targeted against EZH2 (S. M. Elbashir et al., Nature 411:494-498 (2001)), isoliquiritigenin, and those provided in, for example, U.S. Publication Nos. 2009/0012031, 2009/0203010, 2010/0222420, 2011/0251216, 2011/0286990, 2012/0014962, 2012/0071418, 2013/0040906, and 2013/0195843, all of which are incorporated herein by reference; JAK/STAT inhibitors such as lestaurtinib, tofacitinib, ruxohtilib, pacritinib, CYT387, baricitinib, GLPG0636, TG101348, INCB16562, CP-690550, and AZD1480; PKC-β inhibitor such as Enzastaurin; SYK inhibitors such as, but not limited to, GS-9973, R788 (fostamatinib), PRT 062607. R406, (S)-2-(2-((3,5-dimethylphenyl)amino)pyrimidin-4-yl)-N-(1-hydroxypropan-2-yl)-4-methylthiazole-5-carboxamide, R112, GSK143, BAY61-3606, PP2, PRT 060318, R348, and those provided in for example, U.S. Publication Nos. 2003/0113828, 2003/0158195, 2003/0229090, 2005/0075306, 2005/0232969, 2005/0267059, 2006/0205731, 200610247262, 2007/0219152, 2007/0219195, 2008/0114024, 2009/0171089, 2009/0306214, 2010/0048567, 2010/0152159, 2010/0152182, 2010/0316649, 2011/0053897, 2011/0112098, 2011/0245205, 2011/0275655, 2012/0027834, 2012/0093913, 2012/0101275, 2012/0130073, 2012/0142671, 2012/0184526, 2012/0220582, 2012/0277192, 2012/0309735, 2013/0040984, 2013/0090309, 2013/0116260, and 2013/0165431, all of which are incorporated herein by reference; SYK/JAK dual inhibitor such as PRT2070; nitrogen mustards such as bendamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomycins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycin C, mycophenolic acid, nogalamycin, olivomycins, peplomycin, porfiromycin, puromycin quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, camnofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacaibazine; mannomustine; mitobronitol; mitolactol; pipobroman; gacytosine; arabinoside (Ara-C); cyclophosphamide; thiotepa; taxanes, e.g., paclitaxel (e.g., TAXOL™) and docetaxel (e.g., TAXOTERE™) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin, aminopterin; xeloda; ibandronate; camptothecin-11 (CPT-11); topoisomerase inhibitor RFS 2000; difluoromethylornithine (DMFO). Where desired, the compounds or pharmaceutical composition as provided herein can be used in combination with commonly prescribed anti-cancer drugs such as Herceptin®, Avastin®, Erbitux®, Rituxan®, Taxol®, Anrmidex®, Taxotere®, ABVD, AVICINE, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antincoplastic, antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, crizotinib, cell-cycle nonspecific antincoplastic agents, dichloroacetic acid, discodermolide, elsamitrucin, enocitabine, epothilone, eribulin, everolimus, exatecan, exisulind, fermginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitor, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354, each incorporated herein by reference. Additional examples of hedgehog inhibitors include, but are not limited to, GDC-0449 (also known as RG3616 or vismodegib) described in, e.g., Von Hoff D, et al., *N. Engl. J. Med.* 2009; 361(12):1164-72; Robarge K. D, et al., *Bioorg Med Chem Lett.* 2009; 19(19):5576-81; Yauch, R. L, et al. (2009) *Science* 326: 572-574; Sciencexpress: 1-3 (10.1126/science.1179386); Rudin, C, et al. (2009) *New England J of Medicine* 361-366 (10.1056/nejma0902903); BMS-833923 (also known as XL139) described in, e.g., in Siu L, et al., *J. Clin. Oncol.* 2010: 28:15s (suppl; abstr 2501); and National Institute of Health Clinical Trial Identifier No. NCT006701891; LDE-225 described, e.g., in Pan S, et al., *ACS Med. Chem. Lett.*, 2010; 1(3); 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M, et al., *J. Pharmacol. Exp. Ther.* 2009; 329(3):995-1005; 1-piperazinyl-4-aylphthalazines or analogues thereof, described in Lucas B. S, et al., *Bioorg. Med. Chem. Lett.* 2010; 20(12):3618-22.

Other hormonal therapy and chemotherapeutic agents include, but are not limited to, anti-estrogens (e.g., tamoxifen, raloxifene, and megestrol acetate), LHRH agonists (e.g., goserelin and leuprolide), anti-androgens (e.g., flutamide and bicalutamide), photodynamic therapies (e.g., vertoporfin (BPD-MA), phthalocyanine photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), *vinca* alkaloids (e.g., vincristine, vinblastine, vindesine, and vinorelbine), taxoids or taxanes (e.g., paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYO-TAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirn, and EICAR), ribonucleotide reductase inhibitors (e.g., hydroxyurea and deferoxamine), uracil analogs (e.g. 5-fluorouracil (5-FU), floxuridine, doxifluridine, raltitrexed, tegafur-uracil, capecitabine), cytosine analogs (e.g., cytarabine (ara C, cytosine arabinoside), and fludarabine), purine analogs (e.g., mercaptopurine and thioguanine), Vitamin D3 analogs (e.g. EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracyclines (e.g., daunorubicin, doxorubicin, pegylated liposomal doxorubicin, idarubicin, epirubicin, pirarubicin, zorubicin, mitoxantrone), MDR inhibitors (e.g., verapamil), Ca2+ ATPase inhibitors (e.g., thapsigargin), thalidomide, lenalidomide (REVLIMID®), tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®), CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezonmib (Velcade)), mTOR inhibitors (e.g., rapamycin, temsirolimus (CCI-779), everolimnus (RAD-001), ridaforolimus, AP23573 (Ariad), AZD8055 (AstraZeneca), BEZ235 (Novartis), BGT226 (Novartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbazine, prednisolone, dexamethasone, camptothecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immuno-stimulants and/or immuno-modulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumunmab), Rituxan (rituximab), Bexxar (tositumomab), or Perjeta (pertuzumab)).

In one embodiment, the biotherapeutic agent is an anti-CD37 antibody such as, but not limited to, IMGN529, K7153A and TRU-016. In another embodiment, the biotherapeutic agent is an anti-CD20 antibody such as, but not limited to, $^{131}$I tositumomab, $^{90}$Y ibritumomab, $^{111}$I ibritumomab, obinutuzumab and ofatumumab. In another embodiment, the biotherapeutic agent is an anti-CD52 antibody such as, but not limited to, alemtuzumab.

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504), Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors provided herein and those PI3K inhibitors not provided herein). In some embodiment, the PI3K inhibitor is an inhibitor of delta and gamma isoforms of PI3K. In some embodiment, the PI3K inhibitor is an inhibitor of delta isoform of PI3K. In some embodiment, the PI3K inhibitor is an inhibitor of gamma isoform of PI3K. In some embodiments, the PI3K inhibitor is an inhibitor of alpha isoform of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088990, WO 09/088086, WO 2011/008302, WO 2010/036380, WO 2010/006086, WO 09/114870, WO 05/113556; US 2009/0312310, and US 2011/0046165, each incorporated herein by reference. Additional PI3K inhibitors that can be used in combination with the pharmaceutical compositions, include but are not limited to, AMG-319, GSK 2126458, GDC-0980, GDC-0941, Sanofi XL147, XL499, XL756, XL147, PF-4691502, BKM 120, CAL-101 (GS-1101), CAL 263, SF1126, PX-886, and a dual PI3K inhibitor (e.g., Novartis BEZ235). In one embodiment, the PI3K inhibitor is an isoquinolinone.

In one embodiment, the PI3K gamma selective compound selectively inhibits PI3K gamma isoform over PI3K delta isoform. In one embodiment, the PI3K gamma selective compound has a delta/gamma selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment the PI3K gamma selective compound has a delta/gamma selectivity ratio in the range of from greater than 1 to about 5, from about 5 to about 10, from about 10 to about 50, from about 50 to about 850, or greater than about 850. In one embodiment, the delta/gamma selectivity ratio is determined by dividing the compound's $IC_{50}$ against PI3K delta isoform by the compound's $IC_{50}$ against PI3K gamma isoform.

In one embodiment, the PI3K delta selective compound selectively inhibits PI3K delta isoform over PI3K gamma isoform. In one embodiment, the PI3K delta selective compound has a gamma/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective compound has a gamma/delta selectivity ratio in the range of from greater than 1 to about 5, from about 5 to about 10, from about 10 to about 50, from about 50 to about 850, or greater than about 850. In one embodiment, the gamma/delta selectivity ratio is determined by dividing the inhibitor's ICs against PI3K gamma isoform by the inhibitor's $IC_{50}$ against PI3K delta isoform.

In certain embodiments, the PI3K inhibitor is a PI3K delta selective compound. In one embodiment, the PI3K delta selective compound selectively inhibits PI3K delta isoform over PI3K alpha isoform. In one embodiment, the PI3K delta selective compound has an alpha/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective compound has an alpha/delta selectivity ratio in the range of from greater than 1 to about 5, from about 5 to about 10, from about 10 to about 50, from about 50 to about 850, or greater than about 850. In one embodiment, the alpha/delta selectivity ratio is determined by dividing the inhibitor's $IC_{50}$ against PI3K alpha isoform by the inhibitor's $IC_{50}$ against PI3K delta isoform.

In certain embodiments, the PI3K inhibitor is a PI3K delta selective compound. In one embodiment, the PI3K delta selective compound selectively inhibits PI3K delta isoform over PI3K beta isoform. In one embodiment, the PI3K delta selective compound has a beta/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective compound has a beta/delta selectivity ratio in the range of from greater than 1 to about 5, from about 5 to about 10, from about 10 to about 50, from about 50 to about 850, or greater than about 850. In one embodiment, the beta/delta selectivity ratio is determined by dividing the compound's $IC_{50}$ against PI3K beta isoform by the compound's $IC_{50}$ against PI3K delta isoform.

In one embodiment, the PI3K delta selective compound is GS-1101 (5-fluoro-3-phenyl-2-([S)]-1-[9H-purin-6-ylamino]-propyl)-3H-quinazolin-4-one), or AMG319, or a mixture thereof. In one embodiment, the PI3K delta selective compound is GS1101.

In some embodiments, provided herein is a method for using a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of a compound provided herein in this combination therapy can be determined as described herein.

Radiation therapy can be administered through one of several methods, or a combination of methods, including without limitation, external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, 1-131, I-125. Y-90, Re-186. Re-188, Sm-153. Bi-212, P-32, and radioactive isotopes of Lu). Suitable radiation sources for use as a cell conditioner as provided herein include both solids and liquids. By way of non-limiting example, the radiation source can be a radionuclide, such as I-125, I-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of 1-125 or 1-131, or a radioactive fluid can be produced using a slurry of a suitable fluid containing small particles of solid radionuclides, such as Au-198, Y-90. Moreover, the radionuclide (s) can be embodied in a gel or radioactive micro spheres.

Without being limited by any theory, a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound provided herein, or a pharmaceutically acceptable form (e.g., pharmaceutically acceptable salts, hydrates, solvates, isomers, prodrugs, and isotopically labeled derivatives) thereof, which amount is effective in sensitizing abnormal cells to treatment with radiation. The amount of the compound used in this method can be determined according to the means for ascertaining effective amounts of such compounds described herein.

In one embodiment, a compound as provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, can be used in combination with an amount of one or more substances selected from anti-angiogenesis agents, signal transduction inhibitors, and antiproliferative agents, glycolysis inhibitors, or autophagy inhibitors.

Other therapeutic agents, such as MMP-2 (matrix-metalloproteinase 2) inhibitors, MMP-9 (matrix-metalloproteinase 9) inhibitors, and COX-I1 (cyclooxygenase 11) inhibitors, can be used in conjunction with a compound provided herein, or a pharmaceutically acceptable form thereof, or a pharmaceutical composition described herein. Such therapeutic agents include, for example, rapanycin, tensirolimus (CCI-779), everolimnus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999). U.S. Pat. No. 5,863, 949 (issued Jan. 26, 1999), U.S. Pat. No. 5,861,510 (issued Jan. 19, 1999), and European Patent Publication 780.386 (published Jun. 25, 1997), all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-1, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drags which elevate cAMP levels such as adenosine, LY204002, N6-mercaptopurine riboside, and vinblastine. In addition, antisense or siRNAs that inhibit expression of proteins including, but not limited to ATG5 (which are implicated in autophagy), can also be used.

In some embodiments, provided herein is a method of and/or a pharmaceutical composition for treating a cardiovascular disease in a subject which comprises an amount of a compound provided herein, or a pharmaceutically acceptable form (e.g., pharmaceutically acceptable salts, hydrates, solvates, isomers, prodrugs, and isotopically labeled derivatives) thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

In one embodiment, a compound provided herein or a pharmaceutically acceptable form (e.g., pharmaceutically acceptable salts, hydrates, solvates, isomers, prodrugs, and isotopically labeled derivatives) thereof, or a pharmaceutical composition as provided herein, can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with a compound provided herein, or a pharmaceutically acceptable form (e.g., pharmaceutically acceptable salts, hydrates, solvates, isomers, prodrugs, and isotopically labeled derivatives) thereof, include any suitable drugs usefully delivered by inhalation for example, analgesics, e.g., codeine, dihydromorphine, ergotanune, fentanyl or morphine; anginal preparations, e.g., diltiazem; atiallergics, e.g., cromoglycate, ketotifen or nedocromil; anti-infectives, e.g., cephalosporinns, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia: catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids. β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosonuasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other, P3-Lactam antibiotics, an agent containing an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound provided herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immuno-modulation, such as immuno-modulators, immuno-suppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and anti-platelet drugs are also contemplated by the methods herein.

In exemplary embodiments, for treating renal carcinoma, one can combine a compound provided herein, or a pharmaceutically acceptable form (e.g., pharmaceutically acceptable salts, hydrates, solvates, isomers, prodrugs, and isotopically labeled derivatives) thereof, or a pharmaceutical composition as provided herein, with sorafenib and/or avastin. For treating an endometrial disorder, one can combine a compound provided herein with doxorubincin, taxotere (taxol), and/or cisplatin (carboplatin). For treating ovarian cancer, one can combine a compound provided herein with cisplatin, carboplatin, docetaxel, doxorubincin, topotecan, and/or tamoxifen. For treating breast cancer, one can combine a compound provided herein with paclitaxel or docetaxel, gemcitabine, capecitabine, tamoxifen, letrozole, erlotinib, lapatinib, PD0325901, bevacizumab, trastuzumab, OSI-906, and/or OSI-930. For treating lung cancer, one can combine a compound as provided herein with paclitaxel, docetaxel, gemcitabine, cisplatin, pemetrexed, erlotinib, PD0325901, and/or bevacizumab.

In some embodiments, the disorder to be treated, prevented and/or managed is a hematological cancer, e.g., lymphoma (e.g., T-cell lymphoma; NHL), myeloma (e.g., multiple myeloma), and leukemia (e.g., CLL), and a compound provided herein is used in combination with: HDAC inhibitors such as vorinostat, romidepsin and ACY-1215; mTOR inhibitors such as everolimus; anti-folates such as pralatrexate; nitrogen mustard such as bendamustine; gemcitabine, optionally in further combination with oxaliplatin; rituximab-cyclophosphamide combination; PI3K inhibitors such as GS-1101, XL 499, GDC-0941, and AMG-319; angiogenesis inhibitors such as pomalidomide or BTK inhibitors such as ibrutinib, AVL-292, Dasatinib, LFM-AI3, ONO-WG-307, and GDC-0834. In some embodiments, the disorder to be treated, prevented and/or managed is DLBCL, and a compound provided herein, or a pharmaceutically acceptable derivative (e.g., salt or solvate) thereof, is used in combination with HDAC inhibitors provided herein. In one particular embodiment, the HDAC inhibitor is ACY-1215.

In some embodiments, the disorder to be treated, prevented and/or managed is DLBCL, and a compound provided herein, or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is DLBCL, and a compound provided herein, or a pharmaceutically acceptable derivative (e.g., salt or solvate) thereof, is used in combination with IRAK inhibitors provided herein. In one particular embodiment, the IRAK4 inhibitor is ND-2110 or ND-2158.

In some embodiments, the disorder to be treated, prevented and/or managed is WM, and a compound provided herein, or a pharmaceutically acceptable derivative (e.g., salt or solvate) thereof, is used in combination with BTK inhibitors provided herein. In one particular embodiment, the BTK inhibitor is ibrutinib. In one embodiment, the BTK inhibitor is AVL-292.

In some embodiments, the disorder to be treated, prevented and/or managed is WM, and a compound provided herein, or a pharmaceutically acceptable derivative (e.g., salt or solvate) thereof, is used in combination with IRAK4 inhibitors provided herein. In one particular embodiment, the IRAK4 inhibitor is ND-2110 or ND-2158.

In some embodiments, the disorder to be treated, prevented and/or managed is T-ALL, the subject/patient has a PTEN deficiency, and a compound provided herein, or a pharmaceutically acceptable derivative (e.g., salt or solvate) thereof, is used in combination with doxorubicin and/or vincristine.

In certain embodiments, wherein inflammation (e.g., arthritis, asthma) is treated, prevented and/or managed, a compound provided herein can be combined with, for example: PI3K inhibitors such as GS-1101, XL 499, GDC-0941, and AMG-319; BTK inhibitors such as ibrutinib and AVL-292; JAK inhibitors such as tofacitinib, fostamatinib, and GLPG0636.

In certain embodiments wherein asthma is treated, prevented and/or managed, a compound provided herein can be combined with, for example: beta 2-agonists such as, but not limited to, albuterol (Proventil®, or Ventolin®), salmeterol (Serevent®), formoterol (Foradil®), metaproterenol (Alupent®), pirbuterol (MaxAir®), and terbutaline sulfate; corticosteroids such as, but not limited to, budesonide (e.g., Pulmicort®), flunisolide (e.g., AeroBid Oral Aerosol Inhaler® or Nasalide Nasal Aerosol®), fluticasone (e.g., Flonase® or Flovent®) and triamcinolone (e.g., Azmacort®); mast cell stabilizers such as cromolyn sodium (e.g., Intal® or Nasalcrom®) and nedocromil (e.g., Tilade®); xanthine derivatives such as, but not limited to, theophylline (e.g., Aminophyllin®, Theo-24® or Theolair®); leukotriene receptor antagonists such as, but are not limited to, zafirlukast (Accolate®), montelukast (Singulair®), and zileuton (Zyflo®); and adrenergic agonists such as, but are not limited to, epinephrine (Adrenalin, Bronitin®, EpiPen® or Primatene Mist®).

In certain embodiments wherein arthritis is treated, prevented and/or managed, a compound provided herein can be combined with, for example: TNF antagonist (e.g., a TNF antibody or fragment, a soluble TNF receptor or fragment, fusion proteins thereof, or a small molecule TNF antagonist); other biologic antirhheumatics (e.g., IL-6 antagonists, IL-1 antagonists, costimulatory modulators); an antirheumatic (e.g., methotrexate, auranofin, aurothioglucose, azathioprine, etanercept, gold sodium thiomalate, chloroquine, hydroxychloroquine sulfate, leflunomide, sulfasalazine, penicillamine); a muscle relaxant; a narcotic; a non-steroid anti-inflammatory drug (NSAID); an analgesic; an anesthetic; a sedative; a local anesthetic; a neuromuscular blocker, an antimicrobial (e.g., an aminoglycoside, an anti-fungal, an antiparasitic, an antiviral, a carbapenem, cephalosporin, a fluoroquinolone, a macrolide, a penicillin, a sulfonamide, a tetracycline, another antimicrobial); an antipsoriatic; a corticosteroid; an anabolic steroid; a cytokine or a cytokine antagonist; a calcineurin inhibitor (e.g., cyclosporine, tacrolimus).

In some embodiments, a compound provided herein, or an enantiomer or a mixture of enantiomers thereof, or a pharmaceutically acceptable salt, solvate, hydrate, co-crystal, clathrate, or polymorph thereof) is administered in combination with an agent for the treatment of rheumatoid arthritis. Examples of agents for the treatment of rheumatoid arthritis include, but are not limited to, various NSAIDs, corticosteroids, sulfasalazine, auranofin, methotrexate, azathioprine, penicillamine, cyclosporine, Arava (leflunomide), TNF inhibitors (e.g., Enbrel (etanercept), Remicade (infliximab), Humira (adalimumab), Simponi (golimumab), and Cimzia (certolizumab)), IL-1 inhibitors (e.g., Kineret (anakinra)), T-cell costimulatory modulators (e.g., Orencia (abatacept)), Anti-CD20 (e.g., Rituxan (rituximab)), and IL-6 inhibitors (e.g., Actemra (tocilizumab)). In one embodiment, the agent is Cimzia (ccrtolizumab). In another embodiment, the agent is Actemra (tocilizumab).

In some embodiments, a compound provided herein, or an enantiomer or a mixture of enantiomers thereof, or a pharmaceutically acceptable salt, solvate, hydrate, co-crystal, clathrate, or polymorph thereof) is administered in combination with an agent for rheumatology. Examples of agents for rheumatology include, but are not limited to, Rayos (prednisone), Stendra (avanafil), Actemra (tocilizumab), Duexis (ibuprofen and famotidine), Actemra (tocilizumab), Krystexxa (pegloticase), Vimovo (naproxen+esomeprazole), Cimzia (certolizumab pegol), Colctys (colchicine), Pennsaid (diclofenac sodium topical solution), Simponi (golimumab), Uloric (febuxostat), Orencia (abatacept), Elaprase (idursulfase), Orencia (abatacept), Vioxx (rofecoxib), Enbrel (etanercept), Humira (adalimumab), Remicade (infliximab), Bextra, Kineret, Remicade (infliximab), Supartz, Mobic (meloxicam), Vivelle (estradiol transdermal system), Lodine XL (etodolac), Arava, Salagen, Arthrotec, Etodolac, Ketoprofen, Synvisc, Tolmetin Sodium, Azulfidine EN-tabs Tablets (sulfasalazine delayed release tablets, USP), and Naprelan (naproxen sodium).

In some embodiments, the second agent is selected from belimumab, AGS-009, rontalizumab, vitamin D3, sifalimumab, AMG 811, IFNα Kinoid, CEP33457, epratuzumab, LY2127399, Ocrelizumab, Atacicept, A-623, SBI-087, AMG557, laquinimod, rapamycin, cyclophosphamide, azathioprine, mycophenolate, leflunomide, methotrexate, CNTO 136, tamibarotene, N-acetylcysteine, CDP7657, hydroxychloroquine, rituxiniab, carfilzomib, bortezonub, ONX 0914, IMO-3100, DV 179, sulfasalazine, and chloroquine. In one embodiment, the second agent is methotrexate, sulfasalazine, chloroquine, or hydroxychloroquine. In one embodiment, the second agent is methotrexate.

In certain embodiments wherein psoriasis is treated, prevented and/or managed, a compound provided herein can be combined with, for example: budesonide, epidermal growth factor, corticosteroids, cyclosporine, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporine, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55

TNF receptor, soluble p75 TNF receptor, sIL-1RI, sIL-1RII, sIL-6R, anti-inflammatory cytokines, IL-4, IL-10, IL-11, IL-13 and TGFβ.

In certain embodiments wherein fibrosis or fibrotic condition of the bone marrow is treated, prevented and/or managed, a compound provided herein can be combined with, for example, a Jak2 inhibitor (including, but not limited to, INCB018424, XL019, TG101348, or TG101209), an immuno-modulator, e.g., an IMID® (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

In certain embodiments wherein fibrosis or fibrotic condition of the heart is treated, prevented and/or managed, a compound provided herein can be combined with, for example, eplerenone, furosemide, pycnogenol, spironolactone, TcNC 100692, torasemide (e.g., prolonged release form of torasemide), or combinations thereof.

In certain embodiments wherein fibrosis or fibrotic condition of the kidney is treated, prevented and/or managed, a compound provided herein can be combined with, for example, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, or combinations thereof.

In certain embodiments wherein fibrosis or fibrotic condition of the skin is treated, prevented and/or managed, a compound provided herein can be combined with, for example, Bosentan (Tracleer), p144, pentoxifylline; pirfenidone; pravastatin, STI571, Vitamin E, or combinations thereof.

In certain embodiments wherein fibrosis or fibrotic condition of the gastrointestinal system is treated, prevented and/or managed, a compound provided herein can be combined with, for example, ALTU-135, bucelipase alfa (INN), DCI1020, EUR-1008 (ZENPEP™), ibuprofen, Lym-X-Sorb powder, pancrease MT, pancrelipase (e.g., pancrelipase delayed release), pentade canoic acid (PA), repaglinide, TheraCLEC™, triheptadecanoin (THA), ULTRASE MT20, ursodiol, or combinations thereof.

In certain embodiments wherein fibrosis or fibrotic condition of the lung is treated, prevented and/or managed, a compound provided herein can be combined with, for example, 18-FDG, AB0024, ACT-064992 (macitentan), aerosol interferon-gamma, aerosolized human plasma-derived alpha-1 antitrypsin, alpha1-proteinase inhibitor, ambrisentan, amikacin, amiloride, amitriptyline, anti-pseudomonas IgY gargle, ARIKACE™, AUREXIS® (tefibazunmab), AZAPRED, azathioprine, azithromycin azithromycin, AZLI, aztreonam lysine. BIBF 120, Bio-25 probiotic, bosentan, Bramitob®, calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), dornase alfa (PULMOZYME®), EPI-hNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline. Moli1901, MP-376 (levofloxacin solution for inhalation), mucoid exopolysaccharide *P. aeruginosa* immune globulin IV, mycophenolate mofetil, n-acetylcysteine. N-acetylcysteine (NAC), NaCl 6%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhDNAse, SB656933, SB-656933-AAA, sildenafil, tamoxifen technetium [Tc-99m] sulfur colloid and Indium [In-111] DTPA, tetrathiomolybdate, thalidomide, ticarcillin-clavulanate, tiotropium bromide, tiotropium RESPIMATO inhaler, tobramycin (GERNEBCIN®), treprostinil, uridine, valganciclovir (VALCYTE®), vardenafil, vitamin D3, xylitol, zileuton, or combinations thereof.

In certain embodiments wherein fibrosis or fibrotic condition of the liver is treated, prevented and/or managed, a compound provided herein can be combined with, for example, adefovir dipivoxil, candesartan, colchicine, combined ATG, mycophenolate mofetil, and tacrolimus, combined cyclosporine microemulsion and tacrolimus, elastometry, everolimus, FG-3019. Fuzheng Huayu, G1262570, glycyrrhizin (monoammonium glycyrrhizinate, glycine, L-cysteine nonohydrochloride), interferon gamma-1b, irbesartan, losartan, oltipraz, ORAL IMPACTh, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, or combinations thereof.

In certain embodiments wherein cystic fibrosis is treated, prevented and/or managed, a compound provided herein can be combined with, for example, 552-02, 5-methyltetrahydrofolate and vitamin B12, Ad5-CB-CFTR. Adeno-associated virus-CFTR vector, albuterol, alendronate, alpha tocopherol plus ascorbic acid, amiloride HCl, aquADEK™, ataluren (PTC124), AZD1236, AZD9668, azithromycin, bevacizumab, biaxin (clarithromycin). BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexacnoic acid (DHA), doxycycline, ECGC, recombinant human IGF-1, educed glutathione sodium salt, ergocalciferol (vitamin D2), fluorometholone, gadobutrol (GADOVIST®, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b. IoGen (molecular iodine), iosartan potassium, isotonic saline, itraconazole, IV gallium nitrate (GANITE®) infusion, ketorolac acetate, lansoprazole, L-arginine, linezolid, lubiprostone, neropenem, miglustal, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocottienol, unconjugated Isoflavones 100, vitamin: choline bitartrate (2-hydroxyethyl) trimethylammonium salt 1:1, VX-770, VX-809, Zinc acetate, or combinations thereof.

In some embodiments, a compound provided herein is administered in combination with an agent that inhibits IgE production or activity. In some embodiments, the PI3K inhibitor (e.g., PI3Kδ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

In certain embodiments wherein scleroderma is treated, prevented and/or managed, a compound provided herein can be combined with, for example: an immunosuppressant (e.g., methotrexate, azathioprine (Imuran®), cyclosporine, mycophenolate mofetil (Cellcept®), and cyclophosphamide (Cytoxan®)); T-cell-directed therapy (e.g., halofuginone, basiliximab, alemtuzumab, abatacept rapamycin); B-cell directed therapy (e.g., rituximab); autologous hematopoietic stem cell transplantation; a chemokine ligand receptor antagonist (e.g., an agent that targets the CXCL12/CSCR4 axis (e.g., AMD3100)); a DNA methylation inhibitor (e.g., 5-azacytidine); a histone deacetylase inhibitor (e.g., trichostatin A); a stalin (e.g., atorvastatin, simvastatin, pravastatin); an endothelin receptor antagonist (e.g., Bosentan®); a phosphodiesterase type V inhibitor (e.g., Sildenafil®); a prostacyclin analog (e.g., trepostinil); an inhibitor of cytokine synthesis and/or signaling (e.g., Imatinib mesylate, Rosiglitazone, rapamycin, antitransforming growth factor β1 (anti-TGFβ1) antibody, mycophenolate mofetil, an anti-IL-6 antibody (e.g., tocilizumab)); corticosteroids; nonsteroidal anti-inflammatory drugs; light therapy; and blood pressure medications (e.g., ACE inhibitors).

In certain embodiments wherein inflammatory myopathies are treated, prevented and/or managed, a compound provided herein can be combined with, for example: topical creams or ointments (e.g., topical corticosteroids, tacrolimus, pimecrolimus); cyclosporine (e.g., topical cyclosporine); an anti-interferon therapy, e.g., AGS-009, Rontalizumab (rhuMAb IFNalpha), Vitamin D3, Sifalimumab (MEDI-545), AMG 811, IFNα Kinoid, or CEP33457. In some embodiments, the other therapy is an IFN-α therapy, e.g., AGS-009. Rontalizumab, Vitamin D3, Sifalimunab (MEDI-545) or IFNα Kinoid; corticosteroids such as prednisone (e.g., oral prednisone); immunosuppressive therapies such as methotrexate (Trexall®, Methotrexate®, Rheumatrex®), azathioprine (Azasan®, Imuran®), intravenous immunoglobulin, tacrolimus (Prograf®), pimecrolimus, cyclophosphamide (Cytoxan®), and cyclosporine (Gengraf®, Neoral®, Sandimmune®); anti-malarial agents such as hydroxychloroquine (Plaquenil®) and chloroquine (Aralen®); total body irradiation; rituximab (Rituxan®); TNF inhibitors (e.g., etanercept (Enbrel®) infliximab (Remicade®)); AGS-009; Rontalizumab (rhuMAb IFNalpha); Vitamin D3; Sifalimumab (MEDI-545); AMG 811; IFNα Kinoid; CEP33457; agents that inhibit IgE production such as TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2; agents that inhibit IgE activity such as anti-IgE antibodies (e.g., Omalizumab and TNX-90); and additional therapies such as physical therapy, exercise, rest, speech therapy, sun avoidance, heat therapy, and surgery.

In certain embodiments wherein myositis (e.g., dermatomyositis) is treated, prevented and/or managed, a compound provided herein can be combined with, for example: corticosteroids; corticosteroid sparing agents such as, but not limited to, azathioprine and methotrexate; intravenous immunoglobulin; immunosuppressive agents such as, but not limited to, tacrolimus, cyclophosphamide and cyclosporine; rituximab; TNFα inhibitors such as, but not limited to, etanercept and infliximab; growth hormone; growth hormone secretagogues such as, but not limited to, MK-0677, L-162752, L-163022, NN703 ipamorelin, hexarelin, GPA-748 (KP102, GHRP-2), and LY444711 (Eli Lilly); other growth hormone release stimulators such as, but not limited to, Geref, GHRH (1-44). Somatorelin (GRF 1-44), ThGRF genotropin, L-DOPA, glucagon, and vasopressin and insulin-like growth factor.

In certain embodiments wherein Sjögren's syndrome is treated, prevented and/or managed, a compound provided herein can be combined with, for example: pilocarpine; cevimeline; nonsteroidal anti-inflammatory drugs; arthritis medications; antifungal agents; cyclosporine; hydroxychloroquine; prednisone; azathioprine; and cyclophamide.

Further therapeutic agents that can be combined with a compound provided herein can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

In one embodiment, the compounds described herein can be used in combination with the agents provided herein or other suitable agents, depending on the condition being treated. Hence, in some embodiments, a compound provided herein, or a pharmaceutically acceptable form thereof, will be co-administered with other agents as described above. When used in combination therapy, a compound described herein, or a pharmaceutically acceptable form thereof, can be administered with a second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound provided herein and any of the agents described above can be simultaneously administered, wherein both agents are present in separate formulations. In another alternative, a compound provided herein can be administered just followed by any of the agents described above, or vice versa. In the separate administration protocol, a compound provided herein and any of the agents described above can be administered a few minutes apart, or a few hours apart, or a few days apart.

Administration of a compound provided herein, or a pharmaceutically acceptable form thereof, can be effected by any method that enables delivery of the compound to the site of action. An effective amount of a compound provided herein, or a pharmaceutically acceptable form thereof, can be administered in either single or multiple doses by any of the accepted modes of administration of agents having similar utilities, including rectal, buccal, intranasal, and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound provided herein, or a pharmaceutically acceptable form thereof, is administered in a pharmaceutical composition that comprises one or more agents, and the agent has a shorter half-life than the compound provided herein, unit dose forms of the agent and the compound as provided herein can be adjusted accordingly.

In some embodiments, the compound provided herein and the second agent are administered as separate compositions, e.g., pharmaceutical compositions. In some embodiments, the PI3K modulator and the agent are administered separately, but via the same route (e.g., both orally or both intravenously). In other embodiments, the PI3K modulator and the agent are administered in the same composition, e.g., pharmaceutical composition.

In some embodiments, a compound provided herein, or an enantiomer or a mixture of enantiomers thereof, or a pharmaceutically acceptable salt, solvate, hydrate, co-crystal, clathrate, or polymorph thereof) is administered in combination with an agent for pulmonary or respiratory diseases. Examples of agents for pulmonary or respiratory diseases include, but are not limited to, Dymista (azelastine hydrochloride and fluticasone propionate), Kalydeco (ivacaftor), Qnasl (beclomethasone dipropionate) nasal aerosol, Rayos (prednisone) delayed-release tablets, Surfaxin (lucinactant), Tudorza Pressair (aclidinium bromide inhalation powder), Arcapta (indacaterol mnaleate inhalation powder), Daliresp (roflumilast), Xalkori (crzotinib), Cayston (aztreonam for inhalation solution), Dulera (mometasone furoate+fomoterol fumarate dihydrate), Teflaro (ceftaroline fosamil), Adcira (tadalafil), Tyvaso (treprostinil), Alvesco (ciclesonide), Patanase (olopatadine hydrochloride), Letains (anmbrisentan), Xyzal (levocetirizine dihydrochloride), Brovana (arformoterol tartrate), Tygacil (tigecycline), Ketek (telithromycin), Spiriva HandiHaler (tiotropium bromide), Aldurazyme (laronidase), Iressa (gefitinib), Xolair (omalizumab), Zemaira (alphal-proteinase inhibitor), Clarinex, Qvar (beclomethasone dipropionate), Remodulin (treprostinil), Xopenex, Avelox I.V. (moxifloxacin hydrochloride), DuoNeb (albuterol sulfate and ipratropium bromide), Foradil Aerolizer (formoterol fumarate inhalation powder), Invanz, NasalCrom Nasal Spray, Tavist (clemastine fumarate), Tracleer (bosentan), Ventolin HFA (albuterol sulfate inhalation aerosol), Biaxin XL (clarithromycin extended-release tablets), Cefazolin and Dextrose USP, Tri-Nasal Spray (triamcinolone acetonide spray), Accolate, Cafcit Injection, Proventil HFA Inhalation Aerosol, Rhinocort Aqua Nasal Spray, Tequin, Tikosyn Capsules, Allegra-D, Clemastine fumarate syrup, Curosurf, Dynabac, Infasurf, Priftin, Pulmozyme (dornase alfa), Sclerosol Intrapleural Aerosol, Singulair, Synagis, Ceftin (cefuroxime axetil), Cipro (ciprofloxacin HCl), Claritin RediTabs (10 mg loratadine rapidly-disintegrating tablet), Flonase Nasal Spray, Flovent Rotadisk, Metaprotereol Sulfate Inhalation Solution (5%), Nasacort AQ (triamcinolone acetonide) Nasal Spray, Omnicef, Raxar (grepafloxacin), Serevent, Tilade (nedocromil sodium), Tobi, Vanceril 84 meg Double Strength (beclomethasone dipropionate, 84 mcg) Inhalation Aerosol, Zagam (sparfloxacin) tablets, Zyflo (Zileuton), Accolate, Allegra (fexofenadine hydrochloride), Astelin nasal spray, Atrovent (ipratropium bromide), Augmentin (amoxicillin/clavulanate), Azmacort (triamcinolone acetonide) Inhalation Aerosol, Breathe Right, Claritin Syrup (loratadine), Claritin-D 24 Hour Extended Release Tablets (10 mg loratadine, 240 mg pseudoephedrine sulfate), Covera-HS (verapamil), Nasacort AQ (triamcinolone acetonide) Nasal Spray, OcuHist, Pulmozyme (dornase alfa), RespiGam (Respiratory Syncitial Virus Immune Globulin Intravenous), Tavist (clemastine fumarate), Tripedia (Diptheria and Tetanus Toxoids and Acellular Pertussis Vaccine Absorbed), Vancenase AQ 84 mcg Double Strength, Visipaque (iodixanol), Zosyn (sterile piperacillin sodium/tazobactanl sodium), Cedax (ceftibuten), and Zyrtec (cetirizine HCl), In one embodiment, the agent for pulmonary or respiratory diseases is Arcapta, Daliresp, Dulera, Alvesco, Brovana, Spiriva HandiHaler, Xolair, Qvar, Xopenex, DuoNeb, Foradil Aerolizer, Accolate, Singulair, Flovent Rotadisk, Tilade, Vanceril, Zyflo, or Azmacort Inhalation Aerosol. In one embodiment, the agent for pulmonary or respiratory diseases is Spiriva HandiHaler.

In some embodiments, a compound provided herein, or an enantiomer or a mixture of enantiomers thereof, or a pharmaceutically acceptable salt, solvate, hydrate, co-crystal, clathrate, or polymorph thereof) is administered in combination with an agent for immunology or infectious diseases. Examples of agents for immunology or infectious diseases include, but are not limited to, Horizant (gabapentin enacarbil). Qnasl (beclomethasone dipropionate) nasal aerosol. Rayos (prednisone) delayed-release tablets, Stribild (ehlvitegravir, cobicistat, emtricitabine, tenofovir disoproxil fumarate), Tudorza Pressair (aclidinium bromide inhalation powder), Arcapta (indacaterol maleate inhalation powder), Benlysta (belimumab), Complera (emtricitabine/rilpivirine/tenofovir disoproxil fumarate), Daliresp (roflumilast), Dificid (fidaxomicin), Edurant (rilpivirine), Firazyr (icatibant), Gralise (gabapentin), Incivek (telaprevir), Nulojix (belatacept), Victrelis (boceprevir), Cayston (aztreonam for inhalation solution), Egrifta (tesamorelin for injection), Menveo (meningitis vaccine), Oravig (miconazole), Prevnar 13 (Pneumococcal 13-valent Conjugate Vaccine), Teflaro (ceftaroline fosamil), Zortress (everolimus), Zymaxid (gatifloxacin ophthalmic solution), Bepreve (bepotastine besilate ophthalmic solution), Berinert (C1 Esterase Inhibitor (Human)), Besivance (besifloxacin ophthalmic suspension), Cervarix [Human Papillonmavirus Bivalent (Types 16 and 18) Vaccine, Recombinant], Coartem (artemether/lumefantrine), Hiberix (Haemophilus b Conjugate Vaccine; Tetanus Toxoid Conjugate), Ilaris (canakinumab), Ixiaro (Japanese Encephalitis Vaccine, Inactivated, Adsorbed), Kalbitor (ecallantide), Qutenza (capsaicin), Vibativ (telavancin), Zirgan (ganciclovir ophthalmic gel), Aptivus (tipranavir), Astepro (azelastine hydrochloride nasal spray), Cinryze (C1 Inhibitor (Human)), Intelence (etravirine), Moxatag (amoxicillin), Rotarix (Rotavirus Vaccine, Live, Oral), Tysabri (natalizumab), Viread (tenofovir disoproxil fumarate), Altabax (retapamulin), AzaSite (azithromycin), Doribax (doripenem), Extina (ketoconazole), Isentress (raltegravir), Selzentry (maraviroc), Veramyst (fluticasone furoate), Xyzal (levocetirizine dihydrochloride), Eraxis (anidulafungin), Gardasil (quadrivalent human papillomavirus (types 6, 11, 16, 18) recombinant vaccine), Noxafil (posaconazole), Prezista (danmnavir), Rotateq (rotavirus vaccine, live oral pentavalent), Tyzeka (telbivudine), Veregen (kunecatechins), Aptivus (tipranavir), Baraclude (entecavir), Tygacil (tigecycline), Ketek (telithromycin), Tindamax, tinidazole, Xifaxan (rifaximin), Amevive (alefacept), FluMist (Influenza Virus Vaccine), Fuzeon (enfuvirtide), Lexiva (fosamprenavir calcium), Revataz (atazanavir sulfate), Alinia (nitazoxanide), Clarinex, Daptacel, Fluzone Preservative-free, Hepsera (adefovir dipivoxil), Pediarix Vaccine, Pegasys (peginterferon alfa-2a), Restasis (cyclosporine ophthalmic emulsion), Sustiva, Vfend (voriconazole), Avelox I.V. (moxifloxacin hydrochloride), Cancidas, Peg-Intron (peginterferon alfa-2b), Rebetol (ribavirin), Spectracef, Twimix, Valcyte (valganciclovir HCl), Vired (tenofovir disoproxil fumarate), Xigris (drotrecogin alfa [activated]), ABREVA (docosanol), Biaxin XL (clarithromycin extended-release tablets), Cefazolin and Dextrose USP, Children's Motrin Cold, Evoxac, Kaletra Capsules and Oral Solution, Lanmisil (terbinafine hydrochloride) Solution (1%), Lotrisone (clotrimazole/betamethasone dipropionate) lotion, Malarone (atovaquone;

proguanil hydrochloride) Tablet, Rapamune (sirolimus) Tablets, Rid Mousse, Tri-Nasal Spray (triamcinolone acetonide spray), Trivagizole 3 (clotrimazole) Vaginal Cream, Trizivir (abacavir sulfate; lamivudine; zidovudine AZT) Tablet, Agenerase (amprenavir), Cleocin (clindamycin phosphate), Fanlvir (famciclovir), Norvir (ritonavir), Panretin Gel, Rapamune (sirolimus) oral solution, Relenza, Synercid I.V., Tanliflu capsule, Vistide (cidofovir), Allegra-D, CellCept, Clenmastine fumarate syrup, Cleocin (clindamycin phosphate), Dynabac, REBETRON™ Combination Therapy, Simulect, Timentin, Viroptic, INFANRIX (Diphtheria and Tetanus Toxoids and Acellular Pertussis Vaccine Adsorbed), Acyclovir Capsules, Aldara (imiquimod), Aphthasol, Combivir, Condylox Gel 0.5% (pokofilox), Famvir (famciclovir), Flagyl ER, Flonase Nasal Spray, Fortovase, INFERGEN (interferon alfacon-1), Intron A (interferon alfa-2b, recombinant), Norvir (ritonavir), Rescriptor Tablets (delavirdine mesylate tablets), SPORANOX (itraconazole), Stromectol (ivermectin), Taxol, Trovan, VIRACEPT (nelfinavir mesylate), Zerit (stavudine), Albenza (albendazole), Apthasol (Amlexanox), Carrington patch, Confide, Crixivan (Indinavir sulfate), Gastrocrom Oral Concentrate (cromolyn sodium), Havrix Lamisil (terbinafine hydrochloride) Tablets, Leukine (sargramostim), Oral Cytovene, RespiGam (Respiratory Syncitial Virus Immune Globulin Intravenous), Videx (didanosine), Viramune (nevirapine), Vistide (cidofovir), Vitrasert Implant, Zithromax (azithronmycin), Cedax (ceftibuten), Clarithromycin (Biaxin), Epivir (lamivudine), Intron A (Interferon alfa-2b, recombinant), Invirase (saquinavir), Valtrex (valacyclovir HCl), Western blot confirmatory device, Zerit (stavudine), and Zyrtec (cetirizine HCl).

In some embodiments, the second agent is an HDAC inhibitor, such as, e.g., belinostat, vorinostat, panobinostat ACY-1215, or romidepsin.

In some embodiments, the second agent is an mTOR inhibitor, such as, e.g., everolimus (RAD 001).

In some embodiments, the second agent is a proteasome inhibitor, such as, e.g., bortezomib or carfilzomib.

In some embodiments, the second agent is a PKC-β inhibitor, such as, e.g., Enzastaurin (LY317615).

In some embodiments, the second agent is a JAK/STAT inhibitor, such as, e.g., INCB16562 or AZD1480.

In some embodiments, the second agent is an anti-folate, such as, e.g., pralatrexate.

In some embodiments, the second agent is a farnesyl transferase inhibitor, such as, e.g., tipifarnib.

In some embodiments, the second agent is an antibody or a biologic agent, such as, e.g., alemtuzumab, rituximab, ofatunumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein, or a pharmaceutically acceptable derivative (e.g., salt or solvate) thereof, is used in combination bendamustine and one additional active agent. In one embodiment, the cancer or hematological malignancy is iNHL.

In some embodiments, a compound provided herein, or a pharmaceutically acceptable derivative (e.g., salt or solvate) thereof, is used in combination rituximab and one additional active agent. In one embodiment, the cancer or hematological malignancy is iNHL.

In some embodiments, a compound provided herein, or a pharmaceutically acceptable derivative (e.g., salt or solvate) thereof, is used in combination bendamustine and rituximab. In one embodiment, the cancer or hematological malignancy is iNHL.

In some embodiments, a compound provided herein, or a pharmaceutically acceptable derivative (e.g., salt or solvate) thereof, is used in combination fludarabine, cyclophosphamide, and rituximab. In one embodiment, the cancer or hematological malignancy is CLL.

In some embodiments, a compound provided herein, or a pharmaceutically acceptable derivative (e.g., salt or solvate) thereof, is used in combination with an antibody or a biologic agent, such as, e.g., alemtuzumab, rituximab, ofatumumab, or brentuximab vedotin (SGN-035). In one embodiment, the second agent is rituximab. In one embodiment, the second agent is rituximab and the combination therapy is for treating, preventing, and/or managing iNHL, FL, splenic marginal zone, nodal marginal zone, extranodal marginal zone, and/or SLL.

In some embodiments, a compound provided herein, or a pharmaceutically acceptable derivative (e.g., salt or solvate) thereof, is used in combination with an antibody-drug conjugate, such as, e.g., inotuzumab ozogamicin, or brentuximab vedotin.

In some embodiments, a compound provided herein, or a pharmaceutically acceptable derivative (e.g., salt or solvate) thereof, is used in combination with a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, a compound provided herein, or a pharmaceutically acceptable derivative (e.g., salt or solvate) thereof, is used in combination with one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R-CHOP (Rituximab, Cyclophosphamide. Doxorubicin or Hydroxydaunomycin, Vincristine or Oncovin, Prednisone).

In some embodiments, a compound provided herein, or a pharmaceutically acceptable derivative (e.g., salt or solvate) thereof, is used in combination with an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein, or a pharmaceutically acceptable derivative (e.g., salt or solvate) thereof, and a second active agent (e.g., IL-15 antibodies, IL-21 antibodies, IL-4 antibodies, IL-7 antibodies, IL-2 antibodies, IL-9 antibodies, JAK1 inhibitors, JAK3 inhibitors, pan-JAK inhibitors, BTK inhibitors. SYK inhibitors, and/or PI3K delta inhibitors).

Further without being limited by a particular theory, it was found that a compound provided herein does not affect BTK or MEK pathway. Accordingly, in some embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is iNHL. In another embodiment, the cancer or hematological malignancy is CLL.

In other embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a MEK inhibitor. In one embodiment, the MEK inhibitor is trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxyl]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2-yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with an EZH2 inhibitor. In one embodiment, the EZH2 inhibitor is EPZ-6438, GSK-126, GSK-343, Ell, or 3-deazancplanocin A (DNNep). In one embodiment, the cancer or hematological malignancy is DLBCL. In another embodiment, the cancer or hematological malignancy is iNHL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a bcl-2 inhibitor. In one embodiment, the BCL2 inhibitor is ABT-199 (4-[4-[[2-(4-Chlorophenyl)-4,4-dimethylcyclohex-1-en-1-yl]methyl] piperazin-1-yl]-N-[[3-nitro-4-[[(tetrahydro-2H-pyran-4-yl) methyl]amino]phenyl]sulfonyl]-2-[(1H-pyrrolo[2,3-b] pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbeznamide), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl) phenyl)sulfonyl)benzamide), GX15-070 (obatoclax mesylate, (2Z)-2-[(5Z)-5-[(3,5-dimethyl-1H-pyrol-2-yl) methylidene]-4-methoxpyrrol-2-ylidene]indole; methanesulfonic acid))), or G3139 (Oblimersen). In one embodiment, the cancer or hematological malignancy is DLBCL. In another embodiment, the cancer or hematological malignancy is iNHL. In another embodiment, the cancer or hematological malignancy is CLL. In another embodiment, the cancer or hematological malignancy is ALL. In another embodiment, the cancer or hematological malignancy is CTCL.

In other embodiments, provided herein is a method of treating or managing iNHL comprising administering to a patient a therapeutically effective amount of a compound provided herein, or a pharmaceutically acceptable derivative (e.g., salt or solvate) thereof, in combination with rituximab. In one embodiment, the patient is an elderly patient. In another embodiment, iNHL is relapsed or refractory.

In other embodiments, provided herein is a method of treating or managing iNHL comprising administering to a patient a therapeutically effective amount of a compound provided herein, or a pharmaceutically acceptable derivative (e.g., salt or solvate) thereof, in combination with bendamustine. In one embodiment, iNHL is relapsed or refractory.

In other embodiments, provided herein is a method of treating or managing iNHL comprising administering to a patient a therapeutically effective amount of a compound provided herein, or a pharmaceutically acceptable derivative (e.g., salt or solvate) thereof, in combination with rituximab, and in further combination with bendamustine. In one embodiment, iNHL is relapsed or refractory.

In other embodiments, provided herein is a method of treating or managing iNHL comprising administering to a patient a therapeutically effective amount of a compound provided herein, or a pharmaceutically acceptable derivative (e.g., salt or solvate) thereof, in combination with lenalidomide. In one embodiment, iNHL is relapsed or refractory.

In other embodiments, provided herein is a method of treating or managing CLL comprising administering to a patient a therapeutically effective amount of a compound provided herein, or a pharmaceutically acceptable derivative (e.g., salt or solvate) thereof, in combination with rituximab. In one embodiment, the patient is an elderly patient. In another embodiment, CLL is relapsed or refractory.

In other embodiments, provided herein is a method of treating or managing CLL comprising administering to a patient a therapeutically effective amount of a compound provided herein, or a pharmaceutically acceptable derivative (e.g., salt or solvate) thereof, in combination with bendamustine. In one embodiment, CLL is relapsed or refractory.

In other embodiments, provided herein is a method of treating or managing CLL comprising administering to a patient a therapeutically effective amount of a compound provided herein, or a pharmaceutically acceptable derivative (e.g., salt or solvate) thereof, in combination with rituximab, and in further combination with bendamustine. In one embodiment, CLL is relapsed or refractory.

In other embodiments, provided herein is a method of treating or managing CLL comprising administering to a patient a therapeutically effective amount of a compound provided herein, or a pharmaceutically acceptable derivative (e.g., salt or solvate) thereof, in combination with lenalidomide. In one embodiment, CLL is relapsed or refractory.

In other embodiments, provided herein is a method of treating or managing DLBCL comprising administering to a patient a therapeutically effective amount of a compound provided herein, or a pharmaceutically acceptable derivative (e.g., salt or solvate) thereof, in combination with rituximab. In one embodiment, the patient is an elderly patient. In another embodiment, DLBCL is relapsed or refractory.

In other embodiments, provided herein is a method of treating or managing DLBCL comprising administering to a patient a therapeutically effective amount of a compound provided herein, or a pharmaceutically acceptable derivative (e.g., salt or solvate) thereof, in combination with bendamustine. In one embodiment, DLBCL is relapsed or refractory.

In other embodiments, provided herein is a method of treating or managing DLBCL comprising administering to a patient a therapeutically effective amount of a compound provided herein, or a pharmaceutically acceptable derivative (e.g., salt or solvate) thereof, in combination with rituximab, and in further combination with bendamustine. In one embodiment, DLBCL is relapsed or refractory.

In other embodiments, provided herein is a method of treating or managing DLBCL comprising administering to a patient a therapeutically effective amount of a compound provided herein, or a pharmaceutically acceptable derivative (e.g., salt or solvate) thereof, in combination with R-GDP (rituximab, cyclophosphamide, vincristine and prednisone). In one embodiment, DLBCL is relapsed or refractory. In another embodiment, the treatment is done subsequent to treatment by R-CHOP.

In other embodiments, provided herein is a method of treating or managing DLBCL comprising administering to a patient a therapeutically effective amount of a compound provided herein, or a pharmaceutically acceptable derivative (e.g., salt or solvate) thereof, in combination with ibrutinib. In one embodiment, DLBCL is relapsed or refractory.

In other embodiments, provided herein is a method of treating or managing T-cell lymphoma (PTCL or CTCL) comprising administering to a patient a therapeutically effective amount of a compound provided herein, or a pharmaceutically acceptable derivative (e.g., salt or solvate) thereof, in combination with rituximab. In one embodiment. T-cell lymphoma is relapsed or refractory.

In other embodiments, provided herein is a method of treating or managing T-cell lymphoma (PTCL or CTCL) comprising administering to a patient a therapeutically effective amount of a compound provided herein, or a pharmaceutically acceptable derivative (e.g., salt or solvate) thereof, in combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein, or a pharmaceutically acceptable derivative (e.g., salt or solvate) thereof, in combination with rituximab, and in further combination with bendamustine. In one embodiment, T-cell lymphoma is relapsed or refractory.

In other embodiments, provided herein is a method of treating or managing T-cell lymphoma (PTCL or CTCL) comprising administering to a patient a therapeutically effective amount of a compound provided herein, or a pharmaceutically acceptable derivative (e.g., salt or solvate) thereof, in combination with romidepsin. In one embodiment, T-cell lymphoma is relapsed or refractory.

In other embodiments, provided herein is a method of treating or managing mantle cell lymphoma comprising administering to a patient a therapeutically effective amount of a compound provided herein, or a pharmaceutically acceptable derivative (e.g., salt or solvate) thereof, in combination with rituximab. In one embodiment, mantle cell lymphoma is relapsed or refractory.

In other embodiments, provided herein is a method of treating or managing mantle cell lymphoma comprising administering to a patient a therapeutically effective amount of a compound provided herein, or a pharmaceutically acceptable derivative (e.g., salt or solvate) thereof, in combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein, or a pharmaceutically acceptable derivative (e.g., salt or solvate) thereof, in combination with rituximab, an din further combination with bendamustine. In one embodiment, mantle cell lymphoma is relapsed or refractory.

In other embodiments, provided herein is a method of treating or managing mantle cell lymphoma comprising administering to a patient a therapeutically effective amount of a compound provided herein, or a pharmaceutically acceptable derivative (e.g., salt or solvate) thereof, in combination with ibrutinib. In one embodiment, mantle cell lymphoma is relapsed or refractory.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a doxorubicin. In one embodiment, the cancer or hematological malignancy is ALL.

In some embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a AraC. In one embodiment, the cancer or hematological malignancy is AML.

In some embodiments, a compound provided herein or a pharmaceutically acceptable form thereof, is used in combination with one or more second agent or second therapy provided herein.

In some embodiments, the second agent is an antibody-drug conjugate, such as, e.g., inotuzumab ozogamicin, or brentuximab vedotin.

In some embodiments, the second agent is a cytotoxic agent, such as, e.g., bendamustine, gemcitabine, oxaliplatin, cyclophosphamide, vincristine, vinblastine, anthracycline (e.g., daunorubicin or daunomycin, doxorubicin), actinomycin, dactinomycin, bleomycin, clofarabine, nelarabine, cladribine, asparaginase, methotrexate, or pralatrexate.

In some embodiments, the second agent is one or more other anti-cancer agents or chemotherapeutic agents, such as, e.g., fludarabine, ibrutinib, fostamatinib, lenalidomide, thalidomide, rituximab, cyclophosphamide, doxorubicin, vincristine, prednisone, or R-CHOP (Rituximab, Cyclophosphamide, Doxorubicin or Hydroxydaunomycin, Vincristine or Oncovin, Prednisone).

In some embodiments, the second agent is an antibody for a cytokine (e.g., an IL-15 antibody, an IL-21 antibody, an IL-4 antibody, an IL-7 antibody, an IL-2 antibody, an IL-9 antibody). In some embodiments, the second agent is a JAK1 inhibitor, a JAK3 inhibitor, a pan-JAK inhibitor, a BTK inhibitor, an SYK inhibitor, or a PI3K delta inhibitor. In some embodiments, the second agent is an antibody for a chemokine.

Without being limited to a particular theory, a targeted combination therapy described herein has reduced side effect and/or enhanced efficacy. For example, in one embodiment, provided herein is a combination therapy for treating CLL with a compound described herein and a second active agent (e.g., IL-15 antibodies, IL-21 antibodies, IL-4 antibodies, IL-7 antibodies, IL-2 antibodies, IL-9 antibodies, JAK inhibitors, JAK3 inhibitors, pan-JAK inhibitors, BTK inhibitors, SYK inhibitors, and/or PI3K delta inhibitors).

Further without being limited by a particular theory, it was found that a compound provided herein does not affect BTK or MEK pathway. Accordingly, in some embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a BTK inhibitor. In one embodiment, the BTK inhibitor is ibrutinib. In one embodiment, the BTK inhibitor is AVL-292. In one embodiment, the cancer or hematological malignancy is DLBCL. In another embodiment, the cancer or hematological malignancy is CLL.

In other embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a MEK inhibitor. In one embodiment, the MEK inhibitor is trametinib, selumetinob, AS703026/MSC1935369, XL-518/GDC-0973, BAY869766/RDEA119, GSK1120212 (trametinib), pimasertib, refametinib, PD-0325901, TAK733, MEK162/ARRY438162, RO5126766, WX-554, RO4987655/CH4987655 or AZD8330. In one embodiment, the cancer or hematological malignancy is DLBCL. In another embodiment, the cancer or hematological malignancy is ALL. In another embodiment, the cancer or hematological malignancy is CTCL.

In other embodiments, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a bcl-2 inhibitor. In one embodiment, the BCL2 inhibitor is ABT-199, ABT-737, ABT-263, GX15-070 (obatoclax mesylate) or G3139 (Genasense). In one embodiment, the cancer or hematological malignancy is DLBCL. In another embodiment, the cancer or hematological malignancy is ALL. In another embodiment, the cancer or hematological malignancy is CTCL.

Further, without being limited by a particular theory, it was found that cancer cells exhibit differential sensitivity profiles to doxorubicin and compounds provided herein. Thus, provided herein is a method of treating or managing cancer or hematological malignancy comprising administering to a patient a therapeutically effective amount of a compound provided herein, or a pharmaceutically acceptable derivative (e.g., salt or solvate) thereof, in combination with a doxorubicin. In one embodiment, the cancer or hematological malignancy is ALL.

Further provided herein are methods of modulating kinase activity by contacting a kinase with an amount of a compound provided herein sufficient to modulate the activity of the kinase. Modulate can be inhibiting or activating kinase activity. In some embodiments, provided herein are methods of inhibiting kinase activity by contacting a kinase with an amount of a compound provided herein sufficient to inhibit the activity of the kinase. In some embodiments, provided herein are methods of inhibiting kinase activity in a solution by contacting said solution with an amount of a compound provided herein sufficient to inhibit the activity of the kinase in said solution. In some embodiments, provided herein are methods of inhibiting kinase activity in a cell by contacting said cell with an amount of a compound provided herein sufficient to inhibit the activity of the kinase in said cell. In some embodiments, provided herein are methods of inhibiting kinase activity in a tissue by contacting said tissue with an amount of a compound provided herein sufficient to inhibit the activity of the kinase in said tissue. In some embodiments, provided herein are methods of inhibiting kinase activity in an organism by contacting said organism with an amount of a compound provided herein sufficient to inhibit the activity of the kinase in said organism. In some embodiments, provided herein are methods of inhibiting kinase activity in an animal by contacting said animal with an amount of a compound provided herein sufficient to inhibit the activity of the kinase in said animal. In some embodiments, provided herein are methods of inhibiting kinase activity in a mammal by contacting said mammal with an amount of a compound provided herein sufficient to inhibit the activity of the kinase in said mammal. In some embodiments, provided herein are methods of inhibiting kinase activity in a human by contacting said human with an amount of a compound provided herein sufficient to inhibit the activity of the kinase in said human. In some embodiments, the % of kinase activity after contacting a kinase with a compound provided herein is less than 1, 5, 10, 20, 30, 40, 50, 60, 70, 80, 90, 95, or 99% of the kinase activity in the absence of said contacting step.

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

EXAMPLES

Chemical Examples

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours.

The terms "solvent," "organic solvent," and "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol. N-methylpyrrolidone ("NMP"), pyridine, and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure, such as, for example, filtration, extraction, crystallization, column chromatography, thin-layer chromatography, or thick-layer chromatography, or a combination of these procedures. Specific illustrations of suitable separation and isolation procedures are given by reference to the examples herein below. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation. Further, atropisomers (i.e., stereoisomers from hindered rotation about single bonds) of compounds provided herein can be resolved or isolated by methods known to those skilled in the art.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In one embodiment, provided herein is a method of preparing a compound provided herein according to a procedure disclosed herein.

In some embodiments, compounds provided herein can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the compounds and is not intended to limit the scope of reactions or reaction sequences that can be used in preparing the compounds provided herein.

General Synthetic Methods

The compounds herein being generally described, it will be more readily understood by reference to the following examples, which are included merely for purposes of illustration of certain aspects and embodiments, and are not intended to limit these aspects and embodiments.

In one embodiment, compounds of Formula I' provided herein can be prepared according to the scheme below:

Scheme 1

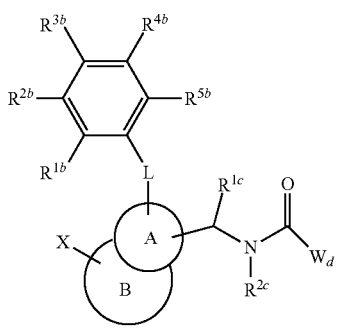

P2

-continued

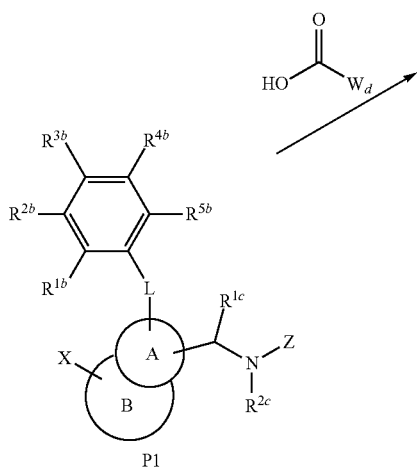

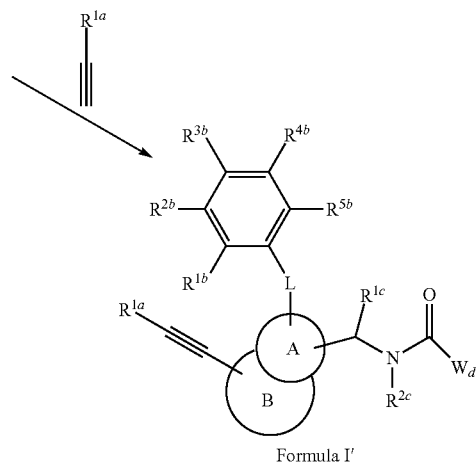

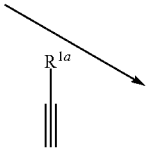

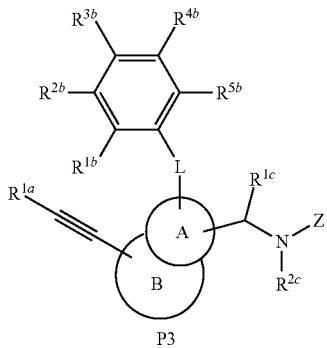

X = Cl, Br
Z is H or Boc

Compound P1 can be treated with $W_d$—C(O)OH to afford compound P2, which can be treated with alkyne to generate a compound of Formula I'. Alternatively, Compound P1 can be treated with the alkyne first to generate compound P3, which can be treated with $W_d$—C(O)OH to afford a compound of Formula I'.

(i) General Conditions for Amide Synthesis:

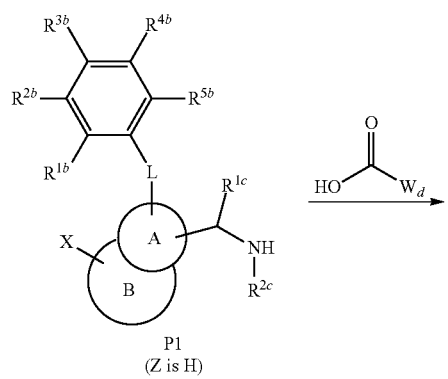

-continued

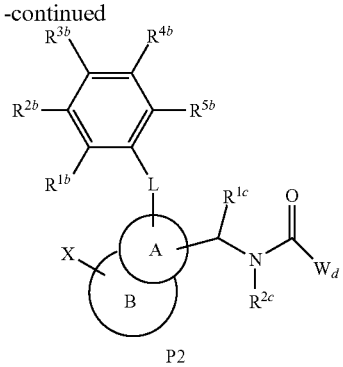

Method A:

To a mixture of amine P1 (Z is H) (0.5 mmol, 1.0 eq), $W_d$—COOH carboxylic acid (0.55 mmol, 1.1 eq), and N,N-diisopropylethylamine (0.17 mL, 1.0 mmol, 2.0 eq) in anhydrous DMF (5 mL), 1-hydroxybenzotriazole hydrate (0.65 mmol, 1.3 eq) and EDC hydrochloride (0.65 mmol, 1.3 eq) are added sequentially and the resulting mixture is stirred at RT for 2-16 h. Ice-water or saturated sodium carbonate solution is added to the reaction mixture and then stirred for 10 min. The precipitate is collected by filtration, rinsed with water and dried in vacuo. The solid collected is further purified by flash column chromatography on silica gel (MeOH/DCM) or reverse phase HPLC (acetonitrile/water/formic acid) to afford the product amide P2.

Method B:

To a mixture of amine P1 (Z is H) (0.53 mmol, 1.0 equiv), $W_d$—COOH carboxylic acid (0.58 mmol, 1.1 eq), and triethylamine (1.6 mmol) in anhydrous DMF (10 mL), 1-hydroxybenzotriazole (0.64 mmol, 1.2 equiv) and EDC hydrochloride (0.64 mmol, 1.2 eq) are added sequentially and the resulting mixture is stirred at 40° C., for 12 h. The mixture is then concentrated and purified using flash silica gel chromatography (10-100% ethyl acetate/petroleum ether) or reverse phase HPLC (acetonitrile/water/formic acid) to afford the product amide P2.

(ii) General Conditions for the Coupling of Alkyne to Aryl Halide:

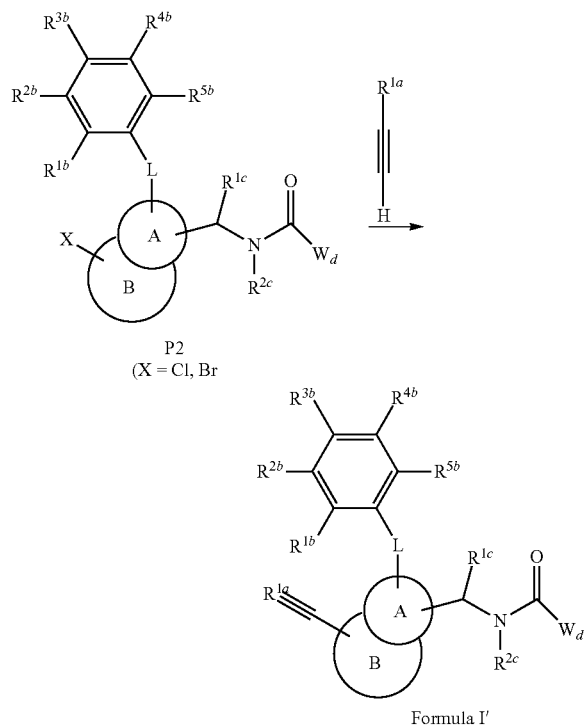

Method C:

A sealed tube vessel is charged with $PdCl_2(MeCN)_2$ (16 mol %), X-Phos (50 mol %), cesium carbonate (1.7 equiv) and propionitrile (3 mL). The mixture is stirred under Ar for 5 min after which compound P2 (0.36 mmol, 1.0 equiv) is added in a solution of propionitrile (2 mL). The mixture is stirred under Ar for an additional 5 min after which alkyne starting material (1.7 equiv) is added in a solution of propionitrile (1 mL). The mixture is sealed and stirred at room temperature for 10 min after which it was heated to 95° C. for 4 h. The reaction is then allowed to cool, diluted with methanol and filtered through a pad of celite. The filtrate is concentrated and purified using flash silica gel chromatography followed by further purification using flash silica gel chromatography or reverse phase HPLC (acetonitrile/water/formic acid) to provide the compound of Formula I'.

Method D:

A mixture of compound P2 (0.45 mmol, 1.0 equiv), alkyne starting material (2.0 equiv), $Cs_2CO_3$ (2.0 equiv), XPhos (50 mol %) and Pd(dppf)Cl$_2$ (50 mol %) in dioxane (20 mL) is heated to 80-100° C. and stirred for 3 h after which the mixture is concentrated. The mixture is purified by flash silica gel chromatography (MeOH/DCM) or reverse phase HPLC (acetonitrile/water/formic acid) to provide the compound of Formula I'.

(iii) General Conditions for Synthesis of Alkene Compounds of Formula II':

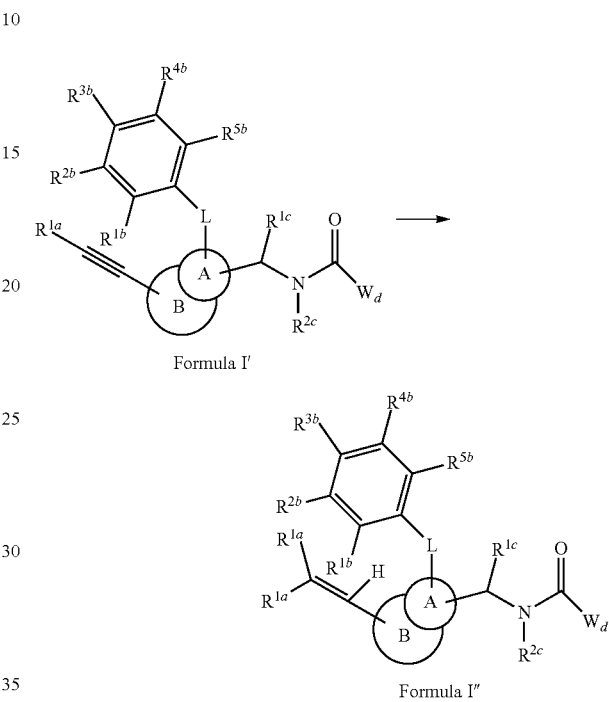

Method E:

To a mixture of alkyne compound of Formula I' (0.12 mmol, 1.0 equiv) dissolved in a mixture of ethanol and ethyl acetate (20 mL, 3:1 v/v), palladium on carbon (10% Pd) is added and the reaction mixture is placed under an atmosphere of $H_2$. The mixture is stirred at RT for 2 d after which it is filtered through a filter disk, concentrated and purified by flash silica gel chromatography (methanol/methylene chloride) or reverse phase HPLC (acetonitrile/water/formic acid) to provide the compound of Formula II' (one of $R^{1a}$ is hydrogen).

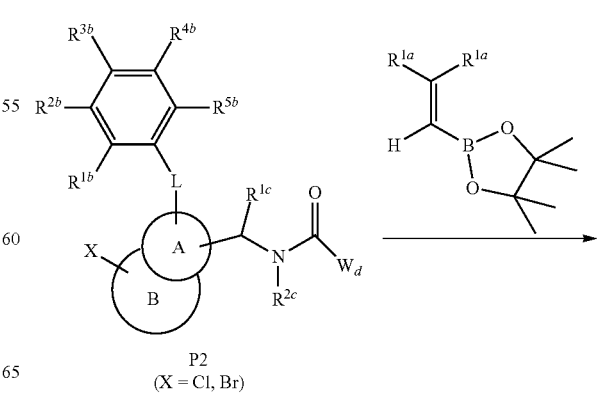

-continued

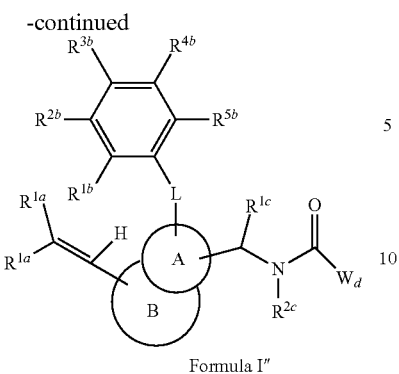

Formula I″

Method F:

Compound P2 (0.22 mmol, 1.0 equiv), PdCl$_2$(Amphos)$_2$ (10 mol %) and sodium carbonate (2.0 equiv) are charged to a 4 mL vial under an Ar atmosphere. A solution of boronate starting material in dioxane/water (1.5 equiv, 2 mL solvent, 4:1 v/v) is added and the reaction mixture is stirred at RT for 5 min under Ar before heating to 85° C. for 1 h. The reaction is allowed to cool, diluted with methylene chloride (15 mL) and washed with water (15 mL). The aqueous layer is then washed with additional methylene chloride (2×15 mL). The organic layers are combined and then washed with water (30 mL), brine (20 mL), dried over sodium sulfate and concentrated to provide crude material which is first purified by flash silica gel chromatography (methanol/methylene chloride) followed by purification using reverse phase HPLC (acetonitrile/water/0.1% formic acid) provide the compound of Formula II′.

(iv) Synthesis of Core Structures:
Compounds with the moiety

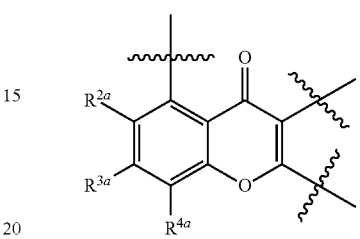

can be synthesized based on the general procedures described in WO2014006572, WO2013164801, or WO2012151525. For example, they can be prepared according to the schemes below.

Scheme 2

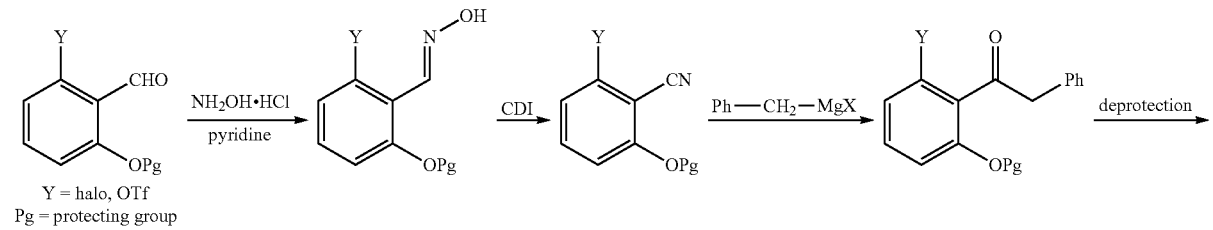

Y = halo, OTf
Pg = protecting group

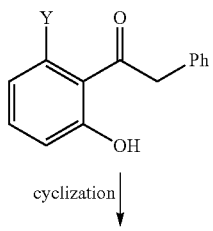

cyclization

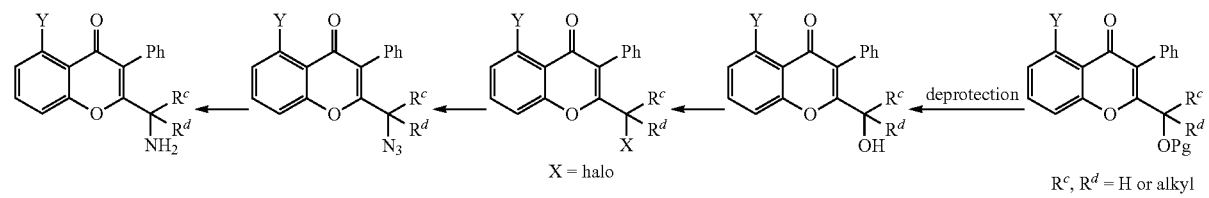

X = halo

R$^c$, R$^d$ = H or alkyl

Scheme 3

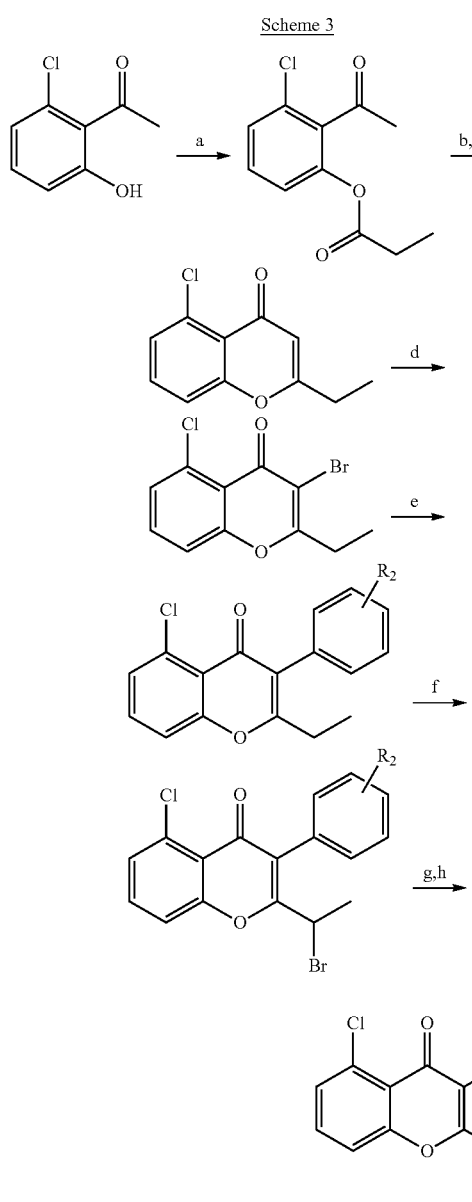

Conditions: a) propionyl chloride, pyridine, 0-15° C.; b) NaH, DMSO, RT; c) dioxane, H₂SO₄, 100° C.; d) NBS, DMF, 15° C.; e) aryl boronate, Pd(dppf)Cl₂, K₂CO₃, Dioxane, water 75° C.; f) Br₂, CCl₄, 60° C.; g) potassium phthalimide, DMF, RT; h) H₂NCH₂CH₂NH₂, MeOH.

Compounds with the moiety

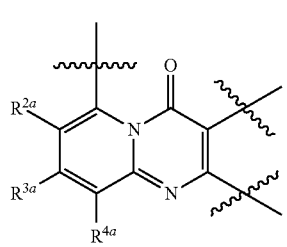

can be synthesized based on the general procedures described in WO2011008487, WO2010151735, Ferrarini et al., *J Het. Chem.*, 1999, 36, 1123-1127, or Li et al. *Bioorg. Med. Chem. Lett.*, 2008, 18, 668-693. For example, they can be synthesized according to the procedures in the scheme below.

Scheme 4

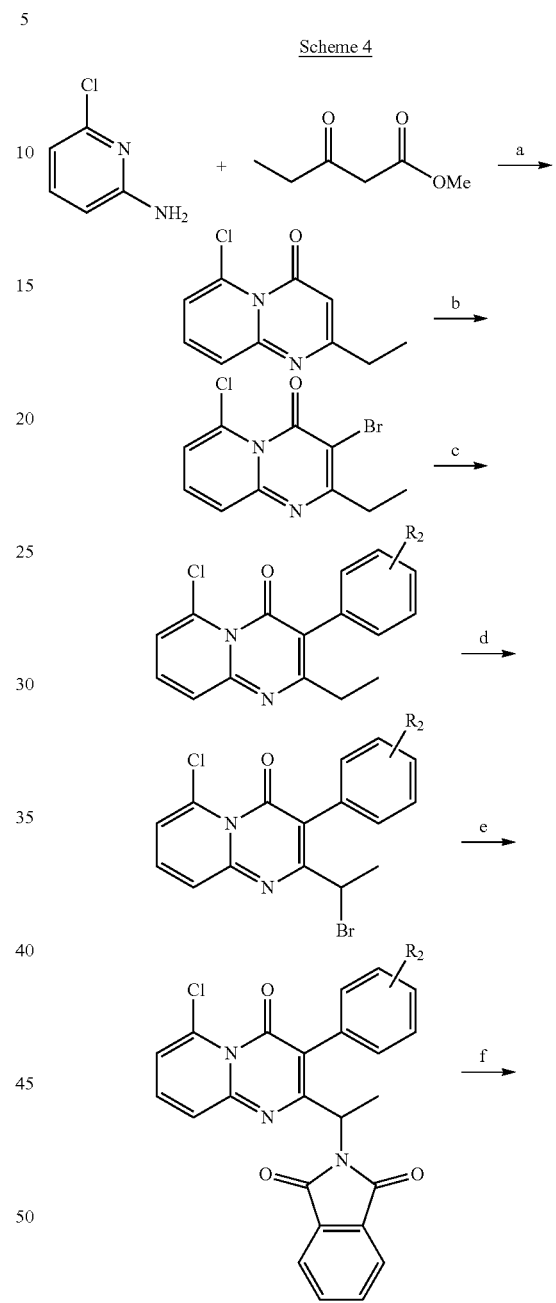

Conditions: a) EtOH, reflux; b) NBS, MeCN, rt; c) aryl boronate, Pd(PPh₃)₄, Na₂CO₃, 80° C., DME; (d) NBS, CCl₄, benzoylperoxide, reflux; (e) K₂CO₃, phthalimide; (f) NH₂NH₂.

483

Compounds with the moiety

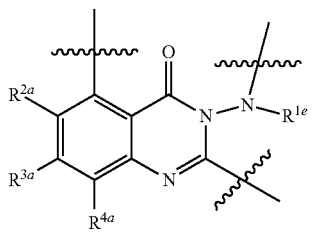

can be synthesized based on the general procedures described in WO2014023083 or US2011/0217300. For example, they can be synthesized according to the procedures in the scheme below.

Scheme 5

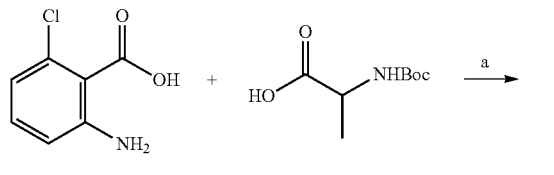

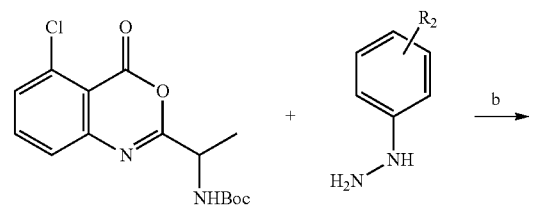

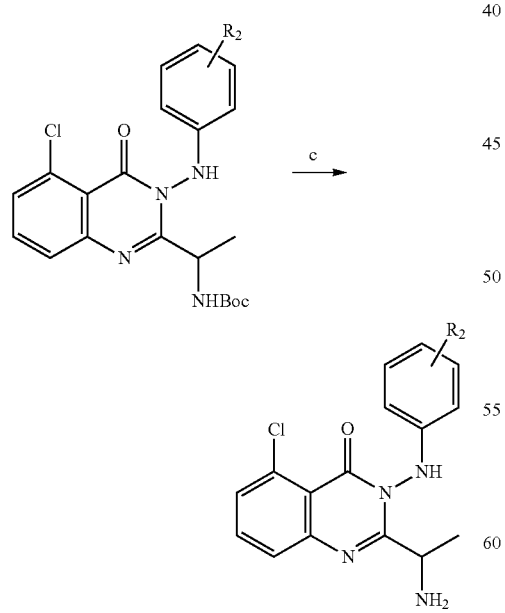

Conditions: a) P(OPh)₃, pyridine, 55° C.; b) 100° C.; c) 4M HCl/dioxane, methanol, RT.

484

Compounds with the moiety

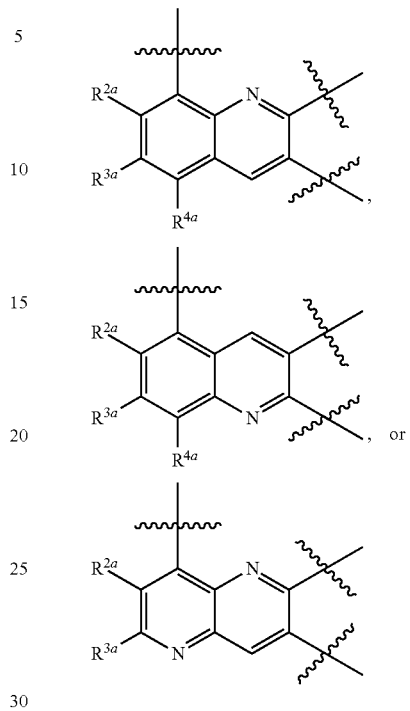

can be synthesized can be synthesized based on the general procedures described in WO2008118468, WO2011075628, US2014/0336182, WO2008150827, and Lanman et al., *Bioorg. Med. Chem. Lett.*, 24(24):5630-5634 (2014). For example, they can be synthesized according to the procedures in the schemes below.

Scheme 6

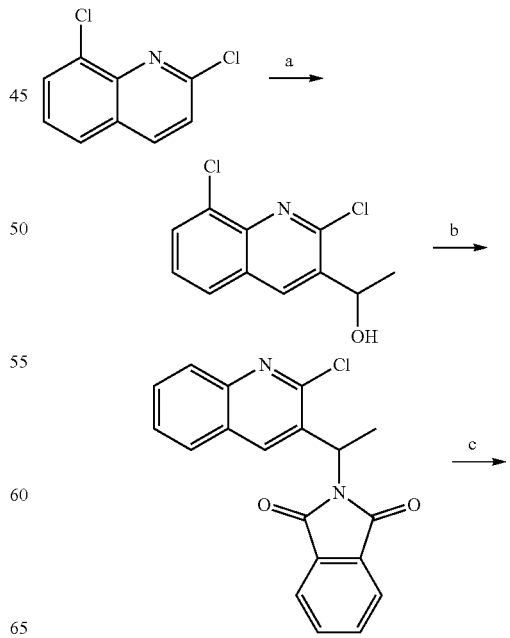

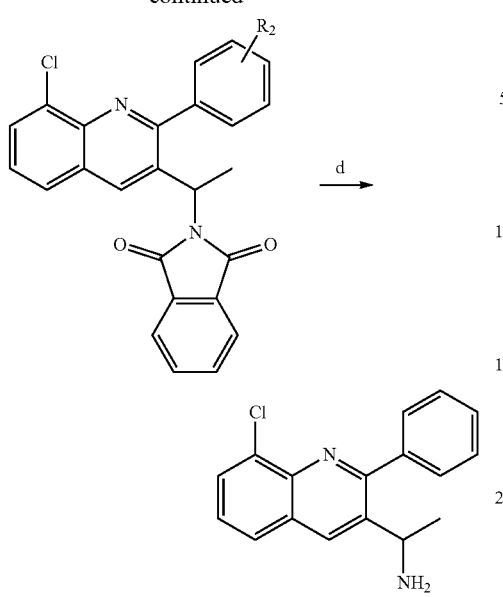

Conditions: a) LDA, THF, acetaldehyde, −78° C.; b) phthalimide, SOCl₂, K₂CO₃, 15-85° C.; c) aryl boronate, Pd(PPh₃)₄, Na₂CO₃, dioxane, H₂O, 85° C.; d) hydrazine hydrate, methanol, 75° C.

Scheme 7

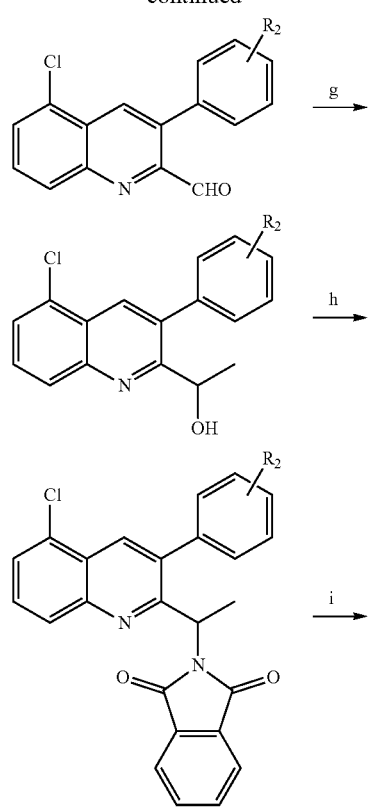

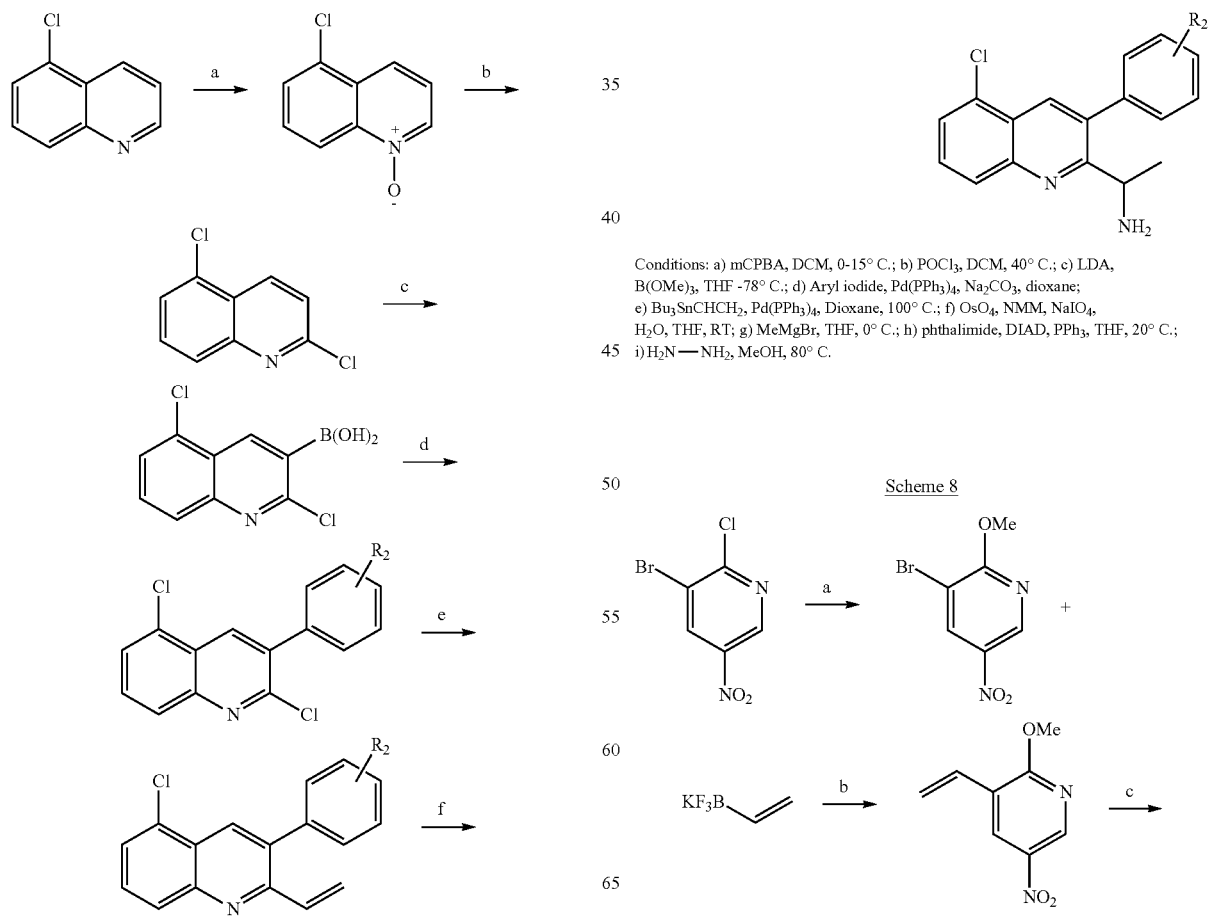

Conditions: a) mCPBA, DCM, 0-15° C.; b) POCl₃, DCM, 40° C.; c) LDA, B(OMe)₃, THF −78° C.; d) Aryl iodide, Pd(PPh₃)₄, Na₂CO₃, dioxane; e) Bu₃SnCHCH₂, Pd(PPh₃)₄, Dioxane, 100° C.; f) OsO₄, NMM, NaIO₄, H₂O, THF, RT; g) MeMgBr, THF, 0° C.; h) phthalimide, DIAD, PPh₃, THF, 20° C.; i) H₂N—NH₂, MeOH, 80° C.

Scheme 8

487
-continued

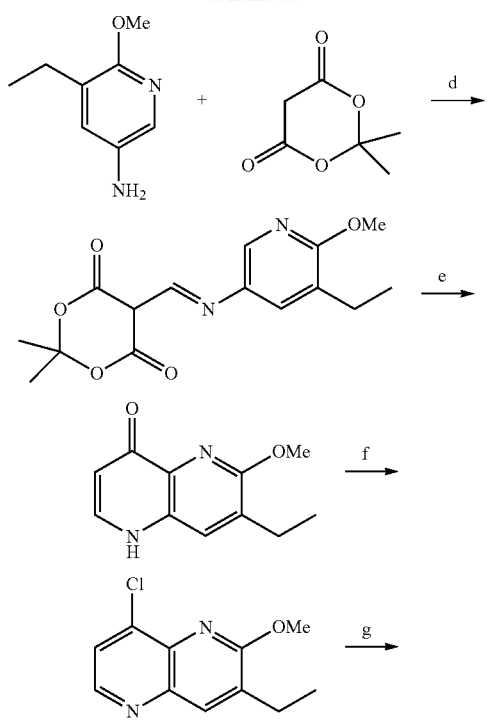

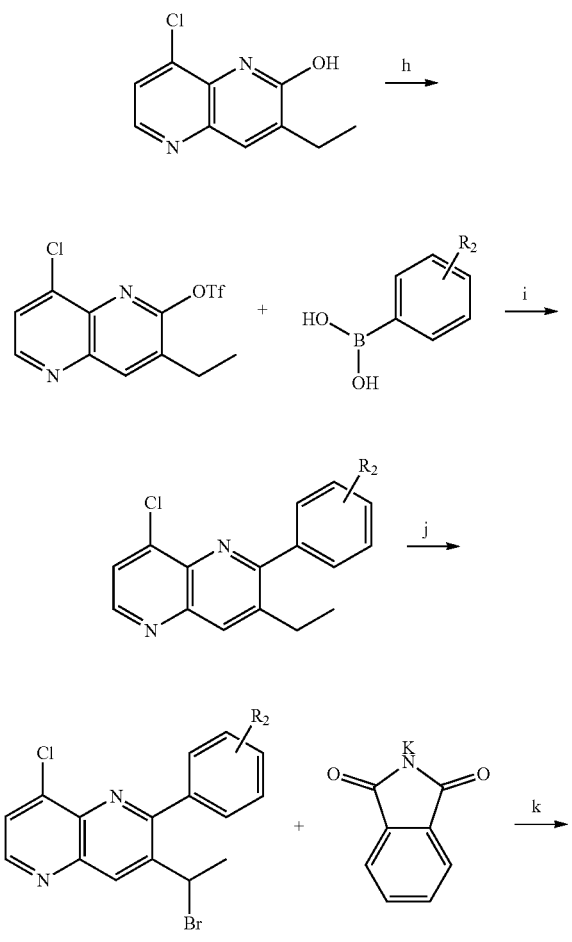

488
-continued

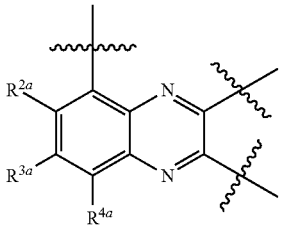

Conditions: a) MeOH; b) K₂CO₃, PdCl₂(Amphos)₂, dioxane, 80° C.; c) H₂, Pd/C, MeOH, rt, 1 atm; (d) CH(OMe)₃, 100° C.; e) PhOPh, 200° C.; f) POCl₃, 100° C. then NaOH; (g) 4M HCl/dioxane; (h) PhNTf₂, K₂CO₃, DMF, rt; (i) PdCl₂dppf, saturated aqueous NaHCO₃, dioxane, 100° C.; (j) Br₂, CCl₄, 60° C.; (k) DMF, rt; (l) H₂N(CH₂)₂NH₂, MeOH.

Compounds with the moiety $$\text{[moiety structure]}$$

can be synthesized based on the general procedures described in WO2013052699, WO2008118468, or Cushing et al., *J. Med. Chem.*, 2015, 58, 480-511. For example, they can be synthesized according to the procedures in the schemes below.

Scheme 9

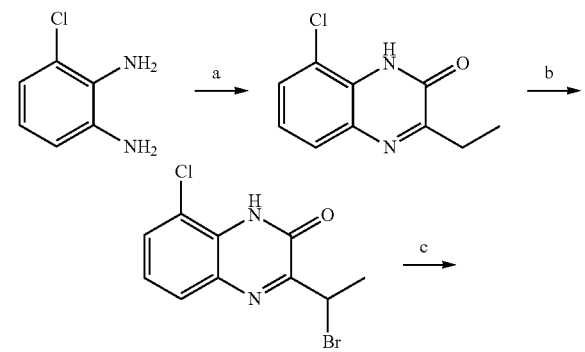

489
-continued

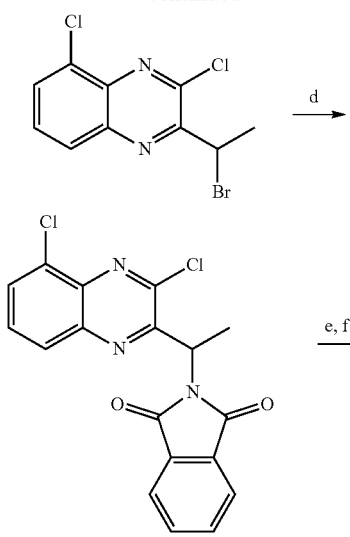

Conditions: a) ethyl 2-oxobutanoate, PPA, 100-160° C.; b) 1,3-dibromo-5,5-dimethylimidazolidine-2,4-dione, benzoyl peroxide, CCl$_4$, 80° C. to reflux; c) POCl$_3$, 110° C.; d) potassium phthalimidie, DMF, rt to 70° C.; e) aryl boronate, Pd(PPh$_3$)$_4$, Na$_2$CO$_3$, 80° C., DME; f) hydrazine hydrate, EtOH, 95° C.

Compounds with the moiety

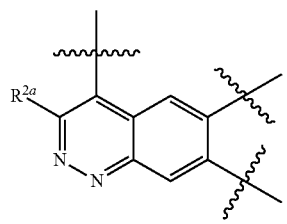

can be synthesized based on the general procedures described in WO2012033144 or Han et al., *ACS Med Chem. Lett.* 6:434-438 (2015). For example, they can be synthesized according to the procedures in the schemes below.

Scheme 10

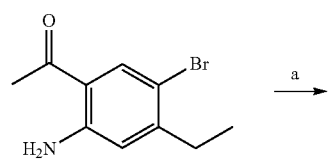

490
-continued

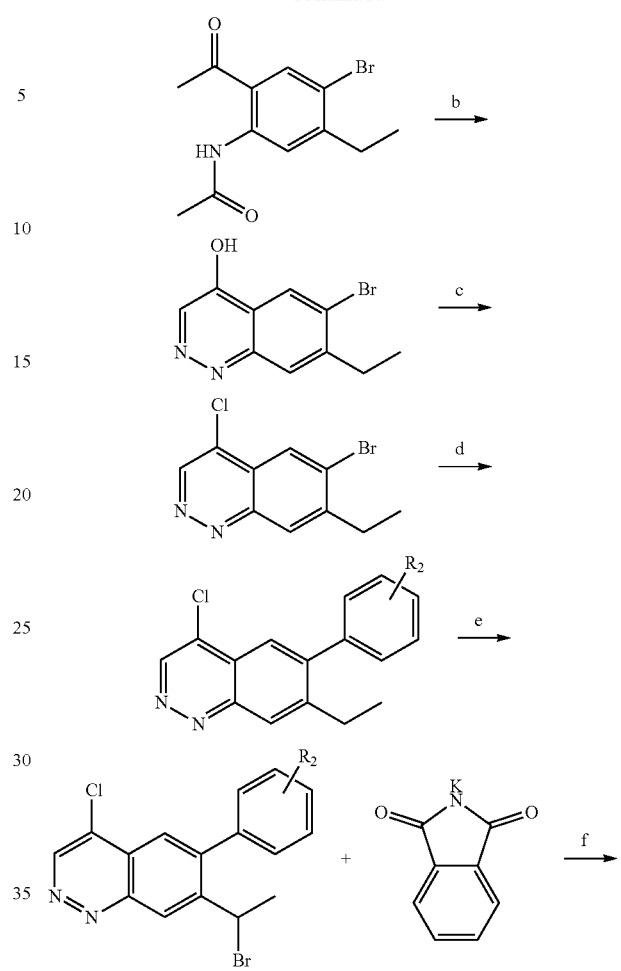

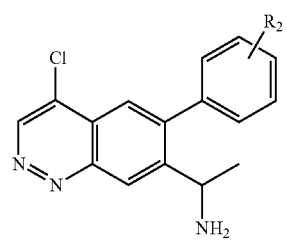

Conditions: a) AcCl, NEt$_3$, DCM, rt; b) NaNO$_2$, concentrated HCl, H$_2$O, THF; c) POCl$_3$, 85° C.; d) aryl boronate, Pd(PPh$_3$)$_4$, K$_2$CO$_3$, dioxane, water, 100° C.; e) Br$_2$, CCl$_4$, 60° C.; (f) DMF, rt; (g) H$_2$N(CH$_2$)$_2$NH$_2$, MeOH.

491
Compounds with the moiety
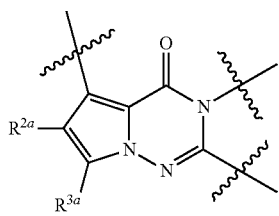
can be synthesized based on the general procedures described in WO2014060431, WO2014060432, WO2012146666, WO2014015675, or Ohta et al., *J. Org. Chem.*, 2009, 74, 8143. For example, they can be synthesized according to the procedures in the schemes below.
Scheme 11
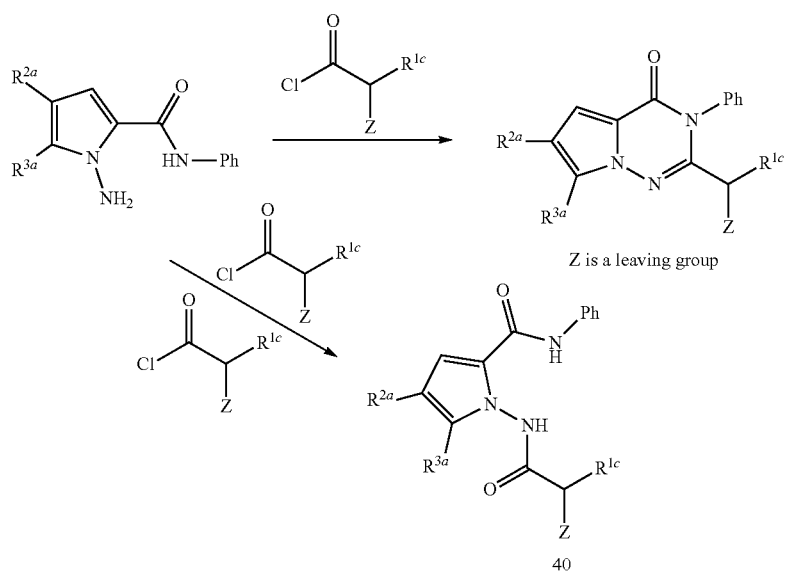
Z is a leaving group
Scheme 12
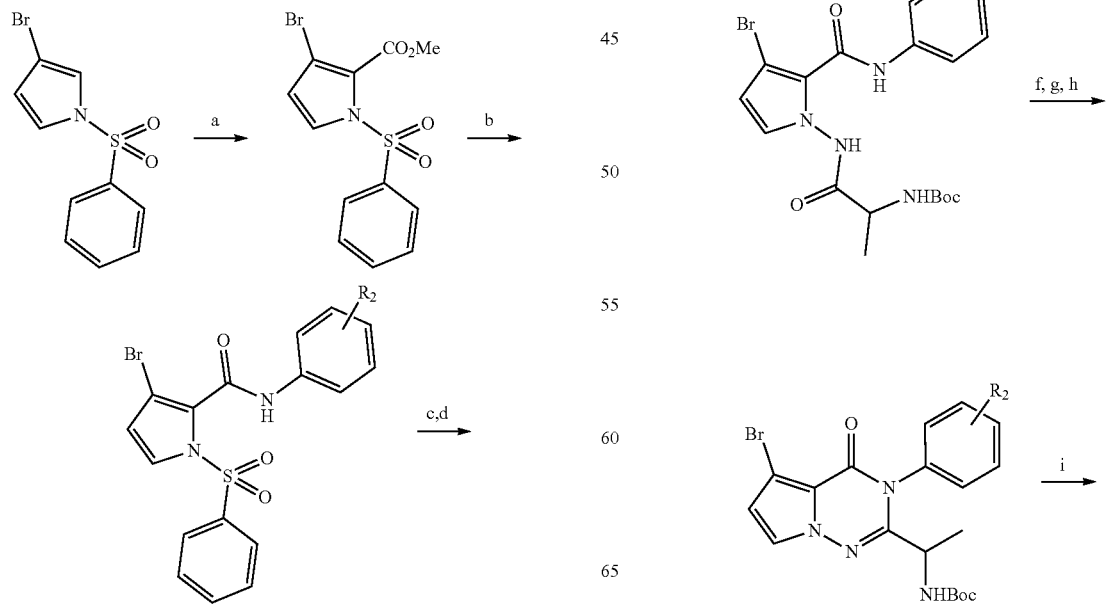
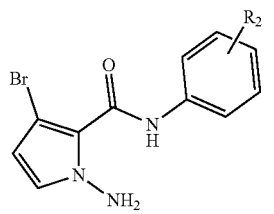

493
-continued

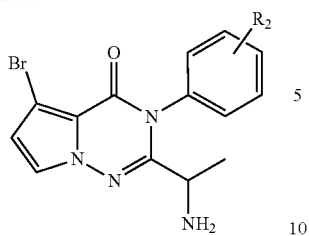

Conditions: a) LDA, THF, -78° C., then methyl chloroformate; b) substituted aniline, AlMe₃, 80° C., then tartaric acid; c) NaOH, H₂O, MeOH, RT; (d) NaOH, NH₄OH, NaOCl, Aliquat 366, water/Et₂O/tBuOMe 0° C. to RT; (e) Boc-alanine, EDC, DMF, RT; (f) Br₂, PPh₃, DCM, RT; (g) NEt₃, DCM, 60° C.; (h) NH₃, MeOH, 60° C.; (i) HCl, dioxane, RT.

Compounds with the moiety

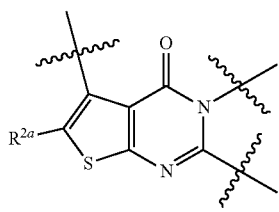

can be synthesized based on the general procedures described in WO2008064018, WO2009064802, or Bowers et al., *Bioorg. Med. Chem. Lett.*, 2011, 21, 1838-1843. For example, they can be synthesized according to the procedures in the scheme below.

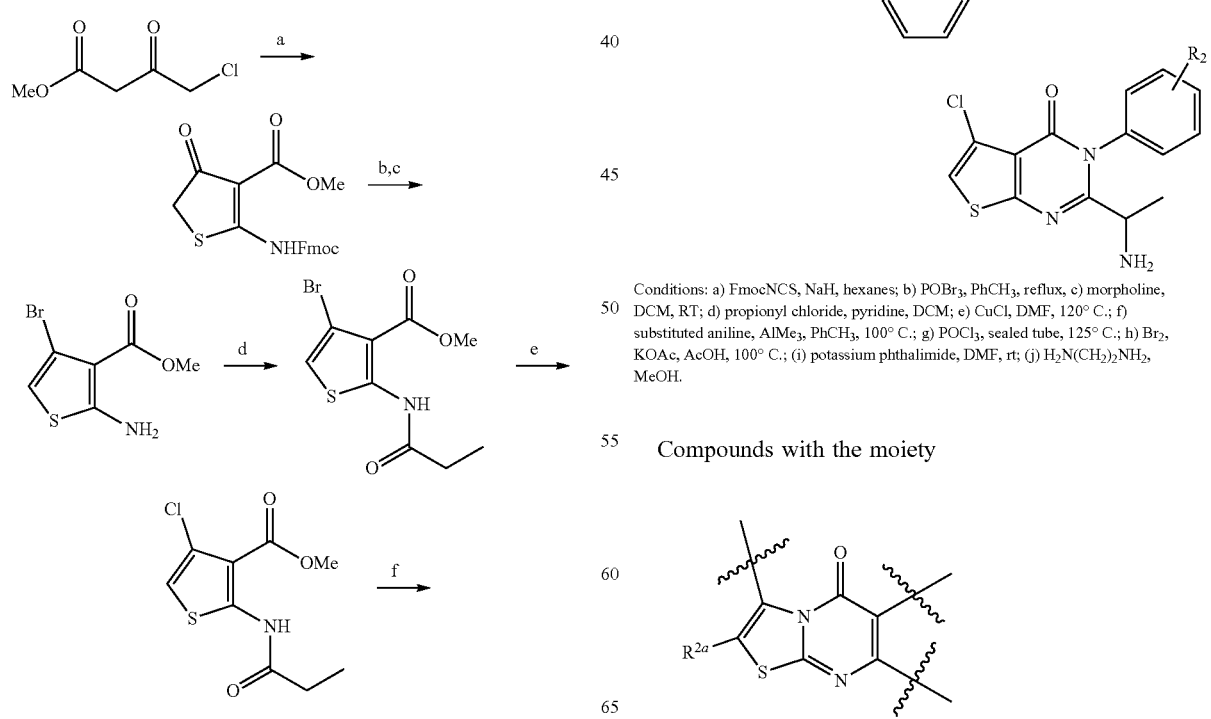

Compounds with the moiety can be synthesized based on the general procedures described in WO2011008487, WO2012125629. For example, they can be synthesized according to the procedures in the scheme below.

Scheme 14

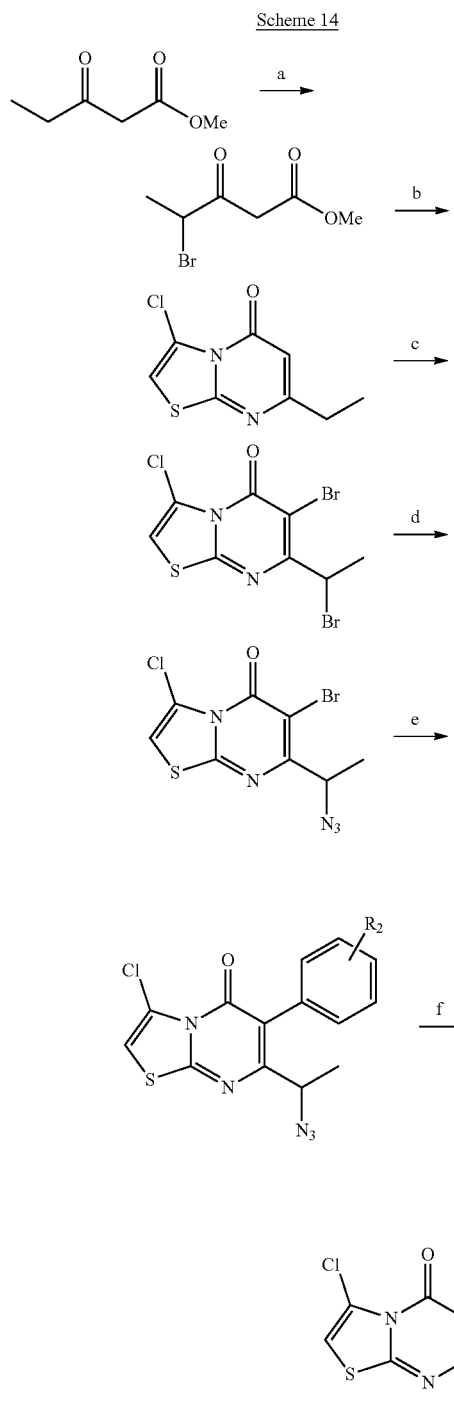

Conditions: a) Br₂, CHCl₃, 0° C. to rt; b) 4-chlorothiazol-2-amine, polyphosphoric acid, 110° C.; c) NBS, MeCN, 80° C.; d) NaN₃, DMF; e) aryl boronic acid, 1M Na₂CO₃, Pd(PPh₃)₄, dioxane, 100° C.; f) PMe₃, THF, water, RT.

Compounds with the moiety

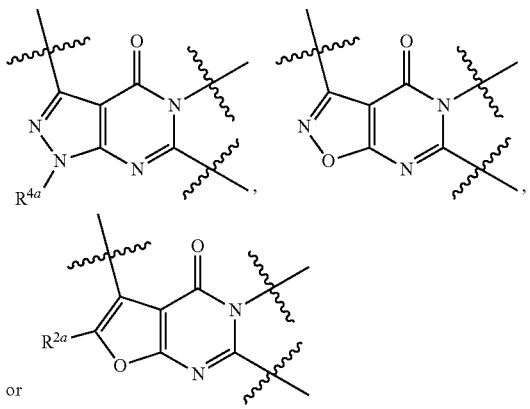

or can be synthesized based on the general procedures described in WO2009064802, WO2011024871, WO2004064836, Tong et al., *Bioorg. Med. Chem. Lett.*, 2008, 18, 5206-5208, or Schlewer et al., *Acta Chemica Scandinavica, Series B: Organic Chemistry and Biochemistry*, B38(10), 815-19 (1984). For example, they can be synthesized according to the procedures in the schemes below.

Scheme 15

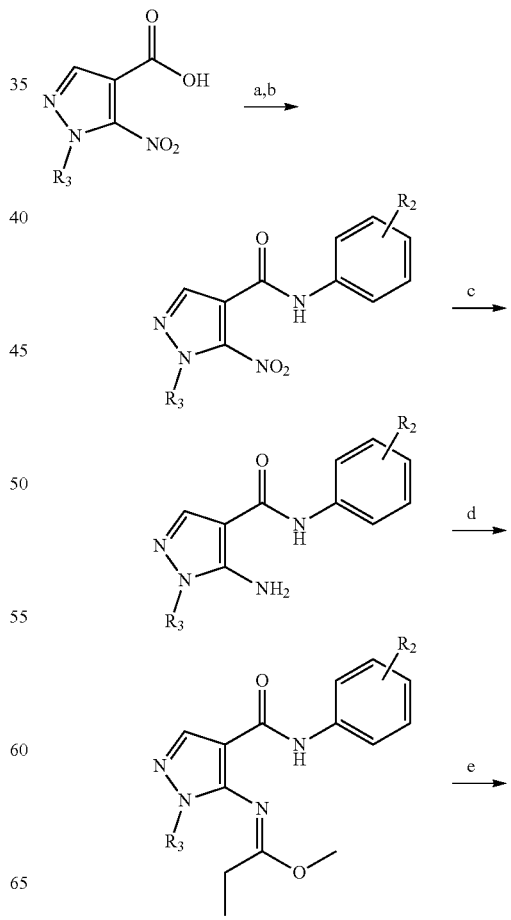

497
-continued

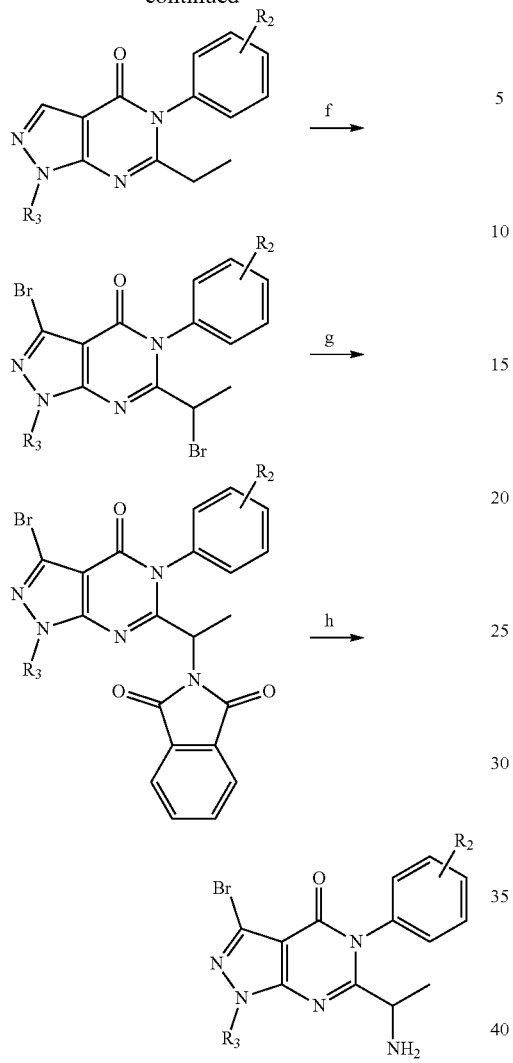

Conditions: a) SOCl₂, DMF (cat), PhCH₃, reflux; b) substituted aniline, DIEA, dioxane, RT; c) zinc, AcOH; d) EtC(OMe)₃, AcOH (cat), 100° C.; e) EtC(OMe)₃, reflux; f) Br₂, KOAc, AcOH, 100° C.; g) potassium phthalimide, DMF, rt; (h) H₂N(CH₂)₂NH₂, MeOH.

Scheme 16

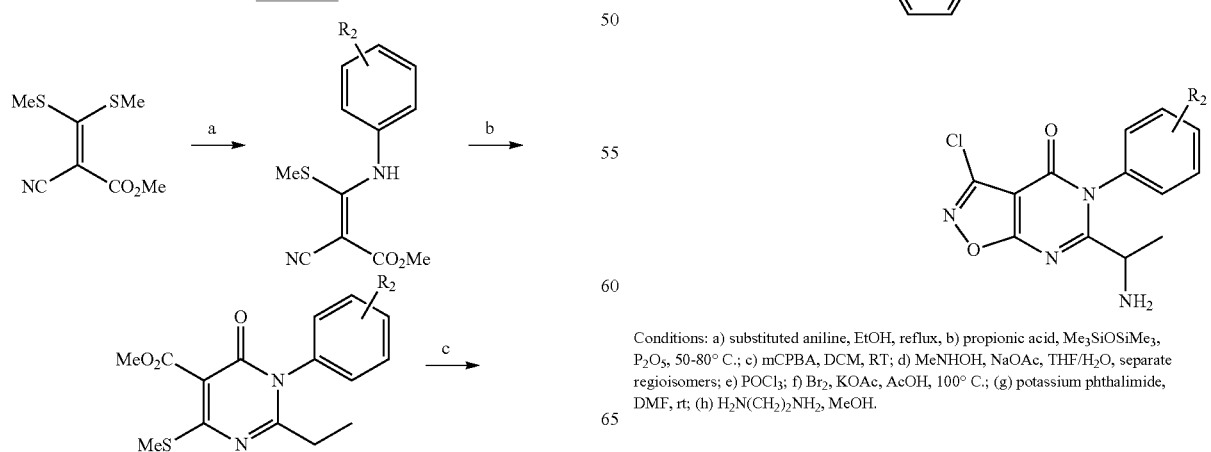

498
-continued

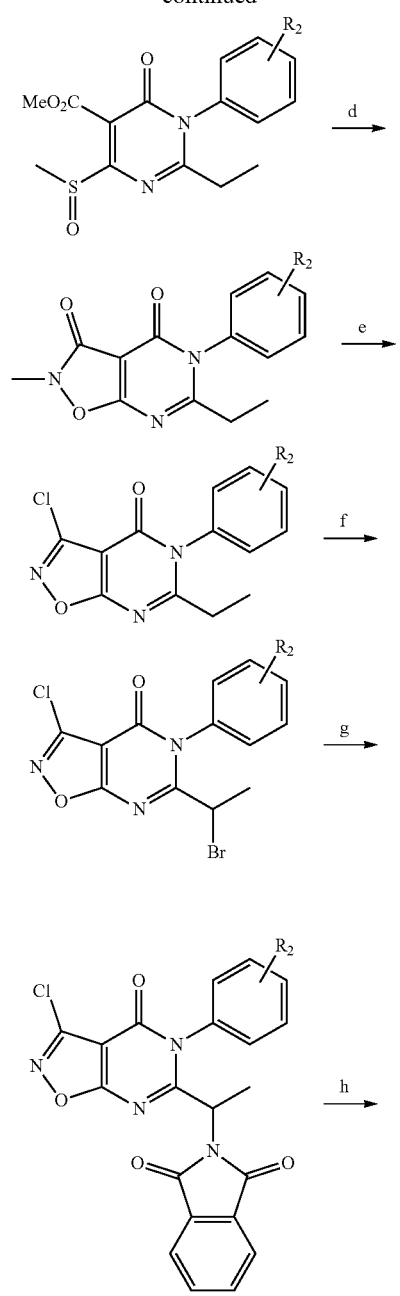

Conditions: a) substituted aniline, EtOH, reflux, b) propionic acid, Me₃SiOSiMe₃, P₂O₅, 50-80° C.; c) mCPBA, DCM, RT; d) MeNHOH, NaOAc, THF/H₂O, separate regioisomers; e) POCl₃; f) Br₂, KOAc, AcOH, 100° C.; (g) potassium phthalimide, DMF, rt; (h) H₂N(CH₂)₂NH₂, MeOH.

Scheme 17

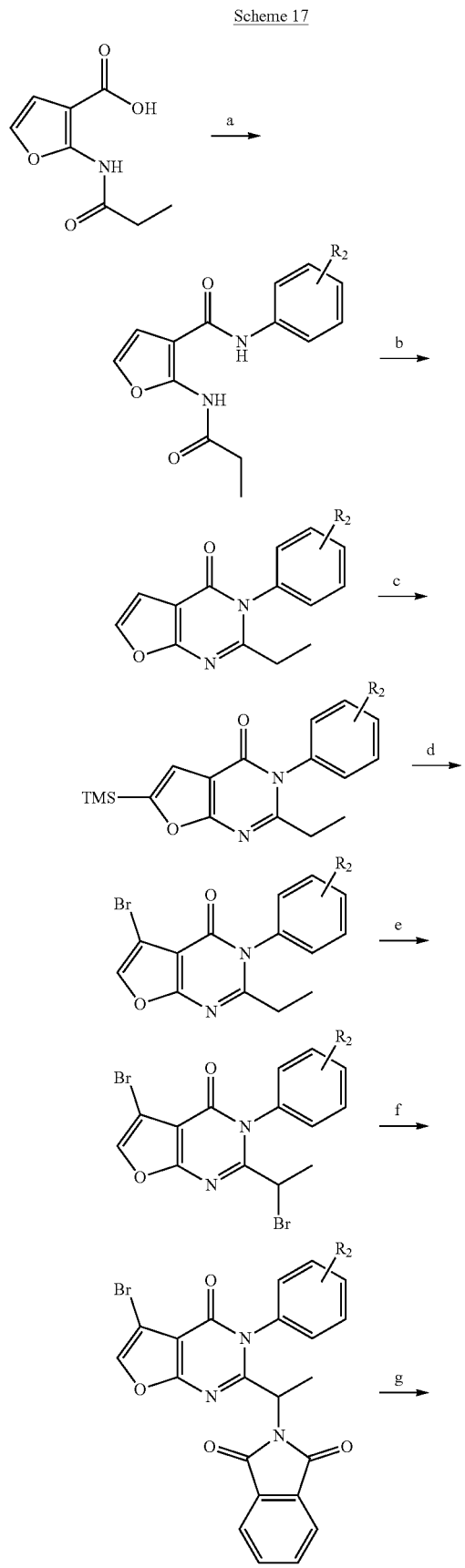

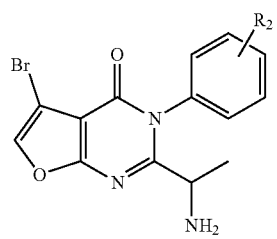

Conditions: a) HATU, substituted aniline, DIEA, DMF, RT; b) POCl$_3$, sealed tube. 125° C.; c) n-BuLi, TMSCl, THF; d) Br$_2$, NaHCO$_3$, water/DCM, RT; e) Br$_2$, KOAc, AcOH, 100° C.; (f) potassium phthalimide, DMF, RT; (g) H$_2$N(CH$_2$)$_2$NH$_2$, MeOH.

Compounds with the moiety

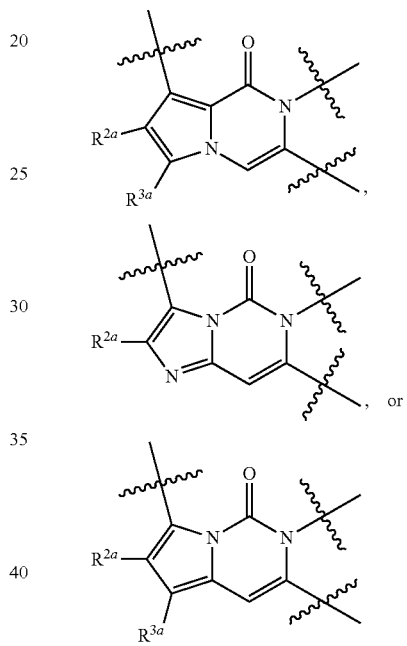

can be synthesized based on the general procedures described in WO2014015675 or WO2014015830. For example, they can be synthesized according to the procedures in the scheme below.

Scheme 18

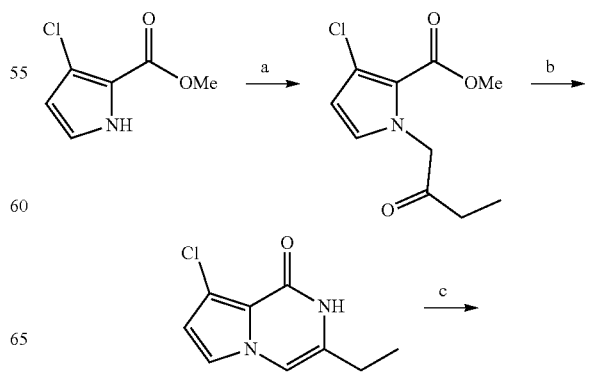

501
-continued

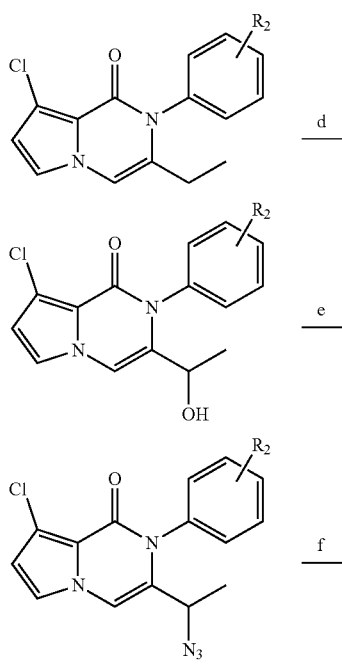

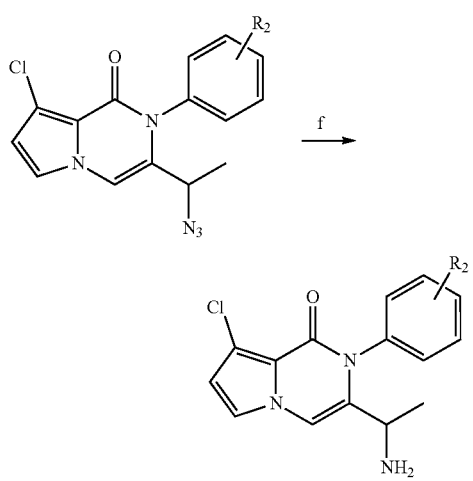

Conditions: a) 1-bromobutan-2-one, NaH, DMF 0° C. to RT; b) 7M NH₃ in MeOH, sealed tube, 130° C.; c) aryl boronic acid, Cu(OAc)₂, pyridine, 4ÅMS, DCM, dry air, RT; d) SeO₂/dioxane, reflux; e) DPPA, DBU, THF, 50-60° C.; f) PPh₃, THF, then concentrated NH₄OH, 50-60° C.

Scheme 19

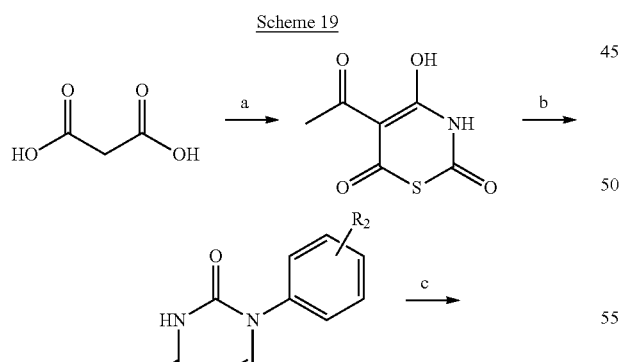

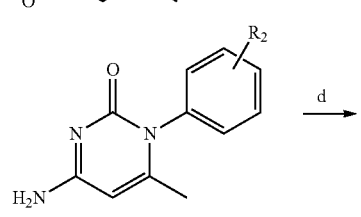

502
-continued

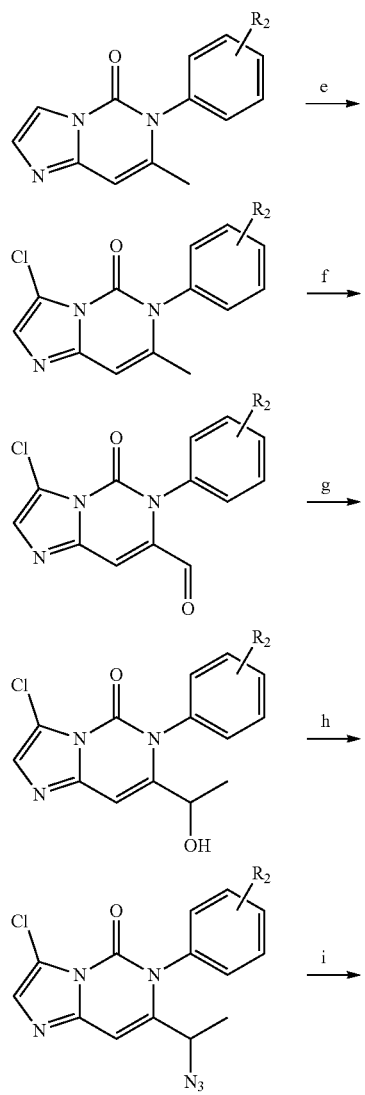

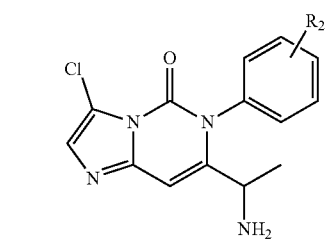

Conditions: a) KSCN, Ac₂O, AcOH; b) subsitututed aniline, DMF, reflux; c) BOP, DBU, NH₃, MeCN, RT; d) 40% 2-chloroacetaldehyde in water, EtOH, 100° C.; e) NCS, DMF, RT; f) SeO₂, dioxane, reflux; g) MeMgBr, THF, -78° C.; h) DPPA, DBU, THF, RT; i) PPh₃, aq. NH₃, THF 60° C.

Scheme 20

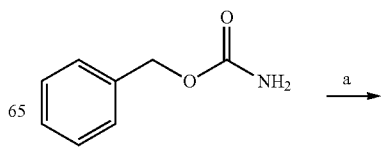

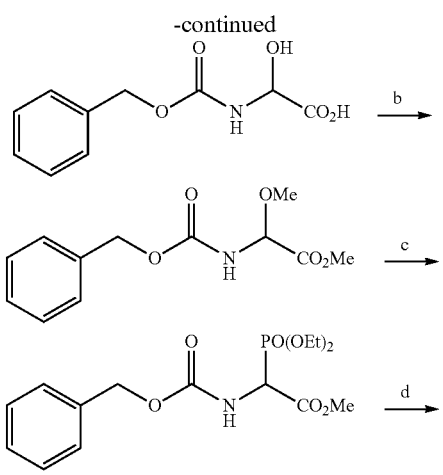
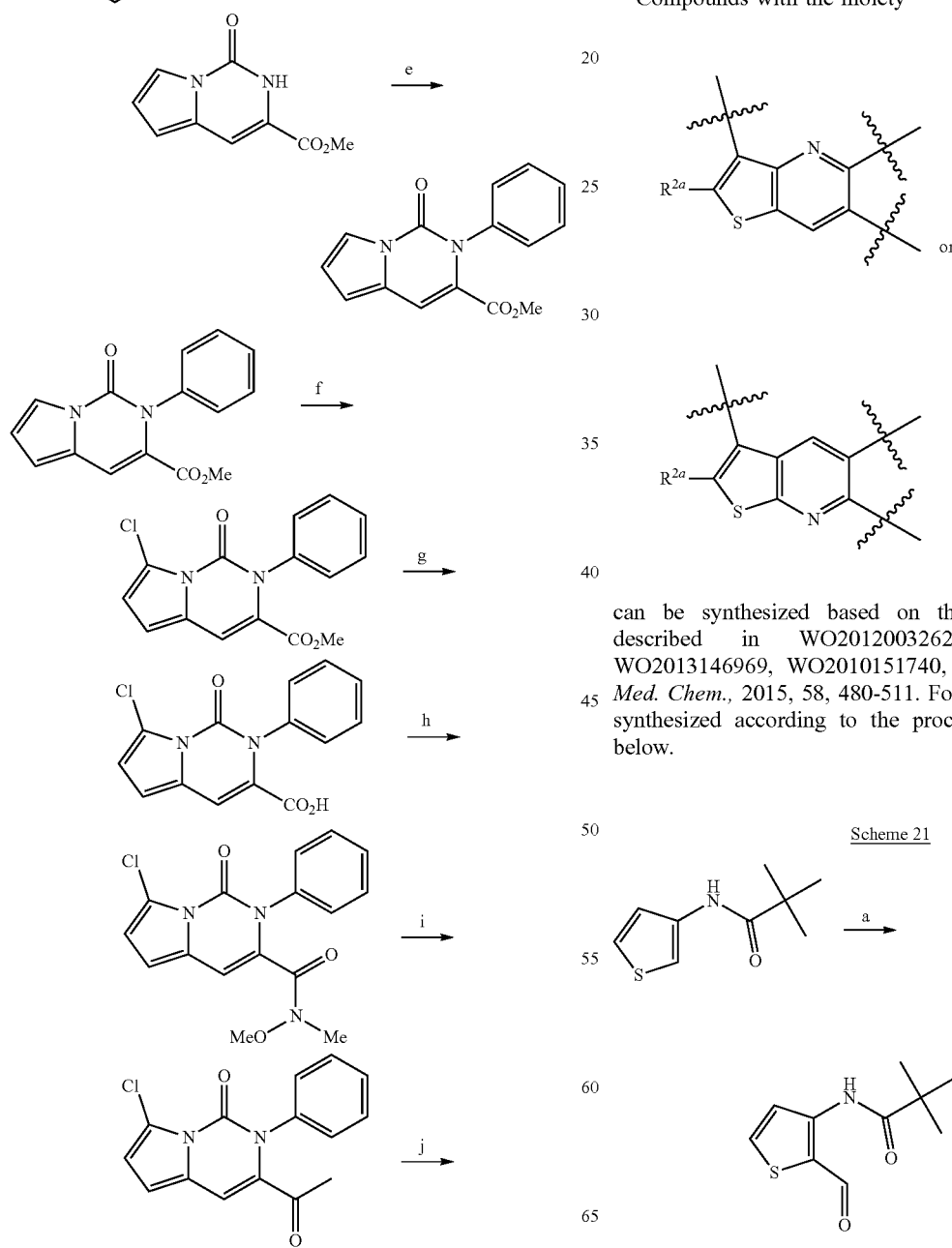

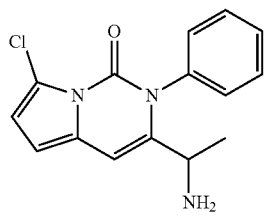

Conditions: a) 2-oxoacetic acid hydrate, Et$_2$O, RT; b) conc. H$_2$SO$_4$, MeOH, 0° C. to RT; c) PBr$_3$, PhCH$_3$, 70° C., then P(OEt)$_3$, 70° C.; d) TMG, DCM, 1H-pyrrole-2-carbaldehyde, -30° C. to RT; e) aryl boronic acid, Cu(OAc)$_2$, pyr, 4Å MS, DCM, RT; f) NCS, DMF, 70° C., separate regioisomers; g) 1N NaOH, EtOH/THF 0° C.; h) N,O-dimethylhydroxylamine-HCl, HBTU, DIEA, DMF, RT; i) MeMgBr in Et$_2$O, THF, 0° C.; j) NH$_4$OAc, NaCNBH$_3$, EtOH, 130° C., MW.

Compounds with the moiety can be synthesized based on the general procedures described in WO2012003262, WO20070259851, WO2013146969, WO2010151740, or Cushing et al., *J. Med. Chem.*, 2015, 58, 480-511. For example, they can be synthesized according to the procedures in the scheme below.

Scheme 21

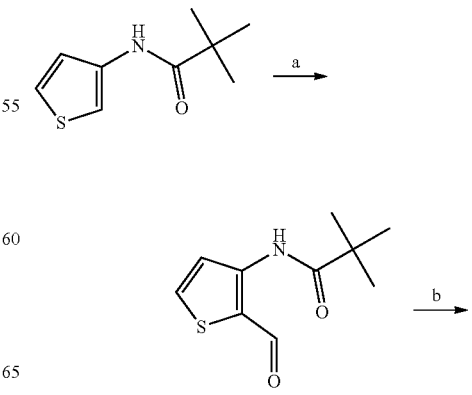

505
-continued

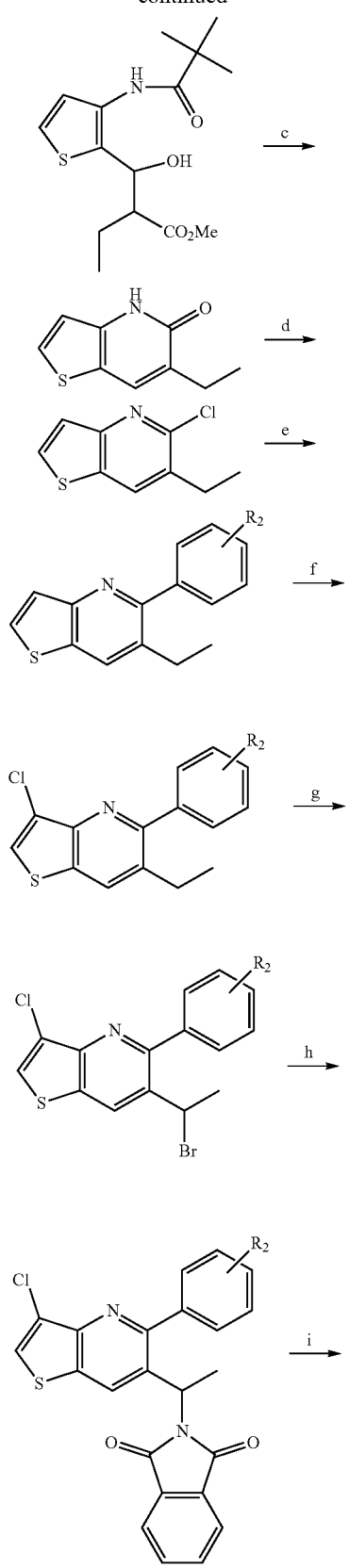

506
-continued

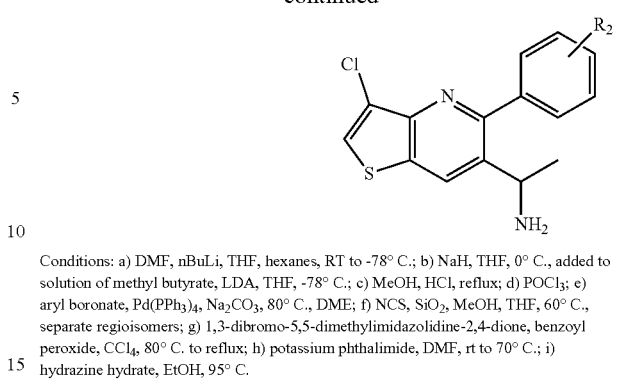

Conditions: a) DMF, nBuLi, THF, hexanes, RT to -78° C.; b) NaH, THF, 0° C., added to solution of methyl butyrate, LDA, THF, -78° C.; c) MeOH, HCl, reflux; d) POCl$_3$; e) aryl boronate, Pd(PPh$_3$)$_4$, Na$_2$CO$_3$, 80° C., DME; f) NCS, SiO$_2$, MeOH, THF, 60° C., separate regioisomers; g) 1,3-dibromo-5,5-dimethylimidazolidine-2,4-dione, benzoyl peroxide, CCl$_4$, 80° C. to reflux; h) potassium phthalimide, DMF, rt to 70° C.; i) hydrazine hydrate, EtOH, 95° C.

Scheme 22

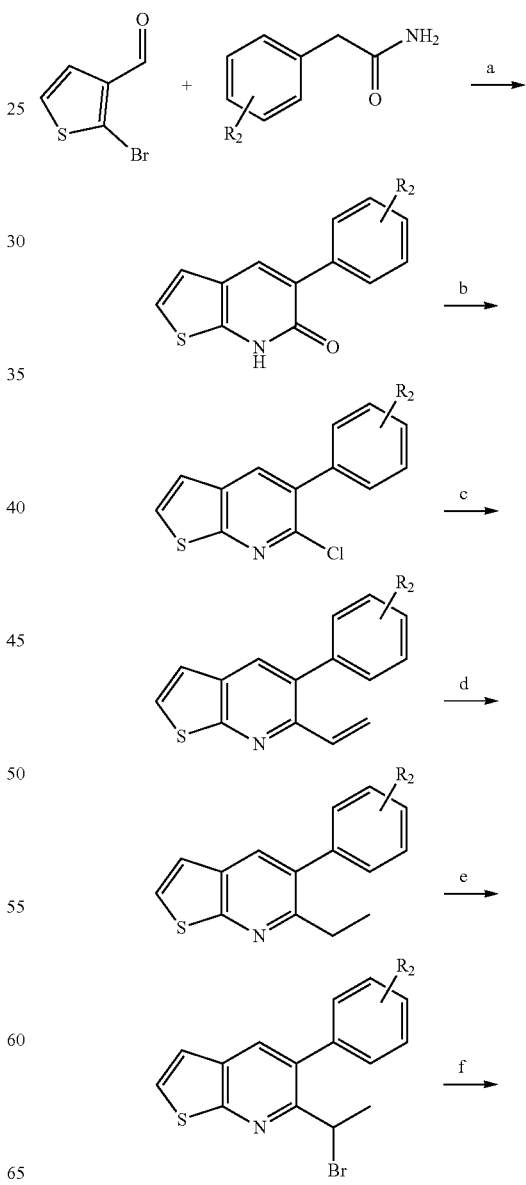

507
-continued

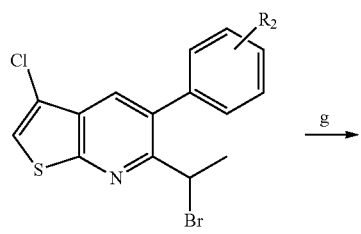

g →

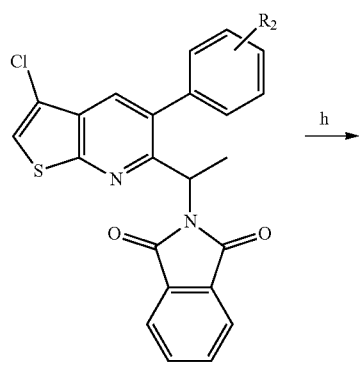

h →

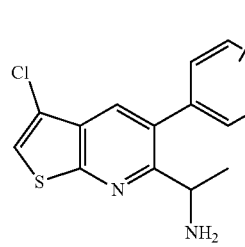

Conditions: a) Cs₂CO₃, Xant-Phos, Pd₂(dba)₃, PhCH₃, 100° C.; b) POCl₃; c) CH₂CHSn(nBu)₃, Pd(PPh₃)₄, dioxane, reflux; d) H₂, Pd/C, MeOH, RT; e) 1,3-dibromo-5,5-dimethylimidazolidine-2,4-dione, benzoyl peroxide, CCl₄, 80° C. to reflux; f) NCS, SiO₂, MeOH, THF, 60° C., separate regioisomers; g) potassium phthalimide, DMF, rt; (h) H₂N(CH₂)₂NH₂, MeOH.

Compounds with the moiety

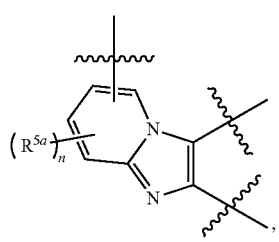
,

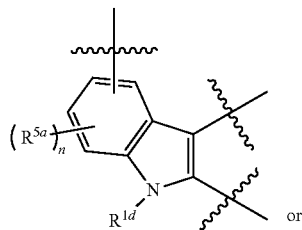
or

508
-continued

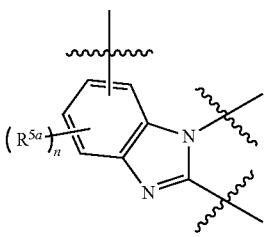

can be synthesized based on the general procedures described in WO2011123751, WO2011075643, WO2008037783, US20110312979, US20120202785, or Li et al., *Bioorg. Med. Chem. Lett.*, 2008, 18, 688-693. For example, they can be synthesized according to the procedures in the schemes below.

Scheme 23

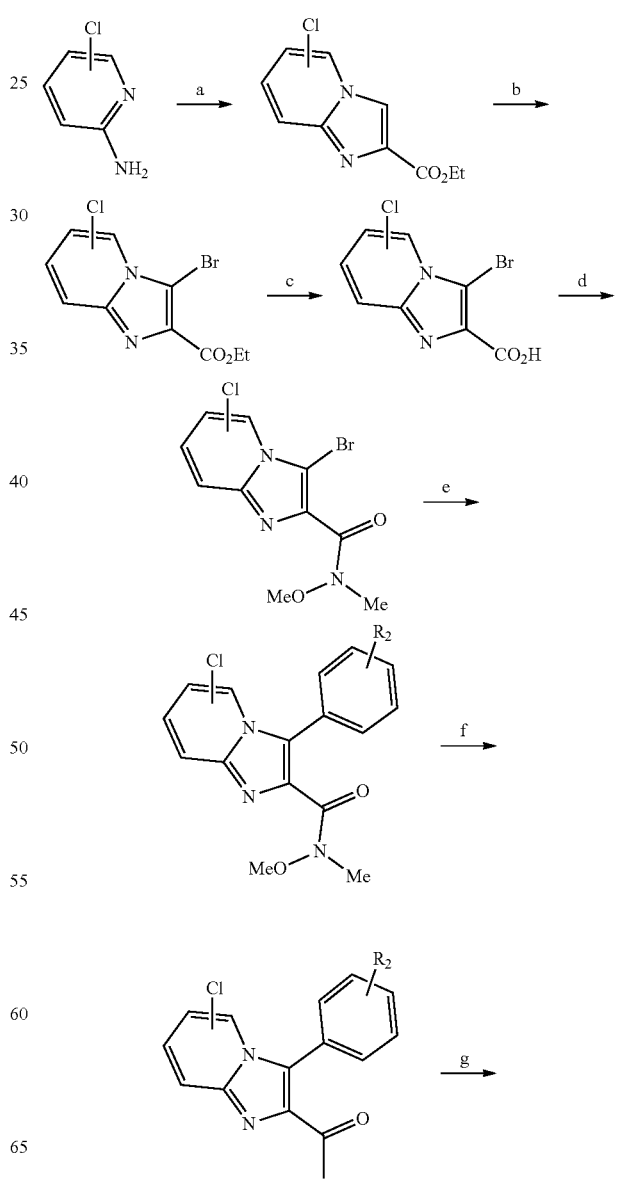

509
-continued

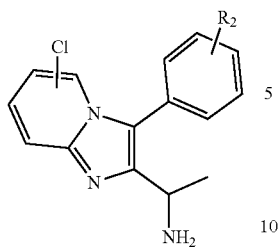

Conditions: a) ethyl bromopyruvate, ethanol, 90° C.; b) NBS, MeCN, RT; c) 1M NaOH, THF, EtOH, RT; d) N,O-dimethylhydroxylamine hydrochloride, DIEA, HBTU, DMF, RT; e) aryl boronic acid, Pd(PPh$_3$)$_4$, Na$_2$CO$_3$, H$_2$O, dioxane, 95° C.; f) MeMgBr, THF, 0° C.; g) NH$_4$OAc, NaBH$_3$CN, MeOH, 65° C.

510
-continued

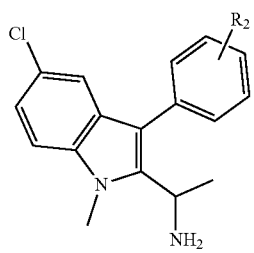

Conditions: a) NBS, Me—THF, RT; b) aryl boronic acid, Pd(PPh$_3$)$_4$, Na$_2$CO$_3$, H$_2$O, dioxane, 95° C.; c) MeMgBr, THF, RT; d) MsCl, DIEA, DCM, RT; e) NaN$_3$, DMF, RT; f) PMe$_3$, THF, RT.

Scheme 24

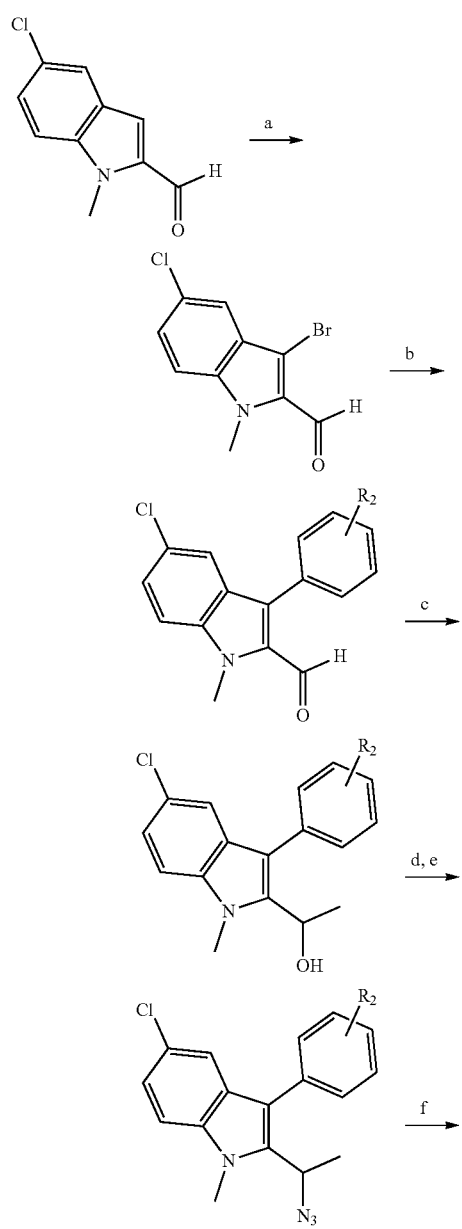

Scheme 25

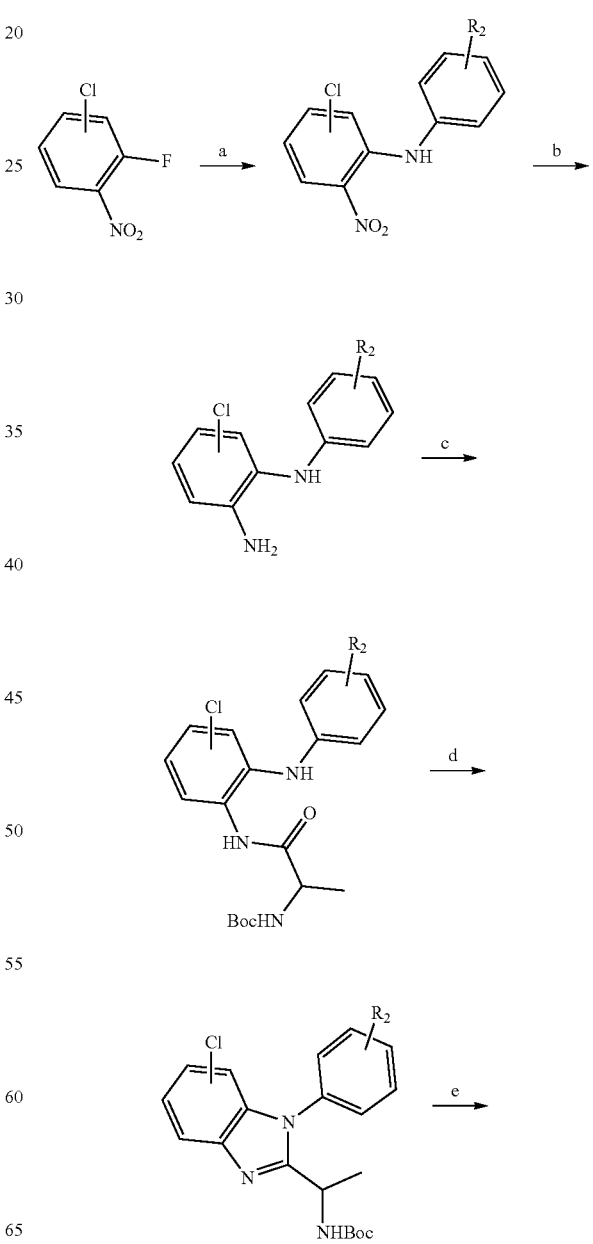

511

-continued

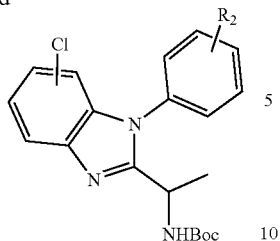

Conditions: a) substituted aniline, DMSO, 100° C.; b) NH₄Cl, Fe, H₂O, MeOH, RT to 100° C.; c) Boc-alanine, HOBt, EDC, NMO, DCM, RT; d) AcOH, 70° C.; e) TFA, DCM rt.

Compounds with the moiety

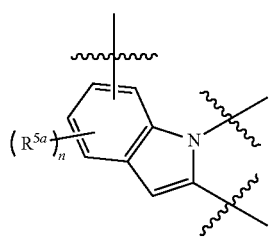

can be synthesized based on the general procedures described in US20110313979 or Jablonowski et al, *J. Med. Chem.*, 2003, 46, 3957-3960. For example, they can be synthesized according to the procedures in the schemes below.

Scheme 26

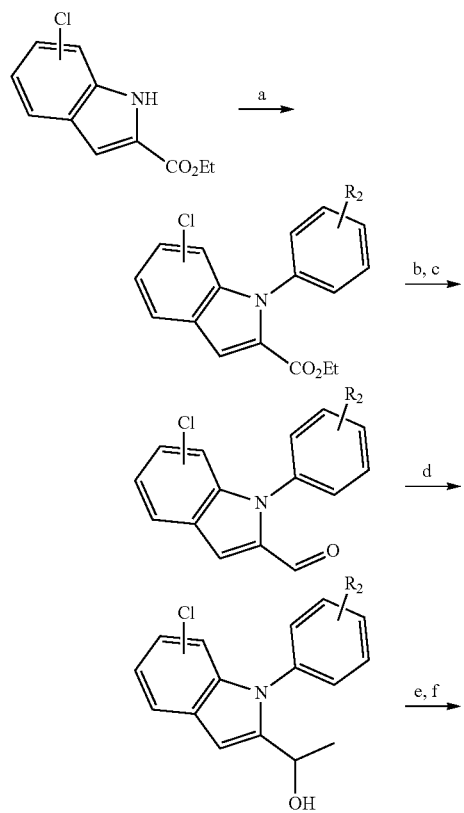

512

-continued

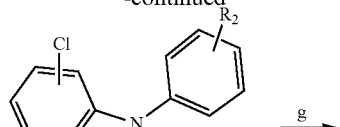

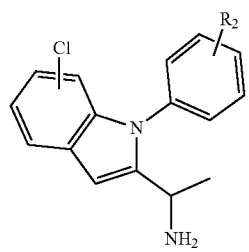

Conditions: a) aryl boronic acid, Cu(OAc)₂, pyridine, 4 Å molecular sieves, DCM, RT; b) LAH, THF, -78° C. to RT; c) Dess-Martin periodinane, DCM, RT; d) MeMgBr, THF, RT; e) MsCl, DIEA, DCM, RT; f) NaN₃, DMF, RT; g) PMe₃, THF, RT.

Compounds with the moiety

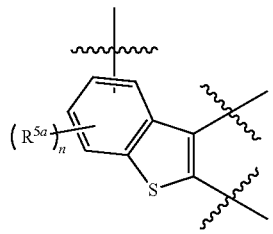

can be synthesized based on the general procedures described in WO2008011560 or WO2011123751. For example, they can be synthesized according to the procedures in the schemes below.

Scheme 27

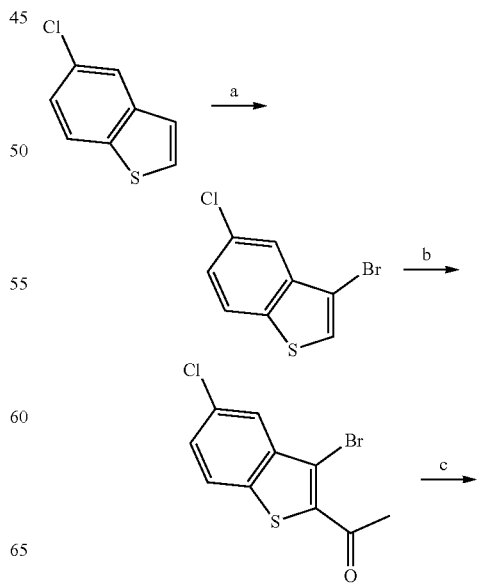

513
-continued

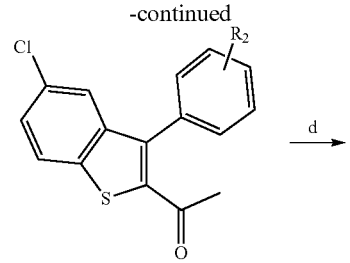
d →

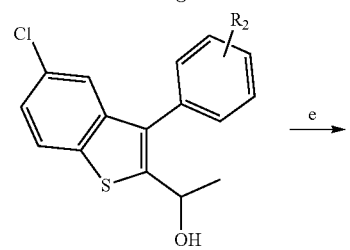
e →

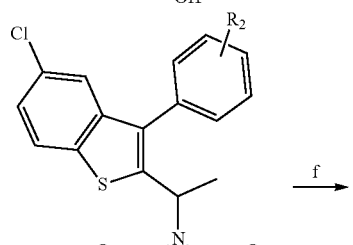
f →

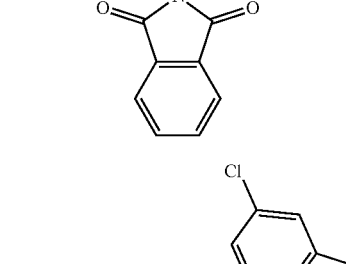

Conditions: 1) Br$_2$, AcONa, DCM, 0° C., then polyphosphoric acid, PhCl, reflux; b) AlCl$_3$, CS$_2$, AcCl, 0° C.; c) aryl boronic acid, PdCl$_2$(PPh$_3$)$_2$, 2N Na$_2$CO$_3$, PhCH$_3$, 110° C.; d) NaBH$_4$, MeOH, RT; e) phthalimide, PPh$_3$, DIAD, THF, 0° C. to RT; f) H$_2$NNH$_2$, EtOH, 50° C.

Compounds with the moiety

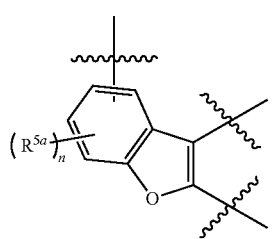

can be synthesized based on the general procedures described in WO2004069829, WO2011123751, US20120202785, or Bachelet et al., *Eur. J. Med. Chem.*, 1985, 20, 425-427. For example, they can be synthesized according to the procedures in the schemes below.

514

Scheme 28

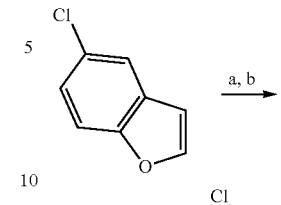
a, b →

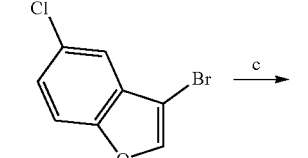
c →

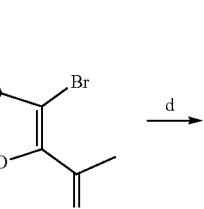
d →

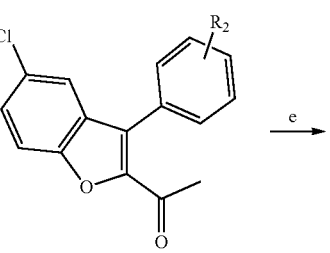
e →

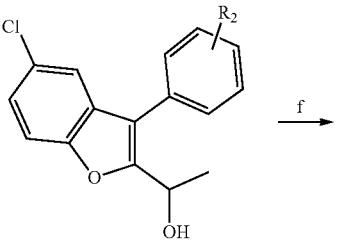
f →

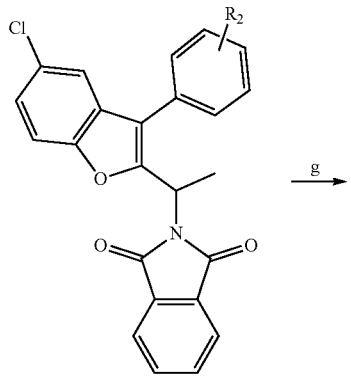
g →

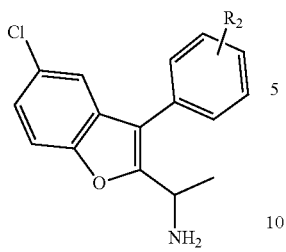

Conditions: a) Br₂, DCM, -30° C. to RT; b) KOH, EtOH, 80° C.; c) AcCl, AlCl₃, DCM, RT; d) aryl boronic acid, PdCl₂(PPh₃)₂, 2N Na₂CO₃, PhCH₃, 110° C.; e) NaBH₄, MeOH, RT; f) phthalimide, PPh₃, DIAD, THF, 0° C. to RT; g) H₂NNH₂, EtOH, 50° C.

Compounds with the moiety

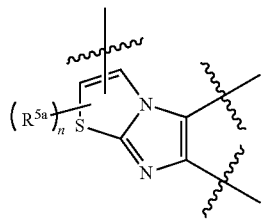

can be synthesized based on the general procedures described in WO2011075643. For example, they can be synthesized according to the procedures in the schemes below.

Scheme 29

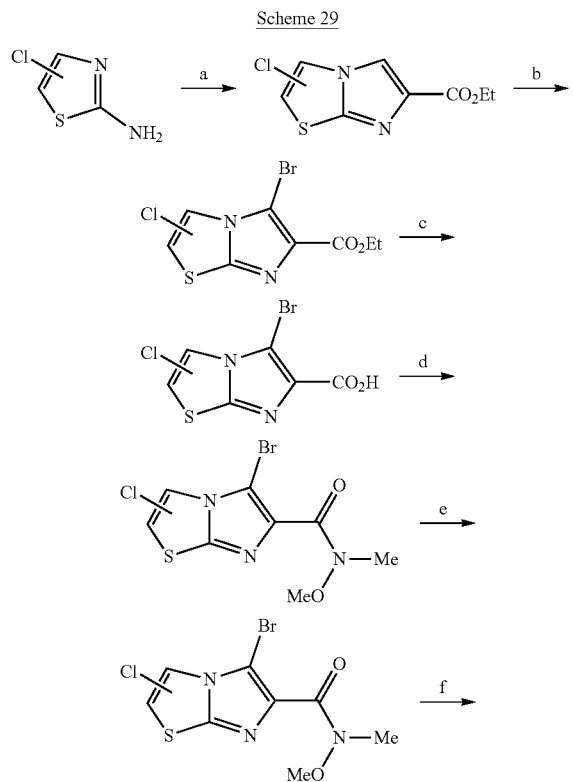

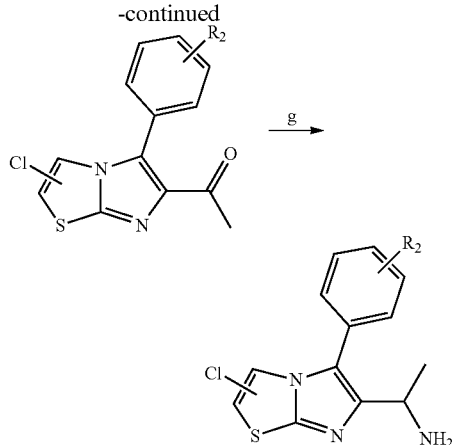

Conditions: a) ethyl bromopyruvate, ethanol, 90° C.; b) NBS, MeCN, RT; c) 1M NaOH, THF, EtOH, RT; d) N,O-dimethylhydroxylamine hydrochloride, DIEA, HBTU, DMF, RT; e) aryl boronic acid, Pd(PPh₃)₄, Na₂CO₃, H₂O, dioxane, 95° C.; f) MeMgBr, THF, 0° C.; g) NH₄OAc, NaBH₃CN, MeOH, 65° C.

(v) General Methods for Alkyne Synthesis:

Method I

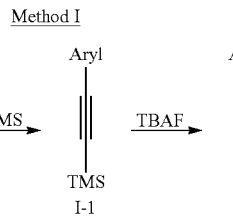

A sealed vessel is charged with PdCl₂(MeCN)₂ and X-Phos (3:1 ratio of X-Phos to PdCl₂(MeCN)₂, 5-15 mol % catalyst), cesium carbonate (1.5-3.0 equiv) and propionitrile (0.5 M). The mixture is stirred for 5 min after which the aryl bromide or aryl iodid substrate was added. After another 5 minutes of stirring TMS-acetylene (3.0 equiv) is added and the flask is sealed and heated at RT for 10 min followed by 1 h of heating at 95° C. The reaction is allowed to cool after which it is concentrated directly onto silica gel and purified using flash silica gel chromatography (gradient of ethyl acetate/hexanes) to provide alkyne I-1.

Alkyne I-1 (1.0 equiv) is then dissolved in tetrahydrofuran (0.13 M) and charged with TBAF (1.1 equiv. 1.0 M in tetrahydrofuran). The resulting mixture is stirred at RT for 6 h after which it is poured into saturated bicarbonate solution and extracted with ethyl acetate. The organic layer is washed with brine and concentrated onto silica gel where it is purified directly by flash silica gel chromatography (gradient of ethyl acetate/hexanes) to provide aryl alkyne I-2.

Method J

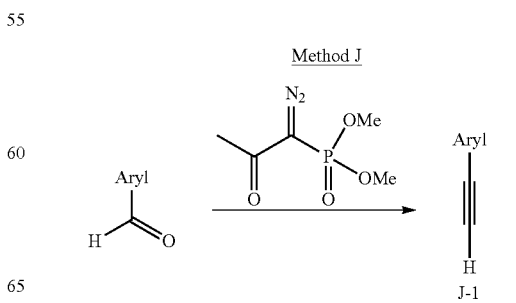

Aldehyde (1.0 equiv) is a dissolved in anhydrous methanol (0.2-0.5 mM) and charged with cesium carbonate (1.0 equiv) and cooled to 0-5° C. Dimethyl (1-diazo-2-oxopropyl)phosphonate (1.0 equiv) is added dropwise after which the reaction is allowed to stir for 1-18 h after which the crude mixture is concentrated onto silica gel and purified directly flash silica gel chromatography to provide the desired alkyne J-1.

Method K

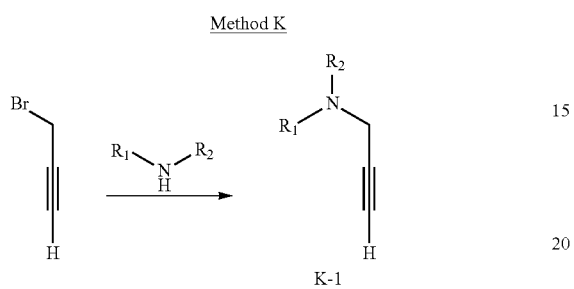

K-1

A secondary amine (1.0 equiv) is dissolved in acetonitrile (0.42 M) and potassium carbonate (1.1 equiv) is added. The white suspension is stirred at 0-5° C. for 5 min after which point propargyl bromide (1.01 equiv) is added dropwise over 3 min. The reaction is then stirred for an additional 15 min at 0-5° C. and then at room temperature for 15 h. The heterogeneous mixture is then filtered. The filtrate is concentrated under reduced pressure, diluted with MTBE and washed with water (2×), brine (1×), dried over sodium sulfate and then filtered through celite. The resulting filtrate is concentrated and purified using flash silica gel chromatography to provide the desired alkyne K-1.

Example 1: Preparation of Compounds 103, 103S and 103R

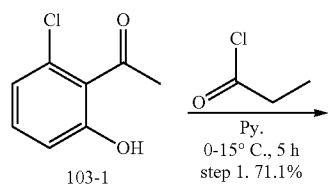

103-1

Py.
0-15° C., 5 h
step 1. 71.1%

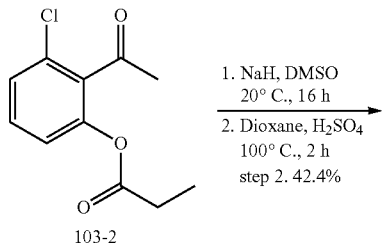

103-2

1. NaH, DMSO
20° C., 16 h
2. Dioxane, $H_2SO_4$
100° C., 2 h
step 2. 42.4%

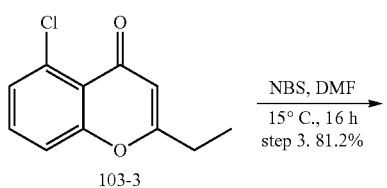

103-3

NBS, DMF
15° C., 16 h
step 3. 81.2%

-continued

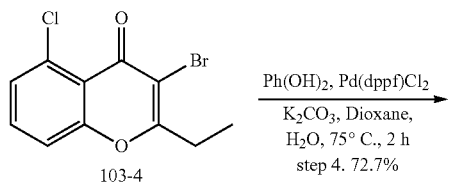

103-4

$Ph(OH)_2$, $Pd(dppf)Cl_2$
$K_2CO_3$, Dioxane,
$H_2O$, 75° C., 2 h
step 4. 72.7%

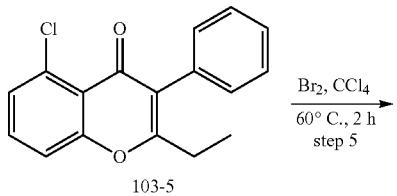

103-5

$Br_2$, $CCl_4$
60° C., 2 h
step 5

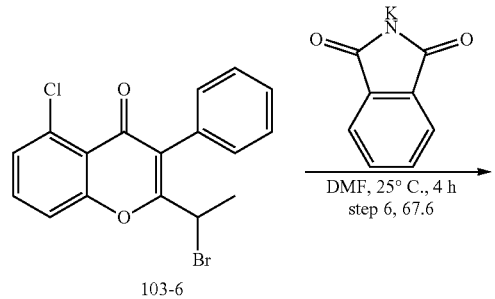

103-6

DMF, 25° C., 4 h
step 6, 67.6

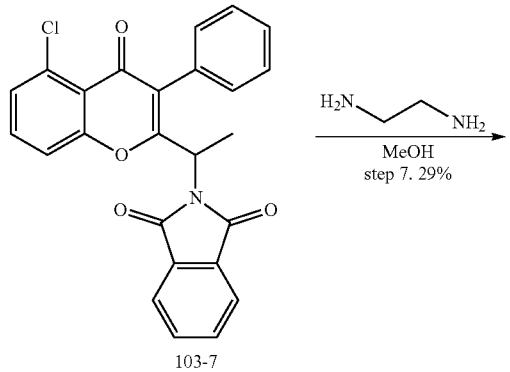

103-7

$H_2N$~~~$NH_2$
MeOH
step 7. 29%

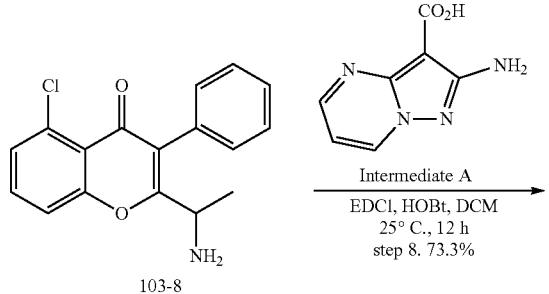

103-8

Intermediate A
EDCl, HOBt, DCM
25° C., 12 h
step 8. 73.3%

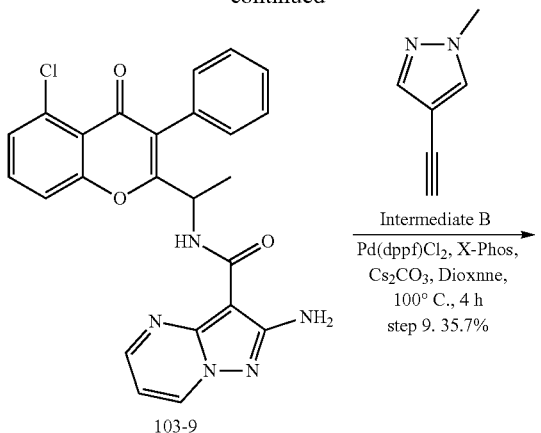

103-9

Intermediate B
Pd(dppf)Cl₂, X-Phos,
Cs₂CO₃, Dioxnne,
100° C., 4 h
step 9. 35.7%

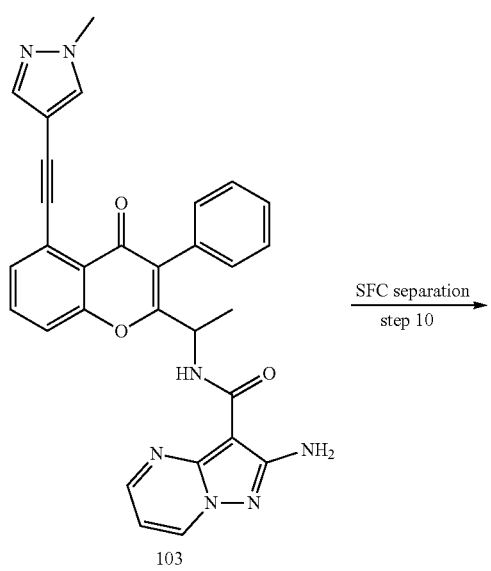

103

SFC separation
step 10

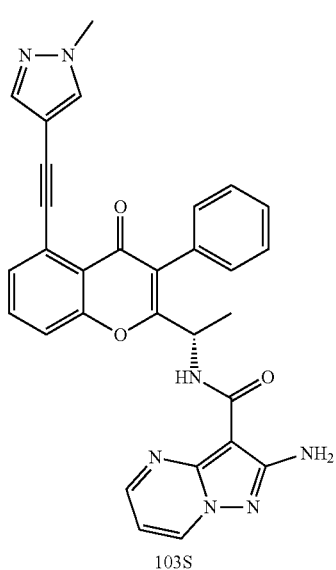

103S

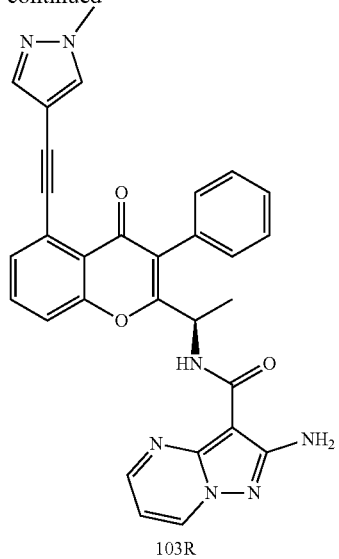

103R

Step 1: Preparation of Compound 103-2

To a solution of compound 103-1 (20 g, 117.24 mmol) in pyridine (300 mL) was added propanoyl chloride (21.7 g, 234.48 mmol) dropwise at 0° C. Then the reaction mixture was allowed to warm to 15° C. and stirred for 5 h. The reaction mixture was filtered and the precipitate was washed with EtOAc (500 ml*3). The filtrate was evaporated under reduced pressure. The residue was purified by silica-gel column (PE/EA=20/1) to give compound 103-2 (21 g, 71.1%) as colorless liquid.

Step 2: Preparation of Compound 103-3

To a solution of compound 103-2 (21 g, 92.6 mmol) in DMSO (150 mL) was added NaH (3.9 g, 97.3 mmol) and kept in 15° C.–20° C. under $N_2$. The mixture was stirred at 15° C. for 16 h. Then the residue was poured into water (300 mL) and adjusted to pH 6~7 with HCl (2 N). The aqueous phase was extracted with ethyl acetate (200 mL*3). The combined organic phase was washed with brine (300 mL), dried with anhydrous $Na_2SO_4$, filtered and concentrated. The residue was dissolved in dioxane (30 mL) and $H_2SO_4$ (95.4 g, 972.8 mmol) was added. The mixture was heated to 100° C. and stirred for 2 h. The mixture was poured into water (500 mL), adjusted pH=8 with saturation $Na_2CO_3$ (aq), then the aqueous phase was extracted with EA (400 mL*3). The combined organic phase was washed with brine (500 mL), dried with anhydrous $Na_2SO_4$, filtered and concentrated to give compound 103-3 (10 g, 42.4%) as a brown solid.

Step 3: Preparation of Compound 103-4

A mixture of compound 103-3 (7 g, 33.6 mmol) and NBS (7.12 g, 40.3 mmol) in DMF (100 mL) was stirred at 15° C. for 16 h. The residue was poured into water (400 mL). The aqueous phase was extracted with ethyl acetate (300 mL*3). The combined organic phase was washed with brine (300 mL), dried with anhydrous $Na_2SO_4$ filtered and concentrated. The residue was purified by silica gel chromatography (column height: 250 mm, diameter: 100 mm, 100-200 mesh silica gel, Petroleum ether/Ethyl acetate=50/1, 30/1) to give compound 103-4 (9 g, 81.2%) as a yellow solid.

Step 4: Preparation of Compound 103-5

A mixture of compound 103-4 (7 g, 24.3 mmol), phenylboronic acid (3 g, 24.3 mmol), Pd(dppf)Cl$_2$ (1.8 g, 2.4 mmol) and K$_2$CO$_3$ (3.4 g, 24.3 mmol) in dioxane (70 mL) and H$_2$O (4 mL) was heated to 80° C. and stirred for 3 h. The mixture was concentrated. The residue was purified by silica gel chromatography (column height: 250 mm, diameter: 100 mm, 100-200 mesh silica gel, PE/EA=100/1, 50/1) to compound 103-5 (6.3 g, 72.7%) as a yellow oil.

Step 5: Preparation of Compound 103-6

A mixture of compound 103-5 (2 g, 7.0 mmol), molecular bromine (1.2 g, 7.4 mmol) in CCl$_4$ (20 mL) was heated to 60° C. and stirred for 2 h. The mixture was concentrated to give compound 103-6 (2.5 g, crude) as a yellow solid.

Step 6: Preparation of Compound 103-7

A mixture of compound 103-6 (2.5 g, 6.9 mmol) and potassium 1,3-dioxoisoindolin-2-ide (2.55 g, 13.8 mmol) in DMF (30 mL) was stirred at 25° C. for 4 h. The residue was poured into water (200 mL). The aqueous phase was extracted with ethyl acetate (200 mL*3). The combined organic phase was washed with brine (200 mL), dried with anhydrous Na$_2$SO$_4$, filtered and concentrated in vacuum. The residue was purified by silica gel chromatography (column height: 250 mm, diameter: 100 mm, 100-200 mesh silica gel, PE/EA=10/1, 5/1) to give compound 103-7 (2 g, 67.6%) as a light yellow solid.

Step 7: Preparation of Compound 103-8

A mixture of compound 103-7 (200 mg, 465.3 umol) and ethane-1,2-diamine (279.6 mg, 4.7 mmol) in MeOH (10 mL) was stirred at 60° C. for 1 h. The residue was purified by silica gel chromatography directly (column height: 250 mm, diameter: 100 mm, 100-200 mesh silica gel, DCM/MeOH=I/O) to give compound 103-8 (80 mg, 29%) as a yellow oil.

Step 8: Preparation of Compound 103-9

A mixture of compound 103-8 (80 mg, 266.9 umol), Intermediate A (71.3 mg, 400.3 umol, commercially available), EDCI (61.4 mg, 320.37 umol), HOBt (43.27 mg, 320.3 umol) and Et$_3$N (54 mg, 533.8 umol) in DMF (5 mL) was stirred at 25° C. for 12 h. The mixture was concentrated. The residue was purified by silica gel chromatography (column height: 250 mm, diameter: 100 mm, 100-200 mesh silica gel, DCM/MeOH=100/1) to give compound 103-9 (150 mg, 73.3%) as a yellow oil.

Step 9: Preparation of Compound 103

A mixture of compound 103-9 (50 mg, 108.7 umol). Intermediate B (17.3 mg, 163.1 umol, prepared according to Method I), Cs$_2$CO$_3$ (35.4 mg, 108.7 umol), XPhos (25.9 mg, 54.4 umol) and Pd(dppf)Cl$_2$ (39.8 mg, 54.4 umol) in dioxane (10 mL) was heated to 80° C. and stirred for 3 h. The mixture was concentrated. The mixture was purified by column chromatography (SiO2, PE:EA=1:1~1:5) to afford the target compound, and the solid was checked by HPLC, then the product was purified by prep-HPLC (TFA acid) to afford Compound 103 (150 mg, 35.7%) as a red solid. ESI-MS m/z: 530.6 [M+H]+.

Step 10: Preparation of Compounds 103S and 103R

Compound 103 was separated by SFC to afford Compound 103S (18.4 mg, 10.99%) and 103R (17 mg, 9.30%). Both are as white solid. ESI-MS nm/z: 530.3 [M+H]+ for Compounds 103S and 103R.

Example 2: Preparation of Compounds 175, 175S and 175R

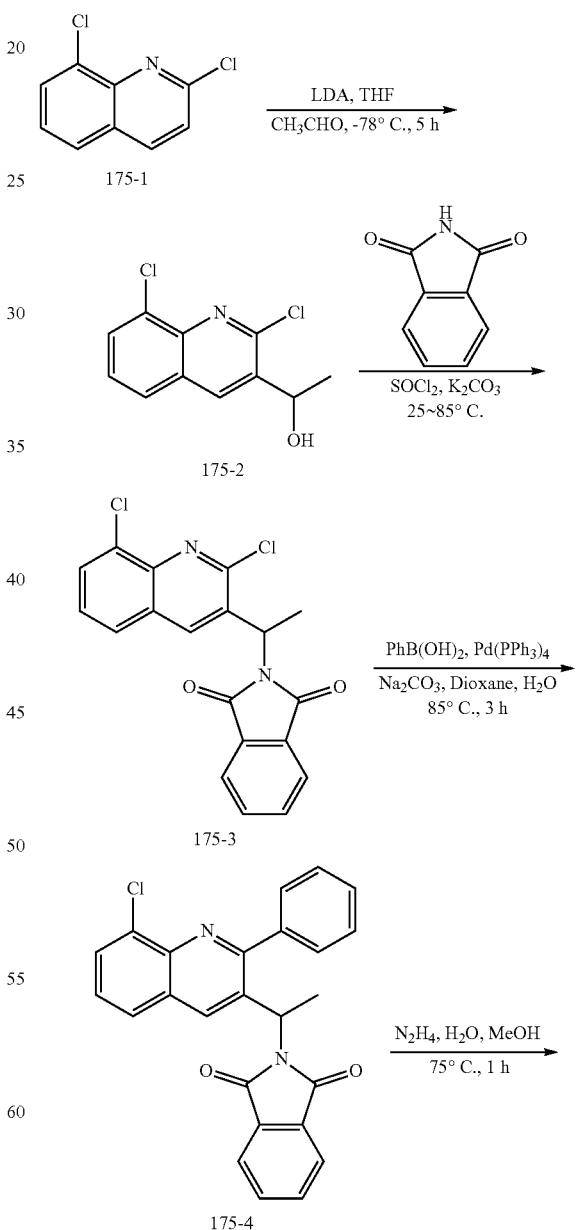

-continued

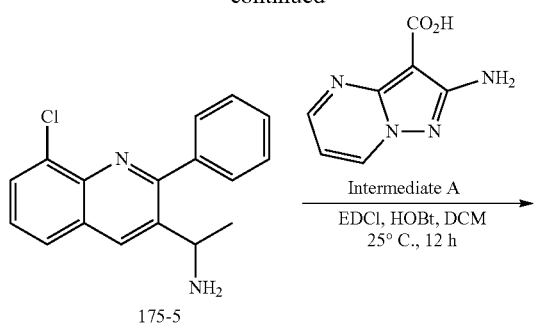

175-5

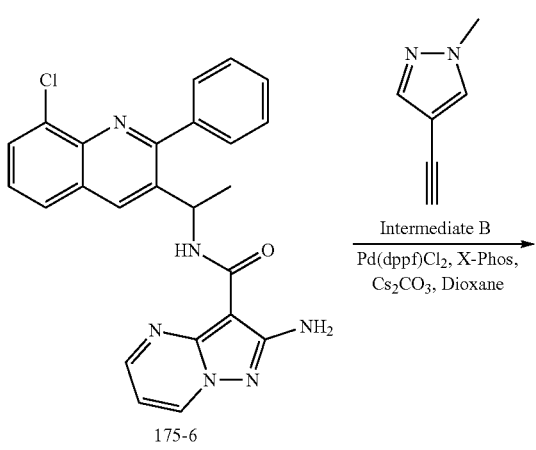

175-6

175S

-continued

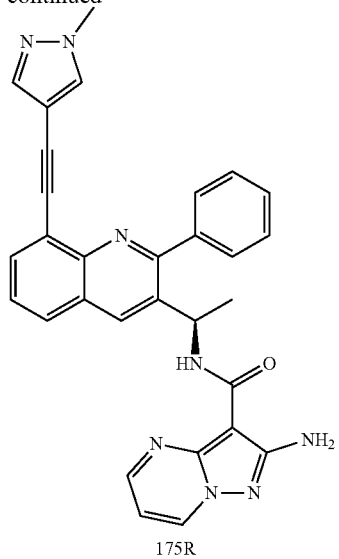

175R

Step 1: Preparation of Compound 175-2

To a solution of compound 175-1 (9.5 g, 0.048 mol) in THF (100 mL) was added LDA (2M, 29 mL, 0.058 mol) at −78° C. under $N_2$. The reaction mixture was stirred for 1 h after addition. Then $CH_3CHO$ (2.5 g, 0.058 mol) was added to the above solution. The reaction mixture was stirred for 4 h at the same temperature. TLC showed the reaction was completed. The reaction mixture was poured into water (100 mL) and extracted with EtOAc (100 mL*3). The organic phase was evaporated under reduced pressure. The residue was purified by silica-gel column to provide compound 175-2 (4 g, 34.5%).

Step 2: Preparation of Compound 175-3

To a solution of compound 175-2 (7.5 g, 0.03 mol) in DCM (80 mL) was added $SOCl_2$ (18 g, 0.16 mol) at 25° C. and stirred for 1 h. Then the reaction mixture was evaporated under reduced pressure. The residue was dissolved into DMF (80 mL) and was added $K_2CO_3$ (8.3 g, 0.06 mol) and phthalimide. The mixture was heated to 85° C., for 1 h. TLC showed the reaction was completed. The reaction mixture was poured into water (100 mL) and extracted with EtOAc (200 mL*3). The organic phase was evaporated under reduced pressure and the residue was purified by silica-gel column (PE/EA=3/1) to provide compound 175-3 (5 g, 45%).

Step 3: Preparation of Compound 175-4

To a suspension compound 175-3 (4.27 g, 11.50 mmol), phenylboronic acid (1.68 g, 13.80 mmol,), $Pd(PPh_3)_4$ (1.33 g, 1.15 mmol,). $Na_2CO_3$ (2.44 g, 23.00 mmol,) in dioxane (40.00 mL) and $H_2O$ (5.00 mL) was heated to 85° C. for 4 h. TLC showed the reaction was completed. The reaction mixture was evaporated under reduced pressure and the residue was purified by silica-gel column (PE/EA=3/I) to provide compound 175-4 (3 g, 63%).

Step 4: Preparation of Compound 175-5

A mixture of compound 175-4 (2.5 g, 0.006 mol), N2H $H_2O$ (3 g, 0.06 mol) in MeOH (30 mL) was heated to 75° C.

for 1 h. The reaction mixture was evaporated under reduced pressure to provide crude product compound 175-5 (2 g).

Step 5: Preparation of Compound 175-6

A solution of compound 175-5 (2 g, 0.007 mol), Intermediate A (1.26 g, 0.007 mol), EDCI (2 g, 0.01 mol), HOBt (1 g, 0.007 mol), TEA (2.1 g, 0.021 mol) in DMF (20 mL) and stirred at 25° C. for 12 h. The reaction mixture was evaporated under reduced pressure and the residue was purified by silica-gel column (PE/EA=1/5) to provide compound 175-6 (1.2 g, 40%).

Step 6: Preparation of Compound Compound 175, 175S, and 175R

To a suspension of compound 175-6 (300.00 mg, 677.35 umol), Intermediate B (107.83 mg, 1.02 mmol), Pd(dppf)Cl₂ (247.81 mg, 338.68 umol), Cs₂CO₃ (220.70 mg, 677.35 umol), x-phos (161.55 mg, 338.68 umol) in dioxane (5.00 mL) was stirred at 100° C. for 4 h under N₂. The reaction mixture was evaporated under reduced pressure and the residue was purified by silica-gel column (PE/EA=1/2). Then it was purified by p-HPLC to provide Compounds 175S (28 mg, 8%) and 175R (30 mg, 8%). Prior to purification by p-HPLC. Compound 175 can be isolated, ESI-MS m/z: 513.3 [M+H]+ for Compounds 175S and 175R.

Example 3: Preparation of Compounds 181, 181S and to 181R

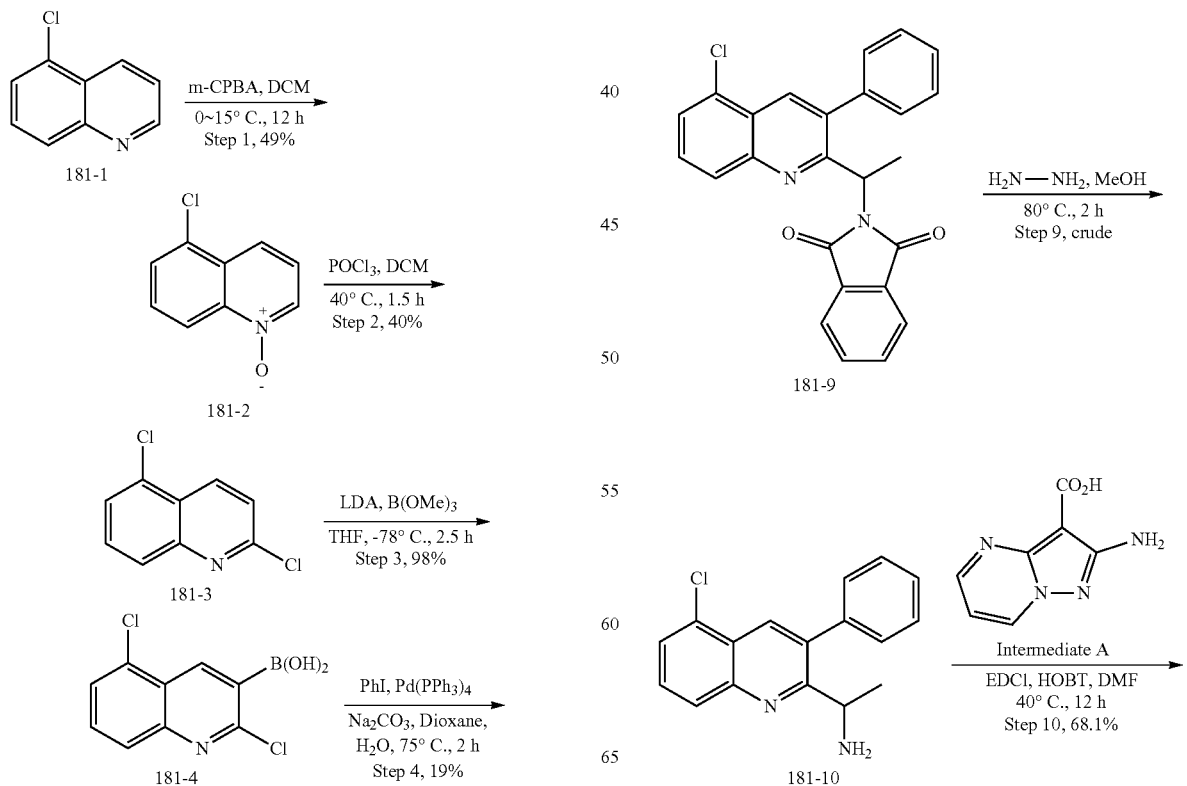

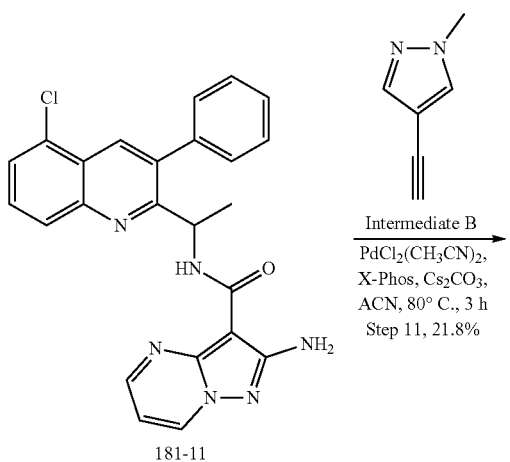

Step 1: Preparation of Compound 181-2 m-CPBA (39 g, 192 mmol) was added to a solution of compound 181-1 (30 g, 183 mmol) in DCM (500 mL) and the mixture was stirred at 15° C. for 12 h. Saturated aqueous Na₂SO₃ (aq, 1000 mL) was added, and the mixture was stirred at 15° C. for another 0.5 hour. The reaction was checked by potassium iodide-starch test paper until the test paper did not change to blue. The mixture was extracted with DCM (500 mL*3). The combined organic phase was washed with brine (500 mL), dried over anhydrous Na₂SO₄ and then filtered. The filtrate was concentrated to give a residue. The residue was purified by silica gel chromatography (column height: 250 mm, diameter: 100 mm, 100-200 mesh silica gel, Petroleum ether/Ethyl acetate=50/1~0/1) to provide compound 181-2 (19 g, 49%) as a yellow solid.

Step 2: Preparation of Compound 181-3

To a solution of compound 181-2 (19 g, 106 mmol) in DCM (250 mL) was added POCl₃ (32 g, 212 mmol). The mixture was heated to 40° C. and stirred for 1.5 h. Saturated aqueous NaHCO₁ (aq, 500 mL) was added and the mixture was stirred at 15° C. for 10 min, then the aqueous phase was extracted with ethyl acetate (300 mL*3). The combined organic phase was washed with brine (500 mL), dried with anhydrous Na₂SO₄, filtered and concentrated in vacuum. The residue was purified by (column height: 250 mm, diameter 100 mm, 100-200 mesh silica gel, PE/EA=50/1-20/1) to provide compound 181-3 (9.8 g, 40%) as a white solid.

Step 3: Preparation of Compound 181-4

To a cold solution of diisopropylamine (8.7 g, 86 mmol) in THF (15 mL) was added drop-wise n-BuLi (2.5 M, 31 mL) at −78° C. The reaction was kept at 15° C. for 0.5 h and cooled to −78° C. before addition of a solution of compound 181-3 (10 g, 51 mmol) in THF (15 mL) drop-wise. The mixture was stirred at this temperature for 1 h, then trimethyl borate (7.9 g, 76 mmol) was added drop-wise and the mixture was stirred at −78° C. for 1 h. The mixture was quenched with water (500 mL), adjusted to pH=4 with HCl (2 N) and extracted with EtOAc (300 mL*3), then the organic layer was washed with brine (500 mL), dried with anhydrous Na$_2$SO$_4$, filtered and concentrated to give solid. The solid was washed with EA (20 mL*2), the solid was concentrated to provide the compound 181-4 (12 g, 98%) as a yellow solid.

Step 4: Preparation of Compound 181-5

A mixture of compound 181-4 (12 g, 50 mmol), iodobenzene (15 g, 74 mmol), Pd(PPh$_3$)$_4$ (5.7 g, 5.0 mmol) and Na$_2$CO$_3$ (15.8 g, 149 mmol) in MeCN (100 mL) and H$_2$O (20 mL) was heated to 75° C. and stirred for 2 h. The residue was poured into water (1000 mL). The aqueous phase was extracted with ethyl acetate (400 mL*3). The combined organic phase was washed with brine (1000 mL), dried with anhydrous Na$_2$SO$_4$, filtered and concentrated in vacuum. The residue was purified by silica gel chromatography (column height: 250 mm, diameter: 100 mm, 100-200 mesh silica gel, Petroleum ether/Ethyl acetate=50/1) to provide compound 181-5 (2.6 g, 19%) as a white solid.

Step 5: Preparation of Compound 181-6

A mixture of compound 181-5 (2.8 g, 10.2 mmol), Pd(PPh$_3$)$_4$ (1.2 g, 1.0 mmol) and tributyl(vinyl)stannane (6.5 g, 20.4 mmol) in dioxane (50 mL) was heated to 100° C. and stirred for 1.5 h. Saturated KF (aq. 300 mL) was added, the mixture was stirred at 20° C. for 10 min. The aqueous phase was extracted with EA (200 mL*3). The combined organic phase was washed with brine (300 mL), dried with anhydrous Na$_2$SO$_4$, filtered and concentrated in vacuum. The residue was purified by silica gel chromatography (column height: 250 mm, diameter: 100 mm, 100-200 mesh silica gel, Petroleum ether/Ethyl acetate=1/0, 100/1) to provide compound 181-6 (3 g, 88%) as a yellow liquid.

Step 6: Preparation of Compound 181-7

To a mixture of compound 181-6 (3 g, 11.3 mmol) and OsO$_4$ (287 mg, 1.1 mmol) in acetone (5 mL) and H$_2$O (2 mL) was added 4-methylmorpholine 4-oxide (4.9 g, 41.7 mmol), and the mixture was stirred at 20° C. for 2 h. The mixture was poured into saturation Na$_2$SO$_3$ (aq, 100 mL). The aqueous phase was extracted with ethyl acetate (30 mL*3). The combined organic phase was washed with brine (50 mL), dried with anhydrous Na$_2$SO$_4$, filtered and concentrated in vacuum. A solution of the residue in THF (10 mL) and H$_2$O (5 mL) was treated with NaIO$_4$ (7.2 g, 33.9 mmol) and OsO$_4$ (287 mg, 1.1 mmol), then the reaction was stirred at 20° C. for another 2 h. Saturated Na$_2$SO$_3$ (aq, 200 mL) was added, and the mixture was stirred at 20° C. for another 0.5 hour. The mixture was extracted with EA (200 mL*3). The combined organic phase was washed with brine (300 mL), dried over Na$_2$SO$_4$, filtered and concentrated. The residue was purified by silica gel chromatography (column height: 250 mm, diameter: 100 mm, 100-200 mesh silica gel, PE/EA=100/1, 20/1) to provide compound 181-6 (1.8 g, 60%) as a yellow solid.

Step 7: Preparation of Compound 181-8

To a solution of compound 181-7 (1.8 g, 6.7 mmol) in THF (30 mL) was added bromo(methyl)magnesium (3 M, 3.36 mL) at 0° C. for 1 h. The residue was poured into water (50 mL) and stirred for 5 min. The aqueous phase was extracted with ethyl acetate (80 mL*3). The combined organic phase was washed with brine (100 mL), dried with anhydrous Na$_2$SO$_4$, filtered and concentrated in vacuum to provide compound 181-8 (1.8 g) as a yellow oil.

Step 8: Preparation of Compound 181-9

A mixture of compound 181-8 (1.8 g, 6.4 mmol), phthalimide (1.1 g, 7.6 mmol), DIAD (1.5 g, 7.6 mmol) and PPh$_3$ (2 g, 7.6 mmol) in THF (5 mL) was stirred at 20° C. for 12 h. The residue was poured into water (200 mL). The aqueous phase was extracted with EA (100 mL*3). The combined organic phase was washed with brine (200 mL), dried with anhydrous Na$_2$SO$_4$, filtered and concentrated in vacuum. The residue was purified by silica gel chromatography (column height: 250 mm, diameter: 100 mm, 100-200 mesh silica gel, Petroleum ether/Ethyl acetate=100/1, 50/1) to provide compound 181-9 (1.5 g, 57.3%) as a yellow solid.

Step 9: Preparation of Compound 181-10

A mixture of compound 181-9 (500 mg, 1.2 mmol) and N$_2$H4.H$_2$O (606 mg, 12.1 mmol) in MeOH (5 mL) was heated to 80° C. and stirred for 2 h. The mixture was filtered and the filtrate was concentrated to give compound 181-10 (360 mg) as a white solid.

Step 10: Preparation of Compound 181-11

A mixture of compound 181-10 (150 mg, 530.5 umol), Et$_3$N (161 mg, 1.6 mmol). Intermediate A (104 mg, 583.5 umol), EDCI (122 mg, 636.6 umol) and HOBt (86 mg, 636.6 umol) in DMF (10 mL) was stirred at 40° C. for 12 h. The mixture was concentrated. The residue was purified by silica gel chromatography (column height: 250 mm, diameter: 100 mm, 100-200 mesh silica gel, Petroleum ether/Ethyl acetate=10/1, 0/I) to give compound 181-11 (200 mg, 68.1%) as a yellow solid.

Steps 11 and 12: Preparation of Compounds 181, 181S and 181R

A mixture of compound 181-11 (200 mg, 451.6 umol). Intermediate B (95.9 mg, 903.14 umol, 2.00 eq), Cs$_2$CO$_3$ (294 mg, 903.1 umol), XPhos (107.6 mg, 225.8 umol) and Pd(dppf)Cl$_2$ (165 mg, 225.8 umol) in dioxane (20 mL) was healed to 80° C. and stirred for 3 h. The mixture was concentrated. The mixture was purified by prep-HPLC (TFA acid) and purified by SFC to afforded 181S (40 mg, 16.8%) and 181R (12 mg, 5.0%) as a light yellow solid. ESI-MS m/z: 513.3 [M+H]+ for Compounds 181S and 181R. Prior to SFC purification, Compound 181 can be isolated.

Example 4: Preparation of Compound 341

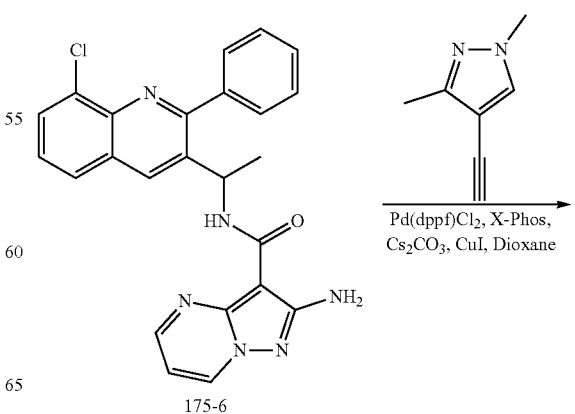

175-6

-continued

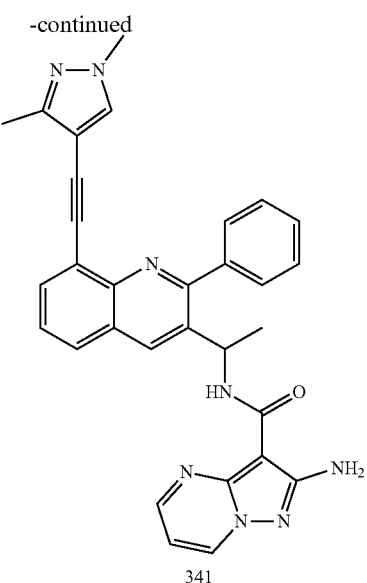

341

To a suspension of compound 175-6 (200.00 mg, 451.57 umol), 4-ethynyl-1,3-dimethyl-1H-pyrazole (81.38 mg, 677.35 umol, prepared according to method J), CuI (8.60 mg, 45.16 umol, Pd(dppf)Cl$_2$ (33.04 mg, 45.16 umol), Cs$_2$CO$_3$ (220.70 mg, 677.35 umol), x-phos (11.25 mg, 135.47 umol) in dioxane (3.00 mL) was heated to 100° C. for 8 h under N$_2$. The reaction mixture was evaporated under reduced pressure and the residue was purified by silica-gel column (PE/EA=1/2) to provide target compound (50 mg, 21%), ESI-MS m/z: 527.3 [M+H]+.

Biological Activity Assessment

Example 222: PI3-Kinase HTRF™ Assay

A PI3-Kinase HTRF® assay kit (cat No. 33-016) purchased from Millipore Corporation is used to screen compounds provided herein. This assay uses specific, high affinity binding of the GRP1 pleckstrin homology (PH) domain to PIP3, the product of a Class 1A or 1B PI3 Kinase acting on its physiological substrate PIP2. During the detection phase of the assay, a complex is generated between the GST-tagged PH domain and biotinylated short chain PIP3. The biotinylated PIP3 and the GST-tagged PH domain recruited fluorophores (Streptavidin-Allophycocyanin and Europium-labeled anti-GST respectively) to form the fluorescence resonance energy transfer (FRET) architecture, generating a stable time-resolved FRET signal. The FRET complex is disrupted in a competitive manner by non-biotinylated PIP3, a product formed in the PI3 Kinase assay.

PI3 Kinase α, β, γ or δ activity is assayed using the PI3 Kinase HTRF®, assay kit (catalogue No. 33-016) purchased from Millipore Corporation. Purified recombinant PI3Kα (catalogue No. 14-602-K), PI3Kβ (catalogue No. 14-603-K), PI3Kγ (catalogue No. 14-558-K), and PI3Kδ (catalogue No. 14-604-K) are obtained from Millipore Corporation. Purified recombinant PI3K enzyme is used to catalyze the phosphorylation of phosphatidylinositol 4,5-bisphosphate (PIP2 at 10 μM) to phosphatidylinositol 3,4,5-trisphosphate (PIP3) in the presence of 10 μM ATP. The assay is carried out in 384-well format and detected using a Perkin Elmer EnVision Xcite Multilabel Reader. Emission ratios are converted into percent inhibitions and imported into GraphPad Prism software. The concentration necessary to achieve inhibition of enzyme activity by 50% (IC$_{50}$) is calculated using concentrations ranging from 20 μM to 0.1 nM (12-point curve), IC$_{50}$ values are determined using a nonlinear regression model available in GraphPad Prism 5.

TABLE 5

In Vitro IC$_{50}$ data for selected compounds.

| Compound no. | PI3K α IC$_{50}$ | PI3K β IC$_{50}$ | PI3K δ IC$_{50}$ | PI3K γ IC$_{50}$ | RAJI p110 δ assay IC$_{50}$ | Raw264.7 p110 γ assay IC$_{50}$ | PI3K δ/ PI3K γ IC$_{50}$ (selectivity) | RAJI δ/ Raw264.7 γ IC$_{50}$ (selectivity) |
|---|---|---|---|---|---|---|---|---|
| 103 | D2 | D2 | D2 | D3 | D4 | B5 | W | X |
| 103S | D2 | D2 | D2 | B3 | D4 | A5 | X | Y |
| 103R | D2 | D2 | D2 | E3 | D4 | C5 | V | X |
| 175S | D2 | D2 | D2 | B3 | B4 | A5 | X | W |
| 175R | D2 | D2 | D2 | E3 | ND | ND | V | ND |
| 181R | D2 | D2 | D2 | E3 | D4 | C5 | V | V |
| 181S | D2 | D2 | D2 | E3 | D4 | C5 | V | Y |
| 341 | D2 | D2 | D2 | E3 | B4 | A5 | W | W |

The data in Table 5 are coded as follows.

| For PI3K α, β, and δ IC$_{50}$: | For PI3K γ IC$_{50}$: | RAJI p110 δ assay IC$_{50}$ | Raw264.7 p110 γ assay IC$_{50}$ |
|---|---|---|---|
| A2 = 1 to <500 nM | A3 = 1 to <100 nM | A4 = 1 to <100 nM | A5 = 1 to <50 nM |
| B2 = 500 to <1000 nM | B3 = 100 to <500 nM | B4 = 100 to <500 nM | B5 = 50 to <100 nM |
| C2 = 1000 to <5000 nM | C3 = 500 to <1000 nM | C4 = 500 to <1000 nM | C5 = 100 to <10000 nM |
| D2 = 5000 to 10000 nM | D3 = 1000 to 5000 nM | D4 = 1000 to 10000 nM | |
| | E3 = >5000 nM | | |

δ/γ IC$_{50}$ selectivity:
V = 0.1 to 1
W = >1 to <10
X = 10 to <50
Y = 50 to <850
ND = not determined

Example 223: Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 224: Expression and Inhibition Assays of p110α/p85α, p110β/p85β, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004), $IC_{50}$ values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM $MgCl_2$), and freshly sonicated phosphatidylinositol (100 µg/ml). Reactions are initiated by the addition of ATP containing 10 µCi of γ-32P-ATP to a final concentration of 10 or 100 µM and allowed to proceed for 5 minutes at room temperature. For TLC analysis, reactions are then terminated by the addition of 105 µL 1N HCl followed by 160 µL $CHCl_3$:MeOH (1:1). The biphasic mixture is vortexed, briefly centrifuged, and the organic phase is transferred to a new tube using a gel loading pipette tip precoated with $CHCl_3$. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 µM). For compounds showing significant activity, $IC_{50}$ determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including, but not limited to, PI 3-Kinase α, θ, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 µL per well. In the first step, each well receives 2 µL of test compound in 20% dimethylsulphoxide resulting in a 2% DMSO final concentration. Next, approximately 14.5 µL of a kinase/PIP2 mixture (diluted in 1× reaction buffer) is added per well for a final concentration of 0.25-0.3 µg/mL kinase and 10 µM PIP2. The plate is sealed and incubated for 15 minutes at room temperature. To start the reaction, 3.5 µL of ATP (diluted in 1× reaction buffer) is added per well for a final concentration of 10 µM ATP. The plate is sealed and incubated for 1 hour at room temperature. The reaction is stopped by adding 5 µL of Stop Solution per well and then 5 µL of Detection Mix is added per well. The plate is sealed, incubated for 1 hour at room temperature, and then read on an appropriate plate reader. Data is analyzed and $IC_{50}$s are generated using GraphPad Prism 5.

Example 225: B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 µL at 50,000 cells/well in B Cell Media (RPMI+10% FBS+Penn/Strep+50 µM bME+5 mM HEPES). A compound provided herein is diluted in B Cell Media and added in a 10 µL volume. Plates are incubated for 30 min at 37° C. and 5% $CO_2$ (0.2% DMSO final concentration). A 50 µL B cell stimulation cocktail is then added containing either 10 µg/mL LPS or 5 µg/mL F(ab')2 Donkey anti-mouse IgM plus 2 ng/mL recombinant mouse IL4 in B Cell Media Plates are incubated for 72 hours at 37° C. and 5% $CO_2$. A volume of 15 µL of Alamar Blue reagent is added to each well and plates are incubated for 5 hours at 37° C. and 5% $CO_2$. Alamar Blue fluoresce is read at 560Ex/590Em, and ICs, or ECs, values are calculated using GraphPad Prism 5.

Example 226: Tumor Cell Line Proliferation Assay

The ability of one or more subject compounds to inhibit tumor cell line proliferation can be determined according to standard procedures known in the art. For instance, an in vitro cellular proliferation assay can be performed to measure the metabolic activity of live cells. The assay is performed in a 96-well microliter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 µL at 5,000 cells/well in Tumor Cell Media. A compound provided herein is diluted in Tumor Cell Media and added in a 10 µL volume. Plates are incubated for 72 hours at 37° C. and 5% $CO_2$. A volume of 10 µL of Alamar Blue reagent is added to each well and plates are incubated for 3 hours at 37° C. and 5% $CO_2$. Alamar Blue fluoresce is read at 560Ex/590Em, and $IC_{50}$ values are calculated using GraphPad Prism 5.

Example 227: Antitumor Activity In Vivo

The compounds described herein can be evaluated in a panel of human and murine tumor models.

Paclitaxel-Refractory Tumor Models
 1. Clinically-Derived Ovarian Carcinoma Model
 This tumor model is established from a tumor biopsy of an ovarian cancer patient. Tumor biopsy is taken from the patient. The compounds described herein are administered to nude mice bearing staged tumors using an every 2 days×5 schedule.
 2. A2780Tax Human Ovarian Carcinoma Xenograft (Mutated Tubulin).
 A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days×5 schedule.
 3. HCT116/VM46 Human Colon Carcinoma Xenograft (Multi-Drug Resistant).
 HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days×5 schedule.
 4. M5076 Murine Sarcoma Model
 M5076 is a mouse fibrosarcoma that is inherently refractory to paclitaxel in vivo. The compounds described herein can be administered to mice bearing staged tumors on an every 2 days×5 schedule. One or more compounds as provided herein can be used in combination with other therapeutic agents in vivo in the multidrug resistant human colon carcinoma xenografts HCT/VM46 or any other model known in the art including those described herein.

In one aspect, compounds provided herein may be evaluated in the following models according to methods known in the art. The dosage and schedule of administration may be varied depending on the model. The results may be evaluated with those of selective delta inhibitors, and combinations of delta and gamma inhibitors, and/or with antibodies that block specific inhibitory receptors.

Pancreatic Models
 KPC model is a transgenic mouse model of pancreatic ductal adenocarcinoma (PDA), in which there is conditional expression of both mutant KrasG12D and p53R 172H alleles in pancreatic cells. Tumors develop spontaneously in this mouse over a period of 3-6 months, and can be used to study prophylactic, as well as therapeutic efficacy with novel agents. Cells from these KPC tumors can also be adoptively transferred into syngeneic B6.129 hybrid mice, creating a model with a shorter latency period and allowing large number of animals with tumors to be synchronously established. See e.g., Cancer Cell 7:468 (2005).
 Pan02 model: The murine pancreatic adenocarcinoma cell line Pan02 is a nonmetastatic tumor line, syngeneic to C57BL/6. It can be studied following s.c. injection into flank, or orthotopically following injection directly into the pancreas. See e.g., Cancer Res. 44: 717-726 (1984).

Lung Models
 LLC Lewis Lung Adenocarcinoma model: LLC cells are derived from a spontaneous lung tumor from a C57BL/6 mouse and can be studied as a s.c. tumor when injected in the flank, or as an orthotopic tumor if injected i.v., following which it localizes to the lung.
 LLC cells have also been modified to express a peptide from ovalbumin (LL2-OVA cells). Use of these cells, following either s.c. or i.v. injection, allows the tracking of OVA-specific CD8+ lymphocytes and measurement of effects of therapy on the adaptive immune response against the tumor. See e.g., Science 330:827 (2010).

Breast Model
 The 4T1 mammary carcinoma is a transplantable tumor cell line that grows in syngeneic BALB/c mice. It is highly tumorigenic and invasive and, unlike most tumor models, can spontaneously metastasize from the primary tumor in the mammary gland to multiple distant sites including lymph nodes, blood, liver, lung, brain, and bone. See e.g., Current Protocols in Immunology Unit 20.2 (2000).

Lymphoma Model
 EL4 is a C57BL/6 T thymoma and EG7 is an OVA-expressing subclone of EL4. The parental EL4 line has been modified to constitutively express luciferase, which allows non-invasive imaging of tumor growth throughout the animal using the Xenogen imaging platform.

Melanoma Model
 B16 murine melanoma cells are syngeneic with C57BL/6 mice and can be studied after s.c. or i.v. injection. Placement at either site will result in metastases to lung and other organs. This model has been extensively studied in terms of the role that inhibitory receptors play in the anti-tumor immune response. See e.g., PNAS 107:4275 (2010).

Example 228: Microsome Stability Assay

The stability of one or more subject compounds is determined according to standard procedures known in the art. For example, stability of one or more subject compounds is established by an in vitro assay. For example, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL of 10.0 mg/mL NADPH; 75 µL of 20.0 mg/mL mouse, rat or human liver microsome; 0.4 µL of 0.2 M phosphate buffer, and 425 µL of ddH$_2$O. Negative control (without NADPH) tube contains 75 µL of 20.0 mg/mL mouse, rat or human liver microsome; 0.4 µL of 0.2 M phosphate buffer, and 525 µL of ddH$_2$O. The reaction is started by adding 1.0 µL of 10.0 mM tested compound. The reaction tubes are incubated at 37° C. 100 µL sample is collected into new Eppendorf tube containing 300 µL cold methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 229: Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37 C, or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

In one embodiment, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs, time, assuming first order kinetics.

Example 230: Kinase Signaling in Blood

PI3K/Akt/mTOR signaling is measured in blood cells using the phosflow method (*Methods Enzymol.* (2007) 434: 131-54). This method is by nature a single cell assay so that cellular heterogeneity can be detected rather than population averages. This allows concurrent distinction of signaling states in different populations defined by other markers. Phosflow is also highly quantitative. To test the effects of one or more compounds provided herein, unfractionated splenocytes, or peripheral blood mononuclear cells are stimulated with anti-CD3 to initiate T-cell receptor signaling. The cells are then fixed and stained for surface markers and intracellular phosphoproteins. Inhibitors provided herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g., 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells are then analyzed by flow cytometry.

Example 231: Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435 (Stem Cell Technologies), supplemented with cytokines (IL-3, IL-6, IL-7, G-CSF, GM-CSF, CF, Flt3 ligand, and erythropoietin) and various concentrations of known chemotherapeutic agents in combination with compounds of the present disclosure. Colonies are counted by microscopy 12-14 days later. This method can be used to test for evidence of additive or synergistic activity.

Example 232: In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1\times10^6$ leukemic cells (e.g., Ph+ human or murine cells, or p190 transduced bone marrow cells). These cells are administered together with a radio-protective dose of about $5\times10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds provided herein in combination with known chemotherapeutic agents can reduce leukemic blood cell counts as compared to treatment with known chemotherapeutic agents (e.g., Gleevec) alone under the conditions tested.

Example 233: Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Slelz.Sle3z model (T. Wu et al. *J. Clin Invest.* 117:2186-2196).

The NZB/W F1 mice that spontaneously develop a systemic autoimmune disease is a model of lupus. The murine NZB/W F1 lupus model has many features of human lupus, and is characterized by elevated levels of anti-nuclear and anti-dsDNA autoantibodies; a critical role for plasmacytoid dendritic cells and IFN-α; T-cell, B-cell, macrophage involvement; pheymolytic anemia; progressive immune complex glomerulonephritis; proteinurea; severity and incidence more pronounced in females; and decreased survival. Treatment with a compound provided herein can be determined by evaluation of urine protein scores, organ weights, plasma anti-dsDNA IgG levels, and histopathology of the kidneys. The mice are treated starting at 20 weeks of age for a profilactic model and at 23 weeks of age for a therapeutic model. Blood and urine samples are obtained throughout the testing period, and tested for antinuclear antibodies (in dilutions of serum) or protein concentration (in urine). Serum is also tested for anti-ssDNA and anti-dsDNA antibodies by ELISA. Glomerulonephritis is assessed in kidney sections stained with H&E at the end of the study, or survival can be an endpoint. For example, the proteozome inhibitor Bortezimib is effective at blocking disease in the NZB/W model in both the profilactic and therapeutic model with reductions in auto-antibody production, kidney damage, and improvements in survival (*Nature Medicine* 14, 748-755 (2008)).

Lupus disease model mice such as R2KO, BXSB or MLR/lpr are treated at about 2 months old, approximately for about two months. Mice are given doses of: vehicle, RAD001 at about 10 mg/kg, or compounds provided herein at approximately 1 mg/kg to about 500 mg/kg. Blood and urine samples are obtained throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This established art model can be employed to demonstrate that the kinase inhibitors provided herein can suppress or delay the onset of lupus symptoms in lupus disease model mice.

Example 234: Murine Bone Marrow Transplant Assay

Female recipient mice are lethally irradiated from a γ ray source. About 1 hr after the radiation dose, mice are injected with about 1×106 leukemic cells from early passage p190 transduced cultures (e.g., as described in *Cancer Genet Cytogenet.* 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment, a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase, p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 μL) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art can be used to demonstrate that effective therapeutic doses of the compounds provided herein can be used for inhibiting the proliferation of leukemic cells.

Example 235: Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds provided herein that inhibit angiogenesis and are thus expected to be useful in treating ocular disorders related to aberrant angiogenesis and/or vascular permeability.

Example 236: Corneal Angiogenesis Assay

A pocket is made in the cornea, and a plug containing an angiogenesis inducing formulation (e.g., VEGF, FGF, or tumor cells), when introduced into this pocket, elicits the ingrowth of new vessels from the peripheral limbal vasculature. Slow-release materials such as ELVAX (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including, but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The results can indicate one or more compounds provided herein inhibit angiogenesis and thus can be useful in treating ocular disorders related to aberrant angiogenesis and/or vascular permeability.

Example 237: Microtiter-Plate Angiogenesis Assay

The assay plate is prepared by placing a collagen plug in the bottom of each well with 5-10 cell spheroids per collagen plug each spheroid containing 400-500 cells. Each collagen plug is covered with 1100 μL of storage medium per well and stored for future use (1-3 days at 37° C., 5% $CO_2$). The plate is sealed with sealing. Test compounds are dissolved in 200 μL assay medium with at least one well including a VEGF positive control and at least one well without VEGF or test compound as a negative control. The assay plate is removed from the incubator and storage medium is carefully pipeted away. Assay medium containing the test compounds are pipeted onto the collagen plug. The plug is placed in a humidified incubator for (37° C., 5% $CO_2$) 24-48 hours. Angiogenesis is quantified by counting the number of sprouts, measuring average sprout length, or determining cumulative sprout length. The assay can be preserved for later analysis by removing the assay medium, adding 1 mL of 10% paraformaldehyde in Hanks BSS per well, and storing at 4° C. The results are expected to identify compounds that inhibit angiogenesis in various cell types tested, including cells of ocular origin.

Example 238: Combination Use of PI3K-δ Inhibitors and Agents that Inhibit IgE Production or Activity The compounds as provided herein can present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy) phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3K-δ can be efficacious in treatment of autoimmune and inflammatory disorders (AIID), for example, rheumatoid arthritis. If any of the compounds causes an undesired level of IgE production, one can choose to administer it in combination with an agent that inhibits IgE production or IgE activity. Additionally, the administration of PI3K-δ or PI3K-δ/γ inhibitors as provided herein in combination with inhibitors of mTOR can also exhibit synergy through enhanced inhibition of the PI3K pathway. Various in vivo and in vitro models can be used to establish the effect of such combination treatment on AIID including, but not limited to: (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3K-δ inhibitors as provided herein with and without mTOR inhibitors such as rapamycin, rapalogs, or nTORC1/C2 inhibitors. The results are expected to show that in the presence of mTOR inhibitors (e.g., rapamycin) alone, there is little to no substantial effect on IgG and IgE response. However, in the presence of PI3K-δ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3K-δ inhibitors alone.

(b) 7NP Assay

Mice are immunized with TNP-Ficoll or TNP-KHL and treated with: vehicle, a PI3K-δ inhibitor, an mTOR inhibitor, for example rapamycin, or a PI3K-δ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3K-δ inhibitor and mTOR inhibitor exhibit a reduction in antigen specific IgG3 response as compared to the mice treated with vehicle alone. Additionally, the mice treated with both PI3K-δ inhibitor and mTOR inhibitor exhibit a decrease in IgE response as compared to the mice treated with PI3K-δ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3K-δ inhibitor, or PI3K-δ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

The combination treatment using a compound as provided herein and rapamycin can provide greater efficacy than treatment with PI3K-δ inhibitor alone.

Example 239: Delayed Type Hypersensitivity Model

DTH is induced by sensitizing 60 BALB/c male mice on day 0 and day 1 with a solution of 0.05% 2,4 dinitrofluorobenzene (DNFB) in a 4:1 acetone/olive oil mixture. Mice are gently restrained while 20 μL of solution is applied to the hind foot pads of each mouse. The hind foot pads of the mice are used as they represent an anatomical site that can be easily isolated and immobilized without anesthesia. On day 5, mice are administered a single dose of vehicle, a compound provided herein at 10, 3, 1, or 0.3 mg/kg, or dexamethasone at a dose of 5 mg/kg by oral gavage. Thirty minutes later mice are anaesthetized, and a solution of 0.25% DNFB in a 4:1 acetone/olive oil solution is applied to the left inner and outer ear surface. This application results in the induction of swelling to the left ear and under these conditions, all animals responded to this treatment with ear swelling. A vehicle control solution of 4:1 acetone/olive oil is applied to the right inner and outer ear. Twenty four hours later, mice are anaesthetized, and measurements of the left and right ear are taken using a digital micrometer. The difference between the two ears is recorded as the amount of swelling induced by the challenge of DNFB. Drag treatment groups are compared to vehicle control to generate the percent reduction in ear swelling. Dexamethasone is routinely used as a positive control as it has broad anti-inflammatory activity.

Example 240: Peptidoglycan-Polysaccharide Rat Arthritic Model (a) Systemic Arthritis Model All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intraperitoneally (i.p.) with a single injection of purified PG-PS 10S Group A, D58 strain (concentration 25 μg/g of bodyweight)

suspended in sterile 0.85% saline. Each animal receives a total volume of 500 microliters administered in the lower left quadrant of the abdomen using a 1 milliliter syringe with a 23 gauge needle. Placement of the needle is critical to avoid injecting the PG-PS 10S into either the stomach or caecum. Animals are under continuous observation until fully recovered from anesthesia and moving about the cage. An acute response of a sharp increase in ankle measurement, typically 20% above baseline measurement can peak in 3-5 days post injection. Treatment with test compounds can be PO, SC, IV or IP. Rats are dosed no more than two times in a 24 hour time span. Treatment can begin on day 0 or any day after that through day 30. The animals are weighed on days 0, 1, 2, 3, 4, 5, 6, 7 and beginning again on day 12-30 or until the study is terminated. Paw/ankle diameter is measured with a digital caliper on the left and right side on day 0 prior to injection and again on day 1, 2, 3, 4, 5, 6 and 7. On day 12, measurements begin again and continue on through day 30. At this time, animals can be anesthetized with isoflurane, as described above, and terminal blood samples can be obtained by tail vein draws for the evaluation of the compound blood levels, clinical chemistry or hematology parameters. Animals are then euthanized with carbon dioxide overdose. A thoracotomy can be conducted as a means of death verification.

(b) Monoarticular Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intra-articular (i.a.) with a single injection of purified PG-PS 100P Group A, D58 strain (concentration 500 µg/mL) suspended in sterile 0.85% saline. Each rat receives a total volume of 10 microliters administered into the tibiotalar joint space using a 1 milliliter syringe with a 27 gauge needle. Animals are under continuous observation until fully recovered from anesthesia and moving about the cage. Animals that respond 2-3 days later with a sharp increase in ankle measurement, typically 20% above baseline measurement on the initial i.a. injection, are included in the study. On day 14, all responders are anesthetized again using the procedure previously described. Animals receive an intravenous (I.V.) injection of PG-PS (concentration 250 µL/mL). Each rat receives a total volume of 400 microliters administered slowly into the lateral tail vein using a 1 milliliter syringe with a 27 gauge needle. Baseline ankle measurements are measured prior to IV injection and continue through the course of inflammation or out to day 10. Treatment with test compounds can be PO, SC, IV or IP. Rats are dosed no more than two times in a 24 hour time span. Treatment can begin on day 0 or any day after that through day 24. The animals are weighed on days 0, 1, 2, 3, 4, 5, and beginning again on day 14-24 or until the study is terminated. Paw/ankle diameter is measured with a digital caliper on the left and right side on day 0 prior to injection and again on day 1, 2, 3, 4, 5, and beginning again on day 14-24 or until the study is terminated. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

Example 241: Mice Models for Asthma

Efficacy of a compound provided herein n treating, preventing and/or managing asthma can be assessed using an conventional animal models including various mice models described in, for example, Nials et al., *Dis Model Mech.* 1(4-5): 213-220 (2008).

(a) Acute Allergen Challenge Models

Several models are known in the art and any of such models can be used. Although various allergens can be used to induce asthma-like conditions, the principle is consistent throughout the methods. Briefly, asthma-like conditions are induced through multiple systemic administration of the allergen (e.g., ova, house dust mite extracts and cockroach extracts) in the presence of an adjuvant such as aluminum hydroxide. Alternatively, an adjuvant-free system can be used, but it usually requires a higher number of exposures to achieve suitable sensitization. Once induced, animals exhibit many key features of clinical asthma such as: elevated levels of IgE; airway inflammation; goblet cell hyperplasia; epithelial hypertrophy; AHR; or specific stimuli; and early and late phase bronchoconstriction. Potential efficacy of a compound thus can be assessed by determining whether one or more of these clinical features are reversed or mitigated.

(b) Chronic Allergen Challenge Models

Chronic allergen challenge models aim to reproduce more of the features of the clinical asthma, such as airway remodeling and persistent AHR, than acute challenge models. While allergens similar to those used in acute allergen challenge models can be used, in chronic allergen challenge models, animals are subjected to repeated exposure of the airways to low levels of allergen for a period of up to 12 weeks. Once induced, animals exhibit key features of human asthma such as: allergen-dependent sensitization; a Th2-dependent allergic inflammation characterized by eosinophilic influx into the airway mucosa; AHR; and airway remodeling as evidenced by goblet cell hyperplasia, epithelial hypertrophy, subepithelial or peribronchiolar fibrosis. Potential efficacy of a compound thus can be assessed by determining whether one or more of these clinical features are reversed or mitigated.

Example 242: Models for Psoriasis

Efficacy of a compound provided herein in treating, preventing and/or managing psoriasis can be assessed using an conventional animal models including various animal models described in, for example, Boehncke et al., *Clinics in Dermatology*, 25: 596-605 (2007).

As an example, the mouse model based on adoptive transfer of $CD4^+CD45RB^{hi}$ T cells described in Hong et al., *J. Immunol.*, 162: 7480-7491 (1999) can be made. Briefly, female BALB/cBY (donor) and C.B.-17/Prkdc scid/scid (recipient) mice are housed in a specific pathogen-free environment and are used between 6 and 8 weeks of age, $CD4^+$ T cells are enriched from BALB/cBy splenocytes using a mouse CD4 enrichment kit. The cells are then labeled with PE-conjugated anti-CD4, FITC-conjugated anti-CD45RB, and APC-conjugated anti-CD25 antibodies. Cells are sorted using a cell sorter, $CD4^+CD45RB^{hi}CD25$ cells are collected. Cells are resuspended in saline and $4\times10^8$ cells/mouse are injected i.p. into C.B.-17/Prkdc scid/scid mice. Mice may be dosed with LPS, cytokines, or antibodies as necessary. Mice are monitored for external signs of skin lesions twice each week. After the termination, ear, back skin, lymph nodes and spleen may be collected for further ex vivo studies.

Example 243: Models for Scleroderma

A compound's efficacy in treating scleroderma can be tested using animal models. An exemplary animal model is a mouse model for scleroderma induced by repeated local injections of bleomycin ("BLM") described, for example, in Yamamoto et al., *J Invest Dermatol* 112: 456-462 (1999), the entirety of which is incorporated herein by reference. This mouse model provides dermal sclerosis that closely resembles systemic sclerosis both histologically and biochemically. The sclerotic changes observed in the model include, but are not limited to: thickened and homogenous collagen bundles and cellular filtrates, gradual increase in number of mast cells; degranulation of mast cells; elevated histamine release; increase in hydroxyproline in skin; presence of anti-nuclear antibody in serum; and strong expression of transforming growth factor β-2 mRNA. Therefore, efficacy of a compound in treating scleroderma can be assessed by monitoring the lessening of one or more of these changes.

Briefly, the following exemplary procedures can be used to generate the mouse model for scleroderma: Specific pathogen-free, female BALB/C mice and C3H mice of 6 weeks old, weighing about 20 g, are purchased and maintained with food and water ad libitum BLM is dissolved in PBS at differing concentrations and sterilized with filtration. Aliquots of each concentration of BLM or PBS are injected subcutaneously into the shaved back of the mice daily for 1-4 weeks with a needle. Alternatively, mice are injected every other day.

Histolopathological and biochemical changes induced can be assessed using any methods commonly practiced in the field. For example, histopathological changes can be assessed using a standard avidine-biotin peroxidase technique with anti-L3T4 monoclonal antibody, anti-Lyt2 monoclonal antibody, anti-mouse pan-tissue-fixed macrophage antibody, anti-stem cell factor monoclonal antibody, anti-transforming growth factor-β polyclonal antibody, and anti-decorin antibody. Cytokine expression of cellular infiltrates can be assessed by using several anti-cytokine antibodies. Hydroxyproline level can be assessed by hydrolyzing skin pieces with hydrochloric acid, neutralizing with sodium hydroxide, and colorimetrically assessing the hydrolates at 560 nm with p-dimethylaminobenzaldehyde. Pepsin-resistant collagen can be assessed by treating collagen sample extracted from biopsied tissues and analyzing by polyacrylamide stacking gel electrophoresis. Mast cells can be identified by toluidine blue, and cells containing metachromatic granules can be counted under high magnification of a light microscope. Serum levels of various cytokines can be assessed by enzyme-linked immunosorbent assay, and mRNA levels of the cytokines can be assessed by reverse-transcriptase polymerase chain reaction. Autoantibodies in serum can be detected using 3T3 fibroblasts as the substrate for the screening.

Example 244: Models for Myositis

A compound's efficacy in treating myositis (e.g., dermatomyositis) can be tested using animal models known in the art. One such example is the familial canine dermatomyositis model described in Hargis et al., *AJP* 120(2): 323-325 (1985). Another example is the rabbit myosin induced mouse model described in Phyanagi et al., *Arthritis & Rheumatism*, 60(10): 3118-3127 (2009).

Briefly, 5-week old male SJL/J mice are used. Purified myosin from rabbit skeletal muscle (6.6 mg/ml) is emulsified with an equal amount of Freund's complete adjuvant and 3.3 mg/ml *Mycobacterium butyricum*. The mice are immunized repeatedly with emulsified rabbit myosin. Once myositis is induced, inflammatory cell filtration and necrotic muscle fiber should be evident in the model. In the muscles of animals, CD4$^+$ T cells are mainly located in the perimysum and CD8$^+$ T cells are mainly located in the endomysium and surround non-necrotic muscle fibers, TNFα, IFNγ and perforin are up-regulated and intercellular adhesion molecule 1 is increased in the muscles.

To assess the efficacy of a compound, following administration of the compound through adequate route at specified dose, the mice are killed and muscle tissues are harvested. The muscle tissue is immediately frozen in chilled isopentane precooled in liquid nitrogen, and then cryostat sections are prepared. The sections are stained with hematoxylin and eosin for counting of number of infiltrated cells. Three sections from each mouse are prepared and photomicrographs are obtained. For immunohistochemical tests, cryostat sections of muscle are dried and fixed in cold acetone at −20° C. The slides are rehydrated in PBS, and then endogeneous peroxidase activity is blocked by incubation in 1% hydrogen peroxide. The sections are incubated overnight with rat anti-mouse CD4 monoclonal antibody, rat anti-mouse CD8 monoclonal antibody, rat anti-mouse F4/80 monoclonal antibody or normal rat IgG in antibody diluent. The samples are washed with PBS and incubated with biotin-conjugated rabbit anti-rat IgG pretreated with 5% normal mouse serum. After washing with PBS, the samples are incubated with streptavidin-horseradish peroxidase. After washing PBS, diaminobenzidine is used for visualization.

Example 245: Models for Sjögren Syndrome

A compound's efficacy in treating Sjögren's syndrome can be tested using animal models known in the art, for example, those described in Chiorini et al., *Journal of Autoimmunity* 33: 190-196 (2009). Examples include: mouse model spontaneously developed in first filial generation of NZB mice crossed to NZW mice (see, e.g., Jonsson et al., *Clin Immunol Immunopathol* 42: 93-101 (1987); mouse model induced by i.p. injection of incomplete Freund's adjuvant (id.; Deshmukh et al., *J Oral Pathol Med* 38: 42-27 (2009)); NOD mouse models wherein Sjögren's phenotype is developed by specific genotypes (see, e.g., Cha et al., *Arthritis Rheum* 46: 1390-1398 (2002); Kong et al., *Clin Exp Rheumatol* 16: 675-681 (1998); Podolin et al., *J Exp Med* 178: 793-803 (1993); and Rasooly et al., *Clin Immunol Immunopathol* 81: 287-292 (1996)); mouse model developed in spontaneous lpr mutation; mouse model developed in Id3 knock-out mice (see, e.g., Li et al., *Immunity* 21: 551-560 (2004)); mouse model developed in PI3K knock-out mice (see, e.g., Oak et al., *Proc Natl Acad Sci USA* 103: 16882-16887 (2006)); mouse model developed in BAFF over-expressing transgenic mice (see, e.g., Groom et al., *J Clin Invest* 109: 59-68 (2002)); mouse model induced by injection of Ro antigen into BALB/c mice (see, e.g., Oh-Hora et al., *Nat. Immunol* 9: 432-443 (2008)); mouse model induced by injection of carbonic anhydrase II (see, e.g., Nishimori et al., *J Immunol* 154: 4865-4873 (1995); mouse model developed in IL-14 over-expressing transgenic mice (see, e.g., Shen et al., *J Immunol* 177: 5676-5686 (2006)); and mouse model developed in IL-12 expressing transgenic mice (see, e.g., McGrath-Morrow et al., *Am J Physiol Lung Cell Mol Physiol* 291: L837-846 (2006)).

Example 246: Models for Immune Complex Mediated Disease

The Arthus reaction is a type 3 immune response to immune complexes, and thus, can be a mechanistic model supporting therapeutic hypothesis for immune complex mediated diseases such as rheumatoid arthritis, lupus and other autoimmune diseases. For example, PI3Kγ and δ deficient mice can be used as experimental models of the Arthus reaction and provide assessment of therapeutic potential of a compound as to the treatment of immune complex mediated diseases. The Arthus reaction can be induced using the following exemplary procedures as described in Konrad et al., *Journal of Biological Chemistry* (2008 283(48): 33296-33303.

PI3Kγ- and PI3Kδ-deficient mice are maintained under div barrier conditions. Mice are anesthetized with ketamine and xylazine, and the trachea is cannulated. Appropriate amount of protein G-purified anti-OVA IgG Ab is applied, and appropriate amount of OVA antigen is given intravenously. For PI3K blocking experiments, wortmanin is given intratracheally together with the application of anti-OVA igG. Mice are killed at 2-4 hours after initiation of inflammation, and desired follow up assessments can be performed using methods known in the art.

Example 247: PI3-Kinase Promega™ Assay

Promega ADP-Glo Max assay kit (Cat. No. V7002) can be utilized to determine $IC_{50}$ values for α, β, δ and γ isoforms of human Class I PI3 kinases (Millipore). Samples of kinase (20 nM α or δ, 40 nM β or γ isoform) are incubated with compound for 15 minutes at room temperature in reaction buffer (15 mM HEPES pH 7.4, 20 mM NaCl, 1 mM EGTA, 0.02% Tween 20, 10 mM $MgCl_2$, 0.2 mg/mL bovine-γ-globulins) followed by addition of ATP/diC8-PtdInsP mixture to give final concentrations of 3 mM ATP and 500 uM $diC_8$-PtdInsP. Reactions are incubated at room temperature for 2 hours followed by addition of 25 uL of stop solution. After a 40-minute incubation at room temperature, 50 uL of Promega detection mix is added followed by incubation for 1 hour at room temperature. Plates are then read on Envision plate reader in luminescence mode. Data are converted to % inhibition using the following equation below:

$$\% \text{ inhibition} = 100 - \left( \left[ \frac{S - Pos}{Neg - Pos} \right] * 100 \right)$$

where S is the sample luminescence, Pos is a positive control without added PI3K, Neg is the negative control without added compound. Data are then plotted as % inhibition vs compound concentration. Data fit to 4 parameter logistic equation to determine $IC_{50}$ values:

$$\% \text{ Inhibition} = \frac{max - min}{1 - \left( \frac{IC_{50}^h}{[I]^h} \right)}$$

Example 248: Isoform-Selective Cellular Assays (a) PI3K-δ Selective Assay

A compound's ability in selectively inhibiting PI3K-δ can be assessed using RAJI cells, i.e., B lymphocyte cells derived from lymphoma patients. Briefly, serum-starved RAJI cells are stimulated with anti-human IgM, thereby causing signaling through the B-cell receptors, as described in, for example, He et al., *Leukemia Research* (2009) 33: 798-802. B-cell receptor signaling is important for the activation, differentiation, and survival of B cells and certain B-cell derived cancers. Reduction of phospho-AKT is indicative of compounds that may inhibit B-cell proliferation and function in certain diseases. By monitoring the reduction of phospho-AKT in stimulated RAJI cells (using for example, phospho-AKT antibodies), a compound's potential efficacy in selectively inhibiting PI3KS can be assessed.

(b) PI3K-γ Selective Assay

A compound's ability in selectively inhibiting PI3K-γ can be assessed using RAW264.7 macrophages. Briefly, serum-starved RAW264.7 cells are stimulated with a known GPCR agonist C5a. See, e.g., Camps et al., *Nature Medicine* (2005) 11(9):936-943. Cells can be treated with test compounds prior to, simultaneously with, or subsequent to the stimulation by C5a. RAW 264.7 cells respond to the complement component fragment C5a through activation of the C5a receptor, and the C5a receptor activates macrophages and induces cell migration. Test compounds' ability to inhibit C5a-mediated AKT phosphorylation is indicative of selective inhibition of PI3K-γ. Thus, by monitoring the reduction of phospho-AKT in stimulated RAW 264.7 cells (using for example, phospho-AKT antibodies), a compound's potential efficacy in selectively inhibiting PI3Kγ can be assessed.

Certain compounds provided herein were tested in RAW 264.7 cell model using procedures as described above. The $IC_{50}$ values for phospho-AKT are summarized in Table 2.

(c) PI3K-α Selective Assay

A compound's ability in selectively inhibiting PI3K-α can be assessed using SKOV-3 cells, i.e., human ovarian carcinoma cell line. Briefly, SKOV-3 cells, in which mutant PI3Kα is constitutively active, can be treated with test compounds. Test compounds' ability to inhibit AKT phosphorylation in SKOV-3 cells, therefore, is indicative of selective inhibition of PI3Kα. Thus, by monitoring the reduction of phospho-AKT in SKOV-3 cells (using for example, phospho-AKT antibodies), a compound's potential efficacy in selectively inhibiting PI3Kα can be assessed.

(d) PI3K-β Selective Assay

A compound's ability in selectively inhibiting PI3K-β can be assessed using 786-O cells, i.e., human kidney carcinoma cell line. Briefly, 786-O cells, in which PI3Kβ is constitutively active, can be treated with test compounds. Test compounds' ability to inhibit AKT phosphorylation in 786-O cells, therefore, is indicative of selective inhibition of PI3K. Thus, by monitoring the reduction of phospho-AKT in 786-O cells (using for example, phospho-AKT antibodies), a compound's potential efficacy in selectively inhibiting PI3Kβ can be assessed.

The present invention is not to be limited in scope by the specific embodiments described herein. Indeed, various modifications of the invention in addition to those described will become apparent to those skilled in the art from the foregoing description. Such modifications are intended to fall within the scope of the appended claims. Various publications, patents and patent applications are cited herein, the disclosures of which are incorporated by reference in their entireties.

What is claimed is:

1. A compound of Formula I' or Formula II':

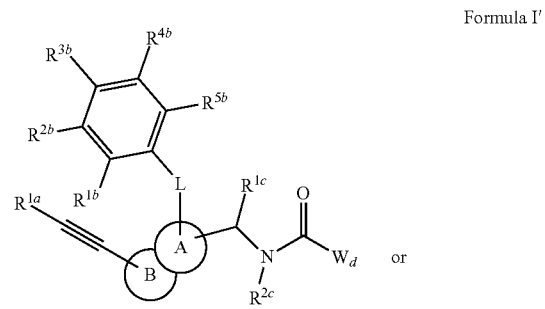

Formula I' or

549
-continued

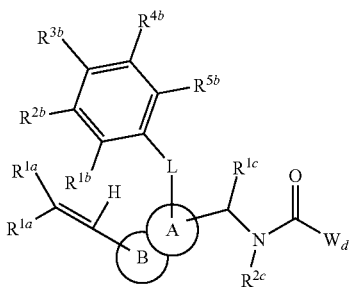
Formula II' or a pharmaceutically acceptable form thereof, wherein

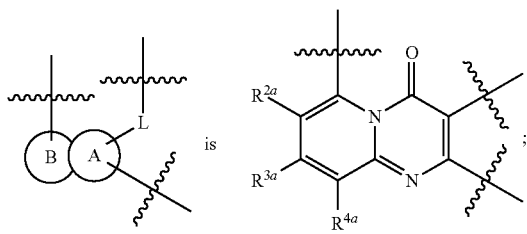
is $W_d$ is a 3-14 membered heteroaryl; wherein the heteroaryl is optionally substituted with $R^{1f}$, $R^{2f}$, $R^{3f}$, $R^{4f}$, and $R^{5f}$;
each instance of $R^{1a}$ is independently selected from the group consisting of hydrogen, $C_1$-$C_8$ alkyl, and 5-6 membered heteroaryl; wherein each of alkyl or heteroaryl is optionally substituted with one or more $R^{11}$;
each instance of $R^{11}$ is independently selected from the group consisting of hydrogen, $C_1$-$C_8$ alkyl, $C_2$-$C_8$ alkenyl, $C_2$-$C_8$ alkynyl, halo, OH, O($C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);
$R^{2a}$, $R^{3a}$, and $R^{4a}$ each is hydrogen;
$R^{1b}$, $R^{2b}$, $R^{3b}$, $R^{4b}$, and $R^{5b}$ each is hydrogen;
$R^{1c}$ is selected from the group consisting of hydrogen, $C_1$-$C_8$ alkyl, $C_2$-$C_8$ alkenyl, $C_2$-$C_8$ alkynyl, halo, OH, O($C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S);
$R^{2c}$ is hydrogen or $C_1$-$C_8$ alkyl;

550

$R^{1f}$ is selected from the group consisting of $NH_2$, $NH(C_1$-$C_8$ alkyl), $N(C_1$-$C_8$ alkyl)$_2$, hydrogen, $C_1$-$C_8$ alkyl, $C_2$-$C_8$ alkenyl, $C_2$-$C_8$ alkynyl, halo, OH, O($C_1$-$C_8$ alkyl), $OCF_3$, $OCF_2H$, $OCFH_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S); and $R^{2f}$, $R^{3f}$, $R^{4f}$, and $R^{5f}$ each is independently selected from the group consisting of hydrogen, $C_1$-$C_8$ alkyl, $C_2$-$C_8$ alkenyl, $C_2$-$C_8$ alkynyl, halo, OH, O($C_1$-$C_8$ alkyl), $OCF_3$, $OCF_2H$, $OCFH_2$, $NH_2$, $NH(C_1$-$C_8$ alkyl), $N(C_1$-$C_8$ alkyl)$_2$, haloalkyl, CN, $NO_2$, $CONH_2$, $CONH(C_1$-$C_8$ alkyl), $CON(C_1$-$C_8$ alkyl)$_2$, COH, $CO(C_1$-$C_8$ alkyl), COOH, $COO(C_1$-$C_8$ alkyl), $NHCO(C_1$-$C_8$ alkyl), $N(C_1$-$C_8$ alkyl)$CO(C_1$-$C_8$ alkyl), (3-14 membered saturated, unsaturated, or aromatic carbocycle), and (3-14 membered saturated, unsaturated, or aromatic heterocycle containing one or more heteroatoms selected from the group consisting of N, O, and S).

2. The compound of claim 1, which is a compound of Formula I':

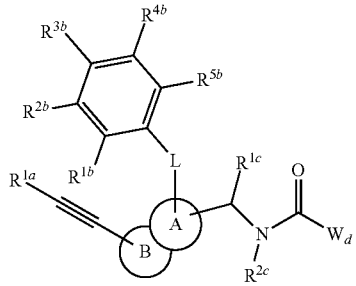
Formula I' or a pharmaceutically acceptable form thereof.

3. The compound of claim 1, which is a compound of Formula II':

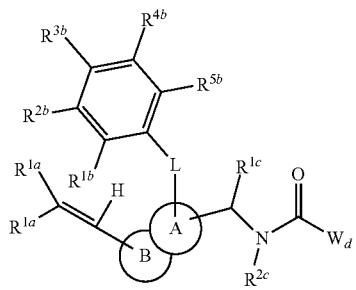
Formula II' or a pharmaceutically acceptable form thereof.

4. The compound of claim 2, wherein the compound of Formula I' is a compound of formula I:

Formula I

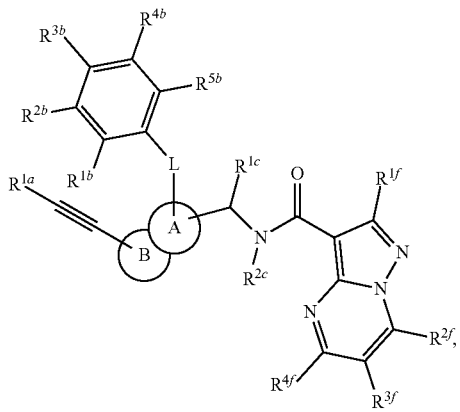

or a pharmaceutically acceptable form thereof.

5. The compound of claim 3, wherein the compound of Formula II' is a compound of formula II:

Formula II

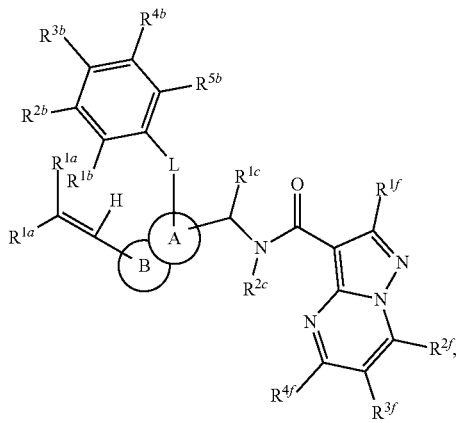

or a pharmaceutically acceptable form thereof.

6. The compound of claim 2, wherein the compound of Formula I' is a compound of the formula:

Formula A2

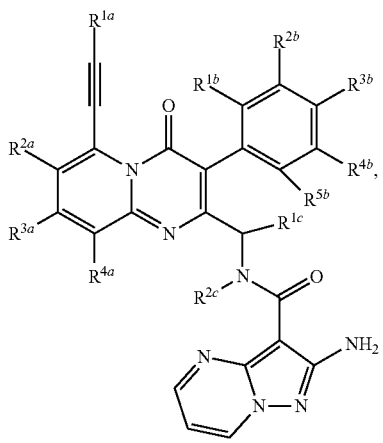

or a pharmaceutically acceptable form thereof.

7. The compound of claim 2, wherein the compound of Formula I' is a compound of the formula:

Formula A2S

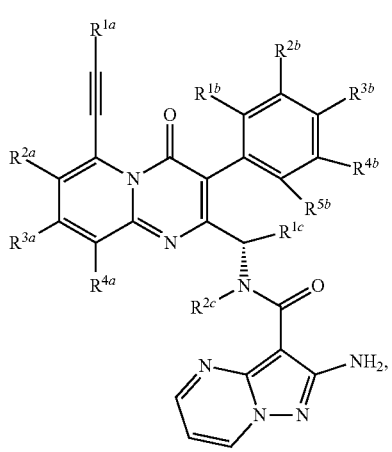

or a pharmaceutically acceptable form thereof.

8. The compound of claim 1, which is

249

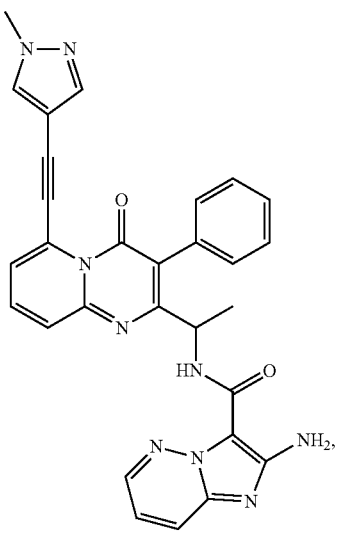

250

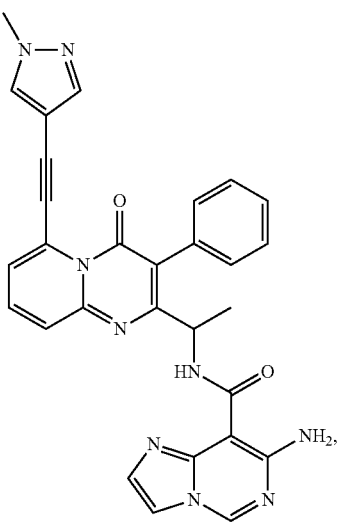

251
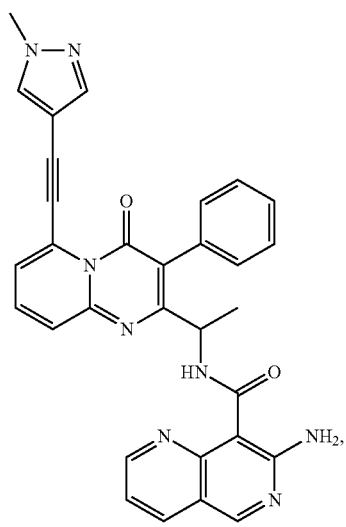
252
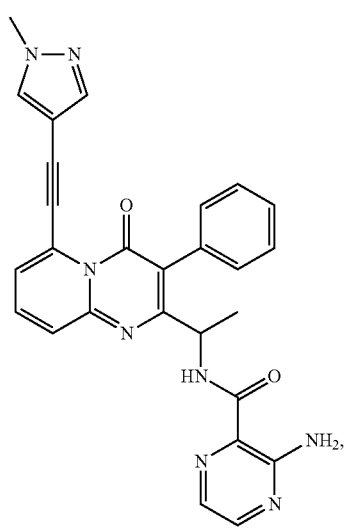
249S
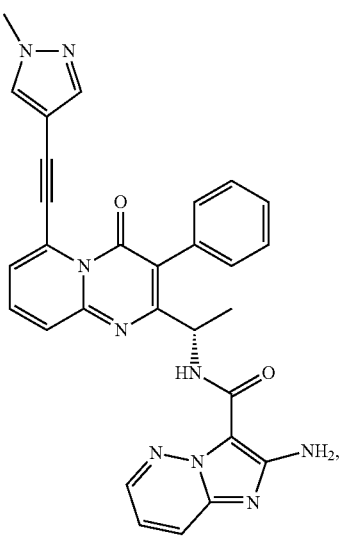
250S
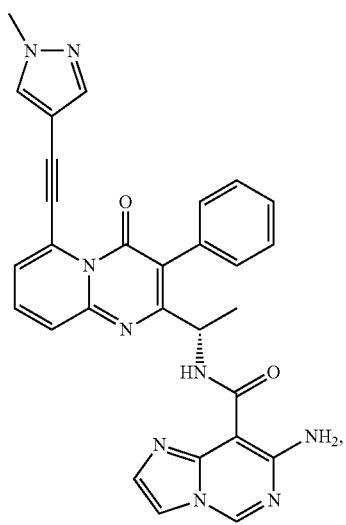
251S
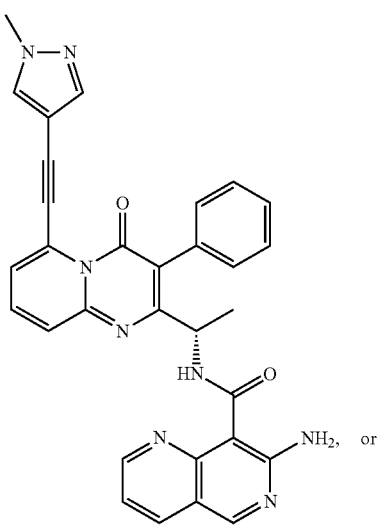
252S
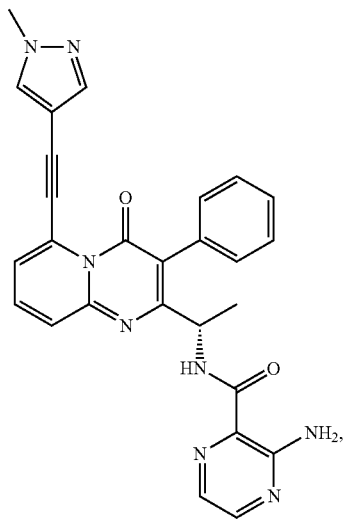
or a pharmaceutically acceptable salt thereof.
9. The compound of claim 4, wherein $R^{1f}$ is $NH_2$, $NH(C_1$-$C_8$ alkyl), or $N(C_1$-$C_8$ alkyl)$_2$.
10. The compound of claim 9, wherein $R^{1f}$ is $NH_2$.

11. The compound of claim 4, wherein $R^{2f}$, $R^{3f}$, and $R^{4f}$ each is independently hydrogen, $C_1$-$C_8$ alkyl, $C_2$-$C_8$ alkenyl, or $C_2$-$C_8$ alkynyl.
12. The compound of claim 11, wherein $R^{2f}$, $R^{3f}$, and $R^{4f}$ are hydrogen.
13. The compound of claim 1, which is
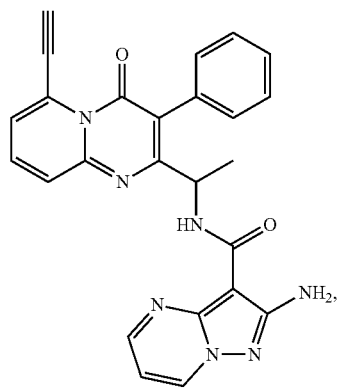
107
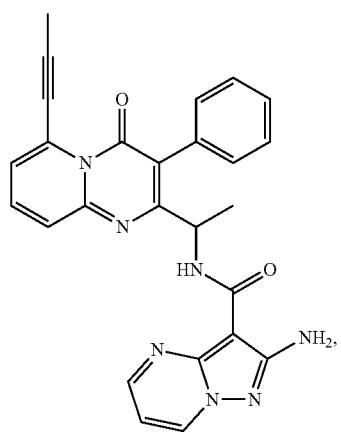
108
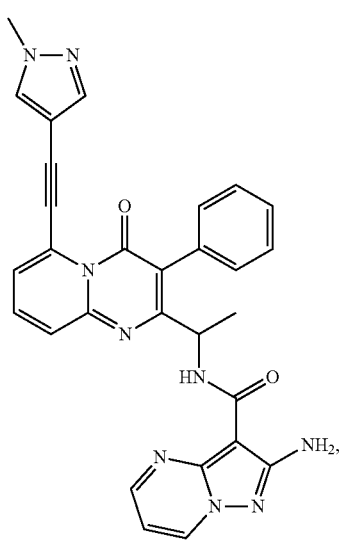
109
-continued
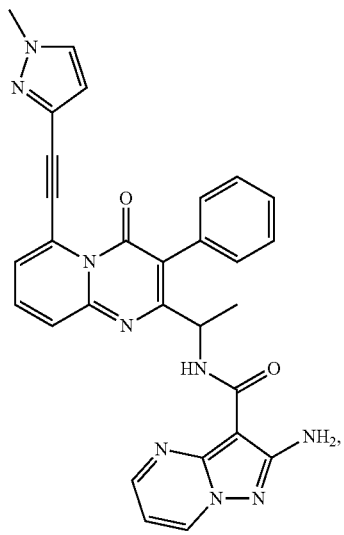
110
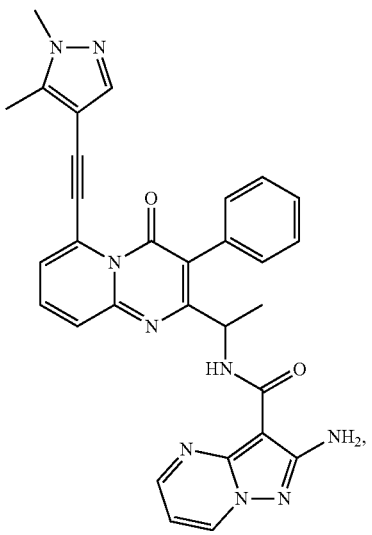
111
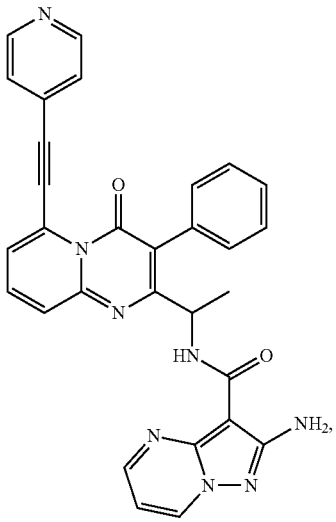
112

557
-continued
107S
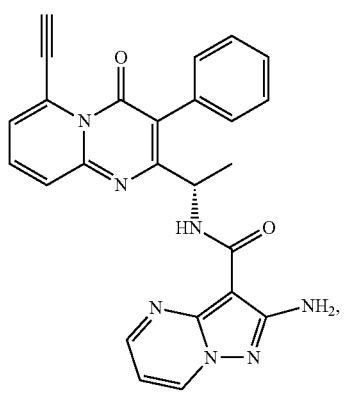
108S
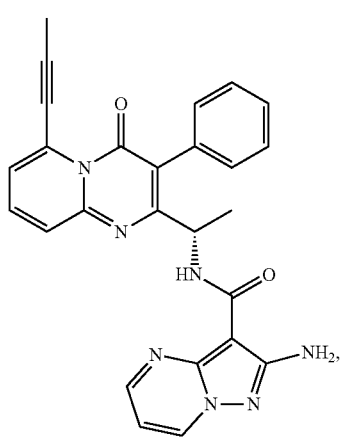
109S
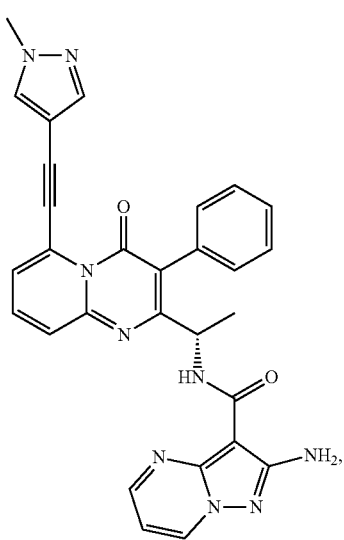
558
-continued
110S
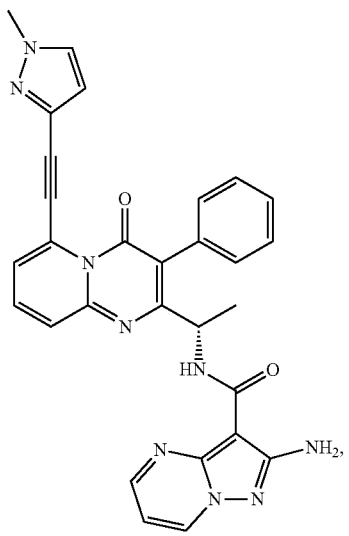
111S
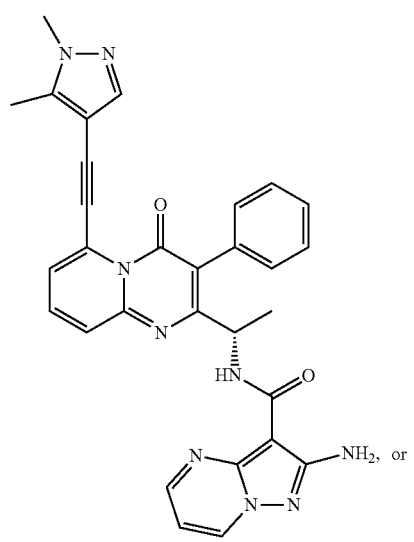
, or
112S
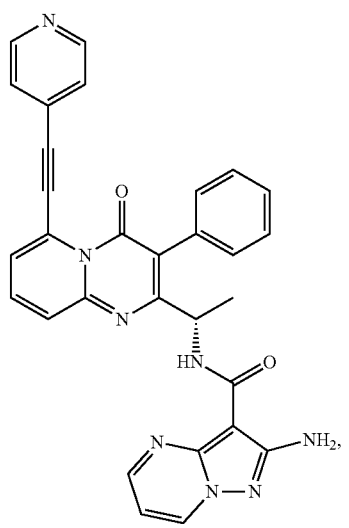
or a pharmaceutically acceptable salt thereof.

14. A pharmaceutical composition comprising a compound of claim 1 and a pharmaceutically acceptable expedient.

15. The pharmaceutical composition of claim 14, further comprising one or more therapeutic agents.

* * * * *